(12) United States Patent
Barbosa, Jr. et al.

(10) Patent No.: US 8,598,174 B2
(45) Date of Patent: Dec. 3, 2013

(54) PYRIDAZINONES, METHOD OF MAKING, AND METHOD OF USE THEREOF

(75) Inventors: Antonio J. M. Barbosa, Jr., Middlebury, CT (US); Peter A. Blomgren, North Branford, CT (US); Kevin S. Currie, North Branford, CT (US); Seung Lee, Branford, CT (US); Jeffrey E. Kropf, Branford, CT (US); Scott A. Mitchell, East Haven, CT (US); Daniel Ortwine, San Ramon, CA (US); William M. Rennells, Schenectady, NY (US); Aaron C. Schmitt, Hamden, CT (US); Jianjun Xu, Madison, CT (US); Wendy B. Young, San Mateo, CA (US); Zhongdong Zhao, Guilford, CT (US); Pavel E. Zhichkin, Delmar, NY (US)

(73) Assignees: Genetech, Inc., South San Francisco, CA (US); Gilead Connecticut, Inc., Foster City, CA (US)

( * ) Notice: Subject to any disclaimer, the term of this patent is extended or adjusted under 35 U.S.C. 154(b) by 0 days.

(21) Appl. No.: 13/128,726

(22) PCT Filed: Nov. 12, 2009

(86) PCT No.: PCT/US2009/064224
§ 371 (c)(1),
(2), (4) Date: Aug. 26, 2011

(87) PCT Pub. No.: WO2010/056875
PCT Pub. Date: May 20, 2010

(65) Prior Publication Data
US 2011/0301145 A1 Dec. 8, 2011

Related U.S. Application Data

(60) Provisional application No. 61/113,953, filed on Nov. 12, 2008, provisional application No. 61/120,669, filed on Dec. 8, 2008, provisional application No. 61/223,983, filed on Jul. 8, 2009.

(51) Int. Cl.
*A61K 31/50* (2006.01)
*A61K 31/501* (2006.01)
*C07D 237/30* (2006.01)

(52) U.S. Cl.
USPC .................................. 514/252.01; 544/224

(58) Field of Classification Search
USPC ................. 544/224, 252.01; 514/252.01, 224
See application file for complete search history.

(56) References Cited

U.S. PATENT DOCUMENTS

| | | | |
|---|---|---|---|
| 2006/0229337 A1 | 10/2006 | Brittelli et al. | |
| 2008/0139557 A1 | 6/2008 | Blomgren et al. | |
| 2009/0105209 A1 | 4/2009 | Dewdney et al. | |

FOREIGN PATENT DOCUMENTS

| | | |
|---|---|---|
| WO | WO 2006/099075 A2 | 9/2006 |
| WO | WO 2008/033854 A1 | 3/2008 |
| WO | WO 2009/053269 A1 | 4/2009 |
| WO | WO 2009/137596 A1 | 11/2009 |

OTHER PUBLICATIONS

Vippagunta et al (2000).*
Pinedo et al (2000).*
McMahon et al (2000).*
International Preliminary Report on Patentability for PCT/US2009/064224 dated May 17, 2011.
International Search Report of PCT/US2009/064224 (Mar. 24, 2010).

* cited by examiner

*Primary Examiner* — Paul V. Ward
(74) *Attorney, Agent, or Firm* — Millen, White, Zelano & Branigan, P.C.

(57) ABSTRACT

Compounds of Formula I that inhibit Btk are described herein. Pharmaceutical compositions comprising at least one compound of Formula I, together with at least one pharmaceutically acceptable vehicle chosen from carriers, adjuvants, and excipients, are described. Methods of treating patients suffering from certain diseases responsive to inhibition of Btk activity and/or B-cell activity are described. Methods for determining the presence of Btk in a sample are described.

(Formula I)

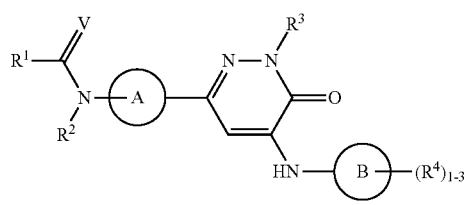

13 Claims, No Drawings

PYRIDAZINONES, METHOD OF MAKING, AND METHOD OF USE THEREOF

This application claims the benefit of the filing date of U.S. Provisional Application Ser. No. 61/113,953 filed Nov. 12, 2008, U.S. Provisional Application Ser. No. 61/120,669 filed Dec. 8, 2008 and U.S. Provisional Application Ser. No. 61/223,983 filed Jul. 8, 2009, which are incorporated by reference herein.

Provided herein are certain substituted pyridazinones, compositions comprising such compounds, and methods of their use.

Protein kinases, the largest family of human enzymes, encompass well over 500 proteins. Bruton's Tyrosine Kinase (Btk) is a member of the Tec family of tyrosine kinases, and is a regulator of early B-cell development as well as mature B-cell activation, signaling, and survival.

B-cell signaling through the B-cell receptor (BCR) can lead to a wide range of biological outputs, which in turn depend on the developmental stage of the B-cell. The magnitude and duration of BCR signals must be precisely regulated. Aberrant BCR-mediated signaling can cause disregulated B-cell activation and/or the formation of pathogenic auto-antibodies leading to multiple autoimmune and/or inflammatory diseases. Mutation of Btk in humans results in X-linked agammaglobulinaemia (XLA). This disease is associated with the impaired maturation of B-cells, diminished immunoglobulin production, compromised T-cell-independent immune responses and marked attenuation of the sustained calcium sign upon BCR stimulation.

Evidence for the role of Btk in allergic disorders and/or autoimmune disease and/or inflammatory disease has been established in Btk-deficient mouse models. For example, in standard murine preclinical models of systemic lupus erythematosus (SLE), Btk deficiency has been shown to result in a marked amelioration of disease progression. Moreover, Btk deficient mice can also be resistant to developing collagen-induced arthritis and can be less susceptible to Staphylococci's-induced arthritis.

A large body of evidence supports the role of B-cells and the humoral immune system in the pathogenesis of autoimmune and/or inflammatory diseases. Protein-based therapeutics (such as Rituxan) developed to deplete B-cells, represent an approach to the treatment of a number of autoimmune and/or inflammatory diseases. Because of Btk's role in B-cell activation, inhibitors of Btk can be useful as inhibitors of B-cell mediated pathogenic activity (such as autoantibody production).

Btk is also expressed in osteoclasts, mast cells and monocytes and has been shown to be important for the function of these cells. For example, Btk deficiency in mice is associated with impaired IgE-mediated mast cell activation (marked diminution of TNF-alpha and other inflammatory cytokine release), and Btk deficiency in humans is associated with greatly reduced TNF-alpha production by activated monocytes.

Thus, inhibition of Btk activity can be useful for the treatment of allergic disorders and/or autoimmune and/or inflammatory diseases such as: SLE, rheumatoid arthritis, multiple vasculitides, idiopathic thrombocytopenic purpura (ITP), myasthenia gravis, allergic rhinitis, and asthma. In addition, Btk has been reported to play a role in apoptosis; thus, inhibition of Btk activity can be useful for cancer, as well as the treatment of B-cell lymphoma and leukemia. Moreover, given the role of Btk in osteoclast function, the inhibition of Btk activity can be useful for the treatment of bone disorders such as osteoporosis.

Provided is a compound of Formula I:

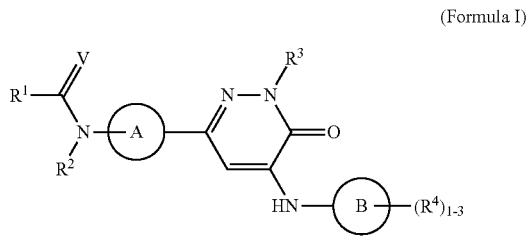

(Formula I)

and pharmaceutically acceptable salts, solvates, prodrugs, and mixtures thereof,
wherein
V is O or NH;
$R^1$ is:

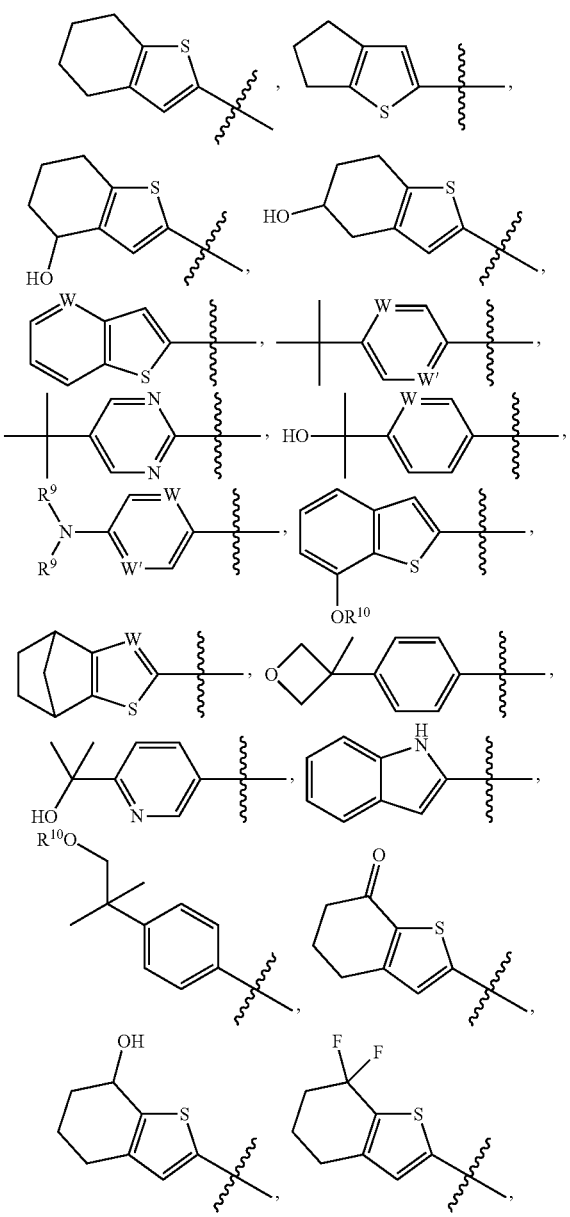

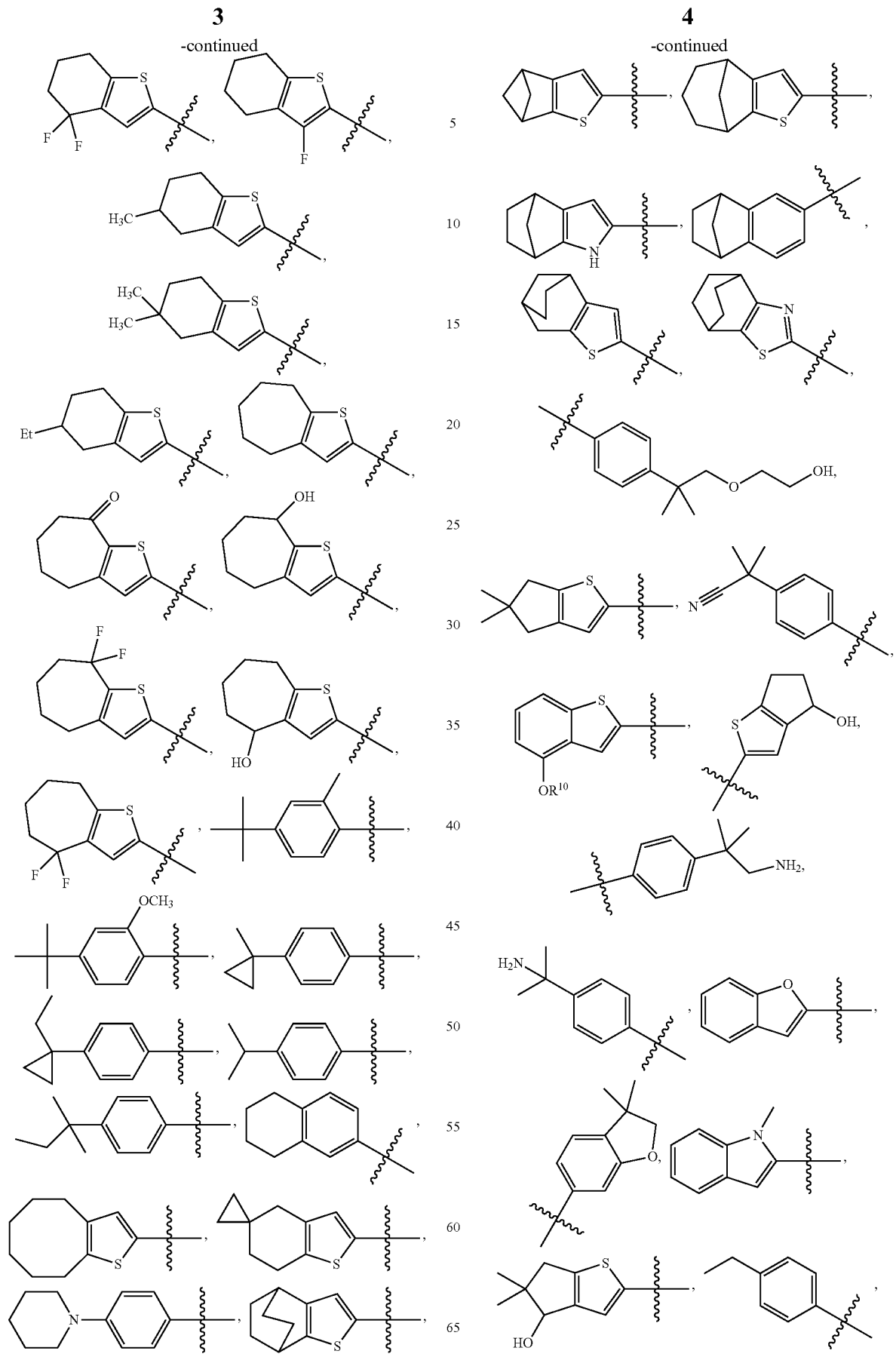

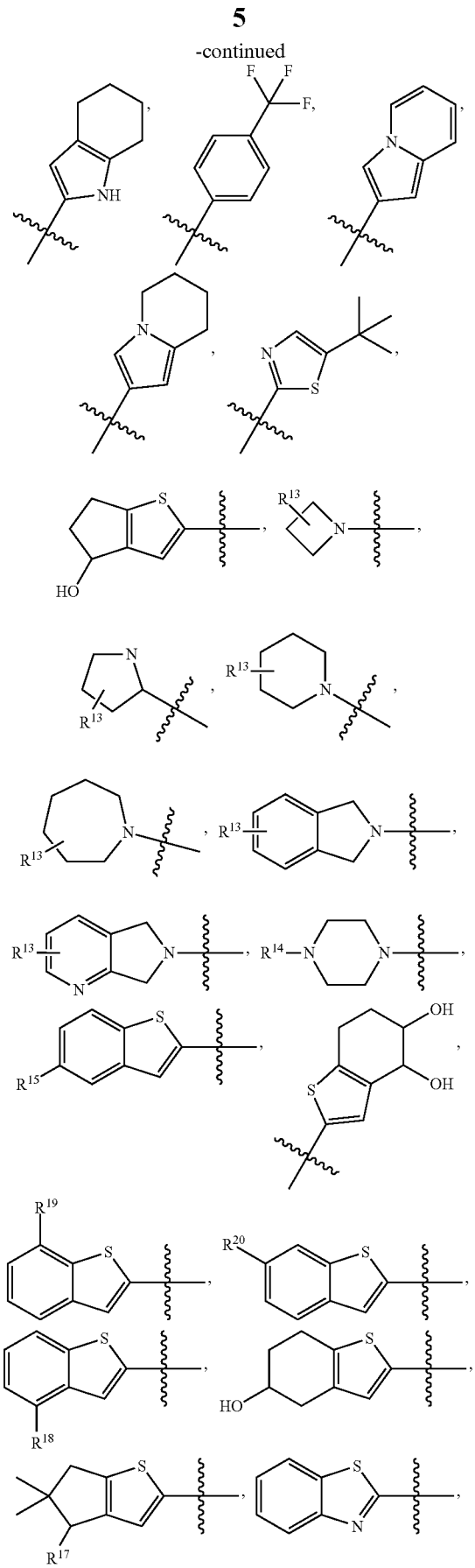

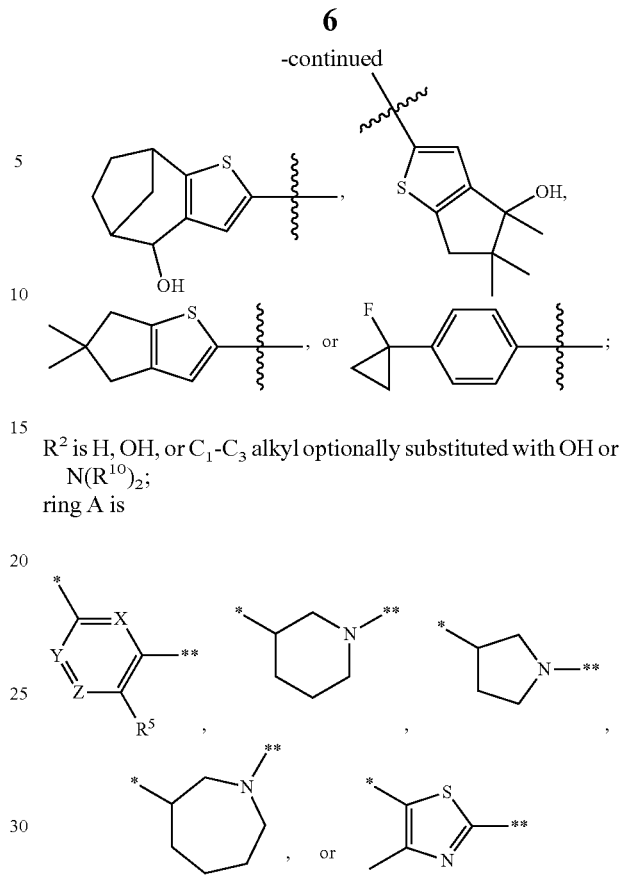

R² is H, OH, or C₁-C₃ alkyl optionally substituted with OH or N(R¹⁰)₂;

ring A is wherein * denotes the point of attachment to R¹CON(R²)— moiety and ** denotes the point of attachment to the pyridazinonyl ring;

R³ is H, CH₃ or CF₃;

ring B is a 5-6 membered heteroaryl having at least one nitrogen ring atom, 5-6 membered heterocyclyl having at least one nitrogen ring atom, or 8-11 membered heterocyclyl having at least one nitrogen ring atom;

each R⁴ is independently H, Rᵃ, —SRᵇ, —NRᵇRᶜ, halo, cyano, nitro, —CORᵇ, —CO₂Rᵇ, —CONRᵇRᶜ, OCORᵇ, OCO₂Rᵃ, OCONRᵇRᶜ, —NRᶜCORᵇ, —NRᶜCO₂Rᵃ, —NRᶜCONRᵇRᶜ, —CO₂Rᵇ, —CONRᵇRᶜ, —NRᶜCORᵇ, —SORᵃ, —SO₂Rᵃ, —SO₂NRᵇRᶜ, or —NRᶜSO₂Rᵃ; or two adjacent R⁴ groups are optionally taken together to form a 5-6 membered ring having 0-2 heteroatoms selected from O, S or N, wherein said 5-6 membered ring is fused to ring B;

Rᵃ is C₁-C₆ alkyl, cycloalkyl, heterocycloalkyl, aryl, or heteroaryl, wherein each member of Rᵃ is optionally substituted with one to three R¹¹ groups;

Rᵇ is H, C₁-C₆ alkyl, cycloalkyl, heterocycloalkyl, aryl, or heteroaryl, wherein each member of Rᵇ except H is optionally substituted with one to three R¹¹ groups;

Rᶜ is H or C₁-C₄ alkyl optionally substituted with one to three R¹¹ groups; or Rᵇ and Rᶜ, and the nitrogen to which they are attached, form an optionally substituted heterocycloalkyl group;

each R¹¹ is independently selected from C₁-C₄ alkyl, cycloalkyl, heterocycloalkyl, aryl, heteroaryl, aryl-C₁-C₄ alkyl-, heteroaryl-C₁-C₄ alkyl-, cycloalkyl-C₁-C₄ alkyl-, heterocycloalkyl-C₁-C₄ alkyl-, C₁-C₄ haloalkyl-, —OC₁-C₄ alkyl, O-heterocycloalkyl, OC₁-C₄ alkylphenyl, —C₁-C₄ alkyl-OH, —OC₁-C₄ haloalkyl, halo, OH, —NH₂, —C₁-C₄ alkyl-NH₂, —NH(C₁-C₄ alkyl), —N(C₁-C₄ alkyl)($C_1$-$C_4$ alkyl), —N($C_1$-$C_4$ alkyl)($C_1$-$C_4$ alkylphenyl), —NH($C_1$-$C_4$ alkylphenyl), —NH-heterocycloalkyl, cyano, nitro, oxo, —$CO_2H$, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2$NH($C_1$-$C_4$ alkyl), —$SO_2$NH(phenyl), —$NHSO_2$($C_1$-$C_4$ alkyl), —$NLISO_2$(phenyl), and $NRSO_2$($C_1$-$C_4$ haloalkyl), wherein said alkyl, cycloalkyl, heterocycloalkyl, aryl, heteroaryl, phenyl and haloalkyl are optionally independently substituted with one to three $R^{12}$ groups;

each $R^{12}$ is independently selected from $C_1$-$C_4$ alkyl, cycloalkyl, heterocycloalkyl, aryl, heteroaryl, aryl-$C_1$-$C_4$ alkyl-, heteroaryl-$C_1$-$C_4$ cycloalkyl-$C_1$-$C_4$ alkyl-, heterocycloalkyl-$C_1$-$C_4$ alkyl-, $C_1$-$C_4$ haloalkyl-, —O$C_1$-$C_4$ alkyl, O-heterocycloalkyl, O$C_1$-$C_4$ alkylphenyl, —$C_1$-$C_4$ alkyl-OH, —O$C_1$-$C_4$ haloalkyl, halo, OH, —$NH_2$, —$C_1$-$C_4$ alkyl-$NH_2$, —NH($C_1$-$C_4$ alkyl), —N($C_1$-$C_4$ alkyl)($C_1$-$C_4$ alkyl), —N($C_1$-$C_4$ alkyl)($C_1$-$C_4$ alkylphenyl), —NH($C_1$-$C_4$ allylphenyl), O-heterocycloalkyl, cyano, nitro, oxo, —$CO_2H$, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2$NH($C_1$-$C_4$—$SO_2$NH(phenyl), —$NHSO_2$($C_1$-$C_4$ alkyl), —$NYISO_2$(phenyl), and $NHSO_2$($C_1$-$C_4$ haloalkyl);

X is N or $CR^6$;
Y is N or $CR^7$;
Z is N or $CR^8$; provided that only of X, Y and Z is N at a time;
$R^5$ is 11 or F;
$R^6$ is H, $CH_3$, F, Cl, CN, $OCH_3$, OH, $CF_3$, $CH_2OH$, $CH_2F$, CH=O, $CH_2OCH_3$, $COCH_3$, or $(CH_2)_2OH$;
$R^7$ is H, $CH_3$, F, Cl, CN or $OCH_3$;
$R^8$ is H, $CH_3$, $CF_3$, F, Cl, CN or $OCH_3$;
W is CH or N;
W' is CH or N;
each $R^9$ is independently $C_1$-$C_3$ alkyl;
each $R^{10}$ is independently H or $CH_3$;
each $R^{13}$ is independently H, halo, $C_1$-$C_6$ alkyl, $C_1$-$C_6$ alkoxy, or $C_1$-$C_6$ haloalkyl;
each $R^{14}$ is independently H, C(=O)H, C(=O)$R^9$, or $C_1$-$C_6$ alkyl wherein said alkyl is optionally substituted with one or more OH groups;
$R^{15}$ is $CH_3$, F, Cl, Br, OH, or $OCH_3$;
$R^{16}$ is F, Cl, Br, $CH_3$, or $CF_3$,
$R^{17}$ is F or $OCH_3$,
$R^{18}$ is F or Cl; and
$R^{19}$ is F or $CH_3$.

Provided is a pharmaceutical composition, comprising a compound of any one of Formulae I, II-a, III-b, IV-a and IV-b, together with at least one pharmaceutically acceptable vehicle chosen from carriers, adjuvants, and excipients.

Provided is a packaged pharmaceutical composition, comprising
a pharmaceutical composition described herein; and
instructions for Using the composition to treat a patient suffering from a disease responsive to inhibition of Btk activity.

Provided is a method for treating a patient having a disease responsive to inhibition of Btk activity, comprising administering to the patient an effective amount of a compound of any one of Formulae I; II-a, II-b, III-a and IV-b.

Provided is a method for treating a patient having a disease chosen from cancer, bone disorders, autoimmune diseases, inflammatory diseases, acute inflammatory reactions, and allergic disorders comprising administering to the patient an effective amount of a compound of any one of Formulae I, II-a, II-b, III-a, III-b, IV-a and IV-b.

Provided is a method for increasing sensitivity of cancer cells to chemotherapy, comprising administering to a patient undergoing chemotherapy with a chemotherapeutic agent an amount of a compound of any one of Formulae I, II-a, II-b, III-b, IV-a and IV-b, sufficient to increase the sensitivity of cancer cells to the chemotherapeutic agent.

Provided is a method of reducing medication error and enhancing therapeutic compliance of a patient being treated for a disease responsive to inhibition of Btk activity, the method comprising providing a packaged pharmaceutical preparation described herein wherein the instructions additionally include contraindication and adverse reaction information pertaining to the packaged pharmaceutical composition.

Provided is a method for inhibiting ATP hydrolysis, the method comprising contacting cells expressing Btk with a compound of any one of Formulae I, II-a, II-b, III-a, III-b, IV-a and IV-b in an amount sufficient to detectably decrease the level of ATP hydrolysis in vitro.

Provided is a method for determining the presence of Btk in a sample, comprising contacting the sample with a compound of any one of Formulae I, II-a, b, III-b, IV-a and IV-b under conditions that permit detection of Btk activity, detecting a level of Btk activity in the sample, and therefrom determining the presence or absence of Mk in the sample.

Provided is a method for inhibiting B-cell activity comprising contacting cells expressing Btk with a compound of any one of Formulae I, II-a, II-b, III-a, III-b, IV-a and IV-b in an amount sufficient to detectably decrease B-cell activity in vitro.

As used in the present specification, the following words and phrases are generally intended to have the meanings as set forth below, except to the extent that the context in which they are used indicates otherwise. The following abbreviations and terms have the indicated meanings throughout.

As used herein, when any variable occurs more than one time in a chemical formula, its definition on each occurrence is independent of its definition at every other occurrence. In accordance with the usual meaning of "a" and "the" in patents, reference, for example, to "a" kinase or compound or "the" kinase or compound is inclusive of one or more kinases or compounds. The broken bond

indicates the point of attachment.

By "optional" or "optionally" is meant that the subsequently described event or circumstance May or may not occur, and that the description includes instances where the event or circumstance occurs and instances in which it does not. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are stoically impractical, synthetically non-feasible and/or inherently unstable.

Unless indicated otherwise, "alkyl" encompasses straight chain and branched hydrocarbon chain having the indicated number of carbon atoms. For example $C_3$-$C_6$ alkyl encompasses both straight and branched chain alkyl of from 1 to 6 carbon atoms. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. When an alkyl residue having a specific number of carbons is named, all geometric isomers having that number of carbons are intended to be encompassed; thus, for example, "butyl" is meant to include n-butyl, sec-butyl, isobutyl and t-butyl; "propyl" includes n-propyl and isopropyl.

Unless indicated otherwise, "cycloalkyl" indicates a saturated hydrocarbon ring group, having the specified number of carbon atoms, usually from 3 to 7 ring carbon atoms. Examples of cycloalkyl groups include cyclopropyl, cyclobutyl, cyclopentyl, and cyclohexyl as well as bridged and caged saturated ring groups such as norbornane.

Unless indicated otherwise, "alkoxy" is meant an alkyl group of the indicated number of carbon atoms attached through an oxygen bridge such as, for example, methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 37 methylpentoxy, and the like. Alkoxy groups will usually have from 1 to 6 carbon atoms attached through the oxygen bridge. "Lower alkoxy" refers to alkoxy groups having one to four carbons.

Unless indicated otherwise, "aryl" encompasses:

5- and 6-membered carbocyclic aromatic rings, for example, benzene;

bicyclic ring systems wherein at least one ring is carbocyclic and aromatic, for example, naphthalene, indane, and tetralin; and tricyclic ring-systems wherein at least one ring is carbocyclic and aromatic, for example fluorene.

For example, aryl includes 5- and 6-Membered carbocyclic aromatic rings fused to a 5- to 7-membered heterocycloalkyl ring containing 1 or more heteroatoms chosen from N, O, and S. For such fused, bicyclic ring systems wherein only one of the rings is a carbocyclic aromatic ring, the point of attachment may be at the carbocyclic aromatic ring or the hetero-Cycloalkyl ring. Bivalent radicals formed from substituted benzene derivatives and having the free valences at ring atoms are named as substituted phenylene radicals. Bivalent radicals derived from univalent polycyclic hydrocarbon radiCals whose names end in "-yl" by removal of one hydrogen atom from the carbon atom with the free valence are named by adding "-idene" to the name of the corresponding univalent radical, e.g., a naphthyl grOup with two points of attachment is termed naphthylidene. Aryl, however, does not encompass or overlap in any way with heteroaryl, separately defined below. Hence, if one or more carbocyclic aromatic rings is fused with a heterocycloalkyl aromatic ring, the resulting ring system is heteroaryl, not aryl, as defined herein.

The term "halo" includes fluoro, chloro, bromo, and iodo, and the term "halogen" includes fluorine, chlorine, bromine, and iodine.

"Haloalkyl" indicates alkyl as defined above having the specified number of carbon atoms, substituted with 1 or more halogen atoms, up to the maximum allowable number of halogen atoms. Examples of haloalkyl include, but are not limited to, trifluoromethyl, difluoromethyl, 2-fluoroethyl, and penta-fluoroethyl.

Unless indicated otherwise, "heteroaryl" encompasses:

5- to 7-membered aromatic, inonocyclic rings containing one or more, for example, from 1 to 4, or in certain embodiments, from 1 to 3, heteroatoms chosen from N, O, and S, with the remaining ring atoms being carbon; and bicyclic heteroeycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring.

For example, heteroaryl includes a 5- to 7-membered heterocycloalkyl, aromatic ring fused to a 5- to 7-membered cycloalkyl ring. For such fused, bicyclic heteroaryl ring systems wherein only one of the rings contains one or more heteroatoms, the point of attachment may be at the heteroaromatic ring or the cycloalkyl ring. When the total number of S and O atoms in the heteroaryl group exceeds I, those heteroatoms are not adjacent to one another. In certain embodiments, the total number of S and O atoms in the heteroaryl group is not more than 2. In certain embodiments, the total number of S and O atoms in the aromatic heterocycle is not more than I. Examples of heteroaryl groups include, but are not limited to, (as numbered from the linkage position assigned priority 1), 2-pyridyl, 3-pyridyl, 4-pyridyl, 2,3-pyrazinyl, 3,4-pyrazinyl, 2,4-pyrimidinyl, 3,5-pyrimidinyl, 2,3-pyrazolinyl, 2,4-imidazolinyl; isoxazolinyl, oxazolinyl, thiazolinyl, thiadiazolinyl, tetrazolyl, thienyl, benzothiophenyl, furanyl, benzofuranyl, benzoimidazolinyl, indolinyl, pyridizinyl, triazolyl, quinolinyl, pyrazolyl, and 5,6,7,8-tetrahydroisoquinoline. Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. Heteroaryl does not encompass or overlap with aryl as defined above. Oxidized forms of the heteroatoms (such as N→O) are also included.

In the term "heteroarylalkyl," heteroaryl and alkyl are as defined herein, and the point of attachment is on the alkyl group. This term encompasses, but is not limited to, pyridylmethyl, thiophenylmethyl, and (pyrrolyl)1-ethyl.

Unless otherwise indicated, "heterocycloalkyl" is meant a monocyclic or bicyclic non-aromatic ring, usually with 3 to 14 ring atoms, containing at least 2 carbon atoms in addition to 1-5 heteroatoms independently selected from oxygen, sulfur, and nitrogen, as well as combinations comprising at least one of the foregoing heteroatoms. Suitable heterocycloalkyl groups include, for example (as numbered from the linkage position assigned priority 1), 2-pyrrolinyl, 2,4-imidazolidinyl, 2,3-pyrazolidinyl, 2-piperidyl, 3-piperidyl, 4-piperidyl, and 2,5-piperzinyl. Morpholinyl groups are also contemplated, including 2-morpholinyl and 3-morpholinyl (numbered wherein the oxygen is assigned priority 1). Substituted heterocycloalkyl also includes ring systems substituted with one or more oxo moieties, such as piperidinyl N-oxide, morpholinyl-N-oxide, 1-oxo-1-thiomorpholinyl and 1,1-dioxo-1-thiomorpholinyl.

The term "substituted", as used herein, means that any one or more hydrogens on the designated atom or group is replaced with a selection from the indicated group, provided that the designated atom's normal valence is not exceeded. When a substituent is oxo (i.e., =O) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility. Unless otherwise specified, substituents are named into the core structure. For example, it is to be understood that when (heteroaryl)alkyl is listed as a possible substituent, the point of attachment of this substituent to the core structure is in the alkyl portion.

As used herein, "modulation" refers to a change in kinase activity as a direct or indirect response to the presence of compounds described herein, relative to the activity of the kinase in the absence of the compound. The change may be an increase in activity or a decrease in activity, and may be due to the direct interaction of the compound with the kinase, or due to the interaction of the compound with one or more other factors that in turn affect kinase activity. For example, the presence of the compound may, for example, increase or decrease kinase activity by directly binding to the kinase, by causing (directly or indirectly) another factor to increase or decrease the kinase activity, or by (directly or indirectly) increasing or decreasing the amount of kinase present in the cell or organism.

Compounds of any one of Formulae I, II-a, II-b, III-a, III-b, IV-a and IV-b include, but are not limited to, optical isomers of Formulae I, II-a, II-b, b, IV-a and IV-b, racemates, and other mixtures thereof. In those situations, the single enantiomers or diastereomers, optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. In addition, compounds include Z- and E-forms (or cis- and trans-forms) of compounds with carbon-carbon double bonds. Where compounds exist in various tautomeric forms, chemical entities of the present invention include all tautomeric forms of the compound. Compounds also include crystal forms including polymorphs and clathrates.

The present invention includes, but is not limited to, compounds of Formulae I, II-a, II-b, IV-a and IV-b and all pharmaceutically acceptable forms thereof. Pharmaceutically acceptable forms of the compounds recited herein include pharmaceutically acceptable salts, solvates, prodrugs, and mixtures thereof. In certain embodiments, the compounds described herein are in the form of pharmaceutically acceptable salts. The compounds of this invention remain part of this invention even when they are in the font of chemical association with other chemical entities in the manner of a chelate or a non-covalent complex. The terms "compound" and "chemical entity" are used interchangeably herein.

"Pharmaceutically acceptable salts" include, but are not limited to salts with inorganic acids, such as hydrochlorate, phosphate, diphosphate, hydrobromate, sulfate, sulfinate, nitrate, and like salts; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, $HOOC—(CH_2)_n—COOH$ where n is 0-4, and like salts. Similarly, pharmaceutically acceptable cations include, but are not limited to sodium, potassium, calcium, aluminum, lithium, and ammonium.

In addition, if the compound is obtained as an acid addition salt, free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

As noted above, prodrugs also fall within the scope of the present invention, for example ester or amide derivatives of the compounds of any one Formulae I, II-a, II-b, III-a, III-b, IV-a and IV-b. The term "prodrugs" includes any compounds that become compounds of any one of Formulae I, II-a, II-b, III-a, III-b, IV-a and IV-b when administered to a patient, e.g., upon metabolic processing of the prodrug. Examples of prodrugs include, but are not limited to, acetate, formate, and benzoate and like derivatives of functional groups (such as alcohol or amine groups) in the compounds of any one of Formulae I, II-a, II-h, III-a, III-b, IV-a and IV-b.

The term "solvate" refers to the chemical entity formed by the interaction of a solvent and a compound. Suitable solvates are pharmaceutically acceptable solvates, such as hydrates, including monohydrates and hemi-hydrates.

The term "chelate" refers to the chemical entity formed by the coordination of a compound to a metal ion at two (or more) points. Such a metal ion include $Ca^{++}$ and $Mg^{++}$.

The term "non-covalent complex" refers to the chemical entity formed by the interaction of a compound and another molecule wherein a covalent bond is not formed between the compound and the molecule. For example, complexation can occur through van der Waals interactions, hydrogen bonding, and electrostatic interactions (also called ionic bonding).

The term "hydrogen bond" refers to a form of association between an electronegative atom (also known as a hydrogen bond acceptor) and a hydrogen atom attached to a second, relatively electronegative atom (also known as a hydrogen bond donor). Suitable hydrogen bond donor and acceptors are well understood in medicinal chemistry (G. C. Pimentel and A. L. McClellan, The Hydrogen Bond, Freeman, San Francisco, 1960; R. Taylor and O. Kennard, "Hydrogen Bond Geometry in organic Crystals", Accounts of Chemical Research, 17, pp. 320-326 (1984)).

The term "active agent" is used to indicate a chemical entity which has biological activity. In certain embodiments, an "active agent" is a compound having pharmaceutical utility. For example an active agent may be an anti-cancer therapeutic.

The term "therapeutically effective amount" of a compound of this invention means an amount effective, when administered to a human or non-human patient, to provide a therapeutic benefit such as amelioration of symptoms, slowing of disease progression, or prevention of disease e.g., a therapeutically effective amount may be an amount sufficient to decrease the symptoms of a disease responsive to inhibition of Btk activity. In some embodiments, a therapeutically effective amount is an amount sufficient to reduce cancer symptoms, the symptoms of bone disorders, the symptoms of an allergic disorder, the symptoms of an autoimmune and/or inflammatory disease, or the symptoms of an acute inflammatory reaction. In some embodiments a therapeutically effective amount is an amount sufficient to decrease the number of detectable cancerous cells in an organism, detectably slow, or stop the growth of a cancerous tumor. In some embodiments, a therapeutically effective amount is an amount sufficient to shrink a cancerous tumor. In certain circumstances a patient suffering from cancer may not present symptoms of being affected. In some embodiments, a therapeutically effective amount of a compound/chemical entity is an amount sufficient to prevent a significant increase or significantly reduce the detectable level of cancerous cells or cancer markers in the patient's blood, serum, or tissues. In methods described herein for treating allergic disorders and/or autoimmune and/or inflammatory diseases and/or acute inflammatory reactions, a therapeutically effective amount may also be an amount sufficient, when administered to a patient, to detectably slow progression of the disease, or prevent the patient to whom the compound/chemical entity is given from presenting symptoms of the allergic disorders and/or autoimmune and/or inflammatory disease, and/or acute inflammatory response. In certain methods described herein for treating allergic disorders and/or autoimmune and/or inflammatory diseases and/or acute inflammatory reactions, a therapeutically effective amount may also be an amount sufficient to produce a detectable decrease in the amount of a marker protein or cell type in the patient's blood or serum. For example, in some embodiments a therapeutically effective amount is an amount of a compound/chemical entity described herein sufficient to significantly decrease the activity of B-cells. In another example, in some embodiments a therapeutically effective amount is an amount of a compound of any one of Formulae I, II-a, II-b, III-a, III-b, IV-a and IV-b sufficient to significantly decrease the number of B-cells. In another example, in some embodiments a therapeutically effective amount is an amount of a compound of any one of Formulae I, II-a, III-b, IV-a and IV-b sufficient to decrease the level of anti-acetylcholine receptor antibody in a patient's blood with the disease myasthenia gravis.

The term "inhibition" indicates a significant decrease in the baseline activity of a biological activity or process. "Inhibition of Btk activity" refers to a decrease in Btk activity as a direct or indirect response to the presence of a compound of any one of Formulae I, II-a, II-b, IV-a and IV-b, relative to the activity of Btk in the absence of such compound. The decrease in activity may be due to the direct interaction of the compound with Btk, or due to the interaction of such compound with one or more other factors that in turn affect Btk activity. For example, the presence of the compound may decrease Btk activity by directly binding to the Btk, by causing (directly or indirectly) another factor to decrease Btk activity, or by (directly or indirectly) decreasing the amount of Btk present in the cell or organism.

Inhibition of Btk activity also refers to observable inhibition of Btk activity in a standard biochemical assay for Btk activity, such as the ATP hydrolysis assay described below. In some embodiments, a compound of any one of Formulae I, II-a, II-b, IV-a and IV-b has an $IC_{50}$ value less than or equal to 1 micromolar. In some embodiments, a compound of any one of Formulae I, II-a, II-b, III-a, III-b, IV-a and IV-b has an $IC_{50}$ value less than or equal to less, than 25 nanomolar. In some embodiments, a compound of any one of Formulae I, II-a, II-b, III-a, IV-a and IV-b has an $IC_{50}$ value less than or equal to 5 nanomolar.

"Inhibition of B-cell activity" refers to a decrease in B-cell activity as a direct or indirect response to the presence of a compound of any one of Formulae II-a, II-b, III-a, III-b, IV-a and IV-b, relative to the activity of B-cells in the absence of such compound. The decrease in activity may be due to the direct interaction of the compound with Btk or with one or more other factors that in turn affect B-cell activity.

Inhibition of B-cell activity also refers to observable inhibition of CD86 expression in a standard assay such as the assay described below. In some embodiments, a compound of any one of Formulae I, II-a, II-b, III-a, III-b, IV-a and IV-b has an $IC_{50}$ value less than or equal to 10 micromolar. In some embodiments, a compound of any one of Formulae I, II-a, II-b, III-a, III-b, IV-a and IV-b has an $IC_{50}$ value less than or equal to less than 0.5 micromolar. In some embodiments, a compound of any one of Formulae I, II-a, II-b, III-a, III-b, IV-a and IV-b has an $IC_{50}$ value less than or equal to 100 nanomolar.

"B cell activity" also includes activation, redistribution, reorganization, or capping of one or more various B cell membrane receptors, e.g., CD40, CD86, and Toll-like receptors TLRs (in particular TLR4), or membrane-bound immunoglobulins, e.g, IgM, IgG, and IgD. Most B cells also have membrane receptors for Fc portion of IgG in the form of either antigen-antibody complexes or aggregated IgG. B cells also carry membrane receptors for the activated components of complement, e.g., C3b, C3d, C4, and Clq. These various membrane receptors and membrane-bound immunoglobulins have membrane mobility and can undergo redistribution and capping that can initiate signal transduction.

B cell activity also includes the synthesis or production of antibodies or immunoglobulins. Immunoglobulins are synthesized by the B cell series and have common structural features and structural units. Five immunoglobulin classes, i.e., IgG, IgA, IgM, IgD, and IgE, are recognized on the basis of structural differences of their heavy chains including the amino acid sequence and length of the polypeptide chain. Antibodies to a given antigen may be detected in all or several classes of immunoglobulins or may be restricted to a single class or subclass of immunoglobulin. Autoantibodies or autoimmune antibodies may likewise belong to one or several classes of immunoglobulins. For example, rheumatoid factors (antibodies to IgG) are most often recognized as an IgM immunoglobulin, but can also IgG or IgA.

In addition, B cell activity also is intended to include a series of events leading to B cell clonal expansion (proliferation) from precursor B lymphocytes and differentiation into antibody-synthesizing plasma cells which takes place in conjunction with antigen-binding and with cytokine signals from other cells.

"Inhibition of B-cell proliferation" refers to inhibition of proliferation of abnormal B-cells, such as cancerous B-cells, e.g. lymphoma B-cells and/or inhibition of normal, non-diseased B-cells. The term "inhibition of B-cell proliferation" indicates no increase or any significant decrease in the number of B-cells, either in vitro or in vivo. Thus an inhibition of B-cell proliferation in vitro would be any significant decrease in the number of B-cells in an in vitro sample contacted with a compound of any one of Formulae I, II-a, H-b, III-a, III-b, IV-a and IV-b as compared to a matched sample not contacted with such compound.

Inhibition of B-cell proliferation also refers to observable inhibition of B-cell proliferation in a standard thymidine incorporation assay for B-cell proliferation, such as the assay described herein. In some embodiments, a compound of any one of Formulae I, II-a, II-b, III-a, III-b, IV-a and IV-b has an $IC_{50}$ value less than or equal to 10 micromolar. In some embodiments, a compound of any one of Formulae I, II-a, Mb, III-b, IV-a and IV-b has an $IC_{50}$ value less than or equal to less than 500 nanomolar. In some embodiments, a compound of any one of Formulae I, II-a, II-b, III-a, III-b, IV-a and IV-b has an $IC_{50}$ value less than or equal to 50 nanomolar.

An "allergy" or "allergic disorder" refers to acquired hypersensitivity to a substance (allergen). Allergic conditions include eczema, allergic rhinitis or coryza, hay fever, bronchial asthma, urticaria (hives) and food allergies, and other atopic conditions.

"Asthma" refers to a disorder of the respiratory system characterized by inflammation, narrowing of the airways and increased reactivity of the airways to inhaled agents. Asthma is frequently, although not exclusively associated with atopic or allergic symptoms.

By "significant" is meant any detectable change that is statistically significant in a standard parametric test of statistical significance such as Student's T-tert, where p<0.05.

A "disease responsive to inhibition of Btk activity" is a disease in which inhibiting Btk kinase provides a therapeutic benefit such as an amelioration of symptoms, decrease in disease progression, prevention or delay of disease onset, or inhibition of aberrant activity of certain cell-types (monocytes, osteoclasts, B-cells, mast cells, myeloid cells, basophils, macrophages, neutrophils, and dendritic cells).

"Treatment or treating" means any treatment of a disease in a patient, including:

a) inhibiting the disease;
b) slowing or arresting the development of clinical symptoms; and/or
c) relieving the disease, that is, causing the regression of clinical symptoms.

"Prevent or preventing" a disease means causing the clinical symptoms of the disease not to develop.

"Patient" refers to an animal, such as a mammal, that has been or will be the object of treatment; observation or experiment. The methods of the invention can be useful in both human therapy and veterinary applications. In some embodiments, the patient is a mammal; in some embodiments the patient is human; and in some embodiments the patient is chosen from cats and dogs.

Provided is a compound of Formula I:

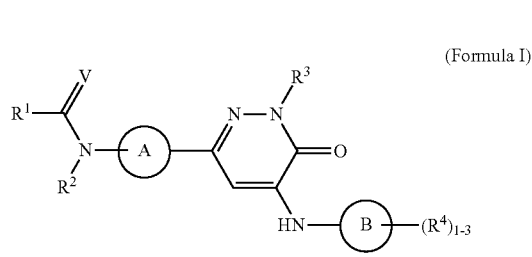

(Formula I)

and pharmaceutically acceptable salts, solvates, prodrugs, and mixtures thereof, wherein V is O or NH;

R$^1$ is:

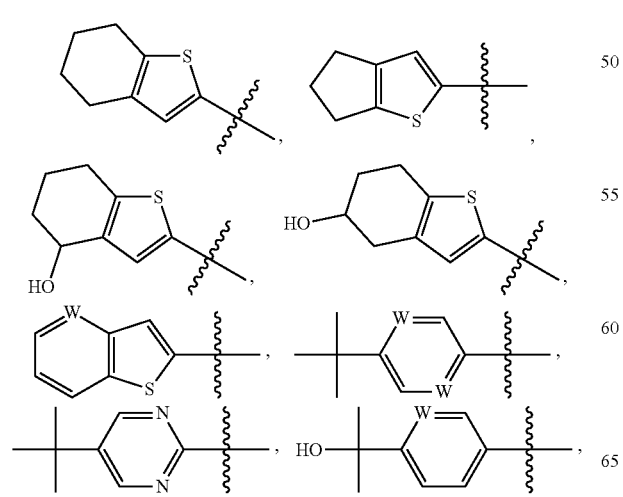

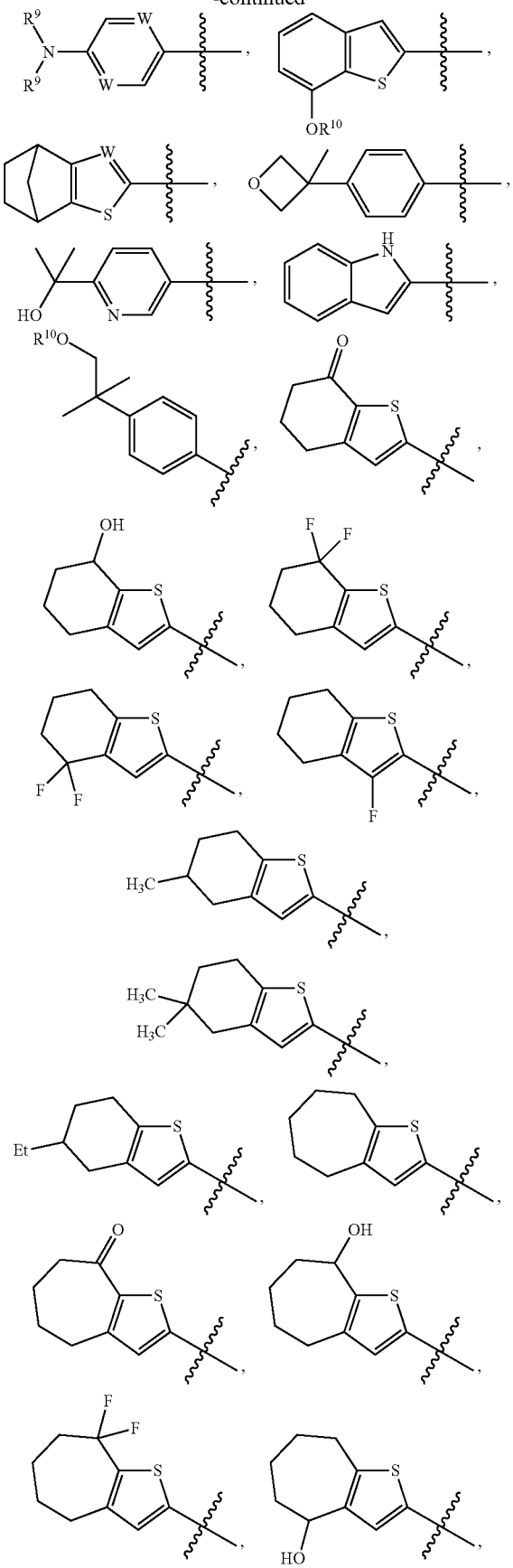

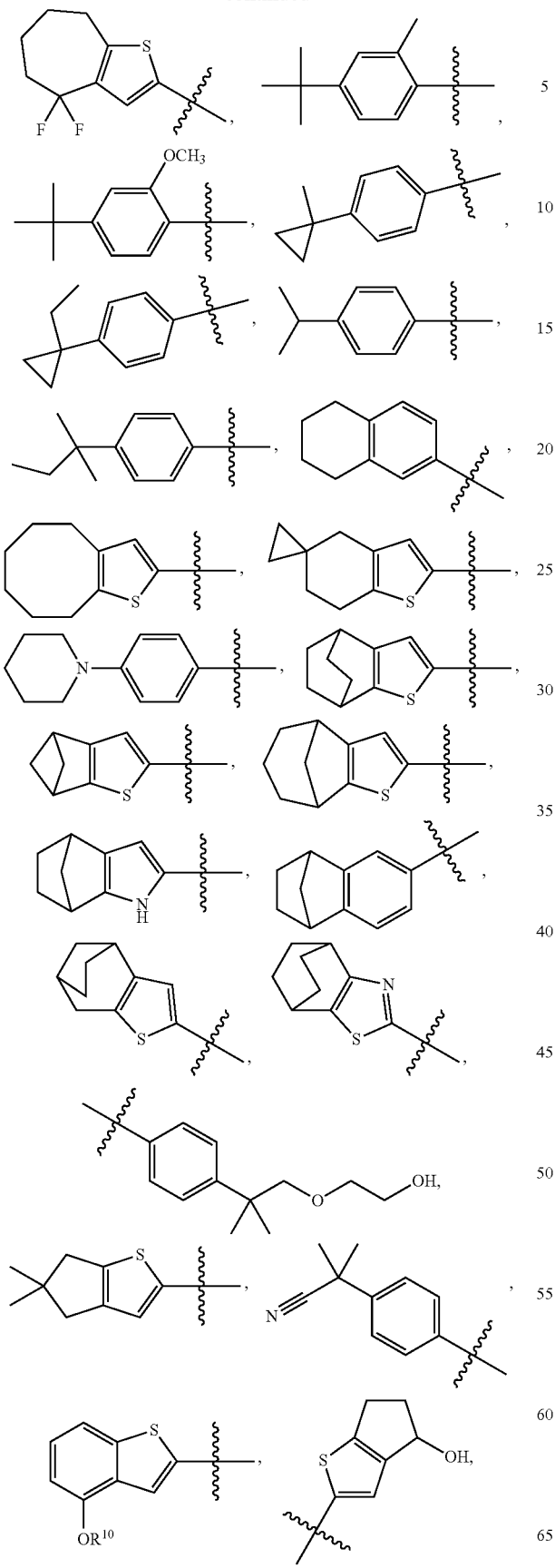
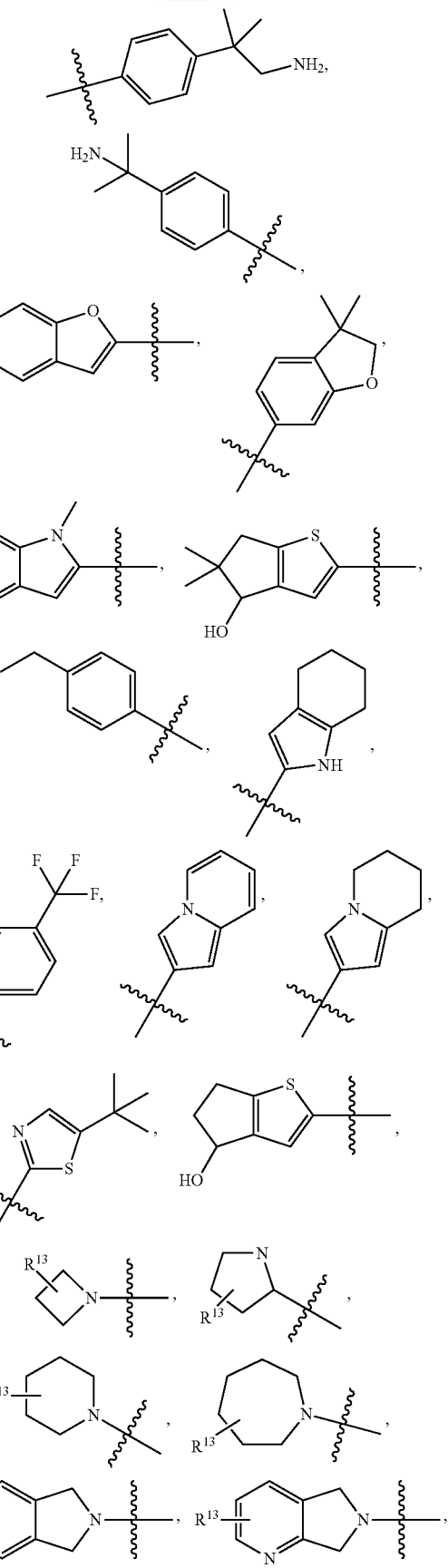

-continued

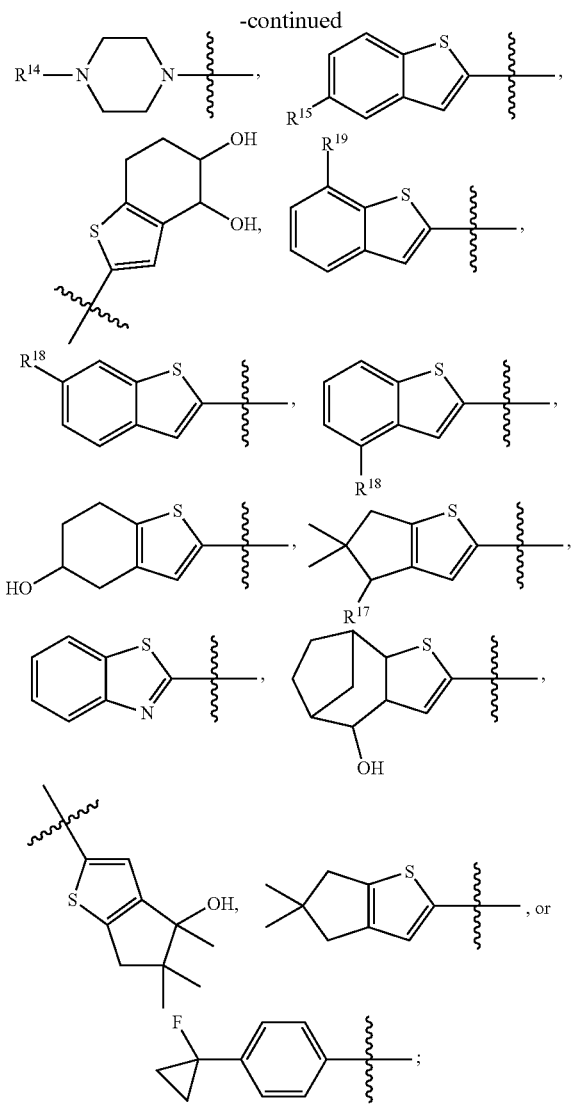

$R^2$ is H, OH, or $C_1$-$C_3$ alkyl optionally substituted with OH or $N(R^{10})_2$;
ring A is

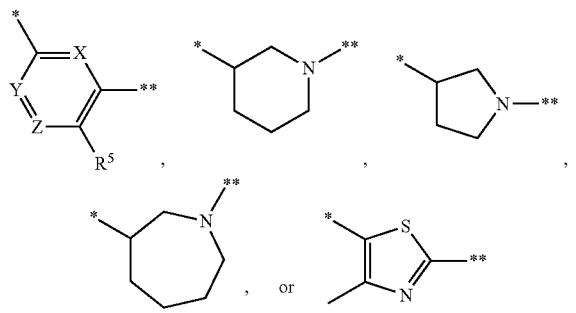

wherein denotes the point of attachment to $R^1CON(R^2)$— moiety and * denotes the point of attachment to the pylidazinortyl ring;
$R^3$ is H, $CH_3$ or $CF_3$;
ring B is a 5-6 membered heteroaryl having at least one nitrogen ring atom, 5-6 membered heterocyclyl having at least one nitrogen ring atom, or 8-11 membered heterocyclyl having at least one nitrogen ring atom;
each $R^4$ is independently H, $R^a$, $OR^b$, —$SR^b$, —$NR^bR^c$, halo, cyano, nitro, —$COR^b$, —$CO_2R^b$, —$CONR^bR^c$, $OCOR^b$, $OCO_2R^a$, $OCONR^bR^a$, —$NR^cCOR^b$, —$NR^cCO_2R^a$, —$NR_cCONR^bR^c$, —$CO_2R^b$, —$CONR^bR^c$, —$NR^cCOR^b$, —$SOR^a$, —$SO_2R^a$, —$SO_2NR^bR^c$, or —$NR^cSO_2R^a$; or two adjacent $R^4$ groups are optionally taken together to form a 5-6 membered ring having 0-2 heteroatoms selected from O, S or N, wherein said 5-6 membered ring is fused to ring B;
$R^a$ is $C_1$-$C_6$ alkyl, cycloalkyl, heterocycloalkyl, aryl, or heteroaryl, wherein each member of $R^a$ is optionally substituted with one to three $R^{11}$ groups;
$R^b$ is H, $C_1$-$C_6$ alkyl, cycloalkyl, heterocycloalkyl, aryl, or heteroaryl, wherein each member of $R^b$ except H is optionally substituted with one to three $R^{11}$ groups;
$R^c$ is H or $C_1$-$C_4$ alkyl optionally substituted with one to three $R^{11}$ groups; or $R^b$ and $R^c$, and the nitrogen to which they are attached, form an optionally substituted heterocycloalkyl group;
each $R^{11}$ is independently selected from $C_1$-$C_4$ alkyl, cycloalkyl, heterocycloalkyl, aryl, heteroaryl, aryl-$C_1$-$C_4$ alkyl-, heteroaryl-$C_1$-$C_4$ alkyl-, cycloalkyl-$C_1$-$C_4$ alkyl-, heterocycloalkyl-$C_1$-$C_4$ alkyl-, $C_3$-$C_4$ haloalkyl-, —$OC_1$-$C_4$ alkyl, O-heterocycloalkyl, $OC_1$-$C_4$ alkylphenyl, alkyl-OH, —$OC_1$-$C_4$ haloalkyl, halo, OH, —$C_1$-$C_4$ alkyl $NH_2$, —$NH(C_1$-$C_4$ alkyl), —$N(C_1$-$C_4$ alkyl)($C_1$-$C_4$ alkyl), —$N(C_1$-$C_4$ alkyl)($C_1$-$C_4$ alkylphenyl), —$NH(C_1$-$C_4$ alkylphenyl), —NH-heterocycloalkyl, cyano, nitro, oxo, —$CO_2H$, —$C(O)OC_1$-$C_4$ alkyl, —$CON(C_1$-$C_4$ alkyl)($C_1$-$C_4$ alkyl), —$CONH(C_1$-$C_4$ alkyl), —$CONH_2$, —$NHC(O)$ ($C_3$-$C_4$ alkyl), —$NHC(O)$(phenyl), —$N(C_1$-$C_4$ alkyl)$C(O)$ ($C_1$-$C_4$ alkyl), —$N(C_1$-$C_4$ alkyl)$C(O)$(phenyl), —$C(O)C_1$-$C_4$ alkyl, —$C(O)C_1$-$C_4$ phenyl, —$C(O)C_1$-$C_4$ haloalkyl, $OC(O)C_1$-$C_4$ alkyl, —$SO_2(C_1$-$C_4$ alkyl), —$SO_2$(phenyl), —$SO_2(C_1$-$C_4$ haloalkyl), —$SO_2NH_2$, —$SO_2NH(C_1$-$C_4$ alkyl), —$SO_2NH$(phenyl), —$NHSO_2(C_1$-$C_4$ alkyl), —$NHSO_2$(phenyl), and $NHSO_2(C_1$-$C_4$ haloalkyl), wherein said alkyl, cycloalkyl, heterocycloalkyl, aryl, heteroaryl, phenyl and haloalkyl are optionally independently substituted with one to three $R^{12}$ groups;
each $R^{12}$ is independently selected from $C_1$-$C_4$ alkyl, cycloalkyl, heterocycloalkyl, aryl, heteroaryl, aryl-$C_1$-$C_4$ alkyl-, heteroaryl-$C_1$-$C_4$ alkyl-, cycloalkyl-$C_1$-$C_4$ alkyl-, heterocycloalkyl-$C_1$-$C_4$ alkyl-, $C_1$-$C_4$ haloalkyl $OC_1$-$C_4$ alkyl, O-heterocycloalkyl, $OC_1$-$C_4$ alkylphenyl, alkyl-OH, —$OC_1$-$C_4$ haloalkyl, halo, OH, —$NH_2$, —$C_1$-$C_4$ alkyl-$NH_2$, —$NH(C_1$-$C_4$ alkyl), —$N(C_1$-$C_4$ alkyl)($C_1$-$C_4$ alkyl), —$N(C_1$-$C_4$ alkyl)($C_1$-$C_4$ alkylphenyl), $NH(C_1$-$C_4$ alkylphenyl), O-heterocycloalkyl, cyano, nitro, oxo, —$CO_2H$, —$C(O)OC_1$-$C_4$ alkyl, —$CON(C_1$-$C_4$ alkyl) ($C_1$-$C_4$ alkyl), —$CONH(C_1$-$C_4$ alkyl), —$CONH_2$, —$NHC(O)(C_1$-$C_4$ alkyl), —$NHC(O)$(phenyl), —$N(C_1$-$C_4$ alkyl)$C(O)(C_1$-$C_4$ alkyl), —$N(C_1$-$C_4$ alkyl)$C(O)$(phenyl), —$C(O)C_1$-$C_4$ alkyl, —$C(O)C_1$-$C_4$ phenyl, haloalkyl, $OC(O)C_1$-$C_4$ alkyl, —$SO_2(C_1$-$C_4$ alkyl), —$SO_2$(phenyl), —$SO_2(C_1$-$C_4$ haloalkyl), —$SO_2NH_2$, $SO_2NH(C_1$-$C_4$ alkyl), —$SO_2NH$ (phenyl), —$NHSO_2(Q$-$C_4$ alkyl), —$NHSO_2(Pherl_\gamma 1)$, and $NHSO_2(C_1$-$C_4$ haloalkyl);
X is N or $CR^6$;
Y is N or $CR^7$;
Z is N or $CR^s$; provided that only of X, Y and Z is N at a time;
$R^5$ is H or F;
$R^6$ is H, $CH_3$, F, Cl, CN, $OCH_3$, OH, $CF_3$, $CH_2OH$, $CH_2F$, CH=O, $CH_2OCH_3$, $COCH_3$, or $(CH_2)_2OH$;
$R^7$ is H, $CH_3$, F, Cl, CN or $OCH_3$;

$R^8$ is H, $CH_3$, $CF_3$, F, Cl, CN or $OCH_3$;

W is CH or N;

W' is CH or N;

each $R^9$ is independently $C_1$-$C_3$ alkyl;

each $R^{10}$ is independently H or $CH_3$;

each $R^{13}$ is independently H, halo, $C_1$-$C_6$ alkyl, $C_1$-$C_6$ alkoxy, or $C_1$-$C_6$ haloalkyl;

each $R^{14}$ is independently H, C(=O)H, C(=O)$R^9$, or $C_1$-$C_6$ alkyl wherein said alkyl is optionally substituted with one or more OH groups;

$R^{15}$ is $CH_3$, F, Cl, Br, OH, or $OCH_3$;

$R^{16}$ is F, Cl, Br, $CH_3$, or $CF_3$, $R^{17}$ is F or $OCH_3$, $R^{18}$ is F or Cl; and $R^{19}$ is F or $CH_3$.

In certain embodiments, the compounds of the present invention are of Formula I wherein:

V is O or NH;

$R^1$ is:

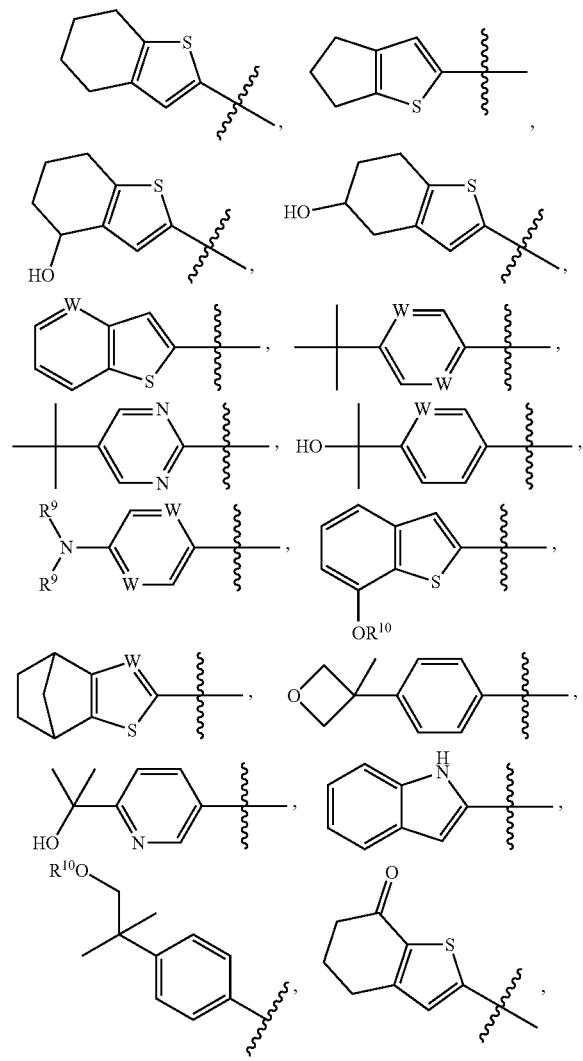

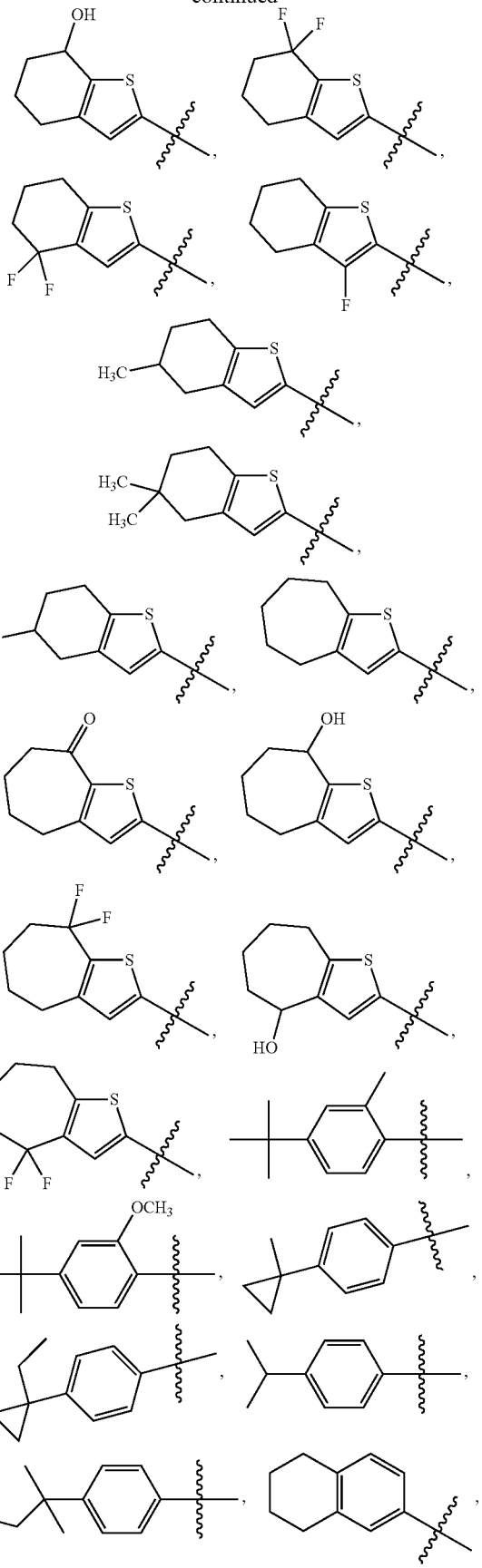

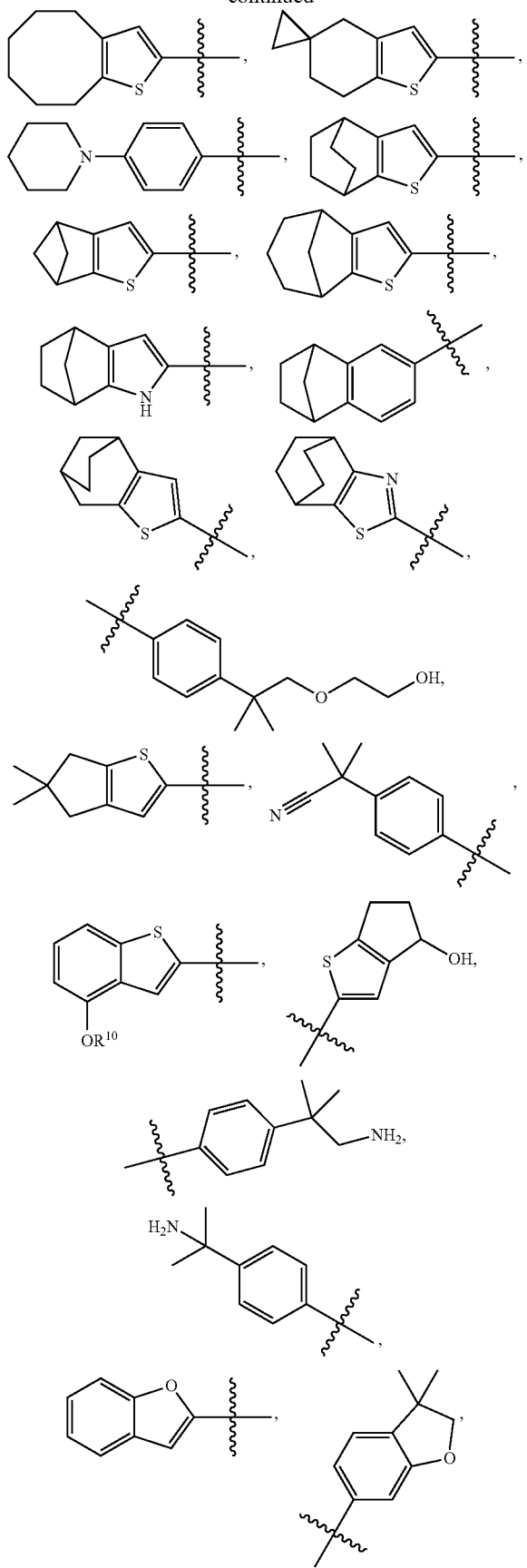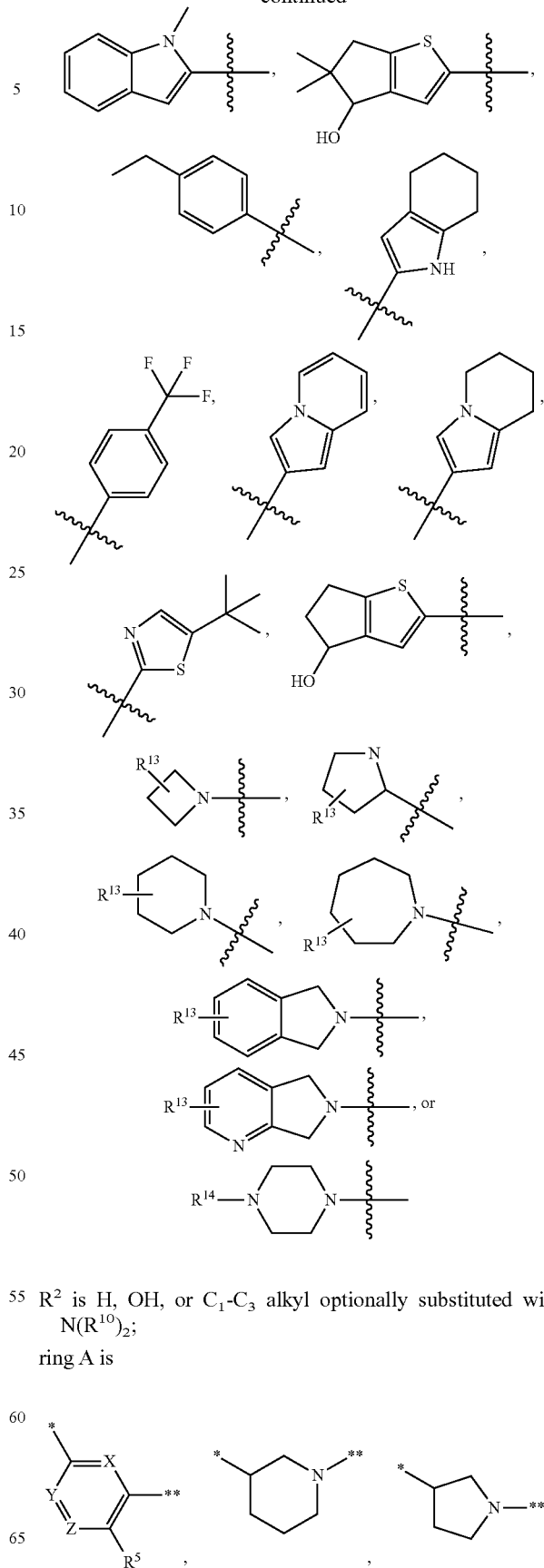
R² is H, OH, or C₁-C₃ alkyl optionally substituted with N(R¹⁰)₂;
ring A is
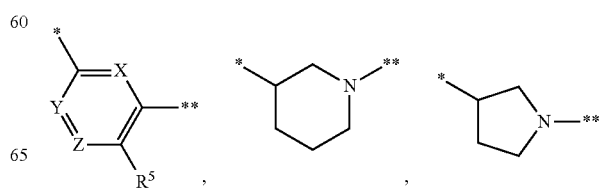

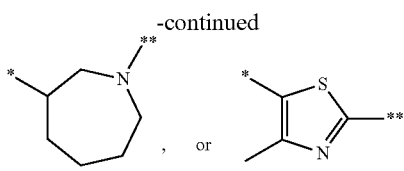
wherein denotes the point of attachment to R¹CON(R²)— moiety and * denotes the point of attachment to the pyridazinonyl ring;

R³ is H, CH₃ or CF₃;

ring B is a 5-6 membered heteroaryl having at least one nitrogen ring atom, 5-6 membered heterocyclyl having at least one nitrogen ring atom, or 8-11 membered heterocyclyl having at least one nitrogen ring atom;

each R⁴ is independently H, R$^a$, OR$^b$, —SR$^b$, —NR$^b$R$^c$, halo, cyano, nitro, —COR$^b$, CO₂R$^b$, —CONR$^b$R$^c$, OCOR$^b$, OCO₂R$^a$, OCONR$^b$R$^c$, —NR$^c$COR$^b$, —NR$^c$CO₂R$^a$, —NR$^c$CONR$^b$R$^c$, CO₂R$^b$, —CONR$^b$R$^c$, —NR$^c$COR$^b$, —SOR$^a$, —SO₂R$^a$, —SO₂NR$^b$R$^c$, or —NR$^c$SO₂R$^a$; or two adjacent R⁴ groups are optionally taken together to form a 5-6 membered ring having 0-2 heteroatoms selected from O, S or N, wherein said 5-6 membered ring is fused to ring B;

R$^a$ is C₁-C₆ alkyl, cycloalkyl, heterocycloalkyl, aryl, or heteroaryl, wherein each member of R$^a$ is optionally substituted with one to three R¹¹ groups;

R$^b$ is H, C₁-C₆ alkyl, cycloalkyl, heterocycloalkyl, aryl, or heteroaryl, wherein each member of R$^b$ except H is optionally substituted with one to three R¹¹ groups;

R$^c$ is H or C₁-C₄ alkyl optionally substituted with one to three R¹¹ groups; or R$^b$ and R$^c$, and the nitrogen to which they are attached, form an optionally substituted heterocycloalkyl group;

each R¹¹ is independently selected from C₁-C₄ alkyl, cycloalkyl, heterocycloalkyl aryl, heteroxyl, aryl-C₁-C₄ alkyl-, heteroaryl-C₁-C₄ alkyl-, cycloalkyl-C₁-C₄ alkyl-, heterocycloalkyl-C₁-C₄ alkyl-, C₁-C₄ haloalkyl-, —OC₁-C₄ alkyl, O-heterocycloalkyl, OC₁-C₄ alkylphenyl, —C₁-C₄ alkyl-OH, —OC₁-C₄ haloalkyl, halo, OH, —NH₂, —C₁-C₄alkyl-NH₂, —NH(C₁-C₄alkyl), —N(C₁-C₄ alkyl)(C₁-C₄ alkyl), —N(C₁-C₄ alkyl)(C₁-C₄ alkylphenyl), —NH(C₁-C₄ alkylphenyl), —NH-heterocycloalkyl, cyano, nitro, oxo, —CO₂H, —C(O)OC₁-C₄ alkyl, —CON (C₁-C₄ alkyl)(C₁-C₄ alkyl), —CONH(C₁-C₄ alkyl), —CONH₂, —NHC(O)(C₁-C₄ alkyl), —NHC(O)(phenyl), —N(C₁-C₄ alkyl)C(O)(C₁-C₄ alkyl); —N(C₁-C₄alkyl)C (O)(phenyl), —C(O)C₁-C₄ alkyl, —C(O)C₁-C₄ phenyl, —C(O)C₁-C₄ haloalkyl, OC(O)C₁-C₄ alkyl, —SO₂(C₁-C₄ alkyl), —SO₂(phenyl), —SO₂(C₁-C₄haloalkyl), —SO₂NH₂, —SO₂NH(C₁-C₄ alkyl), —SO₂NH(phenyl), —NHSO₂(C₁-C₄ alkyl), —NHSO₂(phenyl), and NHSO₂ (C₁-C₄haloalkyl), wherein said alkyl, cycloalkyl, heterocycloalkyl, aryl, heteroaryl, phenyl and haloalkyl are optionally independently substituted with one to three R¹² groups;

each R¹² is independently selected from C₁-C₄ alkyl, cycloalkyl, heterocycloalkyl, aryl, heteroaryl, aryl-C₁-C₄ alkyl-, heteroaryl-C₁-C₄ alkyl-, cycloalkyl-C₁-C₄ alkyl-, heterocycloalkyl-C₁-C₄ alkyl-, C₁-C₄ haloalkyl-, —OC₁-C₄alkyl, O-heterocycloalkyl, —OC₁-C₄alkylphenyl, —C$_r$-C₄ alkyl-OH, —OC₁-C₄ haloalkyl, halo, —OH, —NH₂, —C₁-C₄ alkyl-NH₂, —NH(C₁-C₄ alkyl), —N(C₁-C₄ alkyl)(C₁-C₄ alkyl), —N(C₁-C₄ alkyl)(C₁-C₄ alkylphenyl), —NH(C₁-C₄ alkylphenyl), —O-heterocycloalkyl, cyano, nitro, oxo, —CO₂H, —C(O)OC₁-C₄ alkyl, —CON (C₁-C₄ alkyl)(C₁-C₄ alkyl), —CONH(C₁-C₄ alkyl), —CONH₂, —NHC(O)(C₁-C₄ alkyl), —NHC(O)(phenyl), —N(C₁-C₄ alkyl)C(O)(C₁-C₄ alkyl); —N(C₁-C₄ alkyl)C (O)(phenyl), —C(O)C₁-C₄ alkyl, —C(O)C₁-C₄ phenyl, —C(O)C₁-C₄ haloalkyl, —OC(O)C₁-C₄alkyl, —SO₂(C₁-C₄alkyl), —SO₂(C₁-C₄haloalkyl), —SO₂NH₂, —SO₂NH (C₁-C₄ alkyl), —SO₂NH(phenyl), —NHSO₂(C₁-C₄ alkyl), —NHSO₂(phenyl), and —NHSO₂(C₁-C₄ haloalkyl);

X is N or CR⁶;

Y is N or CR⁷;

Z is N or CR$^a$; provided that only of X; Y and Z is N at a time;

R⁵ is H or F;

R⁶ is H, CH₃, F, Cl, CN, OCH₃, OH, CF₃, or CH₂OH;

R⁷ is H, CH₃, F, Cl, CN or OCH₃;

R⁸ is 11, CH₃, CF₃, F, Cl, CN or OCH₃;

W is CH or N;

W is CH or N;

each R⁹ is independently C₁-C₃ alkyl;

each R¹⁰ is independently H or CH₃;

each R¹³ is independently H, halo, C₁-C₆ alkyl, C₁-C₆ alkoxy, or C₁-C₆ haloalkyl; and each R¹⁴ is independently H, C(=O)H, C(=O)R⁹, or C₁-C₆ alkyl wherein said alkyl is optionally substituted with one or more OH groups.

In certain embodiments, the compounds of the present invention are of Formula I-1 wherein:

(Formula I-1)

R¹ is:

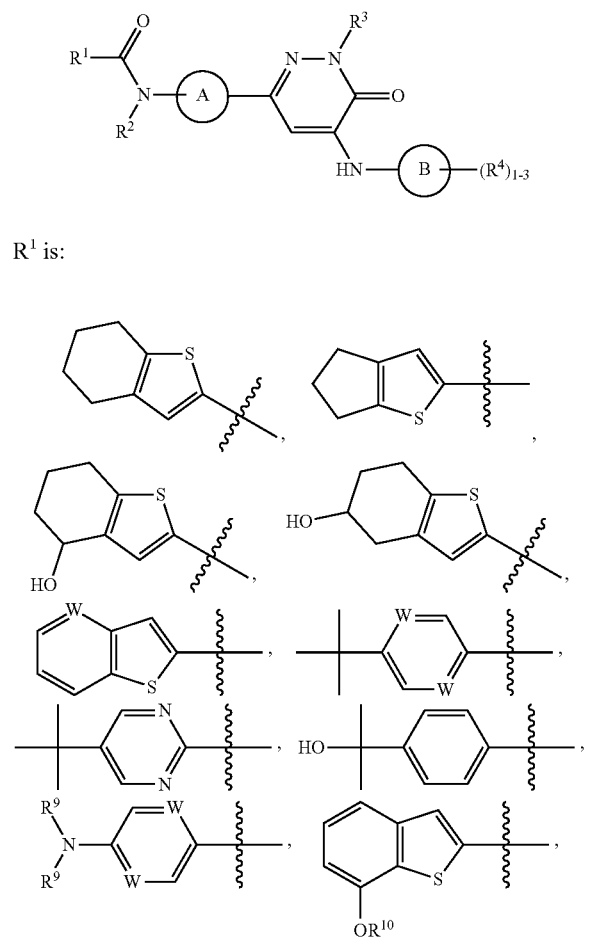

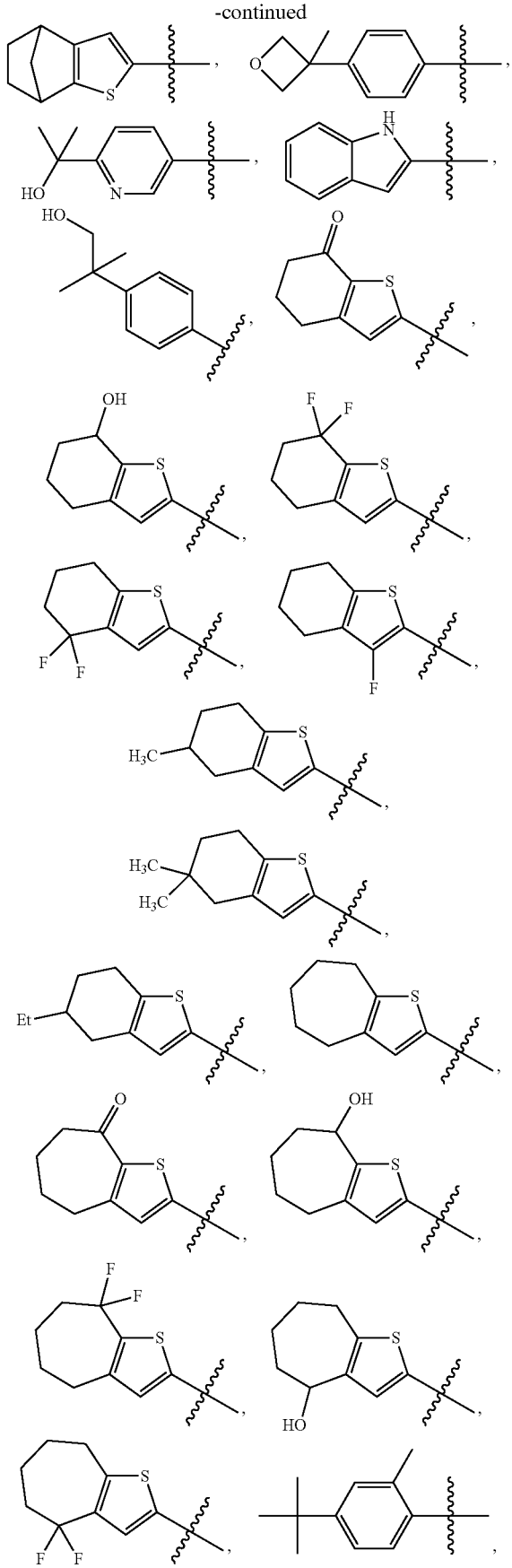
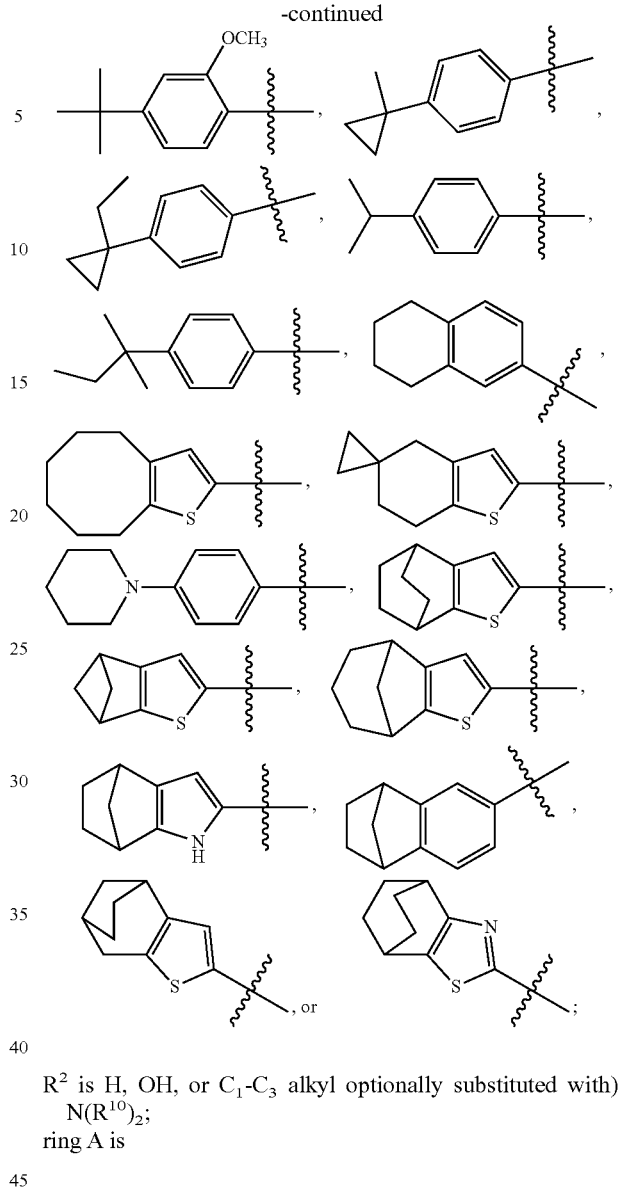

$R^2$ is H, OH, or $C_1$-$C_3$ alkyl optionally substituted with) $N(R^{10})_2$;

ring A is

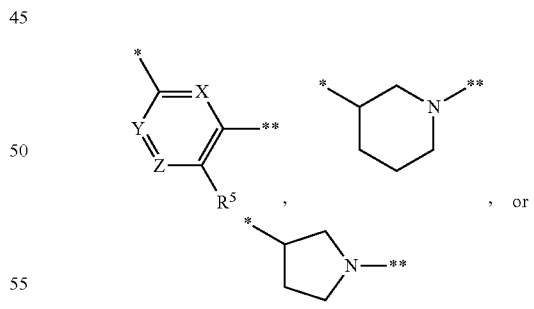

wherein * denotes the point of attachment to $R^1CON(R^2)$— moiety and ** denotes the point of attachment to the pyridazinonyl ring;

$R^3$ is H, $CH_3$ or $CF_3$;

ring B is a 5-6 membered heteroaryl having at least one nitrogen ring atom or 8-11 membered heterotoyclyl having at least one nitrogen ring atom;

each $R^4$ is independently H, —$OR^b$, —$SR^b$, —$NR^bR^c$, halo, cyano, nitro, —$COR^b$, —$CO_2R^b$, —$CONR^bR^c$, $OCOR^b$, —OCO₂Rᵃ, —OCONRᵇRᶜ, —NRᶜCORᵇ, —NRᶜCO₂Rᵃ, —NRᶜCONRᵇRᶜ, —CO₂Rᵇ, —CONRᵇRᶜ, —NRᶜCORᵇ, —SORᵃ, —SO₂Rᵃ, —SO₂NRᵇRᶜ, or NRᶜSO₂Rᵃ; or two adjacent R⁴ groups are optionally taken together to form a 5-6 membered ring having 0-2 heteroatoms selected from O, S or N, wherein said 5-6 membered ring is fused to ring B;

Rᵃ is $C_1$-$C_6$ alkyl, cycloalkyl, heterocycloalkyl, aryl, or heteroaryl, wherein each member of Rᵃ is optionally substituted with one to three $R^{11}$ groups;

Rᵇ is H, $C_1$-$C_6$ alkyl, cycloalkyl, heterocycloalkyl, aryl, or heteroaryl, wherein each member of Rᵇ except H is optionally substituted with one to three $R^{11}$ groups;

Rᶜ is H or $C_1$-$C_4$ alkyl optionally substituted with one or three $R^{11}$ groups; or Rᵇ and Rᶜ, and the nitrogen to which they are attached, form an optionally substituted heterocycloalkyl group;

each $R^{11}$ is independently selected from $C_1$-$C_4$ alkyl, cycloalkyl, heterocycloalkyl, aryl, heteroaryl, aryl-$C_1$-$C_4$ alkyl-, heteroaryl-$C_1$-$C_4$ alkyl-, cycloalkyl-$C_3$-$C_4$ alkyl-, heterocycloalkyl-$C_1$-$C_4$ alkyl-, $C_1$-$C_4$ haloalkyl-, —O$C_1$-$C_4$ alkyl, —O-heterocycloalkyl, —O$C_1$-$C_4$ alkylphenyl, —$C_1$-$C_4$ alkyl-OH, —O$C_1$-$C_4$ haloalkyl, halo, —OH, —NH₂, —$C_1$-$C_4$ alkyl-NH₂, —NH($C_1$-$C_4$ alkyl), —N($C_1$-$C_4$ alkyl)($C_1$-$C_4$ alkyl), —N($C_1$-$C_4$ alkyl)($C_1$-$C_4$ alkylphenyl), —NH($C_3$-$C_4$alkylphenyl), cyano, nitro, oxo, —CO₂H, —C(O)O$C_1$-$C_4$ alkyl, —CON($C_1$-$C_4$ alkyl)($C_1$-$C_4$ alkyl), —CONH($C_1$-$C_4$ alkyl), —CONH₂, —NHC(O)($C_3$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$haloalkyl, —OC(O)$C_1$-$C_4$ alkyl, —SO₂($C_1$-$C_4$ alkyl), —SO₂(phenyl), —SO₂($C_1$-$C_4$haloalkyl), —SO₂NH₂, —SO₂NH($C_1$-$C_4$ alkyl), —SO₂NH(phenyl), —NHSO₂($C_1$-$C_4$ alkyl), —NHSO₂(phenyl), and —NHSO₂($C_1$-$C_4$haloalkyl);

X is N or $CR^6$;

Y is N or $CR^7$;

Z is N or $CR^8$; provided that only of X, Y and Z is N at a time;

R⁵ is H or F;

R⁶ is H, CH₃, F, Cl, CN, OCH₃, OH or C

R⁷ is H, CH₃, F, Cl, CN or OCH₃;

R⁸ is H, CH₃, CF₃, F, Cl, CN or OCH₃;

W is CH or N;

W' is CH or N;

each R⁹ is independently $C_1$-$C_3$ alkyl; and each $R^{10}$ is independently H or CH₃.

In certain embodiments, R³ is H. In certain embodiments, R³ is CH₃.

In certain embodiments, ring A is

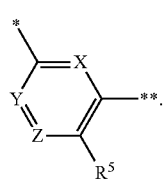

In certain embodiments, the compounds of the present invention are of Formula II-a or II-b, wherein R¹, R², R⁴, R⁵, X, Y and Z are as defined in Formula I.

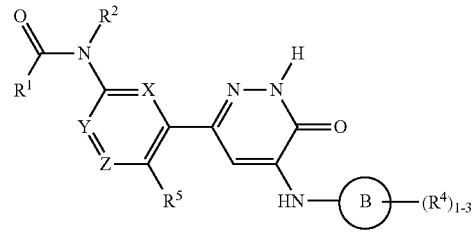

Formula II-a

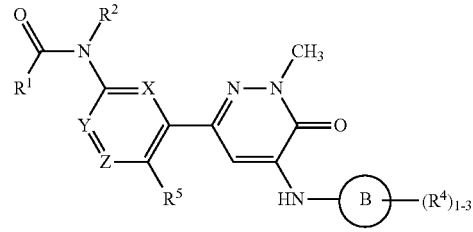

Formula II-b

In certain embodiments, X is $CR^6$.

In certain embodiments, X is N.

In certain embodiments, Y is $CR^7$.

In certain embodiments, Y is N.

In certain embodiments, Y is $CR^8$.

In certain embodiments, Z is N.

In certain embodiments, the compounds of the present invention are of Formula III-a or wherein R¹, R², R⁴, R⁵, R⁶, R⁷ and R⁸ are as defined in Formula I.

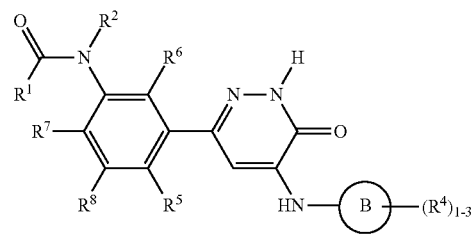

Formula III-a

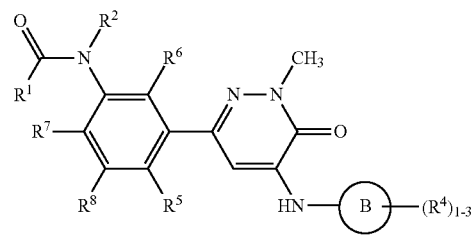

Formula III-b

In certain embodiments, the compounds of the present invention are of Formula IV-a and IV-b, wherein R¹, R², R⁴, R⁵, R⁷ and R⁸ are as defined in Formula I.

Formula IV-a

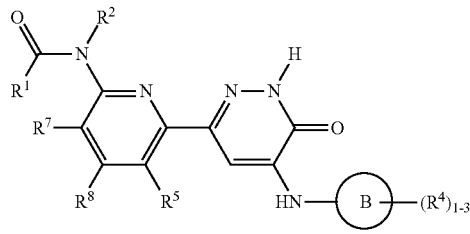

Formula IV-b

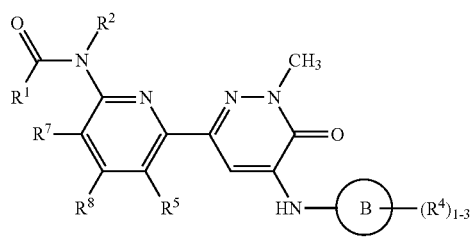

In certain embodiments, R⁵ is H.

In certain embodiments, R⁵ is F.

In certain embodiments, $R^6$ is H, $CH_3$, F, Cl, $CH_2OH$, $CH_2F$, CH=O, $CH_2OCH_3$, or $(CH_2)_2OH$. In certain embodiments, $R^6$ is H, $CH_3$, F, $C_1$ or $CH_2OH$. In certain embodiments, $R^6$ is $CH_3$. In certain embodiments, $R^6$ is H. In certain embodiments, $R^6$ is F. In certain embodiments, $R^6$ is Cl. In certain embodiments, $R^6$ is $CH_2OH$. In certain embodiments, $R^6$ is $CH_2F$, CH=O, $CH_2OCH_3$, or $(CH_2)_2OH$.

In certain embodiments, $R^7$ is chosen from H, F or $CH_3$. In certain embodiments, $R^7$ is F. In certain embodiments, $R^7$ is H. In certain embodiments, $R^7$ is $CH_3$.

In certain embodiments, $R^8$ is H.

In certain embodiments, $R^1$ is chosen from:

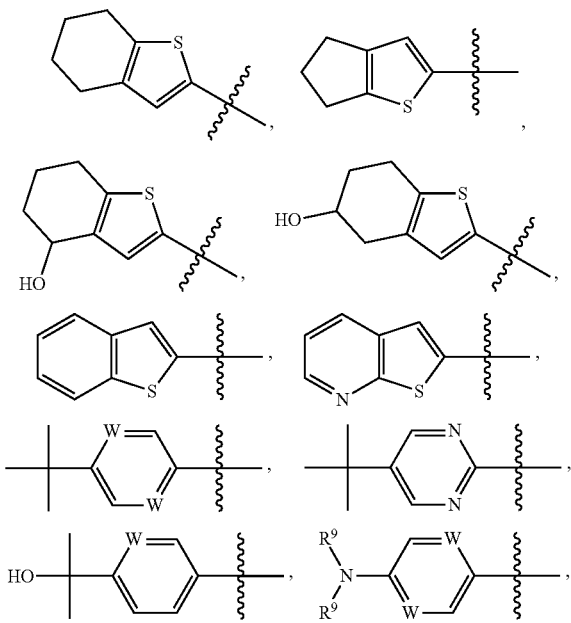

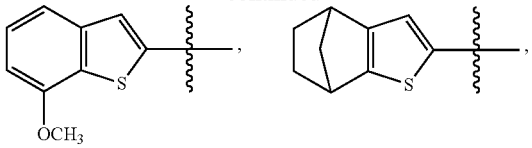

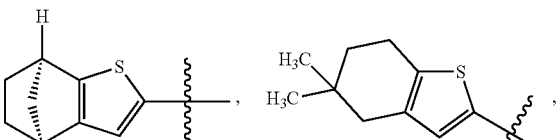

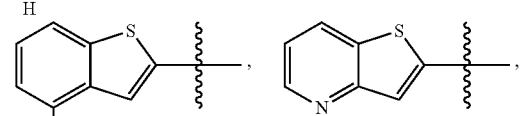

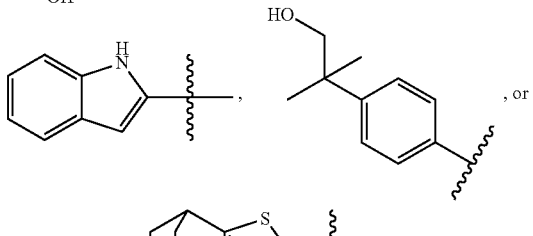

In certain embodiments, $R^1$ is

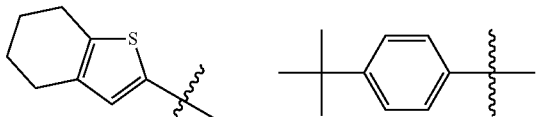

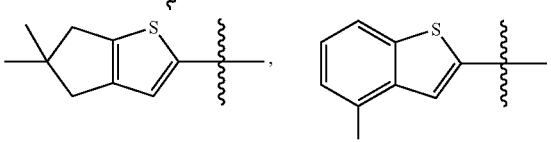

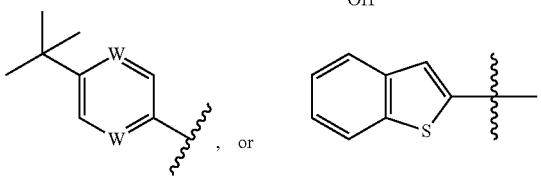

In certain embodiments, $R^2$ is H, $CH_3$ or $CH_2OH$. In certain embodiments, $R^2$ is H or $CH_3$. In certain embodiments, $R^2$ is H. In certain embodiments, $R^2$ is —$(CH_2)_3N(CH_3)_2$. In certain embodiments, $R^2$ is OH. In certain embodiments, $R^2$ is $CH_3$. In certain embodiments, $R^2$ is $CH_2OH$.

In certain embodiments, ring B is a 5-6 membered heteroaryl having at least one nitrogen ring atom. In certain embodiments, ring B is a 5-6 membered heteroaryl having at least one nitrogen ring atom at the 2-position. In certain embodiments, ring B is pyrazolyl, oxazolyl, pyrimidinyl, pyridinyl, pyridazinyl, pyrazinyl, imidazolyl, or thiazolyl. In certain embodiments, ring B is pyrazolyl, oxazolyl, pyrimidinyl, pyridinyl, pyridazinyl, pyrazinyl, or imidazolyl. In certain embodiments, ring B is 2-pyridinyl.

In certain embodiments, ring. B is a 6-membered heterocycloalkyl having at least one nitrogen ring atom. In certain embodiments, ring B is piperidinyl.

In certain embodiments, ring B is an 8-10 membered heterocycloalkyl having at least one nitrogen ring atom. In certain embodiments, ring B is an 8-10 membered heterocycloalkyl having at least one nitrogen ring atom at the 2-position. In certain embodiments, ring B with $(R^4)_{1-3}$ is:

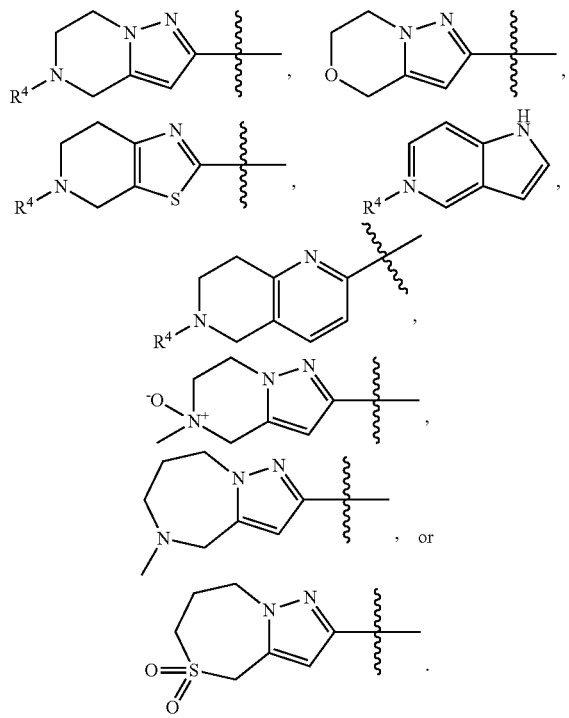

In certain embodiments, ring B with $(R^4)_{1-3}$ is

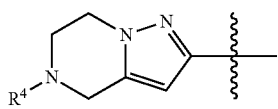

wherein $R^4$ is $CH_3$ or $CD_3$.

In certain embodiments, ring B with $(R^4)_{1-3}$ is:

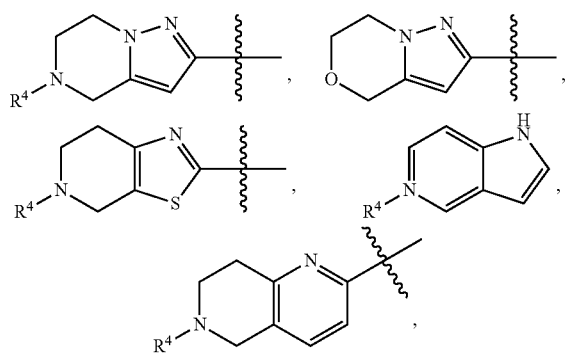

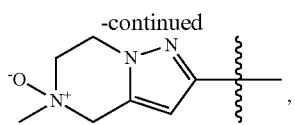

In certain embodiments, ring B with $(R^4)_{1-3}$ is

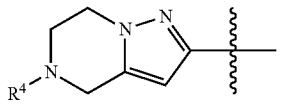

wherein $R^4$ is $CH_3$,

In certain embodiments, ring B with $(R^4)_{1-3}$ is:

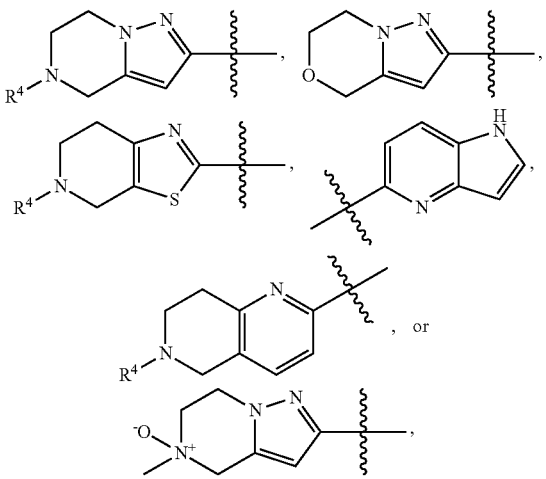

wherein $R^4$ is H, $CH_3$, or $CD_3$.

In certain embodiments, $R^4$ is H, —$R^a$, —$NR^bOR^b$, or $COR^b$. In certain embodiments, $R^4$ is H, —$R^a$, or —$NR^bR^c$. In certain embodiments, $R^a$ is $C_1$-$C_6$ alkyl, cycloalkyl, or heterocycloalkyl, wherein said alkyl, cycloalkyl or heterocycloalkyl is optionally substituted with one to three $R^{11}$ groups.

In certain embodiments, $R^a$ is $C_1$-$C_6$ alkyl, cycloalkyl, or heterocycloalkyl, wherein said alkyl, cycloalkyl or heterocycloalkyl is optionally substituted with one to three $R^{11}$ groups selected from $C_1$-$C_4$ alkyl, —OH, heterocycloalkyl (optionally substituted with one to three $R^{12}$ groups), —$OC_1$-$C_4$ alkyl, —O-heterocycloalkyl, oxo, halo, —$NH_2$, —$NH(C_1$-$C_4$alkyl optionally substituted with one to three $R^{12}$ groups), —$N(C_1$-$C_4$alkyl optionally substituted with one to three $R^{12}$ groups)$_2$, and —NH-heterocycloalkyl.

In certain embodiments, $R^2$ is $C_1$-$C_6$ alkyl, cycloalkyl, or heterocycloalkyl, wherein said alkyl, cycloalkyl or heterocycloalkyl is optionally substituted with one to three $R^{11}$ groups selected from $C_1$-$C_4$ alkyl, —OH, heterocycloalkyl (optionally substituted with one to three $R^{12}$ groups), —$OC_1$-$C_4$ alkyl, —O-heterocycloalkyl, oxo, halo, —$NH_2$, —$NH(C_1$-$C_4$alkyl optionally substituted with one to three $R^{12}$ groups), —$N(C_1$-$C_4$alkyl optionally substituted with one to three $R^{12}$ groups)$_2$, —NH-heterocycloalkyl, wherein each $R^{12}$ is independently selected from OH, F, $NH_2$, $NHCH_3$, $N(CH_3)_2$, and $CH_3$.

In certain embodiments, $R^a$ is $C_1$-$C_6$ alkyl, cycloalkyl, or heterocycloalkyl, wherein said alkyl, cycloalkyl or heterocycloalkyl is optionally substituted with one to three $R^{11}$ groups selected from $C_1$-$C_4$ alkyl, —OH, heterocycloalkyl, —$OC_1$-$C_4$ alkyl, O-heterocycloalkyl, or oxo.

In certain embodiments, $R^b$ is H, heterocycloalkyl, ox $C_1$-$C_6$ alkyl optionally substituted with one to three $R^{11}$ groups and $R^c$ is H or $C_1$-$C_4$ alkyl. In certain embodiments, $R^b$ is H, heterocycloalkyl, or $C_1$-$C_6$ alkyl optionally substituted one to two $R^1$ groups independently selected from OH, $NH_2$, NH($C_1$-$C_4$ alkyl), N($C_1$-$C_4$ alkyl)$_2$ and heterocycloalkyl; and $R^c$ is H or $C_1$-$C_4$ alkyl. In certain embodiments, $R^b$ is $C_1$-$C_6$ alkyl and $R^c$ is $C_1$-$C_4$ alkyl.

In certain embodiments, $R^4$ is H, $CH_3$, $CH_2CH_3$, t-butyl, $CF_3$, —C(OH)($CH_3$)$_2$, —CH(OH)$CH_3$, —$CH_2$NH($CH_2$)$_2$OH, —$CH_2$NH($CH_2$)F, —$CH_2$NH$CH_3$, —$CH_2$N($CH_3$)$_2$, —$CH_2$NH$CH_2$$CF_3$, —$CH_2$OH, —$CH_2$$NH_2$, —$OCH_3$, $NH_2$, —N($CH_3$)($CH_2$)$_2$N$Me_2$, —N($CH_3$)($CH_2$)$_2$OH, —N($CH_3$)($CH_2$)$_2$$NH_2$, —CH(OH)C(O)N($CH_3$)$_2$, —C(O)C(O)N($CH_3$)$_2$, —$CH_2$CH$F_2$, —($CH_2$)$_2$F, —($CH_2$)$_3$F, —O($CH_2$)$_2$N($CH_3$)$_2$, —C($CH_3$)OHC$F_3$,

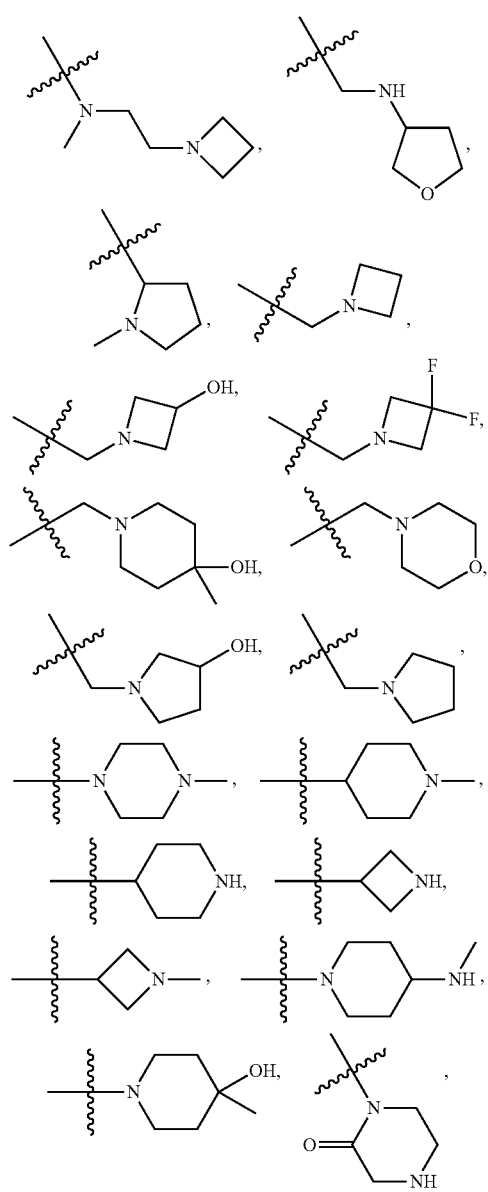

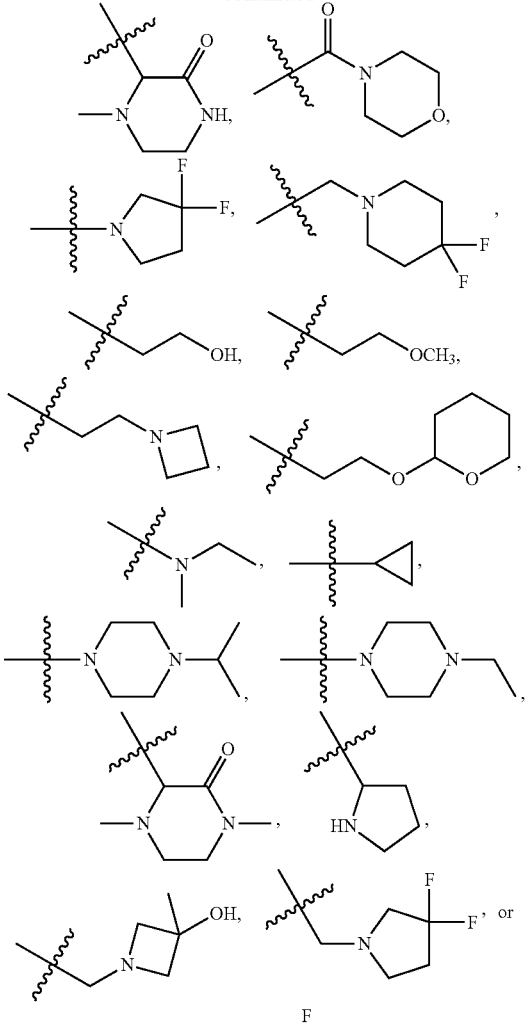

In certain embodiments, $R^4$ is H, $CH_3$, $CH_2CH_3$, t-butyl, $CF_3$, —C(OH)($CH_3$)$_2$, —CH(OH)$CH_3$, —$CH_2$NH($CH_2$)$_2$OH, —$CH_2$NH($CH_2$)F, —$CH_2$NH$CH_3$, —$CH_2$N($CH_3$)$_2$, —$CH_2$NH$CH_2$$CF_3$, —$CH_2$OH, —$CH_2$$NH_2$, —$OCH_3$, $NH_2$, —N($CH_3$)($CH_2$)$_2$NH$CH_2$, —N($CH_3$)($CH_2$)$_2$OH, —N($CH_3$)($CH_2$)$_2$$NH_2$, —CH(O)C(O)N($CH_3$)$_2$, —C(O)C(O)N($CH_3$)$_2$,

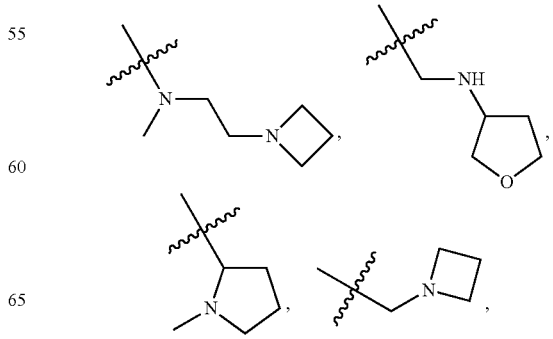

-continued

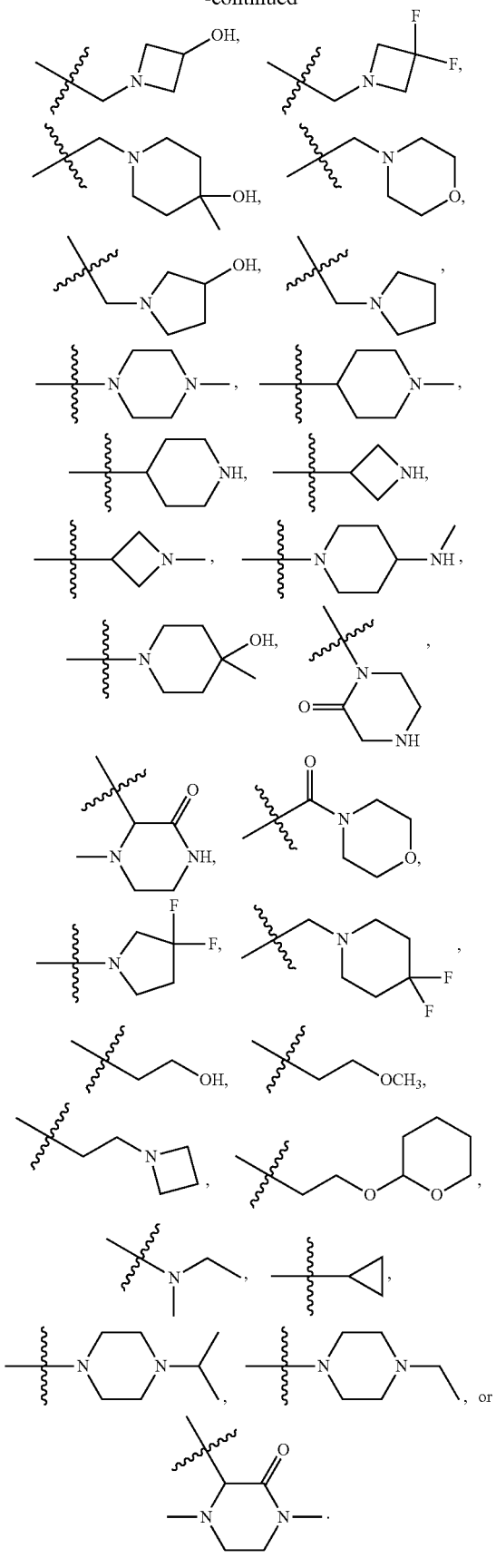

In certain embodiments, each $R^{13}$ is independently H, F, O-t-butyl, t-butyl, or methyl. In certain embodiments, each $R^{14}$ is independently H, —C(=O)CH$_3$, or methyl.

In certain embodiments, $R^1$ contains a thiophene ring fused to a 5, 6, 7 or 8 membered ring as shown herein. In certain embodiments, $R^1$ contains a phenylene or benzo ring as shown herein.

In certain embodiments, the compound of the present invention is chosen from

N-(3-{5-[(1,5-dimethyl-1H-pyrazol-3-yl)amino]-6-oxo-1,6-dihydropyridazin-3-yl}-2,6-difluorophenyl)thieno[3,2-b]pyridine-2-carboxamide;

N-(2-fluoro-5-{5-[(5-methyl-1,2-oxazol-3-yl)amino]-6-oxo-1,6-dihydropyridazin-3-yl}phenyl)-4,5,6,7-tetrahydro-1-benzothiophene-2-carboxamide;

N-{2-fluoro-5-[6-oxo-5-(pyrimidin-4-ylamino)-1,6-dihydropyridazin-3-yl]phenyl}-4,5,6,7-tetrahydro-1-benzothiophene-2-carboxamide;

N-{2-fluoro-5-[5-({1-[2-(oxan-2-yloxy)ethyl]-1H-pyrazol-3-yl}amino)-6-oxo-1,6-dihydropyridazin-3-yl]phenyl}-4,5,6,7-tetrahydro-1-benzothiophene-2-carboxamide;

N-{2-methyl-3-[6-oxo-5-({5-[4-(propan-2-yl)piperazin-1-yl]pyridin-2-yl}amino)-1,6-dihydropyridazin-3-yl]phenyl}-4,5,6,7-tetrahydro-1-benzothiophene-2-carboxamide;

N-(5-{5-[(5-cyclopropyl-1H-pyrazol-3-yl)amino]-6-oxo-,6-dihydropyridazin-3-yl}-2-fluorophenyl)-4,5,6,7-tetrahydro-1-benzothiophene-2-carboxamide;

N-[3-(5-{[5-(4-ethylpiperazin-1-yl)pyridin-2-yl]amino}-1-methyl-6-oxo-1,6-dihydropyridazin-3-yl)-2-methylphenyl]-4,5,6,7-tetrahydro-1-benzothiophene-2-carboxamide;

N-(5-{5-[(1,5-dimethyl-1H-pyrazol-3-yl)amino]-6-oxo-1,6-dihydropyridazin-3-yl}-2-fluorophenyl)-5-hydroxy-4,5,6,7-tetrahydro-1-benzothiophene-2-carboxamide;

N-(3-{5-[(1,5-dimethyl-1H-pyrazol-3-yl)amino]-6-oxo-1,6-dihydropyridazin-3-yl}-6-fluoro-2-6-ethylphenyl)-4,5,6,7-tetrahydro-1-benzothiophene-2-carboxamide;

(1R,7S)—N-(2-fluoro-5-(6-oxo-5-(pyrimidin-4-ylamino)-1,6-dihydropyridazin-3-yl)phenyl)-4,7-methano-4,5,6,7-tetrahydrobenzo[b]thiophene-2-carboxamide;

N-[2-fluoro-5-[5-({5-methyl-4H,5H,6H,7H-pyrazolo[1,5-a]pyrazin-2-yl]amino)-6-oxo-1,6-dihydropyridazin-3-yl]phenyl}-4,5,6,7-tetrahydro-1-benzothiophene-2-carboxamide;

N-[2-fluoro-5-(5-{[1-(2-methoxyethyl)-1,1-pyrazol-3-yl]amino}-6-oxo-1,6-dihydropyridazin-3-yl)phenyl]-4,5,6,7-tetrahydro-1-benzothiophene-2-carboxamide;

4-tert-butyl-N-{2-fluoro-5-[6-oxo-5-(pyrimidin-4-ylamino)-1,6-dihydropyridazin-3-yl]phenyl}benzamide;

N-(3-{5-[(5-cyclopropyl-1H-pyrazol-3-yl)amino]-6-oxo-1,6-dihydropyridazin-3-yl}-2,6-difluorophenyl)-4,5,6,7-tetrahydro-1-benzothiophene-2-carboxamide;

N-{5-[5-({1-[2-(azetidin-1-yl)ethyl]-1H-pyrazol-3-yl}amino)-6-oxo-1,6-dihydropyridazin-3-yl]-2-fluorophenyl}-4,5,6,7-tetrahydro-1-benzothiophene-2-carboxamide;

6-tert-butyl-N-{2-fluoro-5-[6-oxo-5-(pyrimidin-4-ylamino)-1,6-dihydropyridazin-3-yl]phenyl}pyridine-3-carboxamide;

N-{2-fluoro-5-[6-oxo-5-(pyridazin-3-ylamino)-1,6-dihydropyridazin-3-yl]phenyl}-4,5,6,7-tetrahydro-1-benzothiophene-2-carboxamide;

5-tert-butyl-N-{2-fluoro-5-[6-oxo-5-(pyrimidin-4-ylamino)-1,6-dihydropyridazin-3-yl]phenyl}pyrimidine-2-carboxamide;

N-(3-{5-[(1,5-dimethyl-1H-pyrazol-3-yl)amino]-1-methyl-6-oxo-1,6-dihydropyridazin-3-yl}-2,6-difluorophenyl)-4,5,6,7-tetrahydro-1-benzothiophene-2-carboxamide;

N-(5-{5-[(1,5-dimethyl-1H-pyrazol-3-yl)amino]-1,6-dihydropyridazin-3-yl}-2-fluorophenyl)-6-[ethyl(methyl)amino]pyridine-3-carboxamide;

N-(5-{5-[(1,5-dimethyl-1H-pyrazol-3-yl)amino]-6-oxo-1,6-dihydropyridazin-3-yl}-2-fluorophenyl)-4,5,6,7-tetrahydro-1-benzothiophene-2-carboxamide;

N-{2-fluoro-5-[6-oxo-5-(pyrazin-2-ylamino)-1,6-dihydropyridazin-3-yl]phenyl}-4,5,6,7-tetrahydro-1-benzothiophene-2-carboxamide;

5-tert-butyl-N-(5-(5-[(1,5-dimethyl-1H-pyrazol-3-yl)amino]-6-oxo-1,6-dihydropyridazin-3-yl)-2-fluorophenyl)pyridine-2-carboxamide;

N-(5-{5-[(1,5-dimethyl-1H-pyrazol-3-yl)amino]-6-oxo-1,6-dihydropyrazin-3-yl}-2-fluorophenyl)-4-methoxy-1-benzothiophene-2-carboxamide;

4-[ethyl(methyl)amino]-N-{2-fluoro-5-[6-oxo-5-(pyrimidin-4-ylamino)-6-dihydropyridazin-3-yl]phenyl}benzamide;

N-{2-fluoro-5-[6-oxo-5-(pyrimidin-4-ylamino)-1,6-dihydropyridazin-3-yl]phenyl}-1-benzothiophene-2-carboxamide;

N-(5-{5-[(1,5-dimethyl-1H-pyrazol-3-yl)amino]-6-oxo-1,6-dihydropyridazin-3-yl}-2-fluorophenyl)-3-thiatricyclo[5.2.1.0^{2,6}]deca-2(6),4-diene-4-carboxamide;

N-(5-{5-[(1,5-dimethyl-1H-pyrazol-3-yl)amino]-6-oxo-1,6-dihydropyridazin-3-yl}-2-fluorophenyl)-1-benzothiophene-2-carboxamide;

N-(5-{5-[(5-cyclopropyl-1H-pyrazol-3-yl)amino]-1-methyl-6-oxo-1,6-dihydropyridazin-3-yl}-2-fluorophenyl)-4,5,6,7-tetrahydro-1-benzothiophene-2-carboxamide;

N-[2-fluoro-5-(5-{[1-(2-hydroxyethyl)-1H-pyrazol-3-yl]amino}-6-oxo-1,6-dihydropyridazin-3-yl)phenyl]-4,5,6,7-tetrahydro-1-benzothiophene-2-carboxamide;

N-(3-{5-[(1,5-dimethyl-1H-pyrazol-3-yl)amino]-6-oxo-1,6-dihydropyridazin-3-yl}-2,6-difluorophenyl)-4,5,6,7-tetrahydro-1-benzothiophene-2-carboxamide;

5-tert-butyl-N-{2-fluoro-5-[6-oxo-5-(pyrimidin-4-ylamino)-1,6-dihydropyridazin-3-yl]phenyl}pyrazine-2-carboxamide;

N-{2-fluoro-5-[6-oxo-5-(pyrimidin-4-ylamino)-1,6-dihydropyridazin-3-yl]phenyl}-4H,5H,6H-cyclopenta[b]thiophene-2-carboxamide;

N-[3-(5-{[5-(1,4-dimethyl-3-oxopiperazin-2-yl)pyridin-2-yl]amino}-1-methyl-6-oxo-1,6-dihydropyridazin-3-yl)-2,6-difluorophenyl]-4,5,6,7-tetrahydro-1-benzothiophene-2-carboxamide;

N-[3-(5-{[5-(4-ethylpiperazin-1-yl)pyridin-2-yl]amino}-6-oxo-1,6-dihydropyridazin-3-yl)-2-methylphenyl]-4,5,6,7-tetrahydro-1-benzothiophene-2-carboxamide;

N-{3-fluoro-6-[6-oxo-5-(pyilmidin-4-ylamino)-1,6-dihydropyridazin-3-yl]pyridin-2-yl}-4,5,6,7-tetrahydro-1-benzothiophene-2-carboxamide;

N-[2-fluoro-5-(5-{[1-(2-hydroxyethyl)-5-methyl-1H-pyrazol-3-yl]amino}-6-oxo-dihydropyridazin-3-yl)phenyl]-4,5,6,7-tetrahydro-1-benzothiophene-2-carboxamide;

N-(5-{5-[(5-cyclopropyl-1H-pyrazol-3-yl)amino]-6-oxo-1,6-dihydropyridazin-3-yl}-2-fluorophenyl)-5-[ethyl(methyl)amino]pyrazine-2-carboxamide;

N-(5-{5-[(5-cyclopropyl-1H-pyrazol-3-yl)amino]-6-oxo-1,6-dihydropyridazin-3-yl}-2-fluorophenyl)-4-hydroxy-4,5,6,7-tetrahydro-1-benzothiophene-2-carboxamide;

N-(3-{5-[(1,5-dimethyl-1H-pyrazol-3-yl)amino]-6-oxo-1,6-dihydropyridazin-3-yl}2,6-difluorophenyl)-1-benzothiophene-2-carboxamide;

N-(5-{5-[(5-cyclopropyl-1H-pyrazol-3-yl)amino]-6-oxo-1,6-dihydropyridazin-3-yl}-2-fluorophenyl)-4-(2-hydroxypropan-2-yl)benzamide;

5-tert-butyl-N-(5-{5-[(5-cyclopropyl-1H-pyrazol-3-yl)amino]-6-oxo-1,6-dihydropyridazin-3-yl}-2-fluorophenyl)pyrazine-2-carboxamide;

N-(5-{5-[(5-cyclopropyl-1H-pyrazol-3-yl)amino]-6-oxo-1,6-dihydropyridazin-3-yl}-2-fluorophenyl)-4-[1-(2-hydroxyethoxy)-2-methylpropan-2-yl]benzamide N-(5-{5-[(5-cyclopropyl-1H-pyrazol-3-yl)amino]-6-oxo-1,6-dihydropyridazin-3-yl}-2-fluorophenyl)-4-(1-hydroxy-2-methylpropan-2-yl)benzamide;

N-(5-{5-[(5-cyclopropyl-1,1-pyrazol-3-yl)amino]-6-oxo-1,6-dihydropyridazin-3-yl}-2-fluorophenyl)-5,5-dimethyl-4H,5H,6H-cyclopenta[b]thiophene-2-carboxamide;

N-(5-{5-[(1,5-dimethyl-1H-pyrazol-3-yl)amino]-1-methyl-6-oxo-1,6-dihydropyridazin-3-yl}-2-fluorophenyl)-1-benzothiophene-2-carboxamide;

5-tert-butyl-N-{2-fluoro-5-[5-({5-methyl-4H,5H,6H,7H-pyrazolo[1,5-a]pyrazin-2-yl}amino)-6-oxo-1,6-dihydropyridazin-3-yl]phenyl}pyrazine-2-carboxamide;

5-tert-butyl-N-(5-{5-[(1,5-dimethyl-1H-pyrazol-3-yl)amino]-1-methyl-6-oxo-1,6-dihydropyridazin-3-yl}-2-fluorophenyl)pyrazine-2-carboxamide;

4-(1-cyano-1-methylethyl)-N-(5-{5-[(5-cyclopropyl-1H-pyrazol-3-yl)amino]-6-oxo-1,6-dihydropyridazin-3-yl}-2-fluorophenyl)benzamide;

5-tert-butyl-N-(5-{5-[(1,5-dimethyl-1H-pyrazol-3-yl)amino]-6-oxo-1,6-dihydropyridazin-3-yl]-2-fluorophenyl)pyrazine-2-carboxamide;

N-(5-{5-[(5-cyclopropyl-1H-pyrazol-3-yl)amino]-6-oxo-1,6-dihydropyridazin-3-yl}-2-fluorophenyl)-3-thia-5-azatricyclo[5.2.1.0^{2,6}]deca-2(6),4-diene-4-carboxamide;

5-tert-butyl-N-[2-fluoro-5-(5-{[1-(2-hydroxyethyl)-1,1-pyrazol-3-yl]amino}6-oxo-1,6-dihydropyridazin-3-yl)phenyl]pyrazine-2-carboxamide;

N-(5-{5-[(5-cyclopropyl-1H-pyrazol-3-yl)amino]-6-oxo-1,6-dihydropyridazin-3-yl}-2-fluorophenyl)-1-benzothiophene-2-carboxamide;

N-[2-fluoro-5-(5-[1-methyl-5-(trifluoromethyl)-1H-pyrazol-3-yl]amino)-6-oxo-1,6-dihydropyridazin-3-yl)phenyl]-1-benzothiophene-2-carboxamide;

5-tert-butyl-N-[2-fluoro-5-(5-{[5-(4-methylpiperazin-1-yl)pyridin-2-yl]amino}-6-oxo-1,6-dihydropyridazin-3-yl)phenyl]pyrazine-2-carboxamide;

5-tert-butyl-N-(2-fluoro-5-{5-[(6-methylpyridin-2-yl)amino]-6-oxo-1,6-dihydropyridazin-3-yl}phenyl)pyrazine-2-carboxamide;

N-(5-{5-[(1,5-dimethyl-1H-pyrazol-3-yl)amino]-6-oxo-1,6-dihydropyridazin-3-yl}-2-fluorophenyl)-4-(3-methyloxetan-3-yl)benzamide;

N-(5-{5-[(1,5-dimethyl-1H-pyrazol-3-yl)amino]-6-oxo-1,6-dihydropyridazin-3-yl}-2-fluorophenyl)-4-hydroxy-1-benzothiophene-2-carboxamide;

5-tert-butyl-N-[2-fluoro-5-(6-oxo-5-{4H,5H,6H,7H-pyrazolo[1,5-a]pyrazine-2-ylamino-1,6-dihydropyridazin-3-yl}phenyl]pyrazine-2-carboxamide;

N-[2-fluoro-5-(5-{[1-(2-hydroxyethyl)-5-methyl-1H-pyrazol-3-yl]amino}-6-oxo-dihydropyridazin-3-yl)phenyl]-1-benzothiophene-2-carboxamide;

N-[2-fluoro-5-(5-{[1-(2-hydroxyethyl)-1H-pyrazol-3-yl]amino}-6-oxo-1,6-dihydropyridazin-3-yl)phenyl]-1-benzothiophene-2-carboxamide;

N-[2-fluoro-5-(6-oxo-5-{4H,5H,6H,7H-pyrazolo[1,5-a]pyrazin-2-ylamino}-1,6-dihydropyridazin-3-yl)phenyl]-1-benzothiophene-2-carboxamide;

N-[2-fluoro-5-(5-{[5-(4-methylpiperazin-1-yl)pyridin-2-yl]amino}-6-oxo-1,6-dihydropyridazin-3-yl)phenyl]-1-benzothiophene-2-carboxamide;

5-tert-butyl-N-{2-fluoro-5-[1-methyl-5-({5-methyl-4H,5H,6H,7H-pyrazolo[1,5-a]pyrazin-2-yl}amino)-6-oxo-1,6-dihydropyridazin-3-yl]phenyl}pyrazine-2-carboxamide;

N-[2-fluoro-5-(1-methyl-6-oxo-5-{4H,6H,7H-pyrazolo[3,2-c][1,4]oxazin-2-ylamino}-1,6-dihydropyridazin-3-yl)phenyl]-1-benzothiophene-2-carboxamide;

5-tert-butyl-N-[2-fluoro-5-(1-methyl-6-oxo-5-{4H,6H,7H-pyrazolo[3,2-c][1,4]oxazin-2-ylamino}-1,6-dihydropyridazin-3-yl)phenyl]pyrazine-2-carboxamide;

N-(5-{5-[(1,5-dimethyl-1H-pyrazol-3-yl)amino]-6-oxo-1,6-dihydropyridazin-3-yl}-2-fluorophenyl)-4-hydroxy-4,5,6,7-tetrahydro-1-benzothiophene-2-carboxamide;

N-(5-{5-[(1,5-dimethyl-1H-pyrazol-3-yl)amino]-6-oxo-1,6-dihydropyridazin-3-yl}-2-fluorophenyl)-4-(1-hydroxy-2-methylpropan-2-yl)benzamide;

N-(5-{5-[(5-amino-1-methyl-1H-pyrazol-3-yl)amino]-1-methyl-6-oxo-1,6-dihydropyridazin-3-yl}-2-fluorophenyl)-1-benzothiophene-2-carboxamide;

N-[2-fluoro-5-(5-{[5-(1-methylpyrrolidin-2-yl)pyridin-2-yl]amino}-6-oxo-1,6-dihydropyridazin-3-yl)phenyl]-1-benzothiophene-2-carboxamide;

4-tert-butyl-N-[(3R)-1-{5-[(1,5-dimethyl-1H-pyrazol-3-yl)amino]-1-methyl-6-oxo-1,6-dihydropyridazin-3-yl}piperidin-3-yl]benzamide;

N-{2-fluoro-5-[5-({5-methyl-4H,5H,6H,7H-pyrazolo[1,5-a]pyrazin-2-yl}amino)-6-oxo-1,6-dihydropyridazin-3-yl]phenyl}-1-benzothiophene-2-carboxamide;

5-tert-butyl-N-[2-fluoro-5-(6-oxo-5-{4H,6H,7H-pyrazolo[3,2-c][1,4]oxazin-2-ylamino}-1,6-dihydropyridazin-3-yl)phenyl]pyrazine-2-carboxamide;

N-[5-(5-{[5-(azetidin-1-ylmethyl)-1-methyl-1H-pyrazol-3-yl]amino}-1-methyl-6-oxo-1,6-dihydropyridazin-3-yl)-2-fluorophenyl]-1-benzothiophene-2-carboxamide;

N-(5-{5-[(5-amino-1-methyl-1H-pyrazol-3-yl)amino]-1-methyl-6-oxo-1,6-dihydropyridazin-3-yl}-2-fluorophenyl)-5-tert-butylpyrazine-2-carboxamide;

4-tert-butyl-N-(5-{5-[(1,5-dimethyl-1H-pyrazol-3-yl)amino]-1-methyl-6-oxo-1,6-dihydropyridazin-3-yl}-2-fluorophenyl)benzamide;

N-[(3R)-1-{5-[(1,5-dimethyl-1H-pyrazol-3-yl)amino]-1-methyl-6-oxo-1,6-dihydropyridazin-3-yl}piperidin-3-yl]-1-benzothiophene-2-carboxamide;

5-tert-butyl-N-[2-fluoro-5-(5-{[5-(1-methylpyrrolidin-2-yl)pyridin-2-yl]amino}-6-oxo-1,6-dihydropyridazin-3-yl)phenyl]pyrazine-2-carboxamide;

N-{2-fluoro-5-[5-(5-methyl-4H,5H,6H,7H-pyrazolo[1,5-a]pyrazin-2-yl)amino)-6-oxo-1,6-dihydropyridazin-3-yl]phenyl}-5,5-dimethyl-4H,5H,6H-cyclopenta[b]thiophene-2-carboxamide;

N-{2-fluoro-5-[5-({5-methyl-4H,5H,6H,7H-pyrazolo[1,5-a]pyrazin-2-yl}amino)-6-oxo-1,6-dihydropyridazin-3-yl]phenyl}-4-(1-hydroxy-2-methylpropan-2-yl)benzamide;

5-tert-butyl-N-(2-fluoro-5-{5-[(6-methoxypyridin-2-yl)amino]-1-methyl-6-oxo-1,6-dihydropyridazin-3-yl}phenyl)pyrazine-2-carboxamide;

4-tert-butyl-N-(5-{5-[(1,5-dimethyl-1H-pyrazol-3-yl)amino]-6-oxo-1,6-dihydropyridazin-3-yl}-2-fluorophenyl)benzene-1-carboximidamide;

N-{2-fluoro-5-[5-({5-methyl-4H,5H,6H,7H-pyrazolo[1,5-a]pyrazin-2-yl}amino-6-oxo-1,6-dihydropyridazin-3-yl]phenyl}-4-hydroxy-4H,5H,6H-cyclopenta[b]thiophene-2-carboxamide;

N-{2-fluoro-5-[5-({5-methyl-4H,5H,6H,7H-pyrazolo[1,5-a]pyrazin-2-yl}amino)-6-oxo-1,6-dihydropyridazin-3-yl]phenyl}-4-hydroxy-4,5,6,7-tetrahydro-1-benzothiophene-2-carboxamide;

N-[(3R)-1-(1-methyl-5-{[5-(4-methylpiperazin-1-yl)pyridin-2-yl]amino}-6-oxo-1,6-dihydropyridazin-3-yl)piperidin-3-yl]-4,5,6,7-tetrahydro-1-benzothiophene-2-carboxamide;

4-tert-butyl-N-{2-fluoro-5-[5-({5-methyl-4H,5H,6H,7H-pyrazolo[1,5-a]pyrazin-2-yl}amino)-6-oxo-1,6-dihydropyridazin-3-yl]phenyl}benzamide;

4-tert-butyl-N-[(3R)-1-{5-[(1,5-dimethyl-1H-pyrazol-3-yl)amino]-6-oxo-1,6-dihydropyridazin-3-yl}piperidin-3-yl]benzamide;

N-[2-fluoro-5-(5-[5-(1-methylpyrrolidin-2-yl)pyridin-2-yl]amino)-6-oxo-1,6-dihydropyridazin-3-yl)phenyl]-4,5,6,7-tetrahydro-1-benzothiophene-2-carboxamide;

N-[2-fluoro-5-(5-{[5-(4-hydroxy-4-methylpiperidin-1-yl)pyridin-2-yl]amino}-6-oxo-1,6-dihydropyridazin-3-yl)phenyl]-1-benzothiophene-2-carboxamide;

N-{2-fluoro-5-[1-methyl-5-({5-methyl-4H,5H,6H,7H-pyrazolo[1,5-a]pyrazin-2-yl}amino)-6-oxo-1,6-dihydropyridazin-3-yl]phenyl}-6-(2-hydroxypropan-2-yl)pyridine-3-carboxamide;

N-[5-(5-{[5-(azetidin-1-ylmethyl)-1-methyl-1H-pyrazol-3-yl]amino}-6-oxo-1,6-dihydropyridazin-3-yl)-2-fluorophenyl]-1-benzothiophene-2-carboxamide;

4-tert-butyl-N-[2-fluoro-5-(5-{[5-(1-methylpyrrolidin-2-yl)pyridin-2-yl]amino}-6-oxo-1,6-dihydropyridazin-3-yl)phenyl]benzamide;

N-[2-fluoro-5-(6-oxo-5-{[5-(2-oxopiperazin-1-yl)pyridin-2-yl]amino}-1,6-dihydropyridazin-3-yl)phenyl]-4,5,6,7-tetrahydro-1-benzothiophene-2-carboxamide;

N-{2-fluoro-5-[5-({5-methyl-4H,5H,6H,7H-pyrazolo[1,5-a]pyrazin-2-yl}amino)-6-oxo-1,6-dihydropyridazin-3-yl]phenyl}-1H-indole-2-carboxamide;

N-{2-fluoro-5-[5-({5-methyl-4H,5H,6H,7H-pyrazolo[1,5-a]pyrazin-2-yl}amino-6-oxo-1,6-dihydropyridazin-3-yl]phenyl}-5-hydroxy-4,5,6,7-tetrahydro-1-benzothiophene-2-carboxamide;

N-[2-fluoro-5-(6-oxo-5-{4H,6H,7H-pyrazolo[3,2-c][1,4]oxazin-2-ylamino}-1,6-dihydropyridazin-3-yl)phenyl]-1-benzothiophene-2-carboxamide;

N-[5-(5-{[5-(1,4-dimethyl-3-oxopiperazin-2-yl)pyridin-2-yl]amino}-6-oxo-1,6-dihydropyridazin-3-yl)-2-fluorophenyl]-1-benzothiophene-2-carboxamide;

N-{2-fluoro-5-[5-({5-methyl-4H,5H,6H,7H-pyrazolo[1,5-a]pyrazin-2-yl}amino)-6-oxo-1,6-dihydropyridazin-3-yl]phenyl}-4-(2-hydroxypropan-2-yl)benzamide;

5-tert-butyl-N-{2-methyl-3-(5-[(1-methylpyrrolidin-2-yl)pyridin-2-yl]amino}-6-oxo-1,6-dihydropyridazin-3-yl)phenyl]pyrazine-2-carboxamide;

5-tert-butyl-N-{2-methyl-3-[5-({5-methyl-4H,5H,6H,7H-pyrazolo[1,5-a]pyrazin-2-yl}amino)-6-oxo-1,6-dihydropyridazin-3-yl]phenyl}pyrazine-2-carboxamide;

N-(5-{5-[(1,5-dimethyl-1H-pyrazol-3-yl)amino]-6-oxo-1,6-dihydropyridazin-3-yl}-2-fluorophenyl)-6-(2-hydroxypropan-2-yl)pyridine-3-carboxamide;

4-(1-amino-2-methylpropan-2-yl)-N-{2-fluoro-5-[5-({5-methyl-4H,5H,6H,7H-pyrazolo[1,5-a]pyrazin-2-yl}amino)-6-oxo-1,6-dihydropyridazin-3-yl]phenyl}benzamide;

(5S)—N-{2-fluoro-5-[5-({5-methyl-4H,5H,6H,7H-pyrazolo[1,5-a]pyrazin-2-yl}amino)-6-oxo-1,6-dihydropyridazin-3-yl]phenyl}-5-hydroxy-4,5,6,7-tetrahydro-1-benzothiophene-2-carboxamide;

N-{2-methyl-3-[5-({5-methyl-4H,5H,6H,7H-pyrazolo[1,5-a]pyrazin-2-yl}amino)-6-oxo-1,6-dihydropyridazin-3-yl]phenyl}-1-benzothiophene-2-carboxamide;

N-[2-fluoro-5-(5-{[5-(1-methylpyrrolidin-2-yl)pyridin-2-yl] amino}-6-oxo-1,6-dihydropyridazin-3-yl)phenyl]-4-(2-hydroxypropan-2-yl)benzamide;

N-[5-(5-{[5-(1,4-dimethyl-3-oxopiperazin-2-yl)pyridin-2-yl]amino}-6-oxo-1,6-dihydropyridazin-3-yl)-2-fluorophenyl]-4,5,6,7-tetrahydro-1-benzothiophene-2-carboxamide;

N-[(3R)-1-{5-[(1,5-dimethyl-1H-pyrazol-3-yl)amino]-6-oxo-,6-dihydropyridazin-3-yl}piperidin-3-yl]-1-benzothiophene-2-carboxamide;

N-[2-methyl-3-(5-{[5-(1-methylpyrrolidin-2-yl)pyridin-2-yl]amino}-6-oxo-1,6-dihydropyridazin-3-yl)phenyl]-1-benzothiophene-2-carboxamide;

N-[6-fluoro-2-methyl-3-(5-{[5-(1-methylpyrrolidin-2-yl)pyridin-2-yl]amino}-6-oxo-1,6-dihydropyridazin-3-yl)phenyl]-1-benzothiophene-2-carboxamide;

5-tert-butyl-N-{2-fluoro-5-[6-oxo-5-(piperidin-3-ylamino)-1,6-dihydropyridazin-3-yl]phenyl}pyrazine-2-carboxamide;

5-tert-butyl-N-[2-fluoro-5-(5-{[5-(1-methylpyrrolidin-2-yl)pyridin-2-yl]amino}-6-oxo-1,6-dihydropyridazin-3-yl)phenyl]pyridine-2-carboxamide;

N-[2-fluoro-5-(5-{[5-(1-methylpiperidin-4-yl)pyridin-2-yl]amino}-6-oxo-1,6-dihydropyridazin-3-yl)phenyl]-1-benzothiophene-2-carboxamide;

4-tert-butyl-N-[(3S)-1-{5-[(1,5-dimethyl-1H-pyrazol-3-yl)amino]-6-oxo-1,6-dihydropyridazin-3-yl}piperidin-3-yl]benzamide;

4-tert-butyl-N-[2,6-difluoro-3-(5-{[5-(4-hydroxy-4-methylpiperidin-1-yl)pyridin-2-yl]amino}-6-oxo-1,6-dihydropyridazin-3-yl)phenyl]benzamide;

N-{2-fluoro-5-[5-({5-methyl-4H,5H,6H,7H-pyrazolo[1,5-a]pyrazin-2-yl}amino)-6-oxo-1,6-dihydropyridazin-3-yl]phenyl}-5,6,7,8-tetrahydroindolizine-2-carboxamide;

4-(2-aminopropan-2-yl)-N-[2-fluoro-5-(5-{[5-(1-methylpyrrolidin-2-yl)pyridin-2-yl]amino)}-6-oxo-1,6-dihydropyridazin-3-yl)phenyl]benzamide;

N-[2-fluoro-5-(5-{[5-(1-methylpyrrolidin-2-yl)pyridin-2-yl]amino}-6-oxo-1,6-dihydropyridazin-3-yl)phenyl]-N-methyl-1-benzothiophene-2-carboxamide;

N-[2-fluoro-5-(5-{[5-(1-methylpyrrolidin-2-yl)pyridin-2-yl]amino}-6-oxo-1,6-dihydropyridazin-3-yl)phenyl]-4-hydroxy-1-benzothiophene-2-carboxamide;

N-[2-fluoro-5-(5-{[5-(1-methylpyrrolidin-2-yl)pyridin-2-yl]amino}-6-oxo-1,6-dihydropyridazin-3-yl)phenyl]-4-methoxy-1-benzothiophene-2-carboxamide;

N-[2-fluoro-5-(5-[5-(1-methylpyrrolidin-2-yl)pyridin-2-yl]amino)-6-oxo-1,6-dihydropyridazin-3-yl)phenyl]-1-benzofuran-2-carboxamide;

N-[2-fluoro-5-(5-{[5-(1-methylpyrrolidin-2-yl)pyridin-2-yl]amino}-6-oxo-1,6-dihydropyridazin-3-yl)phenyl]-1-methyl-1H-indole-2-carboxamide;

N-[2-fluoro-5-(5-[5-(1-methylpyrrolidin-2-yl)pyridin-2-yl]amino)-6-oxo-1,6-dihydropyridazin-3-yl)phenyl]-4-(1-hydroxy-2-methylpropan-2-yl)benzamide;

5-tert-butyl-N-{2-fluoro-5-[5-({5-methyl-4H,5H,6H,7H-pyrazolo[1,5-a]pyrazin-2-yl}amino)-6-oxo-1,6-dihydropyridazin-3-yl]phenyl}pyridine-2-carboxamide;

N-{2-fluoro-5-[5-({5-[(2-hydroxyethyl)(methyl)amino]pyridin-2-yl}amino)-6-oxo-1,6-dihydropyridazin-3-yl]phenyl}-1-benzothiophene-2-carboxamide;

N-[2-fluoro-5-(6-oxo-5-{[5-(pyrrolidin-1-ylmethyl)pyridin-2-yl]amino}-1,6-dihydropyridazin-3-yl)phenyl]-1-benzothiophene-2-carboxamide;

4-tert-butyl-N-[(3R)-1-[1-methyl-5-({5-methyl-4H,5H,6H,7H-pyrazolo[1,5-a]pyrazin-2-yl}amino)-6-oxo-1,6-dihydropyridazin-3-yl]piperidin-3-yl]benzamide;

N-{3-[5-({5-[(2S)-1,4-dimethyl-3-oxopiperazin-2-yl]pyridin-2-yl}amino)-1-methyl-6-oxo-1,6-dihydropyridazin-3-yl]-2,6-difluorophenyl}-4,5,6,7-tetrahydro-1-benzothiophene-2-carboxamide;

N-{3-[5-({5-[(2R)-1,4-dimethyl-3-oxopiperazin-2-yl]pyridin-2-yl}amino)-1-methyl-6-oxo-1,6-dihydropyridazin-3-yl]-2,6-difluorophenyl}-4,5,6,7-tetrahydro-1-benzothiophene-2-carboxamide;

(4S)—N-{2-fluoro-5-[5-({5-methyl-4H,5H,6H,7H-pyrazolo[1,5-a]pyrazin-2-yl}amino)-6-oxo-1,6-dihydropyridazin-3-yl]phenyl}-4-hydroxy-4H,5H,6H-cyclopenta[b]thiophene-2-carboxamide;

(4R)—N-{2-fluoro-5-[5-({5-methyl-4H,5H,6H,7H-pyrazolo[1,5-a]pyrazin-2-yl}amino)-6-oxo-1,6-dihydropyridazin-3-yl]phenyl}-4-hydroxy-4H,5H,6H-cyclopenta[b]thiophene-2-carboxamide;

N-(2-fluoro-5-{6-oxo-5-[(5-{[(3R)-oxolan-3-ylamino]methyl}pyridin-2-yl)amino]-1,6-dihydropyridazin-3-yl}phenyl)-1-benzothiophene-2-carboxamide;

N-[2-fluoro-5-(5-{[5-(1-methylpyrrolidin-2-yl)pyridin-2-yl]amino}-6-oxo-1,6-dihydropyridazin-3-yl)phenyl]-4-hydroxy-5,5-dimethyl-4H,5H,6H-cyclopenta[b]thiophene-2-carboxamide;

N-[2-fluoro-5-(5-{[5-(1-methylpyrrolidin-2-yl)pyridin-2-yl]amino}-6-oxo-1,6-dihydropyridazin-3-yl)phenyl]-4-(propan-2-yl)benzamide;

N-{2-fluoro-5-[5-({5-methyl-4H,5H,6H,7H-pyrazolo[1,5-a]pyrazin-2-yl}amino)-6-oxo-1,6-dihydropyridazin-3-yl]phenyl}-4-methoxy-1-benzothiophene-2-carboxamide;

N-{2-fluoro-5-[5-({5-methyl-4H,5H,6H,7H-pyrazolo[1,5-a]pyrazin-2-yl})amino)-6-oxo-1,6-dihydropyridazin-3-yl]phenyl}-5,6,7,8-tetrahydronaphthalene-2-carboxamide;

N-[(3R)-1-(5-{[5-(azetidin-1-ylmethyl)-1-methyl-1,1-pyrazol-3-yl]amino}-1-methyl-6-oxo-1,6-dihydropyridazin-3-ylpiperidin-3-yl]4-benzothiophene-2-carboxamide;

N-{2-fluoro-5-[5-({5-methyl-4H,5H,6H,7H-pyrazolo[1,5-a]pyrazin-2-yl}amino)-6-oxo-1,6-dihydropyridazin-3-yl]phenyl}-4-(propan-2-yl)benzamide;

4-ethyl-N-[2-fluoro-5-(5-{[5-(1-methylpyrrolidin-2-yl)pyridin-2-yl]amino}-6-oxo-1,6-dihydropyridazin-3-yl)phenyl]benzamide;

N-{6-fluoro-2-methyl-3-[5-({5-methyl-4H,5H,6H,7H-pyrazolo[1,5-a]pyrazin-2-yl}amino)-6-oxo-1,6-dihydropyridazin-3-yl]phenyl}-1-benzothiophene-2-carboxamide;

N-[2-fluoro-5-(6-oxo-5-{4H,5H-6H,7H-pyrido[4,3-d][1,3]thiazol-2-ylamino}-1,6-dihydropyridazin-3-yl)phenyl]-1-benzothiophene-2-carboxamide;

4-tert-butyl-N-{2-fluoro-5-[5-({5-[(4-hydroxy-4-methylpiperidin-1-yl)methyl]pyridin-2-yl}amino)-1-methyl-6-oxo-1,6-dihydropyridazin-3-yl]phenyl}benzamide;

4-tert-butyl-N-[(3R)-1-(1-methyl-5-{[5-(morpholin-4-ylcarbonyl)pyridin-2-yl]amino}-6-oxo-1,6-dihydropyridazin-3-yl)piperidin-3-yl]benzamide;

5-hydroxy-N-{2-methyl-3-[5-({5-methyl-4H,5H,6H,7H-pyrazolo[1,5-a]pyrazin-2-yl}amino)-6-oxo-1,6-dihydropyridazin-3-yl]phenyl}-4,5,6,7-tetrahydro-1-benzothiophene-2-carboxamide;

N-{2-fluoro-5-[5-({5-[(2R)-1-methylpyrrolidin-2-yl]pyridin-2-yl}amino)-6-oxo-1,6-dihydropyridazin-3-yl]phenyl}-4-hydroxy-4,5,6,7-tetrahydro-1-benzothiophene-2-carboxamide;

N-{2-fluoro-5-[5-({5-[(2S)-1-methylpyrrolidin-2-yl]pyridin-2-yl}amino)-6-oxo-1,6-dihydropyridazin-3-yl]phenyl}-4-hydroxy-4,5,6,7-tetrahydro-1-benzothiophene-2-carboxamide;

N-{2,6-difluoro-3-[5-({5-methyl-4H,5H,6H,7H-pyrazolo[1,5-a]pyrazin-2-yl}amino)-6-oxo-1,6-dihydropyridazin-3-yl]phenyl}-1-benzothiophene-2-carboxamide;

N-{2-methyl-5-[5-({5-methyl-4H,5H,6H,7H-pyrazolo[1,5-a]pyrazin-2-yl}amino)-6-oxo-1,6-dihydropyridazin-3-yl]phenyl}-1-benzothiophene-2-carboxamide;

5-tert-butyl-N-{2-methyl-5-[5-({5-methyl-4H,5H,6H,7H-pyrazolo[1,5-a]pyrazin-2-yl}amino)-6-oxo-1,6-dihydropyridazin-3-yl]phenyl}pyrazine-2-carboxamide;

N-{2-fluoro-5-[5-({5-[(2R)-1-methylpyrrolidin-2-yl]pyridin-2-yl}amino)-6-oxo-L 6-dihydropyridazin-3-yl]phenyl}-5-hydroxy-4,5,6,7-tetrahydro-1-benzothiophene-2-carboxamide;

N-{2-fluoro-5-[5-({5-[(2S)-1-methylpyrrolidin-2-yl]pyridin-2-yl}amino)-6-oxo-1,6-dihydropyridazin-3-yl]phenyl}-5-hydroxy-4,5,6,7-tetrahydro-1-benzothiophene-2-carboxamide;

N-[2-fluoro-5-(6-oxo-5-{1H-pyrrolo[3,2-b]pyridin-5-ylamino}-1,6-dihydropyridazin-3-yl)phenyl]-1-benzothiophene-2-carboxamide;

4-tert-butyl-N-[(3R)-1-(5-{[5-(1,4-dimethyl-3-oxopiperazin-2-yl)pyridin-2-yl]amino}-1-methyl-6-oxo-1,6-dihydropyridazin-3-yl)piperidin-3-yl]benzamide;

N-{2,6-dimethyl-3-[5-({5-methyl-4H,5H,6H,7H-pyrazolo[1,5-a]pyrazin-2-yl}amino)-6-oxo-1,6-dihydropyridazin-3-yl]phenyl}-1-benzothiophene-2-carboxamide;

N-(2-fluoro-5-{5-[(5-{[(2-hydroxyethyl)amino]methyl}pyridin-2-yl)amino)-6-oxo-1,6-dihydropyridazin-3-yl]phenyl)-1-benzothiophene-2-carboxamide;

N-[2-fluoro-5-(5-{[5-(hydroxymethyl)pyridin-2-yl]amino}-6-oxo-1,6-dihydropyridazin-3-yl)phenyl]-1-benzothiophene-2-carboxamide;

N-(2-fluoro-5-{[(5-{[(2-fluoroethyl)amino]methyl}pyridin-2-yl)amino]-6-oxo-1,6-dihydropyridazin-3-yl}phenyl)-1-benzothiophene-2-carboxamide;

N-(2-fluoro-5-{6-oxo-5-[(5-{[(2,2,2-trifluoroethyl)amino]methyl}pyridin-2-yl)amino]-1,6-dihydropyridazin-3-yl}phenyl)-1-benzothiophene-2-carboxamide;

N-(2-fluoro-5-{5-[(5-[(3S)-3-hydroxypyrrolidin-1-yl]methyl)pyridin-2-yl)amino]-6-oxo-1,6-dihydropyridazin-3-yl}phenyl)-1-benzothiophene-2-carboxamide;

N-[3-fluoro-6-(5-{[5-(4-methylpiperazin-1-yl)pyridin-2-yl]amino}-6-oxo-1,6-dihydropyridazin-3-yl)pyridin-2-yl]-4,5,6,7-tetrahydro-1-benzothiophene-2-carboxamide;

N-[2-fluoro-5-(6-oxo-5-{4H,5H,6H,7H-pyrazolo[1,5-a]pyrazin-2-ylamino}-1,6-dihydropyridazin-3-yl)phenyl]-4-hydroxy-4H,5H,6H-cyclopenta[b]thiophene-2-carboxamide;

4-tert-butyl-N-[4-methyl-2-(5-{[5-(1-methylpyrrolidin-2-yl)pyridin-2-yl]amino}-6-oxo-1,6-dihydropyridazin-3-yl)-1,3-thiazol-5-yl]benzamide;

N-(5-{5-[(5-{[2-(azetidin-1-yl)ethyl](methyl)amino}pyridin-2-yl)amino]-6-oxo-1,6-dihydropyridazin-3-yl}-2-fluorophenyl)-1-benzothiophene-2-carboxamide;

N-{5-[5-({5-cyclopropyl-4H,5H,6H,7H-pyrazolo[1,5-a]pyrazin-2-yl}amino)-6-m 1,6-dihydropyridazin-3-yl]-2-fluorophenyl}-1-benzothiophene-2-carboxamide;

N-[(3R)-1-[1-methyl-5-({5-methyl-4H,5H,6H,7H-pyrazolo[1,5-a]pyrazin-2-yl}amino)-6-oxo-1,6-dihydropyridazin-3-yl]piperidin-3-yl]-4,5,6,7-tetrahydro-1-benzothiophene-2-carboxamide;

4-tert-butyl-N-[(3R)-1-[5-({5-methyl-4H,5H,6H,7H-pyrazolo[1,5-a]pyrazin-2-yl}amino)-6-oxo-1,6-dihydropyridazin-3-yl]piperidin-3-yl]benzamide;

4-tert-butyl-N-[(3R)-1-[1-methyl-5-({5-methyl-4H,5H,6H,7H-pyrazolo[1,5-a]pyrazin-2-yl}amino)-6-oxo-1,6-dihydropyridazin-3-yl]pyrrolidin-3-yl]benzamide;

4-tert-butyl-N-{2-fluoro-5-[5-({5-[(methylamino)methyl]pyridin-2-yl}amino)-6-oxo-1,6-dihydropyridazin-3-yl]phenyl}benzamide;

N-[(3R)-1-[1-methyl-5-(5-methyl-4H,5H,6H,7H-pyrazolo[1,5-a]pyrazin-2-yl)amino)-6-oxo-1,6-dihydropyridazin-3-yl]piperidin-3-yl]-1-benzothiophene-2-carboxamide;

N-[(3R)-1-[1-methyl-5-({5-methyl-4H,5H,6H,7H-pyrazolo[1,5-a]pyrazin-2-yl}amino)-6-oxo-1,6-dihydropyridazin-3-yl]piperidin-3-yl]-4,5,6,7-tetrahydro-1H-indole-2-carboxamide;

N-[2-fluoro-5-(6-oxo-5-{4H,5H,6H,7H-pyrazolo[1,5-a]pyrazin-2-ylamino}-1,6-dihydropyridazin-3-yl)phenyl]-4-hydroxy-4,5,6,7-tetrahydro-1-benzothiophene-2-carboxamide;

N-[2-fluoro-5-(5-{[5-(2-hydroxyethyl)-4H,5H,6H,7H-pyrazolo[1,5-a]pyrazin-2-yl]amino}-6-oxo-1,6-dihydropyridazin-3-yl)phenyl]-1-benzothiophene-2-carboxamide;

N-{2-fluoro-5-[5-({5-methyl-4H,5H,6H,7H-pyrazolo[1,5-a]pyrazin-2-yl}amino)-6-oxo-1,6-dihydropyridazin-3-yl]phenyl}-4-(1-methoxy-2-methylpropan-2-yl)benzamide;

N-[2-fluoro-5-(5-{[5-(hydroxymethyl)-1-methyl-1H-pyrazol-3-yl]amino}-6-oxo-1,6-dihydropyridazin-3-yl)phenyl]-1-benzothiophene-2-carboxamide;

4-tert-butyl-N-[6-(5-{[5-(4-methylpiperazin-1-yl)pyridin-2-yl]amino}-6-oxo-1,6-dihydropyridazin-3-yl)pyridin-2-yl]benzamide;

(1S,7R)—N-[(3R)-1-(1-methyl-5-{[5-(morpholin-4-ylcarbonyl)pyridin-2-yl]amino}-6-oxo-1,6-dihydropyridazin-3-yl)piperidin-3-yl]-3-thiatricyclo[5.2.1.0ˆ{2,6}]deca-2(6),4-diene-4-carboxamide;

5-tert-butyl-N-[(3R)-1-[1-methyl-5-({5-methyl-4H,5H,6H,7H-pyrazolo[1,5-a]pyrazin-2-yl}amino)-6-oxo-1,6-dihydropyridazin-3-yl]piperidin-3-yl]pyrazine-2-carboxamide;

N-{3-[5-({5-cyclopropyl-4H,5H,6H,7H-pyrazolo[1,5-a]pyrazin-2-yl}amino)-6-oxo-1,6-dihydropyridazin-3-yl]-6-fluoro-2-methylphenyl}-1-benzothiophene-2-carboxamide;

4-tert-butyl-N-[(3R)-1-(5-{[5-(hydroxymethyl)pyridin-2-yl]amino}-1-methyl-6-oxo-1,6-dihydropyridazin-3-yl)piperidin-3-yl]benzamide;

N-[3-(5-{[5-(azetidin-1-ylmethyl)-1-methyl-1H-pyrazol-3-yl]amino}-6-oxo-1,6-dihydropyridazin-3-yl)-2-fluoro-6-methylphenyl]-1-benzothiophene-2-carboxamide;

N-{2-fluoro-5-[5-({5-methyl-4H,5H,6H,7H-pyrazolo[1,5-a]pyrazin-2-yl}amino)-6-oxo-1,6-dihydropyridazin-3-yl]phenyl}-4-(trifluoromethyl)benzamide;

N-[2-fluoro-5-(5-{[5-(1-methylazetidin-3-yl)pyridin-2-yl]amino}-6-oxo-1,6-dihydropyridazin-3-yl)phenyl]-1-benzothiophene-2-carboxamide;

N-[5-(5-{[5-(azetidin-3-yl)pyridin-2-yl]amino}-6-oxo-1,6-dihydropyridazin-3-yl)-2-fluorophenyl]-4-tert-butylbenzamide;

N-[2-fluoro-5-(6-oxo-5-[5-(2-oxopiperazin-1-yl)pyridin-2-yl]amino)-1,6-dihydropyridazin-3-yl)phenyl]-1-benzothiophene-2-carboxamide;

N-[5-(5-{[5-(azetidin-3-yl)pyridin-2-yl]amino}-6-oxo-1,6-dihydropyridazin-3-yl)-2-fluorophenyl]-1-benzothiophene-2-carboxamide;

5-text-butyl-N-{2,6-dimethyl-3-[5-({5-methyl-4H,5H,6H,7H-pyrazolo[1,5-a]pyrazin-2-yl}amino)-6-oxo-1,6-dihydropyridazin-3-yl]phenyl}pyrazine-2-carboxamide;

4-tert-butyl-N-[(3R)-1-(6-oxo-5-{[5-(pyrrolidin-1-ylmethyl)pyridin-2-yl]amino}-1,6-dihydropyridazin-3-yl)piperidin-3-yl]benzamide;

N-[5-(5-{[5-(azetidin-1-ylmethyl)-1-methyl-1H-pyrazol-3-yl]amino}-6-oxo-1,6-dihydropyridazin-3-yl)-2-fluorophenyl]-4-(2-hydroxypropan-2-yl)benzamide;

4-tert-butyl-N-[2-fluoro-5-(5-{[5-(1-methylazetidin-3-yl)pyridin-2-yl]amino}-6-oxo-1,6-dihydropyridazin-3-yl)phenyl]benzamide;

N-[2-fluoro-5-(1-methyl-6-oxo-5-{[5-(2-oxopiperazin-1-yl)pyridin-2-yl]amino}-1,6-dihydropyridazin-3-yl)phenyl]-1-benzothiophene-2-carboxamide;

N-{2-fluoro-5-[5-({5-methyl-4H,5H,6H,7H-pyrazolo[1,5-a]pyrazin-2-yl}amino)-6-oxo-1,6-dihydropyridazin-3-yl]phenyl}indolizine-2-carboxamide;

N-[3-(5-{[5-(azetidin-1-ylmethyl)-1-methyl-1H-pyrazol-3-yl]amino}-1-methyl-6-oxo-1,6-dihydropyridazin-3-yl)-2-fluoro-6-methylphenyl]-1-benzothiophene-2-carboxamide;

N-[(3R)-1-[1-methyl-5-({5-methyl-4H,5H,6H,7H-pyrazolo[1,5-a]pyrazin-2-yl}amino)-6-oxo-1,6-dihydropyridazin-3-yl]piperidin-3-yl]-5,6,7,8-tetrahydroindolizine-2-carboxamide;

N-{2-fluoro-5-[5-({5-methyl-4H,5H,6H,7H-pyrazolo[1,5-a]pyrazin-2-yl}amino)-6-oxo-1,6-dihydropyridazin-3-yl]phenyl}-3,3-dimethyl-2,3-dihydro-1-benzofuran-6-carboxamide;

4-tert-butyl-N-[(3R)-1-(1-methyl-5-{[5-(morpholin-4-ylcarbonyl)pyridin-2-yl]amino}-6-oxo-1,6-dihydropyridazin-3-yl)piperidin-3-yl]cyclohexane-1-carboxamide;

N-[3-(5-{[5-(1,4-dimethyl-3-oxopiperazin-2-yl)pyridin-2-yl]amino}-1-methyl-6-oxo-1,6-dihydropyridazin-3-yl)-2-fluoro-6-methylphenyl]-4,5,6,7-tetrahydro-1-benzothiophene-2-carboxamide;

4-(1-hydroxy-2-methylpropan-2-yl)-N-[(3R)-1-[1-methyl-5-({5-methyl-4H,5H,6H,7H-pyrazolo[1,5-a]pyrazin-2-yl}amino)-6-oxo-1,6-dihydropyridazin-3-yl]piperidin-3-yl]benzamide;

N-[(3R)-1-[1-methyl-5-({5-methyl-4H,5H,6H,7H-pyrazolo[1,5-a]pyrazin-2-yl}amino)-6-oxo-1,6-dihydropyridazin-3-yl]piperidin-3-yl]-4-(1 methylcyclopropyl)benzamide;

N-[2-fluoro-6-methyl-3-(5-{[5-(4-methylpiperazin-1-yl)pyridin-2-yl]amino}-6-oxo-1,6-dihydropyridazin-3-yl)phenyl]-4-(1-hydroxy-2-methylpropan-2-yl)benzamide;

N-5-(5-{[5-(azetidin-1-ylmethyl)-1-methyl-1H-pyrazol-3-yl amino}-6-oxo-1,6-dihydropyridazin-3-yl)-2-fluorophenyl]-4-(1-hydroxy-2-methylpropan-2-yl)benzamide;

N-[5-(5-{[5-(azetidin-1-ylmethyl)-1-methyl-1H-pyrazol-3-yl]amino}-1-methyl-6-oxo-1,6-dihydropyridazin-3-yl)-2-fluorophenyl]-5,6,7,8-tetrahydroindolizine-2-carboxamide;

N-{6-fluoro-2-methyl-3-[1-methyl-5-({5-methyl-4H,5H,6H,7H-pyrazolo[1,5-a]pyrazin-2-yl}amino)-6-oxo-1,6-dihydropyridazin-3-yl]phenyl}-1-benzothiophene-2-carboxamide;

N-[5-(5-{[5-(azetidin-1-ylmethyl)-1-methyl-1H-pyrazol-3-yl]amino}-6-oxo-1,6-dihydropyridazin-3-yl)-2-methylphenyl]-5-tert-butylpyrazine-2-carboxamide;

N-[5-(5-{[5-(azetidin-1-ylmethyl)-1-ethyl-1H-pyrazol-3-yl]amino}-6-oxo-1,6-dihydropyridazin-3-yl)-2-fluorophenyl]-1-benzothiophene-2-carboxamide;

N-[(3R)-1-[5-({5-[(2-hydroxyethyl)(methyl)amino]pyridin-2-yl}amino)-1-methyl-6-oxo-1,6-dihydropyridazin-3-yl]piperidin-3-yl]-1-benzothiophene-2-carboxamide;

N-[(3R)-1-{5-[({[2-(dimethylamino)ethyl](methyl)amino}pyridin-2-yl)amino]-1-methyl-6-oxo-1,6-dihydropyridazin-3-yl}piperidin-3-yl]-1-benzothiophene-2-carboxamide;

N-[6-fluoro-2-methyl-3-(5-{[1-methyl-5-(morpholin-4-ylmethyl)-1H-pyrazol-3-yl]amino}-6-oxo-1,6-dihydropyridazin-3-yl)phenyl]-1-benzothiophene-2-carboxamide;

N-[5-(5-{[5-(azetidin-1-yl r ethyl)-1-methyl-1H-pyrazol-3-yl]amino}-1-methyl-6-oxo-1,6-dihydropyridazin-3-yl)-2-fluorophenyl]-4-(1-hydroxy-2-methylpropan-2-yl)benzamide;

N-[3-(5-{[5-(azetidin-1-ylmethyl)-1-methyl-1H-pyrazol-3-yl]amino}-1-methyl-6-oxo-1,6-dihydropyridazin-3-yl)-2-fluoro-6-methylphenyl]-4-(1-hydroxy-2-methylpropan-2-yl)benzamide;

N-[2-fluoro-5-(6-oxo-5-{[5-(2-oxopiperazin-1-yl)pyridin-2-yl]amino}-1,6-dihydropyridazin-3-yl)phenyl]-4-(1-hydroxy-2-methylpropan-2-yl)benzamide;

N-[5-(5-{[5-(azetidin-1-ylmethyl)-1-methyl-1H-pyrazol-3-yl]amino}-6-oxo-1,6-dihydropyridazin-3-yl)-2-fluorophenyl]-5,6,7,8-tetrahydroindolizine-2-carboxamide;

5-tert-butyl-N-{2-fluoro-5-[5-({5-methyl-4H,5H,6H,7H-pyrazolo[1,5-a]pyrazin-2-yl}amino)-6-oxo-1,6-dihydropyridazin-3-yl]phenyl}-1,3-thiazole-2-carboxamide;

N-[(3R)-1-(5-{[5-(1,4-dimethyl-3-oxopiperazin-2-yl)pyridin-2-yl]amino}-1-methyl-6-oxo-1,6-dihydropyridazin-3-yl)piperidin-3-yl]-4,5,6,7-tetrahydro-1-benzothiophene-2-carboxamide;

N-{3-[5-({5-[(3,3-difluoroazetidin-1-yl)methyl]-1-methyl-1H-pyrazol-3-yl}amino)-6-oxo-1,6-dihydropyridazin-3-yl]-6-fluoro-2-methylphenyl}-1-benzothiophene-2-carboxamide;

{2-fluoro-6-methyl-3-[5-({5-methyl-4H,5H,6H,7H-pyrazolo[1,5-a]pyrazin-2-yl}amino)-6-oxo-1,6-dihydropyridazin-3-yl]phenyl}-1-benzothiophene-2-carboxamide;

N-[6-fluoro-2-methyl-3-(1-methyl-5-{[5-(1-methylpiperidin-4-yl)pyridin-2-yl]amino}-6-oxo-1,6-dihydropyridazin-3-yl)phenyl]-1-benzothiophene-2-carboxamide;

N-{[5-({5-[(3,3-difluoroazetidin-1-yl)methyl]pyridin-2-yl}amino)-6-oxo-1,6-dihydropyridazin-3-yl}-2-fluorophenyl}-1-benzothiophene-2-carboxamide;

N-[6-fluoro-3-(5-{[5-(2-hydroxyethyl)-4H,5H,6H,7H-pyrazolo[1,5-a]pyrazin-2-yl]amino}-6-oxo-1,6-dihydropyridazin-3-yl)-2-methylphenyl]-1-benzothiophene-2-carboxamide;

N-{3-[5-({6-[(dimethylamino)methyl]pyridazin-3-yl}amino)-1-methyl-6-oxo-1,6-dihydropyridazin-3-yl]-6-fluoro-2-methylphenyl}-1-benzothiophene-2-carboxamide;

N-[3-(5-{[5-(1,4-dimethyl-3-oxopiperazin-2-yl)pyridin-2-yl]amino}-1-methyl-6-oxo-1,6-dihydropyridazin-3-yl)-2-fluoro-6-methylphenyl]-1-benzothiophene-2-carboxamide;

N-(5-{5-[(5-{[2-(dimethylamino)ethyl](methyl)amino}pyridin-2-yl)amino]-1-methyl-6-oxo-1,6-dihydropyridazin-3-yl}-2-fluorophenyl)-1-benzothiophene-2-carboxamide;

4-tert-butyl-N-{1-[1-methyl-5-({5-methyl-4H,5H,6H,7H-pyrazolo[1,5-a]pyrazin-2-yl}amino)-6-oxo-1,6-dihydropyridazin-3-yl]azepan-3-yl}benzamide;

N-[5-(5-{[5-(azetidin-1-ylmethyl)-1-methyl-1H-pyrazol-3-yl]amino}-1-methyl-6-oxo-1,6-dihydropyridazin-3-yl)-2-fluorophenyl]-4-hydroxy-5,5-dimethyl-4H,5H,6H-cyclopenta[b]thiophene-2-carboxamide;

N-[2-fluoro-5-(1-methyl-6-oxo-5-{4H,5H,6H,7H-pyrazolo[1,5-a]pyrazin-2-ylamino}-1,6-dihydropyridazin-3-yl)phenyl]-5,6,7,8-tetrahydroindolizine-2-carboxamide;

N-{3-[5-({5-[(2S)-1,4-dimethyl-3-oxopiperazin-2-yl]pyridin-2-yl}amino)-1-methyl-6-oxo-1,6-dihydropyridazin-3-yl]-2-fluoro-6-methylphenyl}-4,5,6,7-tetrahydro-1-benzothiophene-2-carboxamide;

N-{3-[5-({5-[(2R)-1,4-dimethyl-3-oxopiperazin-2-yl]pyridin-2-yl}amino)-1-methyl-6-oxo-1,6-dihydropyridazin-3-yl]-2-fluoro-6-methylphenyl}-4,5,6,7-tetrahydro-1-benzothiophene-2-carboxamide;

5-tert-butyl-N-{2-methyl-5-[1-methyl-6-oxo-5-(5,6,7,8-tetrahydro-1,6-naphthyridin-2-ylamino)-1,6-dihydropyridazin-3-yl]phenyl}pyrazine-2-carboxamide;

N-[2-fluoro-5-(6-oxo-5-{4H,5H,6H,7H-pyrazolo[1,5-a]pyrazin-2-ylamino}-1,6-dihydropyridazin-3-yl)phenyl]-5,6,7,8-tetrahydroindolizine-2-carboxamide;

N-[2-chloro-6-methyl-3-(5-{[5-(4-methylpiperazin-1-yl)pyridin-2-yl]amino}-6-oxo-1,6-dihydropyridazin-3-yl)phenyl]-1-benzothiophene-2-carboxamide;

N-(6-fluoro-3-{5-[(5-[(3S)-3-hydroxypyrrolidin-1-yl]methyl}-1-methyl-1,1-pyrazol-3-yl)amino]-6-oxo-1,6-dihydropyridazin-3-yl}-2-methylphenyl)-1-benzothiophene-2-carboxamide;

N-[2-chloro-3-(5-[(5-(1,4-dimethyl-3-oxopiperazin-2-yl)pyridin-2-yl]amino)-6-oxo 1,6-dihydropyridazin-3-yl]-6-methylphenyl]-1-benzothiophene-2-carboxamide;

N-{2-fluoro-5-[5-({5-[(3-hydroxyazetidine-1-yl)methyl]-1-methyl-1,1-pyrazol-3-yl}amino)-6-oxo-1,6-dihydropyridazin-3-yl]phenyl}-1-benzothiophene-2-carboxamide;

N-[(3R)-1-[5-({5-[(2S)-1,4-dimethyl-3-oxopiperazin-2-yl]pyridin-2-yl}amino)-1-methyl-6-oxo-1,6-dihydropyridazin-3-yl]piperidin-3-yl]-4,5,6,7-tetrahydro-1-benzothiophene-2-carboxamide;

N-[(3R)-1-[5-({5-[(2R)-1,4-dimethyl-3-oxopiperazin-2-yl]pyridin-2-yl}amino)-1-methyl-6-oxo-1,6-dihydropyridazin-3-yl]piperidin-3-yl]-4,5,6,7-tetrahydro-1-benzothiophene-2-carboxamide;

N-[6-fluoro-3-(5-{[5-(2-hydroxypropan-2-yl)-1-methyl-1H-pyrazol-3-yl]amino}-1-methyl-6-oxo-1,6-dihydropyridazin-3-yl)-2-methylphenyl]-1-benzothiophene-2-carboxamide;

N-{6-fluoro-2-methyl-3-[1-methyl-5-({5-[4-(methylamino)piperidin-1-yl]pyridin-2-yl}amino)-6-oxo-1,6-dihydropyridazin-3-yl]phenyl}-1-benzothiophene-2-carboxamide;

N-{6-fluoro-3-{[5-[(4-hydroxy-4-methylpiperidin-1-yl)methyl]-1-methyl-1H-pyrazol-3-yl}amino)-6-oxo-1,6-dihydropyridazin-3-yl]-2-methylphenyl}-1-benzothiophene-2-carboxamide;

N-(3-{5-[(1,5-dimethyl-1H-pyrazol-3-yl)amino]-6-oxo-1,6-dihydropyridazin-3-yl}-2-methylphenyl)-5,5-dimethyl-4H,5H-6H-cyclopenta[b]thiophene-2-carboxamide;

N-{5-[5-({5-acetyl-4H,5H,6H,7H-pyrazolo[1,5-a]pyrazin-2-yl}amino)-6-oxo-1,6-dihydropyridazin-3-yl]-2-fluorophenyl}-1-benzothiophene-2-carboxamide;

N-(2-fluoro-5-{5-[(5-{[(2-hydroxyethyl)(methyl)amino]methyl}-1-methyl-1H-pyrazol-3-yl)amino]-6-oxo-1,6-dihydropyridazin-3-yl}phenyl)-1-benzothiophene-2-carboxamide;

N-{3-[5-({5-[(2R)-1,4-dimethyl-3-oxopiperazin-2-yl]pyridin-2-yl}amino)-1-methyl-6-oxo-1,6-dihydropyridazin-3-yl]-2-fluoro-6-methylphenyl}-1-benzothiophene-2-carboxamide;

N-{3-[5-({5-[(2S)-1,4-dimethyl-3-oxopiperazin-2-yl]pyridin-2-yl}amino)-1-methyl-6-oxo-1,6-dihydropyridazin-3-yl]-2-fluoro-6-methylphenyl}-1-benzothiophene-2-carboxamide;

N-{6-fluoro-3-[5-({5-[(3-hydroxyazetidine-1-yl)methyl]-1-methyl-1H-pyrazol-3-yl}amino)-6-oxo-1,6-dihydropyridazin-3-yl]-2-methylphenyl}-1-benzothiophene-2-carboxamide;

N-{3-fluoro-6-[1-methyl-5-({5-methyl-4H,5H,6H,7H-pyrazolo[1,5-a]pyrazin-2-yl}amino)-6-oxo-1,6-dihydropyridazin-3-yl]pyridin-2-yl]-4,5,6,7-tetrahydro-1-benzothiophene-2-carboxamide;

4-[ethyl(methyl)amino]-N-[(3R)-1-(1-methyl-5-{[5-(morpholin-4-ylcarbonyl)pyridin-2-yl]amino}-6-oxo-1,6-dihydropyridazin-3-yl)piperidin-3-yl]benzamide;

N-{3-[5-({5-[(3,3-difluoroazetidin-1-yl)methyl]-1-methyl-1H-pyrazol-3-yl}amino)-6-oxo-1,6-dihydropyridazin-3-yl]-2-fluoro-6-methylphenyl}-1-benzothiophene-2-carboxamide;

(4S)—N-[5-(5-{[5-(azetidin-1-ylmethyl)-1-methyl-1H-pyrazol-3-yl]amino}-1-methyl-6-oxo-1,6-dihydropyridazin-3-yl)-2-fluorophenyl]-4-hydroxy 5,5-dimethyl 4H,5H,6H-cyclopenta[b]thiophene-2-e arboxamide;

(4R)—N-[5-(5-{[5-(azetidin-1-ylmethyl)-1-methyl-1H-pyrazol-3-yl]amino}-1-methyl-6-oxo-1,6-dihydropyridazin-3-yl)-2-fluorophenyl]-4-hydroxy-5,5-dimethyl-4H,5H,6H-cyclopenta[b]thiophene-2-carboxamide;

N-[2-fluoro-6-methyl-3-(1-methyl-6-oxo-5-{[5-(2-oxopiperazin-1-yl)pyridin-2-yl]amino}-1,6-dihydropyridazin-3-yl)phenyl]-1-benzothiophene-2-carboxamide;

N-[6-fluoro-3-(5-{[5-(3-hydroxyazetidine-1-yl)pyridin-2-yl]amino}-1-methyl-6-oxo-1,6-dihydropyridazin-3-yl)-2-methylphenyl]-1-benzothiophene-2-carboxamide;

N-{5-[5-({5-[(dimethylamino)methyl]-1,2-oxazol-3-yl}amino)-1-methyl-6-oxo-1,6-dihydropyridazin-3-yl]-2-fluorophenyl}-1-benzothiophene-2-carboxamide;

N-[3-(5-{[5-(aminomethyl)-1-methyl-1H-pyrazol-3-yl]amino}-6-oxo-1,6-dihydropyridazin-3-yl)-6-fluoro-2-methylphenyl]-1-benzothiophene-2-carboxamide;

N-[(3R)-1-[5-({5-[2-aminoethyl)(methyl)amino]pyridin-2-yl}amino)-1-methyl-6-oxo-1,6-dihydropyridazin-3-yl]piperidin-3-yl]-4-tert-butylbenzamide;

5-tert-butyl-N-(2-methyl-5-{1-methyl-5-[(6-methyl-5,6,7,8-tetrahydro-1,6-naphthyridin-2-yl)amino]-6-oxo-1,6-dihydropyridazin-3-yl}phenyl)pyrazine-2-carboxamide;

N-[2-fluoro-5-(5-{[5-(1-hydroxyethyl)pyridin-2-yl]amino}-6-oxo-1,6-dihydropyridazin-3-yl)phenyl]-1-benzothiophene-2-carboxamide;

N-[6-fluoro-3-(5-{[5-(3-hydroxyazetidine-1-yl)pyridin-2-yl]amino}-1-methyl-6-oxo-1,6-dihydropyridazin-3-yl)-2-methylphenyl]-1-benzothiophene-2-carboxamide;

N-{5-[5-({5-[(dimethylamino)methyl]-1,2-oxazol-3-yl}amino)-6-oxo-1,6-dihydropyridazin-3-yl]-2-fluorophenyl}-1-benzothiophene-2-carboxamide;

N-(3-{5-[(1,5-dimethyl-1H-pyrazol-3-yl)amino]-6-oxo-1,6-dihydropyridazin-3-yl}-2-methylphenyl)-4-hydroxy-4H,5H,6H-cyclopenta[b]thiophene-2-carboxamide;

N-[5-(5-{[1-(azetidin-3-yl)-1H-pyrazol-3-yl]amino}-6-oxo-1,6-dihydropyridazin-3-yl)-2-fluorophenyl]-1-benzothiophene-2-carboxamide;

N-{2-methyl-5-[6-oxo-5-(pyrimidin-4-ylamino)-1,6-dihydropyridazin-3-yl]phenyl}-1-benzothiophene-2-carboxamide;

N-[3-(5-{[5-(3,3-difluoropyrrolidin-1-yl)pyridin-2-yl]amino}6 oxo 1,6 dihydropyridazin-3-yl)-2-fluoro-6-methylphenyl]-1-benzothiophene-2-carboxamide;

N-(5-{5-[(1,5-dimethyl-1H-pyrazol-3-yl)amino]-6-oxo-1,6-dihydropyridazin-3-yl}-2-fluorophenyl)-4-hydroxy-4H,5H,6H-cyclopenta[b]thiophene-2-carboxamide;

4-hydroxy-N-{2-methyl-3-[6-oxo-5-(pyrimidin-4-ylamino)-1,6-dihydropyridazin-3-yl]phenyl}-4H,5H,6H-cyclopenta[b]thiophene-2-carboxamide;

4-tert-butyl-N-{5-[5-({5-[(dimethylcarbamoyl)(hydroxy)methyl]pyridin-2-yl}amino)-1-methyl-6-oxo-1,6-dihydropyridazin-3-yl]-2-fluorophenyl}benzamide;

N-[3-(5-{[5-(3,3-difluoropyrrolidin-1-yl)pyridin-2-yl]amino}-1-methyl-6-oxo-1,6-dihydropyridazin-3-yl)-2-fluoro-6-methylphenyl]-1-benzothiophene-2-carboxamide;

4-tert-butyl-N-{5-[5-({5-[(dimethylcarbamoyl)carbonyl]pyridin-2-yl}amino)-1-methyl-6-oxo-1,6-dihydropyridazin-3-yl]-2-fluorophenyl}benzamide;

N-[6-fluoro-2-methyl-3-(6-oxo-5-{-4H,5H,6H,7H-pyrazolo[1,5-a]pyrazin-2-ylamino}-hydropyridazin-3-yl)phenyl]-benzothiophene-2-carboxamide;

N-[5-(5-{[5-(aminomethyl)-1-methyl-1H-pyrazol-3-yl]amino}-6-oxo-1,6-dihydropyridazin-3-yl)-2-methylphenyl]indolizine-2-carboxamide;

5-tert-butyl-N-{2,6-dimethyl-3-[6-oxo-5-(pyrimidin-4-ylamino)-1,6-dihydropyridazin-3-yl]phenyl}pyrazine-2-carboxamide;

N-[(3R)-1-(5-{[1-(azetidin-3-yl)-1H-pyrazol-3-yl]-amino}-1-methyl-6-oxo-1,6-dihydropyridazin-3-yl)piperidin-3-yl]-4-tert-butylbenzamide;

N-{6-fluoro-2-methyl-3-[5-({5-methyl-4H,5H,6H,7H-pyrido[4,3-d][1,3]thiazol-2-yl}amino)-6-oxo-1,6-dihydropyridazin-3-yl]phenyl}-1-benzothiophene-2-carboxamide;

N-[3-(5-{[5-(aminomethyl)piperidin-2-yl]amino}-6-oxo-1,6-dihydropyridazin-3-yl)-6-fluoro-2-methylphenyl]-1-benzothiophene-2-carboxamide;

N{6-fluoro-2-methyl-3-[5-({5-methyl-5-oxo-4H,5H,6H,7H-pyrazolo[1,5-a]pyrazin-2-yl}amino)-6-oxo-1,6-dihydropyridazin-3-yl]phenyl}-1-benzothiophene-2-carboxamide;

4-tert-butyl-N-[(3R)-1-(1-methyl-6-oxo-5-{[1-(piperidin-4-yl)-1H-pyrazol-3-yl]amino}-1,6-dihydropyridazin-3-yl)piperidin-3-yl]benzamide;

N-(3-{5-[(1,5-dimethyl-1H-pyrazol-3-yl)amino]-6-oxo-1,6-dihydropyridazin-3-yl}-2-fluoro-6-methylphenyl)-4-hydroxy-5,5-dimethyl-4H,5H,6H-cyclopenta [b]thiophene-2-carboxamide;

N-{6-fluoro-2-methyl-3-[5-({5-methyl-4H,5H,6H,7H-pyrazolo[1,5-a]pyrazin-2-yl}amino)-6-oxo-1,6-dihydropyridazin-3-yl]phenyl}-4-hydroxy-5,5-dimethyl-4H,5H,6H-cyclopenta[b]thiophene-2-carboxamide;

3-(tert-butoxy)-N-[2-methyl-3-(1-methyl-5-{[5-(morpholin-4-ylcarbonyl)pyridin-2-yl]amino}-6-oxo-1,6-dihydropyridazin-3-yl)phenyl]azetidine-1-carboxamide;

4-tert-butyl-N-{5-[5-({5-[(S)-(dimethylcarbamoyl)(hydroxy)methyl]pyridin-2-yl}amino)-1-methyl-6-oxo-1,6-dihydropyridazin-3-yl]-2-fluorophenyl}benzamide;

4-tert-butyl-N-{5-[5-({5-[(R)-(dimethylcarbamoyl)(hydroxy)methyl]pyridin-2-yl}amino)-1-methyl-6-oxo-1,6-dihydropyridazin-3-yl]-2-fluorophenyl}benzamide;

3-(tert-butoxy)-N-[(3R)-1-(1-methyl-5-{[5-(morpholin-4-ylcarbonyl)pyridin-2-yl]amino}-6-oxo-1,6-dihydropyridazin-3-yl)piperidin-3-yl]azetidine-1-carboxamide;

N-[6-fluoro-3-(5-{[5-(3-fluoropropyl)-4H,5H,6H,7H-pyrazolo[1,5-a]pyrazin-2-yl]amino}-6-oxo-1,6-dihydropyridazin-3-yl)-2-methylphenyl]-1-benzothiophene-2-carboxamide;

N-{3-methyl-6-[5-({5-methyl-4H,5H,6H,7H-pyrazolo[1,5-a]pyrazin-2-yl]amino}-6-oxo-1,6-dihydropyridazin-3-yl)pyridin-2-yl}-1-benzothiophene-2-carboxamide;

N-{2-fluoro-5-[5-({5-[(3-hydroxyazetidine-1-yl)methyl]-1-methyl-1H-pyrazol-3-yl}amino)-1-methyl-6-oxo-1,6-dihydropyridazin-3-yl]phenyl}-1-benzothiophene-2-carboxamide;

N-[2-methyl-3-(1-methyl-5-[5-(morpholin-4-ylcarbonyl)pyridin-2-yl]amino)-6-oxo-1,6-dihydropyridazin-3-yl)phenyl]-2,3-dihydro-1H-isoindole-2-carboxamide;

4-tert-butyl-N-[(3R)-1-(6-oxo-5-{[5-(pyrrolidin-2-yl)pyridin-2-yl]amino}-1,6-dihydropyridazin-3-yl)piperidin-3-yl]benzamide;

N-[2-fluoro-5-(5-{[5-(2-hydroxypropan-2-yl)-1-methyl-1H-pyrazol-3-yl]amino}-6-oxo-1,6-dihydropyridazin-3-yl)phenyl]-1-benzothiophene-2-carboxamide;

N-[2-fluoro-3-(5-[5-(3-hydroxyazetidine-1-yl)pyridin-2-yl]amino)-1-methyl-6-oxo-1,6-dihydropyridazin-3-yl)-6-methylphenyl]-4-hydroxy-5,5-dimethyl-4H,5H,6H-cyclopenta[b]thiophene-2-carboxamide;

N-{6-fluoro-2-methyl-3-[5-({5-methyl-4H,5H,6H,7H-pyrazolo[1,5-a]pyrazin-2-yl}amino)-6-oxo-1,6-dihydropyridazin-3-yl]phenyl}-4,5,6,7-tetrahydro-1-benzothiophene-2-carboxamide;

(4S)—N-(3-{5-[(1,5-dimethyl-1H-pyrazol-3-yl)amino]-6-oxo-1,6-dihydropyridazin-3-yl}-2-fluoro-6-methylphenyl)-4-hydroxy-5,5-dimethyl-4H,5H,6H-cyclopenta[b]thiophene-2-carboxamide;

(4R)—N-(3-{5-[(1,5-dimethyl-1H-pyrazol-3-yl)amino]-6-oxo-1,6-dihydropyridazin-3-yl}-2-fluoro-6-methylphenyl)-4-hydroxy-5,5-dimethyl-4H,5H,6H-cyclopenta[b]thiophene-2-carboxamide;

(4S)—N-6-fluoro-2-methyl-3-[5-({-(5-methyl-4H,5H,6H,7H-pyrazolo[1,5-a]pyrazin-2-yl)amino)-6-oxo-1,6-dihydropyridazin-3-yl]phenyl}-4-hydroxy-5,5-dimethyl-4H,5H,6H-cyclopenta[b]thiophene-2-carboxamide;

(4R)—N-{6-fluoro-2-methyl-3-[5-({5-methyl-4H,5H,6H,7H-pyrazolo[1,5-a]pyrazin-2-yl}amino)-6-oxo-1,6-dihydropyridazin-3-yl]phenyl}-4-hydroxy-5,5-dimethyl-4H,5H,6H-cyclopenta[b]thiophene-2-carbonamide;

N-[2-fluoro-5-(5-{[5-(3-hydroxy-3-methylpyrrolidin-1-yl)pyridin-2-yl]amino}-6-oxo-1,6-dihydropyridazin-3-yl)phenyl]-1-benzothiophene-2-carboxamide;

5-tert-butyl-N-{6-fluoro-2-methyl-3-[5-({5-methyl-4H,5H,6H,7H-pyrazolo[1,5-a]-pyrazin-2-yl}amino)-6-oxo-1,6-dihydropyridazin-3-yl]phenyl}pyrazine-2-carboxamide;

4-tert-butyl-N-{6-fluoro-2-methyl-3-[5-({5-methyl-4H,5H,6H,7H-pyrazolo[1,5-a]pyrazin-2-yl}amino)-6-oxo-1,6-dihydropyridazin-3-yl]phenyl}benzamide;

5-tert-butyl-N-{3-[5-({5-[(3,3-difluoroazetidin-1-yl)methyl]-1-methyl-1,1-pyrazol-3-yl}amino)-6-oxo-1,6-dihydropyridazin-3-yl]-2,6-dimethylphenyl}pyrazine-2-carboxamide;

N-[6-fluoro-3-(5-{[5-(1-hydroxyethyl)-1,3-thiazol-2-yl]amino}-1-methyl-6-oxo-1,6-dihydropyridazin-3-yl)-2-methylphenyl]-1-benzothiophene-2-carboxamide;

N-[3-(5-{[5-(azetidin-1-ylmethyl)-1-methyl-1H-pyrazol-3-yl]amino}-1-methyl-6-oxo-1,6-dihydropyridazin-3-yl)-2-fluoro-6-methylphenyl]-4-hydroxy-5,5-dimethyl-4H,5H,6H-cyclopenta[b]thiophene-2-carboxamide;

N-{6-fluoro-2-methyl-3-[5-({1-[2-(oxan-2-yloxy)ethyl]-1H-pyrazol-3-yl}amino)-6-oxo-1,6-dihydropyridazin-3-yl]phenyl}-1-benzothiophene-2-carboxamide;

N-[6-fluoro-3-(5-{[1-(2-hydroxyethyl)-1H-pyrazol-3-yl]amino}-6-oxo-1,6-dihydropyridazin-3-yl)-2-methylphenyl]-1-benzothiophene-2-carboxamide;

4,4-difluoro-N-{6-fluoro-2-methyl-3-[5-({5-methyl-4H,5H,6H,7H-pyrazolo[1,5-a]pyrazin-2-yl}amino)-6-oxo-1,6-dihydropyridazin-3-yl]phenyl}-4,5,6,7-tetrahydro-1-benzothiophene-2-carboxamide;

N-{5-[5-({5-[2-(dimethylamino)ethoxy]pyridin-2-yl}amino)-1-methyl-6-oxo-1,6-dihydropyridazin-3-yl]-2-fluorophenyl}-1-benzothiophene-2-arboxamide;

N-[2-fluoro-6-methyl-3-(6-oxo-5-{4H,6H,7H-pyrazolo[3,2-c][1,4]oxazin-2-ylamino}-1,6-dihydropyridazin-3-yl)phenyl]-4-hydroxy-5,5-dimethyl-4H,5H,6H-cyclopenta[b]thiophene-2-carboxamide;

4-tert-butyl-N-[(3R)-1-[1-methyl-5-({5-methyl-4H,5H,6H,7H-pyrazolo[1,5-a]pyrazin-2-yl}amino)-6-oxo-1,6-dihydropyridazin-3-yl]azepan-3-yl]benzamide;

N-[6-fluoro-3-(5-{[5-(2-hydroxypropan-2-yl)-1-methyl-1H-pyrazol-3-yl]amino}-6-oxo-1,6-dihydropyridazin-3-yl)-2-methylphenyl]-1-benzothiophene-2-carboxamide;

N-{3-[5-({5-[(3-hydroxyazetidin-1-yl)methyl]-1-methyl-1H-pyrazol-3-yl}amino)-6-oxo-1,6-dihydropyridazin-3-yl]-2,6-dimethylphenyl}-1-benzothiophene-2-carboxamide;

N-[5-(5-{[5-(azetidin-1-ylmethyl)-1-methyl-1H-pyrazol-3-yl]amino}-1-methyl-6-oxo-1,6-dihydropyridazin-3-yl)-2-fluorophenyl]-4-fluoro-5,5-dimethyl-4H,5H,6H-cyclopenta[b]thiophene-2-carboxamide;

N-[6-fluoro-3-(5-[5-(2-fluoroethyl)-4H,5H,6H,7H-pyrazolo[1,5-a]pyrazin-2-yl]amino)-6-oxo-1,6-dihydropyridazin-3-yl)-2-methylphenyl]-1-benzothiophene-2-carboxamide;

N-[3-(5-{[5-(2,2-difluoroethyl)-4H,5H,6H,7H-pyrazolo[1,5-a]pyrazin-2-yl]amino}-6-oxo-1,6-dihydropyridazin-3-yl)-6-fluoro-2-methylphenyl]-1-benzothiophene-2-carboxamide;

4-tert-butyl-N-(3-{5-[(2,6-dimethylpyrimidin-4-yl)amino]-6-oxo-1,6-dihydropyridazin-3-yl}-6-fluoro-2-methylphenyl)benzamide;

(4S)—N-[3-(5-{[5-(azetidin-1-ylmethyl)-1-methyl-1H-pyrazol-3-yl]amino}-1-methyl-6-oxo-1,6-dihydropyridazin-3-yl)-6-fluoro-2-methylphenyl]-4-hydroxy-5,5-dimethyl-4H,5H,6H-cyclopenta[b]thiophene-2-carboxamide;

(4R)—N-[3-(5-{[5-(azetidin-1-ylmethyl)-1-methyl-1H-pyrazol-3-yl]amino}-1-methyl-6-oxo-1,6-dihydropyridazin-3-yl)-6-fluoro-2-methylphenyl]-4-hydroxy-5,5-dimethyl-4H,5H,6H-cyclopenta[b]thiophene-2-carboxamide;

N-[(3R)-1-(5-{[5-(azetidin-3-yl)pyridin-2-yl]amino}-6-oxo-1,6-dihydropyridazin-3-yl)piperidin-3-yl]-4-tert-butylbenzamide;

N-{6-fluoro-2-methyl-3-[5-({5-methyl-4H,5H,6H,7H-pyrazolo[1,5-a]pyrazin-2-yl}amino)-6-oxo-1,6-dihydropyridazin-3-yl]phenyl}-N-methyl-1-benzothiophene-2-carboxamide;

5-tert-butyl-N-{2,6-dimethyl-3-[5-({5-methyl-4H,5H,6H,7H-pyrazolo[1,5-a]pyrazin-2-yl}amino)-6-oxo-1,6-dihydropyridazin-3-yl]phenyl}pyridine-2-carboxamide;

(4S)—N-{2-fluoro-5-[5-({5-[(2S)-1-methylpyrrolidin-2-yl]pyridin-2-yl}amino)-6-oxo-1,6-dihydropyridazin-3-yl]phenyl}-4-hydroxy-5,5-dimethyl-4H,5H,6H-cyclopenta[b]thiophene-2-carboxamide;

(4R)—N-[3-(5-{[5-(azetidin-1-ylmethyl)-1-methyl-1H-pyrazol-3-yl]amino}-1-methyl-6-oxo-1,6-dihydropyridazin-3-yl)-2-fluoro-6-methylphenyl]-4-hydroxy-5,5-dimethyl-4H,5H,6H-cyclopenta[b]thiophene-2-carboxamide;

(4S)—N-[3-(5-{[5-(azetidin-1-ylmethyl)-1-methyl-1H-pyrazol-3-yl]amino}-1-methyl-6-oxo-1,6-dihydropyridazin-3-yl)-2-fluoro-6-methylphenyl]-4-hydroxy-5,5-dimethyl-4H,5H,6H-cyclopenta[b]thiophene-2-carboxamide;

N-{2-methyl-3-[5-({5-methyl-4H,5H,6H,7H-pyrazolo[1,5-a]pyrazin-2-yl}amino)-6-oxo-1,6-dihydropyridazin-3-yl]phenyl}-2,3-dihydro-1H-isoindole-2-carboxamide;

N-{3-fluoro-6-[5-({5-methyl-4H,5H,6H,7H-pyrazolo[1,5-a]pyrazin-2-yl}amino)-6-oxo-1,6-dihydropyridazin-3-yl]pyridin-2-yl}-1-benzothiophene-2-carboxamide;

N-[6-fluoro-3-(5-{[5-(3-hydroxy-3-methylazetidin-1-yl)pyridin-2-yl]amino}-6-oxo-1,6-dihydropyridazin-3-yl)-2-methylphenyl]-1-benzothiophene-2-carboxamide;

N-[2-fluoro-3-(5-{[5-(3-hydroxy-3-methylazetidin-1-yl)pyridin-2-yl]amino}-6-oxo-1,6-dihydropyridazin-3-yl)-6-methylphenyl]-1-benzothiophene-2-carboxamide;

N-[3-(5-{[5-(2,2-difluoroethyl)-4H,5H,6H,7H-pyrazolo[1,5-a]pyrazin-2-yl]amino}-6-oxo-1,6-dihydropyridazin-3-yl)-2-fluoro-6-methylphenyl]-4-hydroxy-5,5-dimethyl-4H,5H,6H-cyclopenta[b]thiophene-2-carboxamide;

N-(3-{5-[(1,5-dimethyl-1H-pyrazol-3-yl)amino]-6-oxo-1,6-dihydropyridazin-3-yl}-6-fluoro-2-methylphenyl)-5-methyl-1-benzothiophene-2-carboxamide;

N-{3-[5-({5-[(3,3-difluoropyrrolidin-1-yl)methyl]-1-methyl-1H-pyrazol-3-yl}amino)-6-oxo-1,6-dihydropyridazin-3-yl]-6-fluoro-2-methylphenyl}-1-benzothiophene-2-carboxamide;

(4S,5R)—N-{2-fluoro-5-[5-({5-methyl-4H,5H,6H,7H-pyrazolo[1,5-a]pyrazin-2-yl}amino)-6-oxo-1,6-dihydropyridazin-3-yl]phenyl}-4,5-dihydroxy tetrahydro-1-benzothiophene-2-carboxamide;

(4R)—N-{2-fluoro-5-[5-({5-[(2S)-1-methylpyrrolidin-2-yl]pyridin-2-yl}amino)-6-oxo-1,6-dihydropyridazin-3-yl]phenyl}-4-hydroxy-5,5-dimethyl-4H,5H,6H-cyclopenta[b]thiophene-2-carboxamide;

(4S)—N-{2-fluoro-5-[5-({5-[(2R)-1-methylpyrrolidin-2-yl]pyridin-2-yl}amino)-6-oxo-1,6-dihydropyridazin-3-yl]phenyl}-4-hydroxy-5,5-dimethyl-4H,5H,6H-cyclopenta[b]thiophene-2-carboxamide;

N-[3-(5-{[5-(2-hydroxypropan-2-yl)-1-methyl-1H-pyrazol-3-yl]amino}-6-oxo-1,6-dihydropyridazin-3-yl)-2,6-dimethylphenyl]-1-benzothiophene-2-carboxamide;

4-tert-butyl-N-[2-(hydroxymethyl)-3-(1-methyl-5-{[5-(morpholin-4-ylcarbonyl)pyridin-2-yl]amino}-6-oxo-1,6-dihydropyridazin-3-yl)phenyl]benzamide;

N-{3-[5-({5-[(4,4-difluoropiperidin-1-yl)methyl]-1-methyl-1H-pyrazol-3-yl}amino)-1-methyl-6-oxo-1,6-dihydropyridazin-3-yl]-6-fluoro-2-methylphenyl}-1-benzothiophene-2-carboxamide;

N-{3-[5-({5-[(4,4-difluoropiperidin-1-yl)methyl]-1-methyl-1H-pyrazol-3-yl}amino)-6-oxo-1,6-dihydropyridazin-3-yl]-6-fluoro-2-methylphenyl}-1-benzothiophene-2-carboxamide;

N-(3-{5-[(1,5-dimethyl-1H-pyrazol-3-yl)amino]-6-oxo-1,6-dihydropyridazin-3-yl}-6-fluoro-2-methylphenyl)-5-fluoro-1-benzothiophene-2-carboxamide;

N-{6-fluoro-2-methyl-3-[5-({5-methyl-4H,5H,6H,7H,8H-pyrazolo[1,5-a][1,4]diazepin-2-yl}amino)-6-oxo-1,6-dihydropyridazin-3-yl]phenyl}-1-benzothiophene-2-carboxamide;

N-(3-{5-[(1,5-dimethyl-1H-pyrazol-3-amino]-6-oxo-1,6-dihydropyridazin-3-yl}-6-fluoro-2-methylphenyl)-6-fluoro-1-benzothiophene-2-carboxamide;

N-(3-{5-[(1,5-dimethyl-1H-pyrazol-3-yl)amino]-6-oxo-1,6-dihydropyridazin-3-yl}-6-fluoro-2-methylphenyl)-7-fluoro-1-benzothiophene-2-carboxamide;

N-[2-(hydroxymethyl)-3-[5-({5-methyl-4H,5H,6H,7H-pyrazolo[1,5-a]pyrazin-2-yl}amino)-6-oxo-1,6-dihydropyridazin-3-yl]phenyl]-1-benzothiophene-2-carboxamide;

(4R)—N-[2-fluoro-6-methyl-3-(6-oxo-5-{4H,6H,7H-pyrazolo[3,2-c][1,4]oxazin-2-ylamino}-1,6-dihydropyridazin-3-yl)phenyl]-4-hydroxy-5,5-dimethyl-4H,5H,6H-cyclopenta[b]thiophene-2-carboxamide;

(4S)—N-[2-fluoro-6-methyl-3-(6-oxo-5-{4H,6H,7H-pyrazolo[1,4]oxazin-2-ylamino}-1,6-dihydropyridazin-3-yl)

phenyl]-4-hydroxy-5,5-dimethyl-4H,5H,6H-cyclopenta[b]thiophene-2-carboxamide;
6-chloro-N-(3-{5-[(1,5-dimethyl-1H-pyrazol-3-yl)amino]-6-oxo-1,6-dihydro pyridazin-3-yl}-6-fluoro-2-methylphenyl)-1-benzothiophene-2-carboxamide;
N-(3-{5-[(1,5-dimethyl-1H-pyrazol-3-yl)amino]-6-oxo-1,6-dihydropyridazin-3-yl}-6-fluoro-2-methylphenyl)-4-fluoro-1-benzothiophene-2-carboxamide;
N-(3-{5-[(1,5-dimethyl-1H-pyrazol-3-yl)amino]-6-oxo-1,6-dihydropyridazin-3-yl}-6-fluoro-2-methylphenyl)-6-methyl-1-benzothiophene-2-carboxamide;
(4R)—N-{2-fluoro-5-[5-({5-[(2R)-1-methylpyrrolidin-2-yl]pyridin-2-yl}amino)-6-oxo-1,6-dihydropyridazin-3-yl]phenyl}-4-hydroxy-5,5-dimethyl-4H,5H,6H-cyclopenta[b]thiophene-2-carboxamide;
(5S)—N-{2-fluoro-5-[5-({5-[2S]-1-methylpyrrolidin-2-yl]pyridin-2-yl}amino)-6-oxo-1,6-dihydropyridazin-3-yl]phenyl}-5-hydroxy-4,5,6,7-tetrahydro-1-benzothiophene-2-carboxamide;
4-tert-butyl-N-[2-formyl-3-(1-methyl-5-{[5-(morpholin-4-ylcarbonyl)pyridin-2-yl]amino}-6-oxo-1,6-dihydropyridazin-3-yl)phenyl]benzamide;
N-(3-{5-[(1,5-dimethyl-1H-pyrazol-3-yl)amino]-6-oxo-1,6-dihydropyridazin-3-yl}-6-fluoro-2-methylphenyl)-6-(trifluoromethyl)-1-benzothiophene-2-carboxamide;
4-tert-butyl-N-[2-(fluoromethyl)-3-(1-methyl-5-{[5-(morpholin-4-ylcarbonyl)pyridin-2-yl]amino}-6-oxo-1,6-dihydropyridazin-3-yl)phenyl]benzamide;
N-(3-{5-[(1,5-dimethyl-1H-pyrazol-3-yl)amino]-6-oxo-1,6-dihydropyridazin-3-yl}-6-fluoro-2-methylphenyl)-4-hydroxy-5,5-dimethyl-4H,5H,6H-cyclopenta[b]thiophene-2-carboxamide;
3-(tert-butoxy)-N-{2-methyl-3-[5-({5-methyl-4H,5H,6H,7H-pyrazolo[1,5-a]pyrazin-2-yl}amino)-6-oxo-1,6-dihydropyridazin-3-yl]phenyl}azetidine-1-carboxamide;
(5R)—N-{2-fluoro-5-[5-({5-[(2S)-1-methylpyrrolidin-2-yl]pyridin-2-yl}amino)-6-oxo-1,6-dihydropyridazin-3-yl]phenyl}-5-hydroxy-4,5,6,7-tetrahydro-1-benzothiophene-2-carboxamide;
(5S)—N-{2-fluoro-5-[5-({5-[(2R)-1-methylpyrrolidin-2-yl]pyridin-2-yl}amino)-6-oxo-1,6-dihydropyridazin-3-yl]phenyl}-5-hydroxy-4,5,6,7-tetrahydro-1-benzothiophene-2-carboxamide;
N-[3-fluoro-6-(5-{[5-(2-hydroxypropan-2-yl)-1-methyl-1H-pyrazol-3-yl]amino}-6-oxo-1,6-dihydropyridazin-3-yl)pyridin-2-yl]-1-benzothiophene-2-carboxamide;
N-{6-fluoro-3-[5-({5-[(3-hydroxy-3-methylazetidin-1-yl)methyl]-1-methyl-1H-pyrazol-3-yl}-amino)-6-oxo-1,6-dihydropyridazin-3-yl]-2-methylphenyl}-1-benzothiophene-2-carboxamide;
N-{6-fluoro-2-methyl-3-[6-oxo-5-(pyrimidin-4-ylamino)-1,6-dihydropyridazin-3-yl]phenyl}-4-hydroxy-5,5-dimethyl-4H,5H,6H-cyclopenta[b]thiophene-2-carboxamide;
N-[5-(5-{[5-(azetidin-1-ylmethyl)-1-methyl-1H-pyrazol-3-yl]amino}-1-methyl-6-oxo-1,6-dihydropyridazin-3-yl)-2-fluorophenyl]-4-methoxy-5,5-dimethyl-4H,5H,6H-cyclopenta[b]thiophene-2-carboxamide;
(5R)—N-{2-fluoro-5-[5-({5-[(2R)-1-methylpyrrolidin-2-yl]pyridin-2-yl}amino)-6-oxo-1,6-dihydropyridazin-3-yl]phenyl}-5-hydroxy-4,5,6,7-tetrahydro-1-benzothiophene-2-carboxamide;
5-tert-butyl-N-[6-fluoro-2-methyl-3-(5-{[5-(1-methylpiperidin-4-yl)pyridin-2-yl]amino}-6-oxo-1,6-dihydropyridazin-3-yl)phenyl]pyrazine-2-carboxamide;
N-[2-fluoro-6-methyl-3-(5-{[5-(1-methylpiperidin-4-yl)pyridin-2-yl]amino}-6-oxo-1,6-dihydropyridazin-3-yl)phenyl]-4-hydroxy-5,5-dimethyl-4H,5H,6H-cyclopenta[b]thiophene-2-carboxamide;
4-chloro-N-(3-{5-[(1,5-dimethyl-1H-pyrazol-3-yl)amino]-6-oxo-1,6-dihydropyridazin-3-yl}-6-fluoro-2-methylphenyl)-1-benzothiophene-2-carboxamide;
N-(3-{5-[(1,5-dimethyl-1H-pyrazol-3-yl)amino]-6-oxo-1,6-dihydropyridazin-3-yl}-6-fluoro-2-methylphenyl)-5-methoxy-1-benzothiophene-2-carboxamide;
5-bromo-N-(3-{5-[(1,5-dimethyl-1H-pyrazol-3-yl)amino]-6-oxo-1,6-dihydro pyridazin-3-yl}-6-fluoro-2-methylphenyl)-1-benzothiophene-2-carboxamide;
6-bromo-N-(3-{5-[(1,5-dimethyl-1H-pyrazol-3-yl)amino]-6-oxo-1,6-dihydro pyridazin-3-yl}-6-fluoro-2-methylphenyl)-1-benzothiophene-2-carboxamide;
N-(3-{5-[(1,5-dimethyl-1H-pyrazol-3-yl)amino]-6-oxo-1,6-dihydropyridazin-3-yl}-6-fluoro-2-methylphenyl)-1,3-benzothiazole-2-carboxamide;
N-{3-[5-({5-[(3,3-difluoroazetidin-1-yl)methyl]-1,2-oxazol-3-yl}amino)-6-oxo-1,6-dihydropyridazin-3-yl]-6-fluoro-2-methylphenyl}-1-benzothiophene-2-carboxamide;
N-{6-fluoro-2-methyl-3-[5-({5-methyl-4H,5H,6H,7H-pyrazolo[1,5-a]pyrazin-2-yl}amino)-6-oxo-1,6-dihydropyridazin-3-yl]phenyl}-7-hydroxy-3-thiatricyclo[6.2.1.0^{2,6}]undeca-2(6),4-diene-4-carboxamide;
N-{6-fluoro-3-[1-(hydroxymethyl)-5-({5-methyl-4H,5H,6H,7H-pyrazolo[1,5-a]pyrazin-2-yl}amino)-6-oxo-1,6-dihydropyridazin-3-yl]-2-methylphenyl}-1-benzothiophene-2-carboxamide;
N-[6-fluoro-2-methyl-3-(6-oxo-5-{[5-(trideuteriomethyl)-4H,5H,6H,7H-pyrazolo[1,5-a]pyrazin-2-yl]amino}-1,6-dihydropyridazin-3-yl)phenyl]-1-benzothiophene-2-carboxamide;
N-(3-{5-[(5-amino-1-methyl-1H-pyrazol-3-yl)amino]-6-oxo-1,6-dihydropyridazin-3-yl}6-fluoro-2-methylphenyl)-1-benzothiophene-2-carboxamide;
5-tert-butyl-N-[2,6-dimethyl-3-(6-oxo-5-{[5-(trideuteriomethyl)-4H,5H,6H,7H-pyrazolo[1,5-a]pyrazin-2-yl]-amino}-1,6-dihydropyridazin-3-yl)phenyl]pyrazine-2-carboxamide;
4-hydroxy-5,5-dimethyl-N-[(3R)-1-[1-methyl-5-({5-methyl-4H,5H,6H,7H-pyrazolo[1,5-a]pyrazin-2-yl}amino)-6-oxo-1,6-dihydropyridazin-3-yl]piperidin-3-yl]-4H,5H,6H-cyclopenta[b]thiophene-2-carboxamide;
4-tert-butyl-N-{3-[5-({5-[(dimethylcarbamoyl)(hydroxy)methyl]pyridin-2-yl}amino)-1-methyl-6-oxo-1,6-dihydropyridazin-3-yl]-6-fluoro-2-methylphenyl}benzamide;
3-(tert-butoxy)-N-(3-{5-[(1,5-dimethyl-1H-pyrazol-3-yl)amino]-6-oxo-1,6-dihydropyridazin-3-yl}-2-methylphenyl)azetidine-1-carboxamide;
(4R)—N-[5-(5-{[5-(azetidin-1-ylmethyl)-1-methyl-1H-pyrazol-3-yl]amino}-1-methyl-6-oxo-1,6-dihydropyridazin-3-yl)-2-fluorophenyl]-4-methoxy-5,5-dimethyl-4H,5H,6H-cyclopenta[b]thiophene-2-carboxamide;
(4S)—N-[5-(5-{[5-(azetidin-1-ylmethyl)-1-methyl-1H-pyrazol-3-yl]amino}-1-methyl-6-oxo-1,6-dihydropyridazin-3-yl)-2-fluorophenyl]-4-methoxy-5,5-dimethyl-4H,5H,6H-cyclopenta[b]thiophene-2-carboxamide;
4-tert-butyl-N-{5-methyl-2-[5-({5-methyl-4H,5H,6H,7H-pyrazolo[1,5-a]pyrazin-2-yl}amino)-6-oxo-1,6-dihydropyridazin-3-yl]-1,3-thiazol-4-yl}benzamide;
N-{6-fluoro-2-methyl-3-[5-({5-methyl-4H,5H,6H,7H-pyrazolo[1,5-a]pyrazin-2-yl}amino)-6-oxo-1,6-dihydropyridazin-3-yl]phenyl}-4-hydroxy-4,5,5-trimethyl-4H,5H,6H-cyclopenta[b]thiophene-2-carboxamide;

N-(3-{5-[(1,5-dimethyl-1H-pyrazol-3-yl)amino]-6-oxo-1,6-dihydropyridazin-3-yl}-6-fluoro-2-methylphenyl)-7-methyl-1-benzothiophene-2-carboxamide;

N-(3-{5-[(1,5-dimethyl-1H-pyrazol-3-yl)amino]-6-oxo-1,6-dihydropyridazin-3-yl}-6-fluoro-2-methylphenyl)-5-hydroxy-1-benzothiophene-2-carboxamide;

4-tert-butyl-N-{3-[5-({5-[(dimethylcarbamoyl)(hydroxy)methyl]pyridin-2-yl}amino)-6-oxo-1,6-dihydropyridazin-3-yl]-6-fluoro-2-methylphenyl}benzamide;

N-{5-[5-({5,5-dioxo-4H,6H,7H-pyrazolo[3,2-c][1,4]thiazin-2-yl}amino)-6-oxo-1,6-dihydropyridazin-3-yl]-2-fluorophenyl}-1-benzothiophene-2-carboxamide;

(4R)—N-[6-fluoro-2-methyl-3-(1-methyl-5-{[1-methyl-5-(pyrrolidin-2-yl)-1H-pyrazol-3-yl]amino}-6-oxo-1,6-dihydropyridazin-3-yl)phenyl]-4-hydroxy-5,5-dimethyl-4H,5H,6H-cyclopenta[b]thiophene-2-carboxamide;

(7R)—N-{6-fluoro-2-methyl-3-[5-({5-methyl-4H,5H,6H,7H-pyrazolo[1,5-a]pyrazin-2-yl}amino)-6-oxo-1,6-dihydropyridazin-3-yl]phenyl}-7-hydroxy-3-thiatricyclo[6.2.1.0ˆ{2,6}]undeca-2(6),4-diene-4-carboxamide;

(7S)—N-{6-fluoro-2-methyl-3-[5-({5-methyl-4H,5H,6H,7H-pyrazolo[1,5-a]pyrazin-2-yl}amino)-6-oxo-1,6-dihydropyridazin-3-yl]phenyl}-7-hydroxy-3-thiatricyclo[6.2.1.0ˆ{2,6}]undeca-2(6),4-diene-4-carboxamide;

(4R)-4-hydroxy-5,5-dimethyl-N-[(3R)-1-[1-methyl-5-({5-methyl-4H,5H,6H,7H-pyrazolo[1,5-a]pyrazin-2-yl}amino)-6-oxo-1,6-dihydropyridazin-3-yl]piperidin-3-yl]-4H,5H,6H-cyclopenta[b]thiophene-2-carboxamide;

(4S)-4-hydroxy-5,5-dimethyl-N-[(3R)-1-[1-methyl-5-({5-methyl-4H,5H,6H,7H-pyrazolo[1,5-a]pyrazin-2-yl}amino)-6-oxo-1,6-dihydropyridazin-3-yl]piperidin-3-yl]-4H,5H,6H-cyclopenta[b]thiophene-2-carboxamide;

4-tert-butyl-N-{3-[5-({5-[(R)-(dimethylcarbamoyl)(hydroxy)methyl]pyridin-2-yl}amino)-1-methyl-6-oxo-1,6-dihydropyridazin-3-yl]-6-fluoro-2-methylphenyl}benzamide;

4-tert-butyl-N-{3-[5-({5-[(S)-(dimethylcarbamoyl)(hydroxy)methyl]pyridin-2-yl}amino)-1-methyl-6-oxo-1,6-dihydropyridazin-3-yl]-6-fluoro-2-methylphenyl}benzamide;

4-tert-butyl-N-{3-[5-({5-[(R)-(dimethylcarbamoyl)(hydroxy)methyl]pyridin-2-yl}amino)-6-oxo-1,6-dihydropyridazin-3-yl]-6-fluoro-2-methylphenyl}benzamide;

4-tert-butyl-N-{3-[5-({5-[(S)-(dimethylcarbamoyl)(hydroxy)methyl]pyridin-2-yl}amino)-6-oxo-1,6-dihydropyridazin-3-yl]-6-fluoro-2-methylphenyl}benzamide;

N-[2-(methoxymethyl)-3-[5-({5-methyl-4H,5H,6H,7H-pyrazolo[1,5-a]pyrazolo-2-yl}amino)-6-oxo-1,6-dihydropyridazin-3-yl]phenyl]-1-benzothiophene-2-carboxamide;

6-fluoro-N-{6-fluoro-2-methyl-3-[5-({5-methyl-4H,5H,6H,7H-pyrazolo[1,5-a]pyrazin-2-yl}amino)-6-oxo-1,6-dihydropyridazin-3-yl]phenyl}-1-benzothiophene-2-carboxamide;

N-[6-fluoro-2-(hydroxymethyl)-3-[1-methyl-5-({5-methyl-4H,5H,6H,7H-pyrazolo[1,5-a]pyrazin-2-yl}amino)-6-oxo-1,6-dihydropyridazin-3-yl]phenyl]-1-benzothiophene-2-carboxamide;

N-{6-fluoro-2-methyl-3-[5-({5-methyl-4H,5H,6H,7H-pyrazolo[1,5-a]pyrazin-2-yl}amino)-6-oxo-1,6-dihydropyridazin-3-yl]phenyl}-4-(1,1,1-trifluoro-2-hydroxypropan-2-yl)benzamide;

4-tert-butyl-N-[2-(hydroxymethyl)-3-[1-methyl-6-oxo-5-(pyrimidin-4-ylamino)-1,6-dihydropyridazin-3-yl]phenyl]benzamide;

N-[2-(hydroxymethyl)-3-[1-methyl-5-({5-methyl-4H,5H,6H,7H-pyrazolo[1,5-a]pyrazin-2-yl}amino)-6-oxo-1,6-dihydropyridazin-3-yl]phenyl]-2,3-dihydro-1H-isoindole-2-carboxamide;

N-{6-fluoro-2-methyl-3-[5-({5-methyl-4H,5H,6H,7H-pyrazolo[1,5-a]pyrazin-2-yl}amino)-6-oxo-1,6-dihydropyridazin-3-yl]phenyl}-4-(2-methoxypropan-2-yl)benzamide;

N-{6-fluoro-2-methyl-3-[5-({5-methyl-4H,5H,6H,7H-pyrazolo[1,5-a]pyrazin-2-yl}amino)-6-oxo-1,6-dihydropyridazin-3-yl]phenyl}-5,5-dimethyl-4H,5H,6H-cyclopenta[b]thiophene-2-carboxamide;

N-[2-(2-hydroxyethyl)-3-[5-({5-methyl-4H,5H,6H,7H-pyrazolo[1,5-a]pyrazin-2-yl}amino)-6-oxo-1,6-dihydropyridazin-3-yl]phenyl]-1-benzothiophene-2-carboxamide;

N-[2-(hydroxymethyl)-3-[5-({5-methyl-4H,5H,6H,7H-pyrazolo[1,5-a]pyrazin-2-yl}amino)-6-oxo-1,6-dihydropyridazin-3-yl]phenyl]-2,3-dihydro-1H-isoindole-2-carboxamide;

N-{6-fluoro-2-methyl-3-[5-({5-methyl-4H,5H,6H,7H-pyrazolo[1,5-a]pyrazin-2-yl}amino)-6-oxo-1,6-dihydropyridazin-3-yl]phenyl}thieno[3,2-b]pyridine-2-carboxamide;

N-{6-fluoro-2-methyl-3-[5-({5-methyl-4H,5H,6H,7H-pyrazolo[1,5-a]pyrazin-2-yl}amino)-6-oxo-1,6-dihydropyridazin-3-yl]phenyl}thieno[2,3-b]pyridine-2-carboxamide;

N-{6-fluoro-2-methyl-3-[5-({5-methyl-4H,5H,6H,7H-pyrazolo[1,5-a]pyrazin-2-yl}amino)-6-oxo-1,6-dihydropyridazin-3-yl]phenyl}-4-[(2R)-1,1,1-trifluoro-2-hydroxypropan-2-yl]benzamide;

N-{6-fluoro-2-methyl-3-[5-({5-methyl-4H,5H,6H,7H-pyrazolo[1,5-a]pyrazin-2-yl}amino)-6-oxo-1,6-dihydropyridazin-3-yl]phenyl}-4-[(2S)-1,1,1-trifluoro-2-hydroxypropan-2-yl]benzamide;

N-[6-fluoro-2-(hydroxymethyl)-3-[5-({5-methyl-4H,5H,6H,7H-pyrazolo[1,5-a]pyrazin-2-yl}amino)-6-oxo-1,6-dihydropyridazin-3-yl]phenyl]-1-benzothiophene-2-carboxamide;

5-tert-butyl-N-[3-(5-{[5-(2,2-difluoroethyl)-4H,5H,6H,7H-pyrazolo[1,5-a]pyrazin-2-yl]amino}-6-oxo-1,6-dihydropyridazin-3-yl)-6-fluoro-2-methylphenyl]pyrazine-2-carboxamide;

N-[5-(5-{[5-(azetidin-1-ylmethyl)-1-methyl-1H-pyrazol-3-yl]amino}-6-oxo-1,6-dihydropyridazin-3-yl)-2-fluorophenyl]-4-fluoro-5,5-dimethyl-4H,5H,6H-cyclopenta[b]thiophene-2-carboxamide;

3-(tert-butoxy)-N-[2-(hydroxymethyl)-3-[5-({5-methyl-4H,5H,6H,7H-pyrazolo[1,5-a]pyrazin-2-yl}amino)-6-oxo-1,6-dihydropyridazin-3-yl]phenyl]benzamide-1-carboxamide;

4-tert-butyl-N-[6-fluoro-2-(hydroxymethyl)-3-[5-({5-methyl-4H,5H,6H,7H-pyrazolo[1,5-a]pyrazin-2-yl}amino)-6-oxo-1,6-dihydropyridazin-3-yl]phenyl]benzamide;

N-[6-fluoro-2-(hydroxymethyl)-3-[1-methyl-5-({5-methyl-4H,5H,6H,7H-pyrazolo[1,5-a]pyrazin-2-yl}amino)-6-oxo-1,6-dihydropyridazin-3-yl]phenyl]-4,5,6,7-tetrahydro-1-benzothiophene-2-carboxamide;

(4R)—N-[5-(5-{[5-(azetidin-1-ylmethyl)-1-methyl-1H-pyrazol-3-yl]amino}-1-methyl-6-oxo-1,6-dihydropyridazin-3-yl)-2-fluorophenyl]-4-fluoro-5,5-dimethyl-4H,5H,6H-cyclopenta[b]thiophene-2-carboxamide;

(4S)—N-[5-(5-{[5-(azetidin-1-ylmethyl)-1-methyl-1H-pyrazol-3-yl]amino}-1-methyl-6-oxo-1,6-dihydropyridazin-3-yl)-2-fluorophenyl]-4-fluoro-5,5-dimethyl-4H,5H,6H-cyclopenta[b]thiophene-2-carboxamide; and N-{6-fluoro-2-methyl-3-[5-({5-methyl-4H,5H,6H,7H-pyrazolo[1,5-a]pyrazin-2-yl}amino)-6-oxo-1,6-dihydropyridazin-3-yl]phenyl}-4-(1-fluorocyclopropyl)benzamide; and pharmaceutically acceptable salts, solvates, and mixtures thereof.

In certain embodiments, the compound of Formula I is chosen from:

| Structure | Name |
|---|---|
| 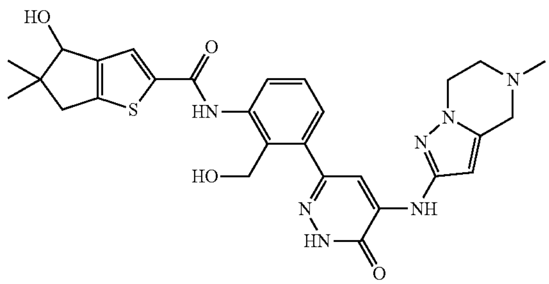 | 4-hydroxy-N-(2-(hydroxymethyl)-3-(5-(5-methyl-4,5,6,7-tetrahydropyrazolo[1,5-a]pyrazin-2-ylamino)-6-oxo-1,6-dihydropyridazin-3-yl)phenyl)-5,5-dimethyl-5,6-dihydro-4H-cyclopenta[b]thiophene-2-carboxamide |
| 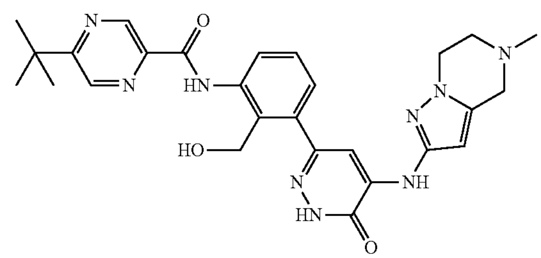 [SMILES: CN1CCn2nc(Nc3cc(-c4cccc(NC(=O)c5cnc(C(C)(C)C)cn5)c4CO)n[nH]c3=O)cc2C1] | 5-tert-butyl-N-(2-(hydroxymethyl)-3-(5-(5-methyl-4,5,6,7-tetrahydropyrazolo[1,5-a]pyrazin-2-ylamino)-6-oxo-1,6-dihydropyridazin-3-yl)phenyl)pyrazine-2-carboxamide |
| 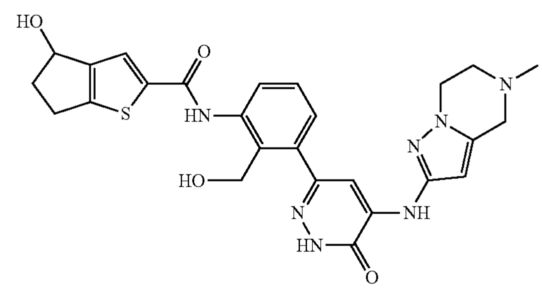 [SMILES: CN1CCn2nc(Nc3cc(-c4cccc(NC(=O)c5cc6c(s5)CCC6O)c4CO)n[nH]c3=O)cc2C1] | 4-hydroxy-N-(2-(hydroxymethyl)-3-(5-(5-methyl-4,5,6,7-tetrahydropyrazolo[1,5-a]pyrazin-2-ylamino)-6-oxo-1,6-dihydropridazin-3-yl)phenyl)-5,6-dihydro-4H-cyclopenta[b]thiophene-2-carboxamide |
| 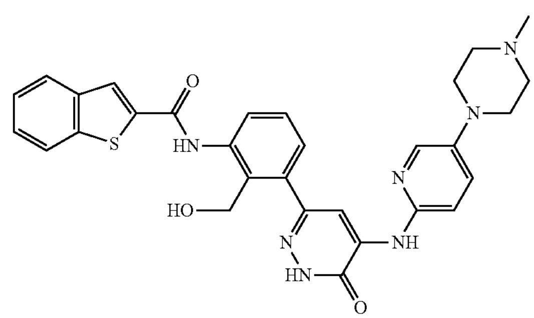 [SMILES: CN1CCN(c2ccc(Nc3cc(-c4cccc(NC(=O)c5cc6ccccc6s5)c4CO)n[nH]c3=O)nc2)CC1] | N-(2-(hydroxymethyl)-3-(5-(5-(4-methylpiperazin-1-yl)pyridin-2-ylamino)-6-oxo-1,6-dihydropyridazin-3-yl)phenyl)benzo[b]thiophene-2-carboxamide |
| 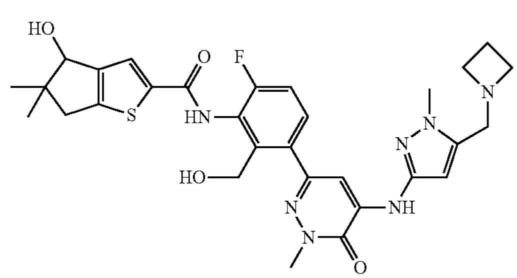 [SMILES: Cn1nc(Nc2cc(-c3ccc(F)c(NC(=O)c4cc5c(s4)CC(C)(C)C5O)c3CO)nn(C)c2=O)cc1CN1CCC1] | N-(3-(5-(5-(azetidin-1-ylmethyl)-1-methyl-1H-pyrazol-3-ylamino)-1-methyl-6-oxo-1,6-dihydropyridazin-3-yl)-6-fluoro-2-(hydroxymethyl)phenyl)-4-hydroxy-5,5-dimethyl-5,6-dihydro-4H-cyclopenta[b]thiophene-2-carboxamide |

| Structure | Name |
|---|---|
| 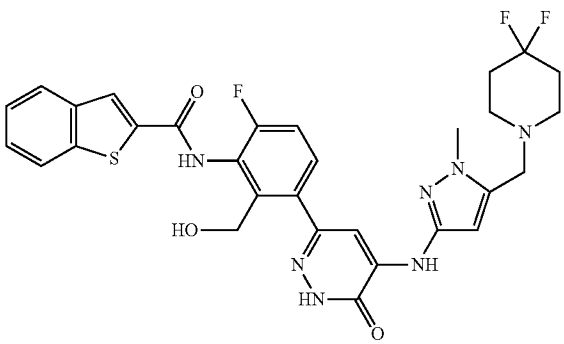 [SMILES: Cn1nc(Nc2cc(-c3ccc(F)c(NC(=O)c4cc5ccccc5s4)c3CO)n[nH]c2=O)cc1CN1CCC(F)(F)CC1] | N-(3-(5-(5-((4,4-difluoropiperidin-1-yl)methyl)-1-methyl-1H-pyrazol-3-ylamino)-6-oxo-1,6-dihydropyridazin-3-yl)-6-fluoro-2-(hydroxymethyl)phenyl)benzo[b]thiophene-2-carboxamide |

The present compounds described herein are potent inhibitors of Btk. While not being bound by any theory, certain compounds have unproved properties in the form of greater efficacy (as measured by, for example, the inhibition of Btk in whole blood and the inhibition of B-cell activation in mice).

Methods for obtaining the novel compounds described herein will be apparent to those of skill in the art, suitable procedures being described, for example, in the reaction schemes I-XI and examples below, and in the references cited herein. See, also, U.S. application Ser. No. 11/371,180 (US2006l0229337), filed Mar. 9, 2006, which is incorporated herein by reference in its entirety; and International patent application WO2008/116064, filed Mar. 20, 2008, which is incorporated herein by reference in its entirety.

Reaction Scheme I

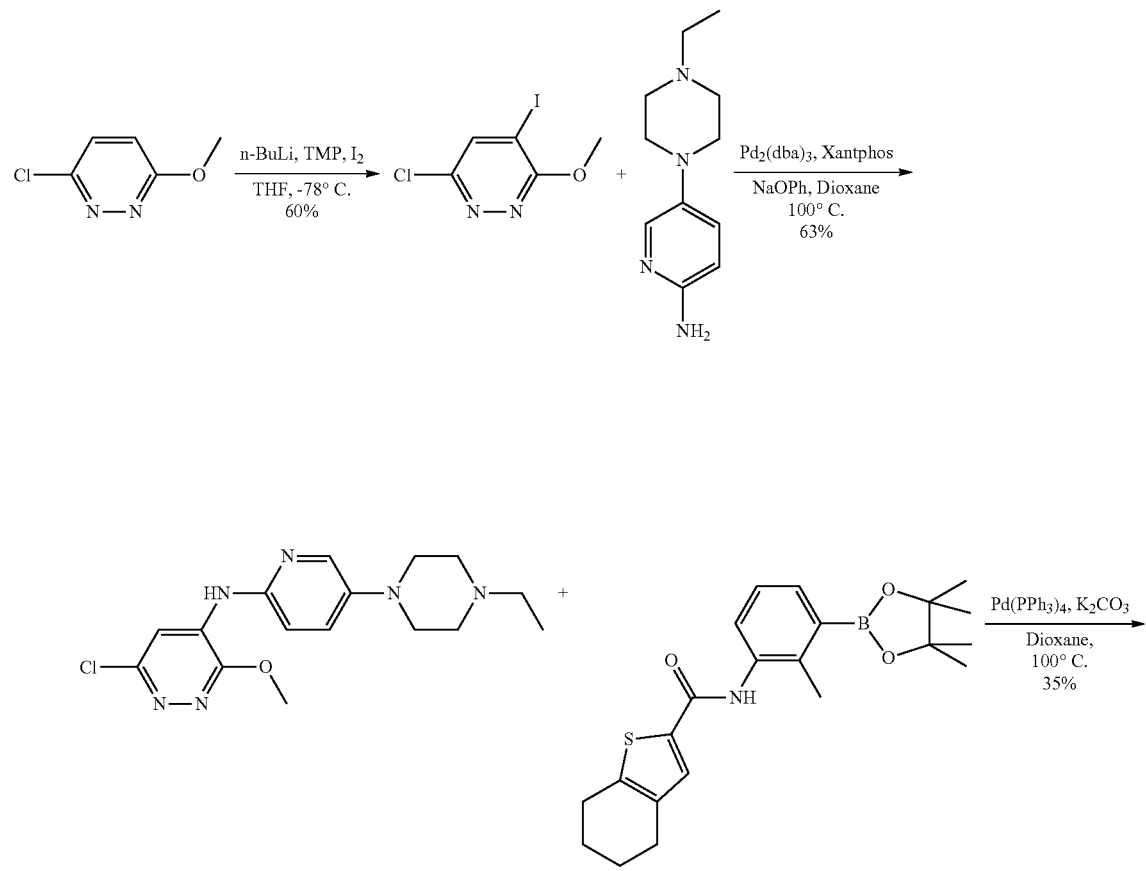

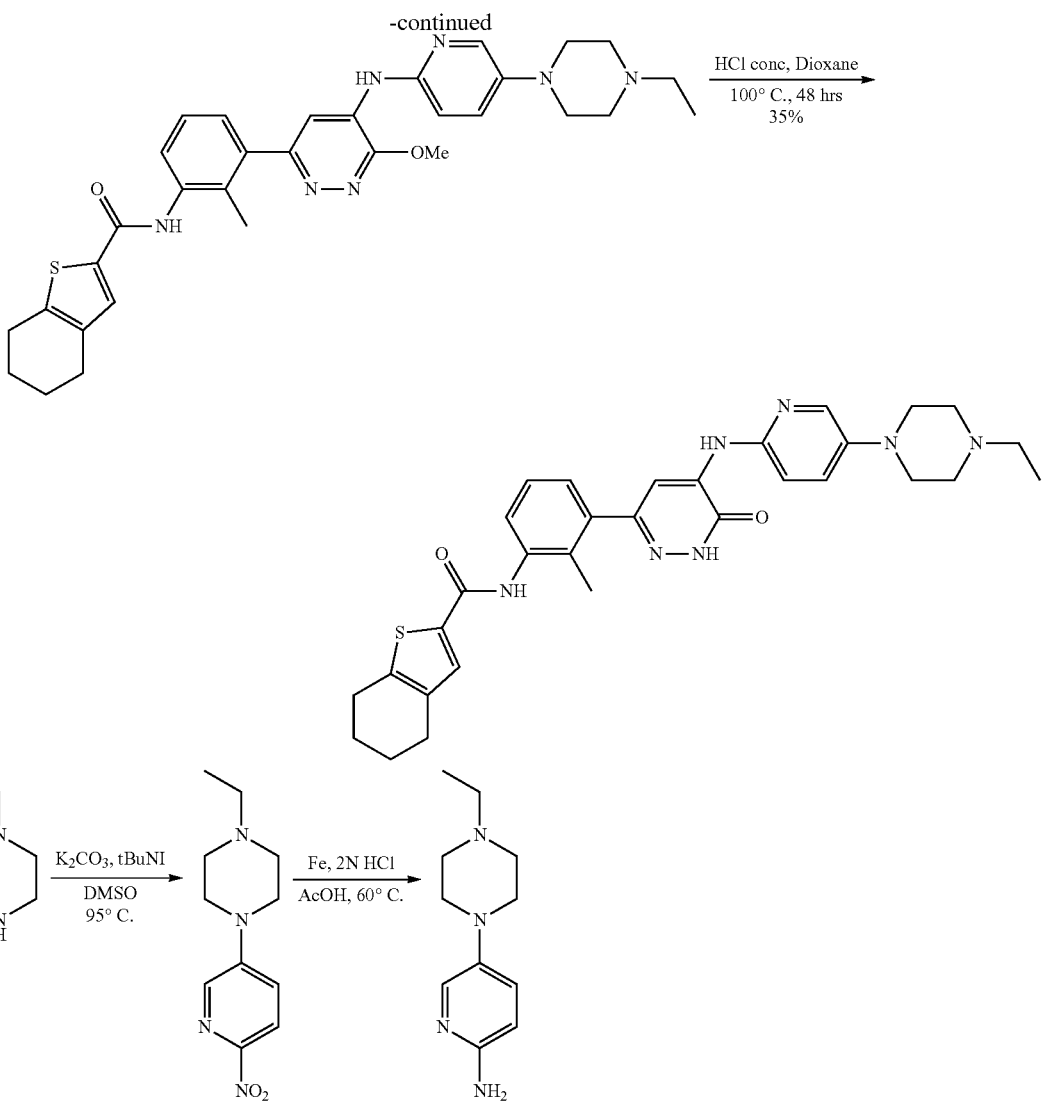
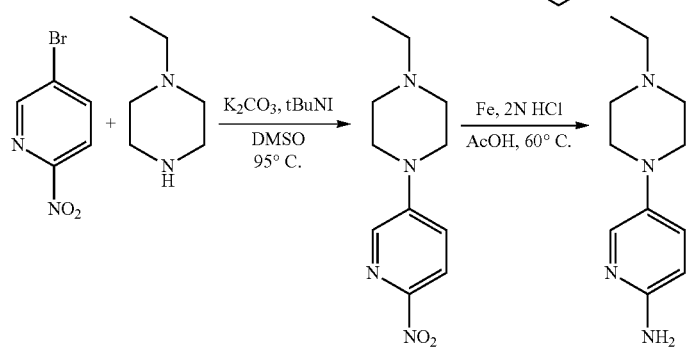
Reaction Scheme II
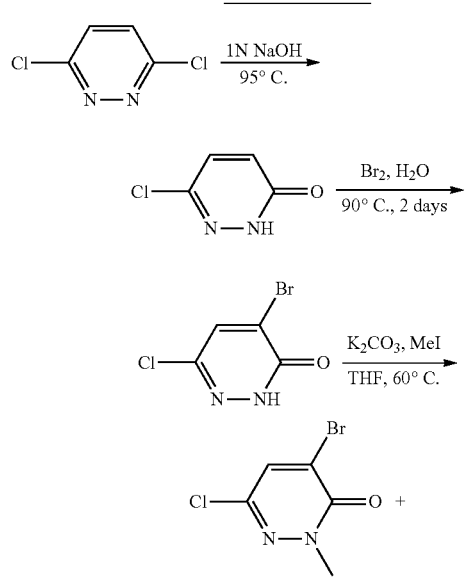
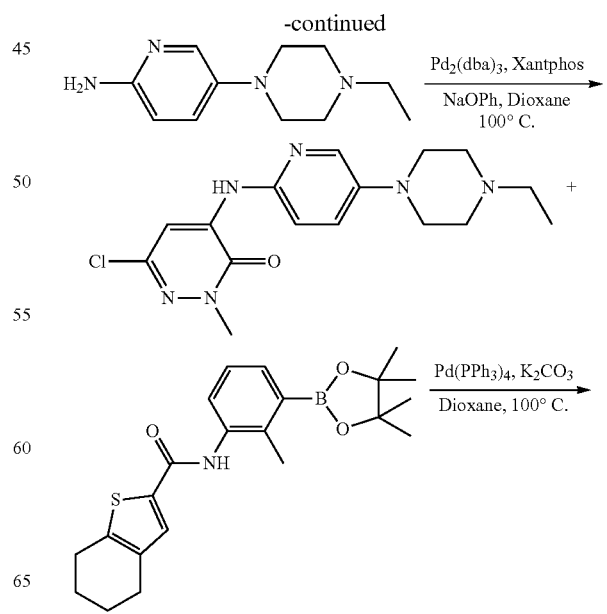

-continued
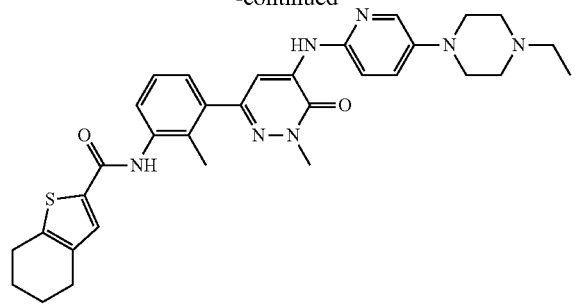
Reaction Scheme III
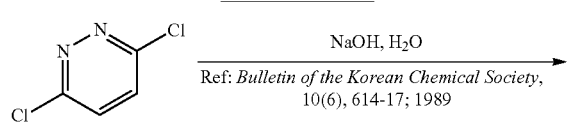
Ref: Bulletin of the Korean Chemical Society, 10(6), 614-17; 1989
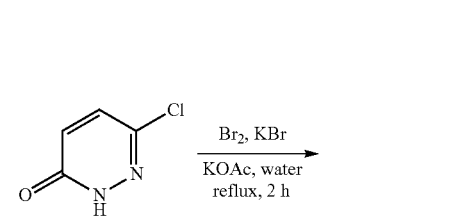
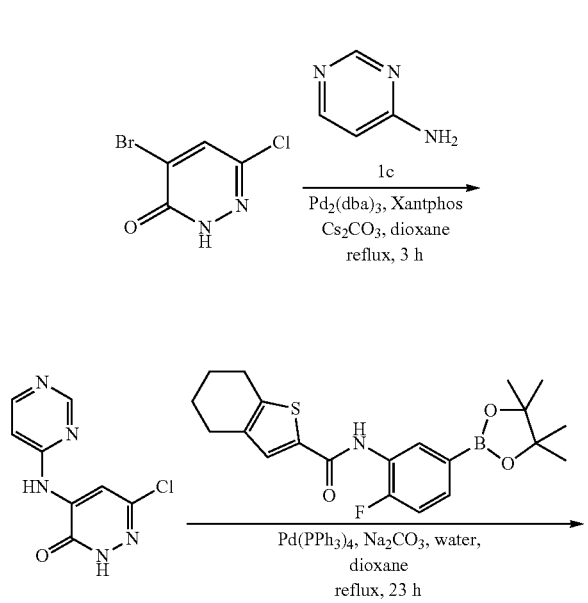
Reaction Scheme IV
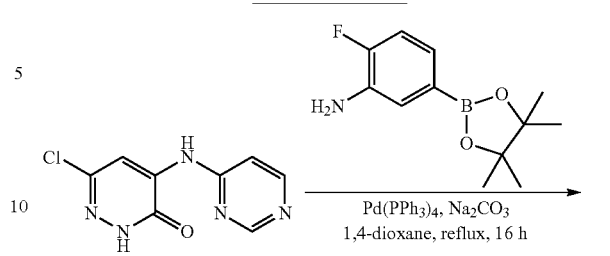
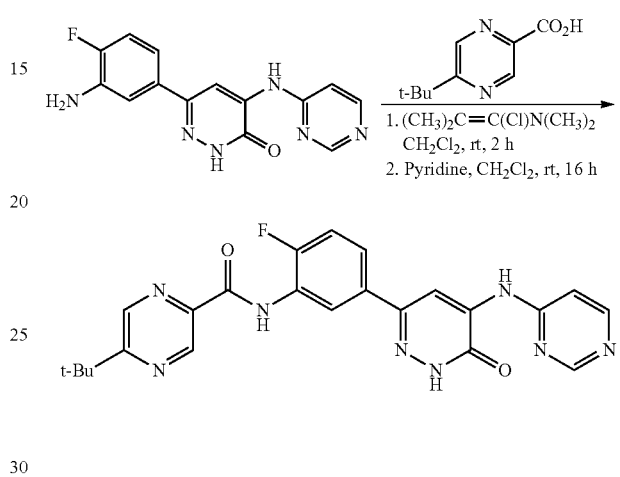
Reaction Scheme V
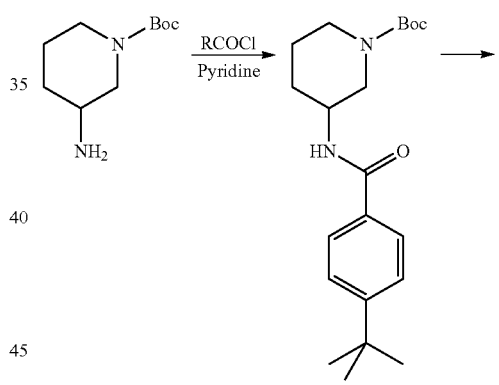
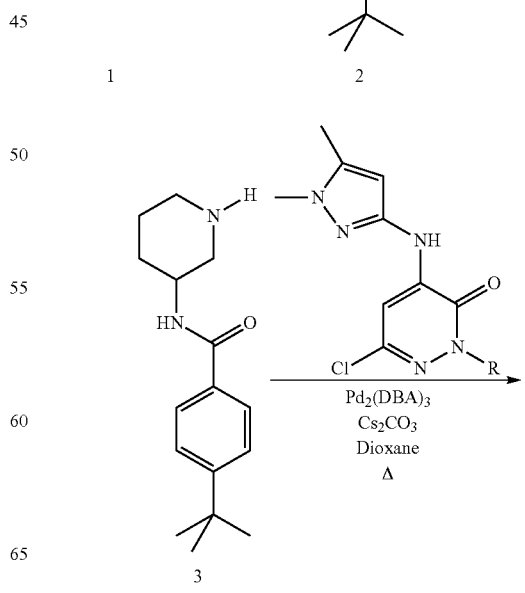

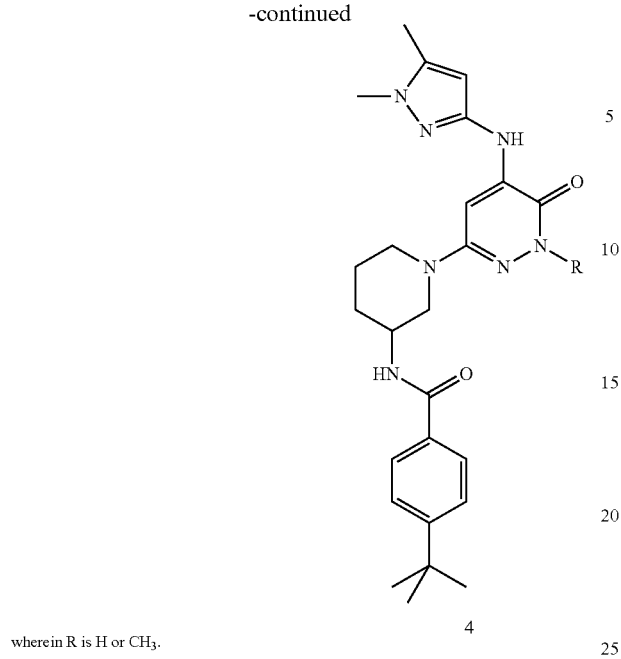
wherein R is H or CH₃.
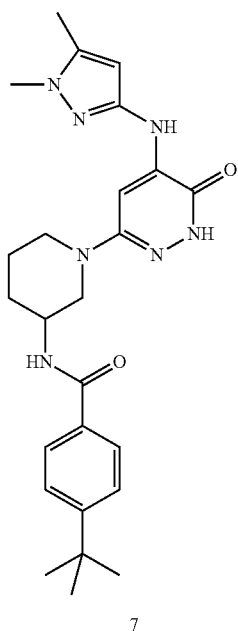
Reaction Scheme VI
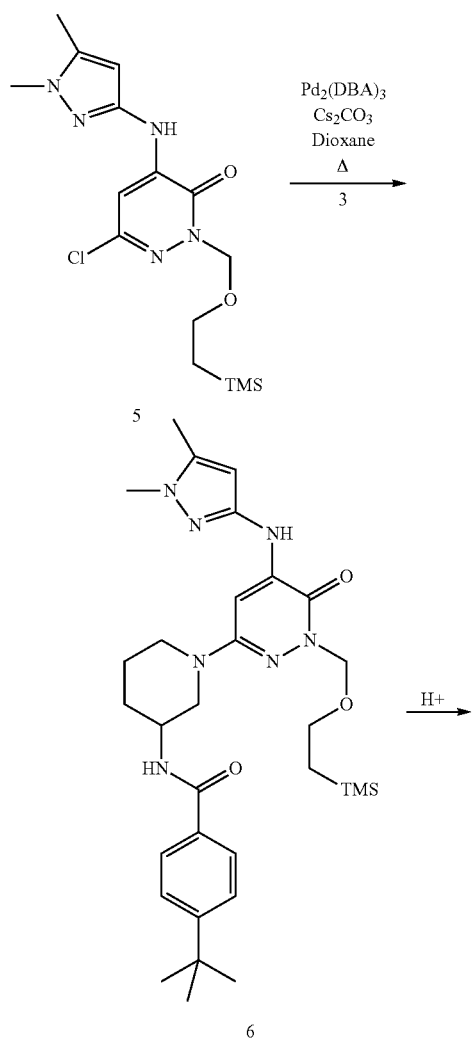
Reaction Scheme VII
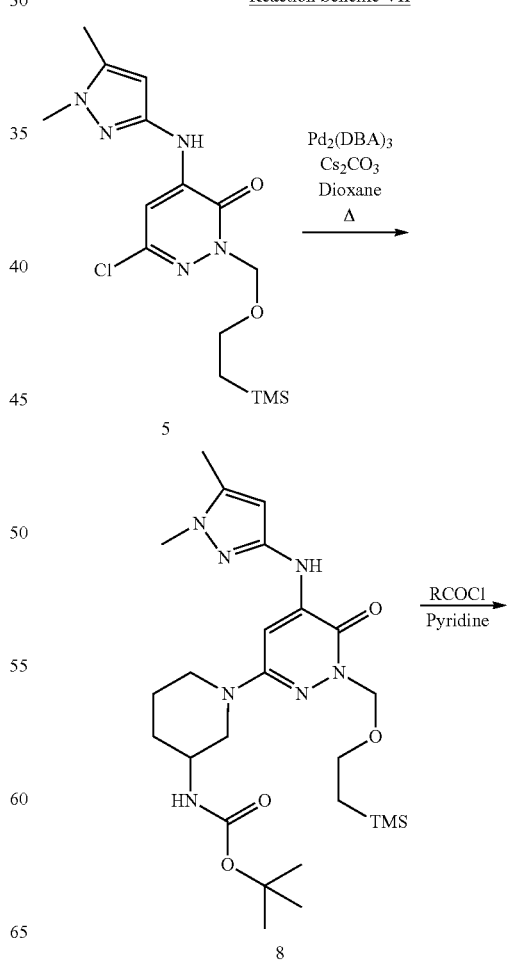

69
-continued
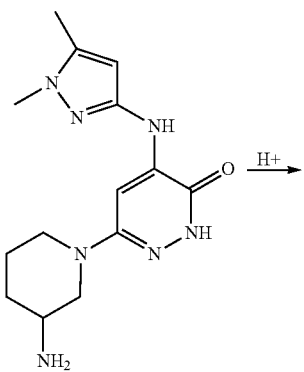
70
-continued
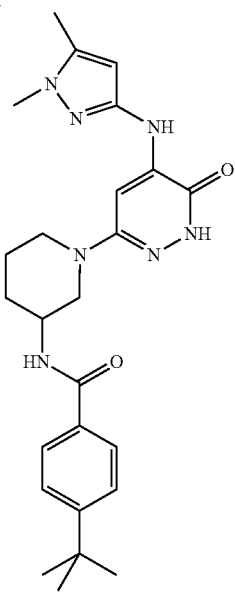
Reaction Scheme VIII
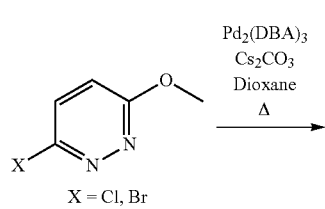
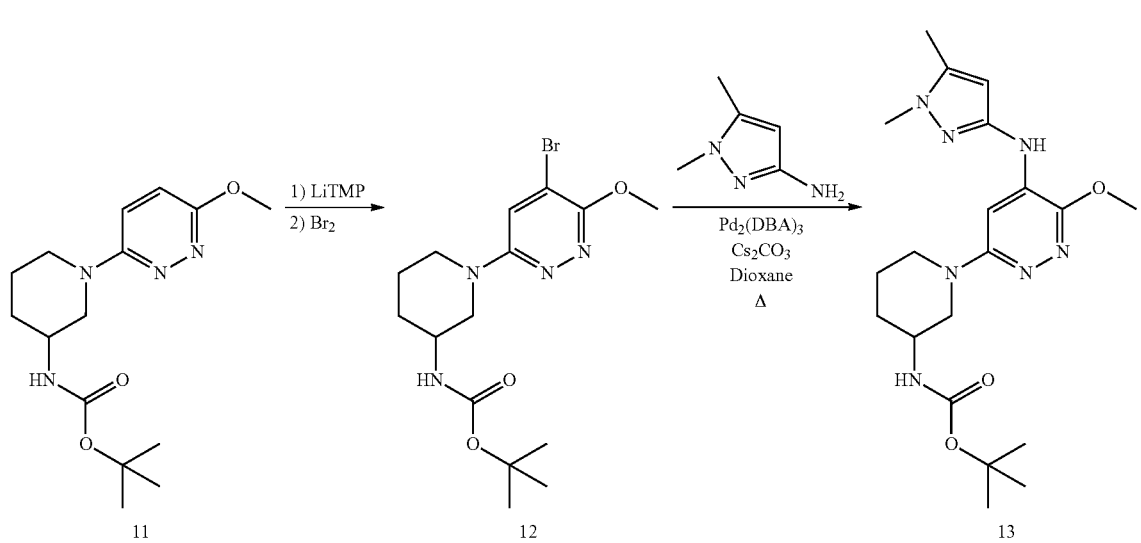

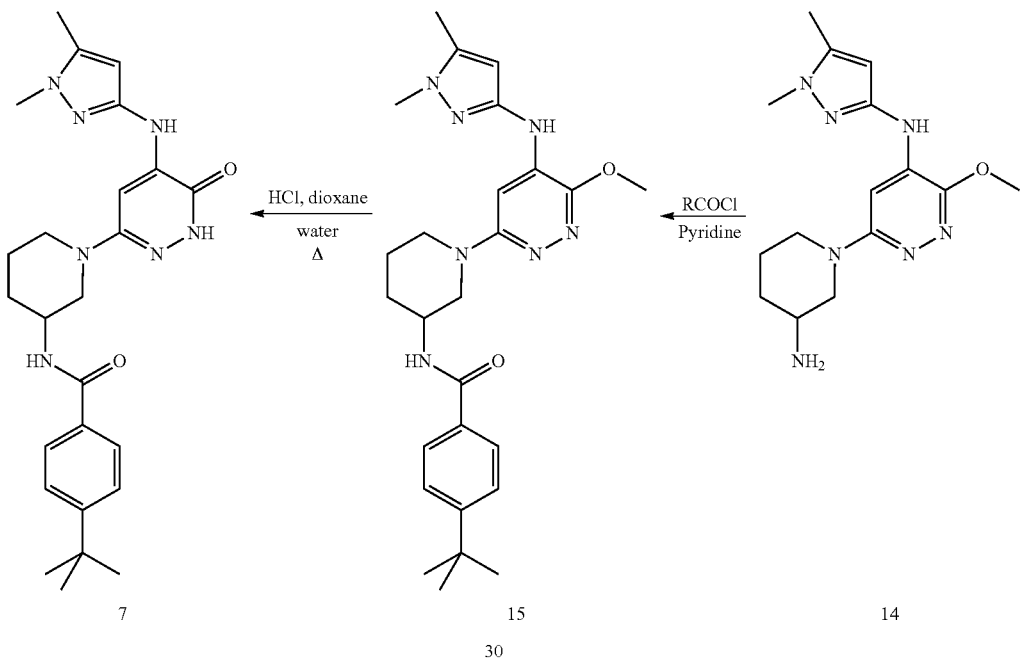
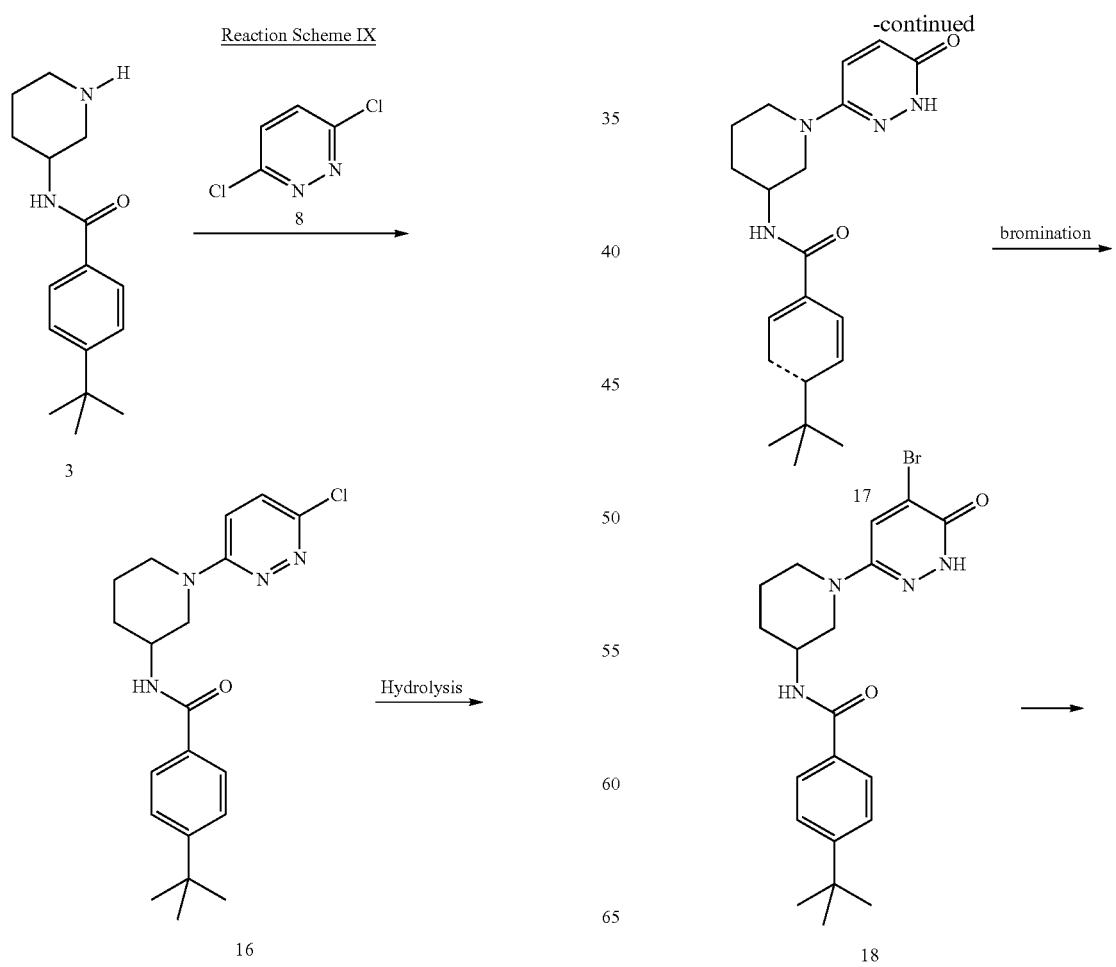
Reaction Scheme IX

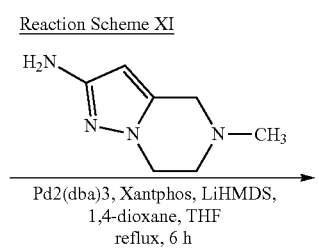
Reaction Scheme XI
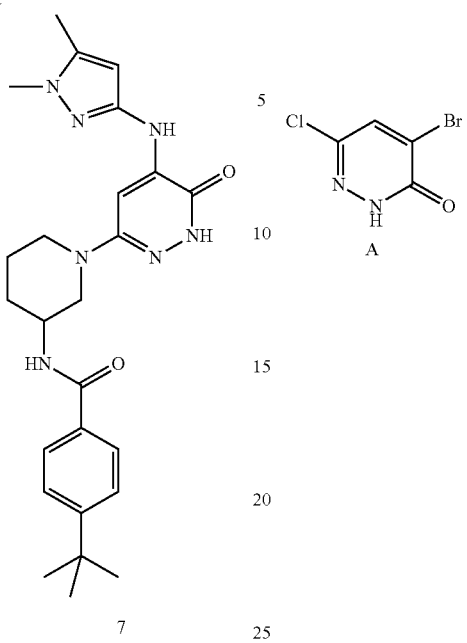
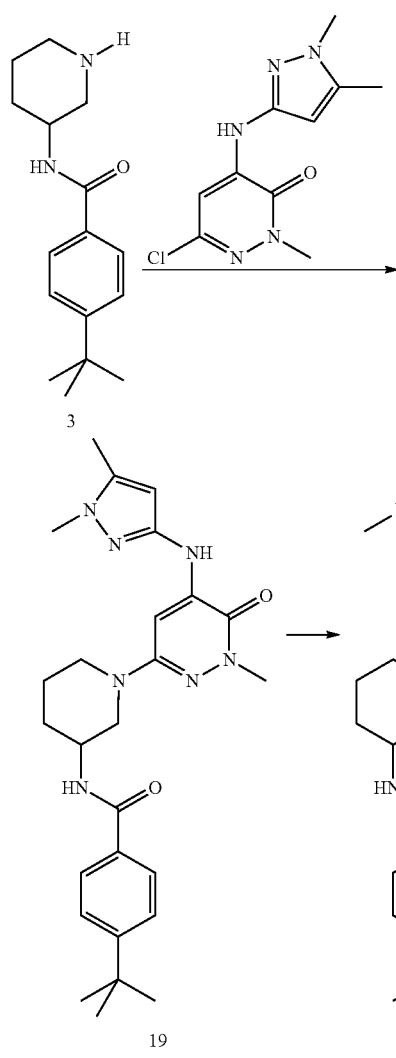
Reaction Scheme X
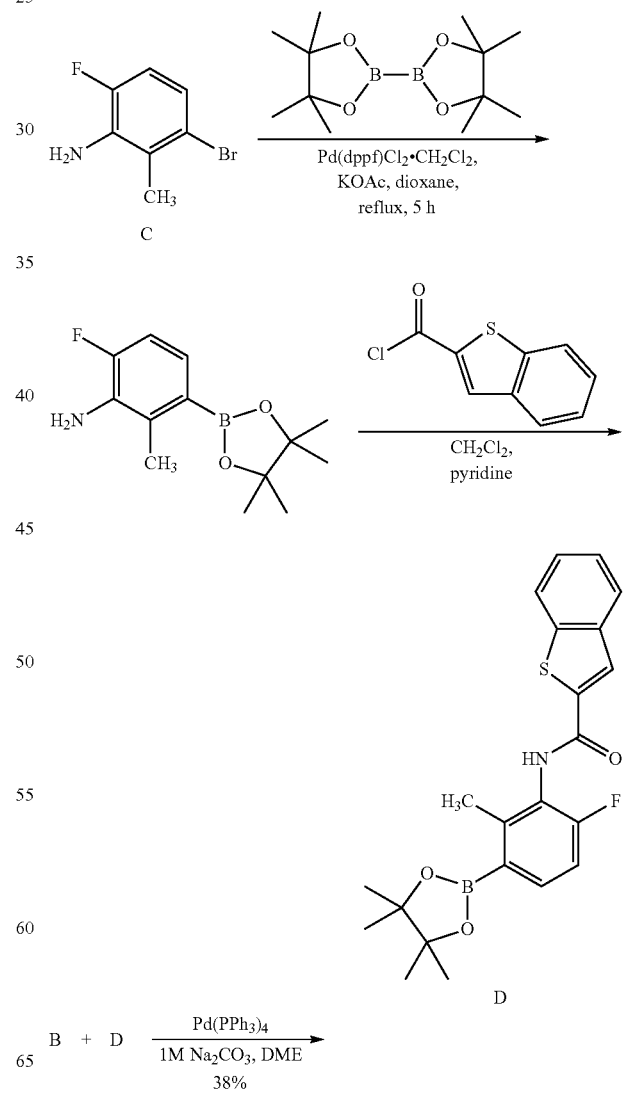
B + D → Pd(PPh₃)₄, 1M Na₂CO₃, DME, 38%

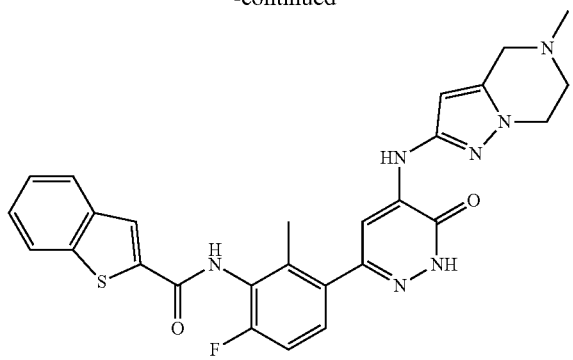

In some embodiments, compounds of any one of Formulae I, II-a, II-b, III-a, III-b, IV-a and IV-b are administered as a pharmaceutical composition or formulation. Accordingly, the invention provides pharmaceutical formulations comprising a compound of any one of Formulae I, II-a, II-b, III-a, III-b, IV-a and IV-b and pharmaceutically acceptable salts, solvates, and mixtures thereof, together with at least one pharmaceutically acceptable vehicle chosen from carriers, adjuvants, and excipients.

Pharmaceutically acceptable vehicles must be of sufficiently high purity and sufficiently low toxicity to render them suitable for administration to the animal being treated. The vehicle can be inert or it can possess pharmaceutical benefits. The amount of vehicle employed in conjunction with the compound is sufficient to provide a practical quantity of material for administration per unit dose of the compound.

Exemplary pharmaceutically acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; synthetic oils; vegetable oils, such as peanut oil, cottonseed oil, sesame oil, olive oil, and corn oil; polyols such as propylene glycol, glycerine, sorbitol, mannitol, and polyethylene glycol; alginic acid; phosphate buffer solutions; emulsifiers, such as the TWEENS; wetting agents, such as sodium lauryl sulfate; coloring agents; flavoring agents; tableting agents; stabilizers; antioxidants; preservatives; pyrogen-free water; isotonic saline; and phosphate buffer solutions.

Optional active agents may be included in a pharmaceutical composition, which do not substantially interfere with the activity of the compound of the present invention.

Effective concentrations of a compound of any one of Formulae I, II-a, II-b, III-a, III-b, IV-a and IV-b and pharmaceutically acceptable salts, solvates, and mixtures thereof, are mixed with a suitable pharmaceutical acceptable vehicle. In instances in which the compound exhibits insufficient solubility, methods for solubilizing compounds may be used. Such methods are known to those of skill in this art, and include, but are not limited to, using cosolvents, such as dimethylsulfoxide (DMSO), using surfactants, such as TWEEN, or dissolution in aqueous sodium bicarbonate.

Upon mixing or addition of the compound of any one of Formulae I, II-a, II-b, III-a, III-b, IV-a and IV-b, the resulting mixture may be a solution, suspension, emulsion or the like. The form of the resulting mixture depends upon a number of factors, including the intended mode of administration and the solubility of the compound in the chosen vehicle. The effective concentration sufficient for ameliorating the symptoms of the disease treated may be empirically determined.

Compounds of any one of Formulae I, II-a, II-b, III-a, III-b, IV-a and IV-b may be administered orally, topically, parenterally, intravenously, by intramuscular injection, by inhalation or spray, sublingually, transdermally, via buccal administration, rectally, as an ophthalmic solution, or by other means, in dosage unit formulations.

Dosage formulations suitable for oral use, include, for example, tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents, such as sweetening agents, flavoring agents, coloring agents and preserving agents, in order to provide pharmaceutically elegant and palatable preparations. In some embodiments, oral formulations contain from 0.1 to 99% of a compound of any one of Formulae I, II-a, II-b, III-a, III-b, IV-a and IV-b. In some embodiments, oral formulations contain at least 5% (weight %) of a compound of Formula I. Some embodiments contain from 25% to 50% or from 5% to 75% of a compound of any one of Formulae I, II-a, II-b, III-a, III-b, IV-a and IV-b.

orally administered compositions also include liquid solutions, emulsions, suspensions, powders, granules, elixirs, tinctures, syrups, and the like. The pharmaceutically acceptable carriers suitable for preparation of such compositions are well known in the art oral formulations may contain preservatives, flavoring agents, sweetening agents, such as sucrose or saccharin, taste-masking agents, and coloring agents.

Typical components of carriers for syrups, elixirs, emulsions and suspensions include ethanol, glycerol, propylene glycol, polyethylene glycol, liquid sucrose, sorbitol and water. Syrups and elixirs may be formulated with sweetening agents, for example glycerol, propylene glycol, sorbitol, or sucrose. Such formulations may also contain a demulcent.

Compounds of any one of Formulae I, II-a, II-b, III-a, III-b, IV-a and IV-b can be incorporated into oral liquid preparations such as aqueous or oily suspensions, solutions, emulsions, syrups, or elixirs, for example. Moreover, formulations containing these chemical entities can be presented as a dry product for constitution with water or other suitable vehicle, before use. Such liquid preparations can contain conventional additives, such as suspending agents (e.g., sorbitol syrup, methyl cellulose, glucose/sugar, syrup, gelatin, hydroxyethyl cellulose, carboxymethyl cellulose, aluminum stearate gel, and hydrogenated edible fats), emulsifying agents (e.g., lecithin, sorbitan monoleate, or acacia), non-aqueous vehicles, which can include edible oils (e.g., almond oil, fractionated coconut oil, silyl esters, propylene glycol and ethyl alcohol), and preservatives (e.g., methyl or propyl p-hydroxybenzoate and sorbic acid).

For a suspension, typical suspending agents include methylcellulose, sodium carboxymethyl cellulose, AVICEL RC-591, tragacanth and sodium alginate; typical wetting agents include lecithin and polysorbate 80; and typical preservatives include methyl paraben and sodium benzoate.

Aqueous suspensions contain the active material(s) in admixture with excipients suitable for the manufacture of aqueous suspensions. Such excipients include suspending agents, for example sodium carboxymethylcellulose, methylcellulose, hydropropylmethylcellulose, sodium alginate, polyvinylpyrrolidone, gum tragacanth and gum acacia; dispersing or wetting agents; naturally-occurring phosphatides, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol substitute, or condensation products of ethylene oxide with partial esters derived from fatty acids and hexitol anhydrides, for example polyethylene sorbitan substitute. The aqueous suspensions may also contain one or more preseivatives, for example ethyl, or n-propyl p-hydroxybenzoate.

Oily suspensions may be formulated by suspending the active ingredients in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Pharmaceutical compositions of the invention may also be in the form of oil-in-water emulsions. The oily phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate:

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above.

Tablets typically comprise conventional pharmaceutically acceptable adjuvants as inert diluents, such as calcium carbonate, sodium carbonate, mannitol, lactose and cellulose; binders such as starch, gelatin and sucrose; disintegrants such as starch, alginic acid and croscarmellose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, can be useful adjuvants for chewable tablets. Capsules (including time release and sustained release formulations) typically comprise one or more solid diluents disclosed above. The selection of carrier components often depends on secondary considerations like taste, cost, and shelf stability.

Such compositions may also be coated by conventional methods, typically with pH or time-dependent coatings, such that the compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methylcellulose phthalate, ethyl cellulose, Eudragit coatings, waxes and shellac.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be sterile injectable solution or suspension in a non-toxic parentally acceptable vehicle, for example as a solution in 1,3-butanediol. Among the acceptable vehicles that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid can be useful in the preparation of injectables.

Compounds of any one of Formulae I, II-a, II-b, III-a, III-b, IV-a and IV-b may be administered parenterally in a sterile medium. Parenteral administration includes subcutaneous injections, intravenous, intramuscular, intrathecal injection or infusion techniques. Compounds of any one of Formulae I, II-a, II-b, III-a, IV-a and IV-b, depending on the vehicle and concentration used, can either be suspended or dissolved in the vehicle. Advantageously, adjuvants such as local anesthetics, preservatives and buffering agents can be dissolved in the vehicle. In many compositions for parenteral administration the carrier comprises at least 90% by weight of the total composition. In some embodiments, the carrier for parenteral administration is chosen from propylene glycol, ethyl oleate, pyrrolidone, ethanol, and sesame oil.

Compounds of any one of Formulae I, II-a, II-b, III-a, III-b, IV-a and IV-b may also be administered in the form of suppositories for rectal administration of the drug. These compositions can be prepared by mixing the drug with a suitable non-irritating excipient that is solid at ordinary temperatures but liquid at rectal temperature and will therefore melt in the rectum to release the drug. Such materials include cocoa butter and polyethylene glycols.

Compounds of any one of Formulae I, II-a, II-b, III-a, III-b, IV-a and IV-b may be formulated for local or topical application, such as for topical application to the skin and mucous membranes, such as in the eye, in the form of gels, creams, and lotions and for application to the eye. Topical compositions may be in any form including, for example, solutions, creams, ointments, gels, lotions, milks, cleansers, moisturizers, sprays, skin patches, and the like.

Such solutions may be formulated as 0.01%-10% isotonic solutions, pH 5-7, with appropriate salts. Compounds of any one of Formulae I, II-a, II-b, III-a, III-b, IV-a and IV-b may also be formulated for transdermal administration as a transdermal patch.

Topical compositions comprising a compound of any one of Formulae I, II-a, II-b, III-a, III-b, IV-a and IV-b can be admixed with a variety of carrier materials well known in the art, such as, for example, water, alcohols, aloe vera gel, allantoin, glycerine, vitamin A and E oils, mineral oil, propylene glycol, PPG-2 myristyl propionate, and the like.

Other materials suitable for use in topical carriers include, for example, emollients, solvents, humectants, thickeners and powders. Examples of each of these types of materials, which can be used singly or as mixtures of one or more materials, are as follows:

Representative emollients include stearyl alcohol, glyceryl monoricinoleate, glyceryl monostearate, propane-1,2-diol, butane-1,3-diol, mink oil, cetyl alcohol, iso-propyl isostearate, stearic acid, iso-butyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, iso-propyl myristate, iso-propyl palmitate, iso-propyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl, linoleate, lauryl lactate, myristyl lactate, decyl oleate, and myristyl myristate; propellants, such as propane, butane, iso-butane, dimethyl ether, carbon dioxide, and nitrous oxide; solvents, such as ethyl alcohol, methylene chloride, iso-propanol, castor oil, ethylene glycol monoethyl ether, diethylene glycol monobutyl ether, diethylene glycol monoethyl ether, dimethyl sulphoxide, dimethyl formamide, tetrahydrofuran; humectants, such as glycerin, sorbitol, sodium 2-pyrrolidone-5-carboxylate, soluble collagen, dibutyl phthalate, and gelatin; and powders, such as chalk, talc, fullers earth, kaolin, starch, gums, colloidal silicon dioxide, sodium polyacrylate, tetra alkyl ammonium smectites, trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, and ethylene glycol monostearate.

Compounds of any one of Formulae I, II-a, II-b, III-a, III-b, IV-a and IV-b may also be topically administered in the form of liposome delivery systems, such as small unilamellar vesicles, large unilamellar vesicles, and multilamellar vesicles. Liposomes can be formed from a variety of phospholipids, such as cholesterol, stearylamine and phosphatidylcholines.

Other compositions useful for attaining systemic delivery of the compound include sublingual, buccal and nasal dosage forms. Such compositions typically comprise one or more of soluble filler substances such as sucrose, sorbitol and mannitol, and binders such as acacia, microcrystalline cellulose, carboxymethyl cellulose, and hydroxypropyl methylcellulose. Glidants, lubricants, sweeteners, colorants, antioxidants and flavoring agents disclosed above may also be included.

Compositions for inhalation typically can be provided in the form of a solution, suspension or emulsion that can be administered as a dry powder or in the form of an aerosol using a conventional propellant (e.g., dichlorodifluoromethane or trichlorofluoromethane).

The compositions of the present invention may also optionally comprise an activity enhancer. The activity enhancer can be chosen from a wide variety of molecules that function in different ways to enhance or be independent of therapeutic effects of the present compounds. Particular classes of activity enhancers include skin penetration enhancers and absorption enhancers.

Pharmaceutical compositions of the invention may also contain additional active agents that can be chosen from a wide variety of molecules, which can function in different ways to enhance the therapeutic effects of a compound of any one of Formulae I, II-a, II-b, III-a, III-b, IV-a and IV-b. These optional other active agents, when present, are typically employed in the compositions of the invention at a level ranging from 0.01% to 15%. Some embodiments contain from 0.1% to 10% by weight of the composition. Other embodiments contain from 0.5% to 5% by weight of the composition.

The invention includes packaged pharmaceutical formulations. Such packaged formulations include a pharmaceutical composition comprising a compound of any one of Formulae I, II-a, II-b, III-a, III-b, IV-a and IV-b and pharmaceutically acceptable salts, solvates, and mixtures thereof, and instructions for using the composition to treat a mammal (typically a human patient). In some embodiments, the instructions are for using the pharmaceutical composition to treat a patient suffering from a disease responsive to inhibition of Btk activity and/or inhibition of B-cell and/or myeloid-cell activity. The invention can include providing prescribing information; for example, to a patient or health care provider, or as a label in a packaged pharmaceutical formulation. Prescribing information may include for example efficacy, dosage and administration, contraindication and adverse reaction information pertaining to the pharmaceutical formulation.

In all of the foregoing the compounds of any one of Formulae I, II-a, II-b, III-a, III-b, IV-a and IV-b can be administered alone, as mixtures, or in combination with other active agents.

Accordingly, the invention includes a method of treating a patient, for example, a mammal, such as a human, having a disease responsive to inhibition of Btk activity, comprising administrating to the patient having such a disease, an effective amount of a compound of any one of Formulae I, II-a, II-b, III-a, III-b, IV-a and IV-b and pharmaceutically acceptable salts, solvates, and mixtures thereof.

To the extent that Btk is implicated in disease, alleviation of the disease, disease symptoms, preventative, and prophylactic treatment is within the scope of this invention. In some embodiments, compounds of any one of Formulae I, II-a, II-b, III-a, III-b, IV-a and IV-b may also inhibit other kinases, such that alleviation of disease, disease symptoms, preventative, and prophylactic treatment of conditions associated with these kinases is also within the scope of this invention.

Methods of treatment also include inhibiting Btk activity and/or inhibiting B-cell and/or myeloid-cell activity, by inhibiting ATP binding or hydrolysis by Btk or by some other mechanism, in vivo, in a patient suffering from a disease responsive to inhibition of Btk activity, by administering an effective concentration of a compound of any one of Formulae I, II-a, II-b, III-a, III-b, IV-a and IV-b and pharmaceutically acceptable salts, solvates, and mixtures thereof. An example of an effective concentration would be that concentration sufficient to inhibit Btk activity in vitro. An effective concentration may be ascertained experimentally, for example by assaying blood concentration of the compound, or theoretically, by calculating bioavailability.

In some embodiments, the condition responsive to inhibition of Btk activity and/or B-cell and/or myeloid-cell activity is cancer, a bone disorder, an allergic disorder and/or an autoimmune and/or inflammatory disease, and/or an acute inflammatory reaction.

The invention includes a method of treating a patient having cancer, a bone disorder, an allergic disorder and/or an autoimmune and/or inflammatory disease, and/or an acute inflammatory reaction, by administering an effective amount of a compound of any one of Formulae I, II-a, II-b, IV-a and IV-b and pharmaceutically acceptable salts, solvates, and mixtures thereof.

In some embodiments, the conditions and diseases that can be affected using compounds of any one of Formulae I, II-a, IV-a and IV-b, include, but are not limited to:
allergic disorders, including but not limited to eczema, allergic rhinitis or coryza, hay fever, bronchial asthma, urticaria (hives) and food allergies, and other atopic conditions;
autoimmune and/or inflammatory diseases, including but not limited to psoriasis, Crohn's disease, irritable bowel syndrome, Sjogren's disease, tissue graft rejection, and hyperacute rejection of transplanted organs, asthma, systemic lupus erythematosus (and associated glomerulonephritis), dermatomyositis, multiple sclerosis, scleroderma, vasculitis (ANCA-associated and other vasculitides), autoimmune hemolytic and thrombocytopenic states, Goodpasture's syndrome (and associated glomerulonephritis and pulmonary hemorrhage), atherosclerosis, rheumatoid arthritis, osteoarthritis, chronic Idiopathic thrombocytopenic purpura (ITP), Addison's disease, Parkinson's disease, Alzheimer's disease, Diabetes mellitus (type 1), septic shock, myasthenia gravis, Ulcerative Colitis, Aplastic anemia, Coeliac disease, Wegener's granulomatosis and other diseases in Which the cells and antibodies arise from and are directed against the individual's own tissues;

acute inflammatory reactions, including birt not limited to skin sunburn, inflammatory pelvic disease, inflammatory bowel disease, urethritis, uvitis, sinusitis, pneumonitis, encephalitis, meningitis, myocarditis, nephritis, osteomyelitis, myositis, hepatitis, gastritis, enteritis, dermatitis, gingivitis, appendicitis, pancreatitis, and cholecystitis;

cancer, including but not limited to hematological malignancies, such as B-cell lymphoma, and acute lymphoblastic leukemia, acute myelogenous leukemia, chronic myelogenous leukemia, chronic and acute lymphocytic leukemia, hairy cell leukemia, Hodgkin's disease, Non-Hodgkin lymphoma, multiple myeloma, and other diseases that are characterized by cancer of the blood or lymphatic system; and bone disorders, including but not limited to osteoporosis.

Btk is a known inhibitor of apoptosis in lymphoma B-cells. Defective apoptosis contributes to the pathogenesis and drug resistance of human leukemias and lymphomas. Thus, further provided is a method of promoting or inducing apoptosis in cells expressing Btk comprising contacting the cell with a compound of any one of Formulae I, II-a, II-b, III-a, III-b, IV-a and IV-b, pharmaceutically acceptable salts, solvates, and mixtures thereof.

The invention provides methods of treatment in which a compound of any one of Formulae I, If-a, II-b, III-a, III-b, IV-a and IV-b, and pharmaceutically acceptable salts, solvates, and mixtures thereof, or a composition (e.g., a pharmaceutical composition thereof), is the only active agent given to a patient and also includes methods of treatment in which a compound of any one of Formulae I, II-a, II-b, III-a, III-b, IV-a and IV-b, and pharmaceutically acceptable salts, solvates, and mixtures thereof, or a composition (e.g., a pharmaceutical composition thereof), is given to a patient in combination with one or more additional active agents. The additional active agent(s) can be given to a patient sequentially or consecutively with a compound or composition of the present invention.

The invention provides methods of treatment of rheumatoid arthritis, systemic lupus erythematosus, multiple sclerosis and/or asthma in which a compound of any one of Formulae I, II-a, II-b, III-a, III-b, IV-a and IV-b, and pharmaceutically acceptable salts, solvates, and mixtures thereof, is the only active agent given to a patient and also includes methods of treatment of rheumatoid arthritis, systemic lupus erythematosus, multiple sclerosis and/or asthma in which a compound of any one of Formulae I, II-a, II-b, III-a, III-b, IV-a and IV-b, and pharmaceutically acceptable salts, solvates, and mixtures thereof, is given to a patient in combination with one or more additional active agents.

Thus in one embodiment the invention provides a method of treating cancer, a bone disorder, an allergic disorder and/or an autoimmune and/or inflammatory disease, and/or an acute inflammatory reaction, which comprises administering to a patient in need thereof an effective amount of a compound of any one of Formulae I, II-a, II-b, III-a, III-b, IV-a and IV-b and pharmaceutically acceptable salts, solvates, and mixtures thereof, together with a second active agent, which can be useful for treating a cancer, a bone disorder, an allergic disorder and/or an autoimmune and/or inflammatory disease, and/or an acute inflammatory reaction. For example the second agent may be an anti-inflammatory agent. Treatment with the second active agent may be prior to, concomitant with, or following treatment with a compound of any one of Formulae I, II-a, II-b, III-a, III-b, IV-a and IV-b and pharmaceutically acceptable salts, solvates, and mixtures thereof. In certain embodiments, a compound of any one of Formulae I, II-a, II-b, III-a, III-b, IV-a and IV-b and pharmaceutically acceptable salts, solvates, and mixtures thereof, is combined with another active agent in a single dosage form. Suitable antitumor therapeutics that may be used in combination with a compound of any one of Formulae I, II-a, II-b, IV-a and IV-b include, but are not limited to, chemotherapeutic agents, for example mitomycin C, carboplatin, taxol, cisplatin, paclitaxel, etoposide, doxombicin, or a combination comprising at least one of the foregoing chemotherapeutic agents. Radiotherapeutic antitumor agents may also be used, alone or in combination with chemotherapeutic agents.

Compounds of any one of Formulae I, II-a, II-b, III-a, III-b, IV-a and IV-b can be useful as chemosensitizing agents, and, thus, can be useful in combination with other chemotherapeutic drags, in particular, drags that induce apoptosis.

A method for increasing sensitivity of cancer cells to chemotherapy, comprising administering to a patient undergoing chemotherapy a chemotherapeutic agent together with a compound of any one of Formulae I, II-a, II-b, III-a, III-b, IV-a and IV-b and pharmaceutically acceptable salts, solvates, and mixtures thereof, in an amount sufficient to increase the sensitivity of cancer cells to the chemotherapeutic agent is also provided herein.

Examples of other chemotherapeutic drugs that can be used in combination with the present compounds include topoisomerase I inhibitors (camplothesin or topotecan), topoisomerase II inhibitors (e.g. daunomycin and etoposide), alkylating agents (e.g. cyclophosphamide, melphalan and BCNU), tubulin directed agents (e.g. taxol and vinblastine), biological agents (e.g. antibodies such as anti CD20 antibody, IDEC 8, immunotoxins, and cytokines), tyrosine kinase inhibitors (e.g., Gleevac) and the like. Such examples of other chemotherapeutic drugs that can be used in combination with the present compounds also include R—CHOP (cyclophosphamide (also called Cytoxan/Neosar), doxorubicin (or Adriamycin), vincristine (Oncovin) and prednisolone), ICE (ifosfamide, carboplatin, and etoposide), DHAP (dexamethasone, cisplatin, and cytarabine), ESHAP (etoposide, methylprednisolone, cytarabine, and cisplatin), gemcitabine, Rituxan®, Treanda®, Chlorambucil, fludarabine, alemtuzumab, and the like.

Included herein are methods of treatment, for example for treating autoimmune and/or inflammatory disease's, in which a compound of any one of Formulae I, II-a, II-b, III-a, III-b, IV-a and IV-b and pharmaceutically acceptable salts, solvates, and mixtures thereof, is administered in combination with an anti-inflammatory agent. Anti-inflammatory agents include but are not limited to NSAIDs, non-specific and COX-2 specific cyclooxygenase enzyme inhibitors, gold compounds, corticosteroids, methotrexate, tumor necrosis factor receptor (TNF) receptors antagonists, immunosuppressants and methotrexate.

Examples of NSAIDs include, but are not limited to ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors (i.e., a compound that inhibits COX-2 with an $IC_{50}$ that is at least 50-fold lower than the $IC_{50}$ for COX-1) such as celecoxib, valdecoxib, lumiracoxib, etoricoxib and/or rofecoxib.

In a further embodiment, the anti-inflammatory agent is a salicylate. Salicylates include but are not limited to acetylsalicylic acid or aspirin, sodium salicylate, and choline and magnesium salicylates.

The anti-inflammatory agent may also be a corticosteroid. For example, the corticosteroid may be chosen from cortisone, dexamethasone, methylprednisolone, prednisolone, prednisolone sodium phosphate, and prednisone.

In additional embodiments the anti-inflammatory therapeutic agent is a gold compound such as gold sodium thiomalate or auranofin.

The invention also includes embodiments in which the anti-inflammatory agent is a metabolic inhibitor such as a dihydrofolate reductase inhibitor, such as methotrexate or a dihydroorotate dehydrogenase inhibitor, such as leflunomide. The second anti-inflammatory agent that may be used in combination with any one or more compounds of the present invention includes biologics and oral agents for treating rheumatoid arthritis.

Other embodiments of the invention pertain to combinations in which at least one anti-inflammatory compound is an anti-C5 monoclonal antibody (such as eculizumab or pexelizumab); a TNF antagonist, such as entanercept, infliximab, and adalimumab (Humira®) which are anti-TNF alpha monoclonal antibodies.

Still other embodiments of the invention pertain to combinations in which at least one active agent is an immunosuppressant compound such as methotrexate, leflunomide, cyclosporine, tacrolinaus, azathioprine, or mycophenolate mofetil.

Still other embodiments of the invention pertain to comminations with Rituxan® (Rituximab) or other agents that work by selectively depleting CD20+ B-cells.

Dosage levels of the order, for example, of from 0.1 mg to 140 mg per kilogram of body weight per day can be useful in the treatment of the above-indicated conditions (0.5 mg to 7 g per patient per day). The amount of active ingredient that may be combined with the vehicle to produce a single dosage form will vary depending upon the host treated and the particular mode of administration. Dosage unit forms will generally contain from 1 mg to 500 mg of an active ingredient.

Frequency of dosage may also vary depending on the compound used and the particular disease treated. In some embodiments, for example, for the treatment of an allergic disorder and/or autoimmune and/or inflammatory disease, a dosage regimen of 4 times daily or less is used In some embodiments, a dosage regimen of 1 or 2 times daily is used. It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease in the patient undergoing therapy.

A labeled form of a compound of the invention can be used as a diagnostic for identifying and/or obtaining compounds that have the function of modulating an activity of a kinase as described herein. The compounds of the invention may additionally be used for validating, optimizing, and standardizing bioassays.

By "labeled" herein is meant that the compound is either directly or indirectly labeled with a label which provides a detectable signal, e.g., radioisotope, fluorescent tag, enzyme, antibodies, particles such as magnetic particles, chemiluminescent tag, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly proVide a detectable signal.

The invention is further illustrated by the following non-limiting examples.

EXAMPLE 1

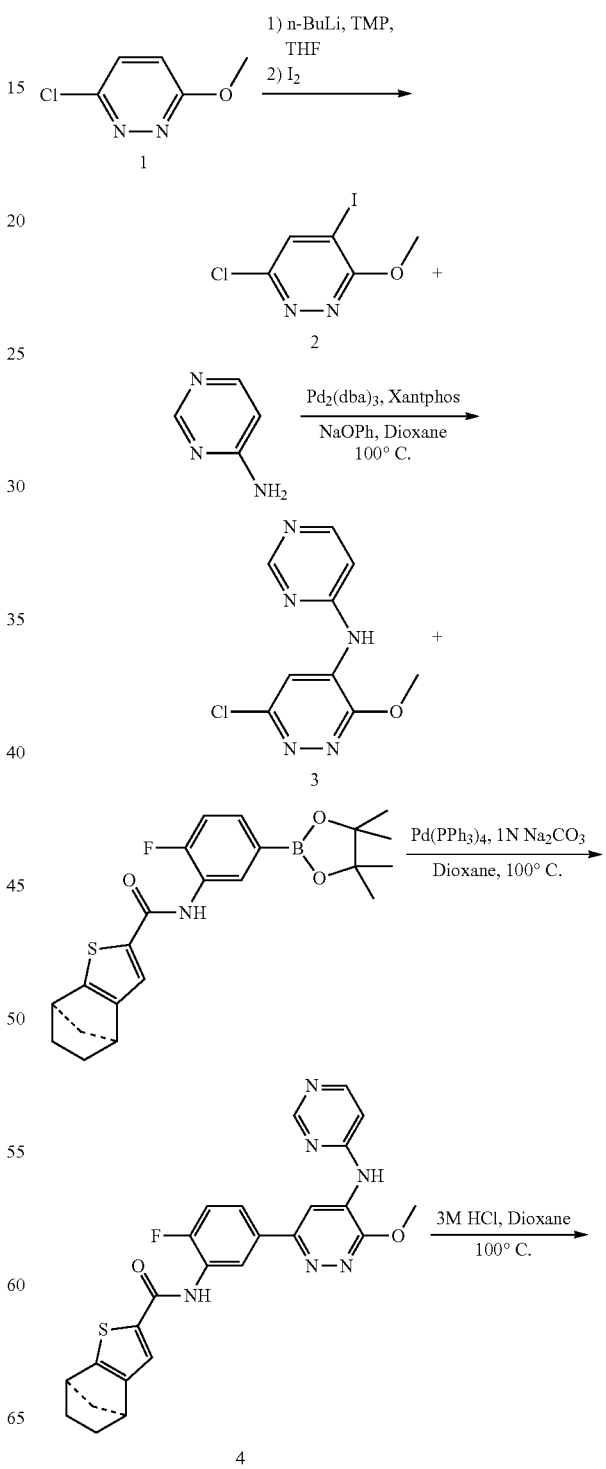

-continued

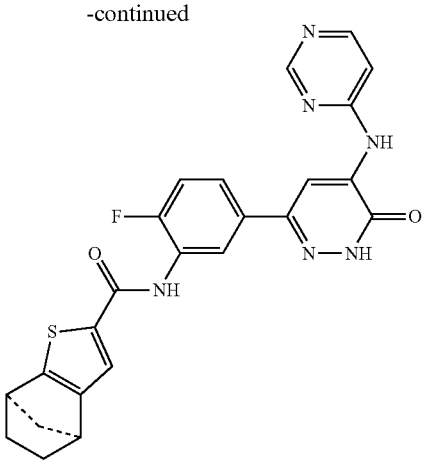

5

6-Chloro-4-iodo-3-methoxypyridazine (2)

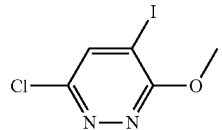

2

In a flask containing THF (350 mL) at −30° C. under nitrogen was added 26 mL (76.1 mmol. 2.93M n-BuLi in hexanes. 2,2,6,6-tetramethylpiperidine (12.9 mL, 76.1 mmol) was then added dropwise and the resulting solution was allowed to warm to 0° C. over 50 min. The solution was then cooled to −78° C. and there was added dropwise 3-chloro-6-methoxypyridazine (1) (5.0 g, 34.6 mmol) in 50 mL THF and the resulting solution stirred at −78° C. for 30 min. Iodine (9.3 g) was then added in three portions and the solution stirred at −78° C. for 2 hrs. The reaction was quenched by the addition of saturated aqueous sodium thiosulfate solution and allowed to warm to room temperature, then diluted with CH$_2$Cl$_2$ and water, the CH$_2$Cl$_2$ layer separated, the aqueous layer extracted once more with CH$_7$Cl$_2$, and the combined CH$_2$Cl$_2$ layers washed with brine, dried over Na$_2$SO$_4$, filtered and concentrated in vacuo. The crude product was purified by column chromatography (silica) eluting with hexane/ethyl acetate to give desired product 2, 5.6 g (60%), ~95% desired regioisomer.

6-Chloro-3-methoxy-N-(pyrimidin-4-yl)pyridazin-4-amine (3)

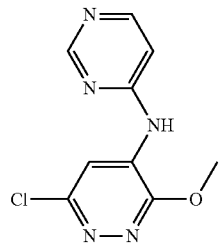

3

In a dried pressure flask was placed compound 2 (1.0 g, 3.70 mmol), 4-aminopyrimidine (352 mg, 3.7 mmol), sodium phenoxide (860 mg, 7.4 mmol), Pd$_2$(dba)$_3$ (170 mg, 5 mol %), and Xantphos (150 mg, 7 mol %). The flask was evacuated and filled with N$_2$ 3× and then 20 mL anhydrous dioxane was added, The mixture was heated at 100° C. for 12 hours. The cooled mixture was diluted with ethyl acetate and water, filtered, separated, the ethyl acetate layer extracted 1× with ethyl acetate, the combined ethyl acetate layers washed with brine 4×, dried over Na$_2$SO$_4$, filtered and concentrated. The product was purified by column chromatography (silica) CH$_2$Cl$_2$/MeOH to give 3.

(1R,7S)—N-(2-Fluoro-5-(6-methoxy-5-(pyrimidin-4-ylamino) pyridazin-3-yl)phenyl)-4,7-methano-4,5,6,7-tetrahydrobenzo[b]thiophene-2-carboxamide (4)

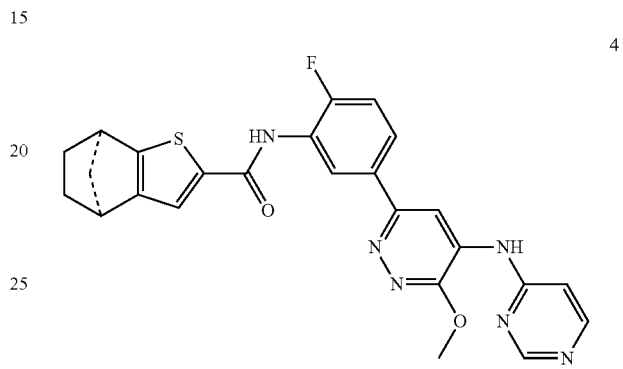

4

In a pressure flask was placed compound 3 (230 mg, 0.968 mmol), (1R, 7S)—N-(2-fluoro-5-(4,4,5,5-tetramethyl-1,3,2-dioxaborolan-2-yl)phenyl)-4,7-methano-4,5,6,7-tetrahydrobenzo-[b]thiophene-2-carboxamide (440 mg, 1.065 mmol), and tetrakis(triphenylphosphine palladium(0) (56 mg, 5 mol %). The flask was evacuated and filled with N$_2$ three times. Then there was added 8 mL anh. dioxane followed by 1M aq. Na2CO3 (2.4 mL, 2.5 eq). The mixture was heated to 100° C. for 12 hours, then allowed to cool and diluted with ethyl acetate and water, filtered, the ethyl acetate separated, the aqueous layer extracted with ethyl acetate, the combined ethyl acetate layers washed with four times with brine, dried over Na$_2$SO$_4$, filtered and concentrated. Purified by column chromatography: Biotage 25M KP NH column to give 4, 370 mg (78%).

(1R,7S)—N-(2-fluoro-5-(6-oxo-5-(pyrimidin-4-ylamino)-1,6-dihydropyridazin-3-yl)phenyl)-4,7-methano-4,5,6,7-tetrahydrobenzo[b]thiophene-2-carboxamide (5)

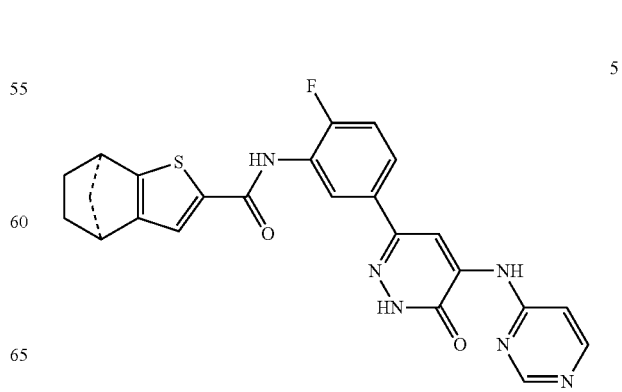

5

In a pressure flask was placed 400 mg of compound 4, 10 mL dioxane and 5 mL 3N HCl were added, the flask sealed and heated to 100° C. until reaction complete (reaction times vary, typically no less than 12 hrs). The mixture was allowed to cool to room temperature, made basic by addition of 3M NaOH, diluted with ethyl acetate, and the ethyl acetate layer separated. The aqueous layer was extracted with ethyl acetate, washed with brine four times, dried over $Na_2SO_4$, filtered and concentrated. Purified by prep HPLC to give 5, exact mass calcd. 474 found 474.92.

EXAMPLE 2

N-{6-fluoro-2-methyl-3-[5-({5-methyl-4H,5H,6H, 7H-pyrazolo[1,5-a]pyrazin-2-yl}amino)-6-oxo-1,6-dihydropyridazin-3-yl]phenyl}-1-benzothiophene-2-carboxamide

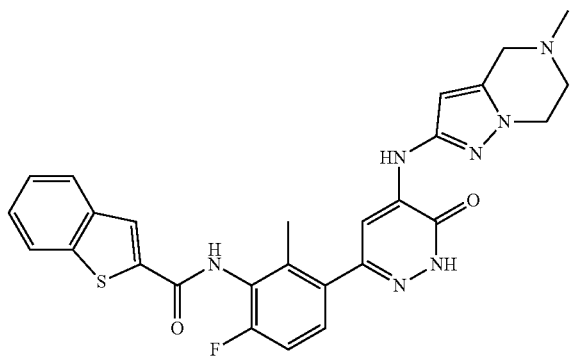 [SMILES: Cc1c(-c2cc(Nc3cc4n(n3)CCN(C)C4)c(=O)[nH]n2)ccc(F)c1NC(=O)c1cc2ccccc2s1]

Synthesis, of 5-methyl-4,5,6,7-tetrahydropyrazolo[1,5-a]pyrazin-2-amine

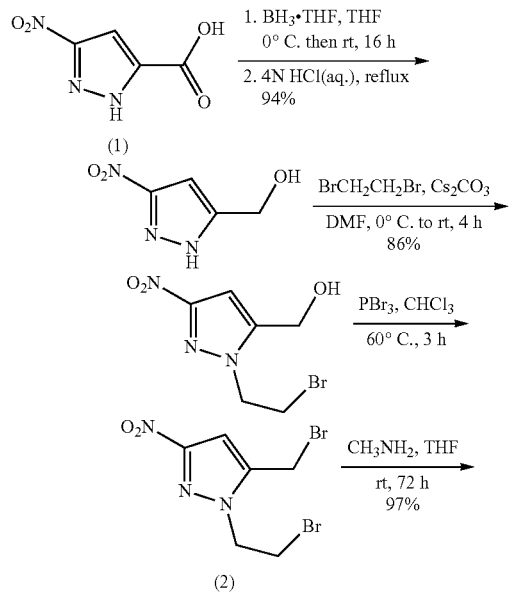

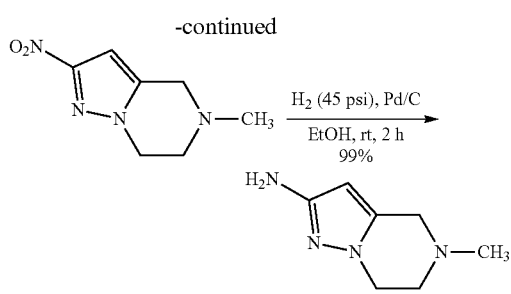

(3-Nitro-1H-pyrazol-5-yl)methanol

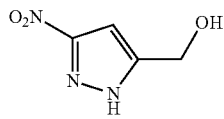

A 3-L three-neck round-bottomed flask equipped with a mechanical stirrer, addition funnel and nitrogen inlet was purged with nitrogen and charged with 3-nitropyrazole-5-carboxylic acid (28.0 g, 178 mmol) and THF (420 mL) and cooled to −5° C. using an ice/acetone bath. Borane-THF complex solution (1.0 M, 535 mL, 535 mmol) was added at a rate that maintained the internal reaction temperature below 5° C. After the addition was complete the cooling bath was removed and the reaction was stirred at room temperature for 18 h. After this time the reaction was cooled to −5° C. using an ice/acetone bath, water (70 mL) and 4N hydrochloric acid (70 mL) was added and the reaction was stirred at reflux for 1 h in order to destroy the borane complex with pyrazole. The reaction was cooled to room temperature and concentrated under reduced pressure to a volume of approximately 30 mL. Ethyl acetate (175 mL) was added and the mixture stirred for 15 min. The aquedus layer was separated and extracted with ethyl acetate (4×200 mL). The combined organic layers were washed with saturated aqueous sodium bicarbonate (2×50 mL), brine (50 mL) and dried over sodium sulfate; the drying agent was removed by filtration, and the filtrate concentrated Under reduced pressure to afford (3-nitro-1H-pyrazol-5-yl)methanol in a 94% yield (24.0 g) as a light yellow solid: $^1H$ NMR (300 MHz, DMSO-$d_6$) δ 13.90 (br s, 1H), 6.87 (s, 1H), 5.58 (t, 1H, J=5.4 Hz), 4.53 (d, 2H, J=5.1 Hz); MS (ESI+) m/z 144.0 (M+H).

(2-Bromoethyl)-3-nitro-1H-pyrazol-5-yl)methanol

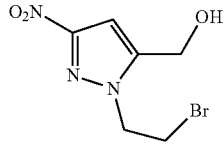 [SMILES: O=[N+]([O-])c1cc(CO)n(CCBr)n1]

A 1-L three-necked round-bottomed flask equipped with a mechanical stirrer and thermoregulator was purged with nitrogen and charged with (3-nitro-1H-pyrazol-5-yl)methanol (25.0 g, 175 mmol), DMF (250 mL), and cesium carbonate (70.0 g, 215 mmol) was heated at 104° C. for 5 min. The reaction mixture was then cooled to 0° C. using an ice/acetone bath and dibromoethane (329 g, 1.75 mol) was added portionwise (no exotherm). The reaction was stirred at 0° C. for 1 then at room temperature for 4 h. After this time a solution of $KH_2PO_4$ (40 g) in water (400 mL) was added slowly. The reaction mixture stirred at room temperature for 30 min. Ethyl acetate (450 mL) was added and the aqueous layer was separated and extracted with ethyl acetate (2×100 mL). The combined organic layers were washed with water (200 mL), brine (200 mL), dried over sodium sulfate, and the drying agent was removed by filtration. The filtrate was concentrated under reduced pressure to afford an 86% yield (37.5 g) of crude (1-(2-bromoethyl)-3-nitro-1H-pyrazol-5-yl)methanol as an orange oil: $^1$H NMR (300 MHz, CDCl$_3$) δ 6.85 (s, 1H), 4.82 (d, 2H, J=5.4 Hz), 4.66 (t, 2H, J=6.3 Hz), 3.83 (t, 2H, J=6.3 Hz); MS (ESI+) m/z 249.9 (M+H). This material was used in the following step directly.

1-(2-Bromoethyl)-5-(bromomethyl)-3-nitro-1H-pyrazole

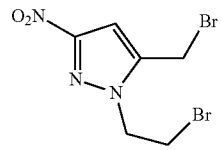 [SMILES: O=[N+]([O-])c1cc(CBr)n(CCBr)n1]

A 500-mL three-necked round-bottomed, flask equipped with a magnetic stirrer, nitrogen inlet and reflux condenser was purged with nitrogen and charged with (1-(2-bromoethyl)-3-nitro-1H-pyrazol-5-yl)methanol (37.0 g, 148 mmol) and chloroform (160 mL). The reaction was cooled to −5° C. using an ice/acetone bath and phosphorous tribromide (40.0 g, 148 mmol) was added portionwise. The cooling bath was removed and the reaction stirred at reflux for 2 h. After this time, the reaction was cooled to −5° C. and saturated aqueous sodium bicarbonate (250 mL) was added until a pH of 8.5 was reached. The mixture was extracted with ethyl acetate (3×150 mL) and the combined organic layers were washed with saturated aqueous sodium carbonate (2×50 mL), brine (75 mL), dried over sodium sulfate and the drying agent was removed by filtration. The filtrate was concentrated under reduced pressure to afford a yellow residue that was dissolved with gentle heating in methylene chloride (60 mL). Hexanes (approximately 20 mL) was added and the solution became cloudy. The mixture was heated until a solid precipitate formed, methylene chloride (9 mL) was added and the solution became clear. The solution was left to cool to room temperature and after 4 h the resulting crystals were collected by vacuum filtration. The filter cake was washed with a ice cold 1:2 mixture of methylene chloride:hexanes (2×20 mL) to afford 1-(2-bromoethyl)-5-(bromomethyl)-3-nitro-1H-pyrazole (19.7 g). The combined filtrates were evaporated and the procedure was performed again to afford an additional 9.70 g of 1-(2-bromoethyl)-5-(bromomethyl)-3-nitro-1H-pyrazole. The solids were combined and dried under high vacuum for 18 h to afford a 57% yield (26.0 g) of 1-(2-bromoethyl)-5-(bromomethyl)-3-nitro-1H-pyrazole as white crystals: mp 95-97° C.; $^1$H NMR (300 MHz, CDCl$_3$) δ 6.93 (s, 1H), 4.63 (t, 2H, J=6.0 Hz), 4.54 (s, 214), 3.86 (t, 2H, J=6.0 HZ).

5-Methyl-2-nitro-4,5,6,7-tetrahydropyrazolo[1,5-a]pyrazine

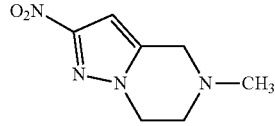

A 1-L Single-neck round-bottomed flask equipped with a magnetic stirrer and nitrogen inlet was charged with THF (350 mL), 1-(2-bromoethyl)-5-(bromomethyl)-3-nitro-1H-pyrazole (10.0 g, 32.2 mmol), 2M methylamine solution in THF (113 mL, 225 mmol) and stirred at room temperature for 72 h. After this time the reaction was concentrated to dryness under reduced pressure, and the resulting solid was stirred with a mixture of ethyl acetate (75 mL) and 10% aqueous potassium carbonate (75 mL). The aqueous layer was separated and extracted with ethyl acetate (2×75 mL). The combined organic extracts were washed with 10% aqueous potassium carbonate (75 mL), followed by brine (50 mL) and (hied over sodium sulfate. The drying agent was removed by filtration, and the filtrate concentrated under reduced pressure to afford 5-methyl-2-nitro-4,5,6,7-tetrahydropyrazolo[1,5-a]pyrazine in a 97% yield (5.70 g) as a yellow solid: $^1$H NMR (300 MHz, CDCl$_3$) δ 6.62 (s, 1H), 4.28 (t, 2H, J=5.4 Hz), 3.67 (s, 2H), 2.95 (t, 2H, J=5.4 Hz), 2.52 (s, 3H); MS (EST+) m/z 183.0 (M+H).

5-Methyl-4,5,6,7-tetrahydropyrazolo[1,5-a]pyrazin-2-amine

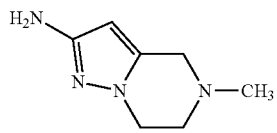

A 500-mL Parr reactor bottle was purged with nitrogen and charged with 10% palladium on carbon (50% wet, 800 mg dry weight) and a solution of 5-methyl-2-nitro-4,5,6,7-tetrahydropyrazolo[1,5-a]pyrazine (4.00 g, 2.20 mmol) in ethanol (160 mL). The bottle was attached to Parr hydrogenator, evacuated, charged with hydrogen gas to a pressure of 45 psi and shaken for 2 h. After this time, the hydrogen was evacuated, and nitrogen was charged into the bottle. Celite 521 (1.0 g) was added, and the mixture was filtered through a pad of Celite 521. The filter cake was washed with ethanol (2×75 mL), and the combined filtrates were concentrated to dryness under reduced pressure to afford a 99% yield of 5-methyl-4,5,6,7-tetrahydropyrazolo[1,5-a]pyrazin-2-amine (3.31 g) as an orange solid: $^1$H NMR (300 MHz, CDCl$_3$) δ 5.34 (s, 1H), 3.98 (t, 2H, J=5.4 Hz), 3.52 (s, 3H), 2.84 (t, 2H, J=5.7 Hz), 2.45 (s, 3H); MS (EST+) m/z 153.1 (M+H).

6-Chloro-4-(5-methyl-4,5,6,7-tetrahydropyrazolo[1,5-a]pyrazin-2-ylamino)pyridazin-3(2H)-one

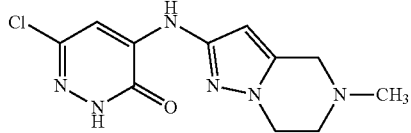 [SMILES: CN1CCn2nc(Nc3cc(Cl)n[nH]c3=O)cc2C1]

A 50-mL single-neck round-bottomed flask equipped with a magnetic stirrer, reflux condenser and nitrogen inlet was charged with 1,4-dioxane (5.0 mL), 5-methyl-4,5,6,7-tetrahydropyrazolo[1,5-a]pyrazin-2-amine (152 mg, 1.00 mmol), 4-bromo-6-chloropyridazin-3(2H)-one (209 mg, 1.00 mmol) and a 1 M THF solution of LiHMDS (5.0 mL, 5.00 mmol). After bubbling nitrogen through the resulting solution for 30 min, Xantphos (49 mg, 0.05 mmol) and tris(dibenzylideneacetone)dipalladium(0) (59 mg, 0.085 mmol) were added, and the reaction mixture was heated at reflux for 3 h. After this time, the reaction was cooled to room temperature, and water (10 mL) was added, The pH was adjusted to 6.5 with 2 N hydrochloric acid. The resulting precipitate was collected by vacuum filtration, washed with water (2×25 mL), absorbed on silica gel and purified by flash chromatography to afford a 74% yield (210 mg) of 6-chloro-4-(5-methyl-4,5,6,7-tetrahydropyrazolo[1,5-a]pyrazin-2-ylamino)pyridazin-3(2H)-one as a light brown solid: $^1$H NMR (300 MHz, DMSO-d$_6$) δ 12.94 (s, 1H), 9.55 (s, 1H), 7.68 (s, 1H), 5.96 (s, 1H), 4.04 (t, 1H, J=5.7 Hz), 3.53 (s, 2H), 2.82 (t, 2H, J=5.7 Hz), 2.36 (s, 3H); MS (ESI+) m/z 281.1 (M+H).

1-Bromo-4-fluoro-2-methyl-3-nitrobenzene (C)

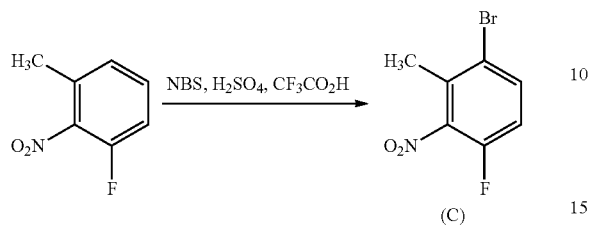

A 250 mL single neck flask equipped with magnetic stirrer was charged with 3-fluoro-2-nitrotoluene (4.75 g, 30.6 mmol) and trifluoroacetic acid (20 mL). Sulfuric acid (96%, 10 mL) was added dropwise over 10 minutes at 0° C. followed by N-bromosuccinimide (8.12 g, 45.6 mmol) in portions over 15 min (causing an exotherm of 3° C.). The reaction was stirred at 0° C. for 20 min and then stirred at mom temperature for 3.5 h. After this time, the reaction mixture was poured in to a 1:1 mixture of ice/water (500 mL), diluted with 95:5 hexanes/methylene chloride (250 mL) and the layers were separated. The aqueous layer was extracted with hexanes (100 mL) and the combined organic layers were washed with water (2×100 mL), saturated aqueous sodium bicarbonate (100 mL), brine (100 mL) and dried over sodium sulfate. The drying agent was removed by filtration, and the filtrate was concentrated under reduced pressure. The crude product was suspended in hexanes (40 mL) and heated until dissolved. The solution was evaporated to a volume to 20 mL and allowed to cool to room temperature overnight. The product was filtered and washed with cold hexanes (3×2 mL) to afford (C) (4.29 g, 60%) as a yellow crystalline solid. The filtrate was concentrated to dryness and the residue was dissolved in hot hexanes (5 mL). After cooling to room temperature, stirring for 2 h, and filtering, an additional 1.30 g of C (18%) was isolated.

3-Bronco-6-fluoro-2-methylaniline

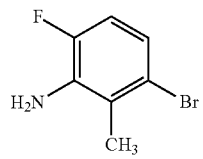

A 100-mL single-neck round-bottomed flask equipped with a magnetic stirrer, reflux condenser and nitrogen inlet was charged with 1-bromo-4-fluoro-2-methyl-3-nitrobenzene (700 mg, 2.58 mmol), tin(11) chloride dihydrate (2.62 g, 11.6 mmol), hydrochloric acid (6.5 mL) and methanol (6.5 mL), and the reaction mixture was heated at 40° C. for 2 h. After this time, potassium carbonate was added to adjust the pH of the solution to 12, and the resulting suspension was extracted with methylene chloride (2×50 mL). The organic extracts were combined and dried over sodium sulfate, filtered and concentrated under reduced pressure. The resulting residue was purified by flash chromatography to afford 3-bromo-6-fluoro-2-methylaniline in a 98% yield (598 mg) as a yellow solid: mp 49-50° C.; $^1$H NMR (500 MHz, CDCl$_3$) δ 6.91 (dd, 1H, T=9.0, 5.0 Hz), 6.76 (dd, 1H, J=10.0, 9.0 Hz), 3.77 (bs, 2H), 2.28 (s, 3H); MS (ESI+) m/z 203.9 (M+H).

6-fluoro-2-methyl-3-(4,4,5,5-tetramethyl-1,3,2-dioxaborolan-2-yl)aniline

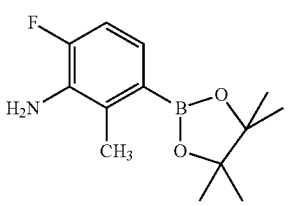 [SMILES: Cc1c(B2OC(C)(C)C(C)(C)O2)ccc(F)c1N]

A 500-mL round-bottomed flask equipped with a magnetic stirrer, reflux condenser and nitrogen inlet was charged with 1,4-dioxane (140 mL), 3-bromo-6-fluoro-2-methylaniline (4 g, 19.6 mmol), bis(pinacolato)diboron (6.0 g, 23.5 mmol) and potassium acetate (5.8 g, 58.8 mmol). After bubbling niuogen through the resulting solution for 30 min, dichloro 1,1'-bis (diphenylphosphino) ferrocene palladium (II) dichloromethane adduct (800 mg, 0.98 mmol) was added, and the reaction mixture was heated to 100° C. for 6 h. After this time, the reaction was cooled to room temperature, and water (50 mL) was added. The aqueous layer was extracted with ethyl acetate (2×25 mL). The combined organics were washed with brine (1×50 mL), dried with sodium sulfate, absorbed on silica gel and purified by flash chromatography to afford a 70% yield (3.45 g) of 6-fluoro-2-methyl-3-(4,4,5,5-tetramethyl-1,3,2-dioxaborolan-2-yl)aniline.

N-(6-fluoro-2-methyl-3-(4,4,5,5-tetramethyl-1,3,2-dioxaborolan-2-yl)phenyl)benzo[b]thiophene-2-carboxamide

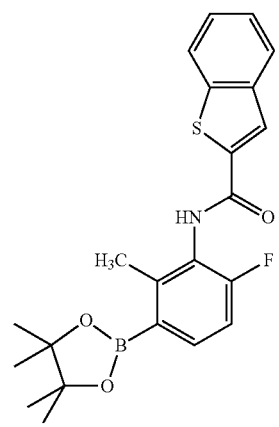 [SMILES: Cc1c(B2OC(C)(C)C(C)(C)O2)ccc(F)c1NC(=O)c1cc2ccccc2s1]

A 200-mL single-neck round-bottomed flask equipped with a magnetic stirrer was purged with nitrogen, charged with 6-fluoro-2-methyl-3-(4,4,5,5-tetramethyl-1,3,2-dioxaborolan-2-yl)aniline (3.45 g, 13.7 mmol), methylene chloride (85 mL), and pyridine (3 mL) and cooled to 0° C. To the resulting solution, benzo[b]thiophene-2-carbonyl chloride (2.7 g, 13.7 mmol) was. The reaction was warmed to room temperature and stirred for 1 h. After this time, aqueous HCl (1M, 50 mL) was added to the reaction. The separated aqueous layer was extracted with dichloromethane (2×25 mL).

The combined organics were washed with aqueous HCl (1M, 2×50 mL), water (1×50 mL) and brine (50 mL), dried over sodium sulfate; filtered and concentrated under reduced pressure. The resulting crude white solid (5.6 g, 99% yield) was used in the next step without further purification.

N-{6-fluoro-2-methyl-3-[5-({5-methyl-4H,5H,6H, 7H-pyrazolo[1,5-a]pyrazin-2-yl}amino)-6-oxo-1,6-dihydropyridazin-3-yl]phenyl}-1-benzothiophene-2-carboxamide A microwave tube equipped with a magnetic stirrer was charged with 6-chloro-4-(5-methyl-4,5,6,7-tetrahydropyrazolo[1,5-a]pyrazin-2-ylamino)pyridazin-3(2H)-one (225 mg, 0.80 mmol), N-(6-fluoro-2-methyl-3-(4,4,5,5-tetramethyl-1,3,2-dioxaborolan-2-yl)phenyl)benzo[b]thiophene-2-carboxamide (463 mg, 1.13 mmol), DME (5 mL) and 1M aqueous sodium carbonate (2 mL). After bubbling Argon while sonicating for 30 sec, Pd(PPh3)4 (65 mg, 0.06 mmol) was added. The mixture was subjected to microwave irradiation at 150° C. for 20 min. After this time, ethyl acetate (10 mL) and water (10 mL) were added. The separated aqueous layer was extracted with ethyl acetate (2×10 mL). The combined organics were washed with brine (50 mL), dried over sodium sulfate, filtered and concentrated under reduced pressure. The resulting residue was purified by column chromatography to afford the title compound N-{6-fluoro-2-methyl-3-[5-({5-methyl-4H,5H,6H,7H-pyrazolo[1,5-a]pyrazin-2-yl}amino)-6-oxo-1,6-dihydropyridazin-3-yl]phenyl}-1-benzothiophene-2-carboxamide (211 mg) in 50% yield.

EXAMPLE 3

The following compounds were prepared following procedures similar to those described in Examples 1-2 and 11-15.

| Structure | Name | MW calcd | MH + m/z obs |
|---|---|---|---|
| 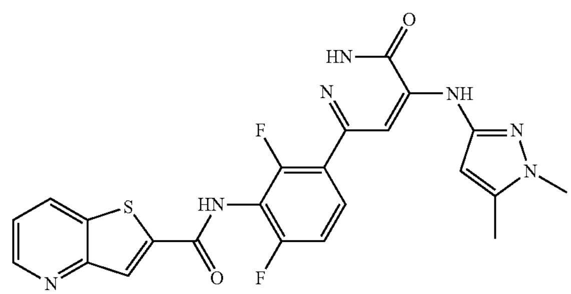 [SMILES: Cc1cc(N/C(=C/C(=N)c2ccc(F)c(NC(=O)c3cc4ncccc4s3)c2F)C(N)=O)nn1C] | N-(3-{5-[(1,5-dimethyl-1H-pyrazol-3-yl)amino]-6-oxo-1,6-dihydropyridazin-3-yl}-2,6-difluorophenyl)thieno[3,2-b]pyridine-2-carboxamide | 493 | 494.1 |
| 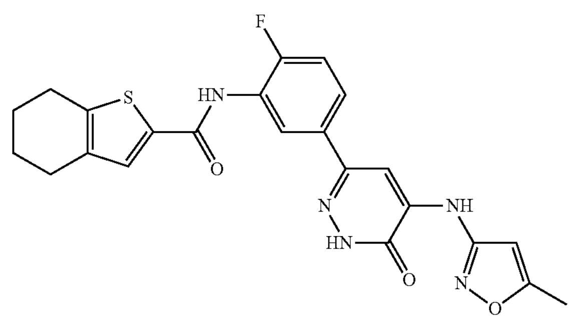 [SMILES: Cc1cc(Nc2cc(-c3ccc(F)c(NC(=O)c4cc5c(s4)CCCC5)c3)n[nH]c2=O)no1] | N-(2-fluoro-5-{5-[(5-methyl-1,2-oxazol-3-yl)amino]-6-oxo-1,6-dihydropyridazin-3-yl}phenyl)-4,5,6,7-tetra hydro-1-benzothiophene-2-carboxamide | 465 | 465.98 |
| 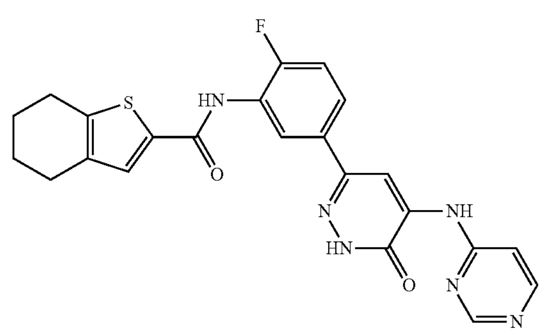 [SMILES: O=C(Nc1cc(-c2cc(Nc3ccncn3)c(=O)[nH]n2)ccc1F)c1cc2c(s1)CCCC2] | N-{2-fluoro-5-[6-oxo-5-(pyrimidin-4-ylamino)-1,6-dihydropyridazin-3-yl] phenyl}-4,5,6,7-tetrahydro-1-benzothiophene-2-carboxamide | 462 | 463 |

-continued

| Structure | Name | MW calcd | MH + m/z obs |
|---|---|---|---|
| 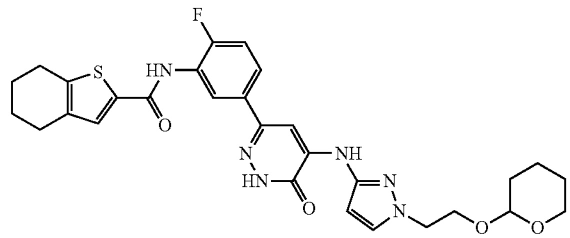 [SMILES: O=C(Nc1cc(-c2cc(Nc3ccn(CCOC4CCCCO4)n3)c(=O)[nH]n2)ccc1F)c1cc2c(s1)CCCC2] | N-{2-fluoro-5-[5-({1-[2-(oxan-2-yloxy)ethyl-1H-pyrazol-3-yl}amino)-6-oxo-1,6-dihydropyridazin-3-yl]phenyl}-4,5,6,7-tetra hydro-1-benzothiophene-2-carboxamide | 578 | 579.44 |
| 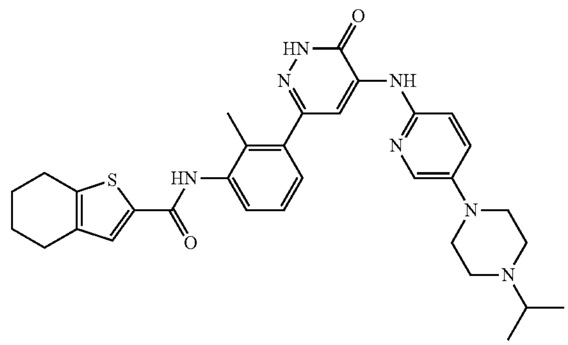 [SMILES: Cc1c(NC(=O)c2cc3c(s2)CCCC3)cccc1-c1cc(Nc2ccc(N3CCN(C(C)C)CC3)cn2)c(=O)[nH]n1] | N-{2-methyl-3-[6-oxo-5-({5-[4-(propan-2-yl)piperazin-1-yl]pyridin-2-yl}amino)-1,6-dihydropyridazin-3-yl]phenyl}-4,5,6,7-tetra hydro-1-benzothiophene-2-carboxamide | 583 | 584.6 |
| 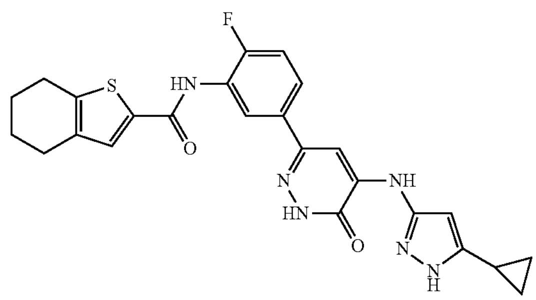 [SMILES: O=C(Nc1cc(-c2cc(Nc3cc(C4CC4)[nH]n3)c(=O)[nH]n2)ccc1F)c1cc2c(s1)CCCC2] | N-(5-{5-[(5-cyclopropyl-1H-pyrazol-3-yl)amino]-6-oxo-1,6-dihydropyridazin-3-yl}-2-fluorophenyl)-4,5,6,7-tetrahydro-1-benzothiophene-2-carboxamide | 490 | 491.57 |
| 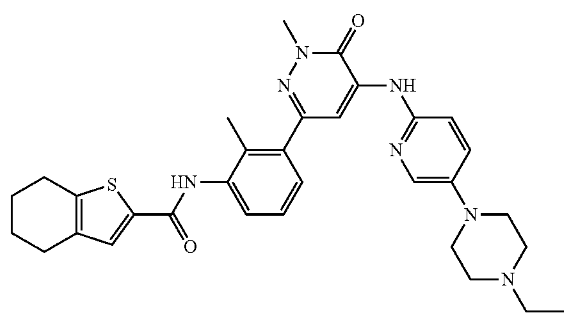 [SMILES: CCN1CCN(c2ccc(Nc3cc(-c4cccc(NC(=O)c5cc6c(s5)CCCC6)c4C)nn(C)c3=O)nc2)CC1] | N-[3-(5-{[5-(4-ethyl piperazin-1-yl)pyridin-2-yl]amino}-1-methyl-6-oxo-1,6-dihydropyridazin-3-yl)-2-methylphenyl]-4,5,6,7-tetrahydro-1-benzothiophene-2-carboxamide | 583 | 666 |
| 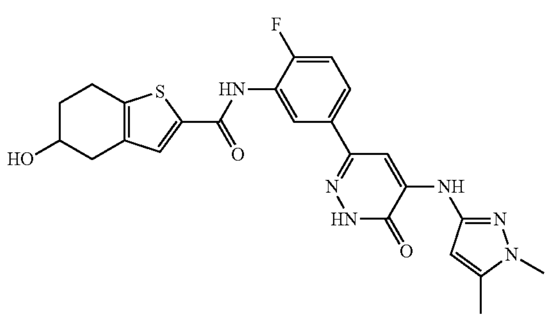 [SMILES: Cc1cc(Nc2cc(-c3ccc(F)c(NC(=O)c4cc5c(s4)CCC(O)C5)c3)n[nH]c2=O)nn1C] | N-(5-{5-[(1,5-dimethyl-1H-pyrazol-3-yl)amino]-6-oxo-1,6-dihydropyridazin-3-yl}-2-fluorophenyl)-5-hydroxy-4,5,6,7-tetrahydro-1-benzothiophene-2-carboxamide | 494 | 495.2 |

-continued

| Structure | Name | MW calcd | MH + m/z obs |
|---|---|---|---|
| | N-(3-{5-[(1,5-dimethyl-1H-pyrazol-3-yl)amino]-6-oxo-1,6-dihydropyridazin-3-yl}-6-fluoro-2-methylphenyl)-4,5,6,7-tetrahydro-1-benzothiophene-2-carboxamide | 492 | 492.6 |
| 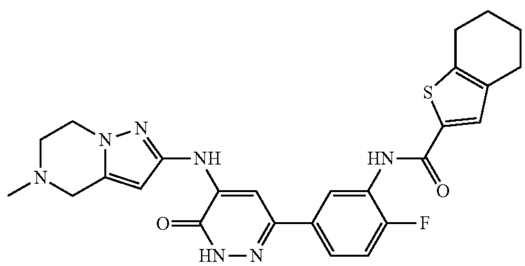 [SMILES: CN1CCn2nc(Nc3cc(-c4ccc(F)c(NC(=O)c5cc6c(s5)CCCC6)c4)n[nH]c3=O)cc2C1] | N-{2-fluoro-5-[5-({5-methyl-4H,5H,6H,7H-pyrazolo[1,5-a]pyrazin-2-yl}amino)-6-oxo-1,6-dihydropyridazin-3-yl]phenyl}-4,5,6,7-tetrahydro-1-benzothiophene-2-carboxamide | 519 | 520.1 |
| | N-[2-fluoro-5-(5-{[1-(2-methoxyethyl)-1H-pyrazol-3-yl]amino}-6-oxo-1,6-dihydropyridazin-3-yl)phenyl]-4,5,6,7-tetra hydro-1-benzothiophene-2-carboxamide | 508 | 508.54 |
| 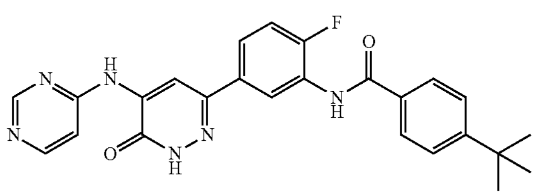 [SMILES: CC(C)(C)c1ccc(C(=O)Nc2cc(-c3cc(Nc4ccncn4)c(=O)[nH]n3)ccc2F)cc1] | 4-tert-butyl-N-{2-fluoro-5-[6-oxo-5-(pyrimidin-4-ylamino)-1,6-dihydropyridazin-3-yl]phenyl}benzamide | 458 | 459.1 |
| 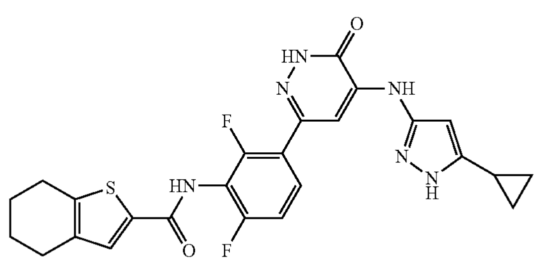 [SMILES: O=C(Nc1c(F)ccc(-c2cc(Nc3cc(C4CC4)[nH]n3)c(=O)[nH]n2)c1F)c1cc2c(s1)CCCC2] | N-(3-{5-[(5-cyclopropyl-1H-pyrazol-3-yl)amino]-6-oxo-1,6-dihydropyridazin-3-yl}-2,6-difluorophenyl)-4,5,6,7-tetrahydro-1-benzo thiophene-2-carboxamide | 508 | 509.51 |
| 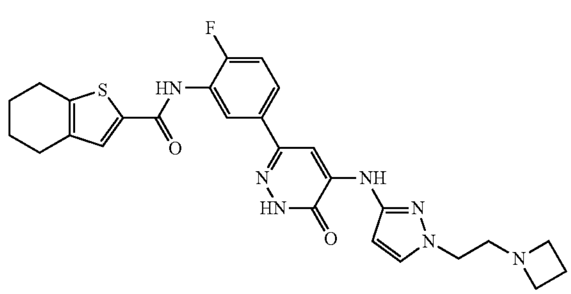 [SMILES: O=C(Nc1cc(-c2cc(Nc3ccn(CCN4CCC4)n3)c(=O)[nH]n2)ccc1F)c1cc2c(s1)CCCC2] | N-{5-[5-({1-[2-(azetidin-1-yl)ethyl]-1H-pyrazol-3-yl}amino)-6-oxo-1,6-dihydropyridazin-3-yl]-2-fluorophenyl}-4,5,6,7-tetrahydro-1-benzo thiophene-2-carboxamide | 533 | 534.5 |

-continued

| Structure | Name | MW calcd | MH + m/z obs |
|---|---|---|---|
| 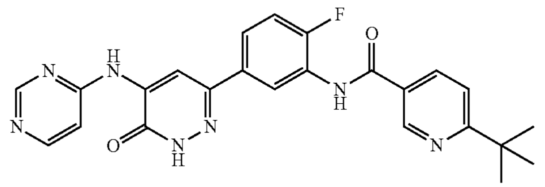 [SMILES: CC(C)(C)c1ccc(C(=O)Nc2cc(-c3cc(Nc4ccncn4)c(=O)[nH]n3)ccc2F)cn1] | 6-tert-butyl-N-{2-fluoro-5-[6-oxo-5-(pyrimidin-4-ylamino)-1,6-dihydropyridazin-3-yl]phenyl}pyridine-3-carboxamide | 459 | 460.5 |
| 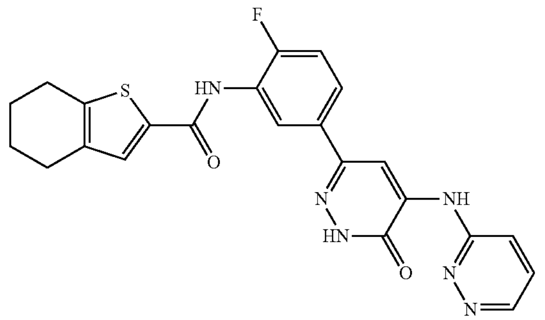 [SMILES: O=C(Nc1cc(-c2cc(Nc3cccnn3)c(=O)[nH]n2)ccc1F)c1cc2c(s1)CCCC2] | N-{2-fluoro-5-[6-oxo-5-(pyridazin-3-ylamino)-1,6-dihydropyridazin-3-yl]phenyl}-4,5,6,7-tetra hydro-1-benzothiophene-2-carboxamide | 462 | 462.9 |
| 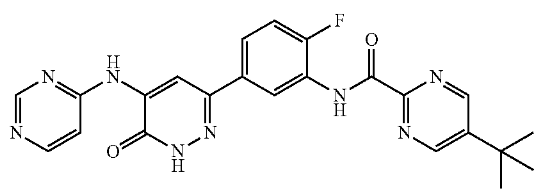 [SMILES: CC(C)(C)c1cnc(C(=O)Nc2cc(-c3cc(Nc4ccncn4)c(=O)[nH]n3)ccc2F)nc1] | 5-tert-butyl-N-{2-fluoro-5-[6-oxo-5-(pyrimidin-4-ylamino)-1,6-dihydropyridazin-3-yl]phenyl}pyrimidine-2-carboxamide | 460 | 461.2 |
| 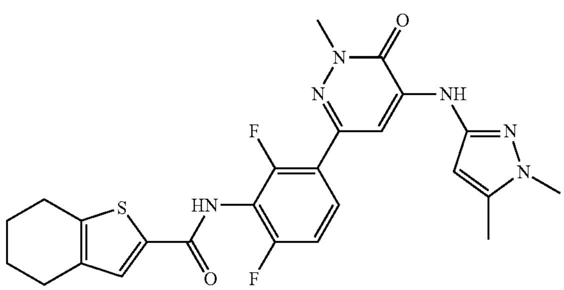 [SMILES: Cc1cc(Nc2cc(-c3ccc(F)c(NC(=O)c4cc5c(s4)CCCC5)c3F)nn(C)c2=O)nn1C] | N-(3-{5-[(1,5-dimethyl-1H-pyrazol-3-yl)amino]-1-methyl-6-oxo-1,6-dihydropyridazin-3-yl}-2,6-difluorophenyl)-4,5,6,7-tetrahydro-1-benzo thiophene-2-carboxamide | 510 | 510.51 |
| 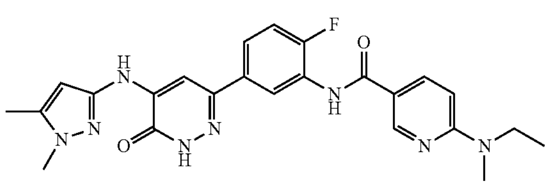 [SMILES: CCN(C)c1ccc(C(=O)Nc2cc(-c3cc(Nc4cc(C)n(C)n4)c(=O)[nH]n3)ccc2F)cn1] | N-(5-{5-[(1,5-dimethyl-1H-pyrazol-3-yl)amino]-6-oxo-1,6-dihydropyridazin-3-yl}-2-fluorophenyl)-6-[ethyl(methyl)amino]pyridine-3-carboxamide | 476 | 476.63 |
| 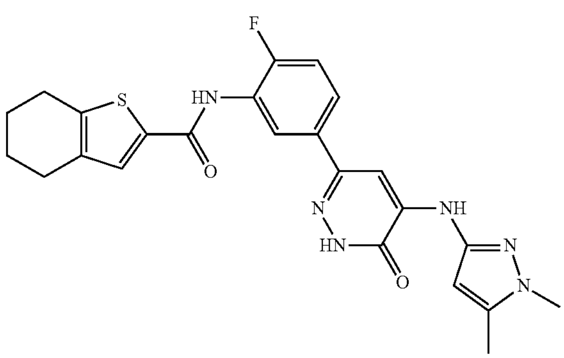 [SMILES: Cc1cc(Nc2cc(-c3ccc(F)c(NC(=O)c4cc5c(s4)CCCC5)c3)n[nH]c2=O)nn1C] | N-(5-{5-[(1,5-dimethyl-1H-pyrazol-3-yl)amino]-6-oxo-1,6-dihydropyridazin-3-yl}-2-fluorophenyl)-4,5,6,7-tetrahydro-1-benzo thiophene-2-carboxamide | 478 | 478.54 |

-continued

| Structure | Name | MW calcd | MH + m/z obs |
|---|---|---|---|
| 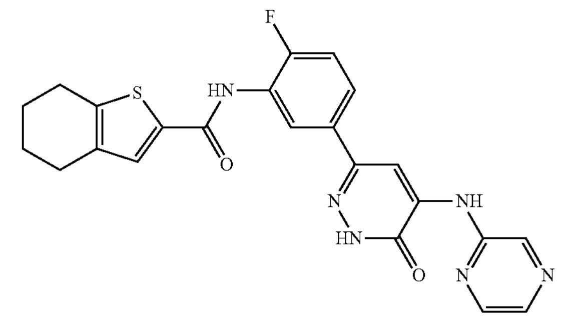 [SMILES: O=C(Nc1cc(-c2cc(Nc3cnccn3)c(=O)[nH]n2)ccc1F)c1cc2c(s1)CCCC2] | N-{2-fluoro-5-[6-oxo-5-(pyrazin-2-ylamino)-1,6-dihydropyridazin-3-yl]phenyl}-4,5,6,7-tetrahydro-1-benzo thiophene-2-carboxamide | 462 | 462.63 |
| 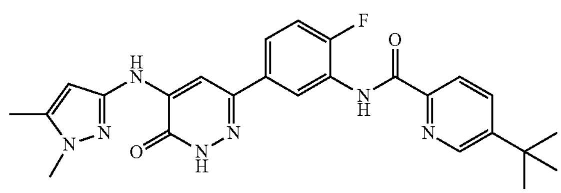 | 5-tert-butyl-N-(5-{5-[(1,5-dimethyl-1H-pyrazol-3-yl)amino]-6-oxo-1,6-dihydropyridazin-3-yl}-2-fluorophenyl)pyridine-2-carboxamide | 475 | 476.2 |
| 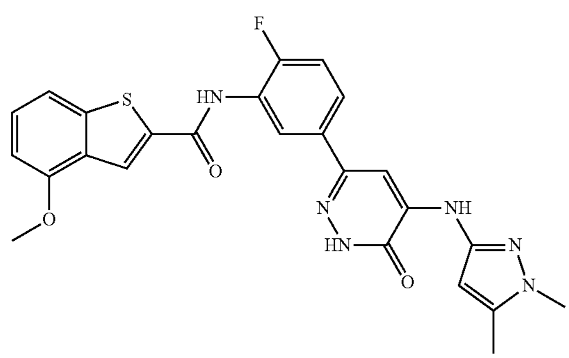 [SMILES: COc1cccc2sc(C(=O)Nc3cc(-c4cc(Nc5cc(C)n(C)n5)c(=O)[nH]n4)ccc3F)cc12] | N-(5-{5-[(1,5-dimethyl-1H-pyrazol-3-yl)amino]-6-oxo-1,6-dihydropyridazin-3-yl}-2-fluorophenyl)-4-methoxy-1-benzothiophene-2-carboxamide | 504 | 505.1 |
| 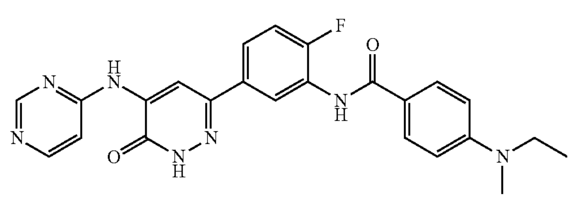 [SMILES: CCN(C)c1ccc(C(=O)Nc2cc(-c3cc(Nc4ccncn4)c(=O)[nH]n3)ccc2F)cc1] | 4-[ethyl(methyl)amino]-N-{2-fluoro-5-[6-oxo-5-(pyrimidin-4-ylamino)-1,6-dihydropyridazin-3-yl]phenyl}benzamide | 459 | 460.1 |
| 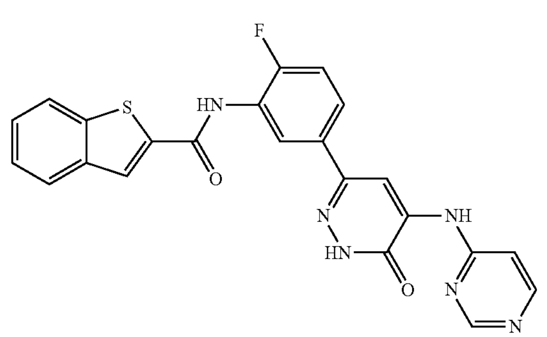 [SMILES: O=C(Nc1cc(-c2cc(Nc3ccncn3)c(=O)[nH]n2)ccc1F)c1cc2ccccc2s1] | N-{2-fluoro-5-[6-oxo-5-(pyrimidin-4-ylamino)-1,6-dihydropyridazin-3-yl]phenyl}-1-benzo thiophene-2-carboxamide | 458 | 459.1 |

| Structure | Name | MW calcd | MH + m/z obs |
|---|---|---|---|
| 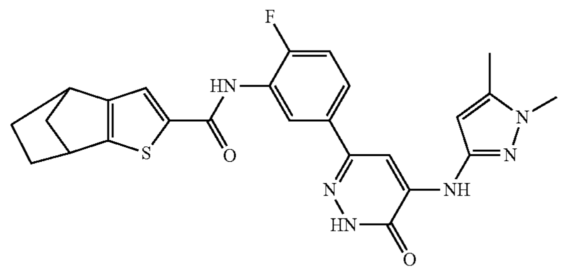 [SMILES: Cc1cc(Nc2cc(-c3ccc(F)c(NC(=O)c4cc5c(s4)C4CCC5C4)c3)n[nH]c2=O)nn1C] | N-(5-{5-[(1,5-dimethyl-1H-pyrazol-3-yl)amino]-6-oxo-1,6-dihydropyridazin-3-yl}-2-fluorophenyl)-3-thiatricyclo[5.2.1.0^{2,6}]deca-2(6),4-diene-4-carboxamide | 490 | 491.02 |
| 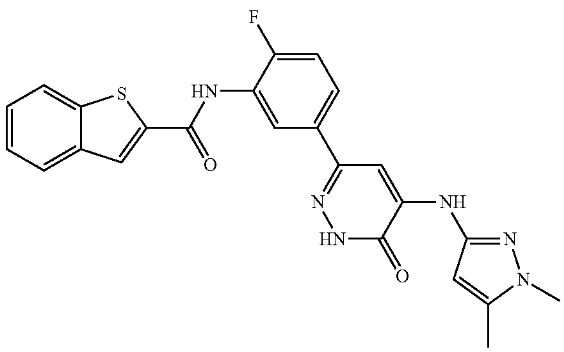 [SMILES: Cc1cc(Nc2cc(-c3ccc(F)c(NC(=O)c4cc5ccccc5s4)c3)n[nH]c2=O)nn1C] | N-(5-{5-[(1,5-dimethyl-1H-pyrazol-3-yl)amino]-6-oxo-1,6-dihydropyridazin-3-yl}-2-fluorophenyl)-1-benzothiophene-2-carboxamide | 474 | 475.1 |
| 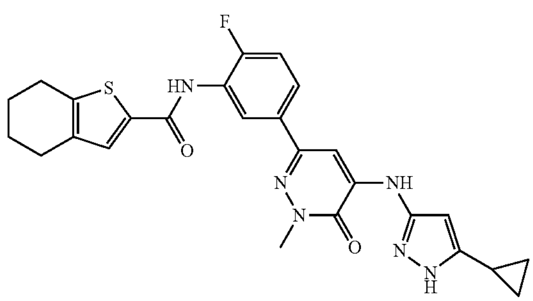 [SMILES: Cn1nc(-c2ccc(F)c(NC(=O)c3cc4c(s3)CCCC4)c2)cc(Nc2cc(C3CC3)[nH]n2)c1=O] | N-(5-{5-[(5-cyclopropyl-1H-pyrazol-3-yl)amino]-1-methyl-6-oxo-1,6-dihydropyridazin-3-yl}-2-fluorophenyl)-4,5,6,7-tetrahydro-1-benzo thiophene-2-carboxamide | 504 | 504.63 |
| 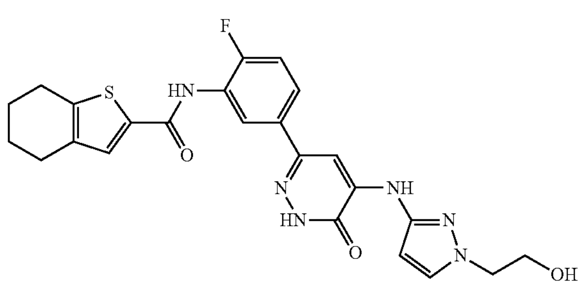 [SMILES: O=C(Nc1cc(-c2cc(Nc3ccn(CCO)n3)c(=O)[nH]n2)ccc1F)c1cc2c(s1)CCCC2] | N-[2-fluoro-5-(5-{[1-(2-hydroxyethyl)-1H-pyrazol-3-yl]amino}-6-oxo-1,6-dihydropyridazin-3-yl)phenyl]-4,5,6,7-tetrahydro-1-benzo thiophene-2-carboxamide | 494 | 495.56 |
| 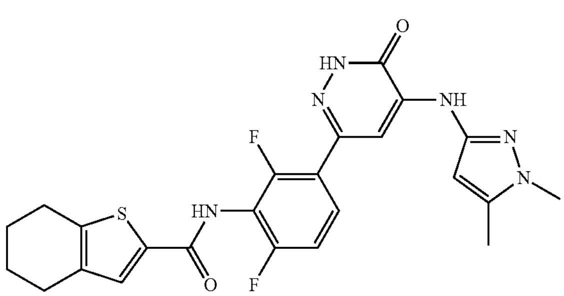 | N-(3-{5-[(1,5-dimethyl-1H-pyrazol-3-yl)amino]-6-oxo-1,6-dihydropyridazin-3-yl}-2,6-difluorophenyl)-4,5,6,7-tetrahydro-1-benzo thiophene-2-carboxamide | 496 | 496.6 |

-continued

| Structure | Name | MW calcd | MH + m/z obs |
|---|---|---|---|
| 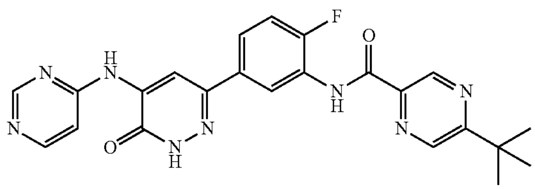 [SMILES: CC(C)(C)c1cnc(C(=O)Nc2cc(-c3cc(Nc4ccncn4)c(=O)[nH]n3)ccc2F)cn1] | 5-tert-butyl-N-{2-fluoro-5-[6-oxo-5-(pyrimidin-4-ylamino)-1,6-dihydro pyridazin-3-yl]phenyl}pyrazine-2-carboxamide | 460 | 461.4 |
| 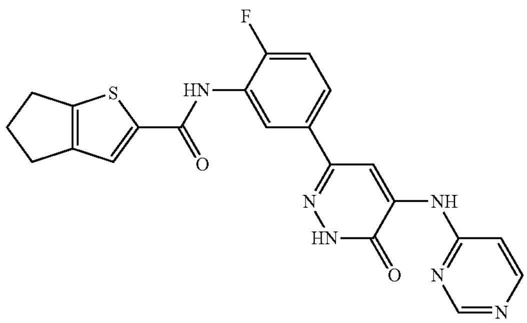 [SMILES: O=C(Nc1cc(-c2cc(Nc3ccncn3)c(=O)[nH]n2)ccc1F)c1cc2c(s1)CCC2] | N-{2-fluoro-5-[6-oxo-5-(pyrimidin-4-ylamino)-1,6-dihydropyridazin-3-yl]phenyl}-4H,5H,6H-cyclopenta[b]thiophene-2-carboxamide | 448 | 449 |
| 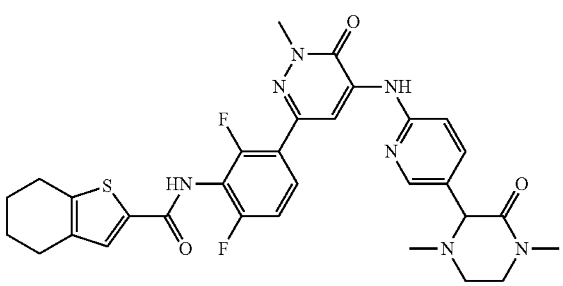 [SMILES: CN1CCN(C)C(c2ccc(Nc3cc(-c4ccc(F)c(NC(=O)c5cc6c(s5)CCCC6)c4F)nn(C)c3=O)nc2)C1=O] | N-[3-(5-{[5-(1,4-dimethyl-3-oxopiperazin-2-yl)pyridin-2-yl]amino}-1-methyl-6-oxo-1,6-dihydropyridazin-3-yl)-2,6-difluorophenyl]-4,5,6,7-tetrahydro-1-benzo thiophene-2-carboxamide | 619 | 620.1 |
| 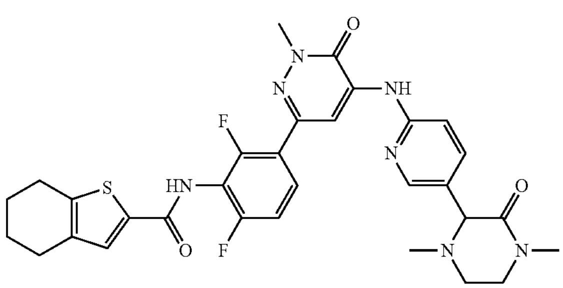 [SMILES: CN1CCN(C)C(c2ccc(Nc3cc(-c4ccc(F)c(NC(=O)c5cc6c(s5)CCCC6)c4F)nn(C)c3=O)nc2)C1=O] | N-[3-(5-{[5-(4-ethylpiperazin-1-yl)pyridin-2-yl]amino}-6-oxo-1,6-dihydropyridazin-3-yl)-2-methylphenyl]-4,5,6,7-tetrahydro-1-benzo thiophene-2-carboxamide | 569 | 570.1 |
| 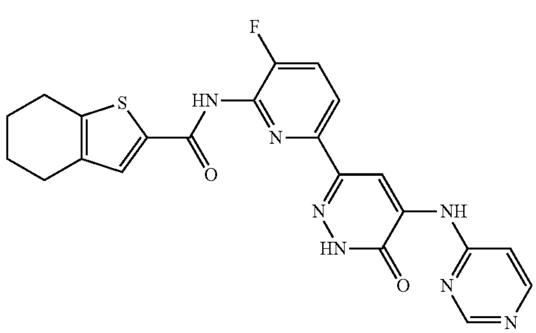 [SMILES: O=C(Nc1nc(-c2cc(Nc3ccncn3)c(=O)[nH]n2)ccc1F)c1cc2c(s1)CCCC2] | N-{3-fluoro-6-[6-oxo-5-(pyrimidin-4-ylamino)-1,6-dihydropyridazin-3-yl]pyridin-2-yl}-4,5,6,7-tetrahydro-1-benzo thiophene-2-carboxamide | 463 | 463.54 |

| Structure | Name | MW calcd | MH + m/z obs |
|---|---|---|---|
| 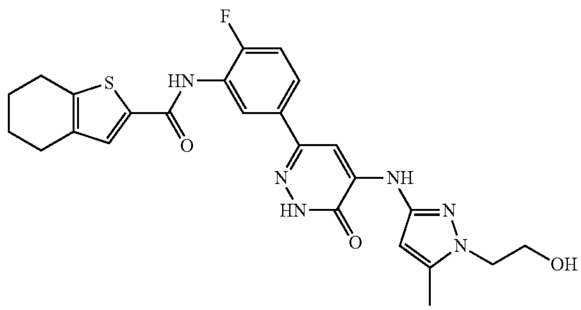 [SMILES: Cc1cc(Nc2cc(-c3ccc(F)c(NC(=O)c4cc5c(s4)CCCC5)c3)n[nH]c2=O)nn1CCO] | N-[2-fluoro-5-(5-{[1-(2-hydroxyethyl)-5-methyl-1H-pyrazol-3-yl]amino}-6-oxo-1,6-dihydropyridazin-3-yl)phenyl]-4,5,6,7-tetrahydro-1-benzo thiophene-2-carboxamide | 508 | 509.1 |
| 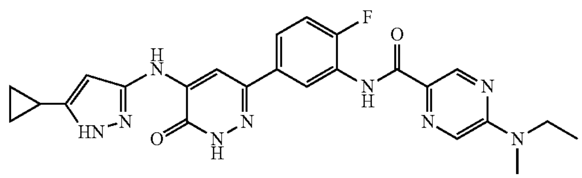 [SMILES: CCN(C)c1cnc(C(=O)Nc2cc(-c3cc(Nc4cc(C5CC5)[nH]n4)c(=O)[nH]n3)ccc2F)cn1] | N-(5-{5-[(5-cyclopropyl-1H-pyrazol-3-yl)amino]-6-oxo-1,6-dihydropyridazin-3-yl}-2-fluorophenyl)-5-[ethyl(methyl)amino]pyrazine-2-carboxamide | 489 | 490.8 |
| 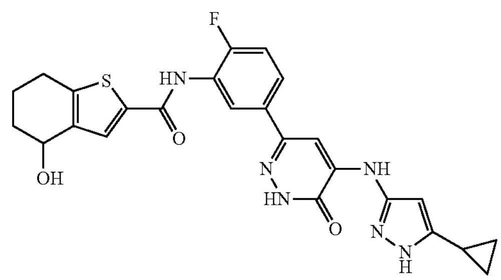 [SMILES: O=C(Nc1cc(-c2cc(Nc3cc(C4CC4)[nH]n3)c(=O)[nH]n2)ccc1F)c1cc2c(s1)CCCC2O] | N-(5-{5-[(5-cyclopropyl-1H-pyrazol-3-yl)amino]-6-oxo-1,6-dihydropyridazin-3-yl}-2-fluorophenyl)-4-hydroxy-4,5,6,7-tetrahydro-1-benzothiophene-2-carboxamide | 506 | 507.2 |
| 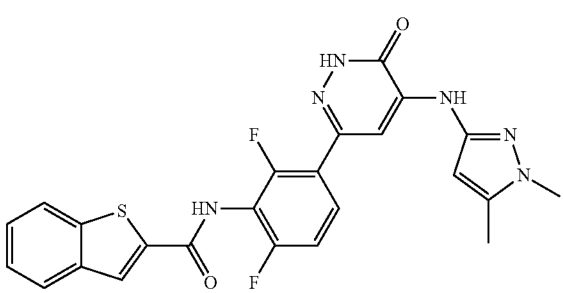 [SMILES: Cc1cc(Nc2cc(-c3ccc(F)c(NC(=O)c4cc5ccccc5s4)c3F)n[nH]c2=O)nn1C] | N-(3-{5-[(1,5-dimethyl-1H-pyrazol-3-yl)amino]-6-oxo-1,6-dihydropyridazin-3-yl}-2,6-difluorophenyl)-1-benzothiophene-2-carboxamide | 492 | 493.1 |
| 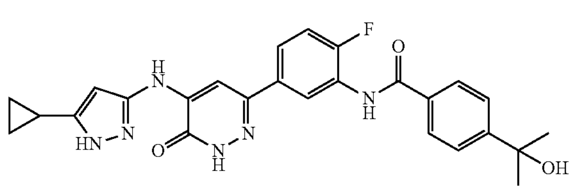 [SMILES: CC(C)(O)c1ccc(C(=O)Nc2cc(-c3cc(Nc4cc(C5CC5)[nH]n4)c(=O)[nH]n3)ccc2F)cc1] | N-(5-{5-[(5-cyclopropyl-1H-pyrazol-3-yl)amino]-6-oxo-1,6-dihydropyridazin-3-yl}-2-fluorophenyl)-4-(2-hydroxypropan-2-yl)benzamide | 488 | 489.2 |
| 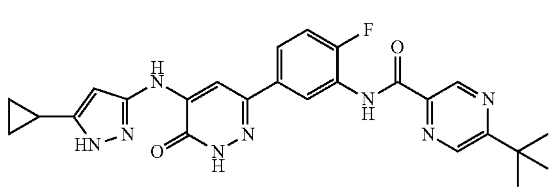 [SMILES: CC(C)(C)c1cnc(C(=O)Nc2cc(-c3cc(Nc4cc(C5CC5)[nH]n4)c(=O)[nH]n3)ccc2F)cn1] | 5-tert-butyl-N-(5-{5-[(5-cyclopropyl-1H-pyrazol-3-yl)amino]-6-oxo-1,6-dihydropyridazin-3-yl}-2-fluorophenyl)pyrazine-2-carboxamide | 488 | 489.3 |

| Structure | Name | MW calcd | MH + m/z obs |
|---|---|---|---|
| 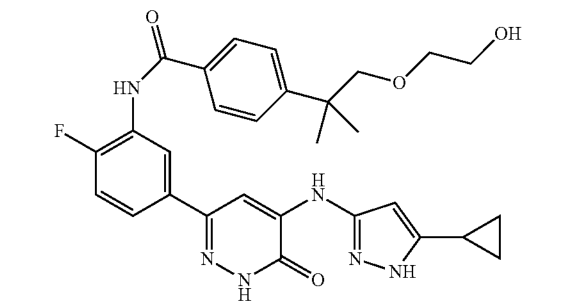 [SMILES: CC(C)(COCCO)c1ccc(C(=O)Nc2cc(-c3cc(Nc4cc(C5CC5)[nH]n4)c(=O)[nH]n3)ccc2F)cc1] | N-(5-{5-[(5-cyclopropyl-1H-pyrazol-3-yl)amino]-6-oxo-1,6-dihydropyridazin-3-yl}-2-fluorophenyl)-4-[1-(2-hydroxyethoxy)-2-methylpropan-2-yl]benzamide | 546 | 547.3 |
| 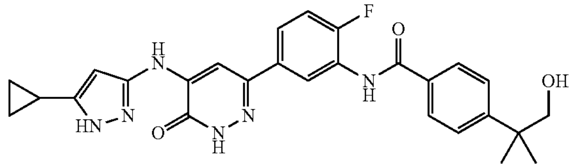 [SMILES: CC(C)(CO)c1ccc(C(=O)Nc2cc(-c3cc(Nc4cc(C5CC5)[nH]n4)c(=O)[nH]n3)ccc2F)cc1] | N-(5-{5-[(5-cyclopropyl-1H-pyrazol-3-yl)amino]-6-oxo-1,6-dihydropyridazin-3-yl}-2-fluorophenyl)-4-(1-hydroxy-2-methylpropan-2-yl)benzamide | 502 | 503.2 |
| 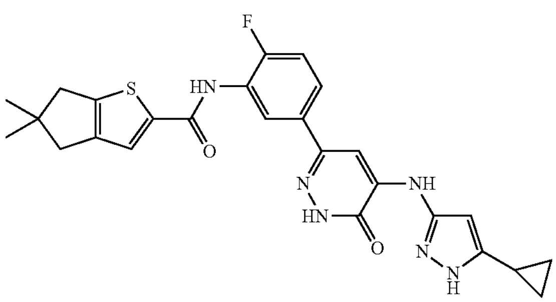 [SMILES: CC1(C)Cc2cc(C(=O)Nc3cc(-c4cc(Nc5cc(C6CC6)[nH]n5)c(=O)[nH]n4)ccc3F)sc2C1] | N-(5-{5-[(5-cyclopropyl-1H-pyrazol-3-yl)amino]-6-oxo-1,6-dihydropyridazin-3-yl}-2-fluorophenyl)-5,5-dimethyl-4H,5H,6H-cyclopenta[b]thiophene-2-carboxamide | 504 | 505.2 |
| 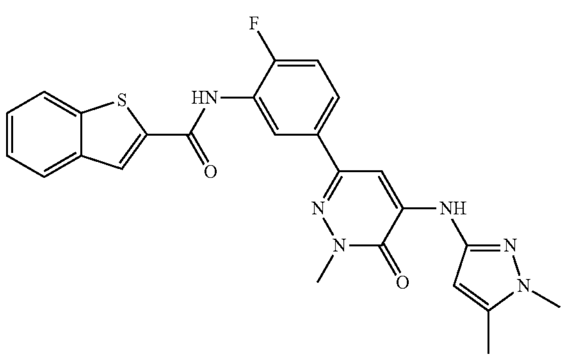 [SMILES: Cc1cc(Nc2cc(-c3ccc(F)c(NC(=O)c4cc5ccccc5s4)c3)nn(C)c2=O)nn1C] | N-(5-{5-[(1,5-dimethyl-1H-pyrazol-3-yl)amino]-1-methyl-6-oxo-1,6-dihydropyridazin-3-yl}-2-fluorophenyl)-1-benzothiophene-2-carboxamide | 488 | 488.52 |
| 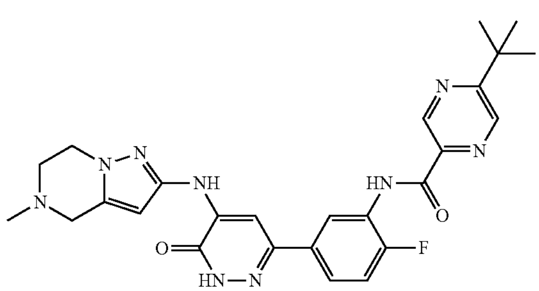 | 5-tert-butyl-N-{2-fluoro-5-[5-({5-methyl-4H,5H,6H,7H-pyrazolo[1,5-a]pyrazin-2-yl}amino)-6-oxo-1,6-dihydropyridazin-3-yl]phenyl}pyrazine-2-carboxamide | 517 | 518.57 |

-continued

| Structure | Name | MW calcd | MH + m/z obs |
|---|---|---|---|
| 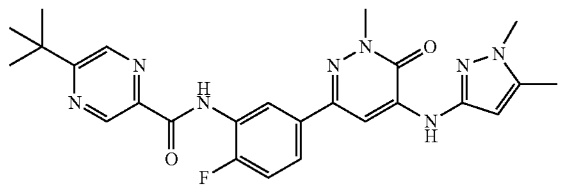 [SMILES: Cc1cc(Nc2cc(-c3ccc(F)c(NC(=O)c4cnc(C(C)(C)C)cn4)c3)nn(C)c2=O)nn1C] | 5-tert-butyl-N-(5-{5-[(1,5-dimethyl-1H-pyrazol-3-yl)amino]-1-methyl-6-oxo-1,6-dihydropyridazin-3-yl}-2-fluorophenyl)pyrazine-2-carboxamide | 490 | 491.2 |
| 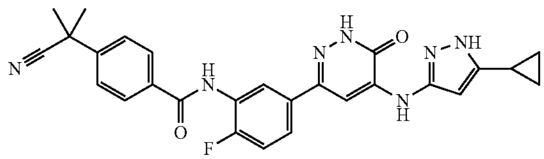 [SMILES: CC(C)(C#N)c1ccc(C(=O)Nc2cc(-c3cc(Nc4cc(C5CC5)[nH]n4)c(=O)[nH]n3)ccc2F)cc1] | 4-(1-cyano-1-methylethyl)-N-(5-{5-[(5-cyclopropyl-1H-pyrazol-3-yl)amino]-6-oxo-1,6-dihydropyridazin-3-yl}-2-fluorophenyl)benzamide | 497 | 498.2 |
| 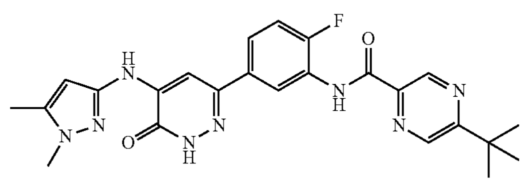 [SMILES: Cc1cc(Nc2cc(-c3ccc(F)c(NC(=O)c4cnc(C(C)(C)C)cn4)c3)n[nH]c2=O)nn1C] | 5-tert-butyl-N-(5-{5-[(1,5-dimethyl-1H-pyrazol-3-yl)amino]-6-oxo-1,6-dihydropyridazin-3-yl}-2-fluorophenyl)pyrazine-2-carboxamide | 476 | 477.2 |
| 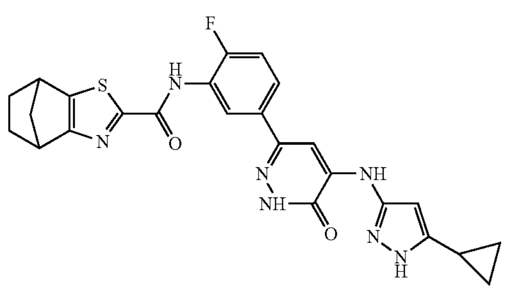 [SMILES: O=C(Nc1cc(-c2cc(Nc3cc(C4CC4)[nH]n3)c(=O)[nH]n2)ccc1F)c1nc2c(s1)C1CCC2C1] | N-(5-{5[(5-cyclopropyl-1H-pyrazol-3-yl)amino]-6-oxo-1,6-dihydropyridazin-3-yl}-2-fluorophenyl)-3-thia-5-azatricyclo[5.2.1.0^{2,6}]deca-2(6),4-diene-4-carboxamide | 503 | 504.2 |
| 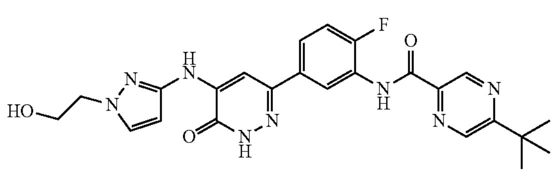 [SMILES: CC(C)(C)c1cnc(C(=O)Nc2cc(-c3cc(Nc4ccn(CCO)n4)c(=O)[nH]n3)ccc2F)cn1] | 5-tert-butyl-N-[2-fluoro-5-(5-{[1-(2-hydroxyethyl)-1H-pyrazol-3-yl]amino}-6-oxo-1,6-dihydropyridazin-3-yl)phenyl]pyrazine-2-carboxamide | 492 | 439.1 |
| 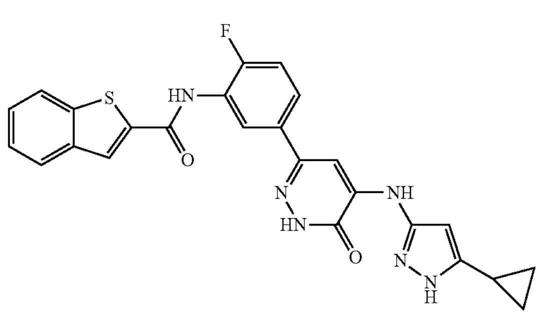 [SMILES: O=C(Nc1cc(-c2cc(Nc3cc(C4CC4)[nH]n3)c(=O)[nH]n2)ccc1F)c1cc2ccccc2s1] | N-(5-{5-[(5-cyclopropyl-1H-pyrazol-3-yl)amino]-6-oxo-1,6-dihydropyridazin-3-yl}-2-fluorophenyl)-1-benzothiophene-2-carboxamide | 486 | 487.1 |

-continued

| Structure | Name | MW calcd | MH + m/z obs |
|---|---|---|---|
| 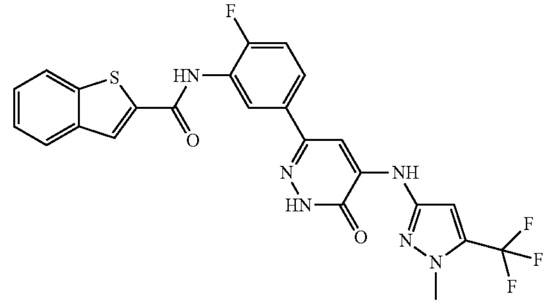 [SMILES: Cn1nc(Nc2cc(-c3ccc(F)c(NC(=O)c4cc5ccccc5s4)c3)n[nH]c2=O)cc1C(F)(F)F] | N-[2-fluoro-5-(5-{[1-methyl-5-(trifluoromethyl)-1H-pyrazol-3-yl]amino}-6-oxo-1,6-dihydropyridazin-3-yl)phenyl]-1-benzothiophene-2-carboxamide | 528 | 529 |
| 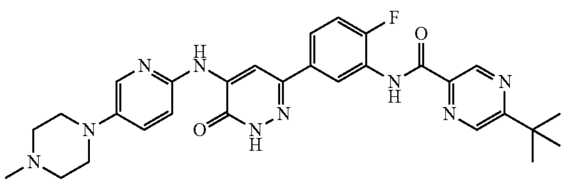 [SMILES: CN1CCN(c2ccc(Nc3cc(-c4ccc(F)c(NC(=O)c5cnc(C(C)(C)C)cn5)c4)n[nH]c3=O)nc2)CC1] | 5-tert-butyl-N-[2-fluoro-5-(5-{[5-(4-methylpiperazin-1-yl)pyridin-2-yl]amino)-6-oxo-1,6-dihydropyridazin-3-yl)phenyl]pyrazine-2-carboxamide | 557 | 558.3 |
| 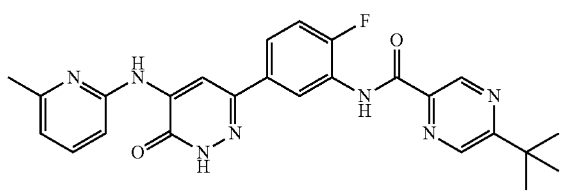 [SMILES: Cc1cccc(Nc2cc(-c3ccc(F)c(NC(=O)c4cnc(C(C)(C)C)cn4)c3)n[nH]c2=O)n1] | 5-tert-butyl-N-(2-fluoro-5-{5-[(6-methylpyridin-2-yl)amino]-6-oxo-1,6-dihydropyridazin-3-yl}phenyl)pyrazine-2-carboxamide | 473 | 474.2 |
| 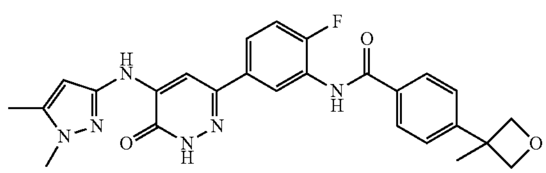 [SMILES: Cc1cc(Nc2cc(-c3ccc(F)c(NC(=O)c4ccc(C5(C)COC5)cc4)c3)n[nH]c2=O)nn1C] | N-(5-{5-[(1,5-dimethyl-1H-pyrazol-3-yl)amino]-6-oxo-1,6-dihydropyridazin-3-yl}-2-fluorophenyl)-4-(3-methyloxetan-3-yl)benzamide | 488 | 489.2 |
| 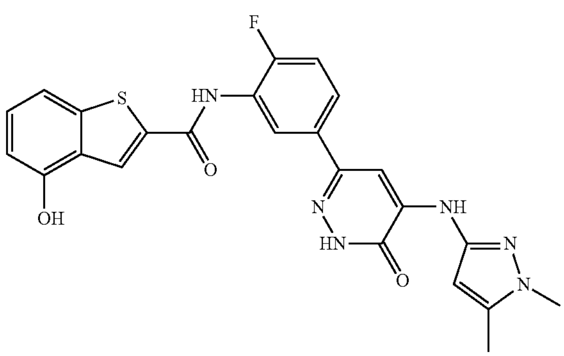 [SMILES: Cc1cc(Nc2cc(-c3ccc(F)c(NC(=O)c4cc5c(O)cccc5s4)c3)n[nH]c2=O)nn1C] | N-(5-{5-[(1,5-dimethyl-1H-pyrazol-3-yl)amino]-6-oxo-1,6-dihydropyridazin-3-yl}-2-fluorophenyl)-4-hydroxy-1-benzothiophene-2-carboxamide | 490 | 491.2 |
| 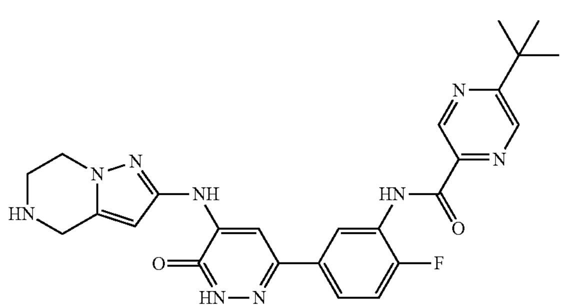 | 5-tert-butyl-N-[2-fluoro-5-(6-oxo-5-{4H,5H,6H,7H-pyrazolo[1,5-a]pyrazin-2-ylamino}-1,6-dihydropyridazin-3-yl)phenyl]pyrazine-2-carboxamide | 503 | 504 |

-continued

| Structure | Name | MW calcd | MH + m/z obs |
|---|---|---|---|
| 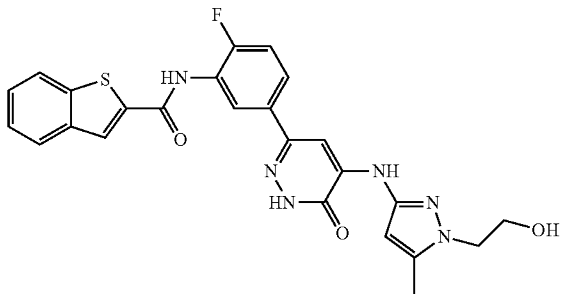 [SMILES: Cc1cc(Nc2cc(-c3ccc(F)c(NC(=O)c4cc5ccccc5s4)c3)n[nH]c2=O)nn1CCO] | N-[2-fluoro-5-(5-{[1-(2-hydroxyethyl)-5-methyl-1H-pyrazol-3-yl]amino}-6-oxo-1,6-dihydropyridazin-3-yl)phenyl]-1-benzothiophene-2-carboxamide | 504 | 505.1 |
| 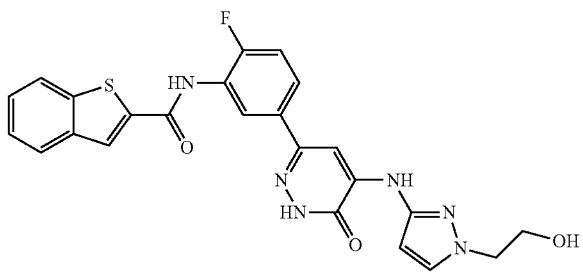 [SMILES: O=C(Nc1cc(-c2cc(Nc3ccn(CCO)n3)c(=O)[nH]n2)ccc1F)c1cc2ccccc2s1] | N-[2-fluoro-5-(5-{[1-(2-hydroxyethyl)-1H-pyrazol-3-yl]amino}-6-oxo-1,6-dihydropyridazin-3-yl)phenyl]-1-benzothiophene-2-carboxamide | 490 | 491 |
| 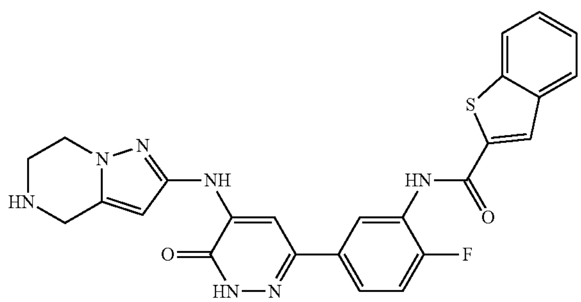 [SMILES: O=C(Nc1cc(-c2cc(Nc3cc4n(n3)CCNC4)c(=O)[nH]n2)ccc1F)c1cc2ccccc2s1] | N-[2-fluoro-5-(6-oxo-5-{4H,5H,6H,7H-pyrazolo[1,5-a]pyrazin-2-ylamino}-1,6-dihydropyridazin-3-yl)phenyl]-1-benzothiophene-2-carboxamide | 501 | 502 |
| 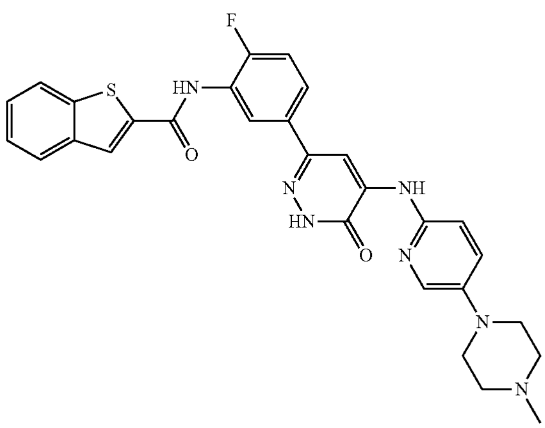 [SMILES: CN1CCN(c2ccc(Nc3cc(-c4ccc(F)c(NC(=O)c5cc6ccccc6s5)c4)n[nH]c3=O)nc2)CC1] | N-[2-fluoro-5-(5-{[5-(4-methylpiperazin-1-yl)pyridin-2-yl]amino}-6-oxo-1,6-dihydropyridazin-3-yl)phenyl]-1-benzothiophene-2-carboxamide | 555 | 556.2 |

-continued

| Structure | Name | MW calcd | MH + m/z obs |
|---|---|---|---|
| 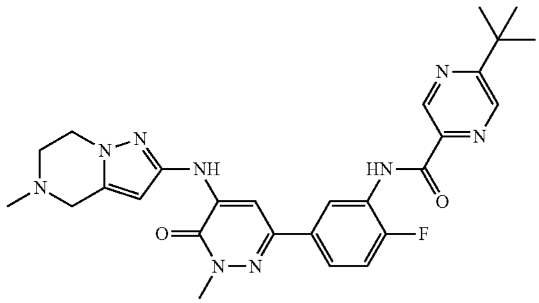 [SMILES: CN1CCn2nc(Nc3cc(-c4ccc(F)c(NC(=O)c5cnc(C(C)(C)C)cn5)c4)nn(C)c3=O)cc2C1] | 5-tert-butyl-N-{2-fluoro-5-[1-methyl-5-({5-methyl-4H,5H,6H,7H-pyrazolo[1,5-a]pyrazin-2-yl}amino)-6-oxo-1,6-dihydropyridazin-3-yl]phenyl}pyrazine-2-carboxamide | 531 | 532.2 |
| 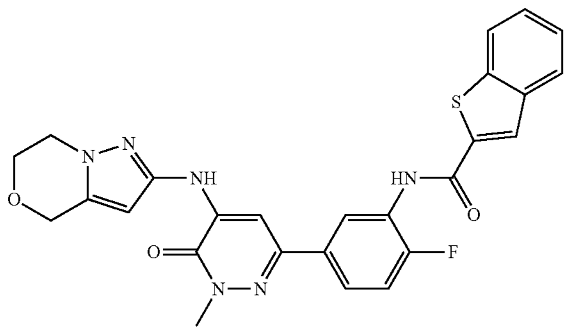 [SMILES: Cn1nc(-c2ccc(F)c(NC(=O)c3cc4ccccc4s3)c2)cc(Nc2cc3n(n2)CCOC3)c1=O] | N-[2-fluoro-5-(1-methyl-6-oxo-5-{4H,6H,7H-pyrazolo[3,2-c][1,4]oxazin-2-ylamino}-1,6-dihydropyridazin-3-yl)phenyl]-1-benzothiophene-2-carboxamide | 516 | 517.1 |
| 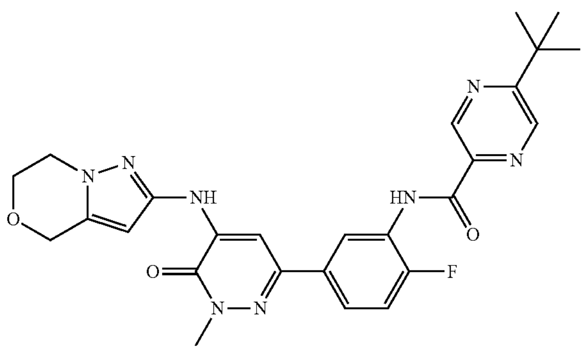 [SMILES: Cn1nc(-c2ccc(F)c(NC(=O)c3cnc(C(C)(C)C)cn3)c2)cc(Nc2cc3n(n2)CCOC3)c1=O] | 5-tert-butyl-N-[2-fluoro-5-(1-methyl-6-oxo-5-{4H,6H,7H-pyrazolo[3,2-c][1,4]oxazin-2-ylamino}-1,6-dihydropyridazin-3-yl)phenyl]pyrazine-2-carboxamide | 518 | 519.1 |
| 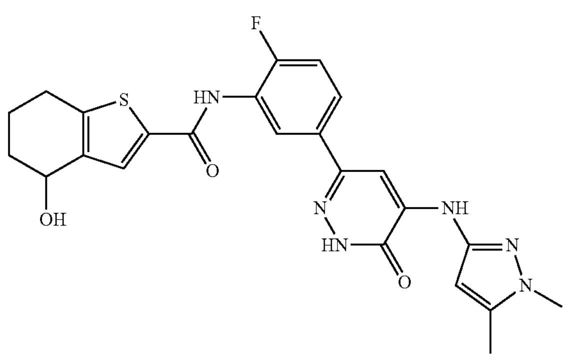 [SMILES: Cc1cc(Nc2cc(-c3ccc(F)c(NC(=O)c4cc5c(s4)CCCC5O)c3)n[nH]c2=O)nn1C] | N-(5-{5-[(1,5-dimethyl-1H-pyrazol-3-yl)amino]-6-oxo-1,6-dihydropyridazin-3-yl}-2-fluorophenyl)-4-hydroxy-4,5,6,7-tetrahydro-1-benzothiophene-2-carboxamide | 494 | 495.2 |
| 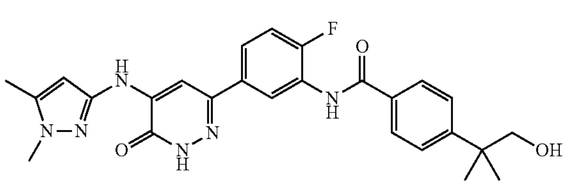 [SMILES: Cc1cc(Nc2cc(-c3ccc(F)c(NC(=O)c4ccc(C(C)(C)CO)cc4)c3)n[nH]c2=O)nn1C] | N-(5-{5-[(1,5-dimethyl-1H-pyrazol-3-yl)amino]-6-oxo-1,6-dihydropyridazin-3-yl}-2-fluorophenyl)-4-(1-hydroxy-2-methylpropan-2-yl)benzamide | 490 | 491.7 |

| Structure | Name | MW calcd | MH + m/z obs |
|---|---|---|---|
| 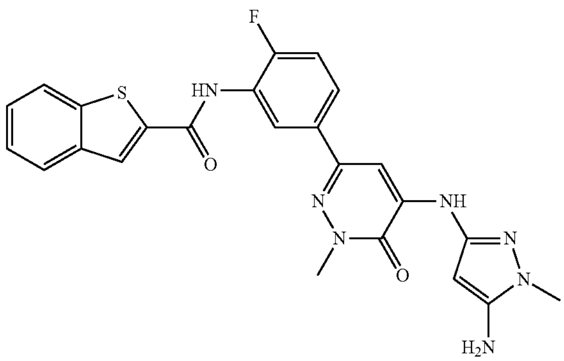 [SMILES: Cn1nc(Nc2cc(-c3ccc(F)c(NC(=O)c4cc5ccccc5s4)c3)nn(C)c2=O)cc1N] | N-(5-{5-[(5-amino-1-methyl-1H-pyrazol-3-yl)amino]-1-methyl-6-oxo-1,6-dihydropyridazin-3-yl}-2-fluorophenyl)-1-benzothiophene-2-carboxamide | 489 | 490.1 |
| 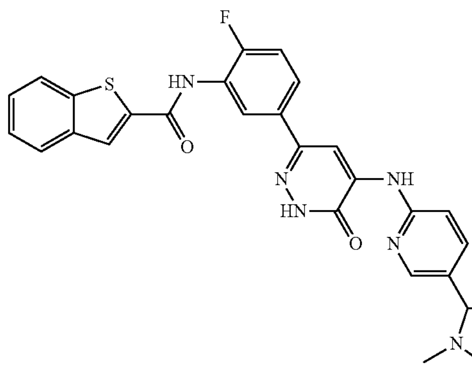 | N-[2-fluoro-5-(5-{[5-(1-methylpyrrolidin-2-yl)pyridin-2-yl]amino}-6-oxo-1,6-dihydropyridazin-3-yl)phenyl]-1-benzothiophene-2-carboxamide | 540 | 541.1 |
| 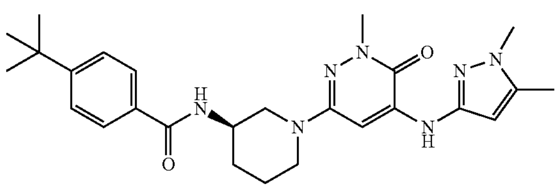 [SMILES: Cc1cc(Nc2cc(N3CCC[C@@H](NC(=O)c4ccc(C(C)(C)C)cc4)C3)nn(C)c2=O)nn1C] | 4-tert-butyl-N-[(3R)-1-{5-[(1,5-dimethyl-1H-pyrazol-3-yl)amino]-1-methyl-6-oxo-1,6-dihydropyridazin-3-yl}piperidin-3-yl]benzamide | 477 | 428.2 |
| 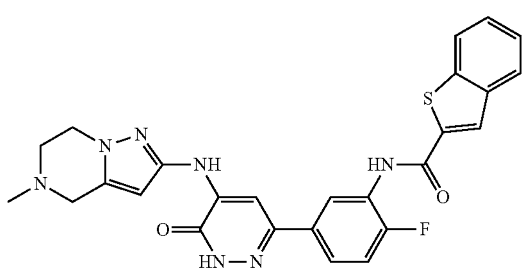 [SMILES: CN1CCn2nc(Nc3cc(-c4ccc(F)c(NC(=O)c5cc6ccccc6s5)c4)n[nH]c3=O)cc2C1] | N-{2-fluoro-5-[5-({5-methyl-4H,5H,6H,7H-pyrazolo[1,5-a]pyrazin-2-yl}amino)-6-oxo-1,6-dihydropyridazin-3-yl]phenyl}-1-benzothiophene-2-carboxamide | 515 | 515.9 |
| 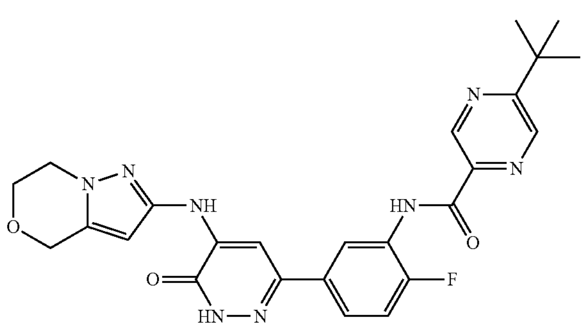 [SMILES: CC(C)(C)c1cnc(C(=O)Nc2cc(-c3cc(Nc4cc5n(n4)CCOC5)c(=O)[nH]n3)ccc2F)cn1] | 5-tert-butyl-N-[2-fluoro-5-(6-oxo-5-{4H,6H,7H-pyrazolo[3,2-c][1,4]oxazin-2-ylamino}-1,6-dihydropyridazin-3-yl)phenyl]pyrazine-2-carboxamide | 504 | 505.1 |

| Structure | Name | MW calcd | MH + m/z obs |
|---|---|---|---|
| 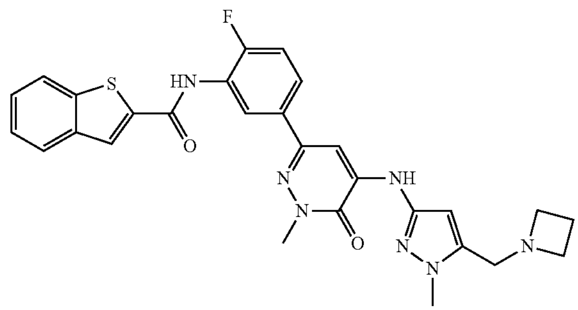 [SMILES: Cn1nc(Nc2cc(-c3ccc(F)c(NC(=O)c4cc5ccccc5s4)c3)nn(C)c2=O)cc1CN1CCC1] | N-[5-(5-{[5-(azetidin-1-ylmethyl)-1-methyl-1H-pyrazol-3-yl]amino}-1-methyl-6-oxo-1,6-dihydropyridazin-3-yl)-2-fluorophenyl]-1-benzothiophene-2-carboxamide | 543 | 544 |
| 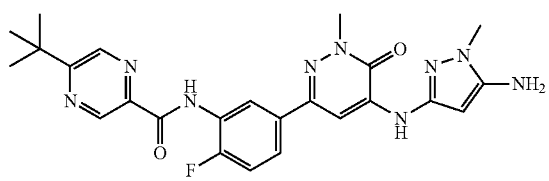 [SMILES: Cn1nc(Nc2cc(-c3ccc(F)c(NC(=O)c4cnc(C(C)(C)C)cn4)c3)nn(C)c2=O)cc1N] | N-(5-{5-[(5-amino-1-methyl-1H-pyrazol-3-yl)amino]-1-methyl-6-oxo-1,6-dihydropyridazin-3-yl}-2-fluorophenyl)-5-tert-butylpyrazine-2-carboxamide | 491 | 492.1 |
| 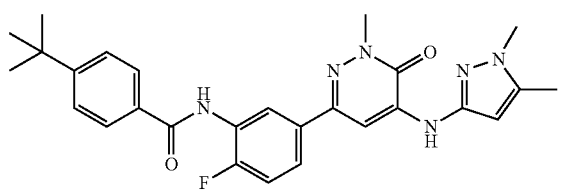 [SMILES: Cc1cc(Nc2cc(-c3ccc(F)c(NC(=O)c4ccc(C(C)(C)C)cc4)c3)nn(C)c2=O)nn1C] | 4-tert-butyl-N-(5-{5-[(1,5-dimethyl-1H-pyrazol-3-yl)amino]-1-methyl-6-oxo-1,6-dihydropyridazin-3-yl}-2-fluorophenyl)benzamide | 488 | 489.1 |
| 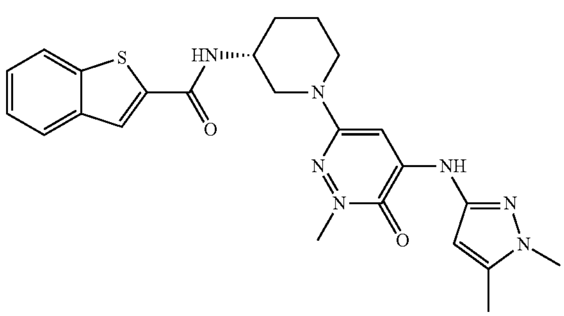 | N-[(3R)-1-{5-[(1,5-dimethyl-1H-pyrazol-3-yl)amino]-1-methyl-6-oxo-1,6-dihydropyridazin-3-yl}piperidin-3-yl]-1-benzothiophene-2-carboxamide | 477 | 478.2 |
| 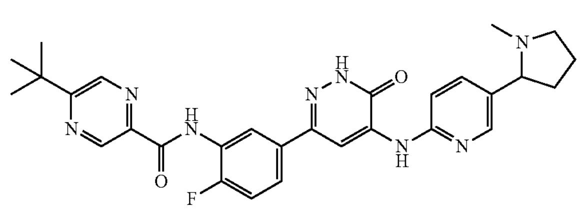 | 5-tert-butyl-N-[2-fluoro-5-(5-{[5-(1-methylpyrrolidin-2-yl)pyridin-2-yl]amino}-6-oxo-1,6-dihydropyridazin-3-yl)phenyl]pyrazine-2-carboxamide | 542 | 543.2 |
| 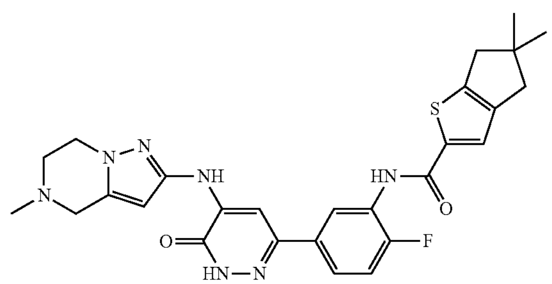 | N-{2-fluoro-5-[5-({5-methyl-4H,5H,6H,7H-pyrazolo[1,5-a]pyrazin-2-yl}amino)-6-oxo-1,6-dihydropyridazin-3-yl]phenyl}-5,5-dimethyl-4H,5H,6H-cyclopenta[b]thiophene-2-carboxamide | 533 | 534.2 |

-continued

| Structure | Name | MW calcd | MH + m/z obs |
|---|---|---|---|
| 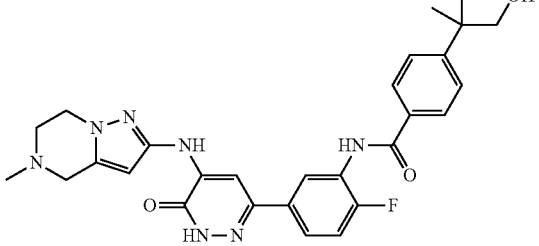 | N-{2-fluoro-5-[5-({5-methyl-4H,5H,6H,7H-pyrazolo[1,5-a]pyrazin-2-yl}amino)-6-oxo-1,6-dihydropyridazin-3-yl]phenyl}-4-(1-hydroxy-2-methylpropan-2-yl)benzamide | 531 | 532.3 |
| 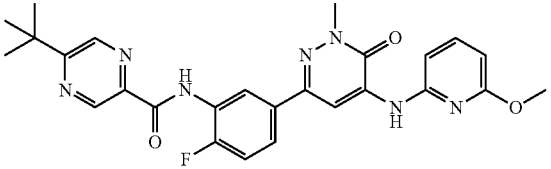 [SMILES: COc1cccc(Nc2cc(-c3ccc(F)c(NC(=O)c4cnc(C(C)(C)C)cn4)c3)nn(C)c2=O)n1] | 5-tert-butyl-N-(2-fluoro-5-{5-[(6-methoxypyridin-2-yl)amino]-1-methyl-6-oxo-1,6-dihydropyridazin-3-yl}phenyl)pyrazine-2-carboxamide | 503 | 504.3 |
| 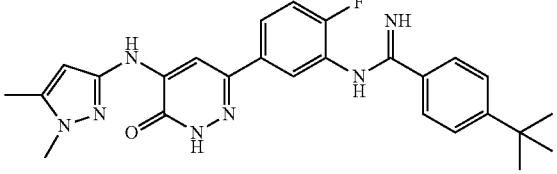 | 4-tert-butyl-N-(5-{5[(1,5-dimethyl-1H-pyrazol-3-yl)amino]-6-oxo-1,6-dihydropyridazin-3-yl}-2-fluorophenyl)benzene-1-carboximidamide | 473 | 474.5 |
| 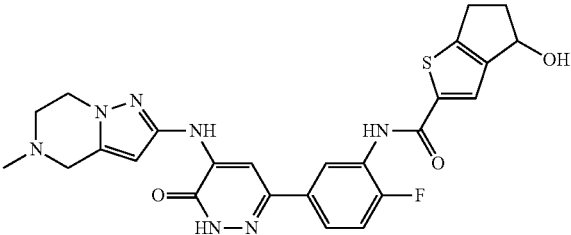 [SMILES: CN1CCn2nc(Nc3cc(-c4ccc(F)c(NC(=O)c5cc6c(s5)CCC6O)c4)n[nH]c3=O)cc2C1] | N-{2-fluoro-5-[5-({5-methyl-4H,5H,6H,7H-pyrazolo[1,5-a]pyrazin-2-yl}amino)-6-oxo-1,6-dihydropyridazin-3-yl]phenyl}-4-hydroxy-4H,5H,6H-cyclopenta[b]thiophene-2-carboxamide | 521 | 522.7 |
| 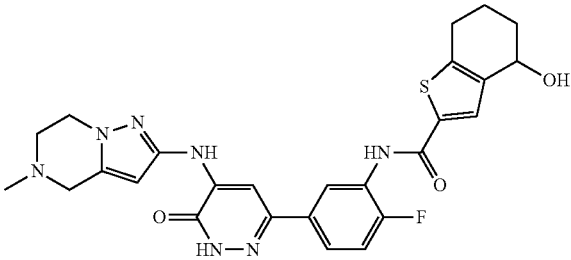 [SMILES: CN1CCn2nc(Nc3cc(-c4ccc(F)c(NC(=O)c5cc6c(s5)CCCC6O)c4)n[nH]c3=O)cc2C1] | N-{2-fluoro-5-[5-({5-methyl-4H,5H,6H,7H-pyrazolo[1,5-a]pyrazin-2-yl}amino)-6-oxo-1,6-dihydropyridazin-3-yl]phenyl}-4-hydroxy-4,5,6,7-tetrahydro-1-benzothiophene-2-carboxamide | 535 | 536.2 |
| 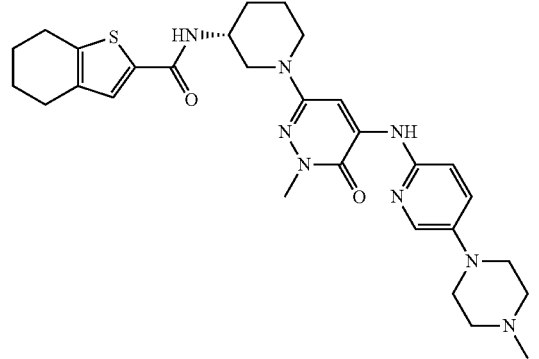 [SMILES: CN1CCN(c2ccc(Nc3cc(N4CCC[C@@H](NC(=O)c5cc6c(s5)CCCC6)C4)nn(C)c3=O)nc2)CC1] | N-[(3R)-1-(1-methyl-5-{[5(4-methylpiperazin-1-yl)pyridin-2-yl]amino}-6-oxo-1,6-dihydropyridazin-3-yl)piperidin-3-yl]-4,5,6,7-tetrahydro-1-benzothiophene-2-carboxamide | 562 | 563.29 |

-continued

| Structure | Name | MW calcd | MH + m/z obs |
|---|---|---|---|
| 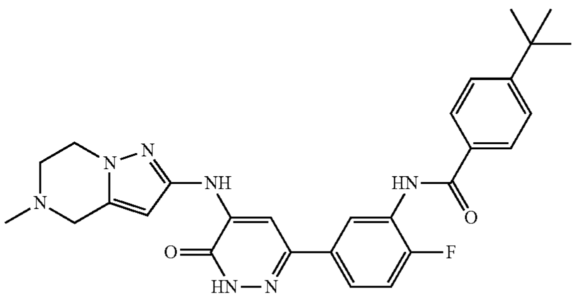 [SMILES: CN1CCn2nc(Nc3cc(-c4ccc(F)c(NC(=O)c5ccc(C(C)(C)C)cc5)c4)n[nH]c3=O)cc2C1] | 4-tert-butyl-N-{2-fluoro-5-[5-({5-methyl-4H,5H,6H,7H-pyrazolo[1,5-a]pyrazin-2-yl}amino)-6-oxo-1,6-dihydropyridazin-3-yl]phenyl}benzamide | 515 | 516.26 |
| 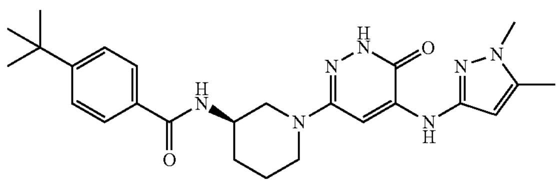 [SMILES: Cc1cc(Nc2cc(N3CCC[C@@H](NC(=O)c4ccc(C(C)(C)C)cc4)C3)n[nH]c2=O)nn1C] | 4-tert-butyl-N-[(3R)-1-{5-[(1,5-dimethyl-1H-pyrazol-3-yl)amino]-6-oxo-1,6-dihydropyridazin-3-yl}piperidin-3-yl]benzamide | 463 | 464.2 |
| 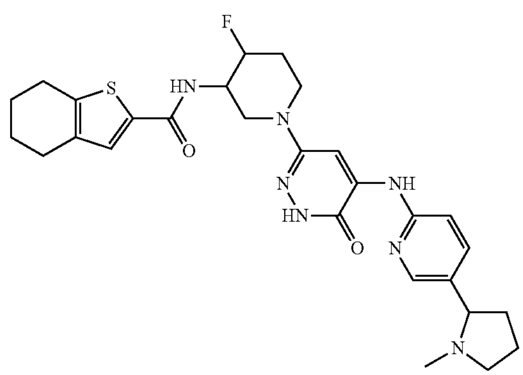 [SMILES: CN1CCCC1c1ccc(Nc2cc(N3CCC(F)C(NC(=O)c4cc5c(s4)CCCC5)C3)n[nH]c2=O)nc1] | N-[2-fluoro-5-(5-{[5-(1-methylpyrrolidin-2-yl)pyridin-2-yl]amino}-6-oxo-1,6-dihydropyridazin-3-yl)phenyl]-4,5,6,7-tetrahydro-1-benzothiophene-2-carboxamide | 544 | 545.2 |
| 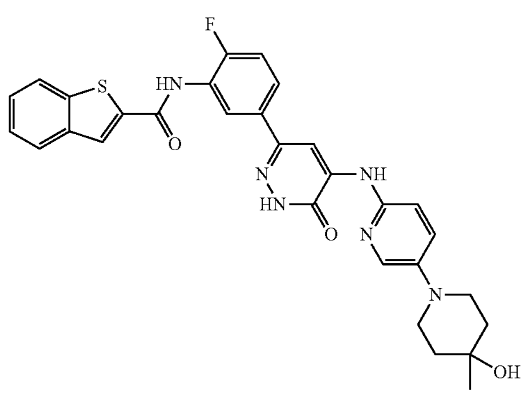 [SMILES: CC1(O)CCN(c2ccc(Nc3cc(-c4ccc(F)c(NC(=O)c5cc6ccccc6s5)c4)n[nH]c3=O)nc2)CC1] | N-[2-fluoro-5-(5-{[5-(4-hydroxy-4-methylpiperidin-1-yl)pyridin-2-yl]amino}-6-oxo-1,6-dihydropyridazin-3-yl)phenyl]-1-benzothiophene-2-carboxamide | 570 | 571 |
| 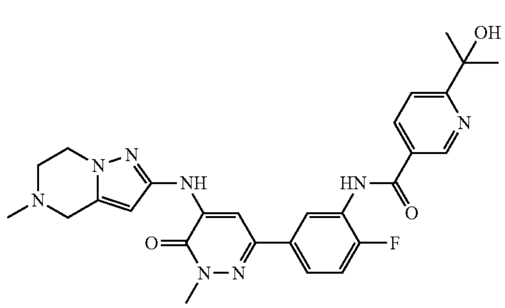 [SMILES: CN1CCn2nc(Nc3cc(-c4ccc(F)c(NC(=O)c5ccc(C(C)(C)O)nc5)c4)nn(C)c3=O)cc2C1] | N-{2-fluoro-5-[1-methyl-5-({5-methyl-4H,5H,6H,7H-pyrazolo[1,5-a]pyrazin-2-yl}amino)-6-oxo-1,6-dihydropyridazin-3-yl]phenyl}-6-(2-hydroxypropan-2-yl)pyridine-3-carboxamide | 532 | 533.1 |

| Structure | Name | MW calcd | MH + m/z obs |
|---|---|---|---|
| 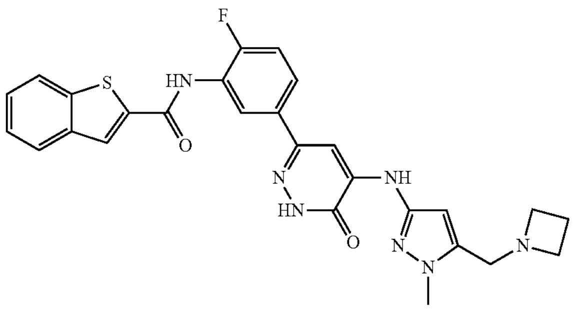 [SMILES: Cn1nc(Nc2cc(-c3ccc(F)c(NC(=O)c4cc5ccccc5s4)c3)n[nH]c2=O)cc1CN1CCC1] | N-[5-(5-{[5-(azetidin-1-ylmethyl)-1-methyl-1H-pyrazol-3-yl]amino}-6-oxo-1,6-dihydropyridazin-3-yl)-2-fluorophenyl]-1-benzothiophene-2-carboxamide | 529 | 530.15 |
| 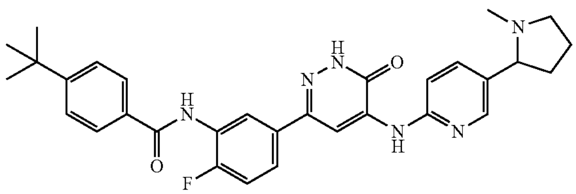 | 4-tert-butyl-N-[2-fluoro-5-(5-{[5-(1-methylpyrrolidin-2-yl)pyridin-2-yl]amino}-6-oxo-1,6-dihydropyridazin-3-yl)phenyl]benzamide | 540 | 541.24 |
| 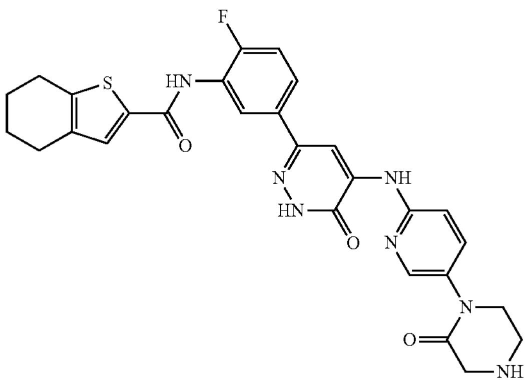 [SMILES: O=C(Nc1cc(-c2cc(Nc3ccc(N4CCNCC4=O)cn3)c(=O)[nH]n2)ccc1F)c1cc2c(s1)CCCC2] | N-[2-fluoro-5-(6-oxo-5-{[5-(2-oxopiperazin-1-yl)pyridin-2-yl]amino}-1,6-dihydropyridazin-3-yl)phenyl]-4,5,6,7-tetrahydro-1-benzothiophene-2-carboxamide | 559 | 560 |
| 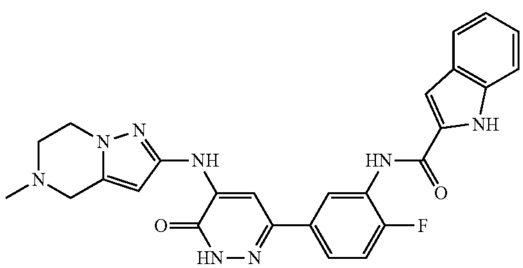 [SMILES: CN1CCn2nc(Nc3cc(-c4ccc(F)c(NC(=O)c5cc6ccccc6[nH]5)c4)n[nH]c3=O)cc2C1] | N-{2-fluoro-5-[5-({5-methyl-4H,5H,6H,7H-pyrazolo[1,5-a]pyrazin-2-yl}amino)-6-oxo-1,6-dihydropyridazin-3-yl]phenyl}-1H-indole-2-carboxamide | 498 | 499.9 |
| 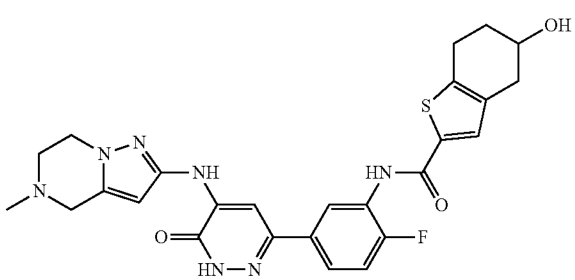 [SMILES: CN1CCn2nc(Nc3cc(-c4ccc(F)c(NC(=O)c5cc6c(s5)CCC(O)C6)c4)n[nH]c3=O)cc2C1] | N-{2-fluoro-5-[5-({5-methyl-4H,5H,6H,7H-pyrazolo[1,5-a]pyrazin-2-yl}amino)-6-oxo-1,6-dihydropyridazin-3-yl]phenyl}-5-hydroxy-4,5,6,7-tetrahydro-1-benzothiophene-2-carboxamide | 535 | 536.2 |

-continued

| Structure | Name | MW calcd | MH + m/z obs |
|---|---|---|---|
| 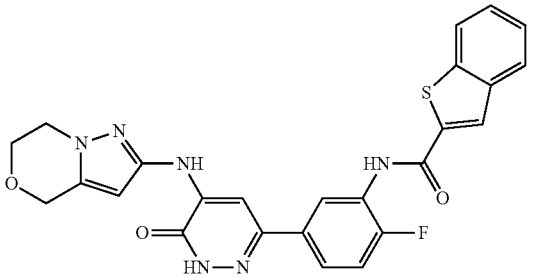 [SMILES: O=C(Nc1cc(-c2cc(Nc3cc4n(n3)CCOC4)c(=O)[nH]n2)ccc1F)c1cc2ccccc2s1] | N-[2-fluoro-5-(6-oxo-5-{4H,6H,7H-pyrazolo[3,2-c][1,4]oxazin-2-ylamino}-1,6-dihydropyridazin-3-yl)phenyl]-1-benzothiophene-2-carboxamide | 502 | 503.19 |
| 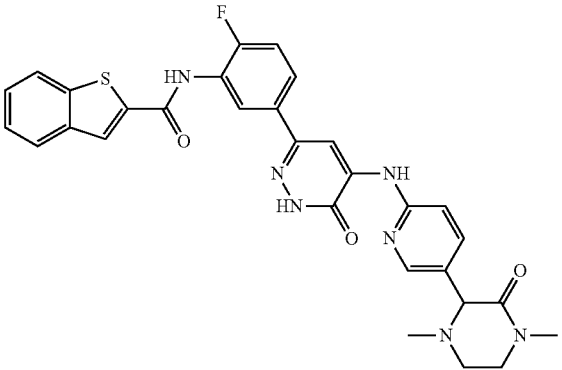 [SMILES: CN1CCN(C)C(c2ccc(Nc3cc(-c4ccc(F)c(NC(=O)c5cc6ccccc6s5)c4)n[nH]c3=O)nc2)C1=O] | N-[5-(5-{[5-(1,4-dimethyl-3-oxopiperazin-2-yl)pyridin-2-yl]amino}-6-oxo-1,6-dihydropyridazin-3-yl)-2-fluorophenyl]-1-benzothiophene-2-carboxamide | 583 | 584.1 |
| 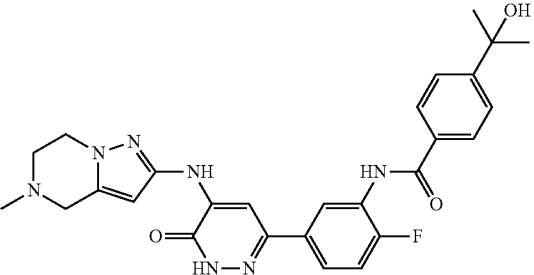 [SMILES: CN1CCn2nc(Nc3cc(-c4ccc(F)c(NC(=O)c5ccc(C(C)(C)O)cc5)c4)n[nH]c3=O)cc2C1] | N-{2-fluoro-5-[5-({5-methyl-4H,5H,6H,7H-pyrazolo[1,5-a]pyrazin-2-yl}amino)-6-oxo-1,6-dihydropyridazin-3-yl]phenyl}-4-(2-hydroxypropan-2-yl)benzamide | 517 | 518.9 |
| 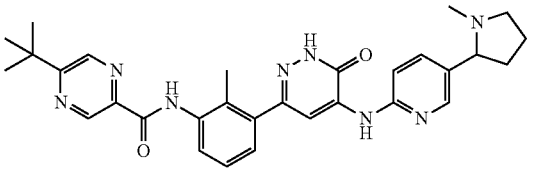 [SMILES: Cc1c(NC(=O)c2cnc(C(C)(C)C)cn2)cccc1-c1cc(Nc2ccc(C3CCCN3C)cn2)c(=O)[nH]n1] | 5-tert-butyl-N-[2-methyl-3-(5-{[5-(1-methylpyrrolidin-2-yl)pyridin-2-yl]amino}-6-oxo-1,6-dihydropyridazin-3-yl)phenyl]pyrazine-2-carboxamide | 538 | 539.2 |
| 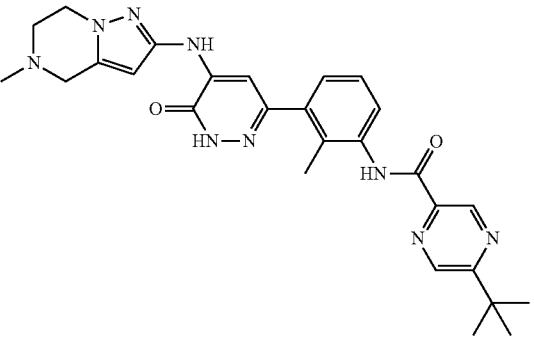 [SMILES: Cc1c(NC(=O)c2cnc(C(C)(C)C)cn2)cccc1-c1cc(Nc2cc3n(n2)CCN(C)C3)c(=O)[nH]n1] | 5-tert-butyl-N-{2-methyl-3-[5-({5-methyl-4H,5H,6H,7H-pyrazolo[1,5-a]pyrazin-2-yl}amino)-6-oxo-1,6-dihydropyridazin-3-yl]phenyl}pyrazine-2-carboxamide | 513 | 515.1 |

-continued

| Structure | Name | MW calcd | MH + m/z obs |
|---|---|---|---|
| 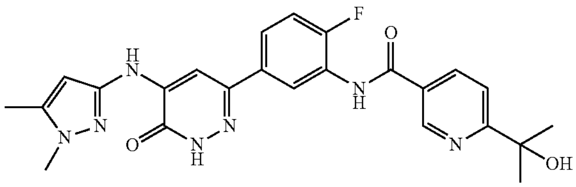 [SMILES: Cc1cc(Nc2cc(-c3ccc(F)c(NC(=O)c4ccc(C(C)(C)O)nc4)c3)n[nH]c2=O)nn1C] | N-(5-{5-[(1,5-dimethyl-1H-pyrazol-3-yl)amino]-6-oxo-1,6-dihydropyridazin-3-yl}-2-fluorophenyl)-6-(2-hydroxypropan-2-yl)pyridine-3-carboxamide | 477 | 478 |
| 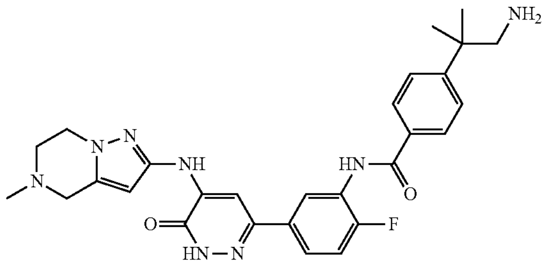 [SMILES: CN1CCn2nc(Nc3cc(-c4ccc(F)c(NC(=O)c5ccc(C(C)(C)CN)cc5)c4)n[nH]c3=O)cc2C1] | 4-(1-amino-2-methylpropan-2-yl)-N-{2-fluoro-5-[5-({5-methyl-4H,5H,6H,7H-pyrazolo[1,5-a]pyrazin-2-yl}amino)-6-oxo-1,6-dihydropyridazin-3-yl]phenyl}benzamide | 530 | 531.3 |
| 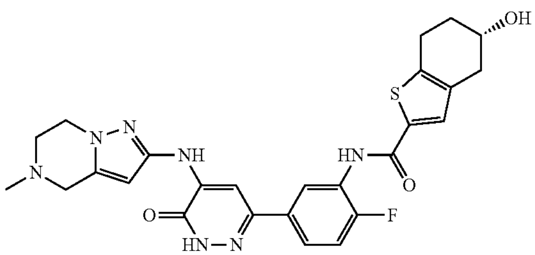 [SMILES: CN1CCn2nc(Nc3cc(-c4ccc(F)c(NC(=O)c5cc6c(s5)CC[C@H](O)C6)c4)n[nH]c3=O)cc2C1] | (5S)-N-{2-fluoro-5-[5-({5-methyl-4H,5H,6H,7H-pyrazolo[1,5-a]pyrazin-2-yl}amino)-6-oxo-1,6-dihydropyridazin-3-yl]phenyl}-5-hydroxy-4,5,6,7-tetrahydro-1-benzothiophene-2-carboxamide | 535 | 536.2 |
| 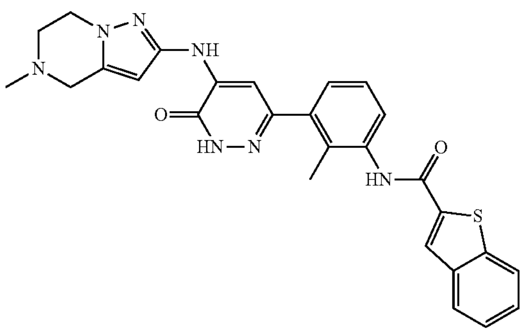 [SMILES: Cc1c(NC(=O)c2cc3ccccc3s2)cccc1-c1cc(Nc2cc3n(n2)CCN(C)C3)c(=O)[nH]n1] | N-{2-methyl-3-[5-({5-methyl-4H,5H,6H,7H-pyrazolo[1,5-a]pyrazin-2-yl}amino)-6-oxo-1,6-dihydropyridazin-3-yl]phenyl}-1-benzothiophene-2-carboxamide | 511 | 512 |
| 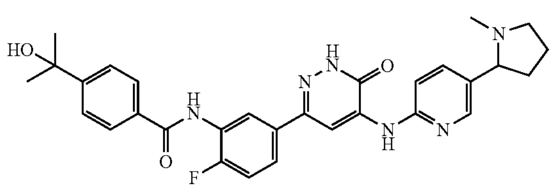 [SMILES: CN1CCCC1c1ccc(Nc2cc(-c3ccc(F)c(NC(=O)c4ccc(C(C)(C)O)cc4)c3)n[nH]c2=O)nc1] | N-[2-fluoro-5-(5-{[5-(1-methylpyrrolidin-2-yl)pyridin-2-yl]amino}-6-oxo-1,6-dihydropyridazin-3-yl)phenyl]-4-(2-hydroxypropan-2-yl)benzamide | 542 | 543.1 |
| 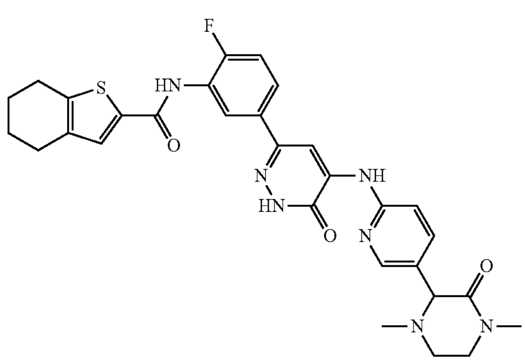 [SMILES: CN1CCN(C)C(c2ccc(Nc3cc(-c4ccc(F)c(NC(=O)c5cc6c(s5)CCCC6)c4)n[nH]c3=O)nc2)C1=O] | N-[5-(5-{[5-(1,4-dimethyl-3-oxopiperazin-2-yl)pyridin-2-yl]amino}-6-oxo-1,6-dihydropyridazin-3-yl)-2-fluorophenyl]-4,5,6,7-tetrahydro-1-benzothiophene-2-carboxamide | 587 | 588.1 |

-continued

| Structure | Name | MW calcd | MH + m/z obs |
|---|---|---|---|
| 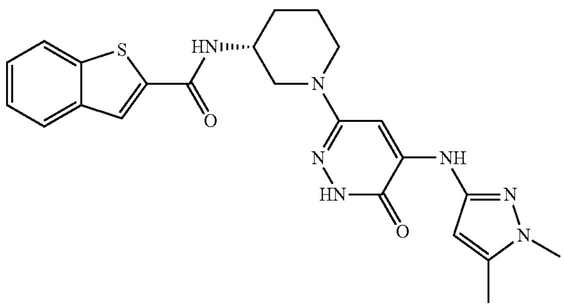 [SMILES: Cc1cc(Nc2cc(N3CCC[C@@H](NC(=O)c4cc5ccccc5s4)C3)n[nH]c2=O)nn1C] | N-[(3R)-1-{5[(1,5-dimethyl-1H-pyrazol-3-yl)amino]-6-oxo-1,6-dihydropyridazin-3-yl}piperidin-3-yl)-1-benzothiophene-2-carboxamide | 463 | 464.23 |
| 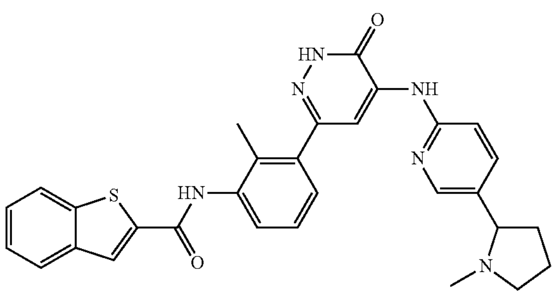 [SMILES: Cc1c(NC(=O)c2cc3ccccc3s2)cccc1-c1cc(Nc2ccc(C3CCCN3C)cn2)c(=O)[nH]n1] | N-[2-methyl-3-(5-{[5-(1-methylpyrrolidin-2-yl)pyridin-2-yl]amino}-6-oxo-1,6-dihydropyridazin-3-yl)phenyl]-1-benzothiophene-2-carboxamide | 537 | 536.65 |
| 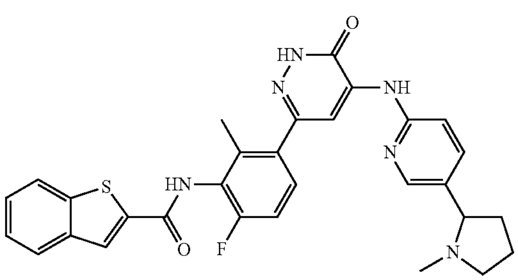 [SMILES: Cc1c(-c2cc(Nc3ccc(C4CCCN4C)cn3)c(=O)[nH]n2)ccc(F)c1NC(=O)c1cc2ccccc2s1] | N-[6-fluoro-2-methyl-3-(5-{[5-(1-methylpyrrolidin-2-yl)pyridin-2-yl]amino}-6-oxo-1,6-dihydropyridazin-3-yl)phenyl]-1-benzothiophene-2-carboxamide | 554 | 555 |
| 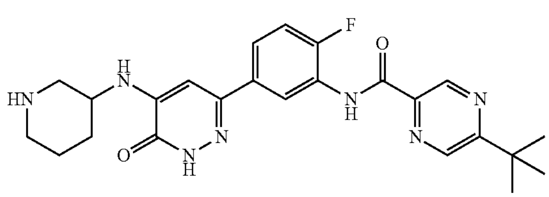 [SMILES: CC(C)(C)c1cnc(C(=O)Nc2cc(-c3cc(NC4CCCNC4)c(=O)[nH]n3)ccc2F)cn1] | 5-tert-butyl-N-{2-fluoro-5-[6-oxo-5-(piperidin-3-ylamino)-1,6-dihydropyridazin-3-yl]phenyl}pyrazine-2-carboxamide | 465 | 464.6 |
| 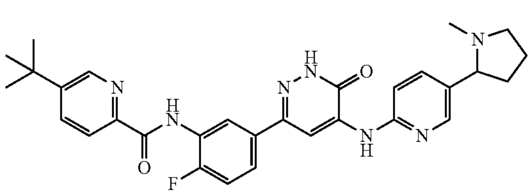 [SMILES: CN1CCCC1c1ccc(Nc2cc(-c3ccc(F)c(NC(=O)c4ccc(C(C)(C)C)cn4)c3)n[nH]c2=O)nc1] | 5-tert-butyl-N-[2-fluoro-5-(5-{[5-(1-methylpyrrolidin-2-yl)pyridin-2-yl]amino}-6-oxo-1,6-dihydropyridazin-3-yl)phenyl]pyridine-2-carboxamide | 541 | 542.1 |

-continued

| Structure | Name | MW calcd | MH + m/z obs |
|---|---|---|---|
| 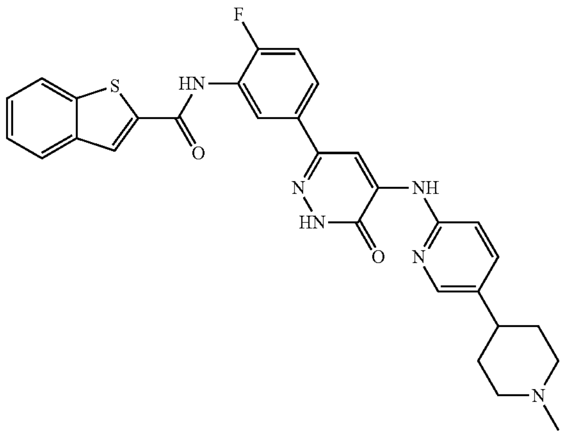 [SMILES: CN1CCC(c2ccc(Nc3cc(-c4ccc(F)c(NC(=O)c5cc6ccccc6s5)c4)n[nH]c3=O)nc2)CC1] | N-[2-fluoro-5-(5-{[5-(1-methylpiperidin-4-yl)pyridin-2-yl]amino}-6-oxo-1,6-dihydropyridazin-3-yl)phenyl]-1-benzothiophene-2-carboxamide | 554 | 555 |
| 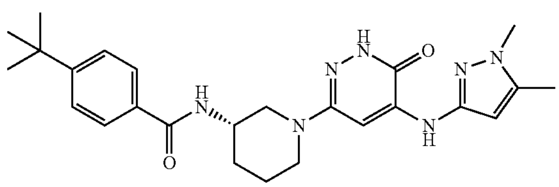 [SMILES: Cc1cc(Nc2cc(N3CCC[C@H](NC(=O)c4ccc(C(C)(C)C)cc4)C3)n[nH]c2=O)nn1C] | 4-tert-butyl-N-[(3S)-1-{5-[(1,5-dimethyl-1H-pyrazol-3-yl)amino]-6-oxo-1,6-dihydropyridazin-3-yl}piperidin-3-yl]benzamide | 463 | 464.23 |
| 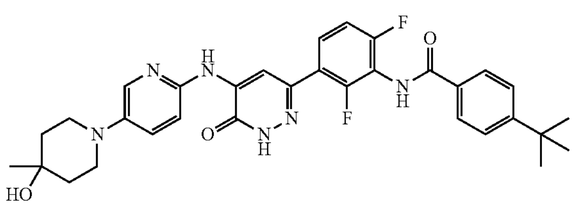 [SMILES: CC1(O)CCN(c2ccc(Nc3cc(-c4ccc(F)c(NC(=O)c5ccc(C(C)(C)C)cc5)c4F)n[nH]c3=O)nc2)CC1] | 4-tert-butyl-N-[2,6-difluoro-3-(5-{[5-(4-hydroxy-4-methylpiperidin-1-yl)pyridin-2-yl]amino}-6-oxo-1,6-dihydropyridazin-3-yl)phenyl]benzamide | 588 | 589.1 |
| 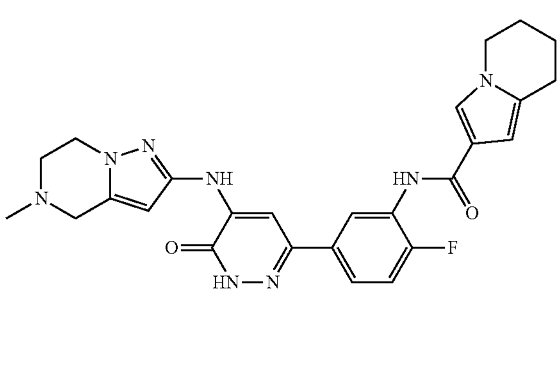 [SMILES: CN1CCn2nc(Nc3cc(-c4ccc(F)c(NC(=O)c5cc6n(c5)CCCC6)c4)n[nH]c3=O)cc2C1] | N-{2-fluoro-5-[5-({5-methyl-4H,5H,6H,7H-pyrazolo[1,5-a]pyrazin-2-yl}amino)-6-oxo-1,6-dihydropyridazin-3-yl]phenyl}-5,6,7,8-tetrahydroindolizine-2-carboxamide | 502 | 503.2 |
| 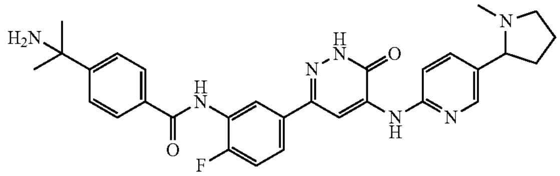 [SMILES: CN1CCCC1c1ccc(Nc2cc(-c3ccc(F)c(NC(=O)c4ccc(C(C)(C)N)cc4)c3)n[nH]c2=O)nc1] | 4-(2-aminopropan-2-yl)-N-[2-fluoro-5-(5-{[5-(1-methylpyrrolidin-2-yl)pyridin-2-yl]amino}-6-oxo-1,6-dihydropyridazin-3-yl)phenyl]benzamide | 541 | 542.3 |

-continued

| Structure | Name | MW calcd | MH + m/z obs |
|---|---|---|---|
| 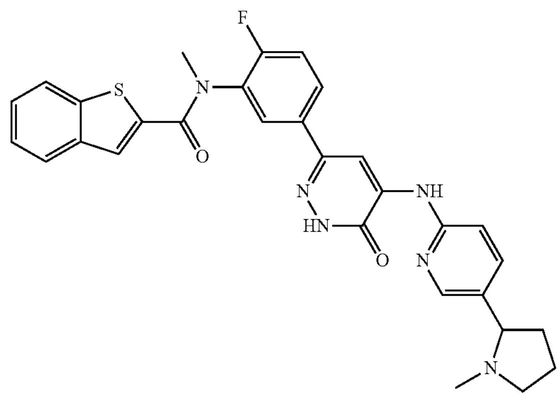 [SMILES: CN(C(=O)c1cc2ccccc2s1)c1cc(-c2cc(Nc3ccc(C4CCCN4C)cn3)c(=O)[nH]n2)ccc1F] | N-[2-fluoro-5-(5-{[5-(1-methylpyrrolidin-2-yl)pyridin-2-yl]amino}-6-oxo-1,6-dihydropyridazin-3-yl)phenyl]-N-methyl-1-benzothiophene-2-carboxamide | 554 | 555.4 |
| 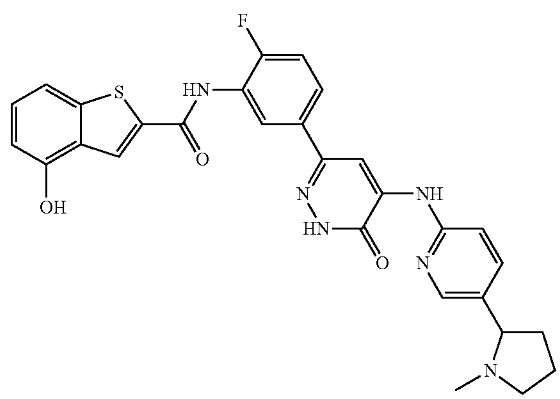 [SMILES: CN1CCCC1c1ccc(Nc2cc(-c3ccc(F)c(NC(=O)c4cc5c(O)cccc5s4)c3)n[nH]c2=O)nc1] | N-[2-fluoro-5-(5-{[5-(1-methylpyrrolidin-2-yl)pyridin-2-yl]amino}-6-oxo-1,6-dihydropyridazin-3-yl)phenyl]-4-hydroxy-1-benzothiophene-2-carboxamide | 556 | 557.2 |
| 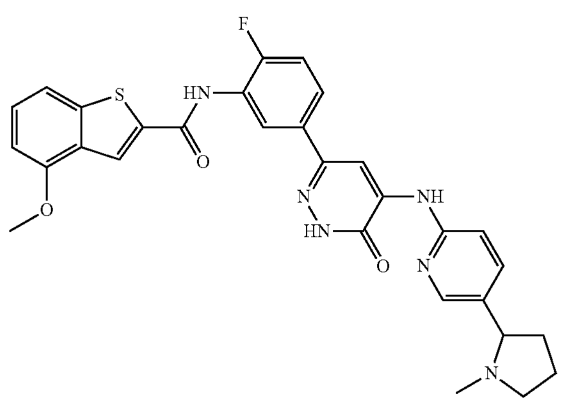 [SMILES: COc1cccc2sc(C(=O)Nc3cc(-c4cc(Nc5ccc(C6CCCN6C)cn5)c(=O)[nH]n4)ccc3F)cc12] | N-[2-fluoro-5-(5-{[5-(1-methylpyrrolidin-2-yl)pyridin-2-yl]amino}-6-oxo-1,6-dihydropyridazin-3-yl)phenyl]-4-methoxy-1-benzothiophene-2-carboxamide | 570 | 571.2 |
| 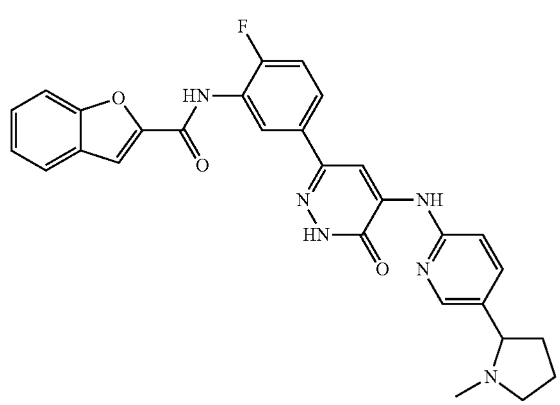 | N-[2-fluoro-5-(5-{[5-(1-methylpyrrolidin-2-yl)pyridin-2-yl]amino}-6-oxo-1,6-dihydropyridazin-3-yl)phenyl]-1-benzofuran-2-carboxamide | 524 | 525.6 |

-continued

| Structure | Name | MW calcd | MH + m/z obs |
|---|---|---|---|
| 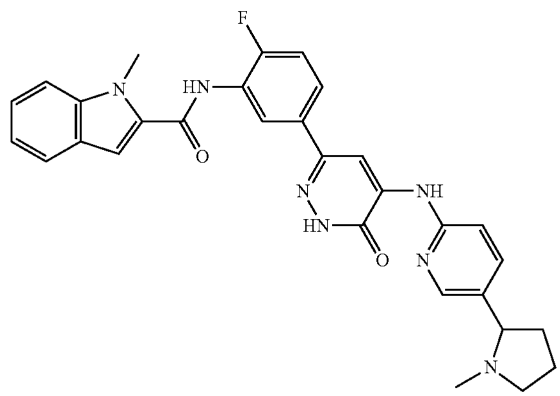 [SMILES: CN1CCCC1c1ccc(Nc2cc(-c3ccc(F)c(NC(=O)c4cc5ccccc5n4C)c3)n[nH]c2=O)nc1] | N-[2-fluoro-5-(5-{[5-(1-methylpyrrolidin-2-yl)pyridin-2-yl]amino}-6-oxo-1,6-dihydropyridazin-3-yl)phenyl]-1-methyl-1H-indole-2-carboxamide | 537 | 538.5 |
| 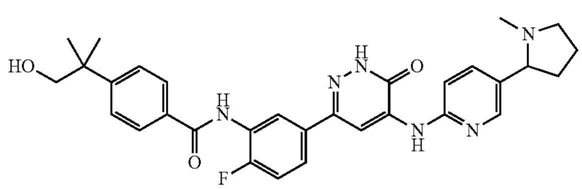 [SMILES: CN1CCCC1c1ccc(Nc2cc(-c3ccc(F)c(NC(=O)c4ccc(C(C)(C)CO)cc4)c3)n[nH]c2=O)nc1] | N-[2-fluoro-5-(5-{[5-(1-methylpyrrolidin-2-yl)pyridin-2-yl]amino}-6-oxo-1,6-dihydropyridazin-3-yl)phenyl]-4-(1-hydroxy-2-methylpropan-2-yl)benzamide | 556 | 557.3 |
| 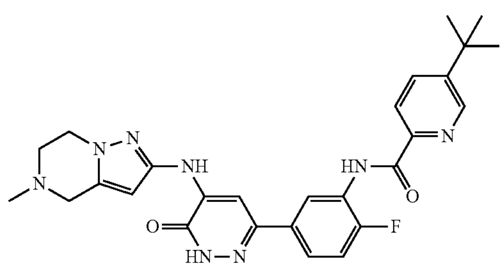 [SMILES: CN1CCn2nc(Nc3cc(-c4ccc(F)c(NC(=O)c5ccc(C(C)(C)C)cn5)c4)n[nH]c3=O)cc2C1] | 5-tert-butyl-N-{2-fluoro-5-[5-({5-methyl-4H,5H,6H,7H-pyrazolo[1,5-a]pyrazin-2-yl}amino)-6-oxo-1,6-dihydropyridazin-3-yl]phenyl}pyridine-2-carboxamide | 516 | 517.2 |
| 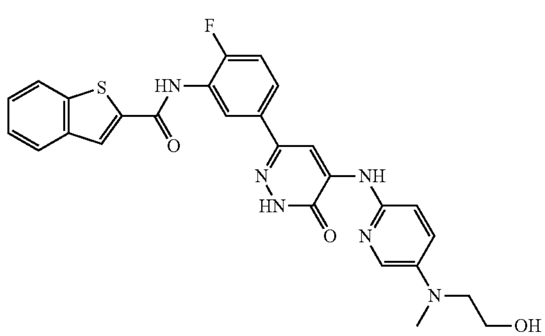 [SMILES: CN(CCO)c1ccc(Nc2cc(-c3ccc(F)c(NC(=O)c4cc5ccccc5s4)c3)n[nH]c2=O)nc1] | N-{2-fluoro-5-[5-({5-[(2-hydroxyethyl)(methyl)amino]pyridin-2-yl}amino)-6-oxo-1,6-dihydropyridazin-3-yl]phenyl}-1-benzothiophene-2-carboxamide | 530 | 531 |
| 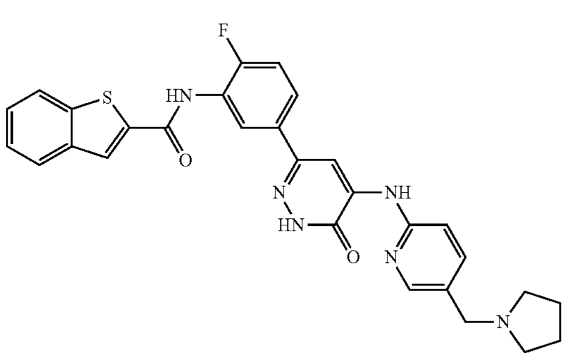 [SMILES: O=C(Nc1cc(-c2cc(Nc3ccc(CN4CCCC4)cn3)c(=O)[nH]n2)ccc1F)c1cc2ccccc2s1] | N-[2-fluoro-5-(6-oxo-5-{[5-(pyrrolidin-1-ylmethyl)pyridin-2-yl]amino}-1,6-dihydropyridazin-3-yl)phenyl]-1-benzothiophene-2-carboxamide | 540 | 541.12 |

-continued

| Structure | Name | MW calcd | MH + m/z obs |
|---|---|---|---|
| 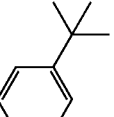 | 4-tert-butyl-N-[(3R)-1-[1-methyl-5-({5-methyl-4H,5H,6H,7H-pyrazolo[1,5-a]pyrazin-2-yl}amino)-6-oxo-1,6-dihydropyridazin-3-yl]piperidin-3-yl]benzamide | 518 | 519.23 |
| 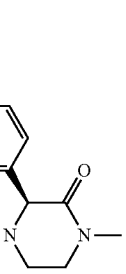 | N-{3-[5-({5-[(2S)-1,4-dimethyl-3-oxopiperazin-2-yl]pyridin-2-yl}amino)-1-methyl-6-oxo-1,6-dihydropyridazin-3-yl]-2,6-difluorophenyl]-4,5,6,7-tetrahydro-1-benzothiophene-2-carboxamide | 619 | 0 |
| 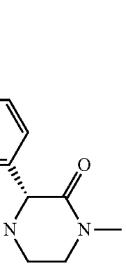 | N-{3-[5-({5-[(2R)-1,4-dimethyl-3-oxopiperazin-2-yl]pyridin-2-yl}amino)-1-methyl-6-oxo-1,6-dihydropyridazin-3-yl]-2,6-difluorophenyl}-4,5,6,7-tetrahydro-1-benzothioithene-2-carboxamide | 619 | 0 |
| 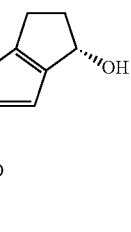 | (4S)-N-{2-fluoro-5-[5-({5-methyl-4H,5H,6H,7H-pyrazolo[1,5-a]pyrazin-2-yl}amino)-6-oxo-1,6-dihydropyridazin-3-yl]phenyl}-4-hydroxy-4H,5H,6H-cyclopenta[b]thiophene-2-carboxamide | 521 | 0 |
| 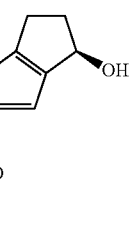 | (4R)-N-{2-fluoro-5-[5-({5-methyl-4H,5H,6H,7H-pyrazolo[1,5-a]pyrazin-2-yl}amino)-6-oxo-1,6-dihydropyridazin-3-yl]phenyl}-4-hydroxy-4H,5H,6H-cyclopenta[b]thiophene-2-carboxamide | 521 | 0 |

| Structure | Name | MW calcd | MH + m/z obs |
|---|---|---|---|
| 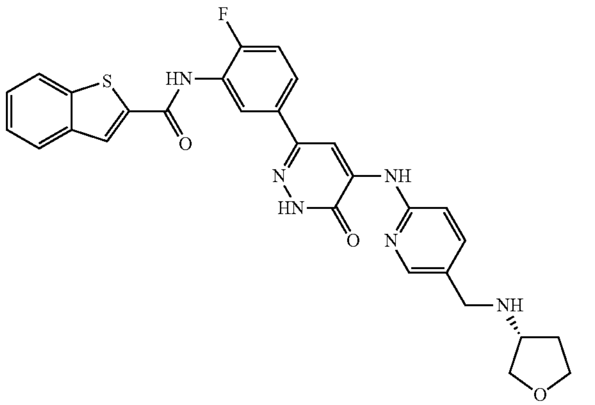 [SMILES: O=C(Nc1cc(-c2cc(Nc3ccc(CN[C@@H]4CCOC4)cn3)c(=O)[nH]n2)ccc1F)c1cc2ccccc2s1] | N-(2-fluoro-5-{6-oxo-5-[(5-{[(3R)-oxolan-3-ylamino]methyl}pyridin-2-yl)amino]-1,6-dihydropyridazin-3-yl}phenyl)-1-benzothiophene-2-carboxamide | 556 | 557.13 |
| 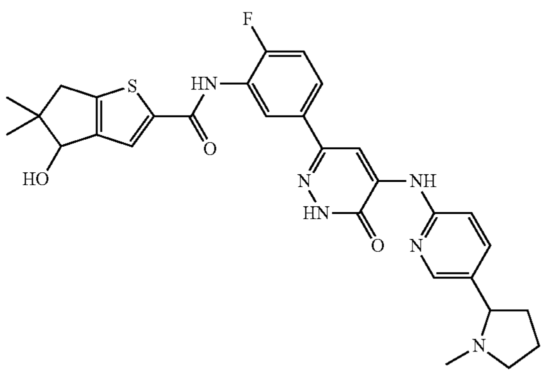 [SMILES: CN1CCCC1c1ccc(Nc2cc(-c3ccc(F)c(NC(=O)c4cc5c(s4)CC(C)(C)C5O)c3)n[nH]c2=O)nc1] | N-[2-fluoro-5-(5-{[5-(1-methylpyrrolidin-2-yl)pyridin-2-yl]amino}-6-oxo-1,6-dihydropyridazin-3-yl)phenyl]-4-hydroxy-5,5-dimethyl-4H,5H,6H-cyclopenta[b]thiophene-2-carboxamide | 574 | 575.4 |
| 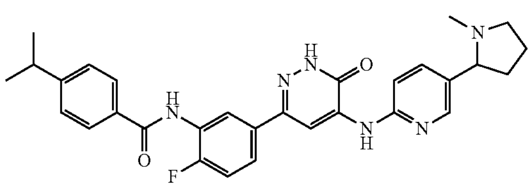 [SMILES: CC(C)c1ccc(C(=O)Nc2cc(-c3cc(Nc4ccc(C5CCCN5C)cn4)c(=O)[nH]n3)ccc2F)cc1] | N-[2-fluoro-5-(5-{[5-(1-methylpyrrolidin-2-yl)pyridin-2-yl]amino}-6-oxo-1,6-dihydropyridazin-3-yl)phenyl]-4-(propan-2-yl)benzamide | 526 | 527.3 |
| 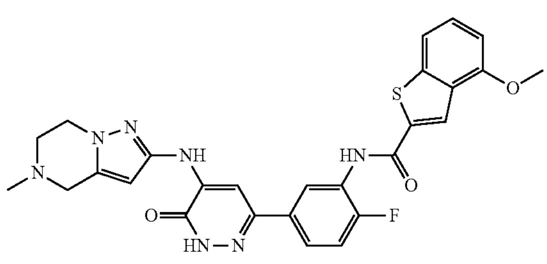 | N-{2-fluoro-5-[5-({5-methyl-4H,5H,6H,7H-pyrazolo[1,5-a]pyrazin-2-yl}amino)-6-oxo-1,6-dihydropyridazin-3-yl]phenyl}-4-methoxy-1-benzothiophene-2-carboxamide | 545 | 546.2 |
| 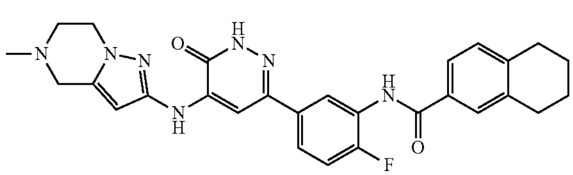 [SMILES: CN1CCn2nc(Nc3cc(-c4ccc(F)c(NC(=O)c5ccc6c(c5)CCCC6)c4)n[nH]c3=O)cc2C1] | N-{2-fluoro-5-[5-({5-methyl-4H,5H,6H,7H-pyrazolo[1,5-a]pyrazin-2-yl}amino)-6-oxo-1,6-dihydropyridazin-3-yl]phenyl}-5,6,7,8-tetrahydronaphthalene-2-carboxamide | 513 | 514.8 |

| Structure | Name | MW calcd | MH + m/z obs |
|---|---|---|---|
| 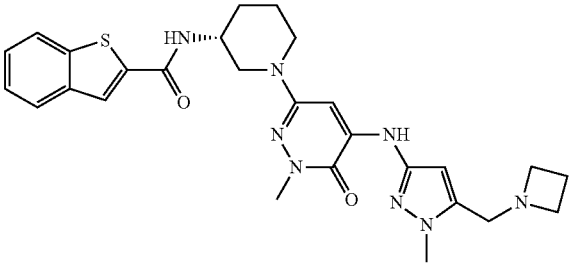 [SMILES: Cn1nc(Nc2cc(N3CCC[C@@H](NC(=O)c4cc5ccccc5s4)C3)nn(C)c2=O)cc1CN1CCC1] | N-[(3R)-1-(5-{[5-(azetidin-1-ylmethyl)-1-methyl-1H-pyrazol-3-yl]amino}-1-methyl-6-oxo-1,6-dihydropyridazin-3-yl)piperidin-3-yl]-1-benzothiophene-2-carboxamide | 532 | 533.17 |
| 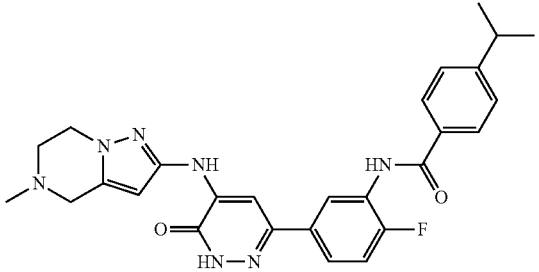 [SMILES: CC(C)c1ccc(C(=O)Nc2cc(-c3cc(Nc4cc5n(n4)CCN(C)C5)c(=O)[nH]n3)ccc2F)cc1] | N-{2-fluoro-5-[5-({5-methyl-4H,5H,6H,7H-pyrazolo[1,5-a]pyrazin-2-yl}amino)-6-oxo-1,6-dihydropyridazin-3-yl]phenyl}-4-(propan-2-yl)benzamide | 501 | 502.4 |
| 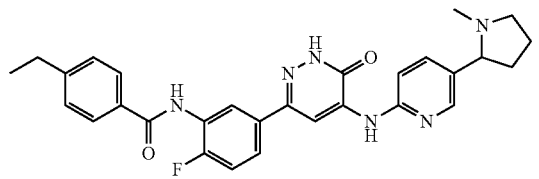 [SMILES: CCc1ccc(C(=O)Nc2cc(-c3cc(Nc4ccc(C5CCCN5C)cn4)c(=O)[nH]n3)ccc2F)cc1] | 4-ethyl-N-[2-fluoro-5-(5-{[5-(1-methylpyrrolidin-2-yl)pyridin-2-yl]amino}-6-oxo-1,6-dihydropyridazin-3-yl)phenyl]benzamide | 512 | 511.7 |
| 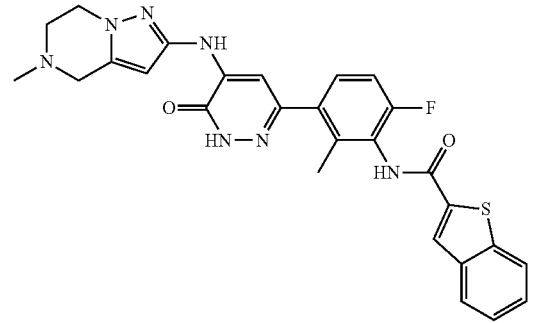 | N-{6-fluoro-2-methyl-3-[5-({5-methyl-4H,5H,6H,7H-pyrazolo[1,5-a]pyrazin-2-yl}amino)-6-oxo-1,6-dihydropyridazin-3-yl]phenyl}-1-benzothiophene-2-carboxamide | 529 | 530.09 |
| 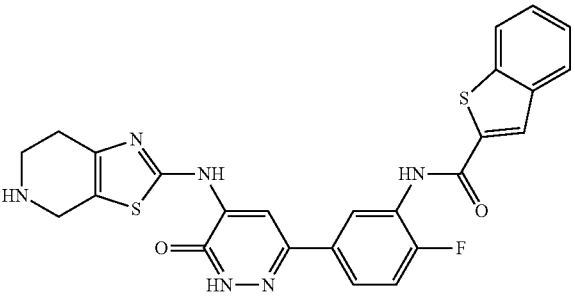 | N-[2-fluoro-5-(6-oxo-5-{4H,5H,6H,7H-pyrido[4,3-d][1,3]thiazol-2-ylamino}-1,6-dihydropyridazin-3-yl)phenyl]-1-benzothiophene-2-carboxamide | 518 | 519 |
| 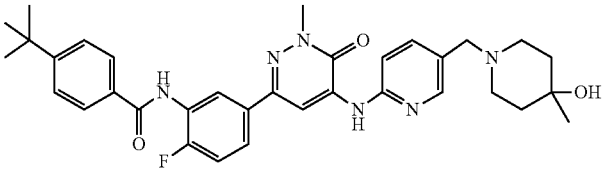 [SMILES: Cn1nc(-c2ccc(F)c(NC(=O)c3ccc(C(C)(C)C)cc3)c2)cc(Nc2ccc(CN3CCC(C)(O)CC3)cn2)c1=O] | 4-tert-butyl-N-{2-fluoro-5-[5-({5-[(4-hydroxy-4-methylpiperidin-1-yl)methyl]pyridin-2-yl}amino)-1-methyl-6-oxo-1,6-dihydropyridazin-3-yl]phenyl}benzamide | 598 | 599.2 |

| Structure | Name | MW calcd | MH + m/z obs |
|---|---|---|---|
| 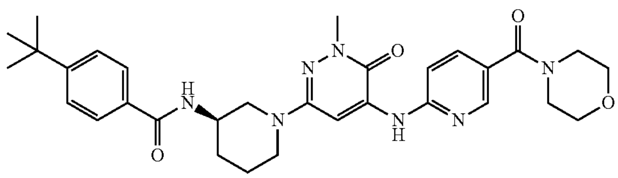 [SMILES: Cn1nc(N2CCC[C@@H](NC(=O)c3ccc(C(C)(C)C)cc3)C2)cc(Nc2ccc(C(=O)N3CCOCC3)cn2)c1=O] | 4-tert-butyl-N-[(3R)-1-(1-methyl-5-{[5-(morpholin-4-ylcarbonyl)pyridin-2-yl]amino}-6-oxo-1,6-dihydropyridazin-3-yl)piperidin-3-yl]benzamide | 573 | 574.18 |
| 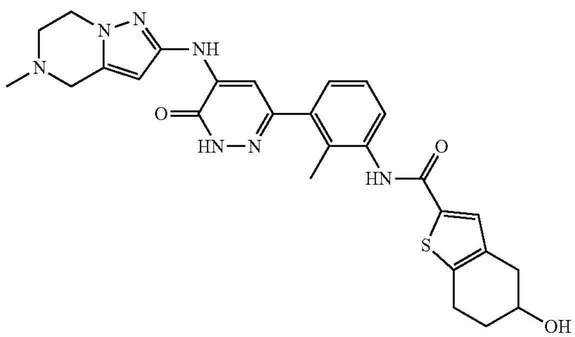 [SMILES: Cc1c(NC(=O)c2cc3c(s2)CCC(O)C3)cccc1-c1cc(Nc2cc3n(n2)CCN(C)C3)c(=O)[nH]n1] | 5-hydroxy-N-{2-methyl-3-[5-({5-methyl-4H,5H,6H,7H-pyrazolo[1,5-a]pyrazin-2-yl}amino)-6-oxo-1,6-dihydropyridazin-3-yl]phenyl}-4,5,6,7-tetrahydro-1-benzothiophene-2-carboxamide | 531 | 532.3 |
| 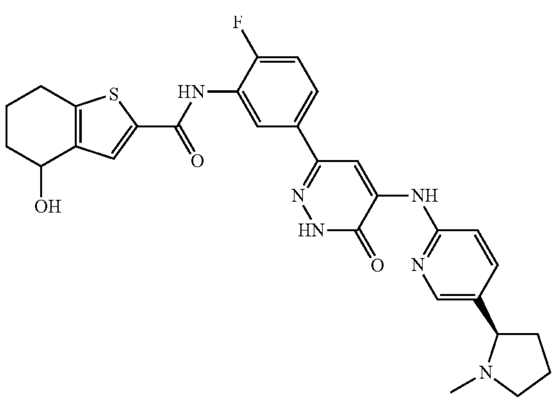 [SMILES: CN1CCC[C@@H]1c1ccc(Nc2cc(-c3ccc(F)c(NC(=O)c4cc5c(s4)CCCC5O)c3)n[nH]c2=O)nc1] | N-{2-fluoro-5-[5-({5-[(2R)-1-methylpyrrolidin-2-yl]pyridin-2-yl}amino)-6-oxo-1,6-dihydropyridazin-3-yl]phenyl}-4-hydroxy-4,5,6,7-tetrahydro-1-benzothiophene-2-carboxamide | 560 | 561.3 |
| 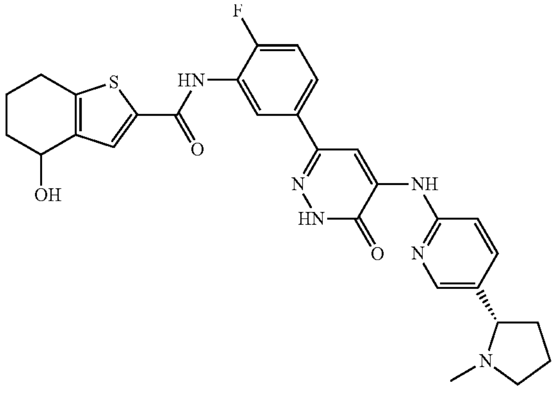 [SMILES: CN1CCC[C@H]1c1ccc(Nc2cc(-c3ccc(F)c(NC(=O)c4cc5c(s4)CCCC5O)c3)n[nH]c2=O)nc1] | N-{2-fluoro-5-[5-({5-[(2S)-1-methylpyrrolidin-2-yl]pyridin-2-yl}amino)-6-oxo-1,6-dihydropyridazin-3-yl]phenyl}-4-hydroxy-4,5,6,7-tetrahydro-1-benzothiophene-2-carboxamide | 560 | 559.4 |

| Structure | Name | MW calcd | MH + m/z obs |
|---|---|---|---|
| 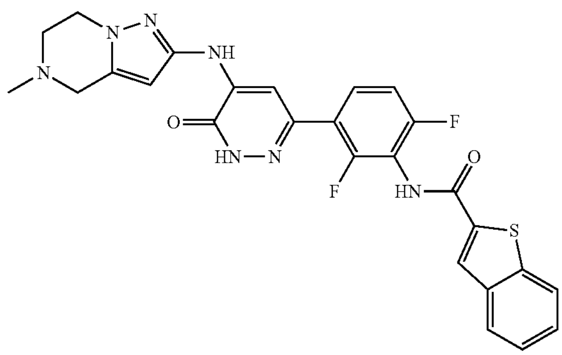 | N-{2,6-difluoro-3-[5-({5-methyl-4H,5H,6H,7H-pyrazolo[1,5-a]pyrazin-2-yl}amino)-6-oxo-1,6-dihydropyridazin-3-yl]phenyl}-1-benzothiophene-2-carboxamide | 533 | 534.2 |
| 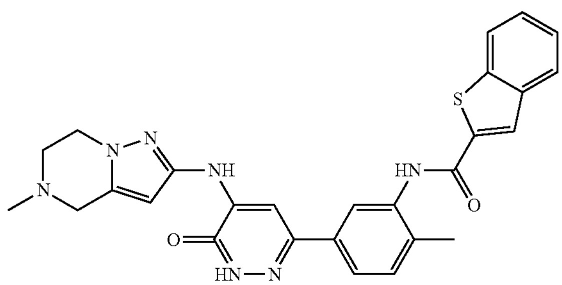 | N-{2-methyl-5-[5-({5-methyl-4H,5H,6H,7H-pyrazolo[1,5-a]pyrazin-2-yl}amino)-6-oxo-1,6-dihydropyridazin-3-yl]phenyl}-1-benzothiophene-2-carboxamide | 511 | 512.1 |
| 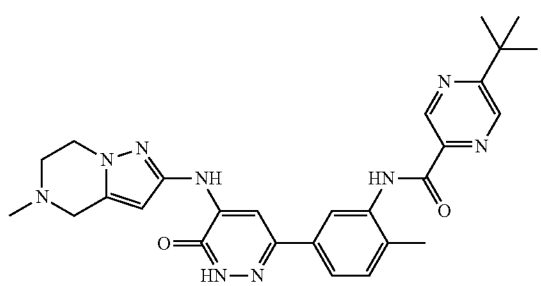 | 5-tert-butyl-N-{2-methyl-5-[5-({5-methyl-4H,5H,6H,7H-pyrazolo[1,5-a]pyrazin-2-yl}amino)-6-oxo-1,6-dihydropyridazin-3-yl]phenyl}pyrazine-2-carboxamide | 513 | 514.18 |
| 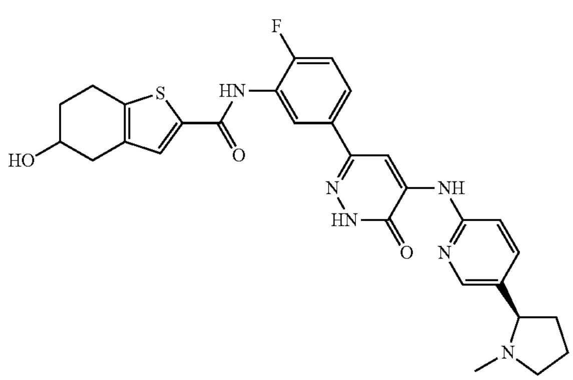 [SMILES: CN1CCC[C@@H]1c1ccc(Nc2cc(-c3ccc(F)c(NC(=O)c4cc5c(s4)CCC(O)C5)c3)n[nH]c2=O)nc1] | N-{2-fluoro-5-[5-({5-[(2R)-1-methylpyrrolidin-2-yl]pyridin-2-yl}amino)-6-oxo-1,6-dihydropyridazin-3-yl]phenyl}-5-hydroxy-4,5,6,7-tetrahydro-1-benzothiophene-2-carboxamide | 560 | 561.2 |

-continued

| Structure | Name | MW calcd | MH + m/z obs |
|---|---|---|---|
| 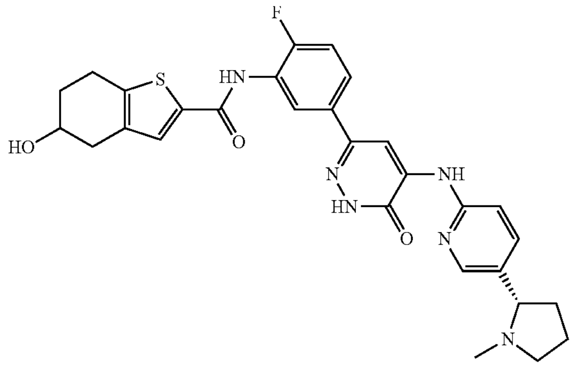 [SMILES: CN1CCC[C@H]1c1ccc(Nc2cc(-c3ccc(F)c(NC(=O)c4cc5c(s4)CCC(O)C5)c3)n[nH]c2=O)nc1] | N-{2-fluoro-5-[5-({5-[(2S)-1-methylpyrrolidin-2-yl]pyridin-2-yl}amino)-6-oxo-1,6-dihydropyridazin-3-yl]phenyl}-5-hydroxy-4,5,6,7-tetrahydro-1-benzothiophene-2-carboxamide | 560 | 461.3 |
| 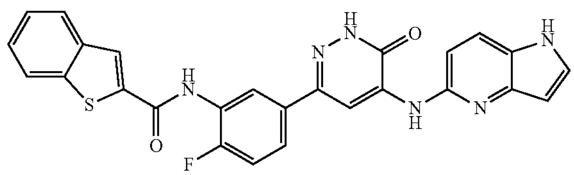 [SMILES: O=C(Nc1cc(-c2cc(Nc3ccc4[nH]ccc4n3)c(=O)[nH]n2)ccc1F)c1cc2ccccc2s1] | N-[2-fluoro-5-(6-oxo-5-{1H-pyrrolo[3,2-b]pyridin-5-ylamino}-1,6-dihydropyridazin-3-yl)phenyl]-1-benzothiophene-2-carboxamide | 496 | 497.2 |
| 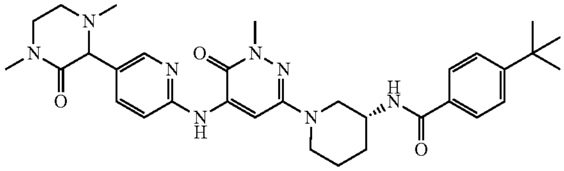 [SMILES: CN1CCN(C)C(c2ccc(Nc3cc(N4CCC[C@@H](NC(=O)c5ccc(C(C)(C)C)cc5)C4)nn(C)c3=O)nc2)C1=O] | 4-tert-butyl-N-[(3R)-1-(5-{[5-(1,4-dimethyl-3-oxopiperazin-2-yl)pyridin-2-yl]amino}-1-methyl-6-oxo-1,6-dihydropyridazin-3-yl)piperidin-3-yl]benzamide | 586 | 587.3 |
| 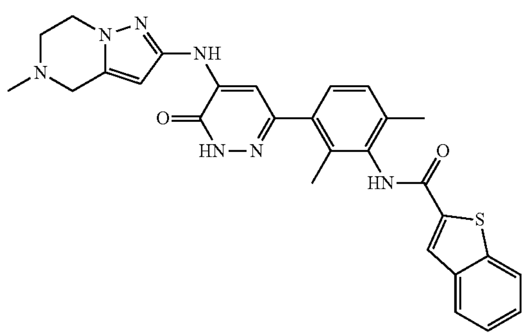 [SMILES: Cc1ccc(-c2cc(Nc3cc4n(n3)CCN(C)C4)c(=O)[nH]n2)c(C)c1NC(=O)c1cc2ccccc2s1] | N-{2,6-dimethyl-3-[5-({5-methyl-4H,5H,6H,7H-pyrazolo[1,5-a]pyrazin-2-yl}amino)-6-oxo-1,6-dihydropyridazin-3-yl]phenyl}-1-benzothiophene-2-carboxamide | 525 | 526.11 |
| 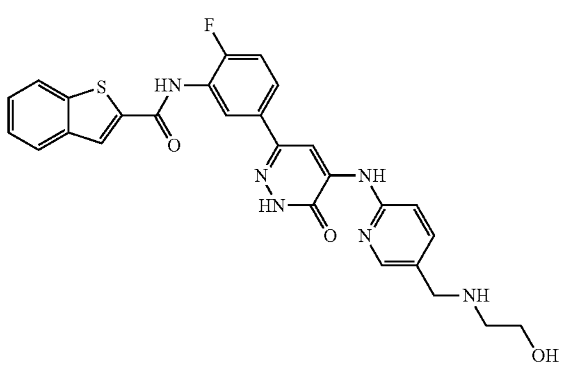 [SMILES: O=C(Nc1cc(-c2cc(Nc3ccc(CNCCO)cn3)c(=O)[nH]n2)ccc1F)c1cc2ccccc2s1] | N-(2-fluoro-5-{5-[(5-{[(2-hydroxyethyl)amino]methyl}pyridin-2-yl)amino]-6-oxo-1,6-dihydropyridazin-3-yl}phenyl)-1-benzothiophene-2-carboxamide | 530 | 532.1 |

-continued

| Structure | Name | MW calcd | MH + m/z obs |
|---|---|---|---|
| 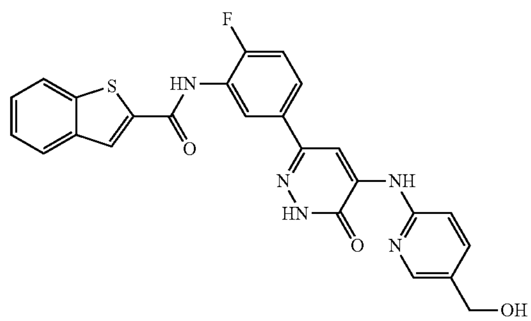 [SMILES: O=C(Nc1cc(-c2cc(Nc3ccc(CO)cn3)c(=O)[nH]n2)ccc1F)c1cc2ccccc2s1] | N-[2-fluoro-5-(5-{[5-(hydroxymethyl)pyridin-2-yl]amino}-6-oxo-1,6-dihydropyridazin-3-yl)phenyl]-1-benzothiophene-2-carboxamide | 487 | 487.9 |
| 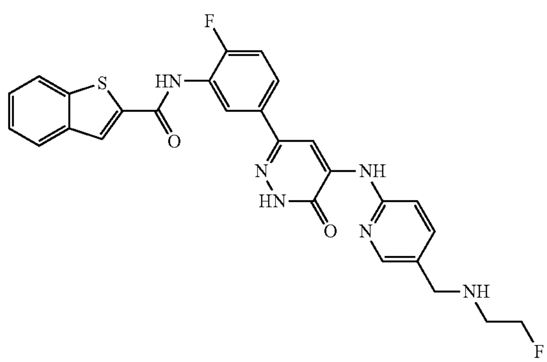 [SMILES: O=C(Nc1cc(-c2cc(Nc3ccc(CNCCF)cn3)c(=O)[nH]n2)ccc1F)c1cc2ccccc2s1] | N-(2-fluoro-5-{5-[(5-{[(2-fluoroethyl)amino]methyl}pyridin-2-yl)amino]-6-oxo-1,6-dihydropyridazin-3-yl}phenyl)-1-benzothiophene-2-carboxamide | 532 | 534 |
| 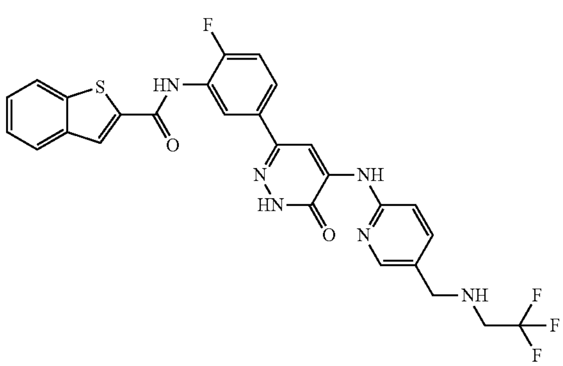 [SMILES: O=C(Nc1cc(-c2cc(Nc3ccc(CNCC(F)(F)F)cn3)c(=O)[nH]n2)ccc1F)c1cc2ccccc2s1] | N-(2-fluoro-5-{6-oxo-5-[(5-{[(2,2,2-trifluoroethyl)amino]methyl}pyridin-2-yl)amino]-1,6-dihydropyridazin-3-yl}phenyl)-1-benzothiophene-2-carboxamide | 568 | 568.9 |
| 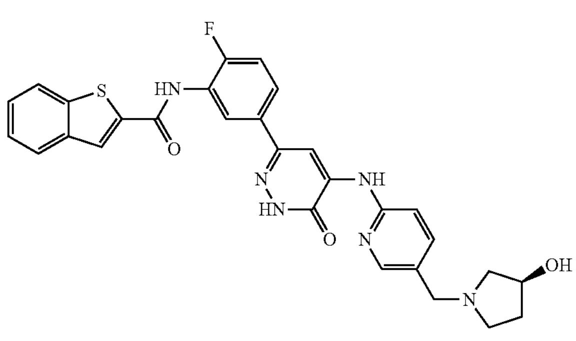 [SMILES: O=C(Nc1cc(-c2cc(Nc3ccc(CN4CC[C@H](O)C4)cn3)c(=O)[nH]n2)ccc1F)c1cc2ccccc2s1] | N-(2-fluoro-5-{5-[(5-{[(3S)-3-hydroxypyrrolidin-1-yl]methyl}pyridin-2-yl)amino]-6-oxo-1,6-dihydropyridazin-3-yl}phenyl)-1-benzothiophene-2-carboxamide | 556 | 558.2 |

| Structure | Name | MW calcd | MH + m/z obs |
|---|---|---|---|
| 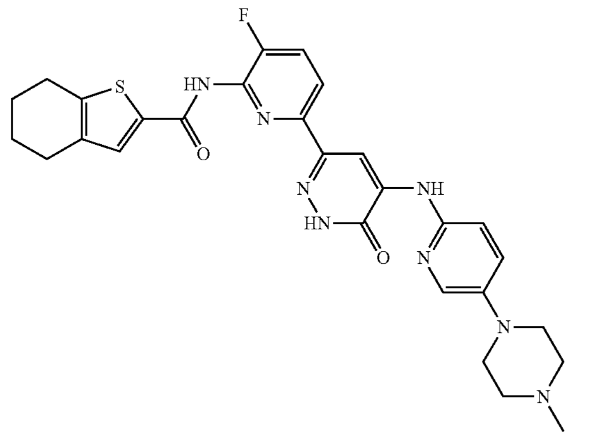 [SMILES: CN1CCN(c2ccc(Nc3cc(-c4ccc(F)c(NC(=O)c5cc6c(s5)CCCC6)n4)n[nH]c3=O)nc2)CC1] | N-[3-fluoro-6-(5-{[5-(4-methylpiperazin-1-yl)pyridin-2-yl]amino}-6-oxo-1,6-dihydropyridazin-3-yl)pyridin-2-yl]-4,5,6,7-tetrahydro-1-benzothiophene-2-carboxamide | 560 | 561 |
| 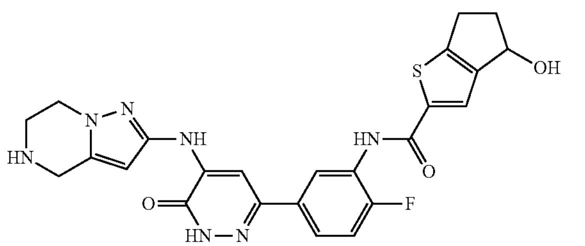 [SMILES: O=C(Nc1cc(-c2cc(Nc3cc4n(n3)CCNC4)c(=O)[nH]n2)ccc1F)c1cc2c(s1)CCC2O] | N-[2-fluoro-5-(6-oxo-5-{4H,5H,6H,7H-pyrazolo[1,5-a]pyrazin-2-ylamino}-1,6-dihydropyridazin-3-yl)phenyl]-4-hydroxy-4H,5H,6H-cyclopenta[b]thiophene-2-carboxamide | 507 | 506.4 |
| 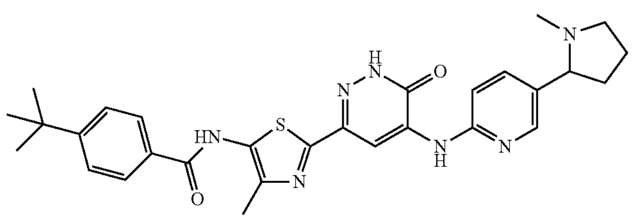 [SMILES: Cc1nc(-c2cc(Nc3ccc(C4CCCN4C)cn3)c(=O)[nH]n2)sc1NC(=O)c1ccc(C(C)(C)C)cc1] | 4-tert-butyl-N-[4-methyl-2-(5-{[5-(1-methylpyrrolidin-2-yl)pyridin-2-yl]amino}-6-oxo-1,6-dihydropyridazin-3-yl)-1,3-thiazol-5-yl]benzamide | 543 | 544.2 |
| 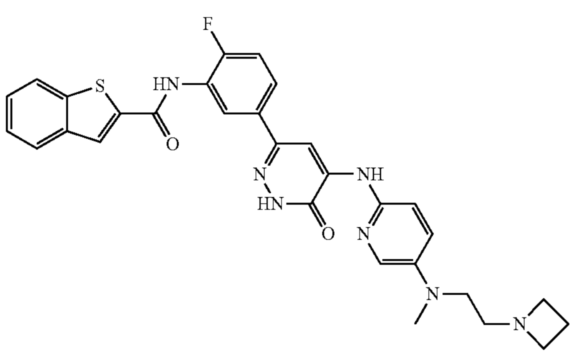 [SMILES: CN(CCN1CCC1)c1ccc(Nc2cc(-c3ccc(F)c(NC(=O)c4cc5ccccc5s4)c3)n[nH]c2=O)nc1] | N-(5-{5-[(5-{[2-(azetidin-1-yl)ethyl](methyl)amino}pyridin-2-yl)amino]-6-oxo-1,6-dihydropyridazin-3-yl}-2-fluorophenyl)-1-benzothiophene-2-carboxamide | 569 | 570 |
| 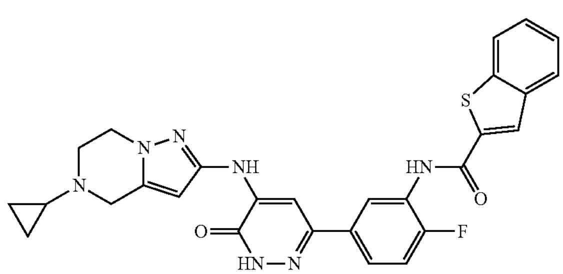 [SMILES: O=C(Nc1cc(-c2cc(Nc3cc4n(n3)CCN(C3CC3)C4)c(=O)[nH]n2)ccc1F)c1cc2ccccc2s1] | N-{5-[5-({5-cyclopropyl-4H,5H,6H,7H-pyrazolo[1,5-a]pyrazin-2-yl}amino)-6-oxo-1,6-dihydropyridazin-3-yl]-2-fluorophenyl}-1-bezothiophene-2-carboxamide | 541 | 541.9 |

-continued

| Structure | Name | MW calcd | MH + m/z obs |
|---|---|---|---|
| 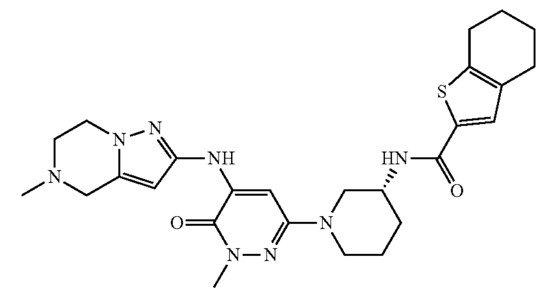 [SMILES: CN1CCn2nc(Nc3cc(N4CCC[C@@H](NC(=O)c5cc6c(s5)CCCC6)C4)nn(C)c3=O)cc2C1] | N-[(3R)-1-[1-methyl-5-({5-methyl-4H,5H,6H,7H-pyrazolo[1,5-a]pyrazin-2-yl}amino)-6-oxo-1,6-dihydropyridazin-3-yl]piperidin-3-yl]-4,5,6,7-tetrahydro-1-benzothiophene-2-carboxamide | 522 | 523.24 |
| 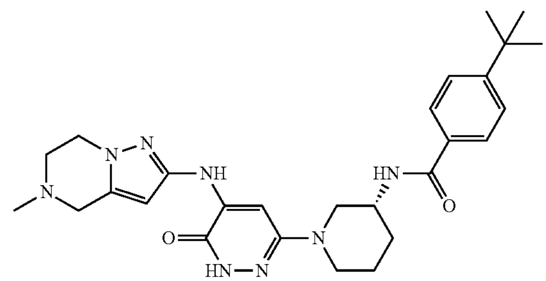 [SMILES: CN1CCn2nc(Nc3cc(N4CCC[C@@H](NC(=O)c5ccc(C(C)(C)C)cc5)C4)n[nH]c3=O)cc2C1] | 4-tert-butyl-N-[(3R)-1-[5-({5-methyl-4H,5H,6H,7H-pyrazolo[1,5-a]pyrazin-2-yl}amino)-6-oxo-1,6-dihydropyridazin-3-yl]piperidin-3-yl]benzamide | 504 | 505.3 |
| 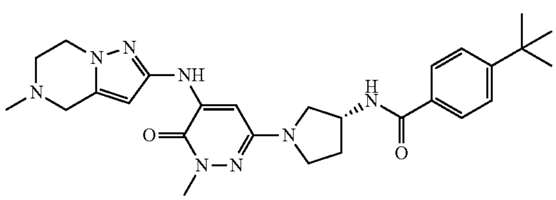 [SMILES: CN1CCn2nc(Nc3cc(N4CC[C@@H](NC(=O)c5ccc(C(C)(C)C)cc5)C4)nn(C)c3=O)cc2C1] | 4-tert-butyl-N-[(3R)-1-[1-methyl-5-({5-methyl-4H,5H,6H,7H-pyrazolo[1,5-a]pyrazin-2-yl}amino)-6-oxo-1,6-dihydropyridazin-3-yl]pyrrolidin-3-yl]benzamide | 504 | 505.3 |
| 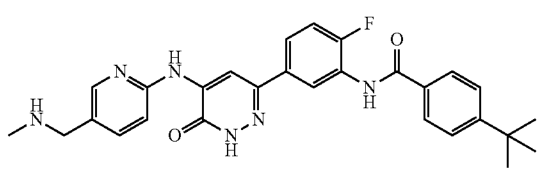 [SMILES: CNCc1ccc(Nc2cc(-c3ccc(F)c(NC(=O)c4ccc(C(C)(C)C)cc4)c3)n[nH]c2=O)nc1] | 4-tert-butyl-N-{2-fluoro-5-[5-({5-[(methylamino)methyl]pyridin-2-yl}amino)-6-oxo-1,6-dihydropyridazin-3-yl]phenyl}benzamide | 500 | 501 |
| 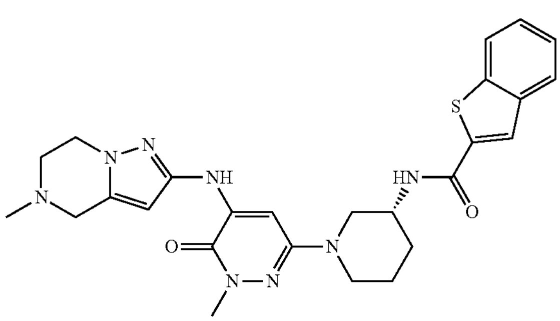 [SMILES: CN1CCn2nc(Nc3cc(N4CCC[C@@H](NC(=O)c5cc6ccccc6s5)C4)nn(C)c3=O)cc2C1] | N-[(3R)-1-[1-methyl-5-({5-methyl-4H,5H,6H,7H-pyrazolo[1,5-a]pyrazin-2-yl}amino)-6-oxo-1,6-dihydropyridazin-3-yl]piperidin-3-yl]-1-benzothiophene-2-carboxamide | 518 | 519.2 |
| 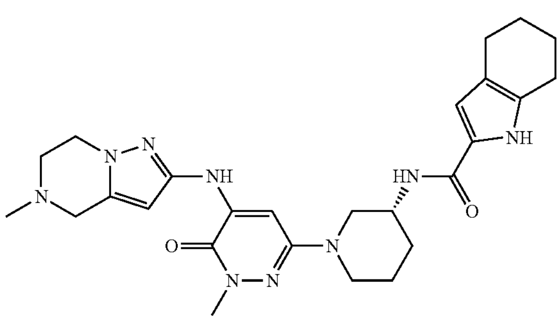 [SMILES: CN1CCn2nc(Nc3cc(N4CCC[C@@H](NC(=O)c5cc6c([nH]5)CCCC6)C4)nn(C)c3=O)cc2C1] | N-[(3R)-1-[1-methyl-5-({5-methyl-4H,5H,6H,7H-pyrazolo[1,5-a]pyrazin-2-yl}amino)-6-oxo-1,6-dihydropyridazin-3-yl]piperidin-3-yl]-4,5,6,7-tetrahydro-1H-indole-2-carboxamide | 505 | 506.3 |

-continued

| Structure | Name | MW calcd | MH + m/z obs |
|---|---|---|---|
| 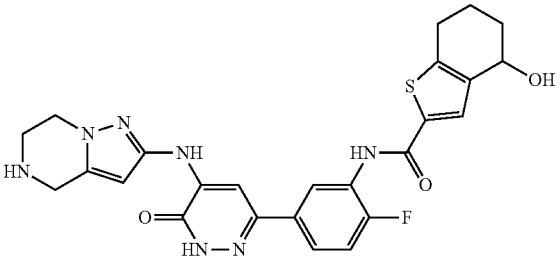 [SMILES: O=C(Nc1cc(-c2cc(Nc3cc4n(n3)CCNC4)c(=O)[nH]n2)ccc1F)c1cc2c(s1)CCCC2O] | N-[2-fluoro-5-(6-oxo-5-{4H,5H,6H,7H-pyrazolo[1,5-a]pyrazin-2-ylamino}-1,6-dihydropyridazin-3-yl)phenyl]-4-hydroxy-4,5,6,7-tetrahydro-1-benzothiophene-2-carboxamide | 521 | 522.5 |
| 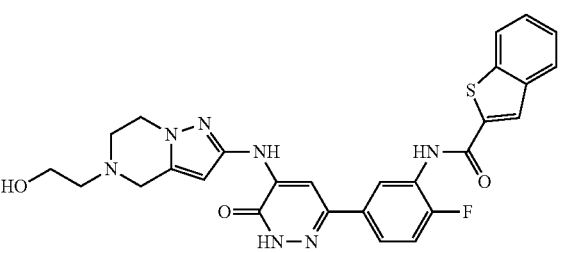 [SMILES: O=C(Nc1cc(-c2cc(Nc3cc4n(n3)CCN(CCO)C4)c(=O)[nH]n2)ccc1F)c1cc2ccccc2s1] | N-[2-fluoro-5-(5-{[5-(2-hydroxyethyl)-4H,5H,6H,7H-pyrazolo[1,5-a]pyrazin-2-yl]amino}-6-oxo-1,6-dihydropyridazin-3-yl)phenyl]-1-benzothiophene-2-cathoxamide | 545 | 546.4 |
| 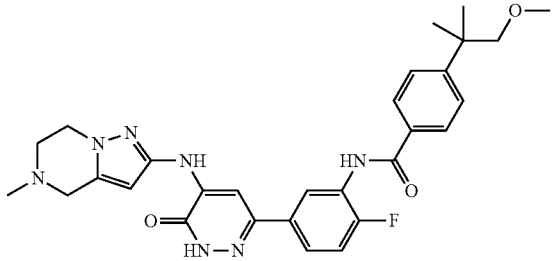 | N-{2-fluoro-5-[5-({5-methyl-4H,5H,6H,7H-pyrazolo[1,5-a]pyrazin-2-yl}amino)-6-oxo-1,6-dihydropyridazin-3-yl]phenyl}-4-(1-methoxy-2-methylpropan-2-yl)benzamide | 545 | 456.2 |
| 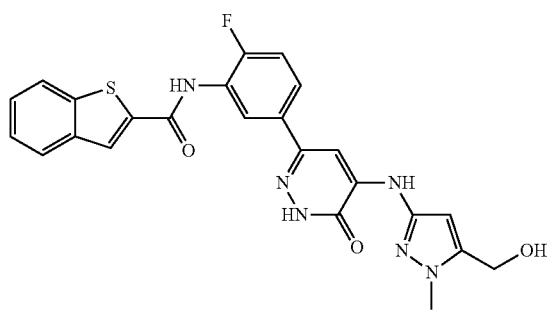 [SMILES: Cn1nc(Nc2cc(-c3ccc(F)c(NC(=O)c4cc5ccccc5s4)c3)n[nH]c2=O)cc1CO] | N-[2-fluoro-5-(5-{[5-(hydroxymethyl)-1-methyl-1H-pyrazol-3-yl]amino}-6-oxo-1,6-dihydropyridazin-3-yl)phenyl]-1-benzothiophene-2-carboxamide | 490 | 491.07 |
| 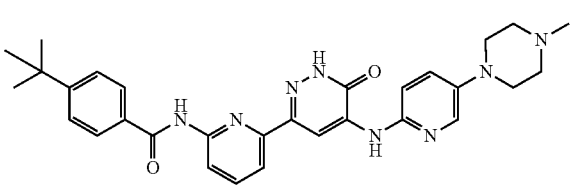 [SMILES: CN1CCN(c2ccc(Nc3cc(-c4cccc(NC(=O)c5ccc(C(C)(C)C)cc5)n4)n[nH]c3=O)nc2)CC1] | 4-tert-butyl-N-[6-(5-{[5-(4-methylpiperazin-1-yl)pyridin-2-yl]amino}-6-oxo-1,6-dihydropyridazin-3-yl)pyridin-2-yl]benzamide | 538 | 539.1 |
| 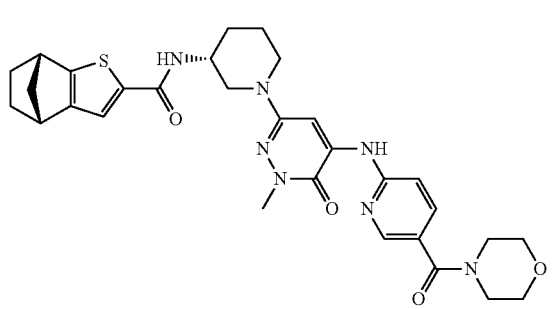 [SMILES: Cn1nc(N2CCC[C@@H](NC(=O)c3cc4c(s3)[C@H]3CC[C@@H]4C3)C2)cc(Nc2ccc(C(=O)N3CCOCC3)cn2)c1=O] | (1S,7R)-N-[(3R)-1-(1-methyl-5-{[5-(morpholin-4-ylcarbonyl)pyridin-2-yl]amino}-6-oxo-1,6-dihydropyridazin-3-yl)piperidin-3-yl]-3-thiatricyclo[5.2.1.0^{2,6}]deca-2(6),4-diene-4-carboxamide | 589 | 570.17 |

-continued

| Structure | Name | MW calcd | MH + m/z obs |
|---|---|---|---|
| 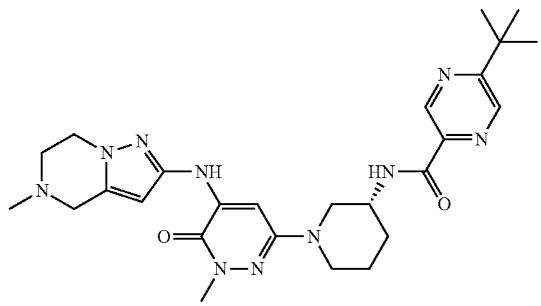 [SMILES: CN1CCn2nc(Nc3cc(N4CCC[C@@H](NC(=O)c5cnc(C(C)(C)C)cn5)C4)nn(C)c3=O)cc2C1] | 5-tert-butyl-N-[(3R)-1-[1-methyl-5-({5-methyl-4H,5H,6H,7H-pyrazolo[1,5-a]pyrazin-2-yl}amino)-6-oxo-1,6-dihydropyridazin-3-yl]piperidin-3-yl]pyrazine-2-carboxamide | 520 | 521.27 |
| 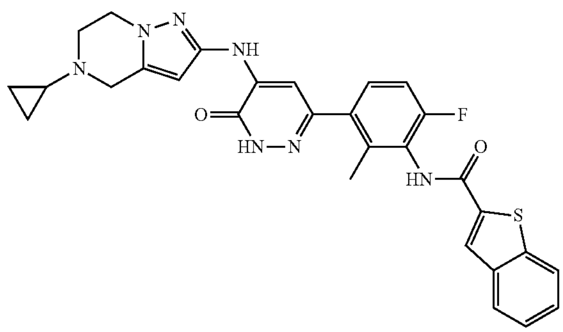 [SMILES: Cc1c(-c2cc(Nc3cc4n(n3)CCN(C3CC3)C4)c(=O)[nH]n2)ccc(F)c1NC(=O)c1cc2ccccc2s1] | N-{3-[5-({5-cyclopropyl-4H,5H,6H,7H-pyrazolo[1,5-a]pyrazin-2-yl}amino)-6-oxo-1,6-dihydropyridazin-3-yl]-6-fluoro-2-methylphenyl}-1-benzothiophene-2-carboxamide | 555 | 556.12 |
| 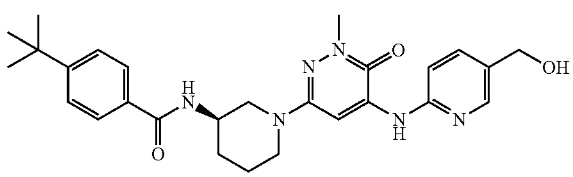 | 4-tert-butyl-N-[(3R)-1-(5-{[5-(hydroxymethyl)pyridin-2-yl]amino}-1-methyl-6-oxo-1,6-dihydropyridazin-3-yl)piperidin-3-yl]benzamide | 490 | 491.2 |
| 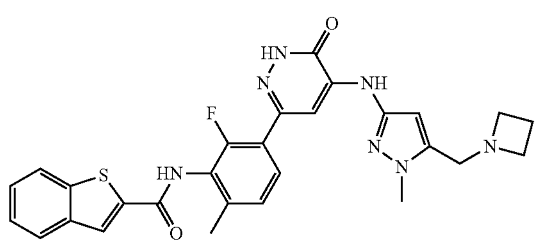 [SMILES: Cc1ccc(-c2cc(Nc3cc(CN4CCC4)n(C)n3)c(=O)[nH]n2)c(F)c1NC(=O)c1cc2ccccc2s1] | N-[3-(5-{[5-(azetidin-1-ylmethyl)-1-methyl-1H-pyrazol-3-yl]amino}-6-oxo-1,6-dihydropyridazin-3-yl)-2-fluoro-6-methylphenyl]-1-benzothiophene-2-carboxamide | 543 | 542.7 |
| 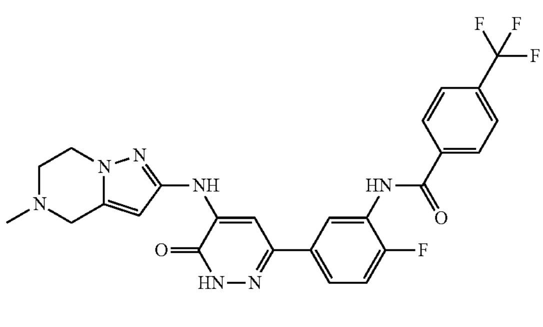 [SMILES: CN1CCn2nc(Nc3cc(-c4ccc(F)c(NC(=O)c5ccc(C(F)(F)F)cc5)c4)n[nH]c3=O)cc2C1] | N-{2-fluoro-5-[5-({5-methyl-4H,5H,6H,7H-pyrazolo[1,5-a]pyrazin-2-yl}amino)-6-oxo-1,6-dihydropyridazin-3-yl]phenyl}-4-(trifluoromethyl)benzamide | 527 | 527.7 |

-continued

| Structure | Name | MW calcd | MH + m/z obs |
|---|---|---|---|
| 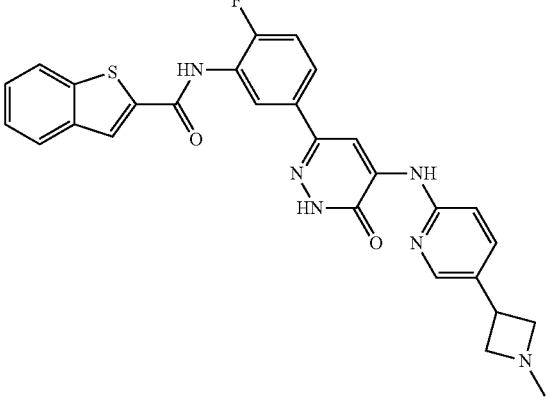 | N-[2-fluoro-5-(5-{[5-(1-methylazetidin-3-yl)pyridin-2-yl]amino}-6-oxo-1,6-dihydropyridazin-3-yl)phenyl]-1-benzothiophene-2-carboxamide | 526 | 527.7 |
| 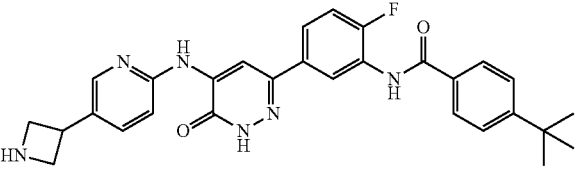 [SMILES: CC(C)(C)c1ccc(C(=O)Nc2cc(-c3cc(Nc4ccc(C5CNC5)cn4)c(=O)[nH]n3)ccc2F)cc1] | N-[5-(5-{[5-(azetidin-3-yl)pyridin-2-yl]amino}-6-oxo-1,6-dihydropyridazin-3-yl)-2-fluorophenyl]-4-tert-butylbenzamide | 512 | 512.7 |
| 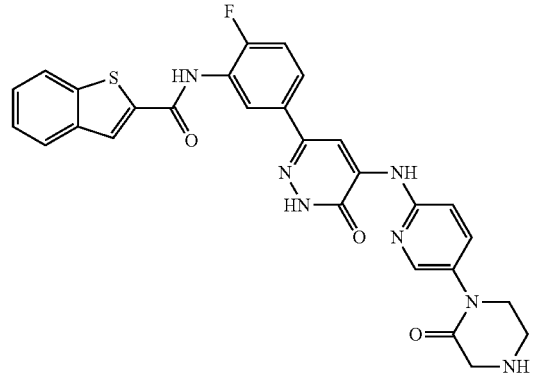 [SMILES: O=C(Nc1cc(-c2cc(Nc3ccc(N4CCNCC4=O)cn3)c(=O)[nH]n2)ccc1F)c1cc2ccccc2s1] | N-[2-fluoro-5-(6-oxo-5-{[5-(2-oxopiperazin-1-yl)pyridin-2-yl]amino}-1,6-dihydropyridazin-3-yl)phenyl]-1-benzothiophene-2-carboxamide | 555 | 556.4 |
| 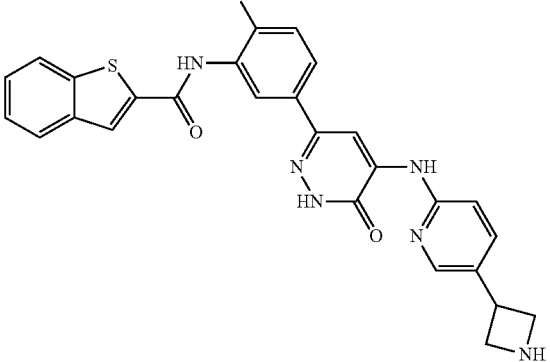 | N-[5-(5-{[5-(azetidin-3-yl)pyridin-2-yl]amino}-6-oxo-1,6-dihydropyridazin-3-yl)-2-fluorophenyl]-1-benzothiophene-2-carboxamide | 512 | 513.5 |

-continued

| Structure | Name | MW calcd | MH + m/z obs |
|---|---|---|---|
| 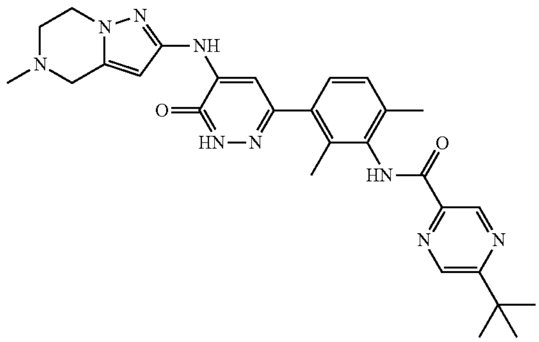 | 5-tert-butyl-N-{2,6-dimethyl-3-[5-({5-methyl-4H,5H,6H,7H-pyrazolo[1,5-a]pyrazin-2-yl}amino)-6-oxo-1,6-dihydropyridazin-3-yl]phenyl}pyrazine-2-carboxamde | 527 | 528.21 |
| 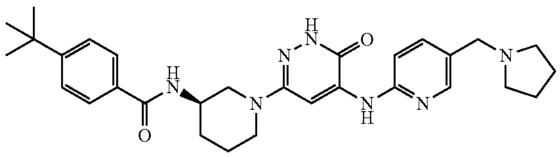 [SMILES: CC(C)(C)c1ccc(C(=O)N[C@@H]2CCCN(c3cc(Nc4ccc(CN5CCCC5)cn4)c(=O)[nH]n3)C2)cc1] | 4-tert-butyl-N-[(3R)-1-(6-oxo-5-{[5-(pyrrolidin-1-ylmethyl)pyridin-2-yl]amino}-1,6-dihydropyridazin-3-yl)piperidin-3-yl]benzamide | 529 | 530.25 |
| 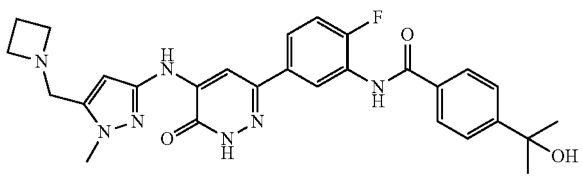 [SMILES: Cn1nc(Nc2cc(-c3ccc(F)c(NC(=O)c4ccc(C(C)(C)O)cc4)c3)n[nH]c2=O)cc1CN1CCC1] | N-[5-(5-{[5-(azetidin-1-ylmethyl)-1-methyl-1H-pyrazol-3-yl]amino}-6-oxo-1,6-dihydropyridazin-3-yl)-2-fluorophenyl]-4-(2-hydroxypropan-2-yl)benzamide | 531 | 532 |
| 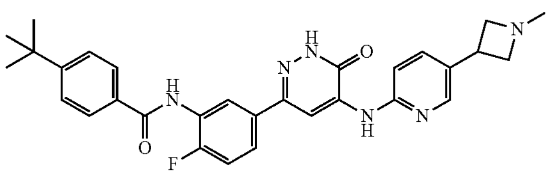 [SMILES: CN1CC(c2ccc(Nc3cc(-c4ccc(F)c(NC(=O)c5ccc(C(C)(C)C)cc5)c4)n[nH]c3=O)nc2)C1] | 4-tert-butyl-N-[2-fluoro-5-(5-{[5-(1-methylazetidin-3-yl)pyridin-2-yl]amino}-6-oxo-1,6-dihydropyridazin-3-yl)phenyl]benzamide | 526 | 527.6 |
| 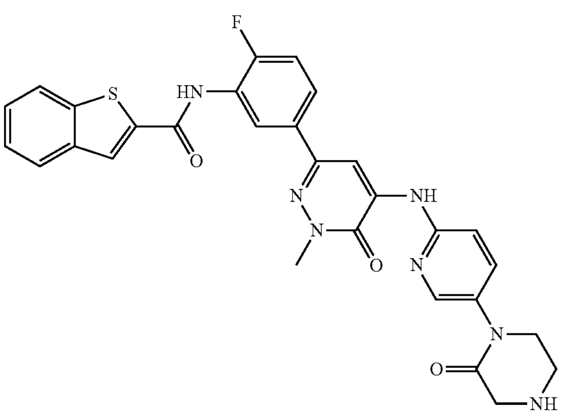 [SMILES: Cn1nc(-c2ccc(F)c(NC(=O)c3cc4ccccc4s3)c2)cc(Nc2ccc(N3CCNCC3=O)cn2)c1=O] | N-[2-fluoro-5-(1-methyl-6-oxo-5-{[5-(2-oxopiperazin-1-yl)pyridin-2-yl]amino}-1,6-dihydropyridazin-3-yl)phenyl]-1-benzothiophene-2-carboxamide | 569 | 570.2 |
| 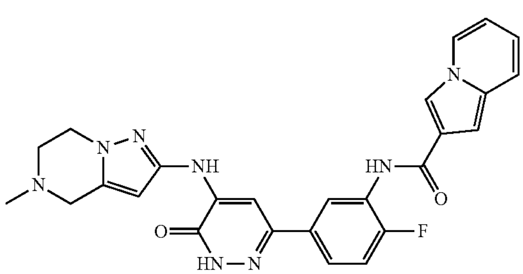 [SMILES: CN1CCn2nc(Nc3cc(-c4ccc(F)c(NC(=O)c5cc6ccccn6c5)c4)n[nH]c3=O)cc2C1] | N-{2-fluoro-5-[5-({5-methyl-4H,5H,6H,7H-pyrazolo[1,5-a]pyrazin-2-yl}amino)-6-oxo-1,6-dihydropyridazin-3-yl]phenyl}indolizine-2-carboxamide | 498 | 499.2 |

-continued

| Structure | Name | MW calcd | MH + m/z obs |
|---|---|---|---|
| 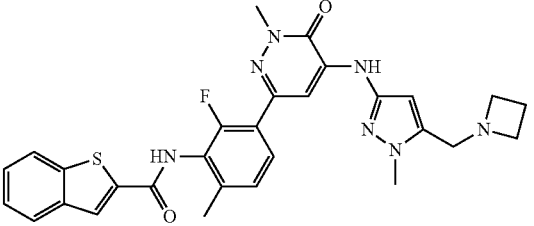 [SMILES: Cc1ccc(-c2cc(Nc3cc(CN4CCC4)n(C)n3)c(=O)n(C)n2)c(F)c1NC(=O)c1cc2ccccc2s1] | N-[3-(5-{[5-(azetidin-1-ylmethyl)-1-methyl-1H-pyrazol-3-yl]amino}-1-methyl-6-oxo-1,6-dihydropyridazin-3-yl)-2-fluoro-6-methylphenyl]-1-benzothiophene-2-carboxamide | 557 | 558.1 |
| 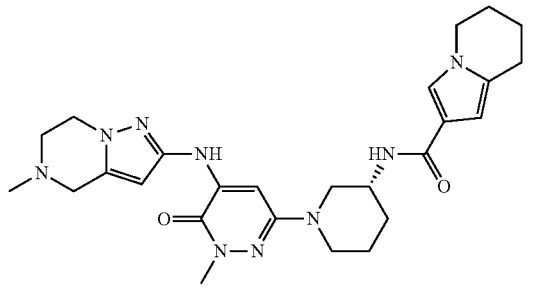 [SMILES: CN1CCn2nc(Nc3cc(N4CCC[C@@H](NC(=O)c5cc6n(c5)CCCC6)C4)nn(C)c3=O)cc2C1] | N-[(3R)-1-[1-methyl-5-({5-methyl-4H,5H,6H,7H-pyrazolo[1,5-a]pyrazin-2-yl}amino)-6-oxo-1,6-dihydropyridazin-3-yl]piperidin-3-yl]-5,6,7,8-tetrahydroindolizine-2-carboxamide | 505 | 506.23 |
| 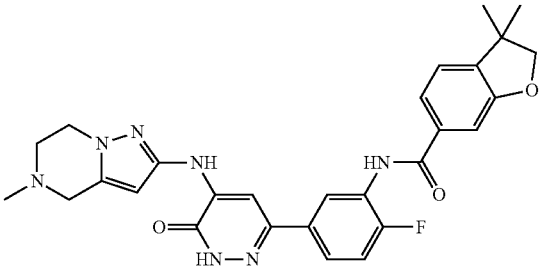 [SMILES: CN1CCn2nc(Nc3cc(-c4ccc(F)c(NC(=O)c5ccc6c(c5)OCC6(C)C)c4)n[nH]c3=O)cc2C1] | N-{2-fluoro-5-[5-({5-methyl-4H,5H,6H,7H-pyrazolo[1,5-a]pyrazin-2-yl}amino)-6-oxo-1,6-dihydropyridazin-3-yl]phenyl}-3,3-dimethyl-2,3-dihydro-1-benzofuran-6-carboxamide | 529 | 530.3 |
| 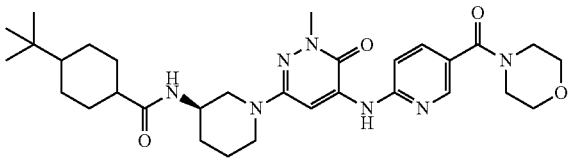 [SMILES: Cn1nc(N2CCC[C@@H](NC(=O)C3CCC(C(C)(C)C)CC3)C2)cc(Nc2ccc(C(=O)N3CCOCC3)cn2)c1=O] | 4-tert-butyl-N-[(3R)-1-(1-methyl-5-{[5-(morpholin-4-ylcarbonyl)pyridin-2-yl]amino}-6-oxo-1,6-dihydropyridazin-3-yl)piperidin-3-yl]cyclohexane-1-carboxamide | 579 | 580.33 |
| 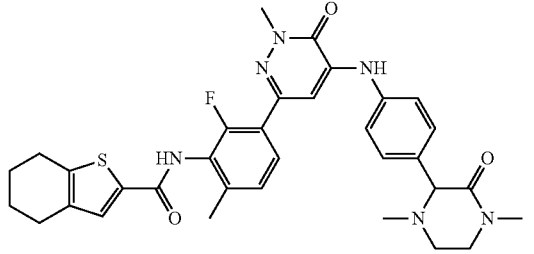 | N-[3-(5-{[5-(1,4-dimethyl-3-oxopiperazin-2-yl)pyridin-2-yl]amino}-1-methyl-6-oxo-1,6-dihydropyridazin-3-yl)-2-fluoro-6-methylphenyl]-4,5,6,7-tetrahydro-1-benzothiophene-2-carboxamide | 615 | 615.8 |
| 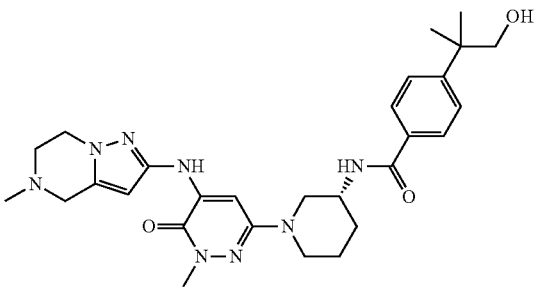 [SMILES: CN1CCn2nc(Nc3cc(N4CCC[C@@H](NC(=O)c5ccc(C(C)(C)CO)cc5)C4)nn(C)c3=O)cc2C1] | 4-(1-hydroxy-2-methylpropan-2-yl)-N-[(3R)-1-[1-methyl-5-({5-methyl-4H,5H,6H,7H-pyrazolo[1,5-a]pyrazin-2-yl}amino)-6-oxo-1,6-dihydropyridazin-3-yl]piperidin-3-yl]benzamide | 534 | 535.23 |

-continued

| Structure | Name | MW calcd | MH + m/z obs |
|---|---|---|---|
| 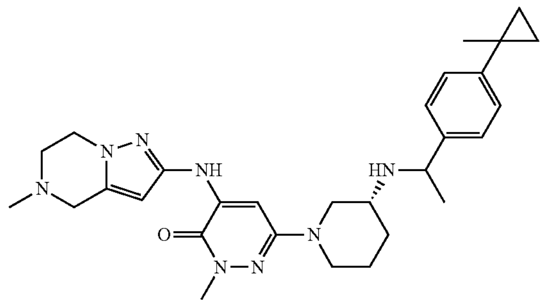 [SMILES: CC(N[C@@H]1CCCN(c2cc(Nc3cc4n(n3)CCN(C)C4)c(=O)n(C)n2)C1)c1ccc(C2(C)CC2)cc1] | N-[(3R)-1-[1-methyl-5-({5-methyl-4H,5H,6H,7H-pyrazolo[1,5-a] pyrazin-2-yl}amino)-6-oxo-1,6-dihydropyridazin-3-yl]piperidin-3-yl]-4-(1-methylcyclopropyl)benzamide | 516 | 517.24 |
| 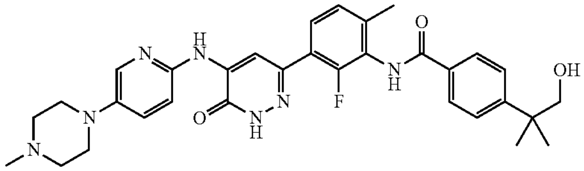 [SMILES: Cc1ccc(-c2cc(Nc3ccc(N4CCN(C)CC4)cn3)c(=O)[nH]n2)c(F)c1NC(=O)c1ccc(C(C)(C)CO)cc1] | N-[2-fluoro-6-methyl-3-(5-{[5-(4-methylpiperazin-1-yl)pyridin-2-yl]amino}-6-oxo-1,6-dihydropyridazin-3-yl)phenyl]-4-(1-hydroxy-2-methylpropan-2-yl)benzamide | 585 | 586.4 |
| 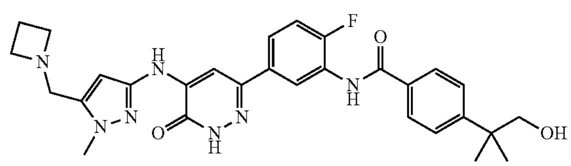 [SMILES: Cn1nc(Nc2cc(-c3ccc(F)c(NC(=O)c4ccc(C(C)(C)CO)cc4)c3)n[nH]c2=O)cc1CN1CCC1] | N-[5-(5-{[5-(azetidin-1-ylmethyl)-1-methyl-1H-pyrazol-3-yl]amino}-6-oxo-1,6-dihydropyridazin-3-yl)-2-fluorophenyl]-4-(1-hydroxy-2-methylpropan-2-yl)benzamide | 545 | 546.3 |
| 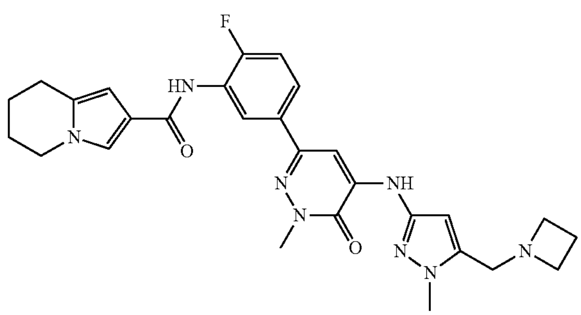 [SMILES: Cn1nc(Nc2cc(-c3ccc(F)c(NC(=O)c4cc5n(c4)CCCC5)c3)nn(C)c2=O)cc1CN1CCC1] | N-[5-(5-{[5-(azetidin-1-ylmethyl)-1-methyl-1H-pyrazol-3-yl]amino}-1-methyl-6-oxo-1,6-dihydropyridazin-3-yl)-2-fluorophenyl]-5,6,7,8-tetrahydroindolizine-2-carboxamide | 530 | 531.2 |
| 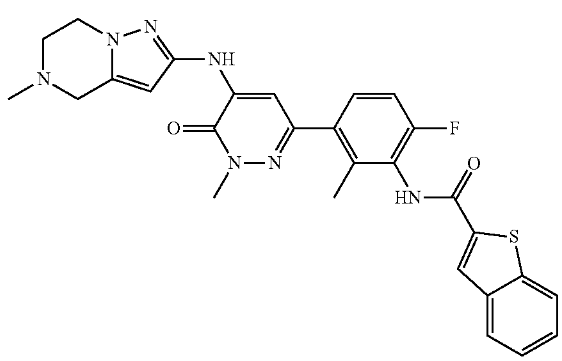 [SMILES: Cc1c(-c2cc(Nc3cc4n(n3)CCN(C)C4)c(=O)n(C)n2)ccc(F)c1NC(=O)c1cc2ccccc2s1] | N-{6-fluoro-2-methyl-3-[1-methyl-5-({5-methyl-4H,5H,6H,7H-pyrazolo[1,5-a]pyrazin-2-yl}amino)-6-oxo-1,6-dihydropyridazin-3-yl]phenyl}-benzothiophene-2-carboxamide | 543 | 544.5 |
| 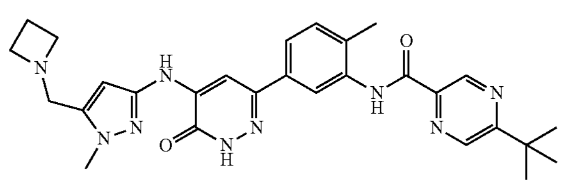 [SMILES: Cc1ccc(-c2cc(Nc3cc(CN4CCC4)n(C)n3)c(=O)[nH]n2)cc1NC(=O)c1cnc(C(C)(C)C)cn1] | N-[5-(5-{[5-(azetidin-1-ylmethyl)-1-methyl-1H-pyrazol-3-yl]amino}-6-oxo-1,6-dihydropyridazin-3-yl)-2-methylphenyl]-5-tert-butylpyrazine-2-carboxamide | 527 | 528 |

-continued

| Structure | Name | MW calcd | MH + m/z obs |
|---|---|---|---|
| 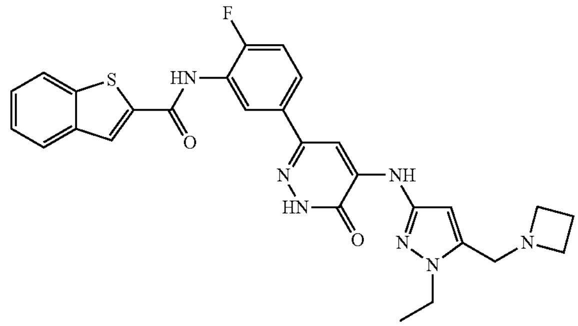 [SMILES: CCn1nc(Nc2cc(-c3ccc(F)c(NC(=O)c4cc5ccccc5s4)c3)n[nH]c2=O)cc1CN1CCC1] | N-[5-(5-{[5-(azetidin-1-ylmethyl)-1-ethyl-1H-pyrazol-3-yl]amino}-6-oxo-1,6-dihydropyridazin-3-yl)-2-fluorophenyl]-1-benzothiophene-2-carboxamide | 543 | 544 |
| 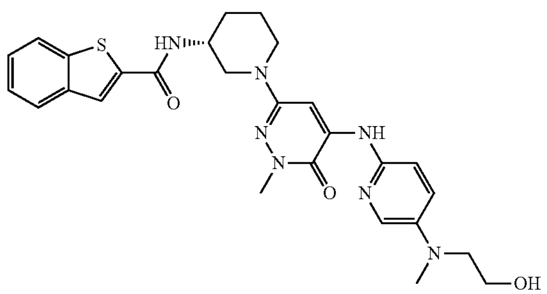 [SMILES: CN(CCO)c1ccc(Nc2cc(N3CCC[C@@H](NC(=O)c4cc5ccccc5s4)C3)nn(C)c2=O)nc1] | N-[(3R)-1-[5-({5-[(2-hydroxyethyl)(methyl)amino]pyridin-2-yl}amino)-1-methyl-6-oxo-1,6-dihydropyridazin-3-yl]piperidin-3-yl]-1-benzothiophene-2-carboxamide | 533 | 534 |
| | N-[(3R)-1-{5[(5-{[2-(dimethylamino)ethyl](methyl)amino}pyridin-2-yl)amino}-1-methyl-6-oxo-1,6-dihydropyridazin-3-yl}piperidin-3-yl]-1-benzothiophene-2-carboxamide | 560 | 561 |
| 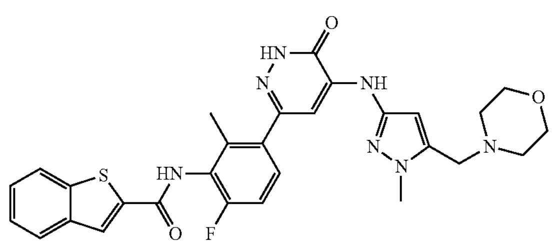 [SMILES: Cc1c(-c2cc(Nc3cc(CN4CCOCC4)n(C)n3)c(=O)[nH]n2)ccc(F)c1NC(=O)c1cc2ccccc2s1] | N-[6-fluoro-2-methyl-3-(5-{[1-methyl-5-(morpholin-4-ylmethyl)-1H-pyrazol-3-yl]amino}-6-oxo-1,6-dihydropyridazin-3-yl)phenyl]-1-benzothiophene-2-carboxamide | 573 | 574 |
| 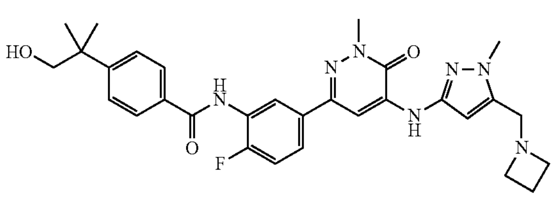 [SMILES: Cn1nc(Nc2cc(-c3ccc(F)c(NC(=O)c4ccc(C(C)(C)CO)cc4)c3)nn(C)c2=O)cc1CN1CCC1] | N-[5-(5-{[5-(azetidin-1-ylmethyl)-1-methyl-1H-pyrazol-3-yl]amino}-1-methyl-6-oxo-1,6-dihydropyridazin-3-yl)-2-fluorophenyl]-4-(1-hydroxy-2-methylpropan-2-yl)benzamide | 559 | 560.2 |
| 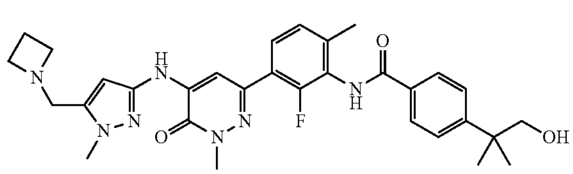 [SMILES: Cc1ccc(-c2cc(Nc3cc(CN4CCC4)n(C)n3)c(=O)n(C)n2)c(F)c1NC(=O)c1ccc(C(C)(C)CO)cc1] | N-[3-(5-{[5-(azetidin-1-ylmethyl)-1-methyl-1H-pyrazol-3-yl]amino}-1-methyl-6-oxo-1,6-dihydropyridazin-3-yl)-2-fluoro-6-methylphenyl]-4-(1-hydroxy-2-methylpropan-2-yl)benzamide | 573 | 574.6 |

-continued

| Structure | Name | MW calcd | MH + m/z obs |
|---|---|---|---|
| 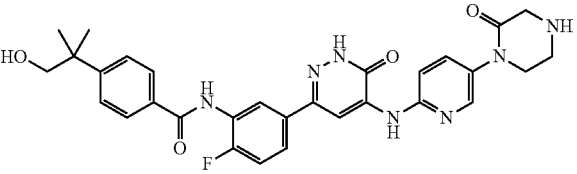 [SMILES: CC(C)(CO)c1ccc(C(=O)Nc2cc(-c3cc(Nc4ccc(N5CCNCC5=O)cn4)c(=O)[nH]n3)ccc2F)cc1] | N-[2-fluoro-5-(6-oxo-5-{[5-(2-oxopiperazin-1-yl)pyridin-2-yl]amino}-1,6-dihydropyridazin-3-yl)phenyl]-4-(1-hydroxy-2-methylpropan-2-yl)benzamide | 571 | 572.3 |
| 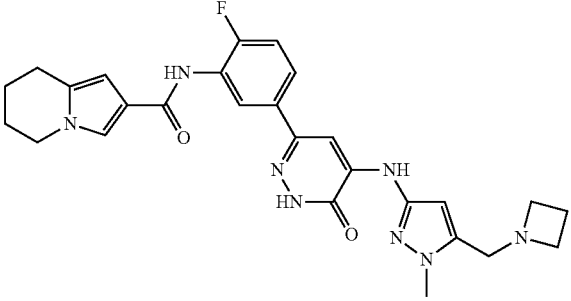 [SMILES: Cn1nc(Nc2cc(-c3ccc(F)c(NC(=O)c4cc5n(c4)CCCC5)c3)n[nH]c2=O)cc1CN1CCC1] | N-[5-(5-{[5-(azetidin-1-ylmethyl)-1-methyl-1H-pyrazol-3-yl]amino}-6-oxo-1,6-dihydropyridazin-3-yl)-2-fluorophenyl]-5,6,7,8-tetrahydroindolizine-2-carboxamide | 516 | 517.5 |
| 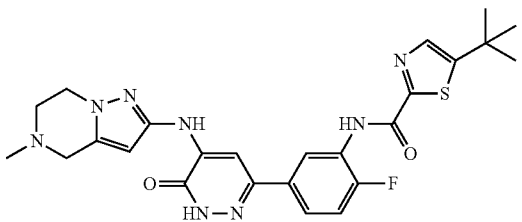 [SMILES: CN1CCn2nc(Nc3cc(-c4ccc(F)c(NC(=O)c5ncc(C(C)(C)C)s5)c4)n[nH]c3=O)cc2C1] | 5-tert-butyl-N-{2-fluoro-5-[5-({5-methyl-4H,5H,6H,7H-pyrazolo[1,5-a]pyrazin-2-yl}amino)-6-oxo-1,6-dihydropyridazin-3-yl]phenyl}-1,3-thiazole-2-carboxamide | 522 | 523.4 |
| 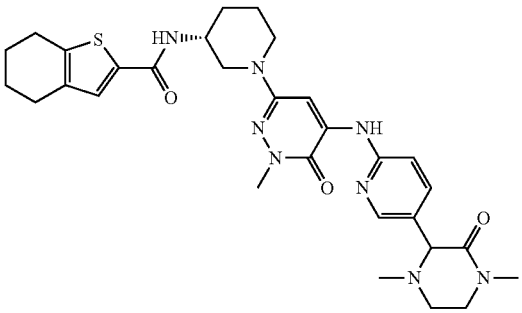 [SMILES: CN1CCN(C)C(c2ccc(Nc3cc(N4CCC[C@@H](NC(=O)c5cc6c(s5)CCCC6)C4)nn(C)c3=O)nc2)C1=O] | N-{(3R)-1-(5-{[5-(1,4-dimethyl-3-oxopiperazin-2-yl)pyridin-2-yl]amino}-1-methyl-6-oxo-1,6-dihydropyridazin-3-yl)piperidin-3-yl]-4,5,6,7-tetrahydro-1-benzothiophene-2-carboxamide | 590 | 591.18 |
| 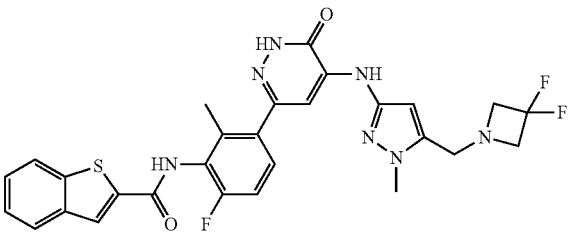 [SMILES: Cc1c(-c2cc(Nc3cc(CN4CC(F)(F)C4)n(C)n3)c(=O)[nH]n2)ccc(F)c1NC(=O)c1cc2ccccc2s1] | N-{3-[5-({5-[(3,3-difluoroazetidin-1-yl)methyl]-1-methyl-1H-pyrazol-3-yl}amino)-6-oxo-1,6-dihydropyridazin-3-yl]-6-fluoro-2-methylphenyl}-1-benzothiophene-2-carboxamide | 579 | 580 |

| Structure | Name | MW calcd | MH + m/z obs |
|---|---|---|---|
| 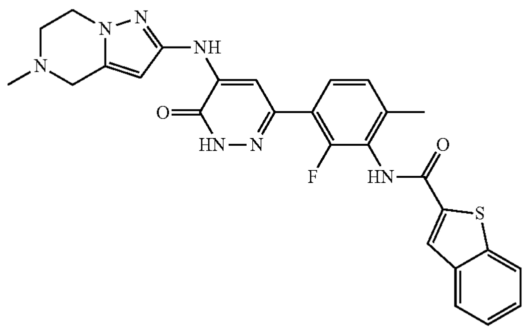 | N-{2-fluoro-6-methyl-3-[5-({5-methyl-4H,5H,6H,7H-pyrazolo[1,5-a]pyrazin-2-yl}amino)-6-oxo-1,6-dihydropyridazin-3-yl]phenyl}-1-benzothiophene-2-carboxamide | 529 | 530 |
| 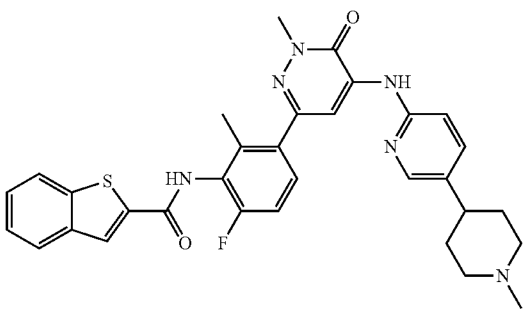 [SMILES: Cc1c(-c2cc(Nc3ccc(C4CCN(C)CC4)cn3)c(=O)n(C)n2)ccc(F)c1NC(=O)c1cc2ccccc2s1] | N-[6-fluoro-2-methyl-3-(1-methyl-5-{[5-(1-methylpiperidin-4-yl)pyridin-2-yl]amino}-6-oxo-1,6-dihydropyridazin-3-yl)phenyl]-1-benzothiophene-2-carboxamide | 582 | 583 |
| 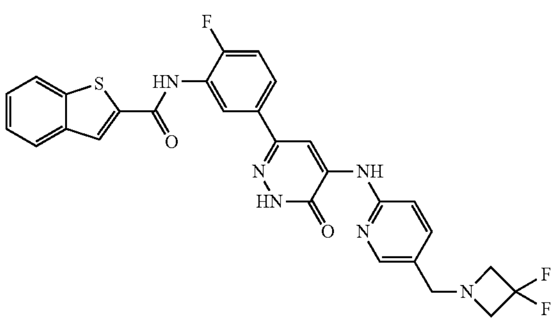 [SMILES: O=C(Nc1cc(-c2cc(Nc3ccc(CN4CC(F)(F)C4)cn3)c(=O)[nH]n2)ccc1F)c1cc2ccccc2s1] | N-{5-[5-({5-[(3,3-difluoroazetidin-1-yl)methyl]pyridin-2-yl}amino)-6-oxo-1,6-dihydropyridazin-3-yl]-2-fluorophenyl}-1-benzothiophene-2-carboxamide | 562 | 563.08 |
| 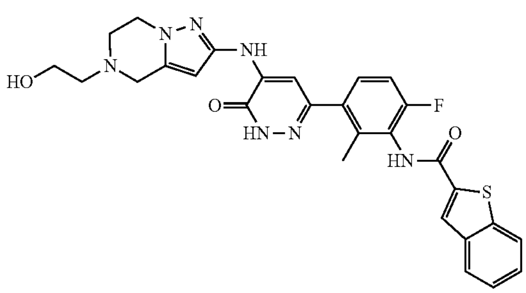 [SMILES: Cc1c(-c2cc(Nc3cc4n(n3)CCN(CCO)C4)c(=O)[nH]n2)ccc(F)c1NC(=O)c1cc2ccccc2s1] | N-[6-fluoro-3-(5-{[5-(2-hydroxyethyl)-4H,5H,6H,7H-pyrazolo[1,5-a]pyrazin-2-yl]amino}-6-oxo-1,6-dihydropyridazin-3-yl)-2-methylphenyl]-1-benzothiophene-2-carboxamide | 559 | 560.3 |
| 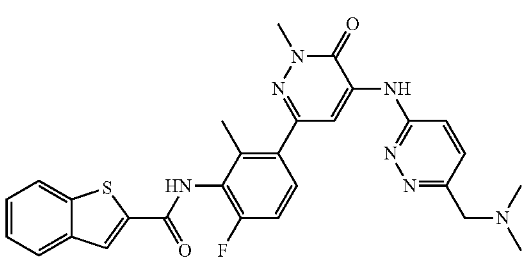 [SMILES: Cc1c(-c2cc(Nc3ccc(CN(C)C)nn3)c(=O)n(C)n2)ccc(F)c1NC(=O)c1cc2ccccc2s1] | N-{3-[5-({6-[(dimethylamino)methyl]pyridazin-3-yl}amino)-1-methyl-6-oxo-1,6-dihydropyridazin-3-yl]-6-fluoro-2-methylphenyl}-1-benzothiophene-2-carboxamide | 543 | 544 |

-continued

| Structure | Name | MW calcd | MH + m/z obs |
|---|---|---|---|
| 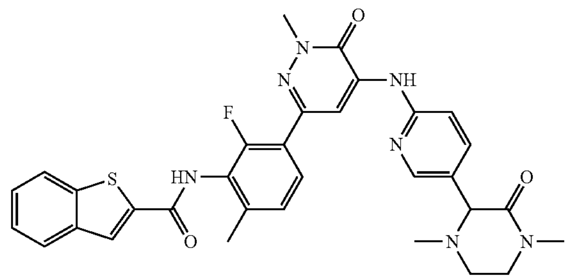 [SMILES: Cc1ccc(-c2cc(Nc3ccc(C4C(=O)N(C)CCN4C)cn3)c(=O)n(C)n2)c(F)c1NC(=O)c1cc2ccccc2s1] | N-[3-(5-{[5-(1,4-dimethyl-3-oxopiperazin-2-yl)pyridin-2-yl]amino}-1-methyl-6-oxo-1,6-dihydropyridazin-3-yl)-2-fluoro-6-methylphenyl]-1-benzothiophene-2-carboxamide | 611 | 612 |
| 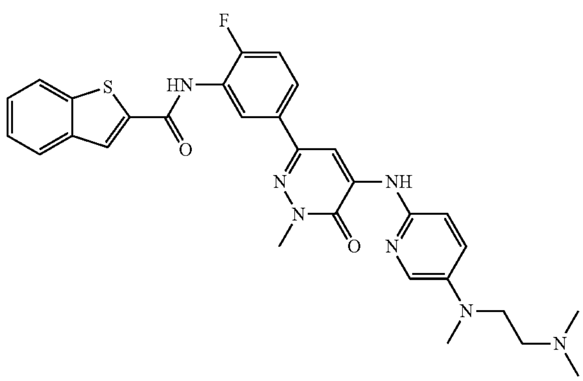 [SMILES: CN(C)CCN(C)c1ccc(Nc2cc(-c3ccc(F)c(NC(=O)c4cc5ccccc5s4)c3)nn(C)c2=O)nc1] | N-(5-{5-[(5{[2-(dimethylamino)ethyl](methyl)amino}pyridin-2-yl)amino]-1-methyl-6-oxo-1,6-dihydropyridazin-3-yl}-2-fluorophenyl)-1-benzothiophene-2-carboxamide | 571 | 572.2 |
| 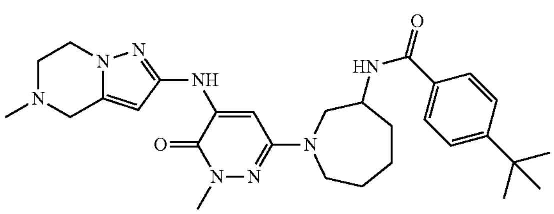 [SMILES: CN1CCn2nc(Nc3cc(N4CCCCC(NC(=O)c5ccc(C(C)(C)C)cc5)C4)nn(C)c3=O)cc2C1] | 4-tert-butyl-N-{1-[1-methyl-5-({5-methyl-4H,5H,6H,7H-pyrazolo[1,5-a]pyrazin-2-yl}amino)-6-oxo-1,6-dihydropyridazin-3-yl]azepan-3-yl}benzamide | 532 | 533.29 |
| 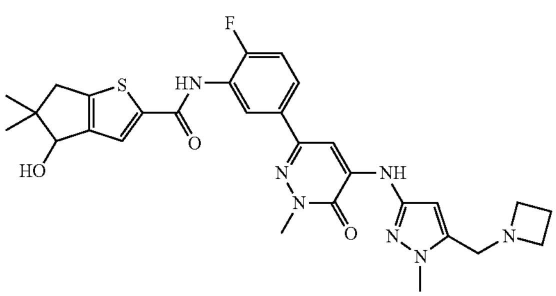 | N-[5-(5-{[5-(azetidin-1-ylmethyl)-1-methyl-1H-pyrazol-3-yl]amino}-1-methyl-6-oxo-1,6-dihydropyridazin-3-yl)-2-fluorophenyl]-4-hydroxy-5,5-dimethyl-4H,5H,6H-cyclopenta[b]thiophene-2-carboxamide | 577 | 578.2 |
| 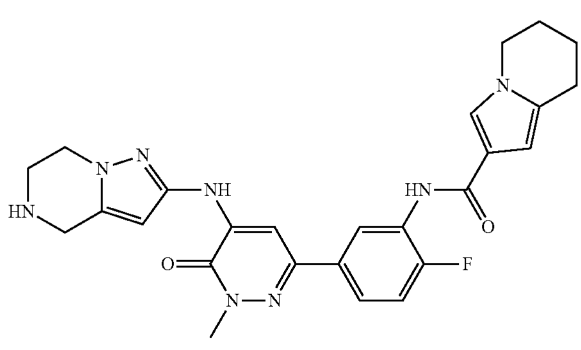 [SMILES: Cn1nc(-c2ccc(F)c(NC(=O)c3cc4n(c3)CCCC4)c2)cc(Nc2cc3n(n2)CCNC3)c1=O] | N-[2-fluoro-5-(1-methyl-6-oxo-5-{4H,5H,6H,7H-pyrazolo[1,5-a]pyrazin-2-ylamino-1,6-dihydropyridazin-3-yl)phenyl]-5,6,7,8-tetrahydroindolizine-2-carboxamide | 502 | 503.4 |

| Structure | Name | MW calcd | MH + m/z obs |
|---|---|---|---|
| 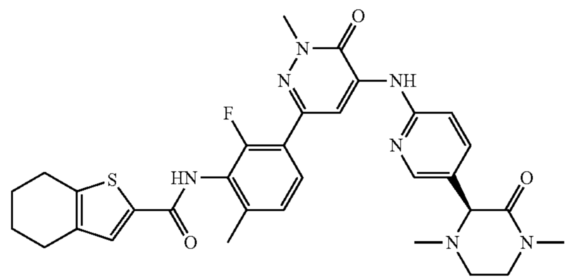 | N-{3-[5-({5-[(2S)-1,4-dimethyl-3-oxopiperazin-2-yl]pyridin-2-yl}amino)-1-methyl-6-oxo-1,6-dihydropyridazin-3-yl]-2-fluoro-6-methylphenyl}-4,5,6,7-tetrahydro-1-benzothiophene-2-carboxamide | 615 | 0 |
| 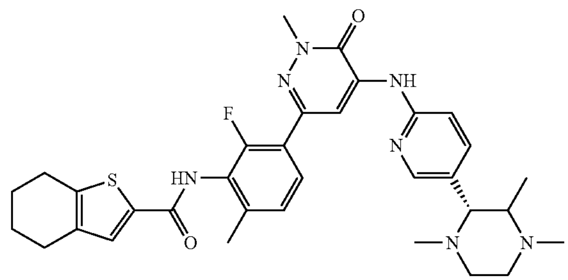 [SMILES: Cc1ccc(-c2cc(Nc3ccc([C@@H]4C(C)N(C)CCN4C)cn3)c(=O)n(C)n2)c(F)c1NC(=O)c1cc2c(s1)CCCC2] | N-{3-[5-({5-[(2R)-1,4-dimethyl-3-oxopiperazin-2-yl]pyridin-2-yl}amino)-1-methyl-6-oxo-1,6-dihydropyridazin-3-yl]-2-fluoro-6-methylphenyl}-4,5,6,7-tetrahydro-1-benzothiophene-2-carboxamide | 615 | 0 |
| 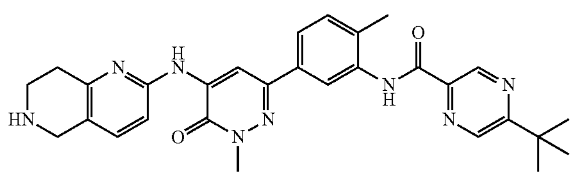 [SMILES: Cc1ccc(-c2cc(Nc3ccc4c(n3)CCNC4)c(=O)n(C)n2)cc1NC(=O)c1cnc(C(C)(C)C)cn1] | 5-tert-butyl-N-{2-methyl-5-[1-methyl-6-oxo-5-(5,6,7,8-tetrahydro-1,6-naphthyridin-2-ylamino)-1,6-dihydropyridazin-3-yl]phenyl}pyrazine-2-carboxamide | 524 | 525.27 |
| 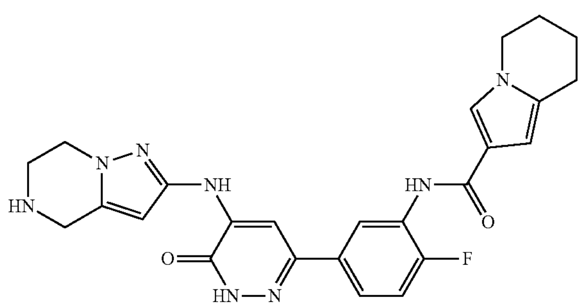 [SMILES: O=C(Nc1cc(-c2cc(Nc3cc4n(n3)CCNC4)c(=O)[nH]n2)ccc1F)c1cc2n(c1)CCCC2] | N-[2-fluoro-5-(6-oxo-5-{4H,5H,6H,7H-pyrazolo[1,5-a]pyrazin-2-ylamino}-1,6-dihydropyridazin-3-yl)phenyl]-5,6,7,8-tetrahydroindolizine-2-carboxamide | 488 | 489.5 |
| 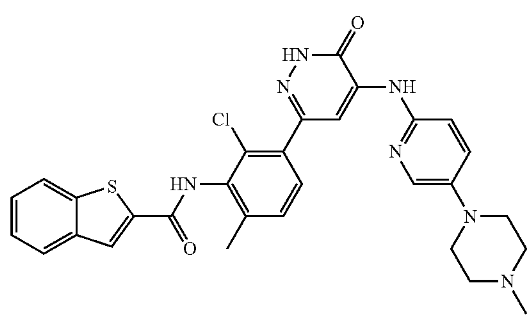 [SMILES: Cc1ccc(-c2cc(Nc3ccc(N4CCN(C)CC4)cn3)c(=O)[nH]n2)c(Cl)c1NC(=O)c1cc2ccccc2s1] | N-[2-chloro-6-methyl-3-(5-{[5-(4-methylpiperazin-1-yl)pyridin-2-yl]amino}-6-oxo-1,6-dihydropyridazin-3-yl)phenyl]-1-benzothiophene-2-carboxamide | 585 | 586.2 |
| 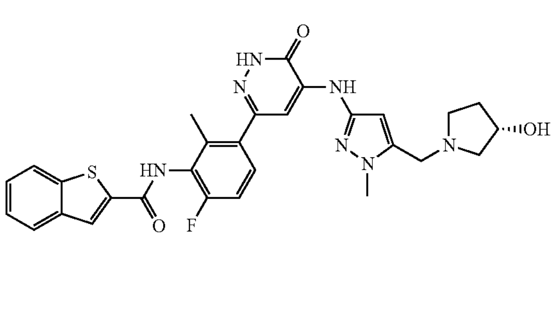 [SMILES: Cc1c(-c2cc(Nc3cc(CN4CC[C@H](O)C4)n(C)n3)c(=O)[nH]n2)ccc(F)c1NC(=O)c1cc2ccccc2s1] | N-(6-fluoro-3-{5-[(5-{[(3S)-3-hydroxypyrrolidin-1-yl]methyl}-1-methyl-1H-pyrazol-3-yl)amino]-6-oxo-1,6-dihydropyridazin-3-yl}-2-methylphenyl)-1-benzothiophene-2-carboxamide | 573 | 574.2 |

-continued

| Structure | Name | MW calcd | MH + m/z obs |
|---|---|---|---|
| 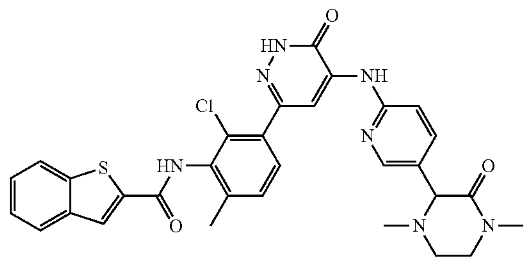 [SMILES: Cc1ccc(-c2cc(Nc3ccc(C4C(=O)N(C)CCN4C)cn3)c(=O)[nH]n2)c(Cl)c1NC(=O)c1cc2ccccc2s1] | N-[2-chloro-3-(5-{[5-(1,4-dimethyl-3-oxopiperazin-2-yl)pyridin-2-yl]amino}-6-oxo-1,6-dihydropyridazin-3-yl)-6-methylphenyl]-1-benzothiophene-2-carboxamide | 613 | 614.2 |
| 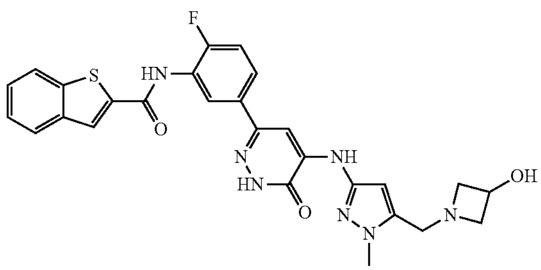 [SMILES: Cn1nc(Nc2cc(-c3ccc(F)c(NC(=O)c4cc5ccccc5s4)c3)n[nH]c2=O)cc1CN1CC(O)C1] | N-{2-fluoro-5-[5-({5-[(3-hydroxyazetidin-1-yl)methyl]-1-methyl-1H-pyrazol-3-yl}amino)-6-oxo-1,6-dihydropyridazin-3-yl]phenyl}-1-benzothiophene-2-carboxamide | 545 | 546 |
| 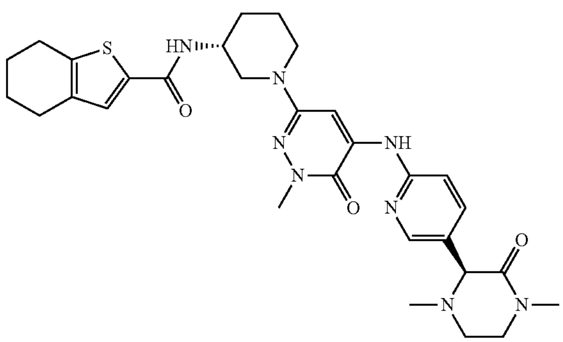 [SMILES: CN1CCN(C)[C@@H](c2ccc(Nc3cc(N4CCC[C@@H](NC(=O)c5cc6c(s5)CCCC6)C4)nn(C)c3=O)nc2)C1=O] | N-[(3R)-1-[5-({5-[(2S)-1,4-dimethyl-3-oxopiperazin-2-yl]pyridin-2-yl}amino)-1-methyl-6-oxo-1,6-dihydropyridazin-3-yl]piperidin-3-yl]-4,5,6,7-tetrahydro-1-benzothiophene-2-carboxamide | 590 | 0 |
| 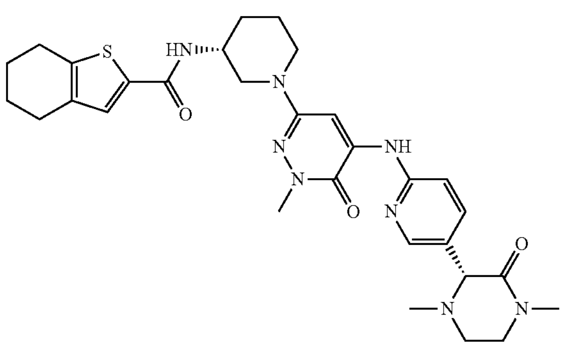 [SMILES: CN1CCN(C)[C@H](c2ccc(Nc3cc(N4CCC[C@@H](NC(=O)c5cc6c(s5)CCCC6)C4)nn(C)c3=O)nc2)C1=O] | N-[(3R)-1-[5-({5-[(2R)-1,4-dimethyl-3-oxopiperazin-2-yl]pyridin-2-yl}amino)-1-methyl-6-oxo-1,6-dihydropyridazin-3-yl]piperidin-3-yl]-4,5,6,7-tetrahydro-1-benzothiophene-2-carboxamide | 590 | 0 |
| 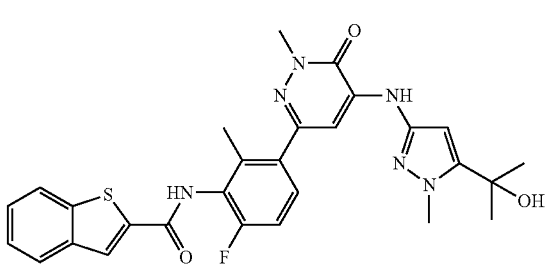 [SMILES: Cc1c(-c2cc(Nc3cc(C(C)(C)O)n(C)n3)c(=O)n(C)n2)ccc(F)c1NC(=O)c1cc2ccccc2s1] | N-[6-fluoro-3-(5-{[5-(2-hydroxypropan-2-yl)-1-methyl-1H-pyrazol-3-yl]amino}-1-methyl-6-oxo-1,6-dihydropyridazin-3-yl)-2-methylphenyl]-1-benzothiophene-2-carboxamide | 546 | 547 |

-continued

| Structure | Name | MW calcd | MH + m/z obs |
|---|---|---|---|
| 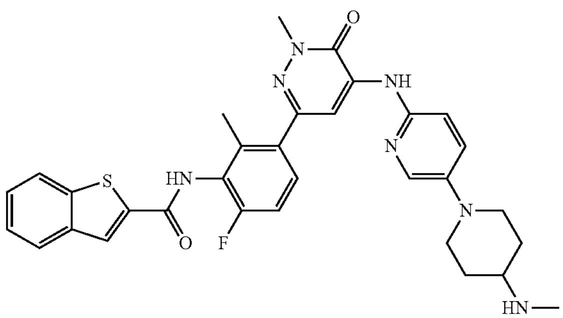 [SMILES: CNC1CCN(c2ccc(Nc3cc(-c4ccc(F)c(NC(=O)c5cc6ccccc6s5)c4C)nn(C)c3=O)nc2)CC1] | N-{6-fluoro-2-methyl-3-[1-methyl-5-({5-[4-(methylamino)piperidin-1-yl]pyridin-2-yl}amino)-6-oxo-1,6-dihydropyridazin-3-yl]phenyl}-1-benzothiophene-2-carboxamide | 597 | 598.2 |
| 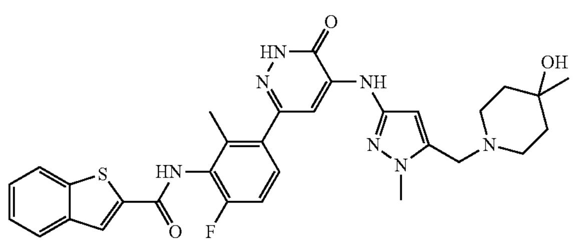 [SMILES: Cc1c(-c2cc(Nc3cc(CN4CCC(C)(O)CC4)n(C)n3)c(=O)[nH]n2)ccc(F)c1NC(=O)c1cc2ccccc2s1] | N-{6-fluoro-3-[5-({5-[(4-hydroxy-4-methylpiperidin-1-yl)methyl]-1-methyl-1H-pyrazol-3-yl}amino)-6-oxo-1,6-dihydropyridazin-3-yl]-2-methylphenyl}-1-benzothiophene-2-carboxamide | 601 | 602.7 |
| 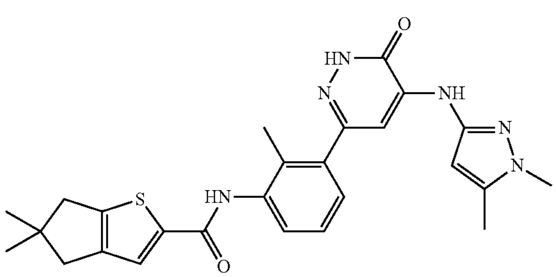 | N-(3-{5-[(1,5-dimethyl-1H-pyrazol-3-yl)amino]-6-oxo-1,6-dihydropyridazin-3-yl}-2-methylphenyl)-5,5-dimethyl-4H,5H,6H-cyclopenta[b]thiophene-2-carboxamide | 488 | 489.2 |
| 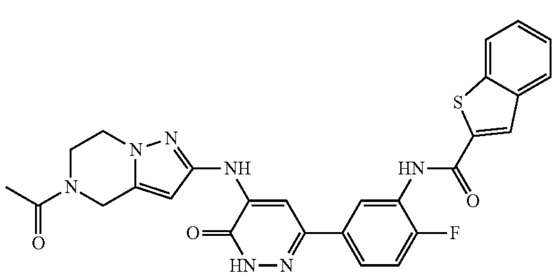 [SMILES: CC(=O)N1CCn2nc(Nc3cc(-c4ccc(F)c(NC(=O)c5cc6ccccc6s5)c4)n[nH]c3=O)cc2C1] | N-{5-[5-({5-acetyl-4H,5H,6H,7H-pyrazolo[1,5-a]pyrazin-2-yl}amino)-6-oxo-1,6-dihydropyridazin-3-yl]-2-fluorophenyl}-1-benzothiophene-2-carboxamide | 543 | 544.7 |
| 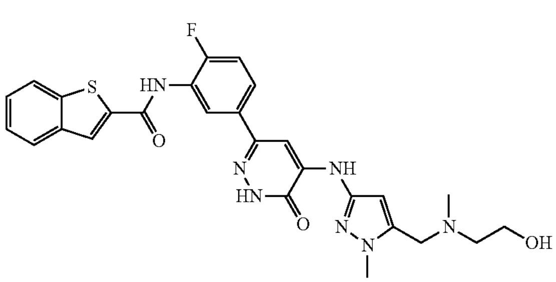 [SMILES: CN(CCO)Cc1cc(Nc2cc(-c3ccc(F)c(NC(=O)c4cc5ccccc5s4)c3)n[nH]c2=O)nn1C] | N-(2-fluoro-5-{5-[(5-{[(2-hydroxyethyl)(methyl)amino]methyl}-1-methyl-1H-pyrazol-3-yl)amino]-6-oxo-1,6-dihydropyridazin-3-yl}phenyl)-1-benzothiophene-2-carboxamide | 547 | 548.2 |

-continued

| Structure | Name | MW calcd | MH + m/z obs |
|---|---|---|---|
| 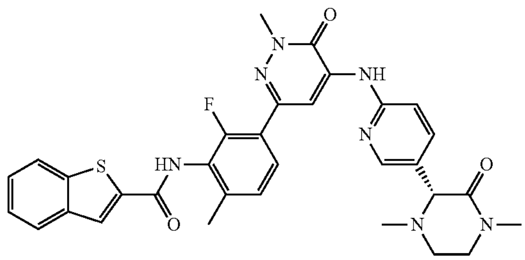 | N-{3-[5-({5-[(2R)-1,4-dimethyl-3-oxopiperazin-2-yl]pyridin-2-yl}amino)-1-methyl-6-oxo-1,6-dihydropyridazin-3-yl]-2-fluoro-6-methylphenyl}-1-benzothiophene-2-carboxamide | 611 | 612.2 |
| 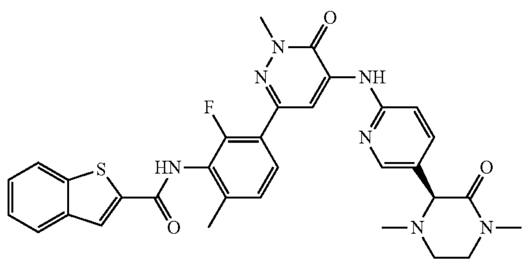 [SMILES: Cc1ccc(-c2cc(Nc3ccc([C@H]4C(=O)N(C)CCN4C)cn3)c(=O)n(C)n2)c(F)c1NC(=O)c1cc2ccccc2s1] | N-{3-[5-({5-[(2S)-1,4-dimethyl-3-oxopiperazin-2-yl]pyridin-2-yl}amino)-1-methyl-6-oxo-1,6-dihydropyridazin-3-yl]-2-fluoro-6-methylphenyl}-1-benzothiophene-2-carboxamide | 611 | 612.2 |
| 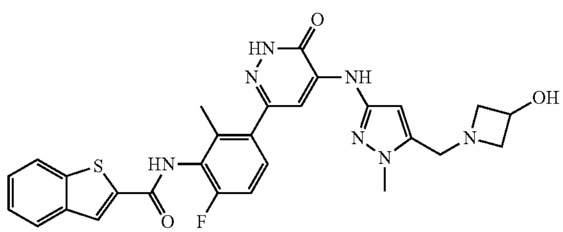 [SMILES: Cc1c(-c2cc(Nc3cc(CN4CC(O)C4)n(C)n3)c(=O)[nH]n2)ccc(F)c1NC(=O)c1cc2ccccc2s1] | N-{6-fluoro-3-[5-({5-[(3-hydroxyazetidin-1-yl)methyl]-1-methyl-1H-pyrazol-3-yl}amino)-6-oxo-1,6-dihydropyridazin-3-yl]-2-methylphenyl}-1-benzothiophene-2-carboxamide | 559 | 560 |
| 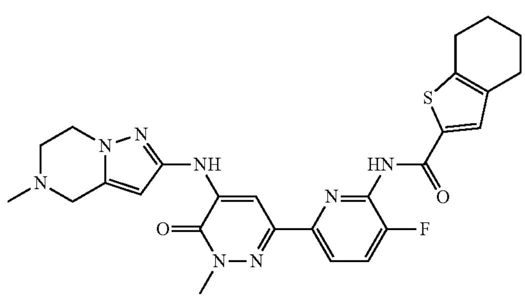 [SMILES: CN1CCn2nc(Nc3cc(-c4ccc(F)c(NC(=O)c5cc6c(s5)CCCC6)n4)nn(C)c3=O)cc2C1] | N-{3-fuoro-6-[1-methyl-5-({5-methyl-4H,5H,6H,7H-pyrazolo[1,5-a]pyrazin-2-yl}amino)-6-oxo-1,6-dihydropyridazin-3-yl]pyridin-2-yl}-4,5,6,7-tetrahydro-1-benzothiophene-2-carboxamide | 534 | 534.8 |
| 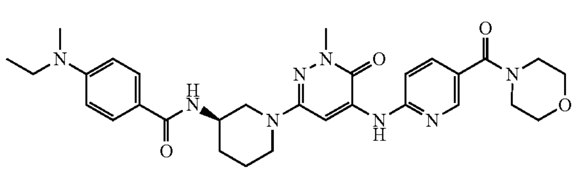 [SMILES: CCN(C)c1ccc(C(=O)N[C@@H]2CCCN(c3cc(Nc4ccc(C(=O)N5CCOCC5)cn4)c(=O)n(C)n3)C2)cc1] | 4-[ethyl(methyl)amino]-N-[(3R)-1-(1-methyl-5-{[5-(morpholin-4-ylcarbonyl)pyridin-2-yl]amino}-6-oxo-1,6-dihydropyridazin-3-yl)piperidin-3-yl]benzamide | 574 | 575.3 |
| 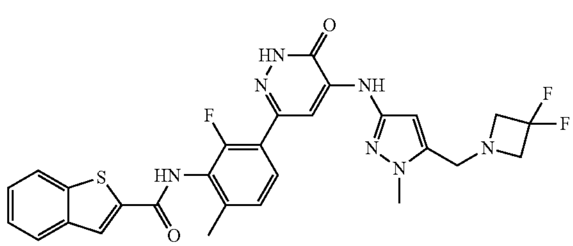 | N-{3-[5-({5-[(3,3-difluoroazetidin-1-yl)methyl]-1-methyl-1H-pyrazol-3-yl}amino)-6-oxo-1,6-dihydropyridazin-3-yl]-2-fluoro-6-methylphenyl}-1-benzothiophene-2-carboxamide | 579 | 580 |

| Structure | Name | MW calcd | MH + m/z obs |
|---|---|---|---|
| 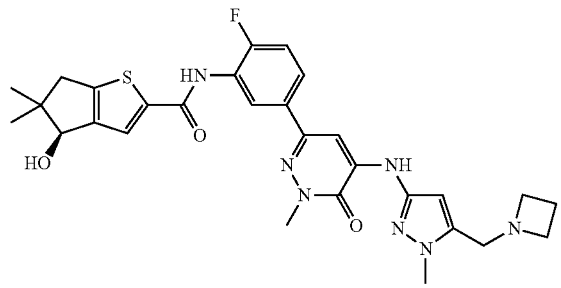 [SMILES: Cn1nc(Nc2cc(-c3ccc(F)c(NC(=O)c4cc5c(s4)CC(C)(C)[C@@H]5O)c3)nn(C)c2=O)cc1CN1CCC1] | (4S)-N-[5-(5-{[5-(azetidin-1-ylmethyl)-1-methyl-1H-pyrazol-3-yl]amino}-1-methyl-6-oxo-1,6-dihydropyridazin-3-yl)-2-fluorophenyl]-4-hydroxy-5,5-dimethyl-4H,5H,6H-cyclopenta[b]thiophene-2-carboxamide | 577 | 0 |
| 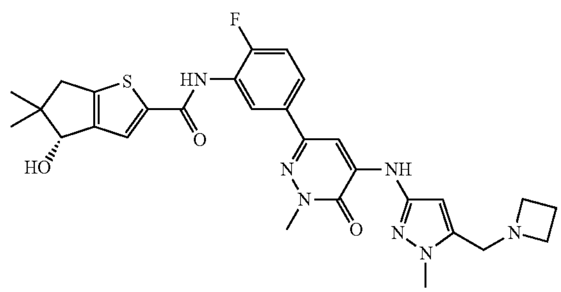 | (4R)-N-[5-(5-{[5-(azetidin-1-ylmethyl)-1-methyl-1H-pyrazol-3-yl]amino}-1-methyl-6-oxo-1,6-dihydropyridazin-3-yl)-2-fluorophenyl]-4-hydroxy-5,5-dimethyl-4H,5H,6H-cyclopenta[b]thiophene-2-carboxamide | 577 | 0 |
| 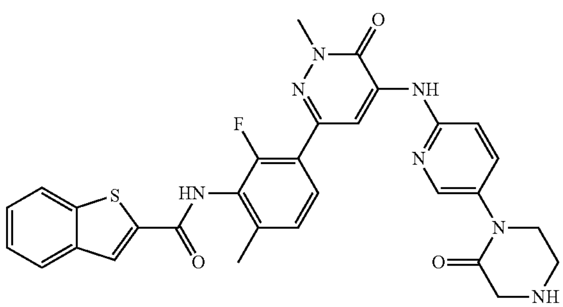 [SMILES: Cc1ccc(-c2cc(Nc3ccc(N4CCNCC4=O)cn3)c(=O)n(C)n2)c(F)c1NC(=O)c1cc2ccccc2s1] | N-[2-fluoro-6-methyl-3-(1-methyl-6-oxo-5-{[5-(2-oxopiperazin-1-yl)pyridin-2-yl]amino}-1,6-dihydropyridazin-3-yl)phenyl]-1-benzothiophene-2-carboxamide | 583 | 584.2 |
| 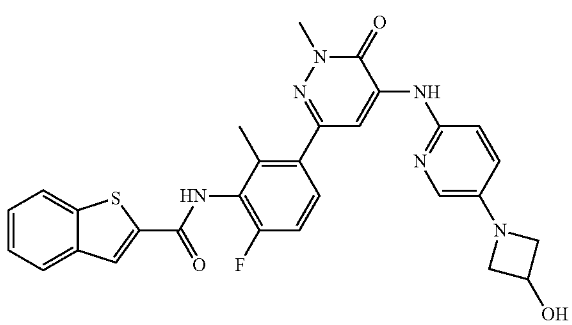 [SMILES: Cc1c(-c2cc(Nc3ccc(N4CC(O)C4)cn3)c(=O)n(C)n2)ccc(F)c1NC(=O)c1cc2ccccc2s1] | N-[6-fluoro-3-(5-{[5-(3-hydroxyazetidin-1-yl)pyridin-2-yl]amino}-1-methyl-6-oxo-1,6-dihydropyridazin-3-yl)-2-methylphenyl]-1-benzothiophene-2-carboxamide | 556 | 557.2 |
| 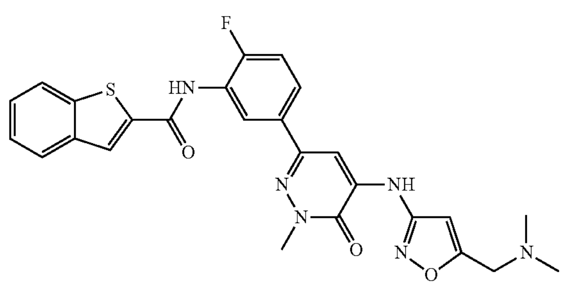 [SMILES: CN(C)Cc1cc(Nc2cc(-c3ccc(F)c(NC(=O)c4cc5ccccc5s4)c3)nn(C)c2=O)no1] | N-{5-[5-({5-[(dimethylamino)methyl]-1,2-oxazol-3-yl}amino)-1-methyl-6-oxo-1,6-dihydropyridazin-3-yl]-2-fluorophenyl}-1-benzothiophene-2-carboxamide | 518 | 519.2 |

-continued

| Structure | Name | MW calcd | MH + m/z obs |
|---|---|---|---|
| 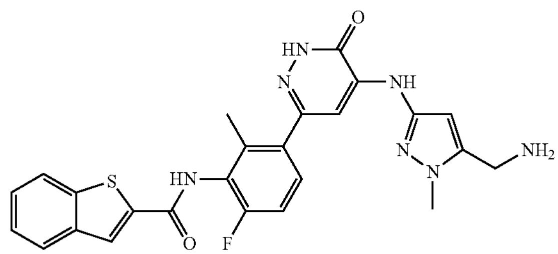 [SMILES: Cc1c(-c2cc(Nc3cc(CN)n(C)n3)c(=O)[nH]n2)ccc(F)c1NC(=O)c1cc2ccccc2s1] | N-[3-(5-{[5-(aminomethyl)-1-methyl-1H-pyrazol-3-yl]amino}-6-oxo-1,6-dihydropyridazin-3-yl)-6-fluoro-2-methylphenyl]-1-benzothiophene-2-carboxamide | 503 | 504.2 |
| 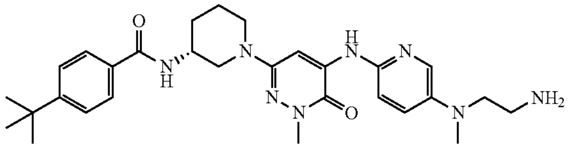 [SMILES: CN(CCN)c1ccc(Nc2cc(N3CCC[C@@H](NC(=O)c4ccc(C(C)(C)C)cc4)C3)nn(C)c2=O)nc1] | N-[(3R)-1-[5-({5-[(2-aminoethyl)(methyl)amino]pyridin-2-yl}amino)-1-methyl-6-oxo-1,6-dihydropyridazin-3-yl]piperidin-3-yl]-4-tert-butylbenzamide | 532 | 533.3 |
| 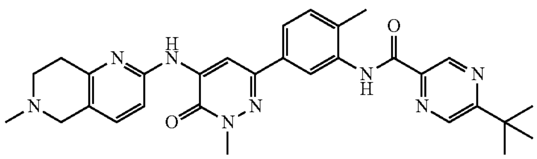 [SMILES: Cc1ccc(-c2cc(Nc3ccc4c(n3)CCN(C)C4)c(=O)n(C)n2)cc1NC(=O)c1cnc(C(C)(C)C)cn1] | 5-tert-butyl-N-(2-methyl-5-{1-methyl-5-[(6-methyl-5,6,7,8-tetrahydro-1,6-naphthyridin-2-yl)amino]-6-oxo-1,6-dihydropyridazin-3-yl}phenyl)pyrazine-2-carboxamide | 538 | 539.1 |
| 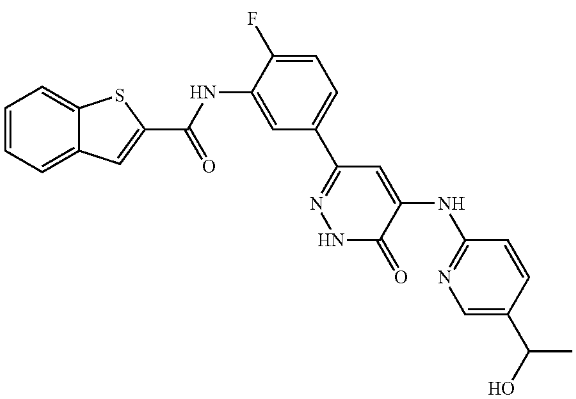 [SMILES: CC(O)c1ccc(Nc2cc(-c3ccc(F)c(NC(=O)c4cc5ccccc5s4)c3)n[nH]c2=O)nc1] | N-[2-fluoro-5-(5-{[5-(1-hydroxyethyl)pyridin-2-yl]amino}-6-oxo-1,6-dihydropyridazin-3-yl)phenyl]-1-benzothiophene-2-carboxamide | 501 | 501.9 |
| 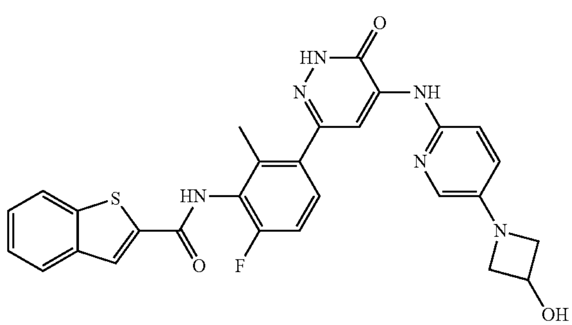 [SMILES: Cc1c(-c2cc(Nc3ccc(N4CC(O)C4)cn3)c(=O)[nH]n2)ccc(F)c1NC(=O)c1cc2ccccc2s1] | N-[6-fluoro-3-(5-{[5-(3-hydroxyazetidin-1-yl)pyridin-2-yl]amino}-6-oxo-1,6-dihydropyridazin-3-yl)-2-methylphenyl]-1-benzothiophene-2-carboxamide | 542 | 543.6 |
| 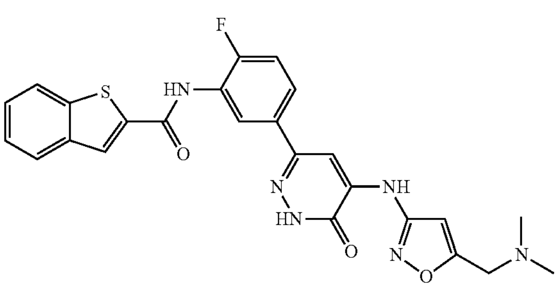 [SMILES: CN(C)Cc1cc(Nc2cc(-c3ccc(F)c(NC(=O)c4cc5ccccc5s4)c3)n[nH]c2=O)no1] | N-{5-[5-({5-[(dimethylamino)methyl]-1,2-oxazol-3-yl}amino)-6-oxo-1,6-dihydropyridazin-3-yl]-2-fluorophenyl}-1-benzothiophene-2-carboxamide | 504 | 505.1 |

-continued

| Structure | Name | MW calcd | MH + m/z obs |
|---|---|---|---|
| 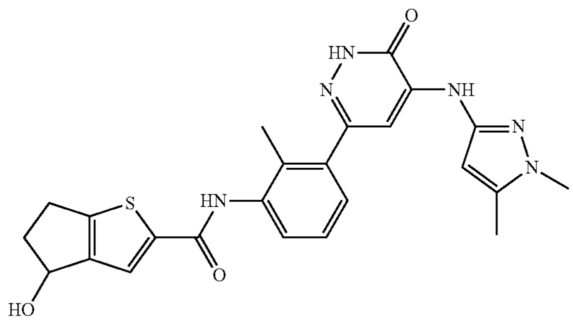 [SMILES: Cc1c(NC(=O)c2cc3c(s2)CCC3O)cccc1-c1cc(Nc2cc(C)n(C)n2)c(=O)[nH]n1] | N-(3-{5-[(1,5-dimethyl-1H-pyrazol-3-yl)amino]-6-oxo-1,6-dihydropyridazin-3-yl}-2-methylphenyl)-4-hydroxy-4H,5H,6H-cyclopenta[b]thiophene-2-carboxamide | 476 | 477.2 |
| 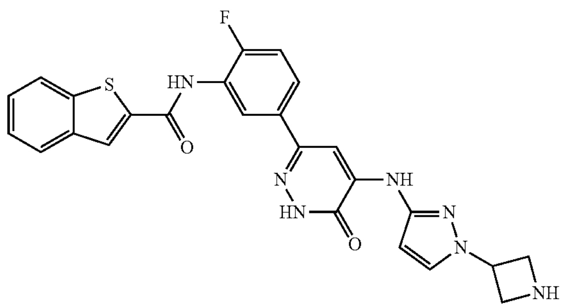 [SMILES: O=C(Nc1cc(-c2cc(Nc3ccn(C4CNC4)n3)c(=O)[nH]n2)ccc1F)c1cc2ccccc2s1] | N-[5-(5-{[1-(azetidin-3-yl)-1H-pyrazol-3-yl]amino}-6-oxo-1,6-dihydropyridazin-3-yl)-2-fluorophenyl]-1-benzothiophene-2-carboxamide | 501 | 502.2 |
| 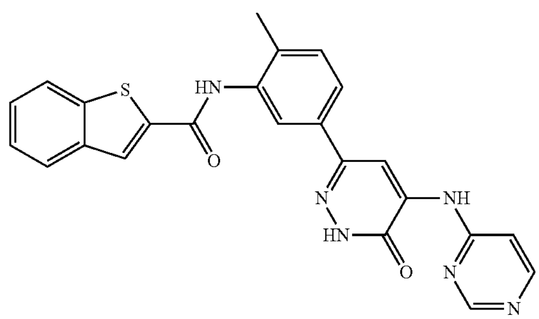 [SMILES: Cc1ccc(-c2cc(Nc3ccncn3)c(=O)[nH]n2)cc1NC(=O)c1cc2ccccc2s1] | N-{2-methyl-5-[6-oxo-5-(pyrimidin-4-ylamino)-1,6-dihydropyridazin-3-yl]phenyl}-1-benzathiophene-2-carboxamide | 454 | 455 |
| 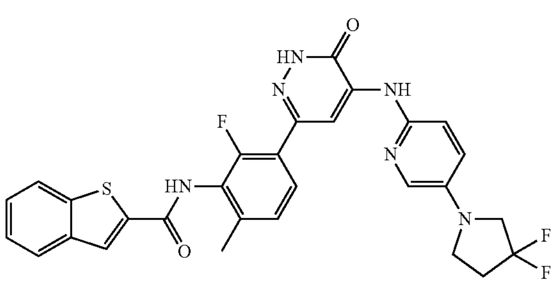 [SMILES: Cc1ccc(-c2cc(Nc3ccc(N4CCC(F)(F)C4)cn3)c(=O)[nH]n2)c(F)c1NC(=O)c1cc2ccccc2s1] | N-[3-(5-{[5-(3,3-difluoropyrrolidin-1-yl)pyridin-2-yl]amino}-6-oxo-1,6-dihydropyridazin-3-yl)-2-fluoro-6-methylphenyl]-1-benzothiophene-2-carboxamide | 576 | 577.2 |
| 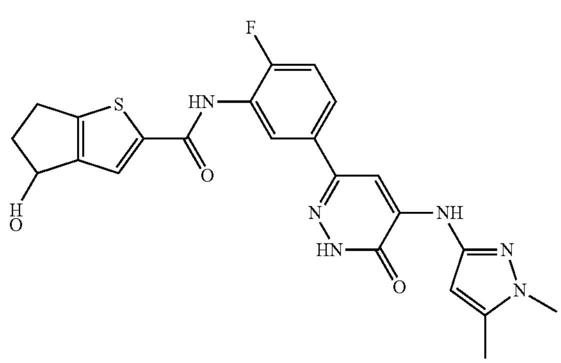 [SMILES: Cc1cc(Nc2cc(-c3ccc(F)c(NC(=O)c4cc5c(s4)CCC5O)c3)n[nH]c2=O)nn1C] | N-(5-{5-[(1,5-dimethyl-1H-pyrazol-3-yl)amino]-6-oxo-1,6-dihydropyridazin-3-yl}-2-fluorophenyl)-4-hydroxy-4H,5H,6H-cyclopenta[b]thiophene-2-carboxamide | 480 | 481.2 |

| Structure | Name | MW calcd | MH + m/z obs |
|---|---|---|---|
| 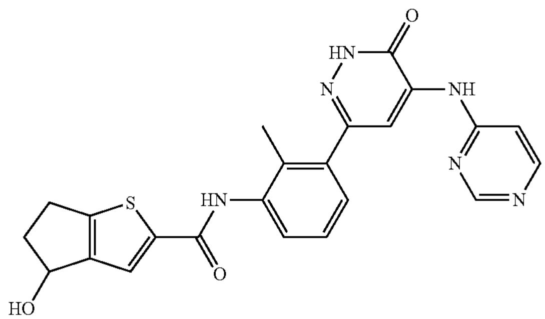 [SMILES: Cc1c(NC(=O)c2cc3c(s2)CCC3O)cccc1-c1cc(Nc2ccncn2)c(=O)[nH]n1] | 4-hydroxy-N-{2-methyl-3-[6-oxo-5-(pyrimidin-4-ylamino)-1,6-dihydropyridazin-3-yl]phenyl}-4H,5H,6H-cyclopenta[b]thiophene-2-carboxamide | 460 | 461.2 |
| 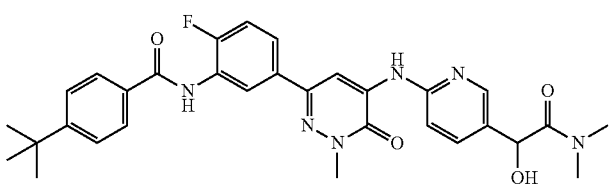 [SMILES: CN(C)C(=O)C(O)c1ccc(Nc2cc(-c3ccc(F)c(NC(=O)c4ccc(C(C)(C)C)cc4)c3)nn(C)c2=O)nc1] | 4-tert-butyl-N-{5-[5-({5-[(dimethylcarbamoyl)(hydroxy)methyl]pyridin-2-yl}amino)-1-methyl-6-oxo-1,6-dihydropyridazin-3-yl]-2-fluorophenyl}benzaande | 572 | 573.3 |
| 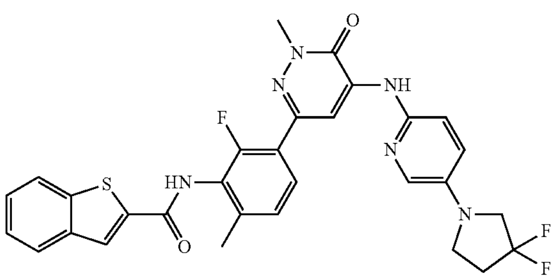 [SMILES: Cc1ccc(-c2cc(Nc3ccc(N4CCC(F)(F)C4)cn3)c(=O)n(C)n2)c(F)c1NC(=O)c1cc2ccccc2s1] | N-[3-(5-{[5-(3,3-difluoropyrrolidin-1-yl)-pyridin-2-yl]amino}-1-methyl-6-oxo-1,6-dihydropyridazin-3-yl)-2-fluoro-6-methylphenyl]-1-benzothiophene-2-carboxamide | 590 | 591.2 |
| 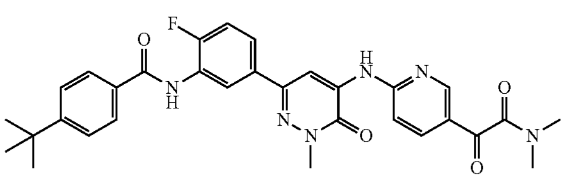 [SMILES: CN(C)C(=O)C(=O)c1ccc(Nc2cc(-c3ccc(F)c(NC(=O)c4ccc(C(C)(C)C)cc4)c3)nn(C)c2=O)nc1] | 4-tert-butyl-N-{5-[5-({5-[(dimethylcarbamoyl)carbonyl]pyridin-2-yl}amino)-1-methyl-6-oxo-1,6-dihydropyridazin-3-yl]-2-fluorophenyl}benzamide | 570 | 571.3 |
| 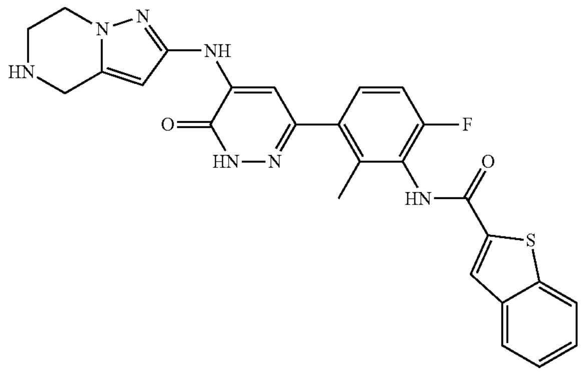 [SMILES: Cc1c(-c2cc(Nc3cc4n(n3)CCNC4)c(=O)[nH]n2)ccc(F)c1NC(=O)c1cc2ccccc2s1] | N-[6-fluoro-2-methyl-3-(6-oxo-5-{4H,5H,6H,7H-pyrazolo[1,5-a]pyrazin-2-ylamino}-1,6-dihydropyridazin-3-yl)phenyl]-1-benzothiophene-2-carboxamide | 515 | 516.2 |

-continued

| Structure | Name | MW calcd | MH + m/z obs |
|---|---|---|---|
| 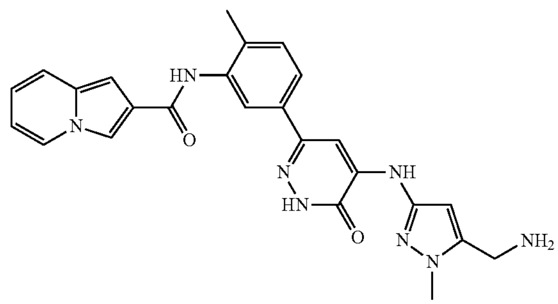 [SMILES: Cc1ccc(-c2cc(Nc3cc(CN)n(C)n3)c(=O)[nH]n2)cc1NC(=O)c1cc2ccccn2c1] | N-[5-(5-{[5-(aminomethyl)-1-methyl-1H-pyrazol-3-yl]amino}-6-oxo-1,6-dihydropyridazin-3-yl)-2-methylphenyl]indolizine-2-carboxamide | 468 | 469.2 |
| 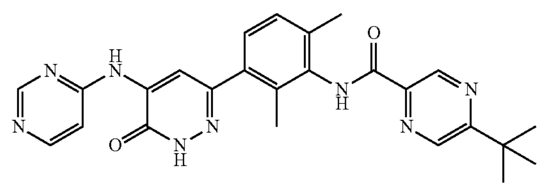 [SMILES: Cc1ccc(-c2cc(Nc3ccncn3)c(=O)[nH]n2)c(C)c1NC(=O)c1cnc(C(C)(C)C)cn1] | 5-tert-butyl-N-{2,6-dimethyl-3-[6-oxo-5-(pyrimidin-4-ylamino)-1,6-dihydropyridazin-3-yl]phenyl}pyrazine-2-carboxamide | 470 | 471.1 |
| 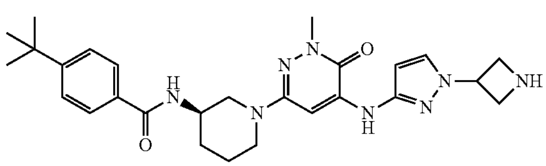 [SMILES: Cn1nc(N2CCC[C@@H](NC(=O)c3ccc(C(C)(C)C)cc3)C2)cc(Nc2ccn(C3CNC3)n2)c1=O] | N-[(3R)-1-(5-{[1-(azetidin-3-yl)-1H-pyrazol-3-yl]amino}-1-methyl-6-oxo-1,6-dihydropyridazin-3-yl)piperidin-3-yl]-4-tert-butylbenzamide | 504 | 505.3 |
| 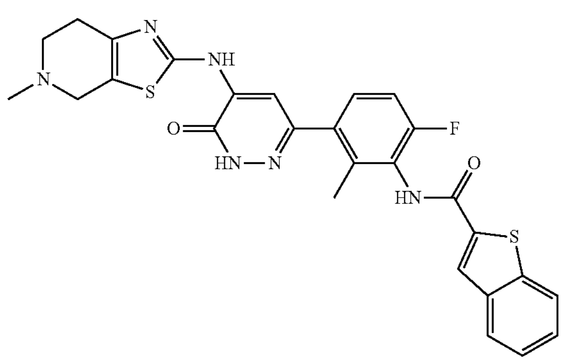 [SMILES: Cc1c(-c2cc(Nc3nc4c(s3)CN(C)CC4)c(=O)[nH]n2)ccc(F)c1NC(=O)c1cc2ccccc2s1] | N-{6-fluoro-2-methyl-3-[5-({5-methyl-4H,5H,6H,7H-pyrido[4,3-d][1,3]thiazol-2-yl}amino)-6-oxo-1,6-dihydropyridazin-3-yl]phenyl}-1-benzothiophene-2-carboxamide | 546 | 546.9 |
| 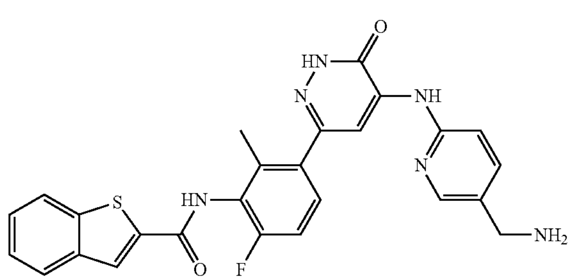 [SMILES: Cc1c(-c2cc(Nc3ccc(CN)cn3)c(=O)[nH]n2)ccc(F)c1NC(=O)c1cc2ccccc2s1] | N-[3-(5-{[5-(aminomethyl)pyridin-2-yl]amino}-6-oxo-1,6-dihydropyridazin-3-yl)-6-fluoro-2-methylphenyl]-1-benzothiophene-2-carboxamide | 500 | 501.0 |

| Structure | Name | MW calcd | MH + m/z obs |
|---|---|---|---|
| 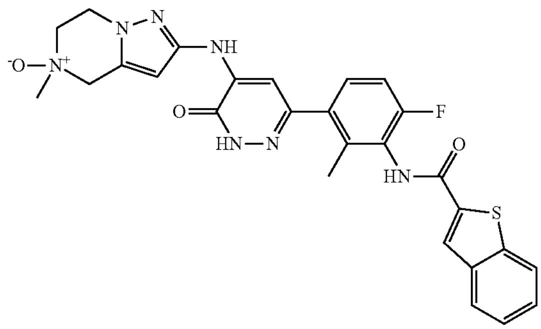 | N-{6-fluoro-2-methyl-3-[5-({5-methyl-5-oxo-4H,5H,6H,7H-pyrazolo[1,5-a]pyrazin-2-yl}amino)-6-oxo-1,6-dihydropyridazin-3-yl]phenyl}-1-benzothiophene-2-carboxamide | 545 | 546 |
| 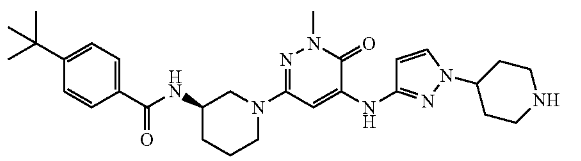 [SMILES: Cn1nc(N2CCC[C@@H](NC(=O)c3ccc(C(C)(C)C)cc3)C2)cc(Nc2ccn(C3CCNCC3)n2)c1=O] | 4-tert-butyl-N-[(3R)-1-(1-methyl-6-oxo-5-{[1-(piperidin-4-yl)-1H-pyrazol-3-yl]amino}-1,6-dihydropyridazin-3-yl)piperidin-3-yl]benzamide | 532 | 533.26 |
| 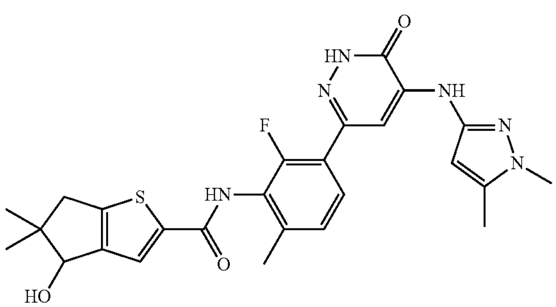 | N-(3-{5-[(1,5-dimethyl-1H-pyrazol-3-yl)amino]-6-oxo-1,6-dihydropyridazin-3-yl}-2-fluoro-5-methylphenyl)-4-hydroxy-5,5-dimethyl-4H,5H,6H-cyclopenta[b]thiophene-2-carboxamide | 522 | 523.2 |

EXAMPLE 4

Biochemical Btk Assay

A generalized procedure for one standard biochemical Btk Kinase Assay that can be used to test compounds disclosed in this application is as follows.

A master mix minus Btk enzyme is prepared containing 1× Cell Signaling kinase buffer (25 mM Tris-HCl, pH 7.5, 5 mM beta-glycerophosphate, 2 mM dithiothreitol, 0.1 mM $Na_3VO_4$, 10 mM $MgCl_2$), 0.5 μM Promega PTK Biotinylated peptide substrate 2, and 0.01% BSA. A master mix plus Btk enzyme is prepared containing 1× Cell Signaling kinase buffer, 0.5 μM PTK Biotinylated peptide substrate 2, 0.01% BSA, and 100 ng/well (0.06 mU/well) Btk enzyme. Btk enzyme is prepared as follows: full length human wildtype Btk (accession number NM-000061) with a C-terminal V5 and 6× His tag was subcloned into pFastBac vector for making baculovirus carrying this epitope-tagged Btk. Generation of baculovirus is done based on Invitrogens instructions detailed in its published protocol "Bac-toBac Baculovirus Expression Systems" (Cat. Nos. 10359-016 and 10608-016). Passage 3 virus is used to infect Sf9 cells to overexpress the recombinant Btk protein. The Btk protein is then purified to homogeneity using Ni-NTA column. The purity of the final protein preparation is greater than 95% based on the sensitive Sypro-Ruby staining. A solution of 200 μM ATP is prepared in water and adjusted to pH7.4 with 1N NaOH. A quantity of 1.25 μL of compounds in 5% DMSO is transferred to a 96-well ½ area Costar polystyrene plate. Compounds are tested singly and with an 11-point dose-responsive curve (starting concentration is 10 μM; 1:2 dilution). A quantity of 18.75 μL of master mix minus enzyme (as a negative control) and master mix plus enzyMe is transferred to appropriate wells in 96-well ½ area costar polystyrene plate. 5 μL of 200 μM ATP is added to that mixture in the 96-well ½ area Costar polystyrene plate for final ATP concentration of 40 μM. The reaction is allowed to incubate for 1 hour at room temperature. The reaction is stopped with Perkin Elmer 1× detection buffer containing 30 mM EDTA, 20 nM SA-APC, and 1 nM. PT66 Ab. The plate is read using time-resolved fluorescence with a Perkin Elmer Envision using excitation filter 330 nm, emission filter 665 nm, and $2^{nd}$ emission filter 615 nm. $IC_{50}$ values are subsequently calculated. Alternatively, the Lanthascreen assay can be used to evaluate Btk activity through quantification of its phosphorylated peptide product. The FRET that occurs between the fluorescein on the peptide product and the terbium on the detection antibody decreases with the addition of inhibitors of Btk that reduce the phosphorylation of the peptide. In a final reaction volume of 25 uL, Btk (h) (0.1 ng/25 ul reaction) is incubated with 50 mM Hepes pH 7.5, 10 mM $MgCl_2$, 2 mM $MnCl_2$, 2 mM DTT, 0.2 mM NaVO4, 0.01% BSA, and 0.4 uM fluorescein poly-GAT. The reaction is initiated by the addition of ATP to 25 uM (Km of ATP). After incubation for 60 minutes at room temperature, the reaction is stopped by the addition of a final concentration of 2 nM Tb-PY20 detection antibody in 60 mM EDTA for 30 minutes at mom temperature. Detection is determined on a Perkin Elmer Envision with 340 nM excitation and emission at 495 and 520 nm.

EXAMPLE 5

Ramos Cell Btk Assay

Another generalized procedure for a standard cellular Btk Kinase Assay that can be used to test compounds disclosed in this application is as follows.

Ramos cells are incubated at a density of $0.5 \times 10^7$ cells/ml in the presence of test compound for 1 hr at 37° C. Cells are then stimulated by incubating with 10 ng/ml anti-human IgM $F(ab)_2$ for 5 minutes at 37° C. Cells are pelleted, lysed, and a protein assay is performed on the cleared lysate. Equal protein amounts of each sample are subject to SDS-PAGE and western blotting with either anti-phosphoBtk(Tyr223) antibody (Cell Signaling Technology #3531; Epitomics, cat. #2207-1) or phosphoBtk(Tyr551) antibody (BD Transduction Labs #558034) to assess Btk autophosphorylation or an anti-Btk antibody (BD Transduction Labs #611116) to control for total amounts of Btk in each lysate.

EXAMPLE 6

B-Cell Proliferation Assay

A generalized procedure for a standard cellular B-cell proliferation assay that can be used to test compounds disclosed in this application is as follows.

B-cells are purified from spleens of 8-16 week old Balb/c mice using a B-cell isolation kit (Miltenyi Biotech, Cat #130-090-862). Testing compounds are diluted in 0.25% DMSO and incubated with $2.5 \times 10^5$ purified mouse splenic B-cells for 30 min prior to addition of 10 µg/ml of an anti-mouse IgM antibody (Southern Biotechnology Associates Cat #1022-01) in a final volume of 100 µl. Following 24 hr incubation, 1 µCi $^3$H-thymidine is added and plates are incubated an additional 36 hr prior to harvest using the manufacturer's protocol for SPA[$^3$H]thymidine uptake assay system (Amersham Biosciences # RPNQ 0130). SPA-bead based fluorescence is counted in a microbeta counter (Wallace Triplex 1450, Perkin Elmer).

EXAMPLE 7

T Cell Proliferation Assay

A generalized procedure for a Standard T cell proliferation assay that can be used to test compounds disclosed in this application is as follows.

T cells are purified from spleens of 8-16 week old Balb/c mice using a Pan T cell isolation kit (Miltenyi Biotech, Cat #1.30-090-861). Testing compounds are diluted in 0.25% DMSO and incubated with $2.5 \times 10^5$ purified mouse splenic T cells in a final volume of 100 µl in flat clear bottom plates precoated for 90 min at −37° C. With 10 µg/ml each of anti-CD3 (BD #553057) and anti-CD28 (BD #553294) antibodies. Following 24 hr incubation, 1 µCi $^3$H-thymidine is added and plates incubated an additional 36 hr prior to harvest using the manufacturer'S protocol for SPA[$^3$H]thymidine uptake assay system (Amersham Biosciences # RPNQ 0130). SPA-bead based fluorescence was counted in a microbeta counter (Wallace Triplex 1450, Perkin Elmer).

EXAMPLE 8

CD86 Inhibition Assay

A generalized procedure for a standard assay for the inhibition of B cell activity that can be used to test compounds disclosed in this application is as follows.

Total mouse splenocytes are purified from spleens of 8-16 week old Balb/c mice by red blood cell lysis (BD Pharmingen 4555899). Testing compounds are diluted to 0.5% DMSO and incubated with $1.25 \times 10^6$ splenocytes in a final volume of 200 it in flat clear bottom plates (Falcon 353072) for 60 min at 37° C. Cells are then stimulated with the addition of 15 µg/ml IgM (Jackson ImmunoResearch 115-006-020), and incubated for 24 hr at 37° C., 5% $CO_2$. Following the 24 hr incubation, cells are transferred to conical bottom clear 96-well plates and pelleted by centrifugation at 1.200×g×5 nm. Cells are preblocked by CD16/CD32 (BD Pharmingen #553142), followed by triple staining with CD19-FITC (BD Pharmingen #553785), CD86-PE (BD Pharmingen #553692), and 7AAD (BD Pharmingen #51-68981E). Cells are sorted on a BD FACSCalibur and gated on the CD19$^+$/7AAD$^-$ population. The levels of CD86 surface expression on the gated population is measured versus test compound concentration.

EXAMPLE 9

B-ALL Cell Survival Assay

The following is a procedure for a standard B-ALL cell survival study using an XTT readout to measure the number of viable cells. This assay can be used to test compounds disclosed in this application for their ability to inhibit the survival of B-ALL cells in culture. One human B-cell acute lymphoblastic leukemia line that can be used is SUP-B15, a human Pre-B-cell ALL line that is available from the ATCC.

SUP-B15 pre-B-ALL cells are plated in multiple 96-well microtiter plates in 100 µl of Iscove's media+20% FBS at a concentration of $5 \times 10^5$ cells/ml. Test compounds are then added with a final conc. of 0.4% DMSO. Cells are incubated at 37° C. with 5% $CO_2$ for up to 3 days. After 3 days cells are split 1:3 into fresh 96-well plates containing the test compound and allowed to grow up to an additional 3 days. After each 24 h period, 50 ul of an XTT solution (Roche) is added to one of the replicate 96-well plates and absorbance readings are taken at 2, 4 and 20 hours following manufacturer's directions. The reading taken with an OD for DMSO only treated cells within the linear range of the assay (0.5-1.5) is then taken and the percentage of viable cells in the compound treated wells are measured versus the DMSO only treated cells.

EXAMPLE 10

The compounds disclosed in Examples 1-3 and 11-16 above are tested in the Btk biochemical assay described herein (Example 4) and all of the compounds of Formula I disclosed in Examples 1-3 and 11-16 above exhibit an $IC_{50}$ value less than or equal to 2 micromolar and certain of those compounds exhibit an $IC_{50}$ value less than or equal to 1 micromolar. Certain of those compounds exhibit an $IC_{50}$ value less than or equal to 25 nM. Certain of those compounds exhibit an $IC_{50}$ value less than or equal to 10 nM. Certain of those compounds exhibit an $IC_{50}$ value less than or equal to 5 nM.

Some of the compounds disclosed herein are tested in an assay for inhibition of B cell activity (under the conditions described in Example 8), and exhibit an $IC_{50}$ value less than or equal to 10 micromolar. Certain of those compounds exhibit an $IC_{50}$ value less than or equal to 0.5 micromolar. Certain of those compounds exhibit an $IC_{50}$ value less than or equal to 100 nM in this assay.

Some of the compounds disclosed herein exhibit both biochemical and cell-based activity. For example, some of the compounds disclosed herein exhibit an $IC_{50}$ value less than or equal to 1 micromolar in the Btk biochemical assay described herein (Example 4) and an $IC_{50}$ value less than or equal to 10 micromolar in at least one of the cell-based assays (other than the T-cell assay) described herein (Examples 5, 6, 8 or 9). Certain of those compounds exhibit an $IC_{50}$ value less than or equal to 50 nM in the Btk biochemical assay described herein (Example 4) and an $IC_{50}$ value less than or equal to 500 nM in at least one of the cell-based assays (other than the cell assay) described herein (Examples 5, 6, 8 or 9). Certain of those compounds exhibit an $IC_{50}$ value less than or equal to 10 nM and an $IC_{50}$ value less than or equal to 100 nM in at least one of the cell-based assays (other than the T-cell assay) described herein (Examples 5, 6, 8 or 9).

EXAMPLE 11

N-[5-(5-{[5-(azetidin-1-ylmethyl)-1-methyl-1H-pyrazol-3-yl]amino}-1-methyl-6-oxo-1,6-dihydropyridazin-3-yl)-2-fluorophenyl]-4-hydroxy 5,5-dimethyl-4H,5H,6H-cyclopenta[b]thiophene-2-carboxamide (29)

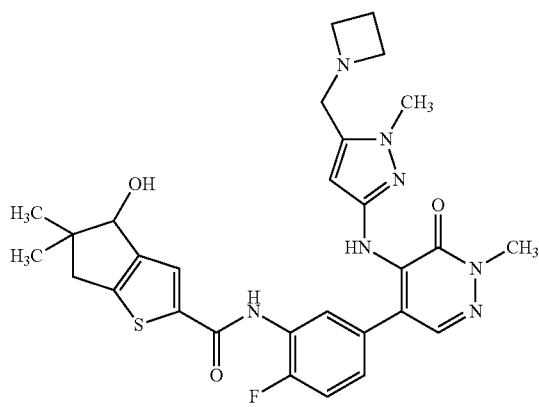

(Z)-5-(ethoxymethylene)-3-methyl-2-thioxothiazolidin-4-one (2)

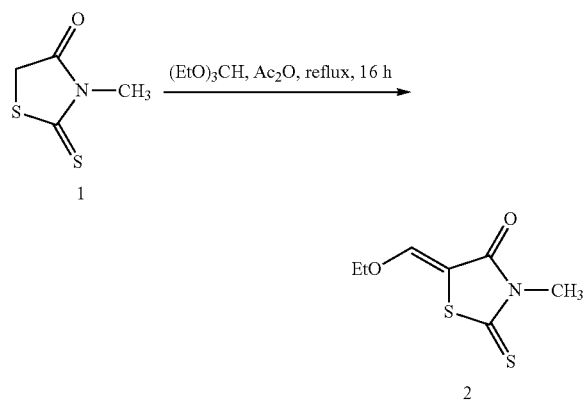

A 250-mL three-neck round-bottomed flask equipped with a magnetic stirrer and reflux condenser was charged with 1 (15.0 g, 102 mmol), triethyl orthoformate (26.7 g, 180 mmol), and acetic anhydride (30 mL). After heating at reflux for 16 h, the reaction mixture was cooled to room temperature and filtered. The filter cake was washed with diethyl ether (20 mL) and dried in an vacuum oven at 45° C. to afford 2 in 85% yield (17.6 g) as a pink solid: mp 110-111° C.; $^1$H NMR (500 MHz, CDCl$_3$) δ 7.75 (s, 1H), 4.25 (q, 2H, =7.5 Hz), 3.42 (s, 3H), 1.42 (t, 3H, =7.5 Hz); MS (ESI+) m/z 204.3 (M+H).

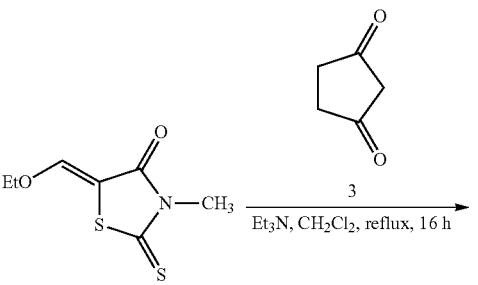

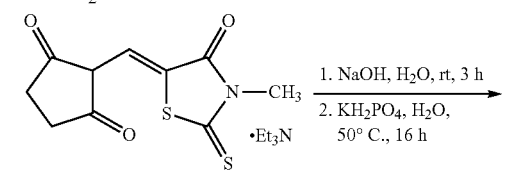

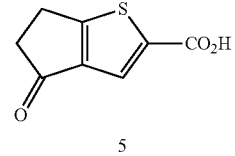

(Z)-2((3-methyl-4-oxo-2-thioxothiazolidin-5-ylidene)methyl)cyclopentane-1,3-dione triethylamine Salt (4)

A 250-mL three-neck round-bottomed flask equipped with a magnetic stirrer and reflux condenser was charged with 2 (5.00 g, 24.6 mmol), triethylamine (2.53 g, 25.1 mmol), 3 (2.56 g, 26.1 mmol) and methylene chloride (50 mL). After heating at reflux for 16 h, the reaction mixture was cooled to room temperature, and the solvent was removed under reduced pressure. The resulting residue was triturated with a mixture of methylene chloride (10 mL), ethyl acetate (10 mL) and diethyl ether (30 mL), and the solid obtained was dried in an vacuum oven at 45° C. to afford 4 in 79% yield (7.19 g) as a pink solid: mp 167-168° C.; $^1$H NMR (500 MHz, DMSO-d$_6$) δ 8.83 (br s, 1H), 7.39 (s, 1H), 3.30 (s, 3H), 3.09 (q, 6H, J=7.5 Hz), 2.20 (s, 4H), 1.18 (t, 9H, J=7.5 Hz).

4-Oxo-5,6-dihydro-4H-cyclopenta[b]thiophene-2-carboxylic Acid (5)

In a 500-mL round-bottomed flask equipped with a magnetic stirrer and reflux condenser, was charged with sodium hydroxide (3.34 g, 83.6 mmol) and water (65 mL). The solution was degassed with nitrogen for 15 min. 4 (7.19 g, 20.2 mmol) was added and the mixture was stirred at room temperature for 3 h. After this time, 1 M aqueous potassium phosphate monobasic was added to adjust the pH of the reaction mixture to 8.0, followed by water (200 mL). After heating at 50° C. for 16 h, the water was evaporated to 50 mL under reduced pressure, and 12 N hydrochloric acid was added to adjust the pH to 2.8 (pH meter). The resulting precipitate was collected by vacuum filtration, washed with water (5 mL) and dried for 16 h under vacuum at 50° C. to afford 5 in 37% yield (1.37 g) as a green solid: mp 195-196° C.; $^1$H NMR (500 MHz, DMSO-$d_6$) δ 13.30 (br s, 1H), 7.64 (s, 1H), 3.23 (t, 2H, J=5.5 Hz), 2.76 (t, 2H, J=5.5 Hz); MS (APCI+) m/z 183.2 (M+H).

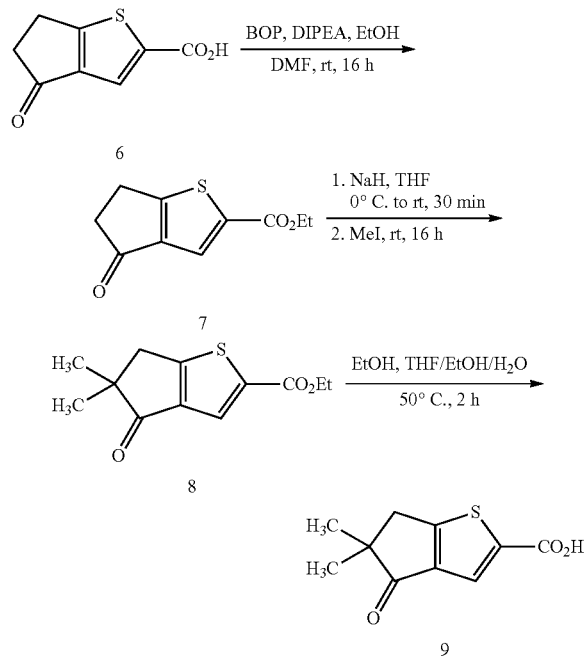

Ethyl 4-Oxo-5,6-dihydro-4H-cyclopenta[b]thiophene-2-carboxylate (7)

A 100-mL single-neck round-bottomed flask equipped with a magnetic stirrer was purged with nitrogen and charged with 6 (1.00 g, 5.49 mmol), ethanol (1.01 g, 22.0 mmol), N,N-diisopropylethylamine (2.84 g, 22.0 mmol) and anhydrous DMF (20 mL). To the resulting solution, benzotriazol-1-yl-oxy-tris(dimethylamino) phosphonium hexafluorophosphate (BOP, 2.67 g, 6.04 mmol) was added, and the reaction was stirred for 16 h. After this time, the reaction mixture was partitioned between ethyl acetate (100 mL) and water (50 mL). The organic layer was separated, and the aqueous layer was re-extracted with ethyl acetate (2×50 mL). The organic layers were combined, washed with water (50 mL) and brine (50 mL), and dried over sodium sulfate. The drying agent was then removed by filtration, and the filtrate was evaporated under reduced pressure to afford a 72% yield (831 mg) of 7 as a brown solid: mp 54-55° C.; $^1$H NMR (500 MHz, CDCl$_3$) δ 7.80 (s, 1H), 4.37 (q, 2H, J=Hz), 3.25 (t, 2H, J=5.5 Hz), 2.97 (t, 2H, J=5.5 Hz), 1.27 (t, 3H, J=7.0 Hz); MS (ESI+) m/z 211.0 (M+H).

Ethyl 5,5-Dimethyl-4-oxo-5,6-dihydro-4H-cyclopenta[b]thiophene-2-carboxylate (8)

A 100-mL single-neck round-bottomed flask equipped with a magnetic stirrer and nitrogen inlet was charged with 60% sodium hydride dispersion in oil (114 mg, 4.76 mmol) and anhydrous THF (5 mL), and the resulting suspension was cooled to 0° C. A solution of 7 (400 mg, 1.90 mmol) in THF (5 mL) was then added, and the reaction mixture was stirred at 0° C. for 30 min. After this time, the cooling bath was removed and the mixture was stirred at room temperature for 30 min, The reaction was then cooled to 0° C., and iodomethane (1.10 g, 7.76 mmol) was added. After 30 min at 0° C., the reaction was allowed to warm to room temperature and stirred for 1.6 h. The solvent was then removed under reduce pressure, and the residue was partitioned between saturated aqueous ammonium, chloride (20 mL) and diethyl ether (40 mL). The organic layer was separated, washed with brine (15 mL) and dried over sodium sulfate. The drying agent was removed by filtration, and the filtrate was concentrated under reduced pressure. The resulting residue was purified by flash chromatography to afford 8 in 69% yield (313 mg) as a yellow solid: mp 41-42° C.; $^1$H NMR (500 MHz, CDCl$_3$) δ 7.82 (s, 1H), 4.36 (q, 2H, J=7.0 Hz), 3.07 (s, 2H), 1.37 (t, 3H, J=7.0 Hz), 1.29 (s, 6H); MS (ESI+) m/z 239.1 (M+H).

5,5-Dimethyl-4-oxo-5,6-dihydro-4H-cyclopenta[b]thiophene-2-carboxylic Acid (9)

A 50-mL single-neck round-bottomed flask equipped with a magnetic stirrer and reflux condenser was charged with 8 (310 mg, 1.30 mmol), THF (2 mL) and ethanol (2 mL). A solution of lithium hydroxide (125 mg, 5.21 mmol) in water (2 mL) was added, and the mixture was stirred at 50° C. for 2 h. After this time, the organic solvents were removed under reduced pressure, water (6 mL) was added, and the pH was adjusted to 3.0 with 2 N hydrochloric acid. The resulting suspension was filtered and the filter cake washed with water (2 mL). The filter cake was dried to constant weight under vacuum at 40° C. to afford a 100% yield (292 mg) of 9 as a white solid: mp 124-125° C.; $^1$H NMR (500 MHz, CDCl$_3$) δ 7.93 (s, 1H), 3.10 (s, 2H), 1.34 (5, 6H); MS (ESI+) m/z 211.0 (M+H).

2-(4-Fluoro-3-nitrophenyl)4,4,5,5-tetramethyl-1,3,2-dioxaborolane (13)

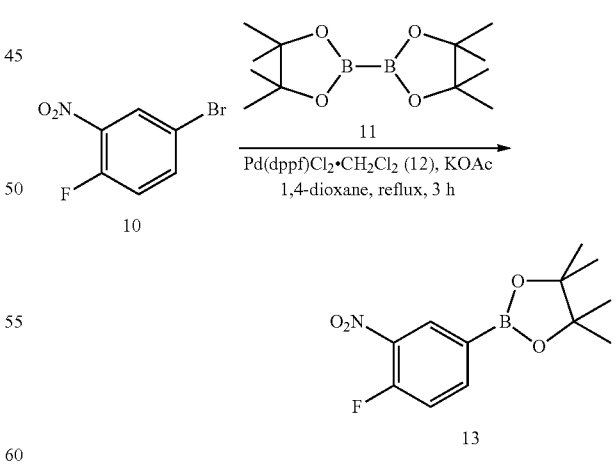

A 25-mL three-neck round-bottomed flask equipped with a magnetic stirrer, reflux condenser and nitrogen inlet was charged with 10 (5.00 g, 23.8 mmol), 11 (6.06 g, 23.8 mmol), potassium acetate (170 mg, 71 mmol), and 1,4-dioxane (300 mL). After bubbling nitrogen through the resulting suspension for 10 min, 12 (1.72 mg, 2.4 mmol) was added. The reaction mixture was heated at reflux for 3 h. After this time, the reaction mixture was cooled to room temperature and diluted with ethyl acetate (400 mL) and water. (400 mL). Celite 521 (80 g) was added, and the mixture was stirred for 5 min. The mixture was filtered through a pad of Celite 521, and the filtrate was washed with saturated aqueous sodium bicarbonate (800 mL) and brine (800 mL), dried over sodium sulfate, filtered and concentrated under reduced pressure to afford an 84% yield (5.10 g) of 13 as a light yellow solid: $^1$H NMR (500 MHz, CDCl$_3$) δ 8.47 (dd, 1H, J=8.0, 1.5 Hz), 8.02 (ddd, 1H, J=8.5, 5.0, 1.5 Hz), 7.27 (dd, 1H, J=11.0, 8.0 Hz), 1:35 (s, 12H).

2-Fluoro-5-(4,4,5,5-tetramethyl-1,3,2-dioxaborolan-2-yl)aniline (14)

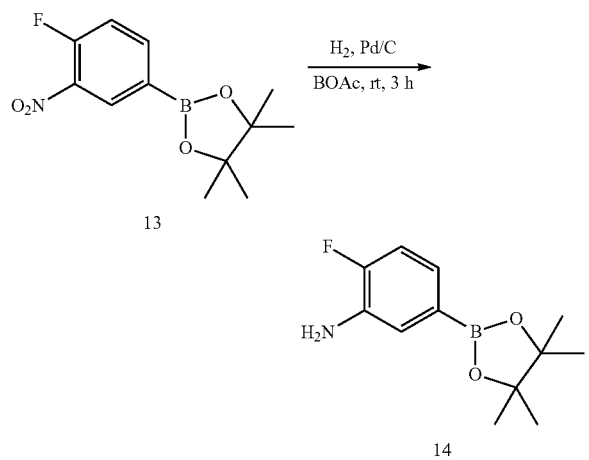

A 500-mL Parr reactor bottle was purged with nitrogen and charged with 13 (6.92 g, 25.9 mmol), ethyl acetate (150 mL) and 10% palladium on carbon (50% wet, 150 mg dry weight). The bottle was attached to Parr hydrogenator, evacuated, charged with hydrogen gas to a pressure of 50 psi and shaken for 2 h. After this time the hydrogen was evacuated and nitrogen charged into the reactor. The catalyst was removed by filtration through a pad of Celite 521 and the filter cake washed with methylene chloride (400 mL). The resulting solution was concentrated under reduced pressure to afford 14 in 100% yield (6.34 g) as a yellow oil: $^1$H NMR (500 MHz, CDCl$_3$) δ 7.22 (dd, 1H, J=8.5, 1.0 Hz), 7.16 (m, 1H), 6.97 (dd, 1H, J=11.5, 8.0 Hz), 3.68 (br s, 2H), 1.33 (m, 12H); MS (ESI+) m/z 238.2 (M+H).

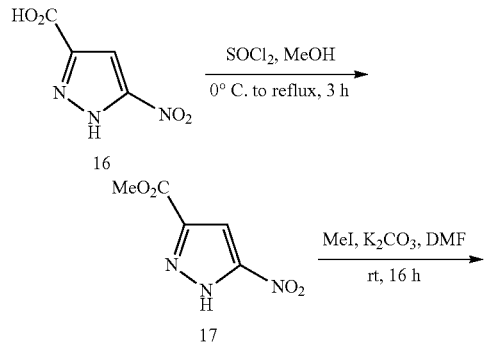

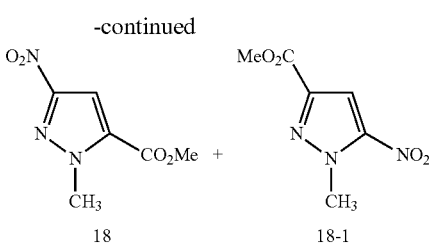

Methyl 5-Nitro-1H-pyrazole-3-carboxylate (17)

A 250-mL single-neck round-bottomed flask equipped with a magnetic stirrer and reflux condenser was purged with nitrogen and charged with 16 (8.63 g, 55.0 mmol) and anhydrous methanol (60 mL), and the reaction mixture was cooled to 0° C. in an ice/water cooling bath. To the resulting solution thionyl chloride (17.2 g, 144 mmol) was added dropwise. After the addition was complete, the bath was removed, and the reaction was heated at reflux for 3 h. After this time, the reaction was concentrated to dryness under reduced pressure to afford a 100% yield of 17 (9.40 g) as a white solid: mp 137-138° C.; $^1$H NMR (300 MHz, DMSO-d$_6$) δ15.24 (bs, 1H), 7.54 (s, 1H), 3.90 (s, 3H); MS (ESI+) m/z 170 (M–H).

Methyl 1-Methyl-3-nitro-1H-pyrazole-5-carboxylate (18) and (18-1)

A 250-mL single-neck round-bottomed flask equipped with a magnetic stirrer was purged with nitrogen and charged with 17 (10.1 g, 59.0 mmol), anhydrous N,N-dimethylformamide (110 mL) and potassium carbonate (14.7 g, 107 mmol), and the reaction was stirred at room temperature for 16 h. After this time the reaction was diluted with water (400 mL) and extracted with methylene chloride (3×250 mL). The combined organic extracts were dried over sodium sulfate, filtered and concentrated under reduced pressure. The resulting residue was subjected to flash chromatography to afford 18 in 66% yield (7.28 g) as a white solid: mp 65-66° C.; $^1$H NMR (300 MHz, DMSO-d$_6$) δ 7.56 (s, 1H), 4.20 (s, 3H), 3.89 (s, 3H) and 18-1 in 15% yield (1.65 g) as a white solid: mp 81-82° C.; $^1$H NMR (300 MHz, DMSO-d$_6$) δ 7.63 (s, 1H), 4.23 (s, 3H), 3.85 (s, 3H).

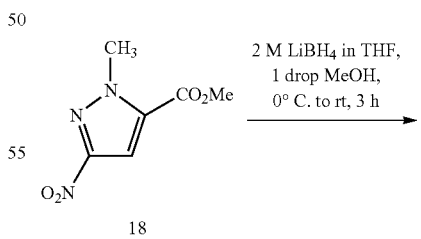

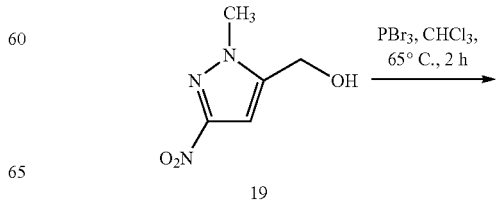

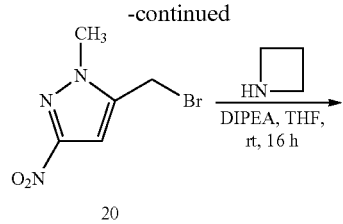

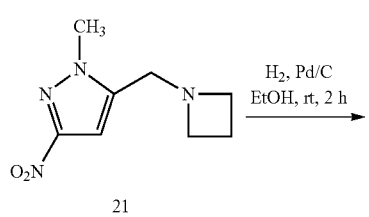

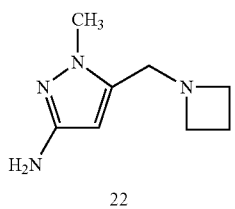

(1-Methyl-3-nitro-1H-pyrazol-5-yl)methanol (19)

A 250-mL three-neck round-bottomed flask equipped with a mechanical stirrer, addition funnel and nitrogen inlet was purged with nitrogen and charged with 18 (2.07 g, 11.2 mmol), THF (50 mL) and cooled to 0° C. using an ice bath. 2 M lithium borohydride solution (11.2 mL, 22.4 mmol) was added dropwise at a rate that maintained the internal reaction temperature below 5° C. After the addition was complete the cooling bath was removed and the reaction was stirred at room temperature for 1 h. After this time a drop of methanol was added and the reaction was stirred for 2 h. The reaction was cooled to 0° C. using an ice bath, and saturated aqueous sodium bicarbonate (150 mL) was added dropwise. The layers were separated, and aqueous layer was extracted with ethyl acetate (3×50 mL). The combined organic layers were washed with brine (50 mL), dried over sodium sulfate and concentrated under reduced pressure The residue was purified by column chromatography to afford a quantative yield (1.83 g) of 19 as an off-white solid: mp 66-68° C.; $^1$H NMR (300 MHz, DMSO-$d_6$) δ 6.94 (s, 1H), 5.56 (t, 1H, J=5.4 Hz), 4.55 (d, 2H, J=5.5 Hz), 3.92 (s, 3H); MS (ESI+) m/z 157.1 (M+H).

5-(Bromomethyl)-1-methyl-3-nitro-1H-pyrazole (20)

A 25-mL three-necked round-bottomed flask equipped with a magnetic stirrer, nitrogen inlet and reflux condenser was purged with nitrogen and charged with 19 (1.83 g, 11.2 mmol) and chloroform (10 mL). The reaction was cooled to 0° C. using an ice bath and phosphorous tribromide (3.02 g, 11.2 mmol) was added dropwise. The cooling bath was removed and the reaction stirred at reflux for 2 h. After this time, the reaction was cooled to 0° C. and diluted with methylene chloride (100 mL). Saturated aqueous sodium bicarbonate (25 mL) was added until a pH of 8.5 was reached. The layers were separated, and the aqueous layer was extracted with methylene chloride (3×20 mL). The combined organic layers were washed with brine (30 mL), dried over sodium sulfate and concentrated under reduced pressure. The residue was purified by column chromatography to afford an 87% yield (1.66 g) of 20 as an off-white solid: mp 41-13° C.; $^1$H NMR (300 MHz, CDCl$_3$) δ 6.91 (s, 1H), 4.44 (s, 2H), 4.01 (s, 3H).

5-(Azetidin-1-ylmethyl)-1-methyl-3-nitro-1H-pyrazole (21)

A 250-mL single-neck round-bottomed flask equipped with a magnetic stirrer and nitrogen inlet was charged with THF (45 mL), 20 (1.66 g, 7.54 mmol), azetidine (531 mg, 9.31 mmol) and stirred at room temperature for 24 h. After this time the reaction was concentrated to dryness under reduced pressure, and the resulting solid was diluted with a mixture of methylene chloride (15 mL) and 10% aqueous potassium carbonate (15 mL). The aqueous layer was separated and extracted with methylene chloride (2×15 mL). The combined organic extracts were dried over sodium sulfate and concentrated under reduced pressure. The residue was purified by column chromatography to afford a 99% yield (1.47 g) of 21 as a yellow oil: $^1$H NMR (300 MHz, CDCl$_3$) δ 6.74 (s, 1H), 3.97 (s, 3H), 3.55 (s, 2H), 3.22 (t, 4H, J=7.2 Hz), 2.10 (pentet, 2H, J=7.2 Hz); MS (ESI+) m/z 197.1 (M+H).

5-(Azetidin-1-ylmethyl)-1-methyl-1H-pyrazol-3-amine (22)

A 500-mL Parr reactor bottle was purged with nitrogen and charged with 10% palladium on carbon (50% wet, 180 mg dry weight) and a solution of 21 (1.00 g, 5.10 mmol) in ethanol (100 mL). The bottle was attached to a Parr hydrogenator, evacuated, charged with hydrogen gas to a pressure of 50 psi and shaken for 2 h. After this time, the hydrogen was evacuated, and nitrogen was charged into the bottle. Celite 521 (1.0 g) was added, and the mixture was filtered through a pad of Celite 521. The filter cake was washed with ethanol (2×25 mL), and the combined filtrates were concentrated to dryness under reduced pressure to afford a 94% yield of 22 (800 mg) as a yellow oil: $^1$H NMR (300 MHz, CDCl$_3$) δ 5.47 (s, 1H), 3.64 (s, 3H), 3.57 (br s, 2H), 3.43 (s, 2H), 3.19 (t, 4H, 0.1=7.2 Hz), 2.06 (quintet, 2H, J=7.2 Hz); MS (ESI+) m/z 167.1 (M+H).

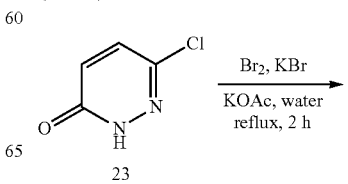

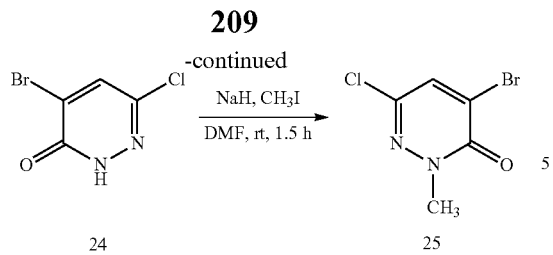

4-Bromo-6-chloropyridazin-3(2H)-one (24)

A 250-mL single-neck round-bottomed flask equipped with a magnetic stirrer and reflux condenser was charged with 6-chloropyridazin-3(2H)-one (23, Bulletin of the Korean Chemical Society, 10(6) 614-17; 1989)) (4.00 g, 30.6 mmol), potassium bromide (10.9 g, 91.9 mmol), potassium acetate (4.51 g, 45.9 mmol) and water (36 mL). Bromine (14.6 g, 91.9 mmol) was added, and the reaction mixture was heated at reflux for 2 h. After this time, the reaction was cooled to room temperature and filtered. The filter cake was washed with a solution of sodium sulfite (7.66 g, 60.7 mmol) in water (400 mL) and again with water (300 mL). The collected solids were dried in a vacuum oven at 50° C. overnight to afford a 100% yield (6.40 g) of 24 as an off-white solid: mp 205-206° C.; $^1$H NMR (500 MHz, DMSO-$d_6$) δ 13.52 (br s, 1H), 8.19 (s, 1H); MS (ESI+) m/z 209.1 (M+H).

4-Bromo-6-chloro-2-methylpyridazin-3(2H)-one (25)

A 250-mL single-necked round bottomed flask equipped with a magnetic stirrer was purged with nitrogen and charged with 24 (1.00 g, 4.77 mmol) and DMF (15 mL). Sodium hydride (60% by weight in oil: 229 mg, 5.73 mmol) was added in one portion. After stirring at room temperature for 10 minutes, iodomethane (1.02 g, 7.16 mmol) was added and the reaction stirred at room temperature for 1.5 h. The reaction was then quenched with aqueous saturated sodium bicarbonate (10 mL) and the resulting solution poured into water (150 mL). The mixture was then extracted with ethyl acetate (250 mL). The organic layer was dried over sodium sulfate. The drying agent was then removed by filtration, and the filtrate was concentrated under reduced pressure to residue. Purification by column chromatography afforded 25 in a 68% yield (722 mg) as a white solid: mp 107-108° C.; $^1$H NMR (300 MHz, CDCl$_3$) δ 7.62 (s, 1H), 3.81 (s, 3H).

4-(5-(Azetidin-1-ylmethyl)-1-methyl-1H-pyrazol-3-ylamino)-6-chloropyridazin-3(2H)-one (26)

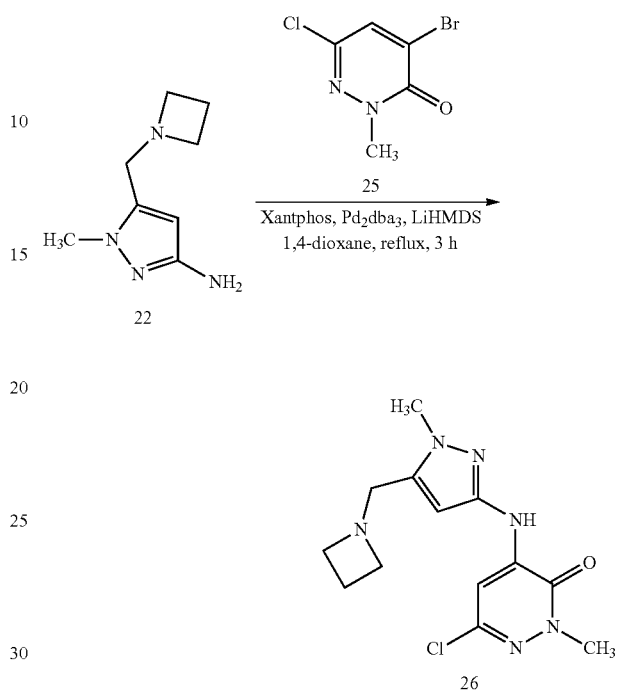

A 100-mL single-neck round-bottomed flask equipped with a magnetic stirrer, reflux condenser and nitrogen inlet was charged with 1,4-dioxane (20 mL), 22 (500 mg, 3.00 mmol), 25 (630 mg, 3.01 mmol) and 1 M THF solution of lithium hexamethyldisilazide (15 mL, 5.00 mmol). After bubbling nitrogen through the resulting solution for 30 min, Xantphos (148 mg, 0.255 mmol) and tris(dibenzylidene acetone)dipalladium(0) (138 mg, 0.150 mmol) were added, and the reaction mixture was heated at reflux for 3 h. After this time, the reaction was cooled to room temperature, and water (20 mL) was added. The pH was adjusted to 7 with 1 N hydrochloric acid. The resulting precipitate was collected by vacuum filtration, washed with water (2×25 mL), absorbed on silica gel and purified by flash chromatography to afford an 66% yield (590 mg) of 26 as a light brown solid: mp 140-141° C. $^1$H NMR (500 MHz, CDCl$_3$) δ 10.63 (s, 1H), 7.78 (s, 1H), 7.46 (s, 1H), 5.84 (s, 1H), 3.81 (s, 3H), 3.52 (s, 2H), 3.23 (t, 4H, J=7.0 Hz), 2.09 (m, 2H); MS (APCI+) m/z 295.8 (M+H).

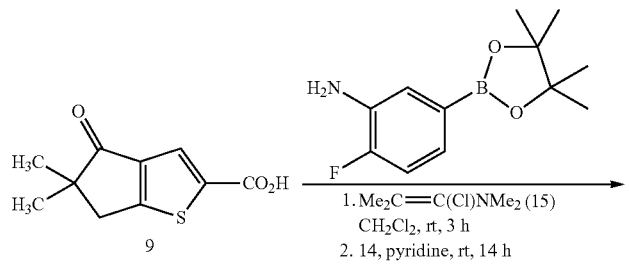

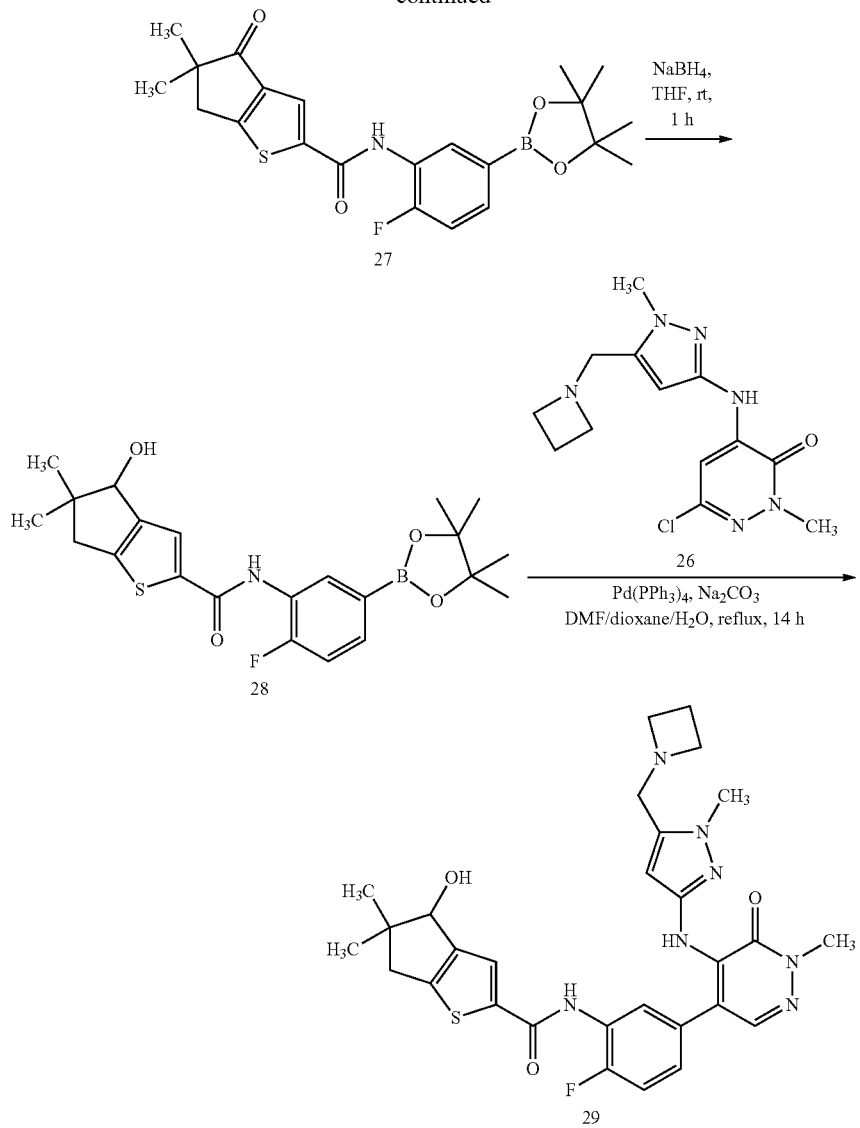

N-(2-Fluoro-5-(4,4,5,5-tetramethyl-1,3,2-dioxaborolan-2-yl)phenyl)-5,5-dimethyl-4-oxo-5,6-dihydro-4H-cyclopenta[b]thiophene-2-carboxamide (27)

A 100-mL single-neck round-bottomed flask equipped with a magnetic stirrer was purged with nitrogen and charged with 9 (270 mg, 1.29 mmol) and methylene chloride (3 mL). The solution Was cooled to 0° C., and 15 (172 mg, 1.29 mmol) was added dropwise. After this addition was complete, the reaction was warmed to room temperature and stirred for 2 h. 14 (305 mg, 1.29 mmol) was then added. After this addition, the reaction was cooled to 0° C., and anhydrous pyridine (306 mg, 3.87 mmol) was added. The cooling bath was removed, and the reaction mixture was stirred at room temperature for 16 h. After this time, the solvents were removed under reduced pressure, and the resulting residue was partitioned between water (10 mL) and methylene chloride (20 mL). The layers were separated, and the aqueous phase was extracted with methylene chloride (2×10 mL). The organic extracts were combined and dried over sodium sulfate, filtered and concentrated under reduced pressure. The resulting residue was purified by flash chromatography to afford 27 in 45% yield (235 mg) as a white solid: mp 88-89° C.; $^1$H NMR (500 MHz, CDCl$_3$) δ 8.73 (d, J=8.5 Hz), 7.87 (s, 1H), 7.62 (s, 1H), 7.56 (t, 1H, J=6.5 Hz), 7.14 (dd, 1H, J=11.0, 8.5 Hz), 3.11 (s, 2H) 1.38 (s, 12H), 1.33 (s, 6H); MS (APCI+) m/z 430.3 (M+H).

N-(2-Fluoro-5-(4,4,5,5-tetramethyl-1,3,2-dioxaborolan-2-yl)phenyl)-4-hydroxy-5,5-dimethyl-5,6-dihydro-4H-cyclopenta[b]thiophene-2-carboxamide (28)

A 100-mL single-neck round-bottomed flask equipped with a magnetic stirrer was charged with 27 (800 mg, 1.86 mmol) and ethanol (5.0 mL). Sodium borohydride (69 mg, 11.82 mmol) was added in one portion. The mixture was stirred at room temperature for 1 h and then neutralized with acetic acid to pH 7. The reaction was concentrated under reduced pressure and triturated with ethyl acetate (10 mL) to give a quantitative yield of 28 as a white semi-solid: $^1$H NMR (500 MHz, CDCl$_3$) δ 8.75 (d, 1H, J=8.5 Hz), 7.78 (s, 1H). 7.53 (m, 2H), 7.10 (m, 1H), 4.58 (s, 1H), 2.88 (d, 1H, J=16.0

Hz), 2.69 (d, 1H, J=16.0 Hz), 1.32 (s, 12H), 1.20 (d, 6H, J=6.5 Hz); MS (APCI+) m/z 431.4 (M+H).

N-(5-(5-(5-(Azetidin-1-ylmethyl)-1-methyl-1H-pyrazol-3-ylamino)-1-methyl-6-oxo-1,6-dihydropyridazin-3-yl)-2-fluorophenyl-4-hydroxy-5,5-dimethyl-5,6-dihydro-4H-cyclopenta[b]thiophene-2-carboxamide (29)

Using the same general procedure as described for the preparation of title compound in Example 2, reaction of 26 (250 mg, 0.809 mmol) with 28 (350 mg, 0.811 mmol) gave a 35% yield (165 mg) of 29 as an off-white solid: mp 110-111° C.; $^1$H NMR (500 MHz, DMSO-$d_6$) δ 10.13 (s, 1H), 9.21 (s, 1H), 8.26 (s, 1H), 8.08 (d, 1H, J=6.5 Hz), 7.90 (s, 1H), 7.53 (s, 1H), 7.42 (t, 1H, J=6.5 Hz), 6.10 (s, 1H), 5.17 (d, 1H, J=6.5 Hz), 4.43 (d, 1H, J=6.5 Hz), 3.77 (d, 6H, J=6.0 Hz), 3.15 (s, 4H), 2.79 (d, 1H, J=16.5 Hz), 2.64 (d, 1H, J=16.5 Hz), 2.07 (s, 2H), 1.98 (m, 2H), 1.13 (s, 3H), 1.08 (s, 3H); MS (APCI+) m/z 578.2 (M+H).

EXAMPLE 12

5-tert-Butyl-N-(2-fluoro-5-(6-oxa-5-(6-(pyridin-4-yl)pyridazin-3-ylamino)-1,6-dihydropyridazin-3-yl)phenyl)pyrazine-2-carboxamide (6g)

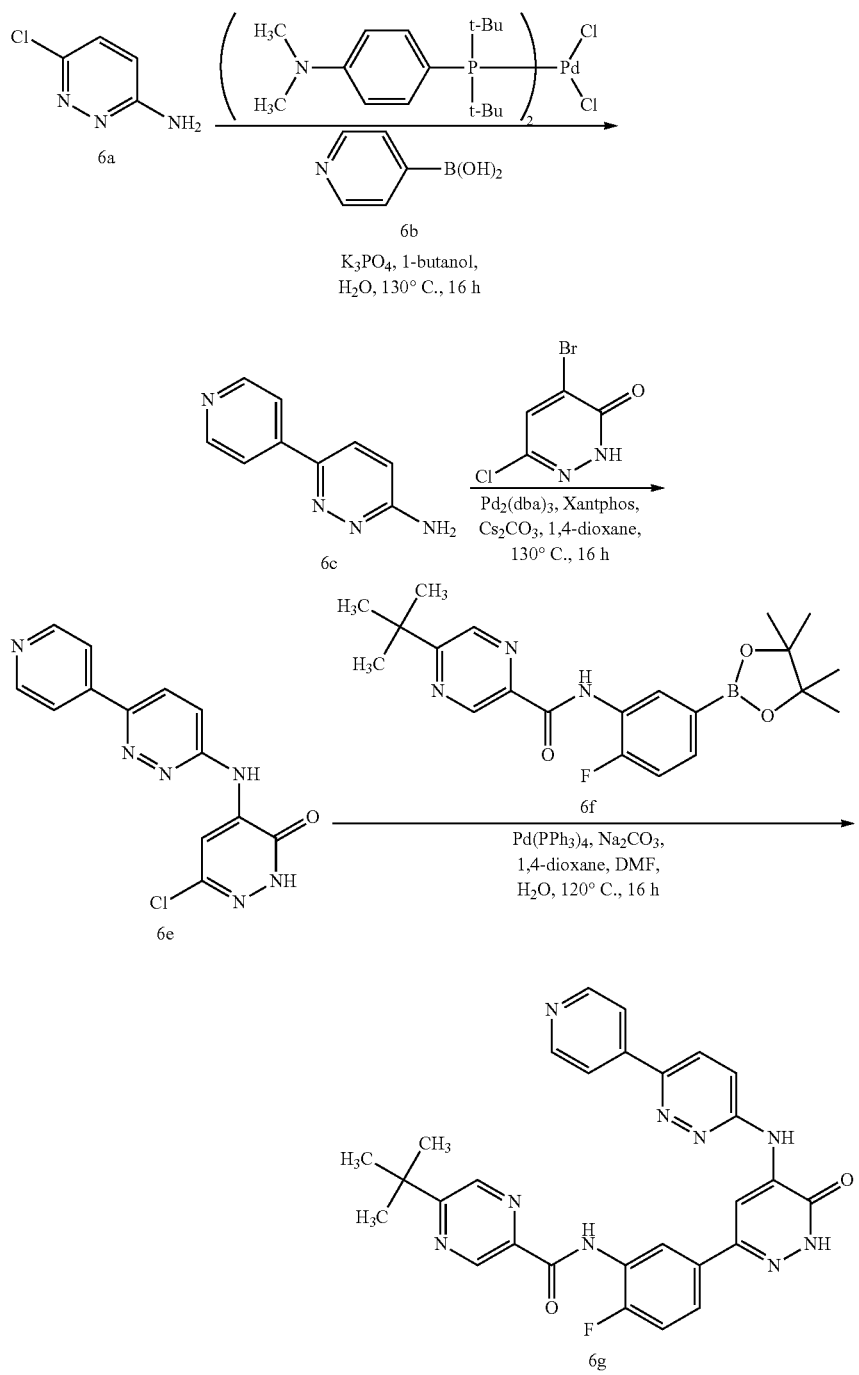

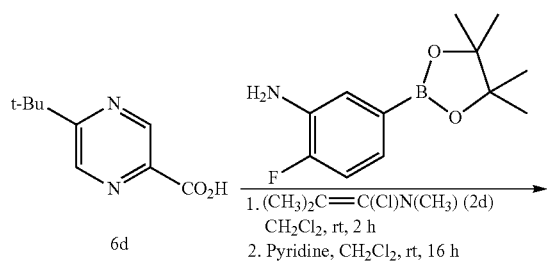 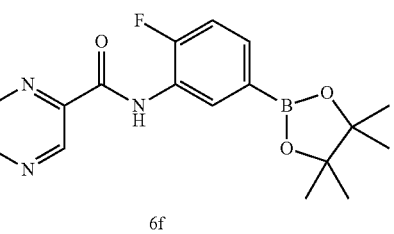

6-(Pyridin-4-yl)pyridazin-3-amine (6c)

A 15-mL pressure tube equipped with a magnetic stirrer and screw cap with a septum was charged with 6a (400 mg, 3.09 mmol), 6b (570 mg, 4.63 mmol), potassium phosphate (692 mg, 6.18 mmol), water (1.5 mL), and 1-butanol (6 mL). After bubbling nitrogen through the resulting suspension for 30 mm, bis(di-tert-butyl(4-dimethylaminophenyl)phosphine)dichloropalladium(II) (547 mg, 0.77 mmol) was added. The tube was sealed, and the reaction mixture was heated for 16 h in a 130° C. bath. After this time, the mixture was cooled to room temperature and diluted with ethyl acetate (100 mL) and water (10 mL). The organic layer was separated and concentrated under reduced pressure. The residue was purified by column chromatography on silica to afford a 42% yield (223 mg) of 6c as an off-white solid: mp 199-201° C.; $^1$H NMR (300 MHz, DMSO-$d_6$) δ 8.64 (d, 2H, J=4.5 Hz), 7.95 (m, 3H), 6.88 (d, 1H, J=9.3 Hz), 6.76 (br s, 2H); MS (ESI+) m/z 173.1 (M+H).

6-Chloro-4-(6-(pyridin-4-yl)pyridazin-3-ylamino)pyridazin-3(2H)-one (6e)

A 25-mL three-neck round-bottomed flask equipped with a reflux condenser, magnetic stirrer and nitrogen inlet was charged with 6c (170 mg, 0.98 mmol), 4-bromo-6-chloropyridazin-3(2H)-one (411 mg, 1.97 mmol), cesium carbonate (956 mg, 8.61 mmol), and 1,4-dioxane (7 mL). After bubbling nitrogen through the resulting suspension for 30 min, Xantphos (48 mg, 0.08 mmol) and tris(dibenzylideneacetone)dipalladium(0) (45 mg, 0.05 mmol) were added, and the reaction mixture was heated for 16 h in a 130° C. bath. After this time, the mixture was cooled to room temperature and concentrated under reduced pressure. The residue was purified by column chromatography on silica to afford a 41% yield (121 mg) of 6e as an off-white solid: mp 263-265° C.; $^1$H NMR (300 MHz, DMSO-$d_6$) δ 13.29 (s, 1H), 1.0.10 (s, 1H), 8.75 (dd, 2H, J=4.8, 1.8 Hz), 8.52 (s, 1H), 8.35 (d, 1H, J=9.3 Hz), 8.11 (dd, 2H, J=4.5, 1.5 Hz), 8.01 (d, 1H, J=9.3 Hz); MS (ESI+) 301.1 (M+H).

5-tert-Butyl-N-(2-fluoro-5-(4,4,5,5-tetramethyl-1,3,2-dioxaborolan-2-yl)phenyl)pyrazine-2-carboxamide (6f)

A 100-mL single-neck round-bottomed flask equipped with a magnetic stirrer was purged with nitrogen and charged with 6d (2.00 g, 11.1 mmol) and methylene chloride (20 mL). The solution was cooled to 0° C., and 2d (1.48 g, 11.1 mmol) was added dropwise. After this addition was complete, the reaction was warmed to room temperature and stirred for 2 h. 2-(4-Fluoro-3-nitrophenyl)-4,4,5,5-tetramethyl-1,3,2-dioxaborolane (2.63 g, 11.1 mmol) was then added. After this addition, the reaction was cooled to 0° C., and anhydrous pyridine (2.63 g, 33.3 mmol) was added. The cooling bath was removed, and the reaction mixture was stirred at room temperature for 16 h. After this time, the solvents were removed under reduced pressure, and the resulting residue was partitioned between water (100 mL) and methylene chloride (200 mL). The layers were separated, and the aqueous phase was extracted with methylene chloride (2×200 mL). The organic extracts were combined and dried over sodium sulfate, filtered and concentrated under reduced pressure. The resulting residue was purified by flash chromatography to afford 6f in 85% yield (3.80 g) as a white solid: mp 156-157° C.; $^1$H NMR (500 MHz, CDCl$_3$) δ 9.91 (s, 1H), 9.40 (s, 1H), 8.92 (d, 1H, J=8.5 Hz), 8.67 (s, 1H), 7.57 (t, 1H, J=7.0 Hz), 7.14 (dd, 1H, J=11.0, 8.5 Hz), 1.46 (s, 9H), 1.34 (s, 12H); MS (ESI+) m/z 400.2 (M+H).

5-tert-Butyl-N-(2-fluoro-5-(6-oxo-5-(6-(pyridin-4-yl)pyridazin-3-ylamino)-1,6-dihydropyridazin-3-yl)phenyl)pyrazine-2-carboxamide (6g)

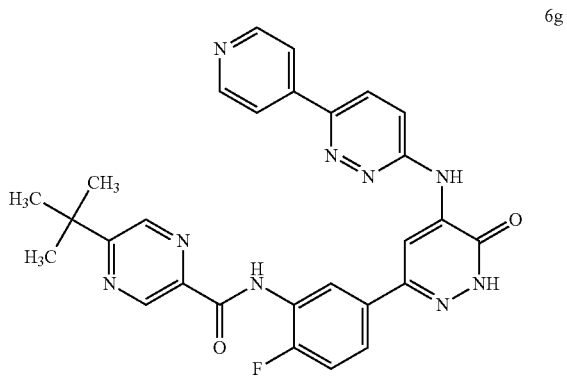 [SMILES: CC(C)(C)c1cnc(C(=O)Nc2cc(-c3cc(Nc4ccc(-c5ccncc5)nn4)c(=O)[nH]n3)ccc2F)cn1]

A 15-mL pressure tube equipped with a magnetic stirrer and screw cap with a septum was charged with 6e (90 rug, 0.30 mmol), 6f (156 mg, 0.39 mmol), sodium carbonate (95 mg, 0.90 mmol), water (0.5 mL), 1,4-dioxane (1.8 mL), and DMF (0.9 mL). After bubbling nitrogen through the resulting suspension for 30 min, tetrakis(triphenylphosphine)palladium(0) (35 mg, 0.03 mmol) was added; the tube was sealed, and the reaction mixture was heated for 16 h in a 120° C. bath. After this time, the mixture was cooled to room temperature and diluted with ethyl acetate (50 mL) and water (5 mL). The organic layer was separated and concentrated under reduced pressure. The residue was purified by column chromatography on silica to afford a 49% yield (79 mg) of 6g as an off-white solid: mp>300° C.; $^1$H NMR (500 MHz, DMSO-$d_6$) δ 13.40 (s, 1H), 10.45 (s, 1H), 9.93 (s, 1H), 9.25 (s, 1H), 9.04 (s, 1H), 8.95 (s, 1H), 8.74 (d, 2H, J=3.3 Hz), 8.54 (d, 1H, J=4.2 Hz), 8.33 (d, 1H, J=5.7 Hz), 8.10 (d, 2H, J=3.0 Hz), 8.02 (d, 1H, J=5.4 Hz), 7.69 (m, 1H), 7.53 (m, 1H), 1.43 (s, 9H); MS (ESI+) m/z 538.2 (M+H).

EXAMPLE 13

5-tert-Butyl-N-(2-fluoro-5-(6-oxo-5-(piperidin-3-ylamino)-1,6-dihydropyridazin-3-yl)phenyl)pyrazine-2-carboxamide (10e)

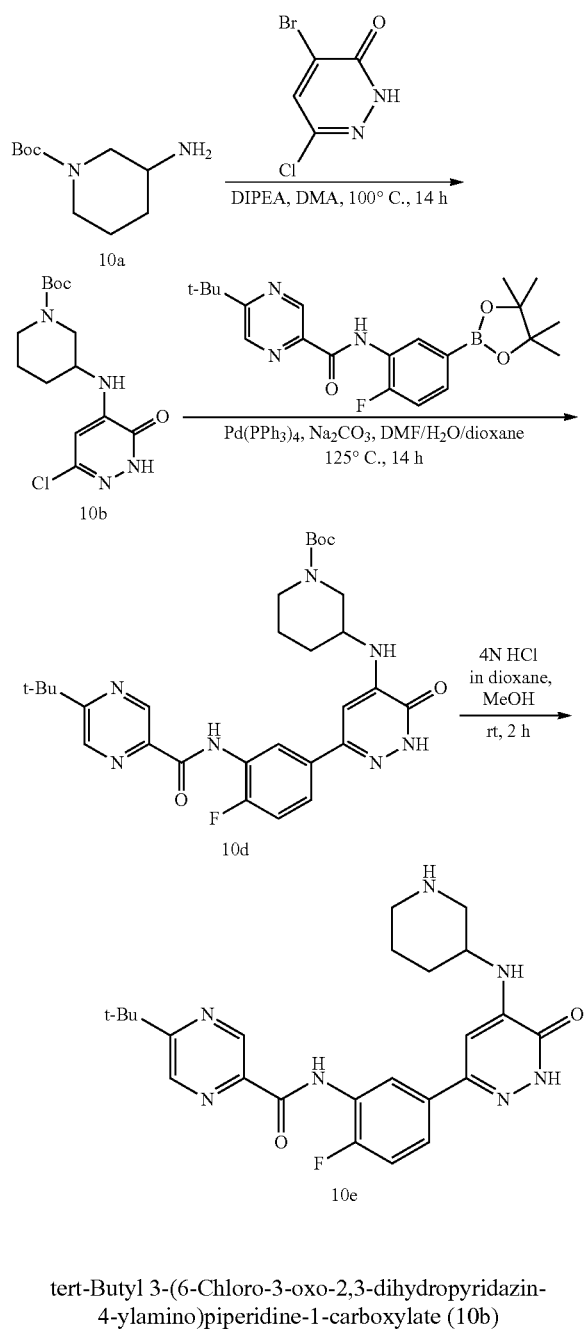

tert-Butyl 3-(6-Chloro-3-oxo-2,3-dihydropyridazin-4-ylamino)piperidine-1-carboxylate (10b)

In a 100-mL single-neck round-bottomed flask equipped with a magnetic stirrer and reflux condenser, 10a (500 mg, 2.49 mmol), 4-bromo-6-chloropyridazin-3(2H)-one (521 mg, 2.49 mmol) and N,N-diisopropylethylamine (350 mg, 2.73 mmol) were mixed With N,N-dimethylacetamide (3 mL), and this mixture was heated at 100° C. (bath temperature) for 14 h under nitrogen. The reaction mixture was diluted with ethyl acetate (200 mL), washed with water (100 mL) and brine (100 ml) and dried over sodium sulfate. The drying agent was removed by filtration, and the filtrate was evaporated under reduced pressure. The resulting residue was purified on a silica gel column eluting the desired product with 30% ethyl acetate in hexanes to afford a 63% yield (520 mg) of Mb as a yellowish solid: mp 195-196° C., $^1$H NMR (500 MHz, DMSO-$d_6$) δ 12.63 (s, 1H), 6.89 (d, 1H, J=6.5 Hz), 6.47 (s, 1H), 4.10 (d, 1H, J=11.5 Hz), 4.00 (d, 1H, J=10.5 Hz), 3.40 (s, 1H), 2.92 (t, 1H, J=10.5 Hz), 2.85 (t, J=10.5 Hz), 1.81 (d, 1H, 0.7=10.0 Hz), 1.72 (m, 1H), 1.39 (m, 11H); MS (APCI+) m/z 329.5 (M+H)

tert-Butyl 3-(6-(3-(5-tert-Butylpyrazine-2-carboxamido)-4-fluorophenyl)-3-oxo-2,3-dihydropyridazin-4-ylamino)piperidine-1-carboxylate (10d)

In a 100-mL single-neck round-bottomed flask equipped with a magnetic stirrer and reflux condenser, 10b (500 mg, 1.52 mmol), 5-tert-Butyl-N-(2-fluoro-5-(4,4,5,5-tetramethyl-1,3,2-dioxaborolan-2-yl)phenyl)pyrazine-2-carboxamide (600 mg, 1.50 mmol) and sodium carbonate (320 mg, 3.01 mmol) were mixed with DMF (8 mL), dioxane (5 mL) and water (2 mL). This mixture was degassed with nitrogen for 30 min. Tetrakis(triphenylphosphine)palladium (175 mg, 0.151 mmol) was added and the mixture was refluxed at 125° C. (bath temperature) for 14 h. The reaction mixture was then cooled to room temperature, and water (100 mL) was added. The resulting precipitate was filtered, and the filter cake was washed with water (250 mL). The filter cake was purified using a silica gel column eluting the desired product with 4-6% methanol in methylene chloride to afford a 36% yield (310 mg) of 10d as a off-white solid: mp 120-121° C.; $^1$H NMR (500 MHz, CDCl$_3$) δ 10.13 (s, 1H), 10.02 (s, 1H), 9.39 (s, 1H), 8.99 (d, 1H, J=7.5 Hz), 8.68 (s, 1H), 7.56 (br s, 1H), 7.22 (m, 1H), 6.88 (s, 1H), 5.15 (s, 1H), 3.85 (s, 1H), 3.64 (m, 1H), 3.50 (m, 3H), 1.92-1.82 (m, 3H, 1.71 (m, 1H), 1.42 (br s, 18H); MS (APCI+) m/z 566.9 (M+H).

5-tert-Butyl-N-(2-fluoro-5-(6-oxo-5-(piperidin-3-ylamino)-1,6-dihydropyridazin-3-yl)phenyl)pyrazine-2-carboxamide (10e)

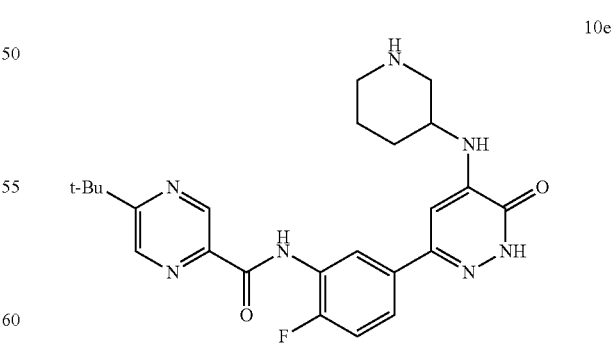

In a 100-mL single-neck round-bottomed flask equipped with a magnetic stirrer 10d (300 mg, 0.530 mmol) was dissolved in methanol (3.0 mL). To this solution 4M hydrogen chloride in dioxane (3 mL) was added, and this mixture was stirred at room temperature for 2 h under nitrogen. The reaction mixture was then concentrated under reduced pressure, and the resulting residue was partitioned between ethyl acetate (20 mL) and water (20 mL). The mixture was neutralized with saturated potassium carbonate to pH 6.5 (pH meter). The aqueous layer was separated and extracted with ethyl acetate (2×50 mL), The combined organic layers were washed with brine (100 mL) and dried over sodium sulfate. The drying agent was removed by filtration and the filtrate was evaporated under reduced pressure. The resulting residue was purified on a silica gel column eluting the desired product with 16% methanol in methylene chloride to afford a 65% yield (161 mg) of 10e as a off-white solid: mp 140-141° C.; $^1$H NMR (500 MHz, DMSO d$_6$) δ 12.79 (s, 1H), 10.37 (s, 1H), 9.23 (s, 1H), 8.92 (s, 1H), 8.48 (d, 1H, J=7.5 Hz), 7.75 (m, 1H), 7.40 (m, 1H), 6.91 (s, 1H), 4.19 (d, 1H, J=9.5 Hz), 4.03 (d, 1H, J=13.0 Hz), 2.99-2.82 (m, 4H), 1.93 (m, 1H), 1.75 (m, 1H), 1.58 (m, 1H), 1.42 (s, 9H), 1.29 (m, 1H); MS (APCI−) m/z 464.6 (M−H).

EXAMPLE 14

N-(2-Fluoro-5-(6-oxo-5-(5-(2-oxopiperazin-1-yl)pyridin-2-ylamino)-1,6-dihydropyridazin-3-yl)phenyl)-4,5,6,7-tetrahydrobenzo[b]thiophene-2-carboxamide (21)

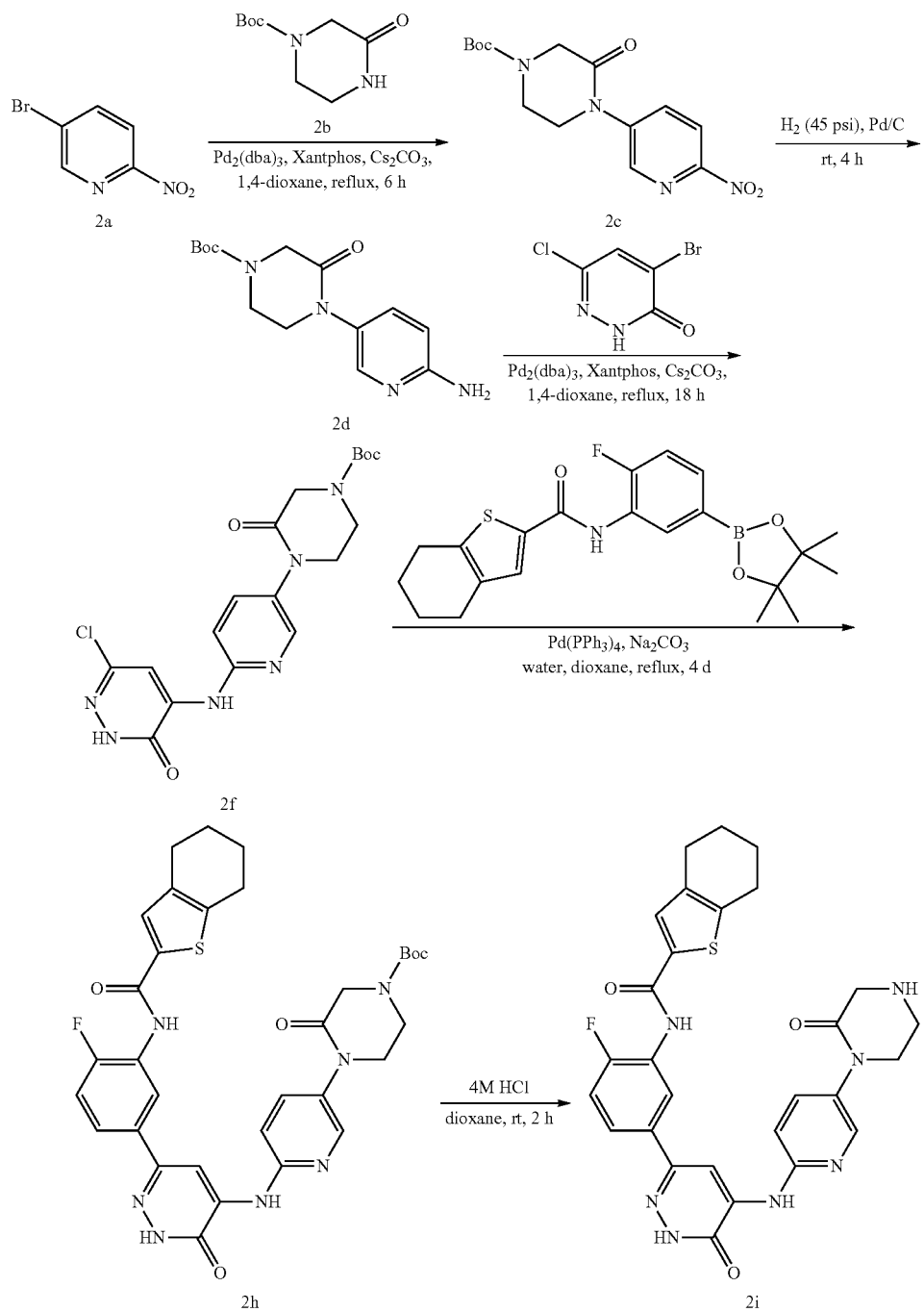

tert-Butyl 4-(6-Nitropyridin-3-yl)-3-oxopiperazine-1-carboxylate (2c)

A 250-mL single-neck round-bottomed flask equipped with a magnetic stirrer and reflux condenser was charged with 2a (1.00 g, 5.00 mmol), 2b (1.01 g, 5.00 mmol), cesium carbonate (3.58 g, 11.0 mmol) and 1,4-dioxane (40 mL). After bubbling nitrogen through the resulting solution for 30 min, Xantphos (246 ing, 0.425 mmol) and tris(dibenzylideneacetone)dipalladium(0) (230 mg, 0.250 mmol) were added, and the reaction mixture was heated at reflux for 6 h. Water (30 mL) and ethyl acetate (150 mL) were added after the reaction mixture was cooled to room temperature. The resulting mixture was filtered through a bed of Celite 521. The organic layer of the filtrate was separated and the aqueous layer was extracted with ethyl acetate (2×50 mL). The combined organic layers were washed with brine (30 mL), dried over sodium sulfate and purified by column chromatography to afford a 96% yield (1.55 g) of 2c as an amber oil: $^1$H NMR (300 MHz, CDCl$_3$) δ 8.67 (d, 1H, J=2.4 Hz), 8.32 (d, 1H, J=8.7 Hz), 8.15 (dd, 1H, J=8.7, 2.4 Hz), 4.33 (s, 1H), 3.89 (m, 4H), 1.48 (s, 9H); MS (ESI+) m/z 323.1 (M+H).

tert-Butyl 4-(6-aminopyridin-3-yl)-3-oxopiperazine-1-carboxylate (2d)

A 250-mL Parr reactor bottle was purged with nitrogen and charged with 10% palladium on carbon (50% wet, 100 mg dry weight) and a solution of 2c (500 mg, 1.55 mmol) in ethanol (20 mL). The bottle was attached to Parr hydrogenator, evacuated, charged with hydrogen gas to a pressure of 45 psi and shaken for 4 h. After this time, the hydrogen was evacuated, and nitrogen was charged into the bottle. Celite 521 (1.0 g) was added, and the mixture was filtered through a pad of Celite 521. The filter cake was washed with ethanol (2×30 mL), and the filtrate was concentrated under reduced pressure to afford a 95% yield of 2d (430 mg) as an amber film: $^1$H NMR (500 MHz, CDCl$_3$) δ 7.98 (d, 1H, J=2.5 Hz), 7.38 (dd, 1H, J=8.5, 2.01 Hz), 6.52 (d, 1H, J=8.5 Hz), 4.54 (s, 1H), 4.26 (s, 2H), 3.78 (t, 2H, J=5.5 Hz), 3.67 (t, 2H, J=5.0 Hz), 1.50 (s, 9H); MS (ESI+) m/z 293.1 (M+H).

tert-Butyl 4-(6-(6-Chloro-3-oxo-2,3-dihydropyridazin-4-ylamino)pyridin-3-yl)-3-oxopiperazine-1-carboxylate (2f)

A 100-mL single-neck round-bottomed flask equipped with a magnetic stirrer and reflux condenser was charged with 2d (558 mg, 1.91 mmol), 4-bromo-6-chloropyridazin-3(2H)-one (400 mg, 1.91 mmol), cesium carbonate (1.37 g, 4.20 mmol), dioxane (25 mL) and DMF (25 mL). After bubbling nitrogen through the resulting solution for 30 min, Xantphos (94 mg, 0.162 mmol) and tris(dibenzylidene acetone)dipalladium(0) (87 mg, 0.096 mmol) were added and the reaction mixture was heated at 125° C. for 18 h. Water (75 mL) was added after the reaction mixture was cooled to room temperature and the pH adjusted to 6.5 with 2N hydrochloric acid. The resulting precipitate was collected by vacuum filtration, absorbed on silica gel and purified by column chromatography to afford a 37% yield (300 mg) of 2f as a tan foam: $^1$H NMR (300 MHz, DMSO-d$_6$) δ13.15 (s, 1H), 9.71 (s, 1H), 8.37 (4, 1H, J=2.7 Hz), 8.29 (s, 1H), 7.76 (dd, 1H, J=9.0, 2.7 Hz), 7.55 (d, 1H, J=9.0 Hz), 4.09 (s, 2H), 3.72 (m, 4H), 1.45 (s, 9H); MS (ESI+) m/z 420.1 (M+H).

tert-Butyl 4-(6-(6-(4-Fluoro-3-(4,5,6,7-tetrahydrobenzo[b]thiophene-2-carboxamido)phenyl)-3-oxo-2,3-dihydropyridazin-4-ylamino)pyridin-3-yl)-3-oxopiperazine-1-carboxylate (2h)

In a 50-mL round-bottomed flask equipped with a magnetic stirrer and reflux condenser, 2f (240 mg, 0.570 mmol), N-(2-fluoro-5-(4,4,5,5-tetramethyl-1,3,2-dioxaborolan-2-yl)phenyl)-4,5,6,7-tetrahydrobenzo[b]thiophene-2-carboxamide (251 mg, 0.630 mmol) and sodium carbonate (181 mg, 1.71 mmol) were mixed with DMF (16.0 mL) and water (3.0 mL). This mixture was degassed with nitrogen for 30 min. Tetrakis(triphenylphosphine)palladium (66 mg, 0.057 mmol) was added and the mixture was stirred at 100° C. (bath temperature) for 4 d. The reaction mixture was then cooled to room temperature, and water (50 mL) was added. The pH was adjusted to 6.5 with 2N hydrochloric acid and the resulting precipitate was filtered, and the filter cake was washed with ater (25 mL) and purified by column chromatography to afford a 27% yield of 2h (100 mg) as a tan foam: $^1$H NMR (300 MHz, DMSO-d$_6$) δ 13.23 (s, 1H), 10.09 (s, 1H), 9.54 (s, 1H), 8.84 (s, 1H), 8.38 (4, 1H, J=2.7 Hz), 8.03 (dd, 1H, J=7.5, 2.1 Hz), 7.75 (d, 1H, J=2.7 Hz), 7.72 (s, 1H), 7.66 (m, 1H), 7.54 (d, 1H, J=9.0 Hz), 7.41 (t, 1H, 3=10.2 Hz), 4.09 (s, 2H), 3.70 (m, 4H), 2.77 (t, 2H, J=5.5 Hz), 2.62 (t, 2H, J=5.0 Hz), 1.79 (m, 4H), 1.45 (s, 9H); MS (ESI+) m/z 659.9 (M+H).

N-(2-Fluoro-5-(6-oxo-5-(5-(2-oxopiperazin-1-yl)pyridin-2-ylamino)-1,6-dihydro pyridazin-3-yl)phenyl)-4,5,6,7-tetrahydrobenzo[b]thiophene-2-carboxamide (2i)

A 10-mL single-neck round bottomed flask equipped with a magnetic stirrer was purged with nitrogen and charged with 2h (75 mg, 0.129 mmol), methanol (2 mL) and 4 M HCl in dioxane (2 mL) and the mixture stirred for 2 h. After this time, ethyl acetate (20 mL) and water (20 mL) were added. The pH was adjusted to 6.5 with aqueous 10% potassium carbonate. The aqueous layer was separated and extracted with ethyl acetate (2×25 mL). The combined organic layers were washed with brine (20 mL) and dried over sodium sulfate. The drying agent was removed by filtration. The filtrate was concentrated under reduced pressure to a residue which was purified by column chromatography to afford a 56% yield of 21 (40 mg) as a white solid: mp 285-287° C.; $^1$H NMR (500 MHz, DMSO-d$_6$) δ13.21 (s, 1H), 10.07 (s, 1H), 9.50 (s, 1H), 8.36 (d, 1H, J=2.5 Hz), 8.04 (dd, 1H, J=7.5, 2.0 Hz), 7.71 (s, 1H), 7.70 (m, 1H), 7.65 (m, 1H), 7.53 (d, 1H, =9.0 Hz), 7.41 (t, 1H, J=9.0 Hz), 3.63 (t, 2H, J=5.5 Hz), 3.42 (s, 2H), 3.04 (t, 2H, J=5.0 Hz), 2.78 (t, 2H, J=5.0 Hz), 2.62 (t, 2H, J=5.5 Hz), 1.78 (m, 4H); MS (ESI+) m/z 560.0 (M+H).

EXAMPLE 15

(R)-4-tert-butyl-N-(1-(5-(1,5-dimethyl-1H-pyrazol-3-ylamino)-1-methyl-6-oxo-1,6-dihydropyridazin-3-yl)piperidin-3-yl)benzamide

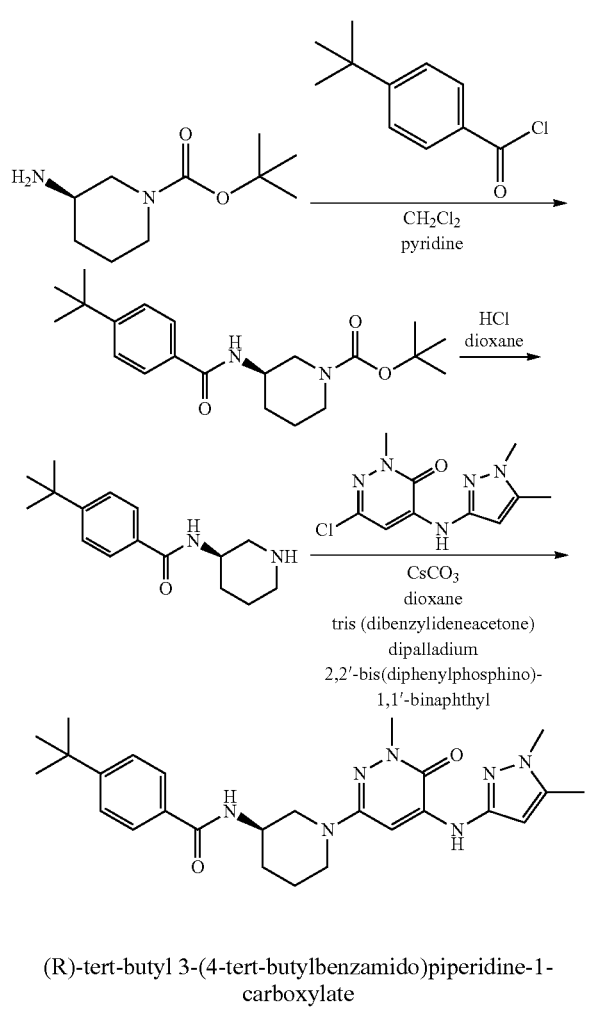

(R)-tert-butyl 3-(4-tert-butylbenzamido)piperidine-1-carboxylate

A 500 mL round bottom flask equipped with a magnetic stirrer was charged with (R)-tert-butyl 3-aminopiperidine-1-carboxylate (1.0 g, 5 mmol), dichloromethane, added pyridine (5 mL), and 4-tert-butylbenzoyl chloride (0.98 g, 5 mmol) and the mixture is let stir for 2 h. The mixture is diluted with 500 mL of dichloromethane and washed with 1N HCl (3×200 mL), NaHCO$_3$ (sat) (1×100 mL), dried over sodium sulfate, and concentrated under reduced pressure. The resulting residue was purified by flash chromatography to afford (R)-tert-butyl 3-(4-tert-butylbenzamido) piperidine-1-carboxylate as a waxy yellow solid in 90% yield (1.62 g, 4.5 mmol).

(R)-4-tert-butyl-N-(piperidin-3-yl)benzamide

A 500 mL round bottom flask equipped with a reflux condenser, and magnetic stirrer was charged with (R)-tert-butyl 3-(4-tert-butylbenzamido) piperidine-1-carboxylate (1.62 g, 4.5 mmol), dioxane (100 mL) and HCl (4N, 25 mL). The mixture was heated to reflux for 3 h cooled to rt, and diluted with ethyl acetate (400 mL). NaHCO$_3$ (sat.) (500 mL) was slowly added with stirring, and the organic layer is dried over sodium sulfate, concentrated under reduced pressure and the resulting residue was purified by flash chromatography to afford an 85% yield of (R)-4-tert-butyl-N-(piperidin-3-yl) benzamide as a white solid (0.99 g, 3.8 mmol)

(R)-4-tert-butyl-N-(1-(5-(1,5-dimethyl-1,1-pyrazol-3-ylamino)-1-methyl-6-oxo-1,6-dihydropyridazin-3-yl)piperidin-3-yl)benzamide A 100-mL pressure flask is equipped with a magnetic stirrer was charged with tert-butyl-N-(piperidin-3-yl)benzamide (130 mg, 0.5 mmol), dioxane (10 mL), 6-chloro-4(1,5-dimethyl-1H-pyrazol-3-ylamino)-2-methylpyridazin-3(2H)-one (127 mg, 0.5 mmol), and cesium carbonate (326 mg, 1 mmol). Argon is bubbled through the solution whilst sonicating for 15 min. Tris(dibenzylideneacetone)dipalladium (0) (46 mg, 0.05 mmol), 2,2'-bis(diphenylphosphino)-1,1'-binaphthyl (66 mg, 0.1 mmol) were then added, the flask was sealed and heated to 120° C. for 8 h. The resulting mixture was diluted with dichloromethane (300 mL) and washed with water (120 mL) filtered through a pad of celite, concentrated and purified by flash chromatography on silica gel to afford a 65% yield of (R)-4-tert-butyl-N-(1-(5-(1,5-dimethyl-1H-pyrazol-3-ylamino)-1-methyl-6-oxo-1,6-dihydropyridazin-3-yl)piperidin-3-yl)benzamide as a white solid (155 mg, 0.325 mmol).

EXAMPLE 16

The following compounds were prepared following procedures similar to those described in Examples 1-2 and 11-15.

| Structure | Name | MW calcd | MH+ m/z obs |
|---|---|---|---|
| 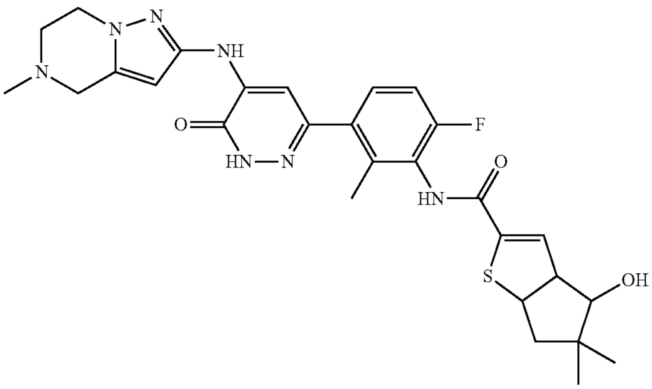 | N-{6-fluoro-2-methyl-3-[5-({5-methyl-4H,5H,6H,7H-pyrazolo[1,5-a]pyrazin-2-yl}amino)-6-oxo-1,6-dihydropyridazin-3-yl]phenyl}-4-hydroxy-5,5-dimethyl-4H,5H,6H-cyclopenta[b]thiophene-2-carboxamide | 563 | 564.2 |
| 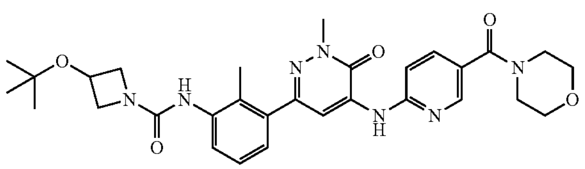 [SMILES: Cc1c(NC(=O)N2CC(OC(C)(C)C)C2)cccc1-c1cc(Nc2ccc(C(=O)N3CCOCC3)cn2)c(=O)n(C)n1] | 3-(tert-butoxy)-N-[2-methyl-3-(1-methyl-5-{[5-(morpholin-4-ylcarbonyl)pyridin-2-yl]amino}-6-oxo-1,6-dihydropyridazin-3-yl)phenyl]azetidine-1-carboxamide | 575 | 576.2 |
| | 4-tert-butyl-N-{5-[5-({5-[(S)-(dimethylcarbamoyl)(hydroxy)methyl]pyridin-2-yl}amino)-1-methyl-6-oxo-1,6-dihydropyridazin-3-yl]-2-fluorophenyl)benzamide | 572 | 573.3 |
| 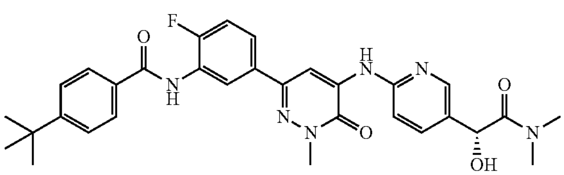 [SMILES: CN(C)C(=O)[C@H](O)c1ccc(Nc2cc(-c3ccc(F)c(NC(=O)c4ccc(C(C)(C)C)cc4)c3)nn(C)c2=O)nc1] | 4-tert-butyl-N-{5-[5-({5-[(R)-(dimethylcarbamoyl)(hydroxy)methyl]pyridin-2-yl}amino)-1-methyl-6-oxo-1,6-dihydropyridazin-3-yl]-2-fluorophenyl)benzamide | 572 | 573.3 |
| 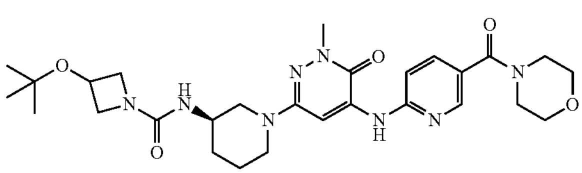 [SMILES: Cn1nc(N2CCC[C@@H](NC(=O)N3CC(OC(C)(C)C)C3)C2)cc(Nc2ccc(C(=O)N3CCOCC3)cn2)c1=O] | 3-(tert-butoxy)-N-[(3R)-1-(1-rnethyl-5-{[5-(morpholin-4-ylcarbonyl)pyridin-2-yl]amino}-6-oxo-1,6-dihydropyridazin-3-yl)piperidin-3-yl]azetidine-1-carboxamide | 568 | 569.2 |
| 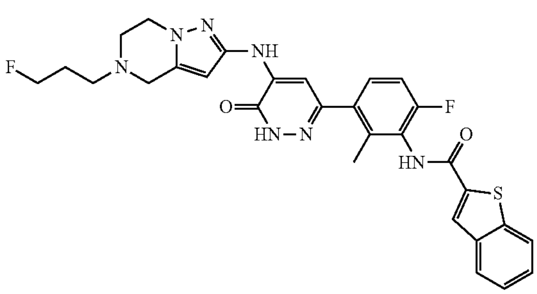 [SMILES: Cc1c(-c2cc(Nc3cc4n(n3)CCN(CCCF)C4)c(=O)[nH]n2)ccc(F)c1NC(=O)c1cc2ccccc2s1] | N-[6-fluoro-3-(5-{[5-(3-fluoropropyl)-4H,5H,6H,7H-pyrazolo[1,5-a]pyrazin-2-yl]amino}-6-oxo-1,6-dihydropyridazin-3-yl)-2-methylphenyl]-1-benzothiophene-2-carboxamide. | 575 | 576.2 |

-continued

| Structure | Name | MW calcd | MH+ m/z obs |
|---|---|---|---|
| | N-(3-methyl-6-[5-({5-methyl-4H,5H,6H,7H-pyrazolo[1,5-a]pyrazin-2-yl}amino)-6-oxo-1,6-dihydropyridazin-3-yl]pyridin-2-yl}-1-benzothiophene-2-carboxamide | 512 | 513.3 |
| 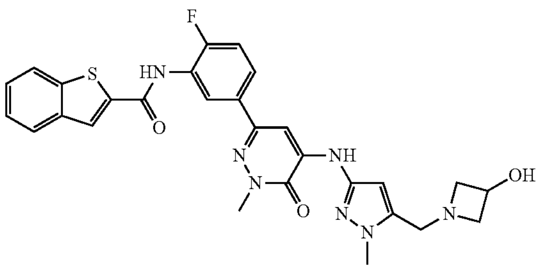 [SMILES: Cn1nc(Nc2cc(-c3ccc(F)c(NC(=O)c4cc5ccccc5s4)c3)nn(C)c2=O)cc1CN1CC(O)C1] | N-{2-fluoro-5-[5-({5-[(3-hydroxyazetidin-1-yl)methyl]-1-methyl-1H-pyrazol-3-yl)amino)-1-methyl-6-oxo-1,6-dihydropyridazin-3-yl]phenyl}-1-benzothiophene-2-carboxamide | 559 | 560.1 |
| 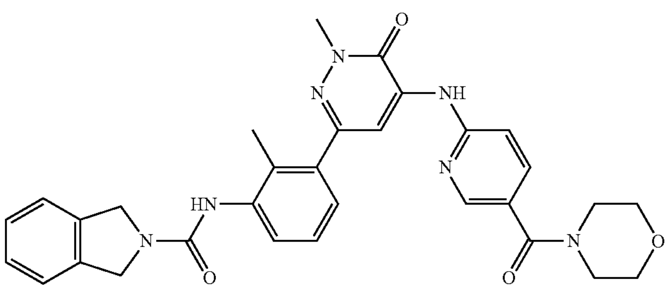 [SMILES: Cc1c(NC(=O)N2Cc3ccccc3C2)cccc1-c1cc(Nc2ccc(C(=O)N3CCOCC3)cn2)c(=O)n(C)n1] | N-[2-methyl-3-(1-methyl-5-{[5-(morpholin-4-ylcarbonyl)pyridin-2-yl]amino}-6-oxo-1,6-dihydropyridazin-3-yl)phenyl]-2,3-dihydro-1H-isoindole-2-carboxamide | 565 | 566.2 |
| 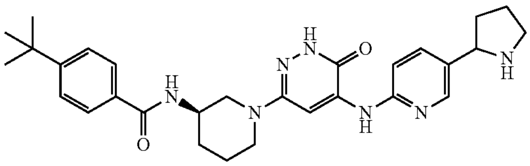 [SMILES: CC(C)(C)c1ccc(C(=O)N[C@@H]2CCCN(c3cc(Nc4ccc(C5CCCN5)cn4)c(=O)[nH]n3)C2)cc1] | 4-tert-butyl-N-[(3R)-1-(6-oxo-5-{[5-(pyrrolidin-2-yl)pyridin-2-yl]amino}-1,6-dihydropyridazin-3-yl)piperidin-3-yl]benzamide | 515 | 516.4 |
| 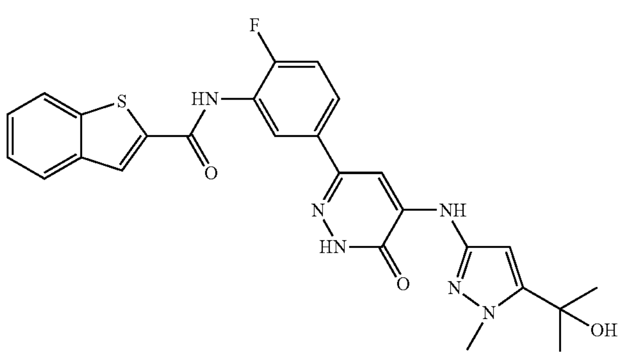 [SMILES: Cn1nc(Nc2cc(-c3ccc(F)c(NC(=O)c4cc5ccccc5s4)c3)n[nH]c2=O)cc1C(C)(C)O] | N-[2-fluoro-5-(5-{[5-(2-hydroxypropan-2-yl)-1-methyl-1H-pyrazol-3-yl]amino}-6-oxo-1,6-dihydropyridazin-3-yl)phenyl]-1-benzothiophene-2-carboxamide | 518 | 519 |

| Structure | Name | MW calcd | MH+ m/z obs |
|---|---|---|---|
| | N-[2-fluoro-3-(5-{[5-(3-hydroxyazetidin-1-yl)pyridin-2-yl]amino}-1-methyl-6-oxo-1,6-dihydropyridazin-3-yl)-6-methylphenyl]-4-hydroxy-5,5-dimethyl-4H,5H,6H-cyclopenta[b]thiophene-2-carboxamide | 590 | 591.1 |
| | N-{6-fluoro-2-methyl-3-[5-({5-methyl-4H,5H,6H,7H-pyrazolo[1,5-a]pyrazin-2-yl}amino)-6-oxo-1,6-dihydropyridazin-3-yl]phenyl}-4,5,6,7-tetrahydro-1-benzothiophene2-carboxamide | 533 | 534.1 |
| 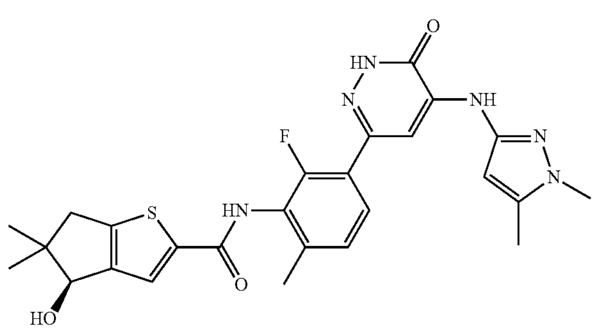 | (4S)-N-(3-{5-[(1,5-dimethyl-1H-pyrazol-3-yl)amino]-6-oxo-1,6-dihydropyridazin-3-yl}-2-fluoro-6-methylphenyl)-4-hydroxy-5,5-dimethyl-4H,5H,6H-cyclopenta[b]thiophene-2carboxamide | 522 | 523.1 |
| 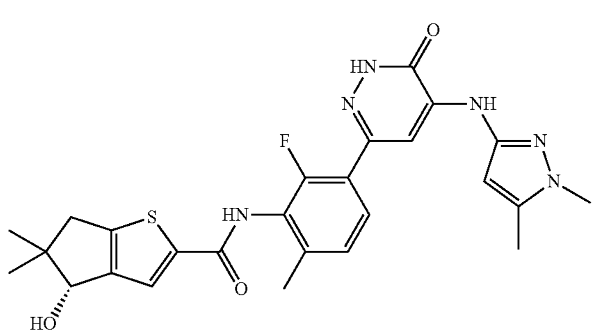 | (4R)-N-(3-{5-[(1,5-dimethyl-1H-pyrazol-3-yl)amino]-6-oxo-1,6-dihydropyridazin-3-yl}-2-fluoro-6-methylphenyl)-4-hydroxy-5,5-dimethyl-4H,5H,6H-cyclopenta[b]thiophene-2-carboxamide | 522 | 523.1 |

-continued

| Structure | Name | MW calcd | MH+ m/z obs |
|---|---|---|---|
| | (4S)-N-{6-fluoro-2-methyl-3-[5-({5-methyl-4H,5H,6H,7H-pyrazolo[1,5-a]pyrazin-2-yl}amino)-6-oxo-1,6-dihydropyridazin-3-yl]phenyl}-4-hydroxy-5,5-dimethyl-4H,5H,6H-cyclopenta[b]thiophene-2-carboxamide | 563 | 564.2 |
| | (4R)-N-{6-fluoro-2-methyl-3-[5-({5-methyl-4H,5H,6H,7H-pyrazolo[1,5-a]pyrazin-2-yl}amino)-6-oxo-1,6-dihydropyridazin-3-yl]phenyl}-4-hydroxy-5,5-dimethyl-4H,5H,6H-cyclopenta[b]thiophene-2-carboxaide | 563 | 564.2 |
| | N-[2-fluoro-5-(5-{[5-(3-hydroxy-3-methylpyrrolidin-1-yl)pridin-2-yl]amino}-6-oxo-1,6-dihydropyridazin-3-yl)phenyl]-1-benzothiophene-2-carboxamide | 556 | 557.2 |

-continued

| Structure | Name | MW calcd | MH+ m/z obs |
|---|---|---|---|
| 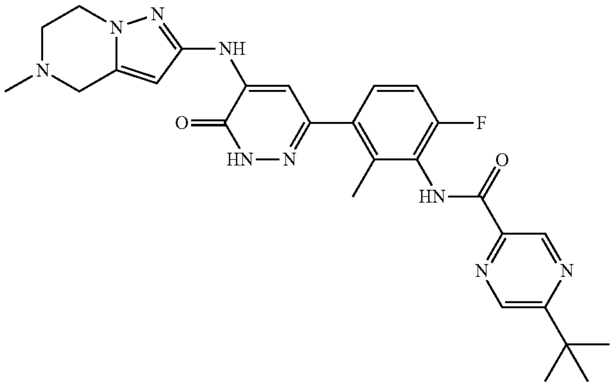 | 5-tert-butyl-N-{6-fluoro-2-methyl-3-[5-({5-methyl-4H,5H,6H,7H-pyrazolo[1,5-a]pyrazin-2-yl}amino)-6-oxo-1,6-dihydropyridazin-3-yl]phenyl)pyrazine-2-carboxamide | 531 | 532.2 |
| 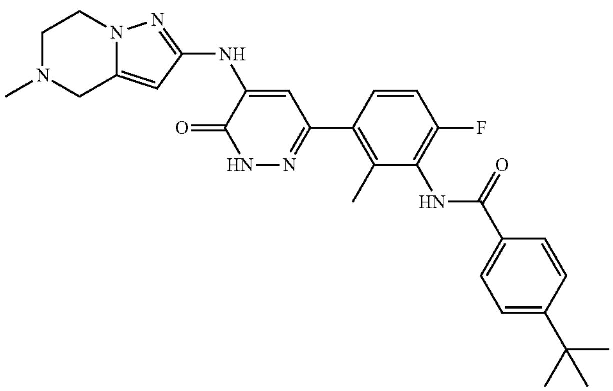 [SMILES: Cc1c(-c2cc(Nc3cc4n(n3)CCN(C)C4)c(=O)[nH]n2)ccc(F)c1NC(=O)c1ccc(C(C)(C)C)cc1] | 4-tert-butyl-N-{6-fluoro-2-methyl-3-[5-({5-methyl-4H,5H,6H,7H-pyrazolo[1,5-a]pyrazin-2-yl}amino)-6-oxo-1,6-dihydropyridazin-3-yl]phenyl)benzamide | 529 | 530.3 |
| 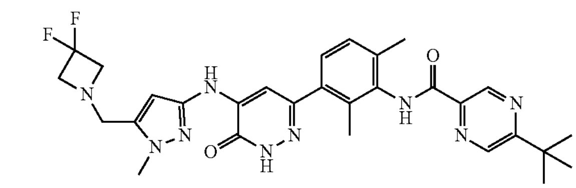 [SMILES: Cc1ccc(-c2cc(Nc3cc(CN4CC(F)(F)C4)n(C)n3)c(=O)[nH]n2)c(C)c1NC(=O)c1cnc(C(C)(C)C)cn1] | 5-tert-butyl-N-{3-[5-({5-[(3,3-difluoroazetidin-1-yl)methyl]-1-methyl-1H-pyrazol-3-yl}amino)-6-oxo-1,6-dihydropyridazin-3-yl]-2,6-dimethylphenyl}pyrazine-2-carboxamide | 577 | 578.2 |
| 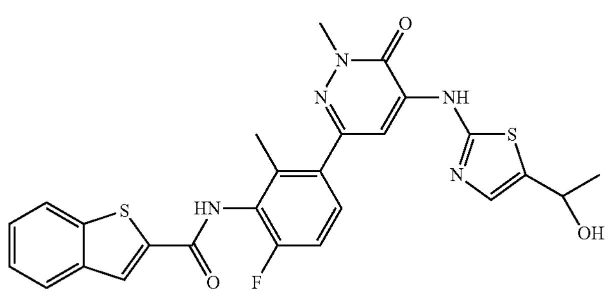 [SMILES: Cc1c(-c2cc(Nc3ncc(C(C)O)s3)c(=O)n(C)n2)ccc(F)c1NC(=O)c1cc2ccccc2s1] | N-[6-fluoro-3-(5-{[5-(1-hydroxyethyl)-1,3-thiazol-2-yl]amino}-1-methyl-6-oxo-1,6-dihydropyridazin-3-yl)-2-methylphenyl]-1-benzothiophene-2-carboxamide | 535 | 536 |
| 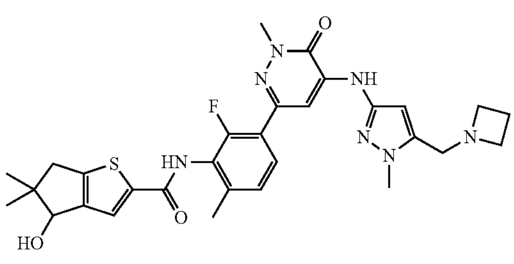 [SMILES: Cc1ccc(-c2cc(Nc3cc(CN4CCC4)n(C)n3)c(=O)n(C)n2)c(F)c1NC(=O)c1cc2c(s1)CC(C)(C)C2O] | N-[3-(5-{[5-(azetidin-1-ylmethyl)-1-methyl-1H-pyrazol-3-yl]amino}-1-methyl-6-oxo-1,6-dihydropyridazin-3-yl)-2-fluoro-6-methylphenyl]-4-hydroxy-5,5-dimethyl-4H,5H,6H-cyclopenta[b]thiophene-2-carboxamide | 591 | 592.2 |

-continued

| Structure | Name | MW calcd | MH+ m/z obs |
|---|---|---|---|
| 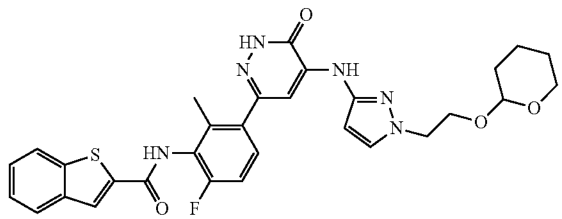 [SMILES: Cc1c(-c2cc(Nc3ccn(CCOC4CCCCO4)n3)c(=O)[nH]n2)ccc(F)c1NC(=O)c1cc2ccccc2s1] | N-{6-fluoro-2-methyl-3-[5-({1-[2-(oxan-2-yloxy)ethyl]-1H-pyrazol-3-yl}amino)-6-oxo-1,6-dihydropyridazin-3-yl]phenyl}-1-benzothiophene-2-carboxamide | 588 | 589.3 |
| 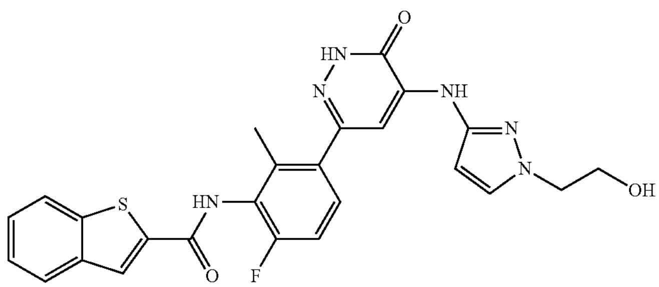 [SMILES: Cc1c(-c2cc(Nc3ccn(CCO)n3)c(=O)[nH]n2)ccc(F)c1NC(=O)c1cc2ccccc2s1] | N-[6-fluoro-3-(5-{[1-(2-hydroxyethyl)-1H-pyrazol-3-yl]amino}-6-oxo-1,6-dihydropyridazin-3-yl)-2-methylphenyl]-1-benzothiophene-2-carboxamide | 504 | 505.09 |
| | 4,4-difluoro-N-{6-fluoro-2-methyl-3-[5-({5-methyl-4H,5H,6H,7H-pyrazolo[1,5-a]pyrazin-2-yl}amino)-6-oxo-1,6-dihydropyridazin-3-yl]phenyl}-4,5,6,7-tetrahydro-1-benzothiophene-2-carboxamide | 569 | 570.7 |
| | N-{5-[5-({5-[2-(dimethylamino)ethoxy]pyridin-2-yl}amino)-1-methyl-6-oxo-1,6-dihydropyridazin-3-yl]-2-fluorophenyl]-1-benzothiophene-2-carboxamide | 558 | 559.2 |

-continued

| Structure | Name | MW calcd | MH+ m/z obs |
|---|---|---|---|
| 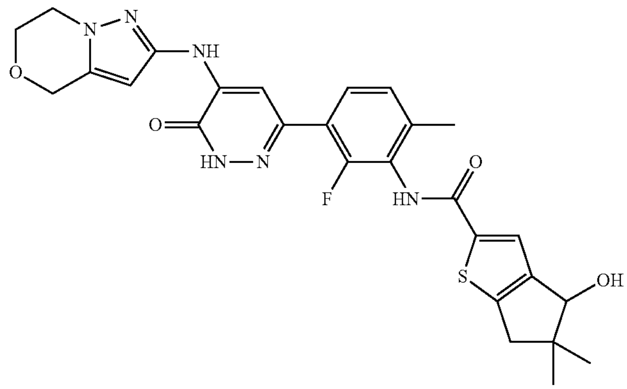 | N-[2-fluoro-6-methyl-3-(6-oxo-5-{4H,6H,7H-pyrazolo[3,2-c][1,4]oxazin-2-ylamino}-1,6-dihydropyridazin-3-yl)phenyl]-4-hydroxy-5,5-dimethyl-4H,5H,6H-cyclopenta[b]thiophene-2-carboxamide | 550 | 551.1 |
| | 4-tert-butyl-N-[(3R)-1-[1-methyl-5-({5-methyl-4H,5H,6H,7H-pyrazolo[1,5-a]pyrazin-2-yl)amino)-6-oxo-1,6-dihydropyridazin-3-yl]azepan-3-yl]benzamide | 532 | 533.3 |
| | N-[6-fluoro-3-(5-{[5-(2-hydroxypropan-2-yl)-1-methyl-1H-pyrazol-3-yl]amino}-6-oxo-1,6-dihydropyridazin-3-yl)-2-methylphenyl]-1-benzothiophene-2-carboxamide | 532 | 533.1 |
| 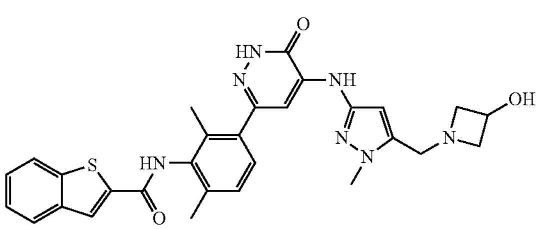 | N-{3-[5-({5-[(3-hydroxyazetidin-1-yl)methyl]-1-methyl-1H-pyrazol-3-yl}amino)-6-oxo-1,6-dihydropyridazin-3-yl]-2,6-dimethylphenyl}-1-benzothiophene-2-carboxamide | 555 | 556.1 |
| 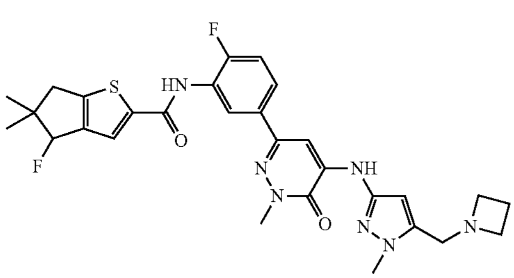 [SMILES: Cn1nc(Nc2cc(-c3ccc(F)c(NC(=O)c4cc5c(s4)CC(C)(C)C5F)c3)nn(C)c2=O)cc1CN1CCC1] | N-[5-(5-{[5-(azetidin-1-ylmethyl)-1-methyl-1H-pyrazol-3-yl]amino}-1-methyl-6-oxo-1,6-dihydropyridazin-3-yl)-2-fluorophenyl]-4-fluoro-5,5-dimethyl-4H,5H,6H-cyclopenta[b]thiophene-2-carboxamide | 579 | 580 |

-continued

| Structure | Name | MW calcd | MH+ m/z obs |
|---|---|---|---|
| | N-[6-fluoro-3-(5-{[5-(2-fluoroethyl)-4H,5H,6H,7H-pyrazolo[1,5-a]pyrazin-2-yl]amino}-6-oxo-1,6-dihydropyridazin-3-yl)-2-methylphenyl]-1-benzothiophene-2-carboxamide | 561 | 562.1 |
| 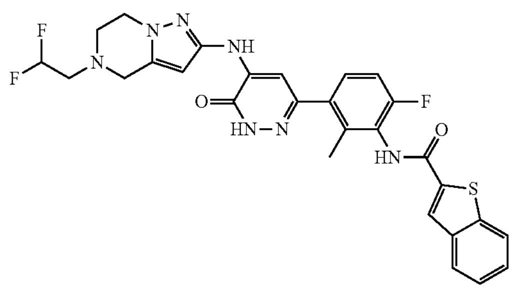 [SMILES: Cc1c(-c2cc(Nc3cc4n(n3)CCN(CC(F)F)C4)c(=O)[nH]n2)ccc(F)c1NC(=O)c1cc2ccccc2s1] | N-[3-(5-{[5-(2,2-difluoroethyl)-4H,5H,6H,7H-pyrazolo[1,5-a]pyrazin-2-yl]amino}-6-oxo-1,6-dihydropyridazin-3-yl)-6-fluoro-2-methylphenyl]-1-benzothiophene-2-carboxamide | 579 | 580.1 |
| 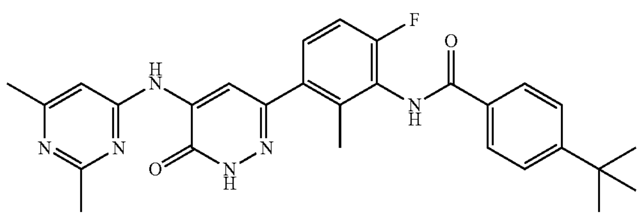 [SMILES: Cc1cc(Nc2cc(-c3ccc(F)c(NC(=O)c4ccc(C(C)(C)C)cc4)c3C)n[nH]c2=O)nc(C)n1] | 4-tert-butyl-N-(3-{5-[(2,6-dimethylpyrimidin-4-yl)amino]-6-oxo-1,6-dihydropyridazin-3-yl}-6-fluoro-2-methylphenyl)benzamide | 500 | 501.3 |
| 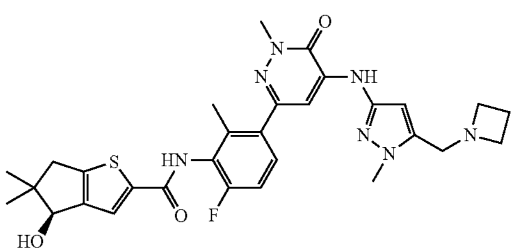 [SMILES: Cc1c(-c2cc(Nc3cc(CN4CCC4)n(C)n3)c(=O)n(C)n2)ccc(F)c1NC(=O)c1cc2c(s1)CC(C)(C)[C@@H]2O] | (4S)-N-[3-(5-{[5-(azetidin-1-ylmethyl)-1-methyl-1H-pyrazol-3-yl]amino]-1-methyl-6-oxo-1,6-dihydropyridazin-3-yl)-6-fluoro-2-methylphenyl]-4-hydroxy-5,5-dimethyl-4H,5H,6H-cyclopenta[b]thiopiene-2-carboxamide | 591 | 592.2 |
| 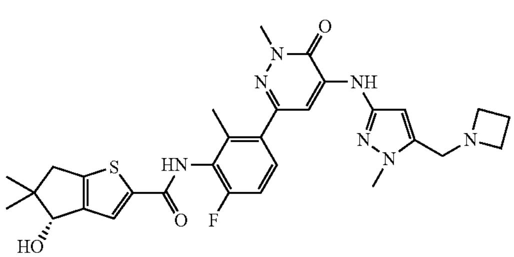 [SMILES: Cc1c(-c2cc(Nc3cc(CN4CCC4)n(C)n3)c(=O)n(C)n2)ccc(F)c1NC(=O)c1cc2c(s1)CC(C)(C)[C@H]2O] | (4R)-N-[3-(5-{[5-(azetidin-1-ylmethyl)-1-methyl-1H-pyrazol-3-yl]amino}-1-methyl-6-oxo-1,6-dihydropyridazin-3-yl)-6-fluoro-2-methylphenyl]-4-hydroxy-5,5-dimethyl-4H,5H,6H-cyclopenta[b]thiophene-2-carboxamide | 591 | 592.2 |
| 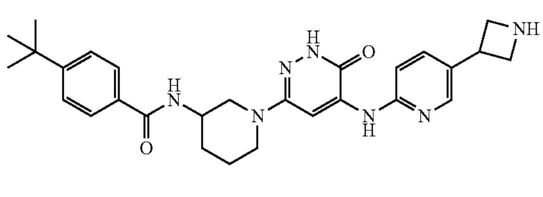 [SMILES: CC(C)(C)c1ccc(C(=O)NC2CCCN(c3cc(Nc4ccc(C5CNC5)cn4)c(=O)[nH]n3)C2)cc1] | N-[(3R)-1-(5-{[5-(azetidin-3-yl)yridine-2-yl]amino}-6-oxo-1,6-dihydropyridazin-3-yl)piperidin-3-yl]-4-tert-butylbenzamide | 501 | 502.3 |

-continued

| Structure | Name | MW calcd | MH+ m/z obs |
|---|---|---|---|
| 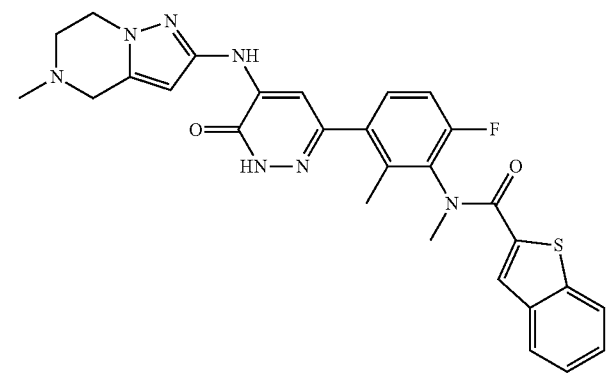 [SMILES: Cc1c(-c2cc(Nc3cc4n(n3)CCN(C)C4)c(=O)[nH]n2)ccc(F)c1N(C)C(=O)c1cc2ccccc2s1] | N-{6-fluoro-2-methyl-3-[5-({5-methyl-4H,5H,6H,7H-pyrazolo[1,5-a]pyrazin-2-yl}amino)-6-oxo-1,6-dihydropyridazin-3-yl]phenyl}-N-methyl-1-benzothiophene-2-carboxamide | 543 | 544.1 |
| 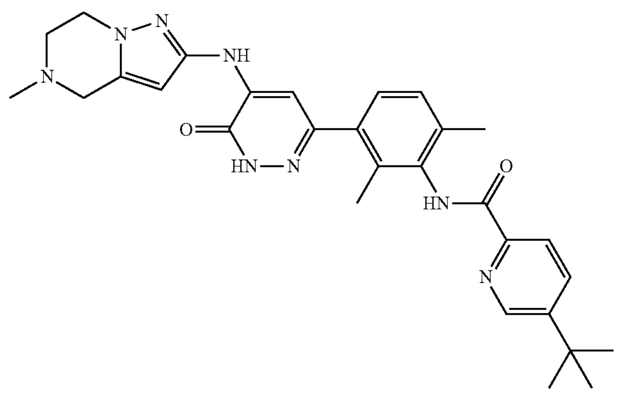 [SMILES: Cc1ccc(-c2cc(Nc3cc4n(n3)CCN(C)C4)c(=O)[nH]n2)c(C)c1NC(=O)c1ccc(C(C)(C)C)cn1] | 5-tert-butyl-N-{2,6-dimethyl-3-[5-({5-methyl-4H,5H,6H,7H-pyrazolo[1,5-a]pyrazin-2-yl}amino)-6-oxo-1,6-dihydropyridazin-3-yl]phenyl}pyridine-2-carboxamide | 526 | 527.3 |
| | (4S)-N-{2-fluoro-5-[5-({5-[(2S)-1-methylpyrrolidin-2-yl]yridine-2-yl}amino)-6-oxo-1,6-dihydropyridazin-3-yl]phenyl}-4-hydroxy-5,5-dimethyl-4H,5H,6H-cyclopenta[b]thiophene-2-carboxamide | 574 | 575.2 |
| 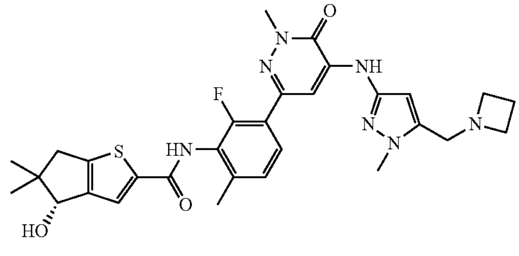 [SMILES: Cc1ccc(-c2cc(Nc3cc(CN4CCC4)n(C)n3)c(=O)n(C)n2)c(F)c1NC(=O)c1cc2c(s1)CC(C)(C)[C@H]2O] | (4R)-N-[3-(5-{[5-(azetidin-1-ylmethyl)-1-methyl-1H-pyrazol-3-yl]amino}-1-methyl-6-oxo-1,6-dihydropyridazin-3-yl)-2-fluoro-6-methylphenyl]-4-hydroxy-5,5-dimethyl-4H,5H,6H-cycloenta[b]thiophene-2-carboxamide | 591 | 592.2 |

-continued

| Structure | Name | MW calcd | MH+ m/z obs |
|---|---|---|---|
| 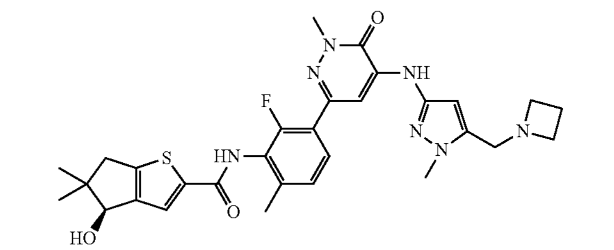 [SMILES: Cc1ccc(-c2cc(Nc3cc(CN4CCC4)n(C)n3)c(=O)n(C)n2)c(F)c1NC(=O)c1cc2c(s1)CC(C)(C)[C@@H]2O] | (4S)-N-[3-(5-{[5-(azetidin-1-ylmethyl)-1-methyl-1H-pyrazol-3-yl]amino-1-methyl-6-oxo-1,6-dihydropyridazin-3-yl)-2-fluoro-6-methylphenyl]-4-hydroxy-5,5-dimethyl-4H,5H,6H-cyclopenta[b]thiophene-2-carboxamide | 591 | 592.2 |
| 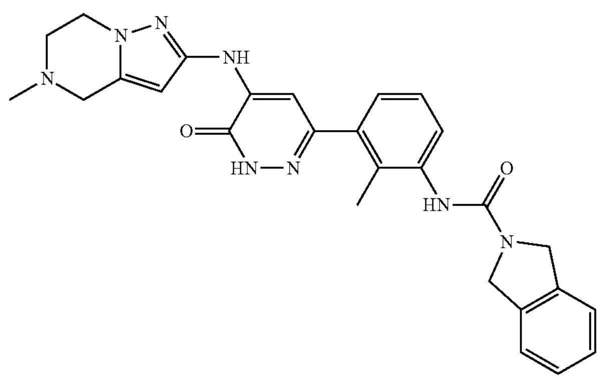 [SMILES: Cc1c(NC(=O)N2Cc3ccccc3C2)cccc1-c1cc(Nc2cc3n(n2)CCN(C)C3)c(=O)[nH]n1] | N-{2-methyl-3-[5-({5-methyl-4H,5H,6H,7H-pyrazolo[1,5-a]pyrazin-2-yl}amino)-6-oxo-1,6-dihydropyridazin-3-yl]phenyl}-2,3-dihydro-1H-isoindole-2-carboxamide | 496 | 497.2 |
| | N-[3-fluoro-6-[5-({5-methyl-4H,5H,6H,7H-pyrazolo[1,5-a]pyrazin-2-yl)amino)-6-oxo-1,6-dihydropyridazin-3-yl] yridine-2-yl]-1-benzothiophene-2-carboxamide | 516 | 517.1 |
| 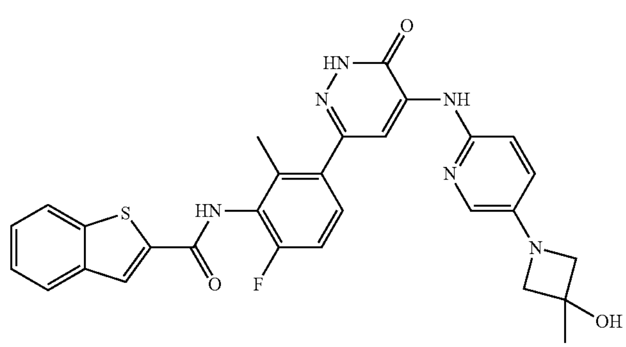 [SMILES: Cc1c(-c2cc(Nc3ccc(N4CC(C)(O)C4)cn3)c(=O)[nH]n2)ccc(F)c1NC(=O)c1cc2ccccc2s1] | N-[6-fluoro-3-(5-{[5-(3-hydroxy-3-methylazetidin-1-yl) yridine-2-yl]amino}-6-oxo-1,6-dihydropyridazin-3-yl)-2-methylphenyl]-1-benzothiophene-2-carboxamide | 556 | 557.1 |

-continued

| Structure | Name | MW calcd | MH+ m/z obs |
|---|---|---|---|
| 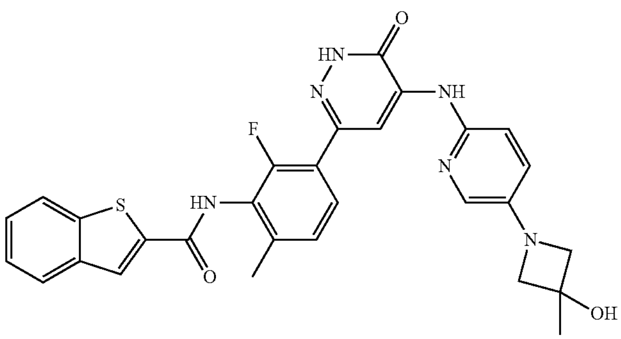 [SMILES: Cc1ccc(-c2cc(Nc3ccc(N4CC(C)(O)C4)cn3)c(=O)[nH]n2)c(F)c1NC(=O)c1cc2ccccc2s1] | N-[2-fluoro-3-(5-{[5-(3-hydroxy-3-methylazetidin-1-yl) yridine-2-yl]amino}-6-oxo-1,6-dihydropyridazin-3-yl)-6-methylphenyl}-1-benzothiophene-2-carboxamide | 556 | 557.1 |
| 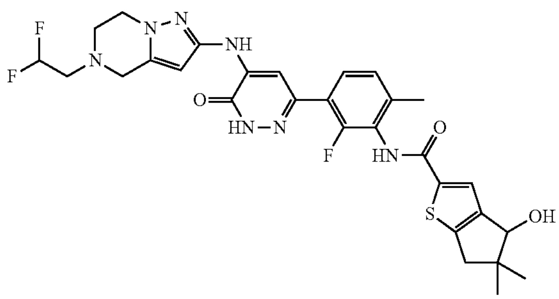 [SMILES: Cc1ccc(-c2cc(Nc3cc4n(n3)CCN(CC(F)F)C4)c(=O)[nH]n2)c(F)c1NC(=O)c1cc2c(s1)CC(C)(C)C2O] | N-[3-(5-{[5-(2,2-difluoroethyl)-4H,5H,6H,7H-pyrazolo[1,5-a]pyrazin-2-yl]amino}-6-oxo-1,6-dihydropyridazin-3-yl)-2-fluoro-6-methylphenyl]-4-hydroxy-5,5-dimethyl-4H-5H-6H-cyclopenta[b]thiophene-2-carboxamide | 613 | 614.1 |
| 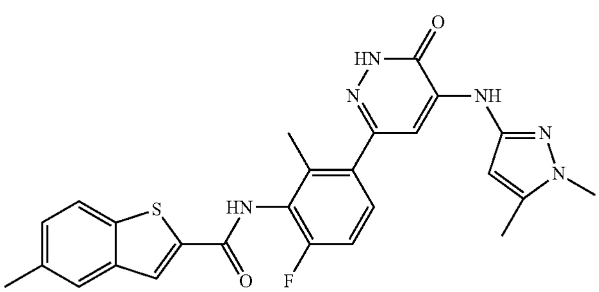 | N-(3-{5-[(1,5-dimethyl-1H-pyrazol-3-yl)amino]-6-oxo-1,6-dihydropyridazin-3-yl}-6-fluoro-2-methylphenyl)-5-methyl-1-benzothiophene-2-carboxamide | 502 | 503 |
| 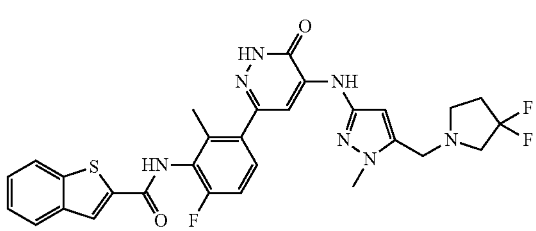 [SMILES: Cc1c(-c2cc(Nc3cc(CN4CCC(F)(F)C4)n(C)n3)c(=O)[nH]n2)ccc(F)c1NC(=O)c1cc2ccccc2s1] | N-[3-({5-[(3,3-difluoropyrrolidin-1-yl)methyl]-1-methyl-1H-pyrazol-3-yl}amino)-6-oxo-1,6-dihydropyridazin-3-yl]-6-fluoro-2-methylphenyl]-1-benzothiophene-2-carboxamide | 593 | 594.2 |
| 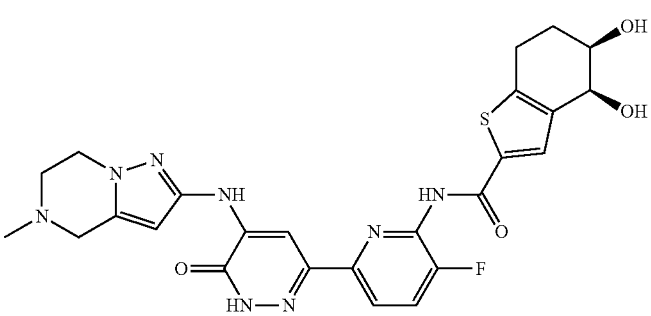 [SMILES: CN1CCn2nc(Nc3cc(-c4ccc(F)c(NC(=O)c5cc6c(s5)CC[C@@H](O)[C@H]6O)n4)n[nH]c3=O)cc2C1] | (4S,5R)-N-{2-fluoro-5-[5-({5-methyl-4H,5H,6H,7H-pyrazolo[1,5-a]pyrazin-2-yl}amino)-6-oxo-1,6-dihydropyridazin-3-yl]phenyl}-4,5-dihydroxy-4,5,6,7-tetrahydro-1-benzothiophene-2-carboxamide | 551 | 552.2 |

-continued

| Structure | Name | MW calcd | MH+ m/z obs |
|---|---|---|---|
| 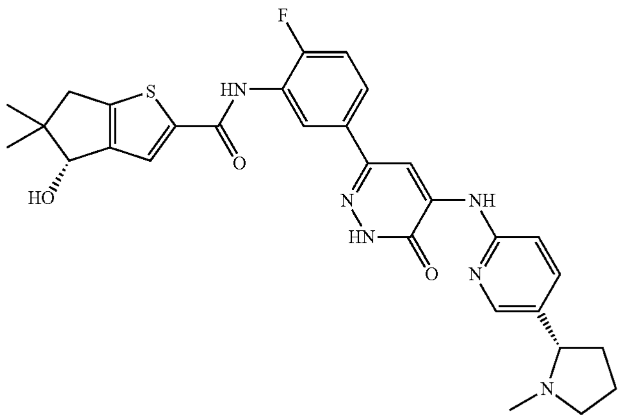 [SMILES: CN1CCC[C@H]1c1ccc(Nc2cc(-c3ccc(F)c(NC(=O)c4cc5c(s4)CC(C)(C)[C@H]5O)c3)n[nH]c2=O)nc1] | (4R)-N-{2-fluoro-5-[5-({5-[(2S)-1-methylpyrrolidin-2-yl] yridine-2-yl}amino)-6-oxo-1,6-dihydropyridazin-3-yl]phenyl}-4-hydroxy-5,5-dimethyl-4H,5H,6H-cyclopenta[b]thiophene-2-carboxamide | 574 | 575.4 |
| 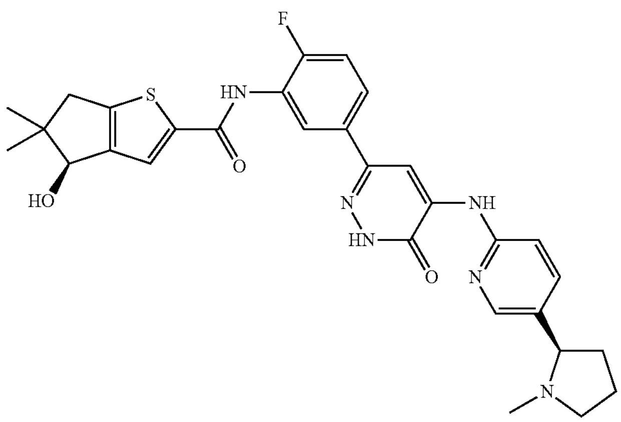 [SMILES: CN1CCC[C@@H]1c1ccc(Nc2cc(-c3ccc(F)c(NC(=O)c4cc5c(s4)CC(C)(C)[C@@H]5O)c3)n[nH]c2=O)nc1] | (4S)-N-{2-fluoro-5-[5-({5-(2R)-1-methylpyrrolidin-2-yl] yridine-2-yl}amino)-6-oxo-1,6-dihydropyridazin-3-yl]phenyl}-4-hydroxy-5,5-dimethyl-4H,5H,6H-cyclopenta[b]thiophene-2-carboxamide | 574 | 572.2 |
| 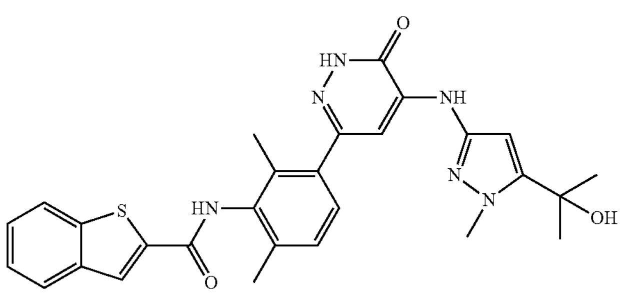 [SMILES: Cc1ccc(-c2cc(Nc3cc(C(C)(C)O)n(C)n3)c(=O)[nH]n2)c(C)c1NC(=O)c1cc2ccccc2s1] | N-[3-(5-{[5-(2-hydroxypropan-2-yl)-1-methyl-1H-pyrazol-3-yl]amino}-6-oxo-1,6-dihydropyridazin-3-yl)-2,6-dimethylphenyl]-1-benzothiophene-2-carboxamide | 528 | 529.2 |
| | 4-tert-butyl-N-[2-(hydroxymethyl)-3-(1-methyl-5-{[5-(morpholin-4-ylcarbonyl) yridine-2-yl]amino}-6-oxo-1,6-dihydropyridazin-3-yl)phenyl]benzamide | 596 | 597.2 |
| 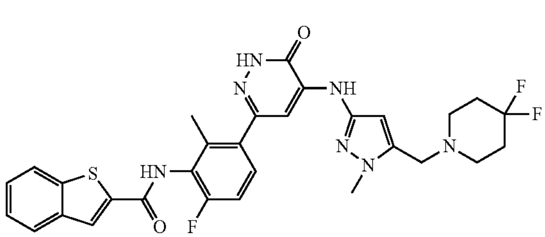 [SMILES: Cc1c(-c2cc(Nc3cc(CN4CCC(F)(F)CC4)n(C)n3)c(=O)[nH]n2)ccc(F)c1NC(=O)c1cc2ccccc2s1] | N-{3-[5-({5-[(4,4-difluoropiperidin-1-yl)methyl]-1-methyl-1H-pyrazol-3-yl}amino)-1-methyl-6-oxo-1,6-dihydropyridazin-3-yl]-6-fluoro-2-methylphenyl}-1-benzothiophene-2-carboxamide | 621 | 622.2 |

-continued

| Structure | Name | MW calcd | MH+ m/z obs |
|---|---|---|---|
| 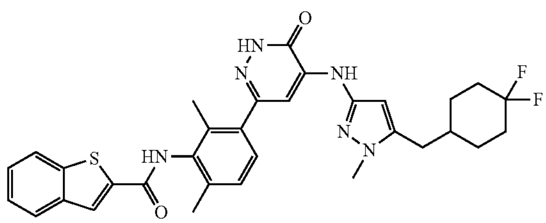 [SMILES: Cc1ccc(-c2cc(Nc3cc(CC4CCC(F)(F)CC4)n(C)n3)c(=O)[nH]n2)c(C)c1NC(=O)c1cc2ccccc2s1] | N-{3-[5-({5-[(4,4-difluoropiperidin-1-yl)methyl-1H-pyrazol-3-yl}amino)-6-oxo-1,6-dihydropyridazin-3-yl]-6-fluoro-2-methylphenyl]-1-benzothiophene-2-carboxamide | 607 | 608.2 |
| 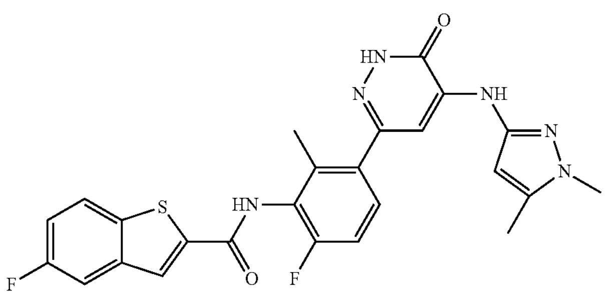 [SMILES: Cc1c(-c2cc(Nc3cc(C)n(C)n3)c(=O)[nH]n2)ccc(F)c1NC(=O)c1cc2cc(F)ccc2s1] | N-(3-{5-[(1,5-dimethyl-1H-pyrazol-3-yl)amino]-6-oxo-1,6-dihydropyridazin-3-yl}-6-fluoro-2-methylphenyl)-5-fluoro-1-benzothiophene-2-carboxamide | 506 | 507 |
| | N-{6-fluoro-2-methyl-3-[5-({5-methyl-4H,5H,6H,7H,8H-pyrazolo[1,5-a][1,4]diazepin-2-yl}amino)-6-oxo-1,6-dihydropyridazin-3-yl]phenyl}-1-benzothiophene-2-carboxamide | 543 | 544.2 |
| 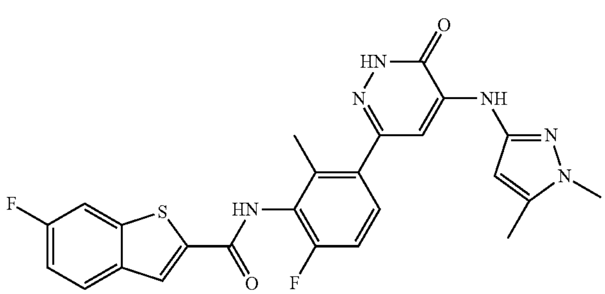 [SMILES: Cc1c(-c2cc(Nc3cc(C)n(C)n3)c(=O)[nH]n2)ccc(F)c1NC(=O)c1cc2ccc(F)cc2s1] | N-(3-{5-[(1,5-dimethyl-1H-pyrazol-3-yl)amino]-6-oxo-1,6-dihydropyridazin-3-yl}-6-fluoro-2-methylphenyl)-6-fluoro-1-benzothiophene-2-carboxamide | 506 | 507 |
| 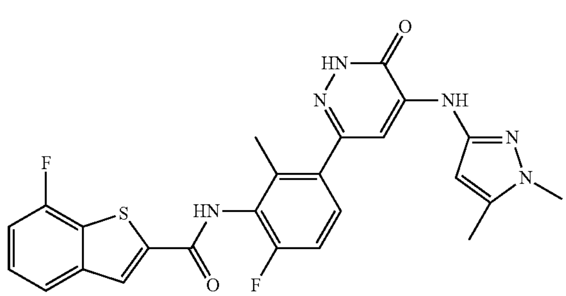 | N-(3-{5-[(1,5-dimethyl-1H-pyrazol-3-yl)amino]-6-oxo-1,6-dihydropyridazin-3-yl}-6-fluoro-2-methylphenyl)-7-fluoro-1-benzothiophene-2-carboxamide | 506 | 507 |

-continued

| Structure | Name | MW calcd | MH+ m/z obs |
|---|---|---|---|
| 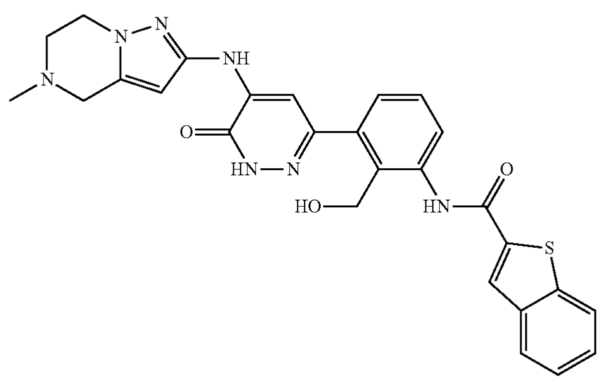 [SMILES: CN1CCn2nc(Nc3cc(-c4cccc(NC(=O)c5cc6ccccc6s5)c4CO)n[nH]c3=O)cc2C1] | N-[2-(hydroxymethyl)-3-[5-({5-methyl-4H,5H,6H,7H-pyrazolo[1,5-a]pyrazin-2-yl}amino)-6-oxo-1,6-dihydropyridazin-3-yl]phenyl]-1-benzothiophene-2-carboxamide | 527 | 528.1 |
| 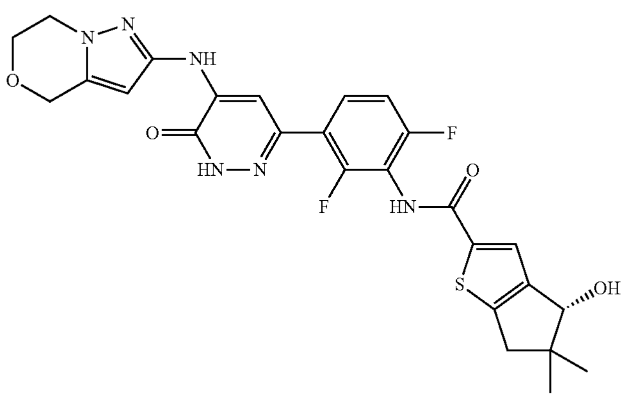 [SMILES: CC1(C)Cc2sc(C(=O)Nc3c(F)ccc(-c4cc(Nc5cc6n(n5)CCOC6)c(=O)[nH]n4)c3F)cc2[C@@H]1O] | (4R)-N-[2-fluoro-6-methyl-3-(6-oxo-5-{4H,6H,7H-pyrazolo[3,2-c][1,4]oxazin-2-ylamino}-1,6-dihydropyridazin-3-yl)phenyl]-4-hydroxy-5,5-dimethyl-4H,5H,6H-cyclopenta[b]thiophene-2-carboxamide | 550 | 551.1 |
| 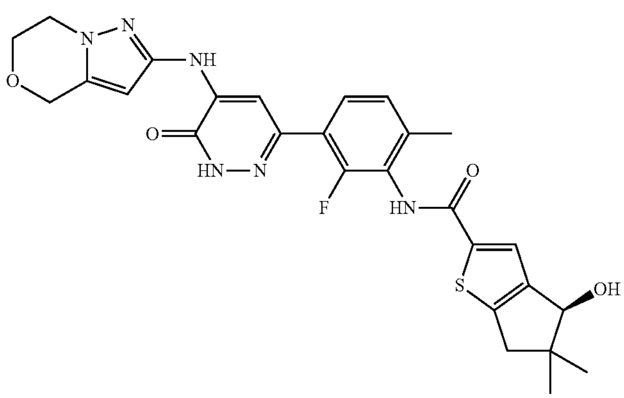 [SMILES: Cc1ccc(-c2cc(Nc3cc4n(n3)CCOC4)c(=O)[nH]n2)c(F)c1NC(=O)c1cc2c(s1)CC(C)(C)[C@@H]2O] | (4S)-N-[2-fluoro-6-methyl-3-(6-oxo-5-{4H,6H,7H-pyrazolo[3,2-c][1,4]oxazin-2-yl)amino}-1,6-dihydropyridazin-3-yl)phenyl]-4-hydroxy-5,5-dimethyl-4H,5H,6H-cyclopenta[b]thiophene-2-carboxamide | 550 | 551.1 |
| 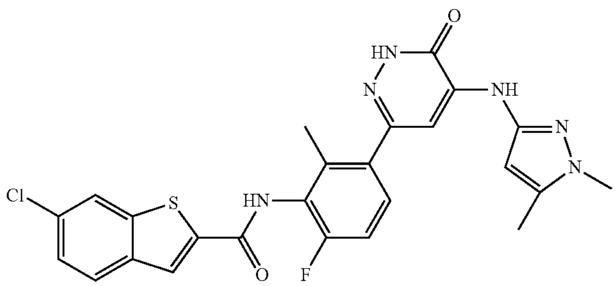 [SMILES: Cc1c(-c2cc(Nc3cc(C)n(C)n3)c(=O)[nH]n2)ccc(F)c1NC(=O)c1cc2ccc(Cl)cc2s1] | 6-chloro-N-(3-{5-[(1,5-dimethyl-1H-pyrazol-3-yl)amino]-6-oxo-1,6-dihydropyridazin-3-yl}-6-fluoro-2-methylphenyl)-1-benzothiophene-2-carboxamide | 522 | 523 |

-continued

| Structure | Name | MW calcd | MH+ m/z obs |
|---|---|---|---|
| 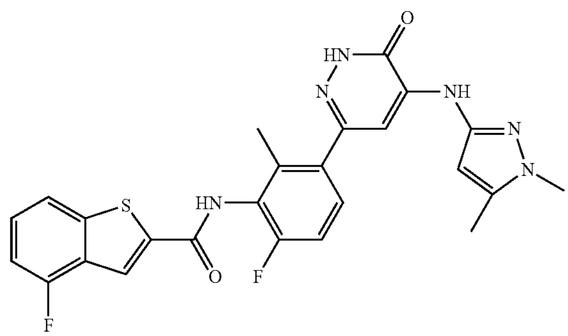 [SMILES: Cc1c(-c2cc(Nc3cc(C)n(C)n3)c(=O)[nH]n2)ccc(F)c1NC(=O)c1cc2c(F)cccc2s1] | N-(3-{5-[(1,5-dimethyl-1H-pyrazol-3-yl)amino]-6-oxo-1,6-dihydropyridazin-3-yl}-6-fluoro-2-methylphenyl)-4-fluoro-1-benzothiophene-2-carboxamide | 506 | 507 |
| 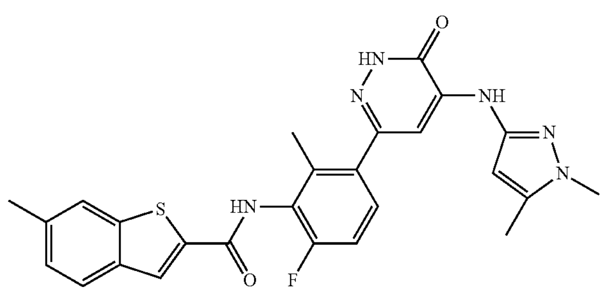 | N-(3-{5-[(1,5-dimethyl-1H-pyrazol-3-yl)amino]-6-oxo-1,6-dihydropyridazin-3-yl}-6-fluoro-2-methylphenyl)-6-methyl-1-benzothiophene-2-carboxamide | 502 | 503 |
| 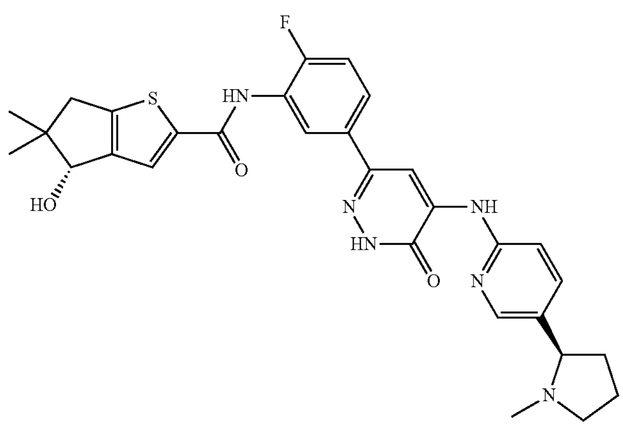 [SMILES: CN1CCC[C@@H]1c1ccc(Nc2cc(-c3ccc(F)c(NC(=O)c4cc5c(s4)CC(C)(C)[C@H]5O)c3)n[nH]c2=O)nc1] | (4R)-N-{2-fluoro-5-[5-({5-[(2R)-1-methylpyrrolidin-2-yl]yridine-2-yl}amino)-6-oxo-1,6-dihydropyridazin-3-yl]phenyl}-4-hydroxy-5,5-dimethyl-4H,5H,6H-cyclopenta[b]thiopbene-2-carboxamide | 574 | 575.8 |
| 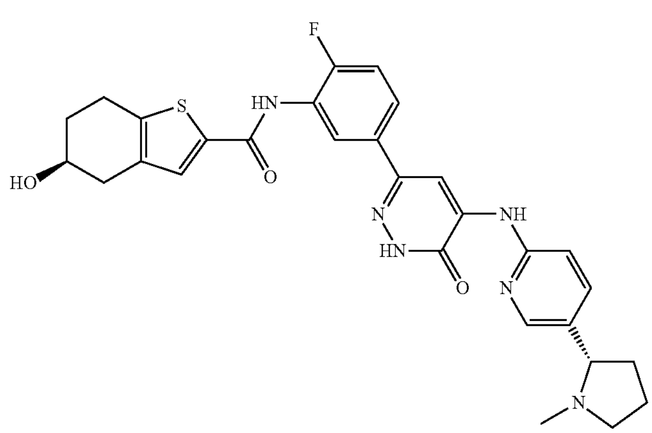 [SMILES: CN1CCC[C@H]1c1ccc(Nc2cc(-c3ccc(F)c(NC(=O)c4cc5c(s4)CC[C@H](O)C5)c3)n[nH]c2=O)nc1] | (5S)-N-{2-fluoro-5-[5-({5-[(2S)-1-methylpyrrolidin-2-yl]yridine-2-yl}amino)-6-oxo-1,6-dihydropyridazin-3-yl]phenyl}-5-hydroxy-4,5,6,7-tetrahydro-1-benzothiophene-2-carboxamide | 560 | 561.2 |

-continued

| Structure | Name | MW calcd | MH+ m/z obs |
|---|---|---|---|
| 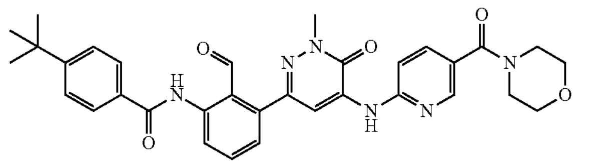 [SMILES: Cn1nc(-c2cccc(NC(=O)c3ccc(C(C)(C)C)cc3)c2C=O)cc(Nc2ccc(C(=O)N3CCOCC3)cn2)c1=O] | 4-tert-butyl-N-[2-formyl-3-(1-methyl-5-{[5-(morpholin-4-ylcarbonyl) yridine-2-yl]amino}-6-oxo-1,6-dihydropyridazin-3-yl)phenyl]benzamide | 594 | 595.14 |
| 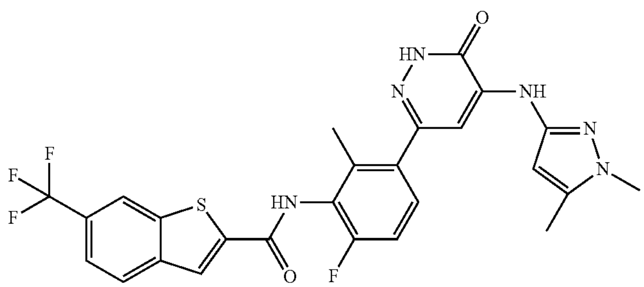 [SMILES: Cc1c(-c2cc(Nc3cc(C)n(C)n3)c(=O)[nH]n2)ccc(F)c1NC(=O)c1cc2ccc(C(F)(F)F)cc2s1] | N-(3-{5-[(1,5-dimethyl-1H-pyrazol-3-yl)amino]-6-oxo-1,6-dihydropyridazin-3-yl}-6-fluoro-2-methylphenyl)-6-(trifluoromethyl)-1-benzothiophene-2-carboxamide | 556 | 557.1 |
| 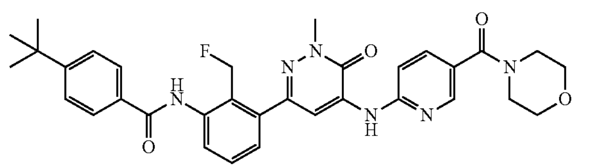 [SMILES: Cn1nc(-c2cccc(NC(=O)c3ccc(C(C)(C)C)cc3)c2CF)cc(Nc2ccc(C(=O)N3CCOCC3)cn2)c1=O] | 4-tert-butyl-N-[2-(fluoromethyl)-3-(1-methyl-5-{[5-(morpholin-4-ylcarbonyl)pyridin-2-yl]amino}-6-oxo-1,6-dihydropyridazin-3-yl)phenyl]benzamide | 598 | 599 |
| 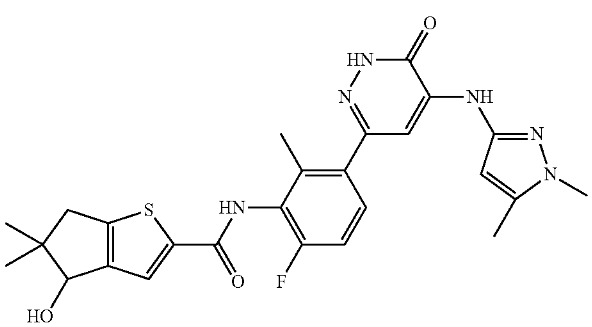 | N-(3-{5-[(1,5-dimethyl-1H-pyrazol-3-yl)amino]-6-oxo-1,6-dihydropyrodazin-3-yl}-6-fluoro-2-methylphenyl)-4-hydroxy-5,5-dimethyl-4H,5H,6H-cyclopenta[b]thiophene-2-carboxamide | 522 | 523.5 |
| 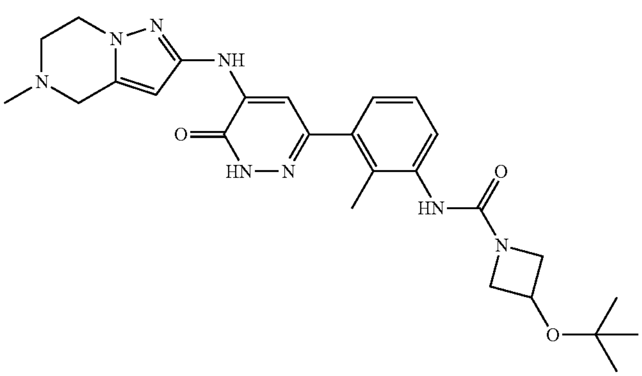 [SMILES: Cc1c(NC(=O)N2CC(OC(C)(C)C)C2)cccc1-c1cc(Nc2cc3n(n2)CCN(C)C3)c(=O)[nH]n1] | 3-(tert-butoxy)-N-{2-methyl-3-[5-({5-methyl-4H,5H,6H,7H-pyrazolo[1,5-a]pyrazin-2-yl}amino)-6-oxo-1,6-dihydropyridazin-3-yl]phenyl}azetidine-1-carboxamide | 506 | 507.3 |

-continued

| Structure | Name | MW calcd | MH+ m/z obs |
|---|---|---|---|
| | (5R)-N-{2-fluoro-5-[5-({5-[(2S)-1-methylpyrrolidin-2-yl]pyridin-2-yl}amino)-6-oxo-1,6-dihydropyridazin-3-yl]phenyl}-5-hydroxy-4,5,6,7-tetrahydro-1-benzothiophene-2-carboxamide | 560 | 561.2 |
| | (5S)-N-{2-fluoro-5-[5-({5-[(2R)-1-methylpyrrolidin-2-yl]pyridin-2-yl}amino)-6-oxo-1,6-dihydropyridazin-3-yl]phenyl}-5-hydroxy-4,5,6,7-tetrahydro-1-benzothiophene-2-carboxamide | 560 | 561.2 |
| 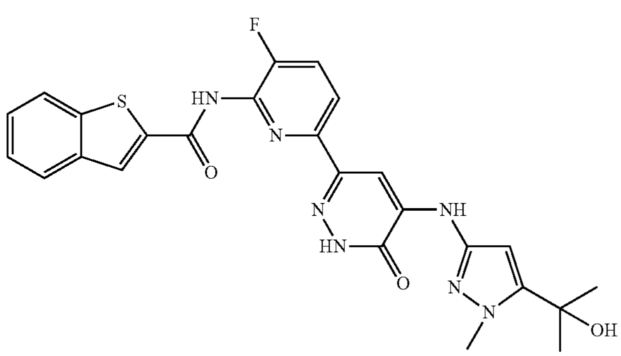 [SMILES: Cn1nc(Nc2cc(-c3ccc(F)c(NC(=O)c4cc5ccccc5s4)n3)n[nH]c2=O)cc1C(C)(C)O] | N-[3-fluoro-6-(5-{[5-(2-hydroxypropan-2-yl)-1-methyl-1H-pyrazol-3-yl]amino)-6-oxo-1,6-dihydropyridazin-3-yl)pyridin-2-yl]-1-benzothiophene-2-carboxamide | 519 | 520.1 |
| 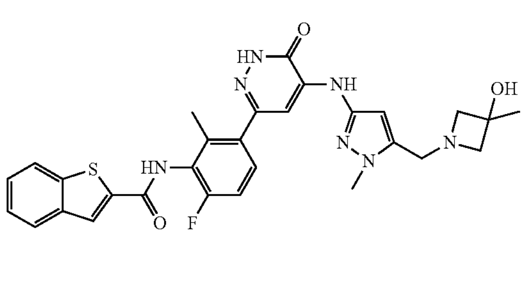 [SMILES: Cc1c(-c2cc(Nc3cc(CN4CC(C)(O)C4)n(C)n3)c(=O)[nH]n2)ccc(F)c1NC(=O)c1cc2ccccc2s1] | N-(6-fluoro-3-[5-({5-[(3-hydroxy-3-methylazetidin-1-yl)methyl]-1-methyl-1H-pyrazol-3-yl}amino)-6-oxo-1,6-dihydropyridazin-3-yl]-2-methylphenyl}-1-benzothiophene-2-carboxamide | 573 | 574.2 |

-continued

| Structure | Name | MW calcd | MH+ m/z obs |
|---|---|---|---|
| 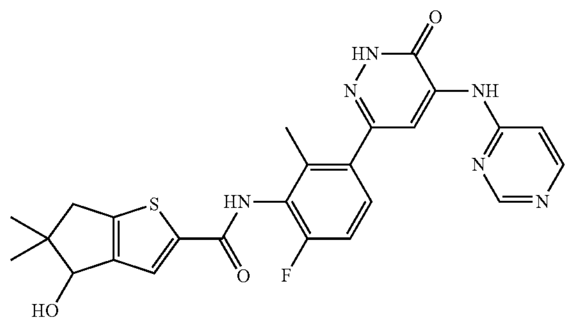 [SMILES: Cc1c(-c2cc(Nc3ccncn3)c(=O)[nH]n2)ccc(F)c1NC(=O)c1cc2c(s1)CC(C)(C)C2O] | N-{6-fluoro-2-methyl-3-[6-oxo-5-(pyrimidin-4-ylamino)-1,6-dihydropyridazin-3-yl]phenyl}-4-hydroxy-5,5-dimethyl-4H,5H,6H-cyclopenta[b]thiophene-2-carboxamide | 506 | 507.4 |
| 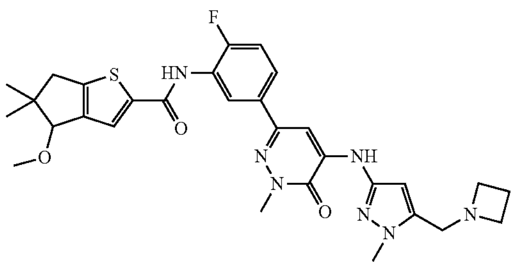 [SMILES: COC1c2cc(C(=O)Nc3cc(-c4cc(Nc5cc(CN6CCC6)n(C)n5)c(=O)n(C)n4)ccc3F)sc2CC1(C)C] | N-[5-(5-{[5-(azetidin-1-ylmethyl)-1-methyl-1H-pyrazol-3-yl]amino)-1-methyl-6-oxo-1,6-dihydropyridazin-3-yl)-2-fluorophenyl]-4-methoxy-5,5-dimethyl-4H,5H,6H-cyclopenta[b]thiophene-2-carboxamide | 591 | 592.2 |
|  | (5R)-N-[2-fluoro-5-[5-({5-[(2R)-1-methylpyrrolidin-2-yl]pyridin-2-yl}amino)-6-oxo-1,6-dihydropyridazin-3-yl]phenyl)-5-hydroxy-4,5,6,7-tetrahydro-1-benzothiophene-2-carboxamide | 560 | 561.2 |
| 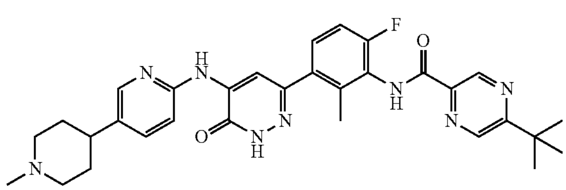 [SMILES: Cc1c(-c2cc(Nc3ccc(C4CCN(C)CC4)cn3)c(=O)[nH]n2)ccc(F)c1NC(=O)c1cnc(C(C)(C)C)cn1] | 5-tert-butyl-N-[6-fluoro-2-methyl-3-(5-{[5-(1-methylpiperidin-4-yl)pyridin-2-yl]amino)-6-oxo-1,6-dihydropyridazin-3-yl)phenyl]pyrazine-2-carboxamide | 570 | 571.3 |
| 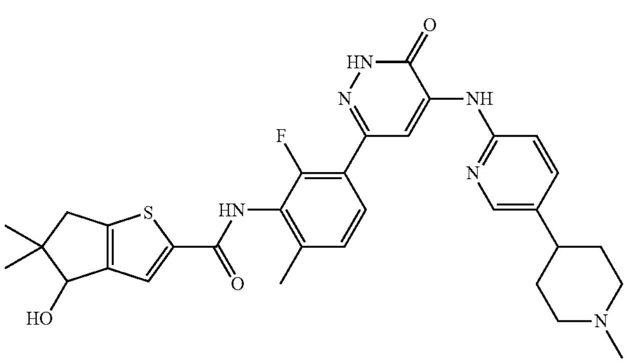 | N-[2-fluoro-6-methyl-3-(5-{[5-(1-methylpiperidin-4-yl)pyridin-2-yl]amino)-6-oxo-1,6-dihydropyridazin-3-yl)phenyl]-4-hydroxy-5,5-dimethyl-4H,5H,6H-cyclopenta[b]thiophene-2-carboxamide | 602 | 603.2 |

-continued

| Structure | Name | MW calcd | MH+ m/z obs |
|---|---|---|---|
| 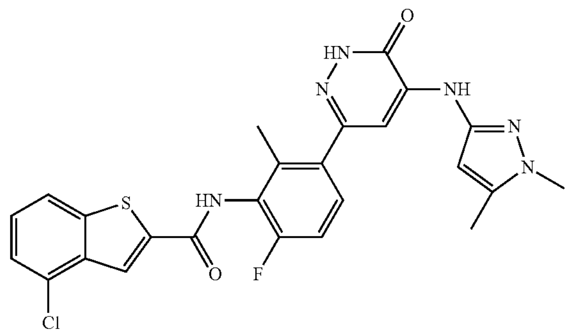 | 4-chloro-N-(3-{5-[(1,5-dimethyl-1H-pyrazol-3-yl)amino]-6-oxo-1,6-dihydropyridazin-3-yl}-6-fluoro-2-methylphenyl)-1-benzothiophene-2-carboxamide | 522 | 523 |
| 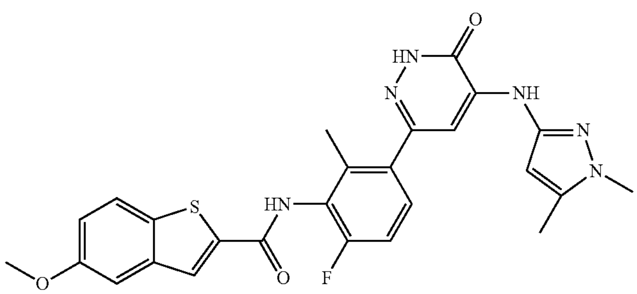 | N-(3-{5-[1,5-dimethyl-1H-pyrazol-3-yl)amino]-6-oxo-1,6-dihydropyridazin-3-yl}-6-fluoro-2-methylphenyl)-5-methoxy-1-benzothiophene-2-carboxamide | 518 | 519 |
| 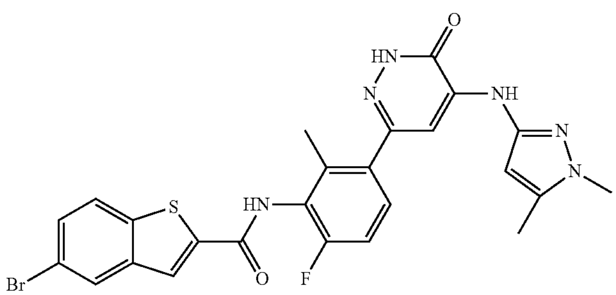 [SMILES: Cc1c(-c2cc(Nc3cc(C)n(C)n3)c(=O)[nH]n2)ccc(F)c1NC(=O)c1cc2cc(Br)ccc2s1] | 5-bromo-N-(3-{5-[1,5-dimethyl-1H-pyrazol-3-yl)amino]-6-oxo-1,6-dihydropyridazin-3-yl}-6-fluoro-2-methylphenyl)-1-benzothiophene-2-carboxamide | 566 | 567 |
| 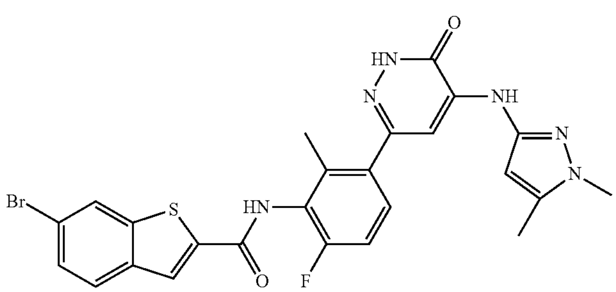 [SMILES: Cc1c(-c2cc(Nc3cc(C)n(C)n3)c(=O)[nH]n2)ccc(F)c1NC(=O)c1cc2ccc(Br)cc2s1] | 6-bromo-N-(3-{5-[(1,5-dimethyl-1H-pyrazol-3-yl)amino]-6-oxo-1,6-dihydropyridazin-3-yl}-6-fluoro-2-methylphenyl)-1-benzothiophene-2-carboxamide | 566 | 567 |
| 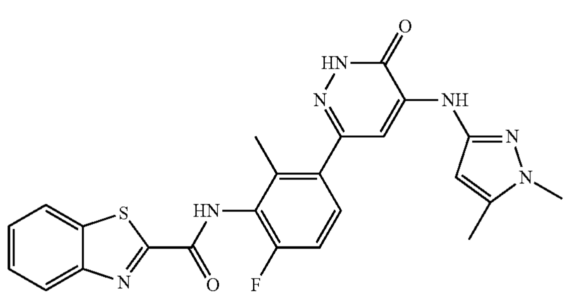 [SMILES: Cc1c(-c2cc(Nc3cc(C)n(C)n3)c(=O)[nH]n2)ccc(F)c1NC(=O)c1nc2ccccc2s1] | N-(3-{5-[(1,5-dimethyl-1H-pyrazol-3-yl)amino]-6-oxo-1,6-dihydropyridazin-3-yl}-6-fluoro-2-methylphenyl)-1,3-benzothiazole-2-carboxamide | 489 | 490 |

-continued

| Structure | Name | MW calcd | MH+ m/z obs |
|---|---|---|---|
| 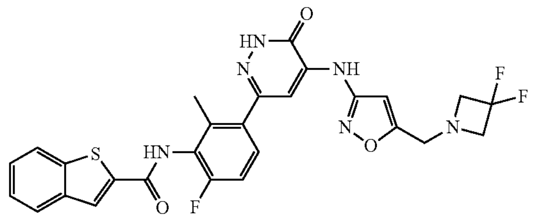 [SMILES: Cc1c(-c2cc(Nc3cc(CN4CC(F)(F)C4)on3)c(=O)[nH]n2)ccc(F)c1NC(=O)c1cc2ccccc2s1] | N-{3-[5-({5-[(3,3-difluoroazetidin-1-yl)methyl]-1,2-oxazol-3-yl}amino)-6-oxo-1,6-dihydropyridazin-3-yl]-6-fluoro-2-methylphenyl}-1-benzothiophene-2-carboxamide | 566 | 567.1 |
| 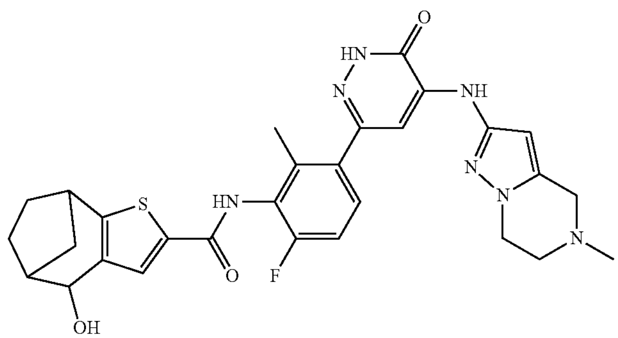 [SMILES: Cc1c(-c2cc(Nc3cc4n(n3)CCN(C)C4)c(=O)[nH]n2)ccc(F)c1NC(=O)c1cc2c(s1)C1CCC(C1)C2O] | N-(6-fluoro-2-methyl-3-[5-({5-methyl-4H,5H,6H,7H-pyrazolo[1,5-a]pyrazin-2-yl}amino)-6-oxo-1,6-dihydropyridazin-3-yl]phenyl-7-hydroxy-3-thiatricyclo[6.2.0^{2,6}]undeca-2(6),4-diene-4-carboxamide | 575 | 576.2 |
| 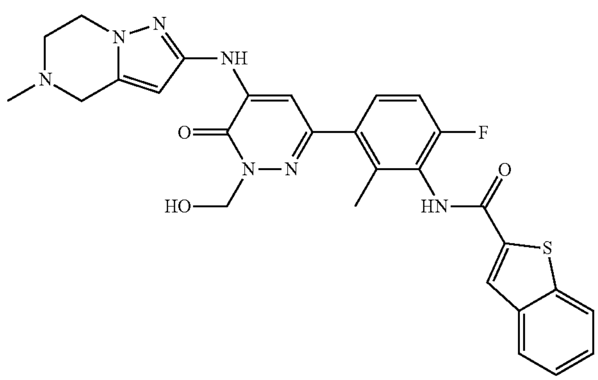 [SMILES: Cc1c(-c2cc(Nc3cc4n(n3)CCN(C)C4)c(=O)n(CO)n2)ccc(F)c1NC(=O)c1cc2ccccc2s1] | N-{6-fluoro-3-[1-(hydroxymethyl)-5-({5-methyl-4H,5H,6H,7H-pyrazolo[1,5-a]pyrazin-2-yl}amino)-6-oxo-1,6-dihydropyridazin-3-yl]-2-methylphenyl}-1-benzothiophene-2-carboxamide | 559 | 560.2 |
| 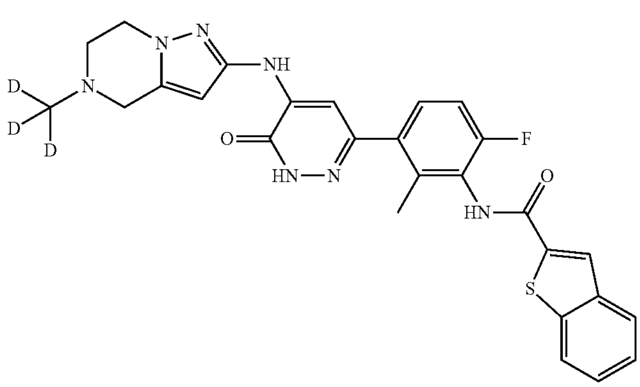 [SMILES: [2H]C([2H])([2H])N1CCn2nc(Nc3cc(-c4ccc(F)c(NC(=O)c5cc6ccccc6s5)c4C)n[nH]c3=O)cc2C1] | N-[6-fluoro-2-methyl-3-(6-oxo-5-{[5-(trideuteriomethyl)-4H,5H,6H,7H-pyrazolo[1,5-a]pyrazin-2-yl]amino}-1,6-dihydropyridazin-3-yl)phenyl]-1-benzothiophene-2-carboxamide | 532 | 533.1 |

-continued

| Structure | Name | MW calcd | MH+ m/z obs |
|---|---|---|---|
| | N-(3-{5-[(5-amino-1-methyl-1H-pyrazol-3-yl)amino]-6-oxo-1,6-dihydropyridazin-3-yl}-6-fluoro-2-methylphenyl)-1-benzothiophene-2-carboxamide | 489 | 490.1 |
| | 5-tert-butyl-N-[2,6-dimethyl-3-(6-oxo-5-{[5-(trideuteriomethyl)-4H,5H,6H,7H-pyrazolo[1,5-a]pyrazin-2-yl]amino}-1,6-dihydropyridazin-3-yl)phenyl]pyrazine-2-carboxamide | 530 | 531.6 |
| | 4-hydroxy-5,5-dimethyl-N-[(3R)-1-[1-methyl-5-({5-methyl-4H,5H,6H,7H-pyrazolo[1,5-a]pyrazin-2-yl)amino)-6-oxo-1,6-dihydropidazin-3yl]piperidin-3-yl)-4H,5H,6H-cyclopenta[b]thiophene-2-carboxamide | 552 | 553.1 |
| | 4-tert-butyl-N-{3-[5-({5-[(dimethylcarbamoyl)(hydroxy)methyl]pyridin-2-yl}amino)-1-methyl-6-oxo-1,6-dihydropyridazin-3-yl]-6-fluoro-2-methylphenyl}benzamide | 586 | 587.3 |
| | 3-(tert-butoxy)-N-(3-(5-{(1,5-dimethyl-1H-pyrazol-3-yl)amino}-6-oxo-1,6-dihydropyridazin-3-yl}-2-methylphenyl)azetidine-1-carboxamide | 465 | 466.5 |

| Structure | Name | MW calcd | MH+ m/z obs |
|---|---|---|---|
| 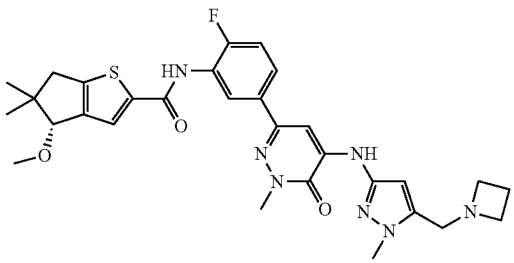 [SMILES: CO[C@H]1c2cc(C(=O)Nc3cc(-c4cc(Nc5cc(CN6CCC6)n(C)n5)c(=O)n(C)n4)ccc3F)sc2CC1(C)C] | (4R)-N-[5-(5-{[5-(azetidin-1-ylmethyl)-1-methyl-1H-pyrazol-3-yl]amino}-1-methyl-6-oxo-1,6-dihydropyridazin-3-yl)-2-fluorophenyl]-4-methoxy-5,5-dimethyl-4H,5H,6H-cyclopenta[b]thiophene-2-carboxamide | 591 | 592.1 |
|  | (4S)-N-[5-(5-({[5-(azetidin-1-ylmethyl)-1-methyl-1H-pyrazol-3-yl]amino}-1-methyl-6-oxo-1,6-dihydropyridazin-3-yl)-2-fluorophenyl]-4-methoxy-5,5-dimethyl-4H,5H,6H-cyclopenta[b]thiophene-2-carboxamide | 591 | 592.1 |
|  | 4-tert-butyl-N-{5-methyl-2-[5-({5-methyl-4H,5H,6H,7H-pyrazolo[1,5-a]pyrazin-2-yl}amino)-6-oxo-1,6-dihydropyridazin-3-yl]-1,3-thiazol-4-yl}benzamide | 518 | 519.2 |
| 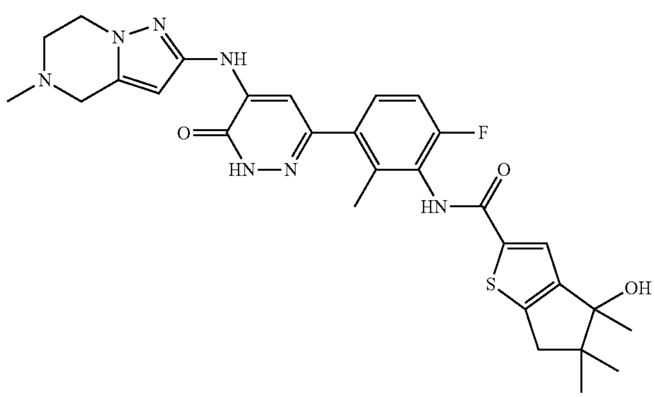 [SMILES: Cc1c(-c2cc(Nc3cc4n(n3)CCN(C)C4)c(=O)[nH]n2)ccc(F)c1NC(=O)c1cc2c(s1)CC(C)(C)C2(C)O] | N-[6-fluoro-2-methyl-3-[5-({5-methyl-4H,5H,6H,7H-pyrazolo[1,5-a]pyrazin-2-yl}amino)-6-oxo-1,6-dihydropyridazin-3-yl]phenyl]-4-hydroxy-4,5,5-trimethyl-4H,5H,6H-cyclopenta[b]thiophene-2-carboxamide | 577 | 578.1 |
| 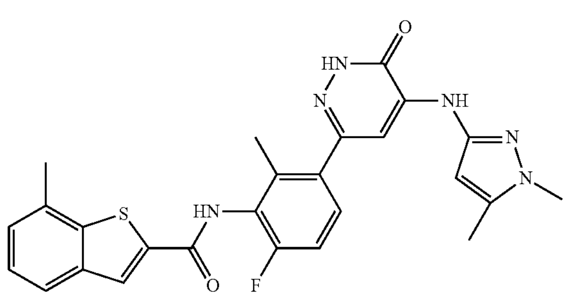 [SMILES: Cc1c(-c2cc(Nc3cc(C)n(C)n3)c(=O)[nH]n2)ccc(F)c1NC(=O)c1cc2cccc(C)c2s1] | N-(3-{5-[(1,5-dimethyl-1H-pyrazol-3-yl)amino]-6-oxo-1,6-dihydropyridazin-3-yl}-6-fluoro-2-methylphenyl)-7-methyl-1-benzothiophene-2-carboxamide | 502 | 503 |

-continued

| Structure | Name | MW calcd | MH+ m/z obs |
|---|---|---|---|
| 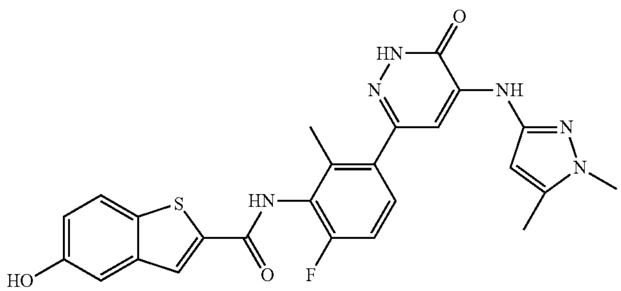 [SMILES: Cc1c(-c2cc(Nc3cc(C)n(C)n3)c(=O)[nH]n2)ccc(F)c1NC(=O)c1cc2cc(O)ccc2s1] | N-(3-{5-[(1,5-dimethyl-1H-pyrazol-3-yl)amino]-6-oxo-1,6-dihydropyridazin-3-yl}-6-fluoro-2-methylphenyl)-5-hydroxy-1-benzothiophene-2-carboxamide | 504 | 505.1 |
| 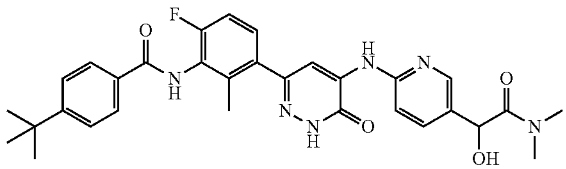 [SMILES: Cc1c(-c2cc(Nc3ccc(C(O)C(=O)N(C)C)cn3)c(=O)[nH]n2)ccc(F)c1NC(=O)c1ccc(C(C)(C)C)cc1] | 4-tert-butyl-N-{3-[5-({5-[(dimethylcarbamoyl)(hydroxy)methyl]pyridin-2-yl}amino)-6-oxo-1,6-dihydropyridazin-3-yl]-6-fluoro-2-methylphenyl}benzamide | 572 | 573.3 |
| 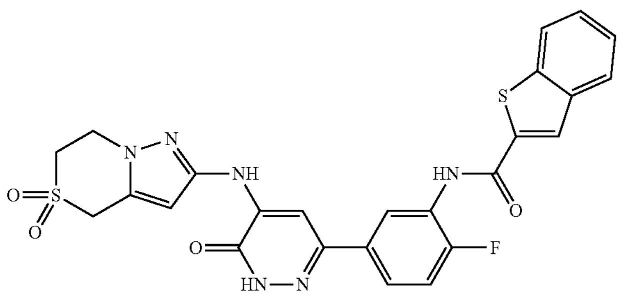 [SMILES: O=C(Nc1cc(-c2cc(Nc3cc4n(n3)CCS(=O)(=O)C4)c(=O)[nH]n2)ccc1F)c1cc2ccccc2s1] | N-{5-[5-({5,5-dioxo-4H,6H,7H-pyrazolo[3,2-c][1,4]thiazin-2-yl}amino)-6-oxo-1,6-dihydropyridazin-3-yl]-2-fluorophenyl}-1-benzothiophene-2-carboxamide | 550 | 550.9 |
| 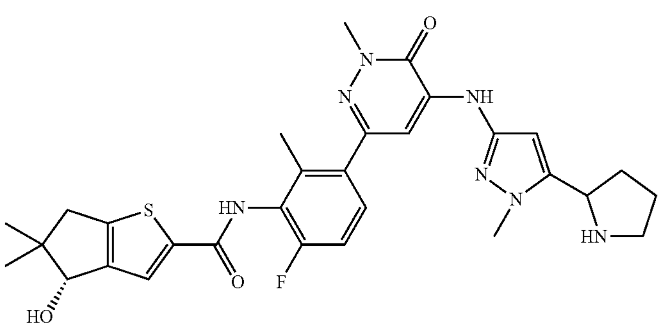 [SMILES: Cc1c(-c2cc(Nc3cc(C4CCCN4)n(C)n3)c(=O)n(C)n2)ccc(F)c1NC(=O)c1cc2c(s1)CC(C)(C)[C@H]2O] | (4R)-N-[6-fluoro-2-methyl-3-(1-methyl-5-{[1-methyl-5-(pyrrolidin-2-yl-1H-pyrazol-3-yl]amino}-6-oxo-1,6-dihydropyridazin-3-yl)phenyl]-4-hydroxy-5,5-dimethyl-4H,5H,6H-cyclopenta[b]thiophene-2-carboxamide | 591 | 592.3 |
| 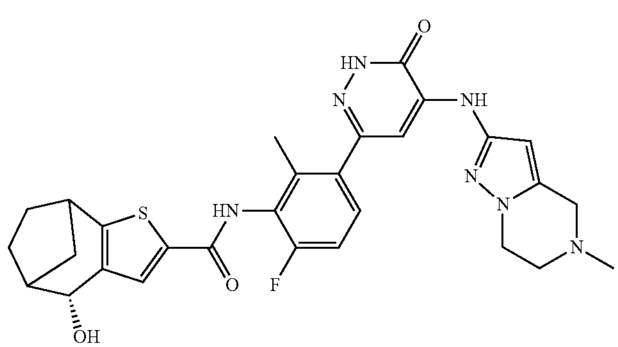 | (7R)-N-{6-fluoro-2-methyl-3-[5-({5-methyl-4H,5H,6H,7H-pyrazolo[1,5-a]pyrazin-2-yl}amino)-6-oxo-1,6-dihydropyridazin-3-yl]phenyl}-7-hydroxy-3-thiatricyclo[6.2.1.0^{2,6}]undeca-2(6),4-diene-4-carboxamide | 575 | 576.2 |

-continued

| Structure | Name | MW calcd | MH+ m/z obs |
|---|---|---|---|
| 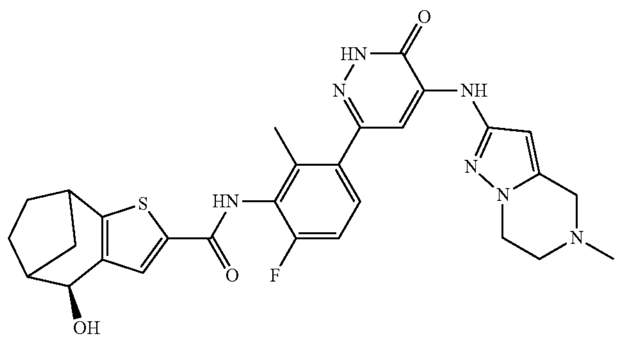 [SMILES: Cc1c(-c2cc(Nc3cc4n(n3)CCN(C)C4)c(=O)[nH]n2)ccc(F)c1NC(=O)c1cc2c(s1)C1CCC(C1)[C@@H]2O] | (7S)-N-{6-fluoro-2-methyl-3-[5-({5-methyl-4H,5H,6H,7H-pyrazolo[1,5-a]pyrazin-2-yl}amino)-6-oxo-1,6-dihydropyridazin-3-yl]phenyl}-7-hydroxy-3-thiatricyclo[6.2.1.0^{2,6}]undeca-2(6),4-diene-4-carboxamide | 575 | 576.2 |
| | (4R)-4-hydroxy-5,5-dimethyl-N-{(3R)-1-[1-methyl-5-({5-methyl-4H,5H,6H,7H-pyrazolo[1,5-a]pyrazin-2-yl}amino)-6-oxo-1,6-dihydropyridazin-3-yl]piperidin-3-yl]-4H,5H,6H-cyclopenta[b]thiophene-2-carboxamide | 552 | 553.3 |
| 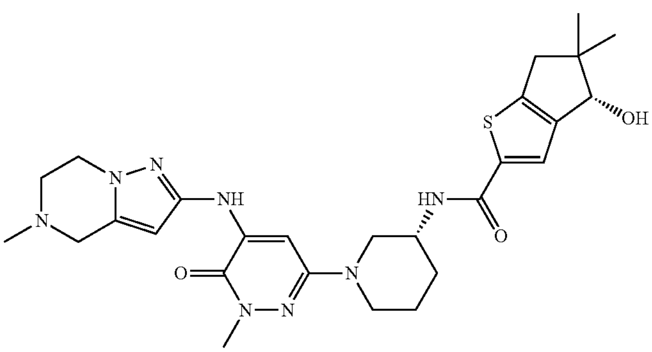 [SMILES: CN1CCn2nc(Nc3cc(N4CCC[C@@H](NC(=O)c5cc6c(s5)CC(C)(C)[C@@H]6O)C4)nn(C)c3=O)cc2C1] | (4S)-4-hydroxy--5,5-dimethyl-N-[(3R)-1-[1-methyl-5-({5-methyl-4H,5H,6H,7H-pyrazolo[1,5-a]pyrazin-2-yl}amino)-6-oxo-1,6-dihydropyridazin-3-yl]piperidin-3-yl]-4H,5H,6H-cyclopenta[b]thiophene-2-carboxamide | 552 | 553.3 |
| 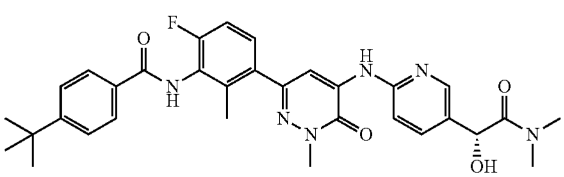 [SMILES: Cc1c(-c2cc(Nc3ccc([C@@H](O)C(=O)N(C)C)cn3)c(=O)n(C)n2)ccc(F)c1NC(=O)c1ccc(C(C)(C)C)cc1] | 4-tert-butyl-N-{3-[5-({5-[(R)-(dimethylcarbamoyl)(hydroxy)methyl]pyridin-2-yl}amino)-1-methyl-6-oxo-1,6-dihydropyridazin-3-yl]-6-fluoro-2-methylphenyl}benzamide | 586 | 587.2 |
| 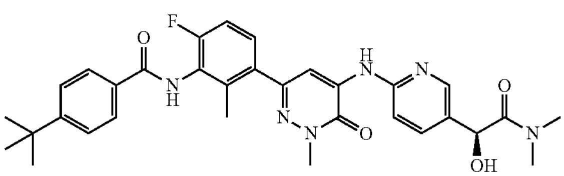 [SMILES: Cc1c(-c2cc(Nc3ccc([C@H](O)C(=O)N(C)C)cn3)c(=O)n(C)n2)ccc(F)c1NC(=O)c1ccc(C(C)(C)C)cc1] | 4-tert-butyl-N-{3-[5-({5-[(S)-(dimethylcarbamoyl)(hydroxy)methyl]pyridin-2-yl}amino)-1-methyl-6-oxo-1,6-dihydropyridazin-3-yl]-6-fluoro-2-methylphenyl}benzamide | 586 | 587.2 |
| 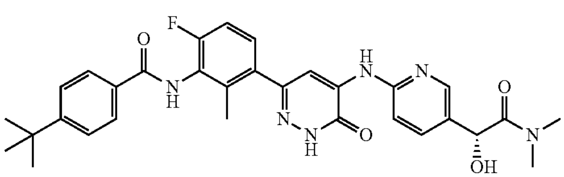 | 4-tert-butyl-N-{3-[5-({5-[(R)-(dimethylcarbamoyl)(hydroxy)methyl]pyridin-2-yl}amino)-6-oxo-1,6-dihydropyridazin-3-yl]-6-fluoro-2-methylphenyl}benzamide | 572 | 572.6 |

-continued

| Structure | Name | MW calcd | MH+ m/z obs |
|---|---|---|---|
| 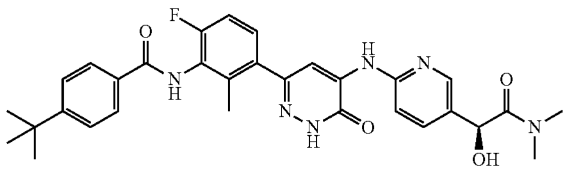 | 4-tert-butyl-N-{3-[5-({5-[(S)-(dimethylcarbamoyl)(hydroxy)methyl]pyridin-2-yl}amino)-6-oxo-1,6-dihydropyridazin-3-yl]-6-fluoro-2-methylphenyl}benzamide | 572 | 572.6 |
| 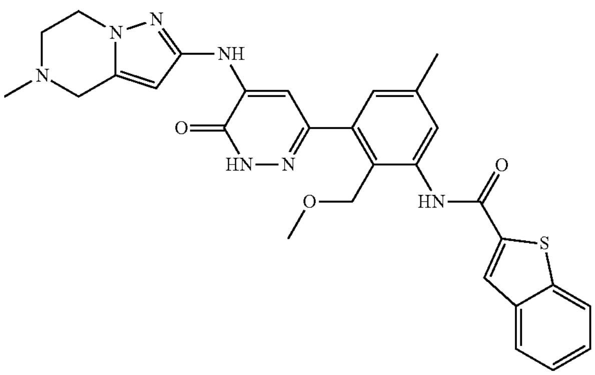 [SMILES: COCc1c(NC(=O)c2cc3ccccc3s2)cc(C)cc1-c1cc(Nc2cc3n(n2)CCN(C)C3)c(=O)[nH]n1] | N-[2-(methoxymethyl)-3-[5-({5-methyl-4H,5H,6H,7H-pyrazolo[1,5-a]pyrazin-2-yl}amino)-6-oxo-1,6-dihydropyridazin-3-yl]phenyl]-1-benzothiophene-2-carboxamide | 541 | 542 |
| | 6-fluoro-N-{6-fluoro-2-methyl-3-[5-({5-methyl-4H,5H,6H,7H-pyrazolo[1,5-a]pyrazin-2-yl}amino)-6-oxo-1,6-dihydropyridazin-3-yl]phenyl}-1-benzothiophene-2-carboxamide | 547 | 548.1 |
| 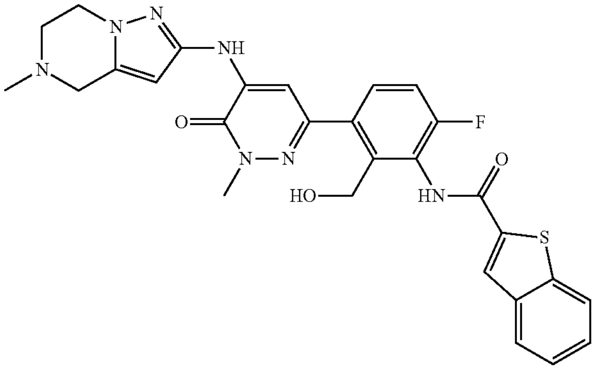 [SMILES: CN1CCn2nc(Nc3cc(-c4ccc(F)c(NC(=O)c5cc6ccccc6s5)c4CO)nn(C)c3=O)cc2C1] | N-[6-fluoro-2-(hydroxymethyl)-3-[1-methyl-5-({5-methyl-4H,5H,6H,7H-pyrazolo[1,5-a]pyrazin-2-yl}amino)-6-oxo-1,6-dihydropyridazin-3-yl]phenyl]-1-benzothiophene-2-carboxamide | 559 | 560.1 |

-continued

| Structure | Name | MW calcd | MH+ m/z obs |
|---|---|---|---|
| 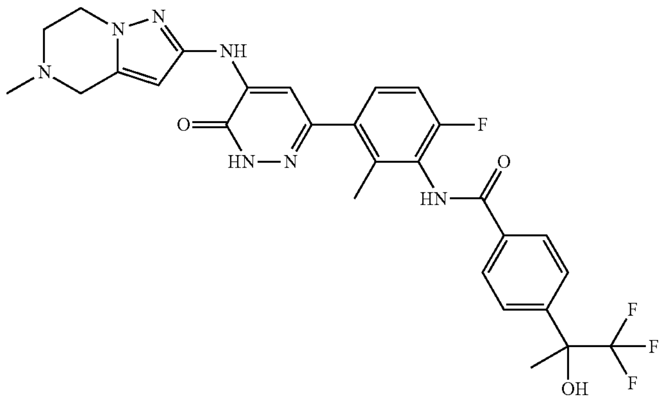 [SMILES: Cc1c(-c2cc(Nc3cc4n(n3)CCN(C)C4)c(=O)[nH]n2)ccc(F)c1NC(=O)c1ccc(C(C)(O)C(F)(F)F)cc1] | N-(6-fluoro-2-methyl-3-[5-({5-methyl-4H,5H,6H,7H-pyrazolo[1,5-a]pyrazin-2-yl}amino)-6-oxo-1,6-dihydropyridazin-3-yl]phenyl}-4-(1,1,1-trifluoro-2-hydroxypropan-2-yl)benzamide | 585 | 586 |
| 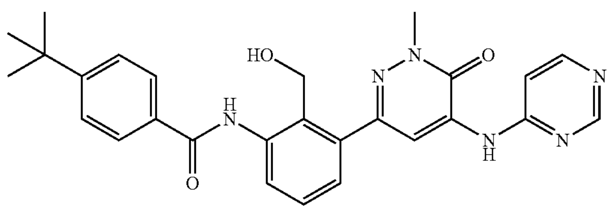 [SMILES: Cn1nc(-c2cccc(NC(=O)c3ccc(C(C)(C)C)cc3)c2CO)cc(Nc2ccncn2)c1=O] | 4-tert-butyl-N-[2-(hydroxymethyl)-3-[1-methyl-6-oxo-5-(pyrimidin-4-ylamino)-1,6-dihydropyridazin-3-yl]phenyl]benzamide | 484 | 485.2 |
| 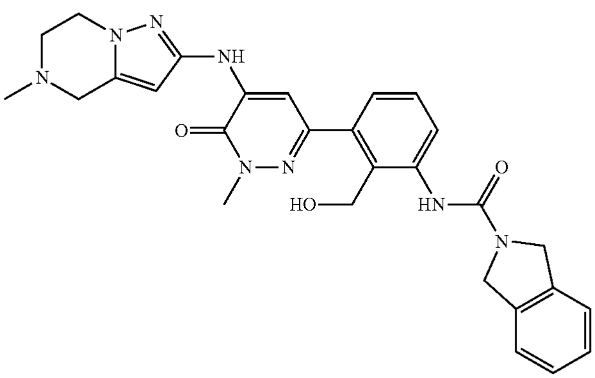 [SMILES: CN1CCn2nc(Nc3cc(-c4cccc(NC(=O)N5Cc6ccccc6C5)c4CO)nn(C)c3=O)cc2C1] | N-[2-(hydroxymethyl)-3-[1-methyl-5-({5-methyl-4H,5H,6H,7H-pyrazolo[1,5-a]pyrazin-2-yl}amino)-6-oxo-1,6-dihydropyridazin-3-yl]phenyl]-2,3-dihydro-1H-isoindole-2-carboxamide | 526 | 527.8 |
| 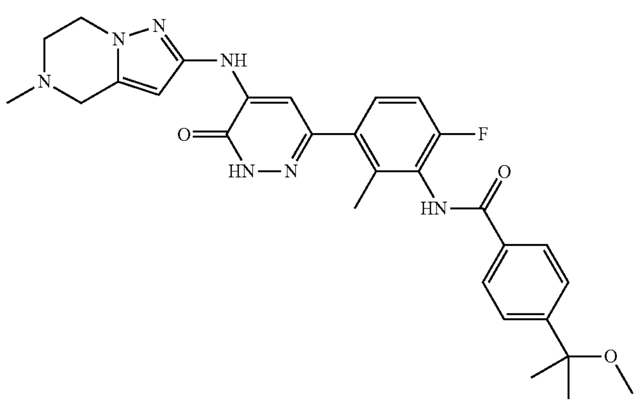 | N-{6-fluoro-2-methyl-3-[5-({5-methyl-4H,5H,6H,7H-pyrazolo[1,5-a]pyrazin-2-yl}amino)-6-oxo-1,6-dihydropyridazin-3-yl]phenyl}-4-(2-methoxypropan-2-yl)benzamide | 545 | 546 |

-continued

| Structure | Name | MW calcd | MH+ m/z obs |
|---|---|---|---|
| 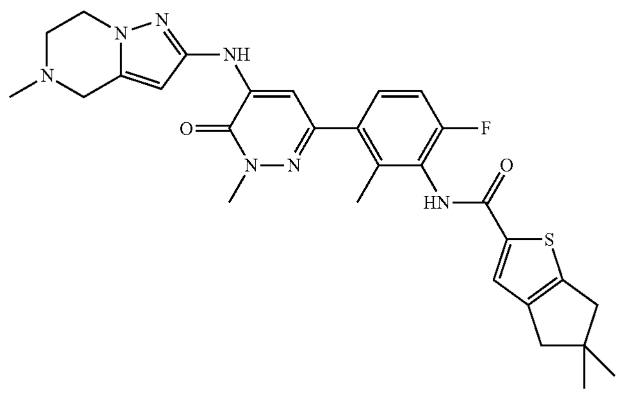 | N-{6-fluoro-2-methyl-3-[5-({5-methyl-4H,5H,6H,7H-pyrazolo[1,5-a]pyrazin-2-yl}amino)-6-oxo-1,6-dihydropyridazin-3-yl]phenyl-5,5-dimethyl-4H,5H,6H-cyclopenta[b]thiophene-2-carboxamide | 547 | 548 |
| 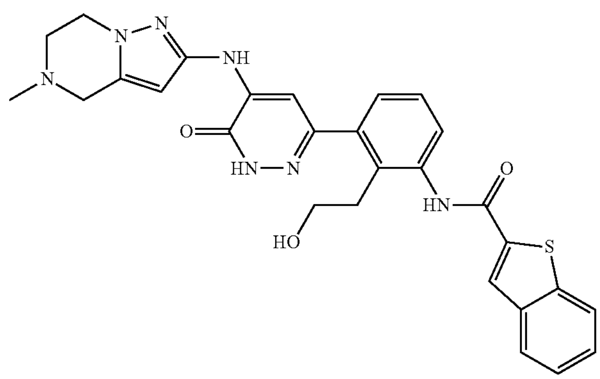 [SMILES: CN1CCn2nc(Nc3cc(-c4cccc(NC(=O)c5cc6ccccc6s5)c4CCO)n[nH]c3=O)cc2C1] | N-[2-(2-hydroxyethyl)-3-[5-({5-methyl-4H,5H,6H,7H-pyrazolo[1,5-a]pyrazin-2-yl}amino)-6-oxo-1,6-dihydropyridazin-3-yl]phenyl)-1-benzothiophene-2-carboxamide | 541 | 542.3 |
| | N-[2-(hydroxymethyl)-3-[5-({5-methyl-4H,5H,6H,7H-pyrazolo[1,5-a]pyrazin-2-yl)amino)-6-oxo-1,6-dihydropyridazin-3-yl]phenyl]-2,3-dihydro-1H-isoindole-2-carboxamide | 512 | 513.2 |
| 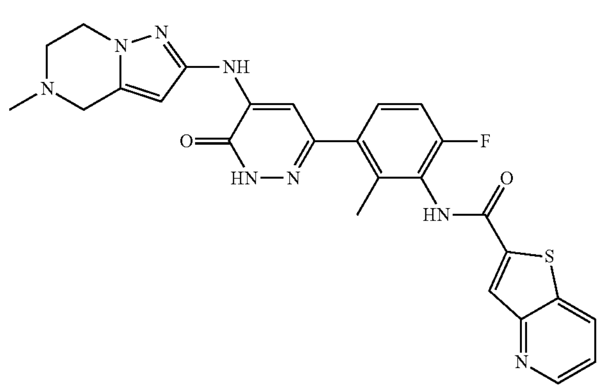 | N-{6-fluoro-2-methyl-3-[5-([5-methyl-4H,5H,6H,7H-pyrazolo[1,5-a]pyrazin-2-yl}amino)-6-oxo-1,6-dihydropyridazin-3-yl]phenyl)thieno[3,2-b]pyridine-2-carboxamide | 530 | 531 |

-continued

| Structure | Name | MW calcd | MH+ m/z obs |
|---|---|---|---|
| | N-(6-fluoro-2-methyl-3-[5-({5-methyl-4H,5H,6H,7H-pyrazolo[1,5-a]pyrazin-2-yl}amino)-6-oxo-1,6-dihydropyridazin-3-yl]phenyl)thieno[2,3-b]pyridine-2-carboxanilde | 530 | 531 |
| 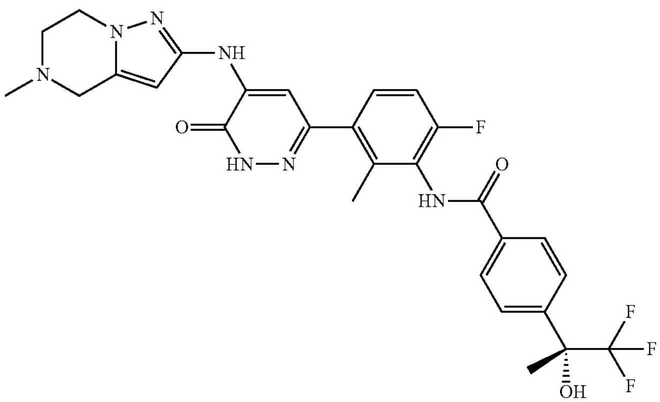 [SMILES: Cc1c(-c2cc(Nc3cc4n(n3)CCN(C)C4)c(=O)[nH]n2)ccc(F)c1NC(=O)c1ccc([C@@](C)(O)C(F)(F)F)cc1] | N-{6-fluoro-2-methyl-3-[5-({5-methyl-4H,5H,6H,7H-pyrazolo[1,5-a]pyrazin-2-yl}amino)-6-oxo-1,6-dihydropyridazin-3-yl]phenyl}-4-[(2R)-1,1,1-trifluoro-2-hydroxypropan-2-yl]benzamide | 585 | 586.2 |
| 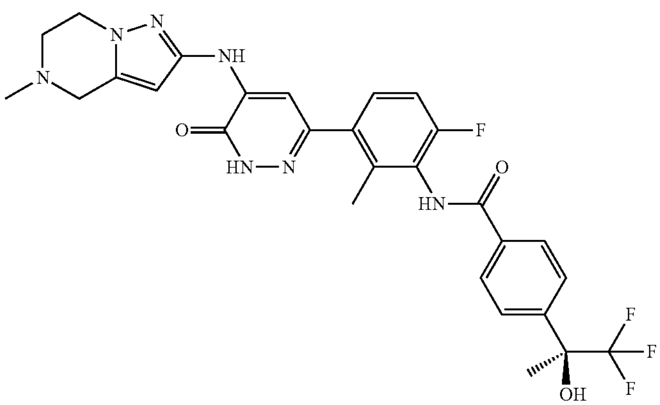 [SMILES: Cc1c(-c2cc(Nc3cc4n(n3)CCN(C)C4)c(=O)[nH]n2)ccc(F)c1NC(=O)c1ccc([C@](C)(O)C(F)(F)F)cc1] | N-{6-fluoro-2-methyl-3-[5-({5-methyl-4H,5H,6H,7H-pyrazolo[1,5-a]pyrazin-2-yl}amino)-6-oxo-1,6-dihydropyridazin-3-yl]phenyl}-4-[(2S)-1,1,1-trifluoro-2-hydroxypropan-2-yl]benzamide | 585 | 586.2 |
| | N-[6-fluoro-2-(hydroxymethyl)-3-(5-({5-methyl-4H,5H,6H,7H-pyrazolo[1,5-a]pyrazin-2-yl}amino)-6-oxo-1,6-dihydropyridazin-3-yl)phenyl]-1-benzothiophene-2-carboxamide | 545 | 546.3 |

-continued

| Structure | Name | MW calcd | MH+ m/z obs |
|---|---|---|---|
| 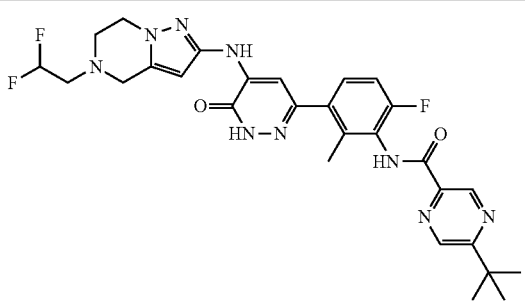 [SMILES: Cc1c(-c2cc(Nc3cc4n(n3)CCN(CC(F)F)C4)c(=O)[nH]n2)ccc(F)c1NC(=O)c1cnc(C(C)(C)C)cn1] | 5-tert-butyl-N-[3-(5-{[5-(2,2-difluoroethyl)-4H,5H,6H,7H-pyrazolo[1,5-a]pyrazin-2-yl]amino}-6-oxo-1,6-dihydropyridazin-3-yl)-6-fluoro-2-methylphenyl]pyrazine-2-carboxamide | 581 | 582 |
| 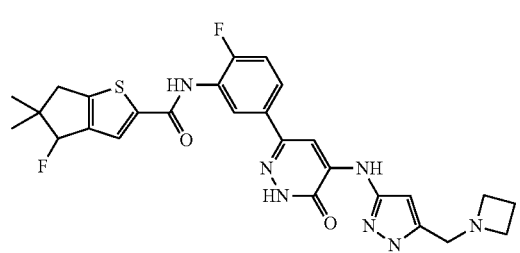 | N-[5-(5-({5-(azetidin)-1-ylmethyl)-1-methyl-1H-pyrazol-3-yl]amino}-6-oxo-1,6-dihydropyridazin-3-yl)-2-fluorophenyl]-4-fluoro-5,5-dimethyl-4H,5H,6H-cyclopenta[b]thiophene-2-carboxamide | 565 | 564 |
| 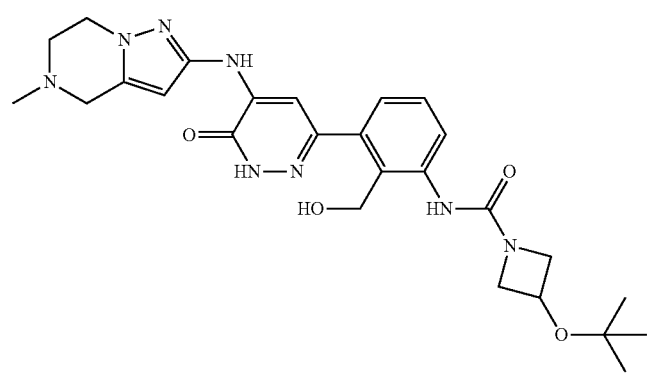 [SMILES: CN1CCn2nc(Nc3cc(-c4cccc(NC(=O)N5CC(OC(C)(C)C)C5)c4CO)n[nH]c3=O)cc2C1] | 3-(tert-butoxy)-N-[2-(hydroxymethyl)-3-[5-({5-methyl-4H,5H,6H,7H-pyrazolo[1,5-a]pyrazin-2-yl}amino)-6-oxo-1,6-dihydropyridazin-3-yl]phenyl]azetidine-1-carboxamide | 522 | 522.6 |
| 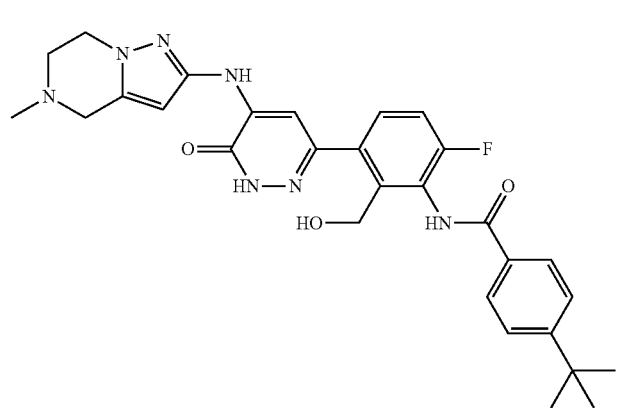 [SMILES: CN1CCn2nc(Nc3cc(-c4ccc(F)c(NC(=O)c5ccc(C(C)(C)C)cc5)c4CO)n[nH]c3=O)cc2C1] | 4-tert-butyl-N-[6-fluoro-2-(hydroxymethyl)-3-[5-({5-methyl-4H,5H,6H,7H-pyrzolo[1,5-a]pyrazin-2-yl]amino)-6-oxo-1,6-dihydropyridazin-3-yl]phenyl]benzamide | 545 | 546.4 |

-continued

| Structure | Name | MW calcd | MH+ m/z obs |
|---|---|---|---|
| 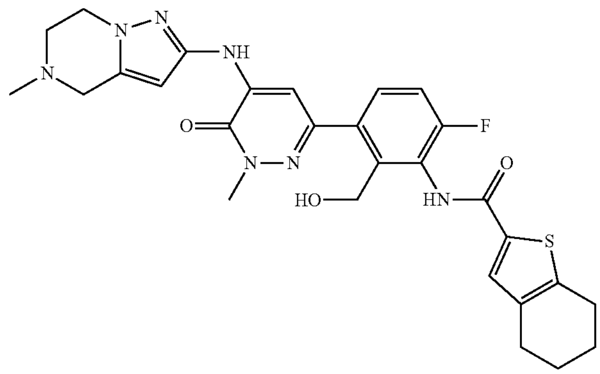 [SMILES: CN1CCn2nc(Nc3cc(-c4ccc(F)c(NC(=O)c5cc6c(s5)CCCC6)c4CO)nn(C)c3=O)cc2C1] | N-[6-fluoro-2-(hydroxymethyl)-3-[1-methyl-5-({5-methyl-4H,5H,6H,7H-pyrazolo-[1,5-a]pyrazin-2-yl}amino)-6-oxo-1,6-dihydropyridazin-3-yl]phenyl]-4,5,6,7-tetrahydro-1-benzothiophene-2-carboxamide | 563 | 564.3 |
| 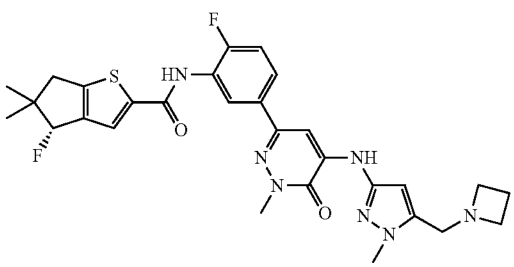 [SMILES: Cn1nc(Nc2cc(-c3ccc(F)c(NC(=O)c4cc5c(s4)CC(C)(C)[C@H]5F)c3)nn(C)c2=O)cc1CN1CCC1] | (4R)-N-[5-(5-{[5-(azetidin-1-ylmethyl)-1-methyl-1H-pyrazol-3yl]amino}-1-methyl-6-oxo-1,6-dihydropyridazin-3-yl)-2-fluorophenyl]-4-fluoro-5,5-dimethyl-4H,5H,6H-cyclopenta[b]thiophene-2-carboxamide | 579 | 578.1 |
| 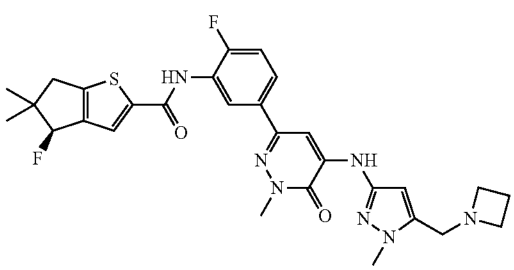 [SMILES: Cn1nc(Nc2cc(-c3ccc(F)c(NC(=O)c4cc5c(s4)CC(C)(C)[C@@H]5F)c3)nn(C)c2=O)cc1CN1CCC1] | (4S)-N-[5-(5-{[5-(azetidin-1-ylmethyl)-1-methyl-1H-pyrazol-3-yl]amino}-1-methyl-6-oxo-1,6-dihydropyridazin-3-yl)-2-fluorophenyl]-4-fluoro-5,5-dimethyl-4H,5H,6H-cyclopenta[b]thiophene-2-carboxamide | 579 | 578.1 |
| | N-{6-fluoro-2-methyl-3-[5-({5-methyl-4H,5H,6H,7H-pyrazolo[1,5-a]pyrazin-2-yl)amino)-6-oxo-1,6-dihydropyridazin-3-yl]phenyl}-4-(1-fluorocyclopropyl)benzamide | 531 | 532 |

While some embodiments have been shown and described, various modifications and substitutions may be made thereto without departing from the spirit and scope of the invention. For example, for claim construction purposes, it is not intended that the claims set forth hereinafter be construed in any way narrower than the literal language thereof, and it is thus not intended that exemplary embodiments from the specification be read into the claims. Accordingly, it is to be understood that the present invention has been described by way of illustration and not limitations on the scope of the claims.

What is claimed is:

1. A compound of Formula I, or a pharmaceutically acceptable salt, hydrate or mixture thereof, wherein

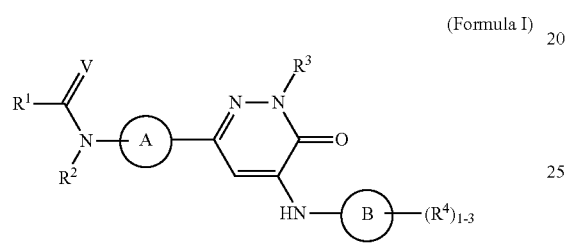

(Formula I)

V is O or NH;
R$^1$ is:

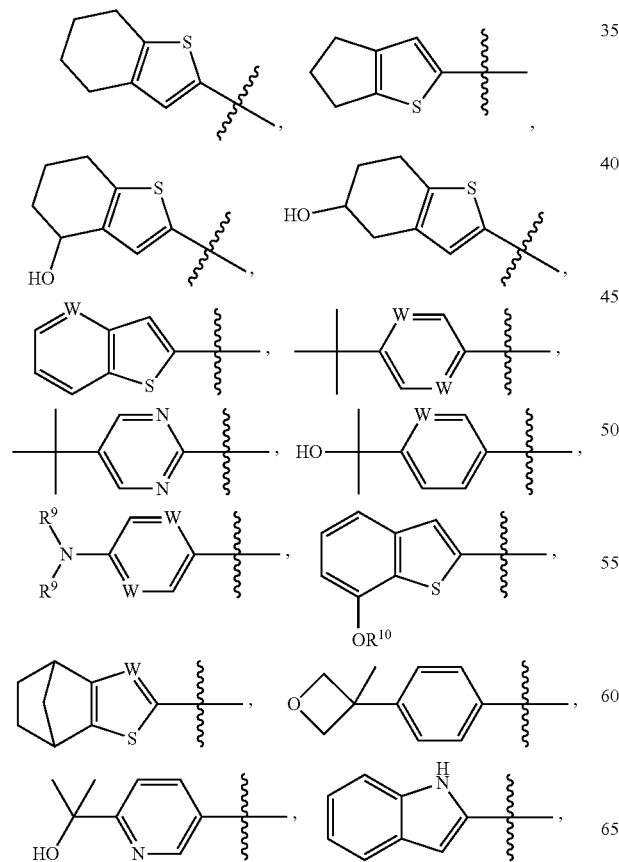

-continued

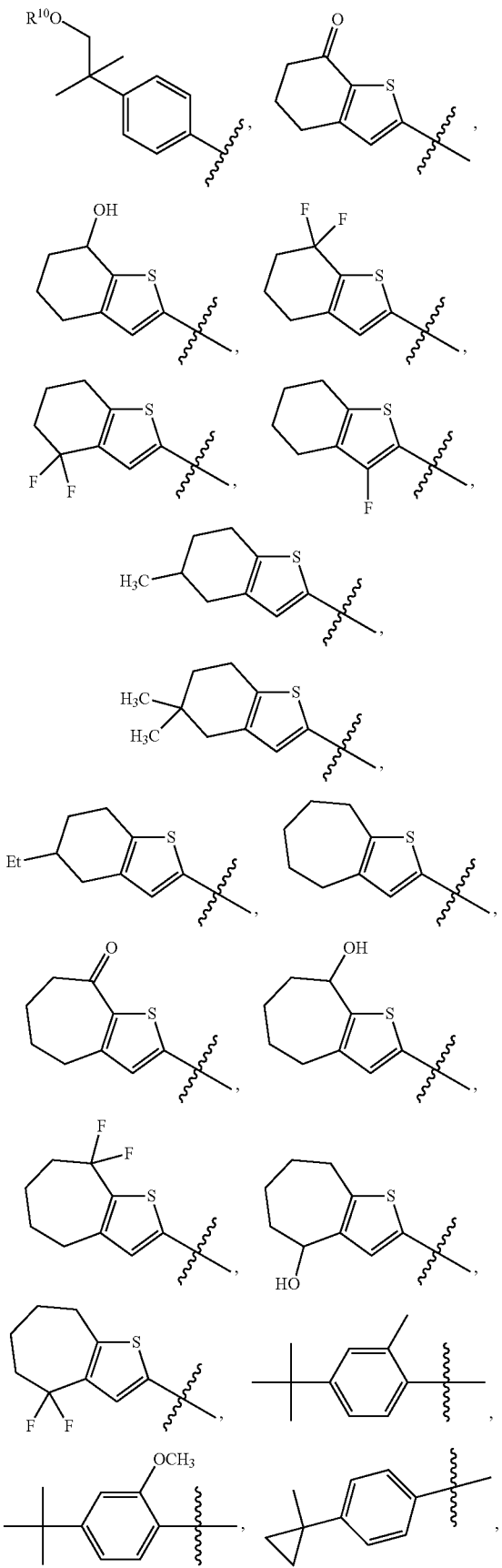

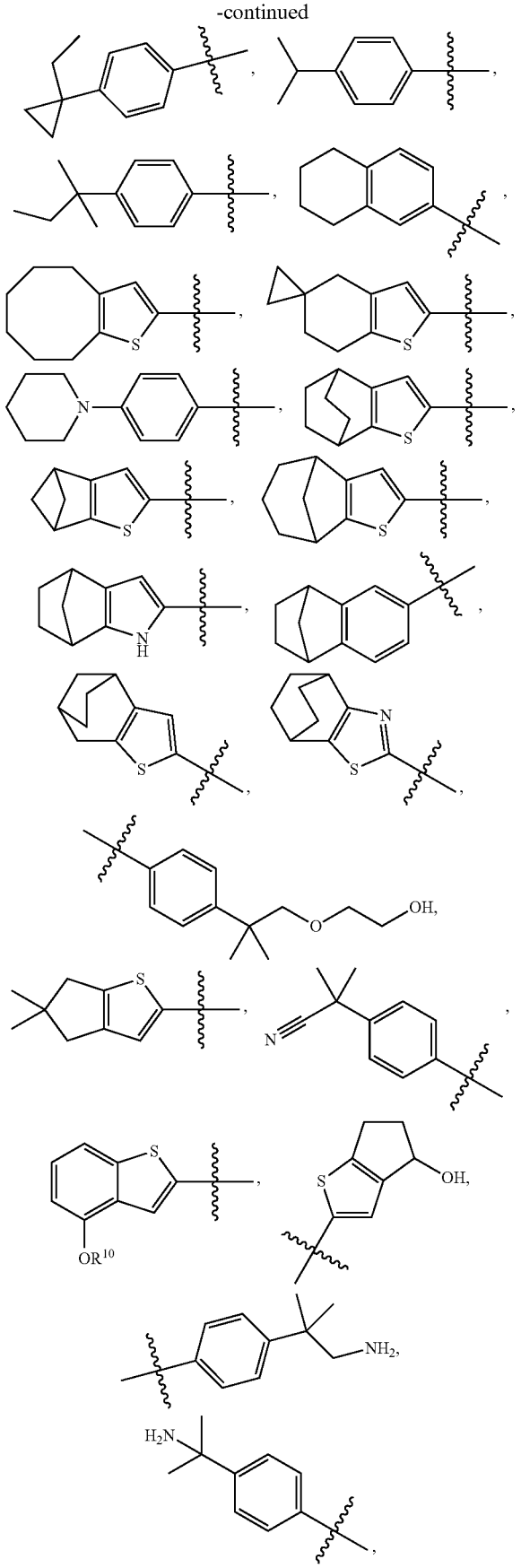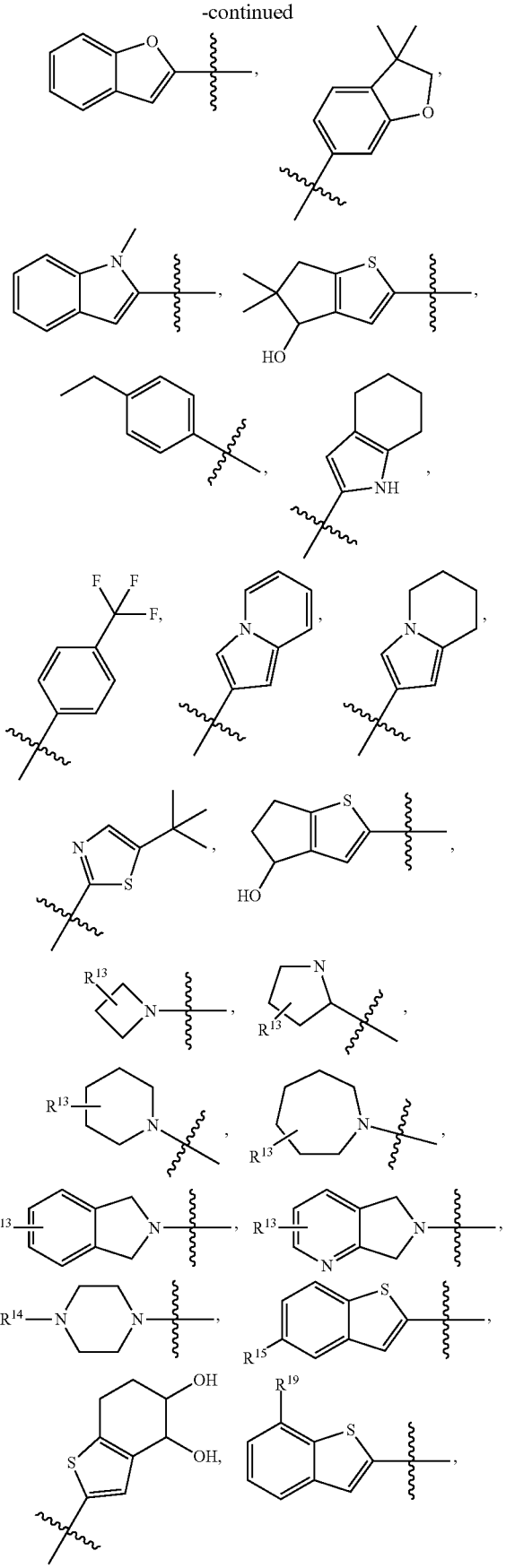

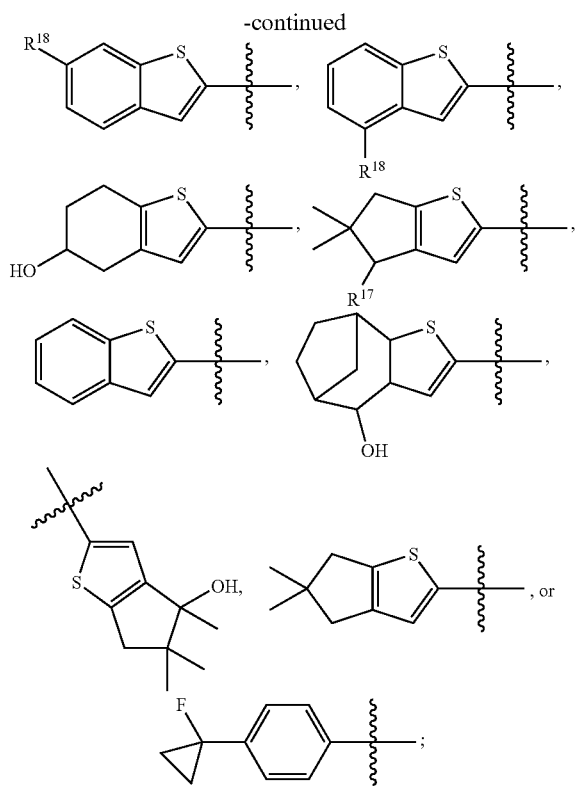

$R^2$ is H, OH, or $C_1$-$C_3$ alkyl optionally substituted with OH or $N(R^{10})_2$;

ring A is

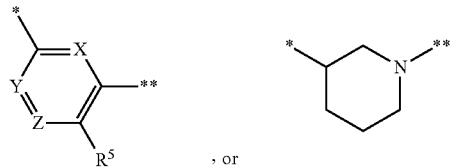

wherein * denotes the point of attachment to $R^1CON(R^2)$— moiety and ** denotes the point of attachment to the pyridazinonyl ring;

$R^3$ is H, $CH_3$ or $CF_3$;

ring B is a 5-6 membered heteroaryl having at least one nitrogen ring atom, or a 5-6 membered heterocyclyl having at least one nitrogen ring atom;

each $R^4$ is independently H, —$R^a$, —$OR^b$, —$SR^b$, —$NR^b R^c$, halo, cyano, nitro, —$COR^b$, —$CO_2 R^b$, —$CONR^b R^c$, —$OCOR^b$, —$OCO_2 R^a$, —$OCONR^b R^c$, —$NR^c COR^b$, —$NR^c CO_2 R^a$, —$NR^c CONR^b R^c$, —$CO_2 R^b$, —$CONR^b R^c$, —$NR^c COR^b$, —$SOR^a$, —$SO_2 R^a$, —$SO_2 NR^b R^c$, or —$NR^c SO_2 R^a$; or two adjacent $R^4$ groups are optionally taken together to form a 5-6 membered ring having 0-2 heteroatoms selected from O, S or N, wherein said 5-6 membered ring is fused to ring B;

$R^a$ is $C_1$-$C_6$ alkyl, cycloalkyl, heterocycloalkyl, aryl, or heteroaryl, wherein each member of $R^a$ is optionally substituted with one to three $R^{11}$ groups;

$R^b$ is H, $C_1$-$C_6$ alkyl, cycloalkyl, heterocycloalkyl, aryl, or heteroaryl, wherein each member of $R^b$ except H is optionally substituted with one to three $R^{11}$ groups;

$R^c$ is H or $C_1$-$C_4$ alkyl optionally substituted with one to three $R^{11}$ groups; or $R^b$ and $R^c$, and the nitrogen to which they are attached, form an optionally substituted heterocycloalkyl group;

each $R^{11}$ is independently selected from $C_1$-$C_4$ alkyl, cycloalkyl, heterocycloalkyl, aryl, heteroaryl, aryl-$C_1$-$C_4$ alkyl-, heteroaryl-$C_1$-$C_4$ alkyl-, cycloalkyl-$C_1$-$C_4$ alkyl-, heterocycloalkyl-$C_1$-$C_4$ alkyl-, $C_1$-$C_4$ haloalkyl-, —$OC_1$-$C_4$ alkyl, —O-heterocycloalkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —NH($C_1$-$C_4$ alkyl), —N($C_1$-$C_4$ alkyl)($C_1$-$C_4$ alkyl), —N($C_1$-$C_4$ alkyl)($C_1$-$C_4$ alkylphenyl), —NH($C_1$-$C_4$ alkylphenyl), —NH-heterocycloalkyl, cyano, nitro, oxo, —$CO_2H$, —C(O)$OC_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2 NH_2$, —$SO_2 NH$($C_1$-$C_4$ alkyl), —$SO_2 NH$(phenyl), —$NHSO_2$($C_1$-$C_4$ alkyl), —$NHSO_2$(phenyl), and —$NHSO_2$($C_1$-$C_4$ haloalkyl), wherein said alkyl, cycloalkyl, heterocycloalkyl, aryl, heteroaryl, phenyl and haloalkyl are optionally independently substituted with one to three $R^{12}$ groups;

each $R^{12}$ is independently selected from $C_1$-$C_4$ alkyl, cycloalkyl, heterocycloalkyl, aryl, heteroaryl, aryl-$C_1$-$C_4$ alkyl-, heteroaryl-$C_1$-$C_4$ alkyl-, cycloalkyl-$C_1$-$C_4$ alkyl-, heterocycloalkyl-$C_1$-$C_4$ alkyl-, $C_1$-$C_4$ haloalkyl-, —$OC_1$-$C_4$ alkyl, —O-heterocycloalkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —NH($C_1$-$C_4$ alkyl), —N($C_1$-$C_4$ alkyl)($C_1$-$C_4$ alkyl), —N($C_1$-$C_4$ alkyl)($C_1$-$C_4$ alkylphenyl), —NH($C_1$-$C_4$ alkylphenyl), —O-heterocycloalkyl, cyano, nitro, oxo, —$CO_2H$, —C(O)$OC_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2 NH_2$, —$SO_2 NH$($C_1$-$C_4$ alkyl), —$SO_2 NH$(phenyl), —$NHSO_2$($C_1$-$C_4$ alkyl), —$NHSO_2$(phenyl), and —$NHSO_2$($C_1$-$C_4$ haloalkyl);

X is N or $CR^6$;
Y is N or $CR^7$;
Z is N or $CR^8$; provided that only one of X, Y and Z is N;
$R^5$ is H or F;
$R^6$ is H, $CH_3$, F, Cl, CN, $OCH_3$, OH, $CF_3$, $CH_2 OH$, $CH_2 F$, CH=O, $CH_2 OCH_3$, $COCH_3$, or $(CH_2)_2 OH$;
$R^7$ is H, $CH_3$, F, Cl, CN or $OCH_3$;
$R^8$ is H, $CH_3$, $CF_3$, F, Cl, CN or $OCH_3$;
W is CH or N;
W' is CH or N;
each $R^9$ is independently $C_1$-$C_3$ alkyl;
each $R^{10}$ is independently H or $CH_3$;
each $R^{13}$ is independently H, halo, $C_1$-$C_6$ alkyl, $C_1$-$C_6$ alkoxy, or $C_1$-$C_6$ haloalkyl;
each $R^{14}$ is independently H, C(=O)H, C(=O)$R^9$, or $C_1$-$C_6$ alkyl wherein said alkyl is optionally substituted with one or more OH groups;
$R^{15}$ is $CH_3$, F, Cl, Br, OH, or $OCH_3$;
$R^{16}$ is F, Cl, Br, $CH_3$, or $CF_3$,
$R^{17}$ is F or $OCH_3$;
$R^{18}$ is F or Cl; and
$R^{19}$ is F or $CH_3$.

2. The compound of claim 1 wherein ring A is:

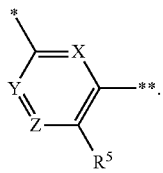

3. The compound of claim 2, wherein the compound is:

Formula III-a

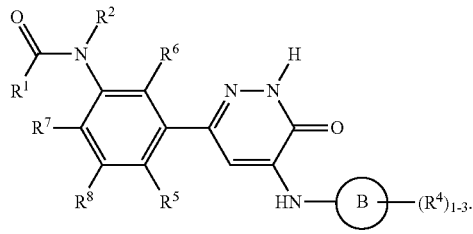

4. The compound of claim 2, wherein the compound is:

Formula III-b

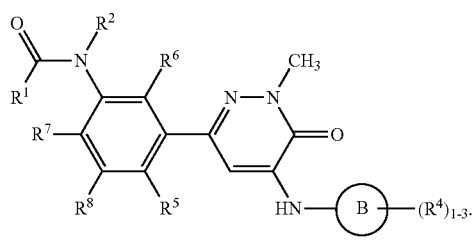

5. The compound of claim 1 wherein ring A is:

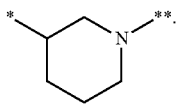

6. The compound of claim 1, wherein $R^1$ is:

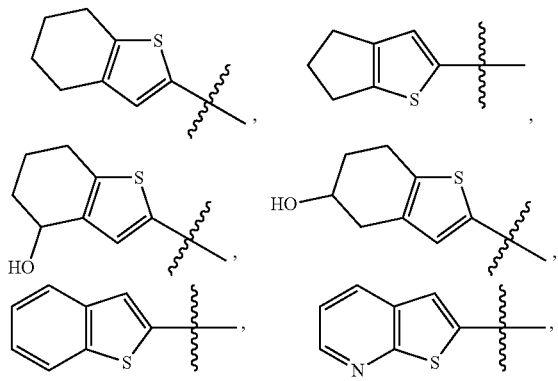

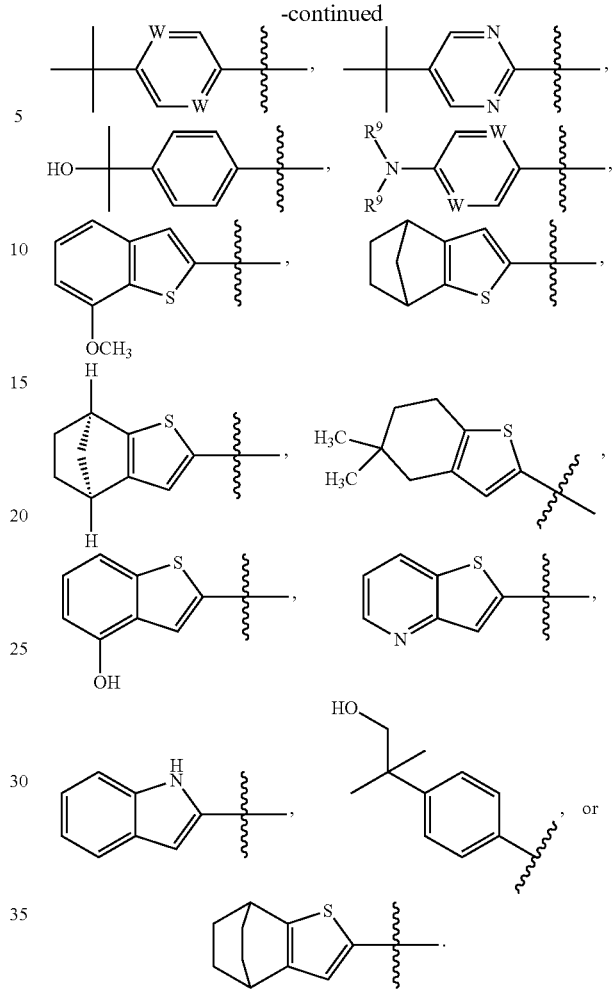

7. The compound of claim 1 that is:
N-(3-{5-[(1,5-dimethyl-1H-pyrazol-3-yl)amino]-6-oxo-1,6-dihydropyridazin-3-yl}-2,6-difluorophenyl)thieno[3,2-b]pyridine-2-carboxamide;
N-(2-fluoro-5-{5-[(5-methyl-1,2-oxazol-3-yl)amino]-6-oxo-1,6-dihydropyridazin-3-yl}phenyl)-4,5,6,7-tetrahydro-1-benzothiophene-2-carboxamide;
N-{2-fluoro-5-[6-oxo-5-(pyrimidin-4-ylamino)-1,6-dihydropyridazin-3-yl]phenyl}-4,5,6,7-tetrahydro-1-benzothiophene-2-carboxamide;
N-{2-fluoro-5-[5-({1-[2-(oxan-2-yloxy)ethyl]-1H-pyrazol-3-yl}amino)-6-oxo-1,6-dihydropyridazin-3-yl]phenyl}-4,5,6,7-tetrahydro-1-benzothiophene-2-carboxamide;
N-{2-methyl-3-[6-oxo-5-({5-[4-(propan-2-yl)piperazin-1-yl]pyridin-2-yl}amino)-1,6-dihydropyridazin-3-yl]phenyl}-4,5,6,7-tetrahydro-1-benzothiophene-2-carboxamide;
N-(5-{5-[(5-cyclopropyl-1H-pyrazol-3-yl)amino]-6-oxo-1,6-dihydropyridazin-3-yl}-2-fluorophenyl)-4,5,6,7-tetrahydro-1-benzothiophene-2-carboxamide;
N-[3-(5-{[5-(4-ethylpiperazin-1-yl)pyridin-2-yl]amino}-1-methyl-6-oxo-1,6-dihydropyridazin-3-yl)-2-methylphenyl]-4,5,6,7-tetrahydro-1-benzothiophene-2-carboxamide;
N-(5-{5-[(1,5-dimethyl-1H-pyrazol-3-yl)amino]-6-oxo-1,6-dihydropyridazin-3-yl}-2-fluorophenyl)-5-hydroxy-4,5,6,7-tetrahydro-1-benzothiophene-2-carboxamide;

N-(3-{5-[(1,5-dimethyl-1H-pyrazol-3-yl)amino]-6-oxo-1,6-dihydropyridazin-3-yl}-6-fluoro-2-methylphenyl)-4,5,6,7-tetrahydro-1-benzothiophene-2-carboxamide;

(1R,7S)—N-(2-fluoro-5-(6-oxo-5-(pyrimidin-4-ylamino)-1,6-dihydropyridazin-3-yl)phenyl)-4,7-methano-4,5,6,7-tetrahydrobenzo[b]thiophene-2-carboxamide;

N-[2-fluoro-5-(5-{[1-(2-methoxyethyl)-1H-pyrazol-3-yl]amino}-6-oxo-1,6-dihydropyridazin-3-yl)phenyl]-4,5,6,7-tetrahydro-1-benzothiophene-2-carboxamide;

4-tert-butyl-N-{2-fluoro-5-[6-oxo-5-(pyrimidin-4-ylamino)-1,6-dihydropyridazin-3-yl]phenyl}benzamide;

N-(3-{5-[(5-cyclopropyl-1H-pyrazol-3-yl)amino]-6-oxo-1,6-dihydropyridazin-3-yl}-2,6-difluorophenyl)-4,5,6,7-tetrahydro-1-benzothiophene-2-carboxamide;

N-{5-[5-({1-[2-(azetidin-1-yl)ethyl]-1H-pyrazol-3-yl}amino)-6-oxo-1,6-dihydropyridazin-3-yl]-2-fluorophenyl}-4,5,6,7-tetrahydro-1-benzothiophene-2-carboxamide;

6-tert-butyl-N-{2-fluoro-5-[6-oxo-5-(pyrimidin-4-ylamino)-1,6-dihydropyridazin-3-yl]phenyl}pyridine-3-carboxamide;

N-{2-fluoro-5-[6-oxo-5-(pyridazin-3-ylamino)-1,6-dihydropyridazin-3-yl]phenyl}-4,5,6,7-tetrahydro-1-benzothiophene-2-carboxamide;

5-tert-butyl-N-{2-fluoro-5-[6-oxo-5-(pyrimidin-4-ylamino)-1,6-dihydropyridazin-3-yl]phenyl}pyrimidine-2-carboxamide;

N-(3-{5-[(1,5-dimethyl-1H-pyrazol-3-yl)amino]-1-methyl-6-oxo-1,6-dihydropyridazin-3-yl}-2,6-difluorophenyl)-4,5,6,7-tetrahydro-1-benzothiophene-2-carboxamide;

N-(5-{5-[(1,5-dimethyl-1H-pyrazol-3-yl)amino]-6-oxo-1,6-dihydropyridazin-3-yl}-2-fluorophenyl)-6-[ethyl(methyl)amino]pyridine-3-carboxamide;

N-(5-{5-[(1,5-dimethyl-1H-pyrazol-3-yl)amino]-6-oxo-1,6-dihydropyridazin-3-yl}-2-fluorophenyl)-4,5,6,7-tetrahydro-1-benzothiophene-2-carboxamide;

N-{2-fluoro-5-[6-oxo-5-(pyrazin-2-ylamino)-1,6-dihydropyridazin-3-yl]phenyl}-4,5,6,7-tetrahydro-1-benzothiophene-2-carboxamide;

5-tert-butyl-N-(5-{5-[(1,5-dimethyl-1H-pyrazol-3-yl)amino]-6-oxo-1,6-dihydropyridazin-3-yl}-2-fluorophenyl)pyridine-2-carboxamide;

N-(5-{5-[(1,5-dimethyl-1H-pyrazol-3-yl)amino]-6-oxo-1,6-dihydropyridazin-3-yl}-2-fluorophenyl)-4-methoxy-1-benzothiophene-2-carboxamide;

4-[ethyl(methyl)amino]-N-{2-fluoro-5-[6-oxo-5-(pyrimidin-4-ylamino)-1,6-dihydropyridazin-3-yl]phenyl}benzamide;

N-{2-fluoro-5-[6-oxo-5-(pyrimidin-4-ylamino)-1,6-dihydropyridazin-3-yl]phenyl}-1-benzothiophene-2-carboxamide;

N-(5-{5-[(1,5-dimethyl-1H-pyrazol-3-yl)amino]-6-oxo-1,6-dihydropyridazin-3-yl}-2-fluorophenyl)-3-thiatricyclo[5.2.1.0^{2,6}]deca-2(6),4-diene-4-carboxamide;

N-(5-{5-[(1,5-dimethyl-1H-pyrazol-3-yl)amino]-6-oxo-1,6-dihydropyridazin-3-yl}-2-fluorophenyl)-1-benzothiophene-2-carboxamide;

N-(5-{5-[(5-cyclopropyl-1H-pyrazol-3-yl)amino]-1-methyl-6-oxo-1,6-dihydropyridazin-3-yl}-2-fluorophenyl)-4,5,6,7-tetrahydro-1-benzothiophene-2-carboxamide;

N-[2-fluoro-5-(5-{[1-(2-hydroxyethyl)-1H-pyrazol-3-yl]amino}-6-oxo-1,6-dihydropyridazin-3-yl)phenyl]-4,5,6,7-tetrahydro-1-benzothiophene-2-carboxamide;

N-(3-{5-[(1,5-dimethyl-1H-pyrazol-3-yl)amino]-6-oxo-1,6-dihydropyridazin-3-yl}-2,6-difluorophenyl)-4,5,6,7-tetrahydro-1-benzothiophene-2-carboxamide;

5-tert-butyl-N-{2-fluoro-5-[6-oxo-5-(pyrimidin-4-ylamino)-1,6-dihydropyridazin-3-yl]phenyl}pyrazine-2-carboxamide;

N-{2-fluoro-5-[6-oxo-5-(pyrimidin-4-ylamino)-1,6-dihydropyridazin-3-yl]phenyl}-4H,5H,6H-cyclopenta[b]thiophene-2-carboxamide;

N-[3-(5-{[5-(1,4-dimethyl-3-oxopiperazin-2-yl)pyridin-2-yl]amino}-1-methyl-6-oxo-1,6-dihydropyridazin-3-yl)-2,6-difluorophenyl]-4,5,6,7-tetrahydro-1-benzothiophene-2-carboxamide;

N-[3-(5-{[5-(4-ethylpiperazin-1-yl)pyridin-2-yl]amino}-6-oxo-1,6-dihydropyridazin-3-yl)-2-methylphenyl]-4,5,6,7-tetrahydro-1-benzothiophene-2-carboxamide;

N-{3-fluoro-6-[6-oxo-5-(pyrimidin-4-ylamino)-1,6-dihydropyridazin-3-yl]pyridin-2-yl}-4,5,6,7-tetrahydro-1-benzothiophene-2-carboxamide;

N-[2-fluoro-5-(5-{[1-(2-hydroxyethyl)-5-methyl-1H-pyrazol-3-yl]amino}-6-oxo-1,6-dihydropyridazin-3-yl)phenyl]-4,5,6,7-tetrahydro-1-benzothiophene-2-carboxamide;

N-(5-{5-[(5-cyclopropyl-1H-pyrazol-3-yl)amino]-6-oxo-1,6-dihydropyridazin-3-yl}-2-fluorophenyl)-5-[ethyl(methyl)amino]pyrazine-2-carboxamide;

N-(5-{5-[(5-cyclopropyl-1H-pyrazol-3-yl)amino]-6-oxo-1,6-dihydropyridazin-3-yl}-2-fluorophenyl)-4-hydroxy-4,5,6,7-tetrahydro-1-benzothiophene-2-carboxamide;

N-(3-{5-[(1,5-dimethyl-1H-pyrazol-3-yl)amino]-6-oxo-1,6-dihydropyridazin-3-yl}-2,6-difluorophenyl)-1-benzothiophene-2-carboxamide;

N-(5-{5-[(5-cyclopropyl-1H-pyrazol-3-yl)amino]-6-oxo-1,6-dihydropyridazin-3-yl}-2-fluorophenyl)-4-(2-hydroxypropan-2-yl)benzamide;

5-tert-butyl-N-(5-{5-[(5-cyclopropyl-1H-pyrazol-3-yl)amino]-6-oxo-1,6-dihydropyridazin-3-yl}-2-fluorophenyl)pyrazine-2-carboxamide;

N-(5-{5-[(5-cyclopropyl-1H-pyrazol-3-yl)amino]-6-oxo-1,6-dihydropyridazin-3-yl}-2-fluorophenyl)-4-[1-(2-hydroxyethoxy)-2-methylpropan-2-yl]benzamide;

N-(5-{5-[(5-cyclopropyl-1H-pyrazol-3-yl)amino]-6-oxo-1,6-dihydropyridazin-3-yl}-2-fluorophenyl)-4-(1-hydroxy-2-methylpropan-2-yl)benzamide;

N-(5-{5-[(5-cyclopropyl-1H-pyrazol-3-yl)amino]-6-oxo-1,6-dihydropyridazin-3-yl}-2-fluorophenyl)-5,5-dimethyl-4H,5H,6H-cyclopenta[b]thiophene-2-carboxamide;

N-(5-{5-[(1,5-dimethyl-1H-pyrazol-3-yl)amino]-1-methyl-6-oxo-1,6-dihydropyridazin-3-yl}-2-fluorophenyl)-1-benzothiophene-2-carboxamide;

5-tert-butyl-N-(5-{5-[(1,5-dimethyl-1H-pyrazol-3-yl)amino]-1-methyl-6-oxo-1,6-dihydropyridazin-3-yl}-2-fluorophenyl)pyrazine-2-carboxamide;

4-(1-cyano-1-methylethyl)-N-(5-{5-[(5-cyclopropyl-1H-pyrazol-3-yl)amino]-6-oxo-1,6-dihydropyridazin-3-yl}-2-fluorophenyl)benzamide;

5-tert-butyl-N-(5-{5-[(1,5-dimethyl-1H-pyrazol-3-yl)amino]-6-oxo-1,6-dihydropyridazin-3-yl}-2-fluorophenyl)pyrazine-2-carboxamide;

N-(5-{5-[(5-cyclopropyl-1H-pyrazol-3-yl)amino]-6-oxo-1,6-dihydropyridazin-3-yl}-2-fluorophenyl)-3-thia-5-azatricyclo[5.2.1.0^{2,6}]deca-2(6),4-diene-4-carboxamide;

5-tert-butyl-N-[2-fluoro-5-(5-{[1-(2-hydroxyethyl)-1H-pyrazol-3-yl]amino}-6-oxo-1,6-dihydropyridazin-3-yl)phenyl]pyrazine-2-carboxamide;
N-(5-{5-[(5-cyclopropyl-1H-pyrazol-3-yl)amino]-6-oxo-1,6-dihydropyridazin-3-yl}-2-fluorophenyl)-1-benzothiophene-2-carboxamide;
N-[2-fluoro-5-(5-{[1-methyl-5-(trifluoromethyl)-1H-pyrazol-3-yl]amino}-6-oxo-1,6-dihydropyridazin-3-yl)phenyl]-1-benzothiophene-2-carboxamide;
5-tert-butyl-N-[2-fluoro-5-(5-{[5-(4-methylpiperazin-1-yl)pyridin-2-yl]amino}-6-oxo-1,6-dihydropyridazin-3-yl)phenyl]pyrazine-2-carboxamide;
5-tert-butyl-N-(2-fluoro-5-{5-[(6-methylpyridin-2-yl)amino]-6-oxo-1,6-dihydropyridazin-3-yl}phenyl)pyrazine-2-carboxamide;
N-(5-{5-[(1,5-dimethyl-1H-pyrazol-3-yl)amino]-6-oxo-1,6-dihydropyridazin-3-yl}-2-fluorophenyl)-4-(3-methyloxetan-3-yl)benzamide;
N-(5-{5-[(1,5-dimethyl-1H-pyrazol-3-yl)amino]-6-oxo-1,6-dihydropyridazin-3-yl}-2-fluorophenyl)-4-hydroxy-1-benzothiophene-2-carboxamide;
N-[2-fluoro-5-(5-{[1-(2-hydroxyethyl)-5-methyl-1H-pyrazol-3-yl]amino}-6-oxo-1,6-dihydropyridazin-3-yl)phenyl]-1-benzothiophene-2-carboxamide;
N-[2-fluoro-5-(5-{[1-(2-hydroxyethyl)-1H-pyrazol-3-yl]amino}-6-oxo-1,6-dihydropyridazin-3-yl)phenyl]-1-benzothiophene-2-carboxamide;
N-[2-fluoro-5-(5-{[5-(4-methylpiperazin-1-yl)pyridin-2-yl]amino}-6-oxo-1,6-dihydropyridazin-3-yl)phenyl]-1-benzothiophene-2-carboxamide;
N-(5-{5-[(1,5-dimethyl-1H-pyrazol-3-yl)amino]-6-oxo-1,6-dihydropyridazin-3-yl}-2-fluorophenyl)-4-hydroxy-4,5,6,7-tetrahydro-1-benzothiophene-2-carboxamide;
N-(5-{5-[(1,5-dimethyl-1H-pyrazol-3-yl)amino]-6-oxo-1,6-dihydropyridazin-3-yl}-2-fluorophenyl)-4-(1-hydroxy-2-methylpropan-2-yl)benzamide;
N-(5-{5-[(5-amino-1-methyl-1H-pyrazol-3-yl)amino]-1-methyl-6-oxo-1,6-dihydropyridazin-3-yl}-2-fluorophenyl)-1-benzothiophene-2-carboxamide;
N-[2-fluoro-5-(5-{[5-(1-methylpyrrolidin-2-yl)pyridin-2-yl]amino}-6-oxo-1,6-dihydropyridazin-3-yl)phenyl]-1-benzothiophene-2-carboxamide;
4-tert-butyl-N-[(3R)-1-{5-[(1,5-dimethyl-1H-pyrazol-3-yl)amino]-1-methyl-6-oxo-1,6-dihydropyridazin-3-yl}piperidin-3-yl]benzamide;
N-[5-(5-{[5-(azetidin-1-ylmethyl)-1-methyl-1H-pyrazol-3-yl]amino}-1-methyl-6-oxo-1,6-dihydropyridazin-3-yl)-2-fluorophenyl]-1-benzothiophene-2-carboxamide;
N-(5-{5-[(5-amino-1-methyl-1H-pyrazol-3-yl)amino]-1-methyl-6-oxo-1,6-dihydropyridazin-3-yl}-2-fluorophenyl)-5-tert-butylpyrazine-2-carboxamide;
4-tert-butyl-N-(5-{5-[(1,5-dimethyl-1H-pyrazol-3-yl)amino]-1-methyl-6-oxo-1,6-dihydropyridazin-3-yl}-2-fluorophenyl)benzamide;
N-[3R)-1-{5-[(1,5-dimethyl-1H-pyrazol-3-yl)amino]-1-methyl-6-oxo-1,6-dihydropyridazin-3-yl}piperidin-3-yl]-1-benzothiophene-2-carboxamide;
5-tert-butyl-N-[2-fluoro-5-(5-{[5-(1-methylpyrrolidin-2-yl)pyridin-2-yl]amino}-6-oxo-1,6-dihydropyridazin-3-yl)phenyl]pyrazine-2-carboxamide;
5-tert-butyl-N-(2-fluoro-5-{5-[(6-methoxypyridin-2-yl)amino]-1-methyl-6-oxo-1,6-dihydropyridazin-3-yl}phenyl)pyrazine-2-carboxamide;
4-tert-butyl-N-(5-{5-[(1,5-dimethyl-1H-pyrazol-3-yl)amino]-6-oxo-1,6-dihydropyridazin-3-yl}-2-fluorophenyl)benzene-1-carboximidamide;
N-[(3R)-1-(1-methyl-5-{[5-(4-methylpiperazin-1-yl)pyridin-2-yl]amino}-6-oxo-1,6-dihydropyridazin-3-yl)piperidin-3-yl]-4,5,6,7-tetrahydro-1-benzothiophene-2-carboxamide;
4-tert-butyl-N-[(3R)-1-{5-[(1,5-dimethyl-1H-pyrazol-3-yl)amino]-6-oxo-1,6-dihydropyridazin-3-yl}piperidin-3-yl]benzamide;
N-[2-fluoro-5-(5-{[5-(1-methylpyrrolidin-2-yl)pyridin-2-yl]amino}-6-oxo-1,6-dihydropyridazin-3-yl)phenyl]-4,5,6,7-tetrahydro-1-benzothiophene-2-carboxamide;
N-[2-fluoro-5-(5-{[5-(4-hydroxy-4-methylpiperidin-1-yl)pyridin-2-yl]amino}-6-oxo-1,6-dihydropyridazin-3-yl)phenyl]-1-benzothiophene-2-carboxamide;
N-[5-(5-{[5-(azetidin-1-ylmethyl)-1-methyl-1H-pyrazol-3-yl]amino}-6-oxo-1,6-dihydropyridazin-3-yl)-2-fluorophenyl]-1-benzothiophene-2-carboxamide;
4-tert-butyl-N-[2-fluoro-5-(5-{[5-(1-methylpyrrolidin-2-yl)pyridin-2-yl]amino}-6-oxo-1,6-dihydropyridazin-3-yl)phenyl]benzamide;
N-[2-fluoro-5-(6-oxo-5-{[5-(2-oxopiperazin-1-yl)pyridin-2-yl]amino}-1,6-dihydropyridazin-3-yl)phenyl]-4,5,6,7-tetrahydro-1-benzothiophene-2-carboxamide;
N-[5-(5-{[5-(1,4-dimethyl-3-oxopiperazin-2-yl)pyridin-2-yl]amino}-6-oxo-1,6-dihydropyridazin-3-yl)-2-fluorophenyl]-1-benzothiophene-2-carboxamide;
5-tert-butyl-N-[2-methyl-3-(5-{[5-(1-methylpyrrolidin-2-yl)pyridin-2-yl]amino}-6-oxo-1,6-dihydropyridazin-3-yl)phenyl]pyrazine-2-carboxamide;
N-(5-{5-[(1,5-dimethyl-1H-pyrazol-3-yl)amino]-6-oxo-1,6-dihydropyridazin-3-yl}-2-fluorophenyl)-6-(2-hydroxypropan-2-yl)pyridine-3-carboxamide;
N-[2-fluoro-5-(5-{[5-(1-methylpyrrolidin-2-yl)pyridin-2-yl]amino}-6-oxo-1,6-dihydropyridazin-3-yl)phenyl]-4-(2-hydroxypropan-2-yl)benzamide;
N-[5-(5-{[5-(1,4-dimethyl-3-oxopiperazin-2-yl)pyridin-2-yl]amino}-6-oxo-1,6-dihydropyridazin-3-yl)-2-fluorophenyl]-4,5,6,7-tetrahydro-1-benzothiophene-2-carboxamide;
N-[(3R)-1-{5-[(1,5-dimethyl-1H-pyrazol-3-yl)amino]-6-oxo-1,6-dihydropyridazin-3-yl}piperidin-3-yl]-1-benzothiophene-2-carboxamide;
N-[2-methyl-3-(5-{[5-(1-methylpyrrolidin-2-yl)pyridin-2-yl]amino}-6-oxo-1,6-dihydropyridazin-3-yl)phenyl]-1-benzothiophene-2-carboxamide;
N-[6-fluoro-2-methyl-3-(5-{[5-(1-methylpyrrolidin-2-yl)pyridin-2-yl]amino}-6-oxo-1,6-dihydropyridazin-3-yl)phenyl]-1-benzothiophene-2-carboxamide;
5-tert-butyl-N-{2-fluoro-5-[6-oxo-5-(piperidin-3-ylamino)-1,6-dihydropyridazin-3-yl]phenyl}pyrazine-2-carboxamide;
5-tert-butyl-N-[2-fluoro-5-(5-{[5-(1-methylpyrrolidin-2-yl)pyridin-2-yl]amino}-6-oxo-1,6-dihydropyridazin-3-yl)phenyl]pyridine-2-carboxamide;
N-[2-fluoro-5-(5-{[5-(1-methylpiperidin-4-yl)pyridin-2-yl]amino}-6-oxo-1,6-dihydropyridazin-3-yl)phenyl]-1-benzothiophene-2-carboxamide;
4-tert-butyl-N-[(3S)-1-{5-[(1,5-dimethyl-1H-pyrazol-3-yl)amino]-6-oxo-1,6-dihydropyridazin-3-yl}piperidin-3-yl]benzamide;
4-tert-butyl-N-[2,6-difluoro-3-(5-{[5-(4-hydroxy-4-methylpiperidin-1-yl)pyridin-2-yl]amino}-6-oxo-1,6-dihydropyridazin-3-yl)phenyl]benzamide;
4-(2-aminopropan-2-yl)-N-[2-fluoro-5-(5-{[5-(1-methylpyrrolidin-2-yl)pyridin-2-yl]amino}-6-oxo-1,6-dihydropyridazin-3-yl)phenyl]benzamide;

N-[2-fluoro-5-(5-{[5-(1-methylpyrrolidin-2-yl)pyridin-2-yl]amino}-6-oxo-1,6-dihydropyridazin-3-yl)phenyl]-N-methyl-1-benzothiophene-2-carboxamide;
N-[2-fluoro-5-(5-{[5-(1-methylpyrrolidin-2-yl)pyridin-2-yl]amino}-6-oxo-1,6-dihydropyridazin-3-yl)phenyl]-4-hydroxy-1-benzothiophene-2-carboxamide;
N-[2-fluoro-5-(5-{[5-(1-methylpyrrolidin-2-yl)pyridin-2-yl]amino}-6-oxo-1,6-dihydropyridazin-3-yl)phenyl]-4-methoxy-1-benzothiophene-2-carboxamide;
N-[2-fluoro-5-(5-{[5-(1-methylpyrrolidin-2-yl)pyridin-2-yl]amino}-6-oxo-1,6-dihydropyridazin-3-yl)phenyl]-1-benzofuran-2-carboxamide;
N-[2-fluoro-5-(5-{[5-(1-methylpyrrolidin-2-yl)pyridin-2-yl]amino}-6-oxo-1,6-dihydropyridazin-3-yl)phenyl]-1-methyl-1H-indole-2-carboxamide;
N-[2-fluoro-5-(5-{[5-(1-methylpyrrolidin-2-yl)pyridin-2-yl]amino}-6-oxo-1,6-dihydropyridazin-3-yl)phenyl]-4-(1-hydroxy-2-methylpropan-2-yl)benzamide;
N-{2-fluoro-5-[5-({5-[(2-hydroxyethyl)(methyl)amino]pyridin-2-yl}amino)-6-oxo-1,6-dihydropyridazin-3-yl]phenyl}-1-benzothiophene-2-carboxamide;
N-[2-fluoro-5-(6-oxo-5-{[5-(pyrrolidin-1-ylmethyl)pyridin-2-yl]amino}-1,6-dihydropyridazin-3-yl)phenyl]-1-benzothiophene-2-carboxamide;
N-(2-fluoro-5-{6-oxo-5-[(5-{[(3R)-oxolan-3-ylamino]methyl}pyridin-2-yl)amino]-1,6-dihydropyridazin-3-yl}phenyl)-1-benzothiophene-2-carboxamide;
N-[2-fluoro-5-(5-{[5-(1-methylpyrrolidin-2-yl)pyridin-2-yl]amino}-6-oxo-1,6-dihydropyridazin-3-yl)phenyl]-4-hydroxy-5,5-dimethyl-4H,5H,6H-cyclopenta[b]thiophene-2-carboxamide;
N-[2-fluoro-5-(5-{[5-(1-methylpyrrolidin-2-yl)pyridin-2-yl]amino}-6-oxo-1,6-dihydropyridazin-3-yl)phenyl]-4-(propan-2-yl)benzamide;
N-[(3R)-1-(5-{[5-(azetidin-1-ylmethyl)-1-methyl-1H-pyrazol-3-yl]amino}-1-methyl-6-oxo-1,6-dihydropyridazin-3-yl)piperidin-3-yl]-1-benzothiophene-2-carboxamide;
4-ethyl-N-[2-fluoro-5-(5-{[5-(1-methylpyrrolidin-2-yl)pyridin-2-yl]amino}-6-oxo-1,6-dihydropyridazin-3-yl)phenyl]benzamide;
4-tert-butyl-N-{2-fluoro-5-[5-({5-[(4-hydroxy-4-methylpiperidin-1-yl)methyl]pyridin-2-yl}amino)-1-methyl-6-oxo-1,6-dihydropyridazin-3-yl]phenyl}benzamide;
4-tert-butyl-N-[(3R)-1-(1-methyl-5-{[5-(morpholin-4-ylcarbonyl)pyridin-2-yl]amino}-6-oxo-1,6-dihydropyridazin-3-yl)piperidin-3-yl]benzamide;
N-{2-fluoro-5-[5-({5-[(2R)-1-methylpyrrolidin-2-yl]pyridin-2-yl}amino)-6-oxo-1,6-dihydropyridazin-3-yl]phenyl}-4-hydroxy-4,5,6,7-tetrahydro-1-benzothiophene-2-carboxamide;
N-{2-fluoro-5-[5-({5-[(2S)-1-methylpyrrolidin-2-yl]pyridin-2-yl}amino)-6-oxo-1,6-dihydropyridazin-3-yl]phenyl}-4-hydroxy-4,5,6,7-tetrahydro-1-benzothiophene-2-carboxamide;
N-{2-fluoro-5-[5-({5-[(2R)-1-methylpyrrolidin-2-yl]pyridin-2-yl}amino)-6-oxo-1,6-dihydropyridazin-3-yl]phenyl}-5-hydroxy-4,5,6,7-tetrahydro-1-benzothiophene-2-carboxamide;
N-{2-fluoro-5-[5-({5-[(2S)-1-methylpyrrolidin-2-yl]pyridin-2-yl}amino)-6-oxo-1,6-dihydropyridazin-3-yl]phenyl}-5-hydroxy-4,5,6,7-tetrahydro-1-benzothiophene-2-carboxamide;
4-tert-butyl-N-[(3R)-1-(5-{[5-(1,4-dimethyl-3-oxopiperazin-2-yl)pyridin-2-yl]amino}-1-methyl-6-oxo-1,6-dihydropyridazin-3-yl)piperidin-3-yl]benzamide;
N-(2-fluoro-5-{5-[(5-{[(2-hydroxyethyl)amino]methyl}pyridin-2-yl)amino]-6-oxo-1,6-dihydropyridazin-3-yl}phenyl)-1-benzothiophene-2-carboxamide;
N-[2-fluoro-5-(5-{[5-(hydroxymethyl)pyridin-2-yl]amino}-6-oxo-1,6-dihydropyridazin-3-yl)phenyl]-1-benzothiophene-2-carboxamide;
N-(2-fluoro-5-{5-[(5-{[(2-fluoroethyl)amino]methyl}pyridin-2-yl)amino]-6-oxo-1,6-dihydropyridazin-3-yl}phenyl)-1-benzothiophene-2-carboxamide;
N-(2-fluoro-5-{6-oxo-5-[(5-{[(2,2,2-trifluoroethyl)amino]methyl}pyridin-2-yl)amino]-1,6-dihydropyridazin-3-yl}phenyl)-1-benzothiophene-2-carboxamide;
N-(2-fluoro-5-{5-[(5-{[(3S)-3-hydroxypyrrolidin-1-yl]methyl}pyridin-2-yl)amino]-6-oxo-1,6-dihydropyridazin-3-yl}phenyl)-1-benzothiophene-2-carboxamide;
N-[3-fluoro-6-(5-{[5-(4-methylpiperazin-1-yl)pyridin-2-yl]amino}-6-oxo-1,6-dihydropyridazin-3-yl)pyridin-2-yl]-4,5,6,7-tetrahydro-1-benzothiophene-2-carboxamide;
N-(5-{5-[(5-{[2-(azetidin-1-yl)ethyl](methyl)amino}pyridin-2-yl)amino]-6-oxo-1,6-dihydropyridazin-3-yl}-2-fluorophenyl)-1-benzothiophene-2-carboxamide;
4-tert-butyl-N-{2-fluoro-5-[5-({5-[(methylamino)methyl]pyridin-2-yl}amino)-6-oxo-1,6-dihydropyridazin-3-yl]phenyl}benzamide;
N-[2-fluoro-5-(5-{[5-(hydroxymethyl)-1-methyl-1H-pyrazol-3-yl]amino}-6-oxo-1,6-dihydropyridazin-3-yl)phenyl]-1-benzothiophene-2-carboxamide;
4-tert-butyl-N-[6-(5-{[5-(4-methylpiperazin-1-yl)pyridin-2-yl]amino}-6-oxo-1,6-dihydropyridazin-3-yl)pyridin-2-yl]benzamide;
(1S,7R)—N-[(3R)-1-(1-methyl-5-{[5-(morpholin-4-ylcarbonyl)pyridin-2-yl]amino}-6-oxo-1,6-dihydropyridazin-3-yl)piperidin-3-yl]-3-thiatricyclo[5.2.1.0^{2,6}]deca-2(6),4-diene-4-carboxamide;
4-tert-butyl-N-[(3R)-1-(5-{[5-(hydroxymethyl)pyridin-2-yl]amino}-1-methyl-6-oxo-1,6-dihydropyridazin-3-yl)piperidin-3-yl]benzamide;
N-[3-(5-{[5-(azetidin-1-ylmethyl)-1-methyl-1H-pyrazol-3-yl]amino}-6-oxo-1,6-dihydropyridazin-3-yl)-2-fluoro-6-methylphenyl]-1-benzothiophene-2-carboxamide;
N-[2-fluoro-5-(5-{[5-(1-methylazetidin-3-yl)pyridin-2-yl]amino}-6-oxo-1,6-dihydropyridazin-3-yl)phenyl]-1-benzothiophene-2-carboxamide;
N-[5-(5-{[5-(azetidin-3-yl)pyridin-2-yl]amino}-6-oxo-1,6-dihydropyridazin-3-yl)-2-fluorophenyl]-4-tert-butylbenzamide;
N-[2-fluoro-5-(6-oxo-5-{[5-(2-oxopiperazin-1-yl)pyridin-2-yl]amino}-1,6-dihydropyridazin-3-yl)phenyl]-1-benzothiophene-2-carboxamide;
N-[5-(5-{[5-(azetidin-3-yl)pyridin-2-yl]amino}-6-oxo-1,6-dihydropyridazin-3-yl)-2-fluorophenyl]-1-benzothiophene-2-carboxamide;
4-tert-butyl-N-[(3R)-1-(6-oxo-5-{[5-(pyrrolidin-1-ylmethyl)pyridin-2-yl]amino}-1,6-dihydropyridazin-3-yl)piperidin-3-yl]benzamide;
N-[5-(5-{[5-(azetidin-1-ylmethyl)-1-methyl-1H-pyrazol-3-yl]amino}-6-oxo-1,6-dihydropyridazin-3-yl)-2-fluorophenyl]-4-(2-hydroxypropan-2-yl)benzamide;

4-tert-butyl-N-[2-fluoro-5-(5-{[5-(1-methylazetidin-3-yl)pyridin-2-yl]amino}-6-oxo-1,6-dihydropyridazin-3-yl)phenyl]benzamide;

N-[2-fluoro-5-(1-methyl-6-oxo-5-{[5-(2-oxopiperazin-1-yl)pyridin-2-yl]amino}-1,6-dihydropyridazin-3-yl)phenyl]-1-benzothiophene-2-carboxamide;

N-[3-(5-{[5-(azetidin-1-ylmethyl)-1-methyl-1H-pyrazol-3-yl]amino}-1-methyl-6-oxo-1,6-dihydropyridazin-3-yl)-2-fluoro-6-methylphenyl]-1-benzothiophene-2-carboxamide;

4-tert-butyl-N-[(3R)-1-(1-methyl-5-{[5-(morpholin-4-ylcarbonyl)pyridin-2-yl]amino}-6-oxo-1,6-dihydropyridazin-3-yl)piperidin-3-yl]cyclohexane-1-carboxamide;

N-[3-(5-{[5-(1,4-dimethyl-3-oxopiperazin-2-yl)pyridin-2-yl]amino}-1-methyl-6-oxo-1,6-dihydropyridazin-3-yl)-2-fluoro-6-methylphenyl]-4,5,6,7-tetrahydro-1-benzothiophene-2-carboxamide;

N-[(3R)-1-[1-methyl-5-({5-methyl-4H,5H,6H,7H-pyrazolo[1,5-a]pyrazin-2-yl}amino)-6-oxo-1,6-dihydropyridazin-3-yl]piperidin-3-yl]-4-(1-methylcyclopropyl)benzamide;

N-[2-fluoro-6-methyl-3-(5-{[5-(4-methylpiperazin-1-yl)pyridin-2-yl]amino}-6-oxo-1,6-dihydropyridazin-3-yl)phenyl]-4-(1-hydroxy-2-methylpropan-2-yl)benzamide;

N-[5-(5-{[5-(azetidin-1-ylmethyl)-1-methyl-1H-pyrazol-3-yl]amino}-6-oxo-1,6-dihydropyridazin-3-yl)-2-fluorophenyl]-4-(1-hydroxy-2-methylpropan-2-yl)benzamide;

N-[5-(5-{[5-(azetidin-1-ylmethyl)-1-methyl-1H-pyrazol-3-yl]amino}-1-methyl-6-oxo-1,6-dihydropyridazin-3-yl)-2-fluorophenyl]-5,6,7,8-tetrahydroindolizine-2-carboxamide;

N-{6-fluoro-2-methyl-3-[1-methyl-5-({5-methyl-4H,5H,6H,7H-pyrazolo[1,5-a]pyrazin-2-yl}amino)-6-oxo-1,6-dihydropyridazin-3-yl]phenyl}-1-benzothiophene-2-carboxamide;

N-[5-(5-{[5-(azetidin-1-ylmethyl)-1-methyl-1H-pyrazol-3-yl]amino}-6-oxo-1,6-dihydropyridazin-3-yl)-2-methylphenyl]-5-tert-butylpyrazine-2-carboxamide;

N-[5-(5-{[5-(azetidin-1-ylmethyl)-1-ethyl-1H-pyrazol-3-yl]amino}-6-oxo-1,6-dihydropyridazin-3-yl)-2-fluorophenyl]-1-benzothiophene-2-carboxamide;

N-[(3R)-1-[5-({5-[(2-hydroxyethyl)(methyl)amino]pyridin-2-yl}amino)-1-methyl-6-oxo-1,6-dihydropyridazin-3-yl]piperidin-3-yl]-1-benzothiophene-2-carboxamide;

N-[(3R)-1-{5-[(5-{[2-(dimethylamino)ethyl](methyl)amino}pyridin-2-yl)amino]-1-methyl-6-oxo-1,6-dihydropyridazin-3-yl}piperidin-3-yl]-1-benzothiophene-2-carboxamide;

N-[6-fluoro-2-methyl-3-(5-{[1-methyl-5-(morpholin-4-ylmethyl)-1H-pyrazol-3-yl]amino}-6-oxo-1,6-dihydropyridazin-3-yl)phenyl]-1-benzothiophene-2-carboxamide;

N-[5-(5-{[5-(azetidin-1-ylmethyl)-1-methyl-1H-pyrazol-3-yl]amino}-1-methyl-6-oxo-1,6-dihydropyridazin-3-yl)-2-fluorophenyl]-4-(1-hydroxy-2-methylpropan-2-yl)benzamide;

N-[2-fluoro-5-(6-oxo-5-{[5-(2-oxopiperazin-1-yl)pyridin-2-yl]amino}-1,6-dihydropyridazin-3-yl)phenyl]-4-(1-hydroxy-2-methylpropan-2-yl)benzamide;

N-[5-(5-{[5-(azetidin-1-ylmethyl)-1-methyl-1H-pyrazol-3-yl]amino}-6-oxo-1,6-dihydropyridazin-3-yl)-2-fluorophenyl]-5,6,7,8-tetrahydroindolizine-2-carboxamide;

N-[(3R)-1-(5-{[5-(1,4-dimethyl-3-oxopiperazin-2-yl)pyridin-2-yl]amino}-1-methyl-6-oxo-1,6-dihydropyridazin-3-yl)piperidin-3-yl]-4,5,6,7-tetrahydro-1-benzothiophene-2-carboxamide;

N-{3-[5-({5-[(3,3-difluoroazetidin-1-yl)methyl]-1-methyl-1H-pyrazol-3-yl}amino)-6-oxo-1,6-dihydropyridazin-3-yl]-6-fluoro-2-methylphenyl}-1-benzothiophene-2-carboxamide;

N-[6-fluoro-2-methyl-3-(1-methyl-5-{[5-(1-methylpiperidin-4-yl)pyridin-2-yl]amino}-6-oxo-1,6-dihydropyridazin-3-yl)phenyl]-1-benzothiophene-2-carboxamide;

N-{5-[5-({5-[(3,3-difluoroazetidin-1-yl)methyl]pyridin-2-yl}amino)-6-oxo-1,6-dihydropyridazin-3-yl]-2-fluorophenyl}-1-benzothiophene-2-carboxamide;

N-{3-[5-({6-[(dimethylamino)methyl]pyridazin-3-yl}amino)-1-methyl-6-oxo-1,6-dihydropyridazin-3-yl]-6-fluoro-2-methylphenyl}-1-benzothiophene-2-carboxamide;

N-[3-(5-{[5-(1,4-dimethyl-3-oxopiperazin-2-yl)pyridin-2-yl]amino}-1-methyl-6-oxo-1,6-dihydropyridazin-3-yl)-2-fluoro-6-methylphenyl]-1-benzothiophene-2-carboxamide;

N-(5-{5-[(5-{[2-(dimethylamino)ethyl](methyl)amino}pyridin-2-yl)amino]-1-methyl-6-oxo-1,6-dihydropyridazin-3-yl}-2-fluorophenyl)-1-benzothiophene-2-carboxamide;

N-[5-(5-{[5-(azetidin-1-ylmethyl)-1-methyl-1H-pyrazol-3-yl]amino}-1-methyl-6-oxo-1,6-dihydropyridazin-3-yl)-2-fluorophenyl]-4-hydroxy-5,5-dimethyl-4H,5H,6H-cyclopenta[b]thiophene-2-carboxamide;

N-{3-[5-({5-[(2S)-1,4-dimethyl-3-oxopiperazin-2-yl]pyridin-2-yl}amino)-1-methyl-6-oxo-1,6-dihydropyridazin-3-yl]-2-fluoro-6-methylphenyl}-4,5,6,7-tetrahydro-1-benzothiophene-2-carboxamide;

N-{3-[5-({5-[(2R)-1,4-dimethyl-3-oxopiperazin-2-yl]pyridin-2-yl}amino)-1-methyl-6-oxo-1,6-dihydropyridazin-3-yl]-2-fluoro-6-methylphenyl}-4,5,6,7-tetrahydro-1-benzothiophene-2-carboxamide;

N-[2-chloro-6-methyl-3-(5-{[5-(4-methylpiperazin-1-yl)pyridin-2-yl]amino}-6-oxo-1,6-dihydropyridazin-3-yl)phenyl]-1-benzothiophene-2-carboxamide;

N-(6-fluoro-3-{5-[(5-{[(3S)-3-hydroxypyrrolidin-1-yl]methyl}-1-methyl-1H-pyrazol-3-yl)amino]-6-oxo-1,6-dihydropyridazin-3-yl}-2-methylphenyl)-1-benzothiophene-2-carboxamide;

N-[2-chloro-3-(5-{[5-(1,4-dimethyl-3-oxopiperazin-2-yl)pyridin-2-yl]amino}-6-oxo-1,6-dihydropyridazin-3-yl)-6-methylphenyl]-1-benzothiophene-2-carboxamide;

N-{2-fluoro-5-[(5-{[3-hydroxyazetidin-1-yl)methyl]-1-methyl-1H-pyrazol-3-yl}amino)-6-oxo-1,6-dihydropyridazin-3-yl]phenyl}-1-benzothiophene-2-carboxamide;

N-[(3R)-1-[5-({5-[(2S)-1,4-dimethyl-3-oxopiperazin-2-yl]pyridin-2-yl}amino)-1-methyl-6-oxo-1,6-dihydropyridazin-3-yl]piperidin-3-yl]-4,5,6,7-tetrahydro-1-benzothiophene-2-carboxamide;

N-[(3R)-1-[5-({5-[(2R)-1,4-dimethyl-3-oxopiperazin-2-yl]pyridin-2-yl}amino)-1-methyl-6-oxo-1,6-dihydropyridazin-3-yl]piperidin-3-yl]-4,5,6,7-tetrahydro-1-benzothiophene-2-carboxamide;

N-[6-fluoro-3-(5-{[5-(2-hydroxypropan-2-yl)-1-methyl-1H-pyrazol-3-yl]amino}-1-methyl-6-oxo-1,6-dihydropyridazin-3-yl)-2-methylphenyl]-1-benzothiophene-2-carboxamide;

N-{6-fluoro-2-methyl-3-[1-methyl-5-({5-[4-(methylamino)piperidin-1-yl]pyridin-2-yl}amino)-6-oxo-1,6-dihydropyridazin-3-yl]phenyl}-1-benzothiophene-2-carboxamide;

N-{6-fluoro-3-[5-({5-[(4-hydroxy-4-methylpiperidin-1-yl)methyl]-1-methyl-1H-pyrazol-3-yl}amino)-6-oxo-1,6-dihydropyridazin-3-yl]-2-methylphenyl}-1-benzothiophene-2-carboxamide;

N-(3-{5-[(1,5-dimethyl-1H-pyrazol-3-yl)amino]-6-oxo-1,6-dihydropyridazin-3-yl}-2-methylphenyl)-5,5-dimethyl-4H,5H,6H-cyclopenta[b]thiophene-2-carboxamide;

N-{5-[5-({5-acetyl-4H,5H,6H,7H-pyrazolo[1,5-a]pyrazin-2-yl}amino)-6-oxo-1,6-dihydropyridazin-3-yl]-2-fluorophenyl}-1-benzothiophene-2-carboxamide;

N-(2-fluoro-5-{5-[(5-{[(2-hydroxyethyl)(methyl)amino]methyl}-1-methyl-1H-pyrazol-3-yl)amino]-6-oxo-1,6-dihydropyridazin-3-yl}phenyl)-1-benzothiophene-2-carboxamide;

N-{3-[5-({5-[(2R)-1,4-dimethyl-3-oxopiperazin-2-yl]pyridin-2-yl}amino)-1-methyl-6-oxo-1,6-dihydropyridazin-3-yl]-2-fluoro-6-methylphenyl}-1-benzothiophene-2-carboxamide;

N-{3-[5-({5-[(2S)-1,4-dimethyl-3-oxopiperazin-2-yl]pyridin-2-yl}amino)-1-methyl-6-oxo-1,6-dihydropyridazin-3-yl]-2-fluoro-6-methylphenyl}-1-benzothiophene-2-carboxamide;

N-{6-fluoro-3-[5-({5-[(3-hydroxyazetidin-1-yl)methyl]-1-methyl-1H-pyrazol-3-yl}amino)-6-oxo-1,6-dihydropyridazin-3-yl]-2-methylphenyl}-1-benzothiophene-2-carboxamide;

N-{3-fluoro-6-[1-methyl-5-({5-methyl-4H,5H,6H,7H-pyrazolo[1,5-a]pyrazin-2-yl}amino)-6-oxo-1,6-dihydropyridazin-3-yl]pyridin-2-yl}-4,5,6,7-tetrahydro-1-benzothiophene-2-carboxamide;

4-[ethyl(methyl)amino]-N-[(3R)-1-(1-methyl-5-{[5-(morpholin-4-ylcarbonyl)pyridin-2-yl]amino}-6-oxo-1,6-dihydropyridazin-3-yl)piperidin-3-yl]benzamide;

N-{3-[5-({5-[(3,3-difluoroazetidin-1-yl)methyl]-1-methyl-1H-pyrazol-3-yl}amino)-6-oxo-1,6-dihydropyridazin-3-yl]-2-fluoro-6-methylphenyl}-1-benzothiophene-2-carboxamide;

(4S)—N-[5-(5-{[5-(azetidin-1-ylmethyl)-1-methyl-1H-pyrazol-3-yl]amino}-1-methyl-6-oxo-1,6-dihydropyridazin-3-yl)-2-fluorophenyl]-4-hydroxy-5,5-dimethyl-4H,5H,6H-cyclopenta[b]thiophene-2-carboxamide;

(4R)—N-[5-(5-{[5-(azetidin-1-ylmethyl)-1-methyl-1H-pyrazol-3-yl]amino}-1-methyl-6-oxo-1,6-dihydropyridazin-3-yl)-2-fluorophenyl]-4-hydroxy-5,5-dimethyl-4H,5H,6H-cyclopenta[b]thiophene-2-carboxamide;

N-[2-fluoro-6-methyl-3-(1-methyl-6-oxo-5-{[5-(2-oxopiperazin-1-yl)pyridin-2-yl]amino}-1,6-dihydropyridazin-3-yl)phenyl]-1-benzothiophene-2-carboxamide;

N-[6-fluoro-3-(5-{[5-(3-hydroxyazetidin-1-yl)pyridin-2-yl]amino}-1-methyl-6-oxo-1,6-dihydropyridazin-3-yl)-2-methylphenyl]-1-benzothiophene-2-carboxamide;

N-{5-[5-({5-[(dimethylamino)methyl]-1,2-oxazol-3-yl}amino)-1-methyl-6-oxo-1,6-dihydropyridazin-3-yl]-2-fluorophenyl}-1-benzothiophene-2-carboxamide;

N-[3-(5-{[5-(aminomethyl)-1-methyl-1H-pyrazol-3-yl]amino}-6-oxo-1,6-dihydropyridazin-3-yl)-6-fluoro-2-methylphenyl]-1-benzothiophene-2-carboxamide;

N-[(3R)-1-[5-({5-[(2-aminoethyl)(methyl)amino]pyridin-2-yl}amino)-1-methyl-6-oxo-1,6-dihydropyridazin-3-yl]piperidin-3-yl]-4-tert-butylbenzamide;

N-[2-fluoro-5-(5-{[5-(1-hydroxyethyl)pyridin-2-yl]amino}-6-oxo-1,6-dihydropyridazin-3-yl)phenyl]-1-benzothiophene-2-carboxamide;

N-[6-fluoro-3-(5-{[5-(3-hydroxyazetidin-1-yl)pyridin-2-yl]amino}-6-oxo-1,6-dihydropyridazin-3-yl)-2-methylphenyl]-1-benzothiophene-2-carboxamide;

N-{5-[5-({5-[(dimethylamino)methyl]-1,2-oxazol-3-yl}amino)-6-oxo-1,6-dihydropyridazin-3-yl]-2-fluorophenyl}-1-benzothiophene-2-carboxamide;

N-(3-{5-[(1,5-dimethyl-1H-pyrazol-3-yl)amino]-6-oxo-1,6-dihydropyridazin-3-yl}-2-methylphenyl)-4-hydroxy-4H,5H,6H-cyclopenta[b]thiophene-2-carboxamide;

N-[5-(5-{[1-(azetidin-3-yl)-1H-pyrazol-3-yl]amino}-6-oxo-1,6-dihydropyridazin-3-yl)-2-fluorophenyl]-1-benzothiophene-2-carboxamide;

N-{2-methyl-5-[6-oxo-5-(pyrimidin-4-ylamino)-1,6-dihydropyridazin-3-yl]phenyl}-1-benzothiophene-2-carboxamide;

N-[3-(5-{[5-(3,3-difluoropyrrolidin-1-yl)pyridin-2-yl]amino}-6-oxo-1,6-dihydropyridazin-3-yl)-2-fluoro-6-methylphenyl]-1-benzothiophene-2-carboxamide;

N-(5-{5-[(1,5-dimethyl-1H-pyrazol-3-yl)amino]-6-oxo-1,6-dihydropyridazin-3-yl}-2-fluorophenyl)-4-hydroxy-4H,5H,6H-cyclopenta[b]thiophene-2-carboxamide;

4-hydroxy-N-{2-methyl-3-[6-oxo-5-(pyrimidin-4-ylamino)-1,6-dihydropyridazin-3-yl]phenyl}-4H,5H,6H-cyclopenta[b]thiophene-2-carboxamide;

4-tert-butyl-N-{5-[5-({5-[(dimethylcarbamoyl)(hydroxy)methyl]pyridin-2-yl}amino)-1-methyl-6-oxo-1,6-dihydropyridazin-3-yl]-2-fluorophenyl}benzamide;

N-[3-(5-{[5-(3,3-difluoropyrrolidin-1-yl)pyridin-2-yl]amino}-1-methyl-6-oxo-1,6-dihydropyridazin-3-yl)-2-fluoro-6-methylphenyl]-1-benzothiophene-2-carboxamide;

4-tert-butyl-N-{5-[5-({5-[(dimethylcarbamoyl)carbonyl]pyridin-2-yl}amino)-1-methyl-6-oxo-1,6-dihydropyridazin-3-yl]-2-fluorophenyl}benzamide;

N-[5-(5-{[5-(aminomethyl)-1-methyl-1H-pyrazol-3-yl]amino}-6-oxo-1,6-dihydropyridazin-3-yl)-2-methylphenyl]indolizine-2-carboxamide;

5-tert-butyl-N-{2,6-dimethyl-3-[6-oxo-5-(pyrimidin-4-ylamino)-1,6-dihydropyridazin-3-yl]phenyl}pyrazine-2-carboxamide;

N-[(3R)-1-(5-{[1-(azetidin-3-yl)-1H-pyrazol-3-yl]amino}-1-methyl-6-oxo-1,6-dihydropyridazin-3-yl)piperidin-3-yl]-4-tert-butylbenzamide;

N-[3-(5-{[5-(aminomethyl)pyridin-2-yl]amino}-6-oxo-1,6-dihydropyridazin-3-yl)-6-fluoro-2-methylphenyl]-1-benzothiophene-2-carboxamide;

4-tert-butyl-N-[(3R)-1-(1-methyl-6-oxo-5-{[1-(piperidin-4-yl)-1H-pyrazol-3-yl]amino}-1,6-dihydropyridazin-3-yl)piperidin-3-yl]benzamide; or N-(3-{5-[(1,5-dimethyl-1H-pyrazol-3-yl)amino]-6-oxo-1,6-dihydropyridazin-3-yl}-2-fluoro-6-methylphenyl)-4-hydroxy-5,5-dimethyl-4H,5H,6H-cyclopenta[b]thiophene-2-carboxamide.

8. The compound of claim 1 that is—:

4-hydroxy-N-(2-(hydroxymethyl)-3-(5-(5-methyl-4,5,6,7-tetrahydropyrazolo[1,5-a]pyrazin-2-ylamino)-6-oxo-1,6-dihydropyridazin-3-yl)phenyl)-5,5-dimethyl-5,6-dihydro-4H-cyclopenta[b]thiophene-2-carboxamide;

5-tert-butyl-N-(2-(hydroxymethyl)-3-(5-(5-methyl-4,5,6,7-tetrahydropyrazolo[1,5-a]pyrazin-2-ylamino)-6-oxo-1,6-dihydropyridazin-3-yl)phenyl)pyrazine-2-carboxamide;

4-hydroxy-N-(2-(hydroxymethyl)-3-(5-(5-methyl-4,5,6,
7-tetrahydropyrazolo[1,5-a]pyrazin-2-ylamino)-6-oxo-
1,6-dihydropyridazin-3-yl)phenyl)-5,6-dihydro-4H-cy-
clopenta[b]thiophene-2-carboxamide;

N-(2-(hydroxymethyl)-3-(5-(5-(4-methylpiperazin-1-yl)
pyridin-2-ylamino)-6-oxo-1,6-dihydropyridazin-3-yl)
phenyl)benzo[b]thiophene-2-carboxamide;

N-(3-(5-(5-(azetidin-1-ylmethyl)-1-methyl-1H-pyrazol-
3-ylamino)-1-methyl-6-oxo-1,6-dihydropyridazin-3-
yl)-6-fluoro-2-(hydroxymethyl)phenyl)-4-hydroxy-5,
5-dimethyl-5,6-dihydro-4H-cyclopenta[b]thiophene-2-
carboxamide; or N-(3-(5-(5-((4,4-difluoropiperidin-1-yl)methyl)-1-me-
thyl-1H-pyrazol-3-ylamino)-6-oxo-1,6-dihydropy-
ridazin-3-yl)-6-fluoro-2-(hydroxymethyl)phenyl)
benzo[b]thiophene-2-carboxamide.

9. A compound that is:

3-(tert-butoxy)-N-[2-methyl-3-(1-methyl-5-{[5-(morpho-
lin-4-ylcarbonyl)pyridin-2-yl]amino}-6-oxo-1,6-dihy-
dropyridazin-3-yl)phenyl]azetidine-1-carboxamide;

4-tert-butyl-N-{5-[5-({5-[(S)-(dimethylcarbamoyl)(hy-
droxy)methyl]pyridin-2-yl}amino)-1-methyl-6-oxo-1,
6-dihydropyridazin-3-yl]-2-fluorophenyl}benzamide;

4-tert-butyl-N-{5-[5-({5-[(R)-(dimethylcarbamoyl)(hy-
droxy)methyl]pyridin-2-yl}amino)-1-methyl-6-oxo-1,
6-dihydropyridazin-3-yl]-2-fluorophenyl}benzamide;

3-(tert-butoxy)-N-[(3R)-1-(1-methyl-5-{[5-(morpholin-
4-ylcarbonyl)pyridin-2-yl]amino}-6-oxo-1,6-dihydro-
pyridazin-3-yl)piperidin-3-yl]azetidine-1-carboxam-
ide;

N-{2-fluoro-5-[5-({5-[(3-hydroxyazetidin-1-yl)methyl]-
1-methyl-1H-pyrazol-3-yl}amino)-1-methyl-6-oxo-1,
6-dihydropyridazin-3-yl]phenyl}-1-benzothiophene-2-
carboxamide;

N-[2-methyl-3-(1-methyl-5-{[5-(morpholin-4-ylcarbo-
nyl)pyridin-2-yl]amino}-6-oxo-1,6-dihydropyridazin-
3-yl)phenyl]-2,3-dihydro-1H-isoindole-2-carboxam-
ide;

4-tert-butyl-N-[(3R)-1-(6-oxo-5-{[5-(pyrrolidin-2-yl)py-
ridin-2-yl]amino}-1,6-dihydropyridazin-3-yl)piperi-
din-3-yl]benzamide;

N-[2-fluoro-5-(5-{[5-(2-hydroxypropan-2-yl)-1-methyl-
1H-pyrazol-3-yl]amino}-6-oxo-1,6-dihydropyridazin-
3-yl)phenyl]-1-benzothiophene-2-carboxamide;

N-[2-fluoro-3-(5-{[5-(3-hydroxyazetidin-1-yl)pyridin-2-
yl]amino}-1-methyl-6-oxo-1,6-dihydropyridazin-3-
yl)-6-methylphenyl]-4-hydroxy-5,5-dimethyl-4H,5H,
6H-cyclopenta[b]thiophene-2-carboxamide;

(4S)—N-(3-{5-[(1,5-dimethyl-1H-pyrazol-3-yl)amino]-
6-oxo-1,6-dihydropyridazin-3-yl}-2-fluoro-6-meth-
ylphenyl)-4-hydroxy-5,5-dimethyl-4H,5H,6H-cyclo-
penta[b]thiophene-2-carboxamide;

(4R)—N-(3-{5-[(1,5-dimethyl-1H-pyrazol-3-yl)amino]-
6-oxo-1,6-dihydropyridazin-3-yl}-2-fluoro-6-meth-
ylphenyl)-4-hydroxy-5,5-dimethyl-4H,5H,6H-cyclo-
penta[b]thiophene-2-carboxamide;

N-[2-fluoro-5-(5-{[5-(3-hydroxy-3-methylpyrrolidin-1-
yl)pyridin-2-yl]amino}-6-oxo-1,6-dihydropyridazin-3-
yl)phenyl]-1-benzothiophene-2-carboxamide;

5-tert-butyl-N-{3-[5-({5-[(3,3-difluoroazetidin-1-yl)me-
thyl]-1-methyl-1H-pyrazol-3-yl}amino)-6-oxo-1,6-di-
hydropyridazin-3-yl]-2,6-dimethylphenyl}pyrazine-2-
carboxamide;

N-[6-fluoro-3-(5-{[5-(1-hydroxyethyl)-1,3-thiazol-2-yl]
amino}-1-methyl-6-oxo-1,6-dihydropyridazin-3-yl)-2-
methylphenyl]-1-benzothiophene-2-carboxamide;

N-[3-(5-{[5-(azetidin-1-ylmethyl)-1-methyl-1H-pyrazol-
3-yl]amino}-1-methyl-6-oxo-1,6-dihydropyridazin-3-
yl)-2-fluoro-6-methylphenyl]-4-hydroxy-5,5-dimethyl-
4H,5H,6H-cyclopenta[b]thiophene-2-carboxamide;

N-{6-fluoro-2-methyl-3-[5-({1-[2-(oxan-2-yloxy)ethyl]-
1H-pyrazol-3-yl}amino)-6-oxo-1,6-dihydropyridazin-
3-yl]phenyl}-1-benzothiophene-2-carboxamide;

N-[6-fluoro-3-(5-{[1-(2-hydroxyethyl)-1-pyrazol-3-yl]
amino}-6-oxo-1,6-dihydropyridazin-3-yl)-2-meth-
ylphenyl]-1-benzothiophene-2-carboxamide;

N-{5-[5-({5-[2-(dimethylamino)ethoxy]pyridin-2-
yl}amino)-1-methyl-6-oxo-1,6-dihydropyridazin-3-
yl]-2-fluorophenyl}-1-benzothiophene-2-carboxamide;

N-[6-fluoro-3-(5-{[5-(2-hydroxypropan-2-yl)-1-methyl-
1H-pyrazol-3-yl]amino}-6-oxo-1,6-dihydropyridazin-
3-yl)-2-methylphenyl]-1-benzothiophene-2-carboxamide;

N-{3-[5-({5-[(3-hydroxyazetidin-1-yl)methyl]-1-methyl-
1H-pyrazol-3-yl}amino)-6-oxo-1,6-dihydropyridazin-
3-yl]-2,6-dimethylphenyl}-1-benzothiophene-2-car-
boxamide;

N-[5-(5-{[5-(azetidin-1-ylmethyl)-1-methyl-1H-pyrazol-
3-yl]amino}-1-methyl-6-oxo-1,6-dihydropyridazin-3-
yl)-2-fluorophenyl]-4-fluoro-5,5-dimethyl-4H,5H,6H-
cyclopenta[b]thiophene-2-carboxamide;

4-tert-butyl-N-(3-{5-[(2,6-dimethylpyrimidin-4-yl)
amino]-6-oxo-1,6-dihydropyridazin-3-yl}-6-fluoro-2-
methylphenyl)benzamide;

(4S)—N-[3-(5-{[5-(azetidin-1-ylmethyl)-1-methyl-1H-
pyrazol-3-yl]amino}-1-methyl-6-oxo-1,6-dihydropy-
ridazin-3-yl)-6-fluoro-2-methylphenyl]-4-hydroxy-5,
5-dimethyl-4H,5H,6H-cyclopenta[b]thiophene-2-
carboxamide;

(4R)—N-[3-(5-{[5-(azetidin-1-ylmethyl)-1-methyl-1H-
pyrazol-3-yl]amino}-1-methyl-6-oxo-1,6-dihydropy-
ridazin-3-yl)-6-fluoro-2-methylphenyl]-4-hydroxy-5,
5-dimethyl-4H,5H,6H-cyclopenta[b]thiophene-2-
carboxamide;

N-[(3R)-1-(5-{[5-(azetidin-3-yl)pyridin-2-yl]amino}-6-
oxo-1,6-dihydropyridazin-3-yl)piperidin-3-yl]-4-tert-
butylbenzamide;

(4S)—N-{2-fluoro-5-[5-({5-[(2S)-1-methylpyrrolidin-2-
yl]pyridin-2-yl}amino)-6-oxo-1,6-dihydropyridazin-3-
yl]phenyl}-4-hydroxy-5,5-dimethyl-4H,5H,6H-cyclo-
penta[b]thiophene-2-carboxamide;

(4R)—N-[3-(5-{[5-(azetidin-1-ylmethyl)-1-methyl-1H-
pyrazol-3-yl]amino}-1-methyl-6-oxo-1,6-dihydropy-
ridazin-3-yl)-2-fluoro-6-methylphenyl]-4-hydroxy-5,
5-dimethyl-4H,5H,6H-cyclopenta[b]thiophene-2-
carboxamide;

(4S)—N-[3-(5-{[5-(azetidin-1-ylmethyl)-1-methyl-1H-
pyrazol-3-yl]amino}-1-methyl-6-oxo-1,6-dihydropy-
ridazin-3-yl)-2-fluoro-6-methylphenyl]-4-hydroxy-5,
5-dimethyl-4H,5H,6H-cyclopenta[b]thiophene-2-
carboxamide;

N-[3-fluoro-6-[5-({5-methyl-4H,5H,6H,7H-pyrazolo[1,
5-a]pyrazin-2-yl}amino)-6-oxo-1,6-dihydropyridazin-
3-yl]pyridin-2-yl]-1-benzothiophene-2-carboxamide;

N-[6-fluoro-3-(5-{[5-(3-hydroxy-3-methylazetidin-1-yl)
pyridin-2-yl]amino}-6-oxo-1,6-dihydropyridazin-3-
yl)-2-methylphenyl]-1-benzothiophene-2-carboxam-
ide;

N-[2-fluoro-3-(5-{[5-(3-hydroxy-3-methylazetidin-1-yl)
pyridin-2-yl]amino}-6-oxo-1,6-dihydropyridazin-3-
yl)-6-methylphenyl]-1-benzothiophene-2-carboxam-
ide;

N-(3-{5-[(1,5-dimethyl-1H-pyrazol-3-yl)amino]-6-oxo-1,6-dihydropyridazin-3-yl}-6-fluoro-2-methylphenyl)-5-methyl-1-benzothiophene-2-carboxamide;

N-{3-[5-({5-[(3,3-difluoropyrrolidin-1-yl)methyl]-1-methyl-1H-pyrazol-3-yl}amino)-6-oxo-1,6-dihydropyridazin-3-yl]-6-fluoro-2-methylphenyl}-1-benzothiophene-2-carboxamide;

(4R)—N-{2-fluoro-5-[5-({5-[(2S)-1-methylpyrrolidin-2-yl]pyridin-2-yl}amino)-6-oxo-1,6-dihydropyridazin-3-yl]phenyl}-4-hydroxy-5,5-dimethyl-4H,5H,6H-cyclopenta[b]thiophene-2-carboxamide;

(4S)—N-{2-fluoro-5-[5-({5-[(2R)-1-methylpyrrolidin-2-yl]pyridin-2-yl}amino)-6-oxo-1,6-dihydropyridazin-3-yl]phenyl}-4-hydroxy-5,5-dimethyl-4H,5H,6H-cyclopenta[b]thiophene-2-carboxamide;

N-[3-(5-{[5-(2-hydroxypropan-2-yl)-1-methyl-1H-pyrazol-3-yl]amino}-6-oxo-1,6-dihydropyridazin-3-yl)-2,6-dimethylphenyl]-1-benzothiophene-2-carboxamide;

4-tert-butyl-N-[2-(hydroxymethyl)-3-(1-methyl-5-{[5-(morpholin-4-ylcarbonyl)pyridin-2-yl]amino}-6-oxo-1,6-dihydropyridazin-3-yl)phenyl]benzamide;

N-{3-[5-({5-[(4,4-difluoropiperidin-1-yl)methyl]-1-methyl-1H-pyrazol-3-yl}amino)-1-methyl-6-oxo-1,6-dihydropyridazin-3-yl]-6-fluoro-2-methylphenyl}-1-benzothiophene-2-carboxamide;

N-{3-[5-({5-[(4,4-difluoropiperidin-1-yl)methyl]-1-methyl-1H-pyrazol-3-yl}amino)-6-oxo-1,6-dihydropyridazin-3-yl]-6-fluoro-2-methylphenyl}-1-benzothiophene-2-carboxamide;

N-(3-{5-[(1,5-dimethyl-1H-pyrazol-3-yl)amino]-6-oxo-1,6-dihydropyridazin-3-yl}-6-fluoro-2-methylphenyl)-5-fluoro-1-benzothiophene-2-carboxamide;

N-(3-{5-[(1,5-dimethyl-1H-pyrazol-3-yl)amino]-6-oxo-1,6-dihydropyridazin-3-yl}-6-fluoro-2-methylphenyl)-6-fluoro-1-benzothiophene-2-carboxamide;

N-(3-{5-[(1,5-dimethyl-1H-pyrazol-3-yl)amino]-6-oxo-1,6-dihydropyridazin-3-yl}-6-fluoro-2-methylphenyl)-7-fluoro-1-benzothiophene-2-carboxamide;

6-chloro-N-(3-{5-[(1,5-dimethyl-1H-pyrazol-3-yl)amino]-6-oxo-1,6-dihydro pyridazin-3-yl}-6-fluoro-2-methylphenyl)-1-benzothiophene-2-carboxamide;

N-(3-{5-[(1,5-dimethyl-1H-pyrazol-3-yl)amino]-6-oxo-1,6-dihydropyridazin-3-yl}-6-fluoro-2-methylphenyl)-4-fluoro-1-benzothiophene-2-carboxamide;

N-(3-{5-[(1,5-dimethyl-1H-pyrazol-3-yl)amino]-6-oxo-1,6-dihydropyridazin-3-yl}-6-fluoro-2-methylphenyl)-6-methyl-1-benzothiophene-2-carboxamide;

(4R)—N-{2-fluoro-5-[5-({5-[(2R)-1-methylpyrrolidin-2-yl]pyridin-2-yl}amino)-6-oxo-1,6-dihydropyridazin-3-yl]phenyl}-4-hydroxy-5,5-dimethyl-4H,5H,6H-cyclopenta[b]thiophene-2-carboxamide;

(5S)—N-{2-fluoro-5-[5-({5-[(2S)-1-methylpyrrolidin-2-yl]pyridin-2-yl}amino)-6-oxo-1,6-dihydropyridazin-3-yl]phenyl}-5-hydroxy-4,5,6,7-tetrahydro-1-benzothiophene-2-carboxamide;

4-tert-butyl-N-[2-formyl-3-(1-methyl-5-{[5-(morpholin-4-ylcarbonyl)pyridin-2-yl]amino}-6-oxo-1,6-dihydropyridazin-3-yl)phenyl]benzamide;

N-(3-{5-[(1,5-dimethyl-1H-pyrazol-3-yl)amino]-6-oxo-1,6-dihydropyridazin-3-yl}-6-fluoro-2-methylphenyl)-6-(trifluoromethyl)-1-benzothiophene-2-carboxamide;

4-tert-butyl-N-[2-(fluoromethyl)-3-(1-methyl-5-{[5-(morpholin-4-ylcarbonyl)pyridin-2-yl]amino}-6-oxo-1,6-dihydropyridazin-3-yl)phenyl]benzamide;

N-(3-{5-[(1,5-dimethyl-1H-pyrazol-3-yl)amino]-6-oxo-1,6-dihydropyridazin-3-yl}-6-fluoro-2-methylphenyl)-4-hydroxy-5,5-dimethyl-4H,5H,6H-cyclopenta[b]thiophene-2-carboxamide;

(5R)—N-{2-fluoro-5-[5-({5-[(2S)-1-methylpyrrolidin-2-yl]pyridin-2-yl}amino)-6-oxo-1,6-dihydropyridazin-3-yl]phenyl}-5-hydroxy-4,5,6,7-tetrahydro-1-benzothiophene-2-carboxamide;

(5S)—N-{2-fluoro-5-[5-({5-[(2R)-1-methylpyrrolidin-2-yl]pyridin-2-yl}amino)-6-oxo-1,6-dihydropyridazin-3-yl]phenyl}-5-hydroxy-4,5,6,7-tetrahydro-1-benzothiophene-2-carboxamide;

N-[3-fluoro-6-(5-{[5-(2-hydroxypropan-2-yl)-1-methyl-1H-pyrazol-3-yl]amino}-6-oxo-1,6-dihydropyridazin-3-yl)pyridin-2-yl]-1-benzothiophene-2-carboxamide;

N-{6-fluoro-3-[5-({5-[(3-hydroxy-3-methylazetidin-1-yl)methyl]-1-methyl-1H-pyrazol-3-yl}amino)-6-oxo-1,6-dihydropyridazin-3-yl]-2-methylphenyl}-1-benzothiophene-2-carboxamide;

N-{6-fluoro-2-methyl-3-[6-oxo-5-(pyrimidin-4-ylamino)-1,6-dihydropyridazin-3-yl]phenyl}-4-hydroxy-5,5-dimethyl-4H,5H,6H-cyclopenta[b]thiophene-2-carboxamide;

N-[5-(5-{[5-(azetidin-1-ylmethyl)-1-methyl-1H-pyrazol-3-yl]amino}-1-methyl-6-oxo-1,6-dihydropyridazin-3-yl)-2-fluorophenyl]-4-methoxy-5,5-dimethyl-4H,5H,6H-cyclopenta[b]thiophene-2-carboxamide;

(5R)—N-{2-fluoro-5-[5-({5-[(2R)-1-methylpyrrolidin-2-yl]pyridin-2-yl}amino)-6-oxo-1,6-dihydropyridazin-3-yl]phenyl}-5-hydroxy-4,5,6,7-tetrahydro-1-benzothiophene-2-carboxamide;

5-tert-butyl-N-[6-fluoro-2-methyl-3-(5-{[5-(1-methylpiperidin-4-yl)pyridin-2-yl]amino}-6-oxo-1,6-dihydropyridazin-3-yl)phenyl]pyrazine-2-carboxamide;

N-[2-fluoro-6-methyl-3-(5-{[5-(1-methylpiperidin-4-yl)pyridin-2-yl]amino}-6-oxo-1,6-dihydropyridazin-3-yl)phenyl]-4-hydroxy-5,5-dimethyl-4H,5H,6H-cyclopenta[b]thiophene-2-carboxamide;

4-chloro-N-(3-{5-[(1,5-dimethyl-1H-pyrazol-3-yl)amino]-6-oxo-1,6-dihydropyridazin-3-yl}-6-fluoro-2-methylphenyl)-1-benzothiophene-2-carboxamide;

N-(3-{5-[(1,5-dimethyl-1H-pyrazol-3-yl)amino]-6-oxo-1,6-dihydropyridazin-3-yl}-6-fluoro-2-methylphenyl)-5-methoxy-1-benzothiophene-2-carboxamide;

5-bromo-N-(3-{5-[(1,5-dimethyl-1H-pyrazol-3-yl)amino]-6-oxo-1,6-dihydro pyridazin-3-yl}-6-fluoro-2-methylphenyl)-1-benzothiophene-2-carboxamide;

6-bromo-N-(3-{5-[(1,5-dimethyl-1H-pyrazol-3-yl)amino]-6-oxo-1,6-dihydro pyridazin-3-yl}-6-fluoro-2-methylphenyl)-1-benzothiophene-2-carboxamide;

N-(3-{5-[(1,5-dimethyl-1H-pyrazol-3-yl)amino]-6-oxo-1,6-dihydropyridazin-3-yl}-6-fluoro-2-methylphenyl)-1,3-benzothiazole-2-carboxamide;

N-{3-[5-({5-[(3,3-difluoroazetidin-1-yl)methyl]-1,2-oxazol-3-yl}amino)-6-oxo-1,6-dihydropyridazin-3-yl]-6-fluoro-2-methylphenyl}-1-benzothiophene-2-carboxamide;

N-(3-{5-[(5-amino-1-methyl-1H-pyrazol-3-yl)amino]-6-oxo-1,6-dihydropyridazin-3-yl}-6-fluoro-2-methylphenyl)-1-benzothiophene-2-carboxamide;

4-tert-butyl-N-{3-[5-({5-[(dimethylcarbamoyl)(hydroxy)methyl]pyridin-2-yl}amino)-1-methyl-6-oxo-1,6-dihydropyridazin-3-yl]-6-fluoro-2-methylphenyl}benzamide;

3-(tert-butoxy)-N-(3-{5-[(1,5-dimethyl-1H-pyrazol-3-yl)amino]-6-oxo-1,6-dihydropyridazin-3-yl}-2-methylphenyl)azetidine-1-carboxamide;

(4R)—N-[5-(5-{[5-(azetidin-1-ylmethyl)-1-methyl-1H-pyrazol-3-yl]amino}-1-methyl-6-oxo-1,6-dihydropyridazin-3-yl)-2-fluorophenyl]-4-methoxy-5,5-dimethyl-4H,5H,6H-cyclopenta[b]thiophene-2-carboxamide;

(4S)—N-[5-(5-{[5-(azetidin-1-ylmethyl)-1-methyl-1H-pyrazol-3-yl]amino}-1-methyl-6-oxo-1,6-dihydropyridazin-3-yl)-2-fluorophenyl]-4-methoxy-5,5-dimethyl-4H,5H,6H-cyclopenta[b]thiophene-2-carboxamide;

N-(3-{5-[(1,5-dimethyl-1H-pyrazol-3-yl)amino]-6-oxo-1,6-dihydropyridazin-3-yl}-6-fluoro-2-methylphenyl)-7-methyl-1-benzothiophene-2-carboxamide;

N-(3-{5-[(1,5-dimethyl-1H-pyrazol-3-yl)amino]-6-oxo-1,6-dihydropyridazin-3-yl}-6-fluoro-2-methylphenyl)-5-hydroxy-1-benzothiophene-2-carboxamide;

4-tert-butyl-N-{3-[5-({5-[(dimethylcarbamoyl)(hydroxy)methyl]pyridin-2-yl}amino)-6-oxo-1,6-dihydropyridazin-3-yl]-6-fluoro-2-methylphenyl}benzamide;

(4R)—N-[6-fluoro-2-methyl-3-(1-methyl-5-{[1-methyl-5-(pyrrolidin-2-yl)-1H-pyrazol-3-yl]amino}-6-oxo-1,6-dihydropyridazin-3-yl)phenyl]-4-hydroxy-5,5-dimethyl-4H,5H,6H-cyclopenta[b]thiophene-2-carboxamide;

4-tert-butyl-N-{3-[5-({5-[(R)-(dimethylcarbamoyl)(hydroxy)methyl]pyridin-2-yl}amino)-1-methyl-6-oxo-1,6-dihydropyridazin-3-yl]-6-fluoro-2-methylphenyl}benzamide;

4-tert-butyl-N-{3-[5-({5-[(S)-(dimethylcarbamoyl)(hydroxy)methyl]pyridin-2-yl}amino)-1-methyl-6-oxo-1,6-dihydropyridazin-3-yl]-6-fluoro-2-methylphenyl}benzamide;

4-tert-butyl-N-{3-[5-({5-[(R)-(dimethylcarbamoyl)(hydroxy)methyl]pyridin-2-yl}amino)-6-oxo-1,6-dihydropyridazin-3-yl]-6-fluoro-2-methylphenyl}benzamide;

4-tert-butyl-N-{3-[5-({5-[(S)-(dimethylcarbamoyl)(hydroxy)methyl]pyridin-2-yl}amino)-6-oxo-1,6-dihydropyridazin-3-yl]-6-fluoro-2-methylphenyl}benzamide;

4-tert-butyl-N-[2-(hydroxymethyl)-3-[1-methyl-6-oxo-5-(pyrimidin-4-ylamino)-1,6-dihydropyridazin-3-yl]phenyl]benzamide;

N-[5-(5-{[5-(azetidin-1-ylmethyl)-1-methyl-1H-pyrazol-3-yl]amino}-6-oxo-1,6-dihydropyridazin-3-yl)-2-fluorophenyl]-4-fluoro-5,5-dimethyl-4H,5H,6H-cyclopenta[b]thiophene-2-carboxamide;

(4R)—N-[5-(5-{[5-(azetidin-1-ylmethyl)-1-methyl-1H-pyrazol-3-yl]amino}-6-oxo-1,6-dihydropyridazin-3-yl)-2-fluorophenyl]-4-fluoro-5,5-dimethyl-4H,5H,6H-cyclopenta[b]thiophene-2-carboxamide; or (4S)—N-[5-(5-{[5-(azetidin-1-ylmethyl)-1-methyl-1H-pyrazol-3-yl]amino}-1-methyl-6-oxo-1,6-dihydropyridazin-3-yl)-2-fluorophenyl]-4-fluoro-5,5-dimethyl-4H,5H,6H-cyclopenta[b]thiophene-2-carboxamide.

10. A pharmaceutical composition, comprising a compound of claim 1, together with at least one pharmaceutically acceptable vehicle chosen from carriers, adjuvants, and excipients.

11. A method for inhibiting ATP hydrolysis, the method comprising contacting cells expressing Btk with a compound of claim 1 in an amount sufficient to detectably decrease the level of ATP hydrolysis in vitro.

12. A method for determining the presence of Btk in a sample, comprising contacting the sample with a compound of claim 1 under conditions that permit detection of Btk activity, detecting a level of Btk activity in the sample, and therefrom determining the presence or absence of Btk in the sample.

13. A method for inhibiting B-cell activity comprising contacting cells expressing Btk with a compound of claim 1, in an amount sufficient to detectably decrease B-cell activity in vitro.

* * * * *

UNITED STATES PATENT AND TRADEMARK OFFICE
CERTIFICATE OF CORRECTION

| | | |
|---|---|---|
| PATENT NO. | : 8,598,174 B2 | Page 1 of 1 |
| APPLICATION NO. | : 13/128726 | |
| DATED | : December 3, 2013 | |
| INVENTOR(S) | : Antonio J. M. Barbosa, Jr. | |

It is certified that error appears in the above-identified patent and that said Letters Patent is hereby corrected as shown below:

On the Title Page, Item (73) Assignee: reads "Genetech, Inc., South San Francisco," should read -- Genentech, Inc., South San Francisco, --.

Signed and Sealed this
Fifteenth Day of April, 2014

Michelle K. Lee
*Deputy Director of the United States Patent and Trademark Office*